US010793563B2

(12) United States Patent
Bleich et al.

(10) Patent No.: US 10,793,563 B2
(45) Date of Patent: Oct. 6, 2020

(54) GCN2 INHIBITORS AND USES THEREOF

(71) Applicants: Merck Patent GmbH, Darmstadt (DE); Vertex Pharmaceuticals Incorporated, Boston, MA (US)

(72) Inventors: Matthew Bleich, Brighton, MA (US); Jean-Damien Charrier, Wantage (GB); Huijun Dong, Arlington, MA (US); Steven Durrant, Abingdon (GB); Meredith Suzanne Eno, Brighton, MA (US); Gorka Etxebarria I Jardi, Abingdon (GB); Simon Everitt, Abingdon (GB); Damien Fraysse, Abingdon (GB); Ronald Knegtel, Abingdon (GB); Igor Mochalkin, Westford, MA (US); Kiri North, Abingdon (GB); Filippos Porichis, Melrose, MA (US); Hui Qiu, Acton, MA (US); Robert Pullin, Abingdon (GB); Pierre-Henri Storck, Abingdon (GB); Heather Clare Twin, Abingdon (GB); Yufang Xiao, Lexington, MA (US)

(73) Assignees: MERCK PATENT GMBH, Darmstadt (DE); VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 16/260,019

(22) Filed: Jan. 28, 2019

(65) Prior Publication Data

US 2019/0233411 A1    Aug. 1, 2019

Related U.S. Application Data

(60) Provisional application No. 62/623,312, filed on Jan. 29, 2018.

(51) Int. Cl.
*C07D 471/04* (2006.01)
*C07D 519/00* (2006.01)
*A61P 35/00* (2006.01)

(52) U.S. Cl.
CPC ......... *C07D 471/04* (2013.01); *C07D 519/00* (2013.01); *A61P 35/00* (2018.01)

(58) Field of Classification Search
CPC .................................................. C07D 471/04
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese |
| 5,602,273 A | 2/1997 | Giese |
| 5,604,104 A | 2/1997 | Giese |
| 5,610,020 A | 3/1997 | Giese |
| 5,650,270 A | 7/1997 | Giese |
| 6,552,065 B2 | 4/2003 | Remiszewski |
| 7,226,926 B2 | 6/2007 | Blackaby |
| 7,390,799 B2 | 6/2008 | Bruncko |
| 8,138,347 B2 | 3/2012 | Knight |
| 8,513,276 B2 | 8/2013 | Berdini |
| 8,895,745 B2 | 11/2014 | Berdini |
| 8,906,682 B2 | 12/2014 | June |
| 2006/0247232 A1 | 11/2006 | Kawashima |
| 2010/0041662 A1 | 2/2010 | Ferrand |
| 2011/0176972 A1 | 7/2011 | Dien-Barataud |
| 2012/0071474 A1 | 3/2012 | Bo |
| 2013/0216498 A1* | 8/2013 | Eastwood .............. A61K 45/06 424/85.6 |
| 2015/0025058 A1 | 1/2015 | Deutsch |
| 2019/0233425 A1 | 8/2019 | Bayly et al. |

FOREIGN PATENT DOCUMENTS

| | | |
|---|---|---|
| WO | WO2000142246 | 6/2001 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |
| WO | WO2006029879 | 3/2006 |
| WO | WO2006078846 | 7/2006 |
| WO | WO2006105021 | 10/2006 |
| WO | WO2006122806 | 11/2006 |
| WO | WO2007005874 | 1/2007 |
| WO | WO2007016176 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | 2008078091 | 7/2008 |

(Continued)

OTHER PUBLICATIONS

International Search Report for PCT/US2019/015473.
International Search Report for PCT/US2019/015469.
Adams et al., "Big opportunities for small molecules in immuno-oncology", Nature Reviews Drug Discovery, vol. 14, No. 9, 2015 (pp. 603-621).
Berge, S. M. et al., "Pharmaceutical Salts", J. Pharmaceutical Sciences, vol. 66, No. 1, Jan. 1977, (pp. 1-19).
Castilho et al., "Keeping the eIF2 alpha kinase Gcn2 in check", Biochimica et Biophysica Acta 1843, 2014, (pp. 1948-1968).
Corthay, "Does the immune system naturally protect against cancer?", Frontiers in Immunology, vol. 5, Article 197, May 2014, (pp. 1-8).
Dong et al., "Uncharged tRNA Activates GCN2 by Displacing the Protein Kinase Moiety from a Bipartite tRNA-Binding Domain", Molecular Cell, vol. 6, Aug. 2000, (pp. 269-279).

(Continued)

*Primary Examiner* — Rebecca L Anderson
(74) *Attorney, Agent, or Firm* — Dechert LLP; Andrea L. C. Reid

(57) ABSTRACT

The present invention provides compounds, compositions thereof, and methods of using the same.

28 Claims, No Drawings

(56) References Cited

FOREIGN PATENT DOCUMENTS

| WO | WO2008109943 | 9/2008 |
|---|---|---|
| WO | WO2008118802 | 10/2008 |
| WO | WO2008132601 | 11/2008 |
| WO | WO2009009116 | 1/2009 |
| WO | 2009050183 | 4/2009 |
| WO | WO2009044273 | 4/2009 |
| WO | WO2009073620 | 6/2009 |
| WO | WO2009114512 | 9/2009 |
| WO | WO2010019570 | 2/2010 |
| WO | WO2010077634 | 7/2010 |
| WO | WO2011028683 | 3/2011 |
| WO | WO2011056652 | 5/2011 |
| WO | WO2011070024 | 6/2011 |
| WO | WO2011090760 | 7/2011 |
| WO | WO2011107553 | 9/2011 |
| WO | WO2011109400 | 9/2011 |
| WO | WO2011131407 | 10/2011 |
| WO | WO2011140249 | 11/2011 |
| WO | WO2012032433 | 3/2012 |
| WO | WO2012142237 | 10/2012 |
| WO | WO2012145493 | 10/2012 |
| WO | WO2013079174 | 6/2013 |
| WO | WO2013087699 | 6/2013 |
| WO | WO2013119716 | 8/2013 |
| WO | 2013131609 | 9/2013 |
| WO | WO2013132044 | 9/2013 |
| WO | WO2013169264 | 11/2013 |
| WO | WO2014008218 | 1/2014 |
| WO | WO2014036357 | 3/2014 |
| WO | 2016071293 | 5/2016 |
| WO | 2019148132 | 1/2019 |
| WO | 2019148136 | 1/2019 |

OTHER PUBLICATIONS

Fallarino et al., "The Combined Effects of Tryptophan Starvation and Tryptophan Catabolites Down-Regulate T Cell Receptor ζ-Chain and Induce a Regulatory Phenotype in Naive T Cells", J Immunol, 2006, 176, (pp. 6752-6761).

Fletcher et al., "L-Arginine Depletion Blunts Antitumor T-cell Responses by Inducing Myeloid-Derived Suppressor Cells", Cancer Res, 2015, (pp. 275-283).

Holmgaard et al., "Indoleamine 2,3-dioxygenase is a critical resistance mechanism in antitumor T cell immunotherapy targeting CTLA-4", Journal of Exp Med., vol. 210, No. 7, 2013, (pp. 1389-1402).

Munn et al., "Expression of indoleamine 2,3-dioxygenase by plasmacytoid dendritic cells in tumor-draining lymph nodes", J. Clin. Invest. 114(2), Jul. 2004, (pp. 280-290).

Munn et al., "GCN2 Kinase in T Cells Mediates Proliferative Arrest and Anergy Induction in Response to Indoleamine 2,3-Dioxygenase", Immunity, vol. 22, May 2005, (pp. 633-642).

Okazaki, T et al., "A rheostat for immune responses—the unique properties of PD-1 and their advantage for clinical application", Nat. Immunol 14(12), Dec. 2013, (pp. 1212-1218).

Pilotte et al., "Reversal of tumoral immune resistance by inhibition of tryptophan 2,3-dioxygenase", Proc. Natl. Acad. Sci. U.S.A., vol. 109, No. 7, Feb. 2012, (pp. 2497-2502).

Ramirez et al., "Defining causative factors contributing in the activation of hedgehog signaling in diffuse large B-cell lymphoma", Leuk. Res., vol. 36(10), Oct. 2012 (pp. 1267-1273).

Ravishankar et al., "The amino acid sensor GCN2 inhibits inflammatory responses to apoptotic cells promoting tolerance and suppressing systemic autoimmunity", Proc. Natl. Acad. Sci. U.S.A., vol. 112(34), Aug. 2015, (pp. 10774-10779).

Rodriguez et al., "L-arginine availability regulates T-lymphocyte cell-cycle progression", Blood, vol. 109, No. 4, Feb. 2007, (pp. 1568-1573).

Rodriguez et al., "L-Arginine Deprivation Regulates Cyclin D3 mRNA Stability in Human T Cells by Controlling HuR Expression", J Immunol, vol. 185, 2010, (pp. 5198-5204).

Ross et al., "Bispecific T cell engager (BiTE®) antibody constructs can mediate bystander tumor cell killing", PLoS One vol. 12, No. 8, Aug. 2017, (pp. 1-24).

Rostovtsev et al., "A Stepwise Huisgen Cycloaddition Process: Copper(I)-Catalyzed Regioselective "Ligation" of Azides and Terminal Alkynes" Angew. Chem. , vol. 41, 2002; (pp. 2708-2711).

Spranger et al., "Mechanism of tumor rejection with doublets of CTLA-4, PD-1/PD-L1, or IDO blockade involves restored IL-2 production and proliferation of $CD8^+$ T cells directly within the tumor microenvironment", Journal for ImmunoTherapy of Cancer, 2:3, 2014, (pp. 1-14).

Sun et al., "Carbohydrate and Protein Immobilization onto Solid Surfaces by Sequential Diels-Alder and Azide-Alkyne Cycloadditions", Bioconjugate Chem., vol. 17, 2006, (pp. 52-57).

Toogood, "Small molecule immuno-oncology therapeutic agents," Bioorganic & Medicinal Chemistry Letters, vol. 28, 2018, (pp. 319-329).

Uyttenhove et al., "Evidence for a tumoral immune resistance mechanism based on tryptophan degradation by indoleamine 2,3-dioxygenase", Nature Medicine, vol. 9, No. 10, Oct. 2003, (pp. 1269-1274).

Vattem and Wek, "Reinitiation involving upstream ORFs regulates ATF4 mRNA translation in mammalian cells", Proc. Natl. Acad. Sci USA, vol. 101(31), Aug. 2004, (pp. 11269-11274).

Wang et al., "Amino Acid Deprivation Promotes Tumor Angiogenesis through the GCN2/ATF4 Pathway", NeoPlasia, vol. 15, No. 8, Aug. 2013, (pp. 989-997).

Wek et al., "Juxtaposition of domains homologous to protein kinases and histidyl-tRNA synthetases in GCN2 protein suggest a mechanism for coupling GCN4 expression to amino acid availability", Proc. Nat. Acad. Sci, U.S.A., vol. 86, Jun. 1989, (pp. 4579-4583).

Whyte et al., "Suppressor of cytokine signaling (SOCS)1 is a key determinant of differential macrophage activation and function", Journal of Leukocyte Biology, vol. 90, Nov. 2011, (pp. 845-854).

Ye et al., "The GCN2-ATF4 pathway is critical for tumour cell survival and proliferation in response to nutrient deprivation", The EMBO Journal, vol. 29, 2010, (pp. 2082-2096).

Zea et al., "Arginase-Producing Myeloid Suppressor Cells in Renal Cell Carcinoma Patients: A Mechanism of Tumor Evasion", Cancer Res., vol. 65 (8), 2005, (pp. 3044-3048).

Zhang et al., "The GCN2 eIF2α Kinase is Required for Adaptation to Amino Acid Deprivation in Mice", Molecular and Cellular Biology, vol. 22, No. 19, Oct. 2002, (pp. 6681-6688).

Haning et al., "Comparison of different heterocyclic scaffolds as substrate analog PDE5 inhibitors", Bioorganic & Medicinal Chemistry Letters 15, vol. 15, 2005, pp. 3900-3907.

Popowycz, Inc., "Pyrazolo[1,5-a]=1,3,5-triazine as a Purine Bioisostere: Access to Potent Cyclin-Dependent Kinase Inhibitor (R)-Roscovitine Analogue", J. Med. Chem 2009, vol. 52, pp. 655-663.

Third Party Observation as submitted in PCT/US2019/015473 dated May 29, 2020, 7 pages.

* cited by examiner

GCN2 INHIBITORS AND USES THEREOF

CROSS-REFERENCE TO RELATED APPLICATIONS

This application claims the benefit under 35 U.S.C. § 119(e) of U.S. Provisional Application No. 62/623,312, filed Jan. 29, 2018, the content of which is incorporated herein in its entirety by reference.

TECHNICAL FIELD OF THE INVENTION

The present invention relates to compounds and methods useful for inhibiting General amino acid Control Non-derepressible 2 kinase ("GCN2"). The invention also provides pharmaceutically acceptable compositions comprising compounds of the present invention and methods of using said compositions in the treatment of various disorders.

BACKGROUND OF THE INVENTION

GCN2 (General amino acid Control Non-derepressible 2) is a ubiquitously expressed protein kinase involved in cellular responses to amino acid deficiency across eukaryotes (Castilho et al., 2014). Cellular deficiency in one or more amino acids causes the accumulation of uncharged cognate transfer RNAs (tRNAs), which are bound directly by GCN2, leading to kinase activation and phosphorylation of eukaryotic initiation factor 2 α (eIF2α) on Serine 51 (Wek et al., 1989; Dong et al., 2000). Phosphorylation of eIF2α results in initiation of protein translation, which causes a reduction in the translation of most mRNAs leading to reduced global utilization of amino acids. Simultaneously, eIF2α phosphorylation increases the translation of a specific subset of mRNAs containing certain upstream open reading frames in their 5' untranslated regions (5'-UTRs), such as the transcription factor ATF4 in mammals (Vattem and Wek, 2004), which promotes restoration of protein homeostasis. GCN2 is therefore a critical determinant of cell fate in response to amino acid depletion.

Induction of cellular responses to amino acid deficiency is emerging as an important mechanism for regulation of the mammalian immune system, particularly in certain disease settings including cancer and autoimmunity. Various immunosuppressive cell types implicated in the control of immune responses in these settings, including tolerogenic dendritic cells, myeloid derived suppressor cells (MDSCs), tolerogenic/M2 macrophages and cancer cells themselves, have each been reported to use the depletion of amino acids to suppress T-cell responses (Munn et al., 2004; Munn et al., 2005; Rodriguez et al., 2010; Whyte et al., 2011; Uyttenhove et al., 2003). This is achieved by the intracellular transport of amino acids coupled with the overexpression of amino acid catabolizing enzymes in these cells, such as the tryptophan catabolizing enzymes indoleamine 2,3 dioxygenase (IDO) and tryptophan 2,3 dioxygenase (TDO), and the arginine catabolizing enzymes arginase 1 and 2 (ARG1, ARG2). As a result, these cells can reduce the local extracellular concentrations of specific amino acids wherever they reside, and therefore induce GCN2 activity in nearby T-cells in an antigen-specific manner (Munn et al., 2004). In the mouse system both in vitro and in vivo, the depletion of local tryptophan or arginine concentrations, for example by IDO- or ARG1-expressing dendritic cells, has been reported to induce proliferative arrest and anergy in T-cells in a GCN2-dependent manner (Munn et al., 2005; Rodriguez et al., 2007; Fletcher et al., 2015). In addition, the induction and/or maintenance of MDSCs and immunosuppressive regulatory T-cells (T-regs) may also be dependent on GCN2 activity under amino acid depleted conditions (Fletcher et al., 2015; Fallarino et al., 2006). Finally, other work implicates the activation of GCN2 by IDO within tolerogenic macrophages as a key mechanism for suppressing systemic autoimmune responses to apoptotic cells (Ravishankar et al., 2015). These findings identify GCN2 as a potentially key effector of the immunosuppressive effects of amino acid depletion associated with various disease states.

Incipient cancers need to evade host anti-cancer immunity in order to thrive (Corthay, 2014). This can be achieved by modulating tumor antigen presentation and/or by using tumor immune evasion mechanisms to actively suppress immune attack. High expression of amino acid catabolising enzymes such as IDO and ARG1 has been observed across a large proportion of cancer patients with various tumor types, both in the cancer cells themselves and in immunosuppressive host cell types that accumulate in tumors, tumor-draining lymph nodes and/or the peripheral circulation (Uyttenhove et al., 2003; Pilotte et al., 2012; Zea et al., 2005). Amino acid depletion may therefore be a powerful and widespread immune evasion mechanism whereby anti-cancer immunity is restrained. Consistently, amino acid depletion in both tumors and tumor-draining lymph nodes has been established as a resistance mechanism to existing immuno-oncology agents, including checkpoint receptor blocking antibodies, in several syngeneic mouse tumor models (Holmgaard et al., 2013; Spranger et al., 2014). On this basis, inhibitors of IDO and TDO are now being progressed in clinical trials for cancer and inhibitors of additional amino acid catabolases are in preclinical development. Accordingly, inhibitors of GCN2 may also be useful for cancer treatment by disrupting the nodal effector signal of amino acid depletion in the immune system and enabling an anti-cancer immune response. Genetic ablation of GCN2 is well tolerated in mice under standard growth conditions (Zhang et al., 2002), and inhibitors of GCN2 may have broader utility than inhibitors of individual amino acid catabolases because GCN2 responds to depletion of several different amino acids.

In addition, GCN2 activation and overexpression has been observed in various human tumors compared with normal tissues (Ye et al., 2010; Wang et al., 2013). Depletion of GCN2 reduced the growth of mouse embryonic fibroblasts and human cancer cells in vitro under severe amino acid or glucose depleted conditions, and blocked the growth of human tumor xenografts in mice (Ye et al., 2010). GCN2 inhibitors may therefore have direct anti-cancer effects due to the frequent disruption of nutrient supply in the tumor microenvironment.

For these reasons, there is a need for the development of potent and selective inhibitors of GCN2 for the treatment of cancer, either as single agents or in combination, for example with anti-CTLA4 and anti-PD1/PD-L1 checkpoint blocking antibodies.

SUMMARY OF THE INVENTION

It has now been found that compounds of this invention, and pharmaceutically acceptable compositions thereof, are effective as inhibitors of GCN2 kinase. Such compounds have the general formula I:

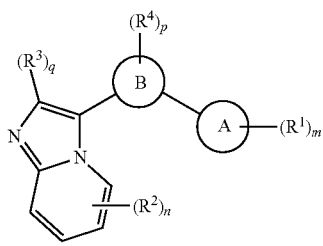

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating GCN2 kinase. Such diseases, disorders, or conditions include those described herein.

Compounds provided by this invention are also useful for the study of the GCN2 enzyme in biological and pathological phenomena; the study of intracellular signal transduction pathways occurring in bodily tissues; and the comparative evaluation of new GCN2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of GCN2 protein kinase. In some embodiments, a provided compound inhibits GCN2.

In certain embodiments, the present invention provides a compound of formula I:

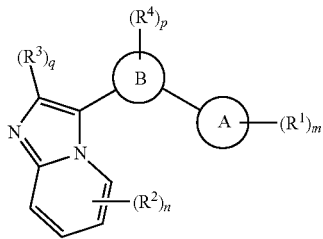

I or a pharmaceutically acceptable salt thereof, wherein:
Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur, or Het, wherein Het is a 4-8 membered saturated monocyclic heterocyclic ring having 1-2 heteroatoms independently selected from nitrogen, oxygen, or sulfur, a 7-12 membered saturated spirocyclic heterocyclic ring having 1-4 heteroatoms independently selected from nitrogen, oxygen, or sulfur, a 7-12 membered saturated bicyclic heterocyclic ring having 1-3 heteroatoms independently selected from nitrogen, oxygen, or sulfur, or a 7-12 membered saturated bridged bicyclic heterocyclic ring having 1-2 heteroatoms independently selected from nitrogen, oxygen, or sulfur;
Ring B is

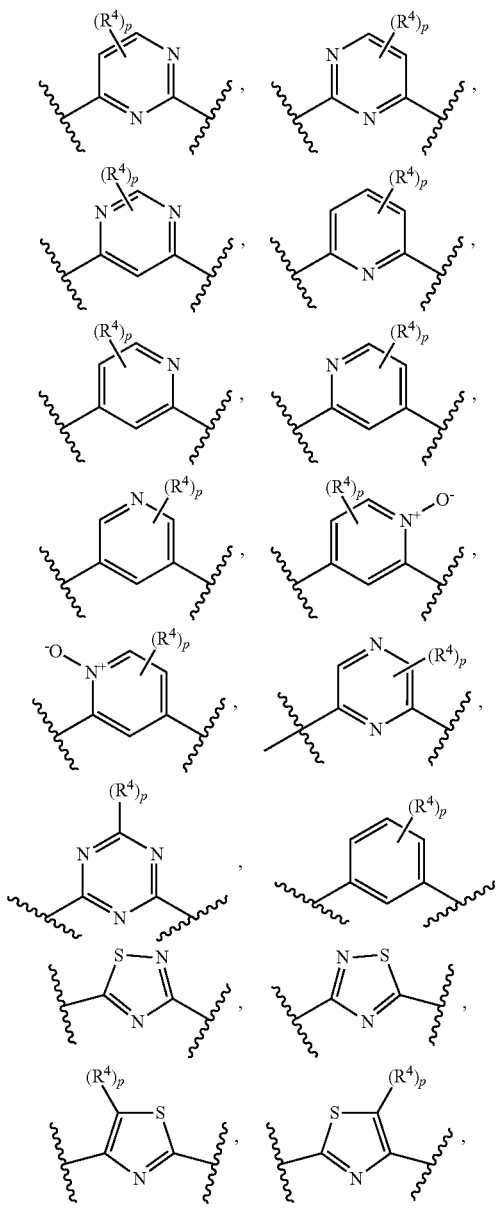

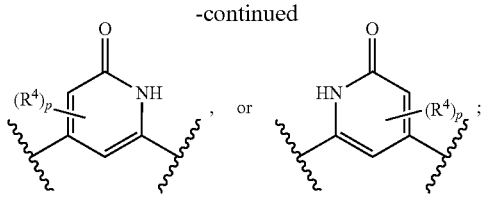

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent $C_{2-4}$ alkylene chain;

two R groups are optionally taken together with their intervening atoms to form an optionally substituted 3-7-membered saturated or partially unsaturated monocyclic ring having 0-4 heteroatoms independently selected from nitrogen, oxygen or sulfur;

each R' is independently hydrogen or a $C_{1-3}$ aliphatic group optionally substituted with halogen;

each of $R^1$ is independently hydrogen, halogen, —CN, —$NO_2$, —C(O)R, —C(O)OR, —C(O)$NR_2$, —C(O)NRS(O)$_2$R, —C(O)N=S(O)$R_2$, —$NR_2$, —NRC(O)R, —NRC(O)$NR_2$, —NRC(O)OR, —NRS(O)$_2$R, —NRS(O)$_2NR_2$, —OR, —ON(R)SO$_2$R, —P(O)$R_2$, —SR, —S(O)R, —S(O)$_2$R, —S(O)(NH)R, —S(O)$_2$N(R)$_2$, —S(NH$_2$)$_2$(O)OH, —N=S(O)$R_2$, —$CH_3$, —$CH_2$OH, —$CH_2NHSO_2CH_3$, —$CH_3$, —$CH_2$OH, —$CH_2NHSO_2CH_3$, —$CD_3$, —$CD_2$NRS(O)$_2$R, or R; or:

two $R^1$ groups are optionally taken together to form =O or =NH; or two $R^1$ groups are optionally taken together to form a bivalent $C_{2-4}$ alkylene chain;

each of $R^2$ is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from $C_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur;

$R^3$ is hydrogen, halogen, —CN, —OR', —N(R')$_2$, or an optionally substituted group selected from $C_{1-3}$ aliphatic, phenyl, or a 5-6 membered monocyclic heteroaromatic ring having 1-4 heteroatoms independently selected from nitrogen, oxygen, or sulfur;

$R^4$ is hydrogen, halogen, —CN, —OR, —N=S(O)$R_2$, —N(R)$_2$, or an optionally substituted group selected from $C_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur;

m is 0, 1, 2, 3, 4 or 5;

n is 0, 1, or 2;

p is 0 or 1; and q is 0 or 1.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

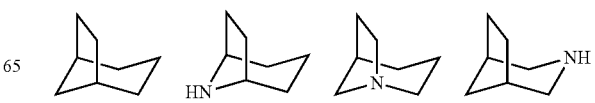

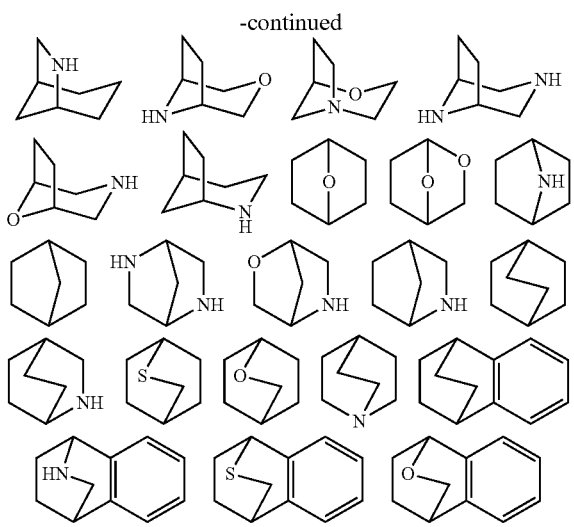

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

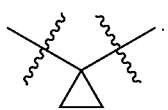

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —(CH$_2$)$_{0-4}$ S(O)(NR°)R°; —N(R°)S(O)$_2$NR°$_2$; N(R°)S(O)$_2$R°; —N(R°)S(O)(NR°)R°$_2$; —N(OR°)R°; —N=S(O)R°$_2$; —N(OR°)SO$_2$R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene) C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*)$_2$)$_{2-3}$O—, or —S(C(R*)$_2$)$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$ (C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, $R^x$, of a provided compound comprises one or more deuterium atoms.

As used herein, the term "inhibitor" is defined as a compound that binds to and/or inhibits GCN2 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a GCN2 protein kinase activity between a sample comprising a compound of the present invention, or composition thereof, and a GCN2 protein kinase, and an equivalent sample comprising a GCN2 protein kinase, in the absence of said compound, or composition thereof.

3. Description of Exemplary Embodiments

As described above, in certain embodiments, the present invention provides a compound of formula I:

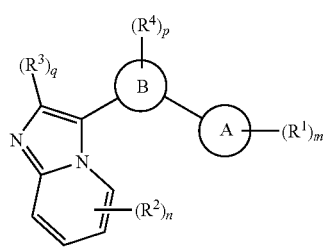

or a pharmaceutically acceptable salt thereof, wherein:
Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur, or Het, wherein Het is a 4-8 membered saturated monocyclic heterocyclic ring having 1-2 heteroatoms independently selected from nitrogen, oxygen, or sulfur, a 7-12 membered saturated spirocyclic heterocyclic ring having 1-4 heteroatoms independently selected from nitrogen, oxygen, or sulfur, a 7-12 membered saturated bicyclic heterocyclic ring having 1-3 heteroatoms independently selected from nitrogen, oxygen, or sulfur, or a 7-12 membered saturated bridged bicyclic heterocyclic ring having 1-2 heteroatoms independently selected from nitrogen, oxygen, or sulfur;

Ring B is

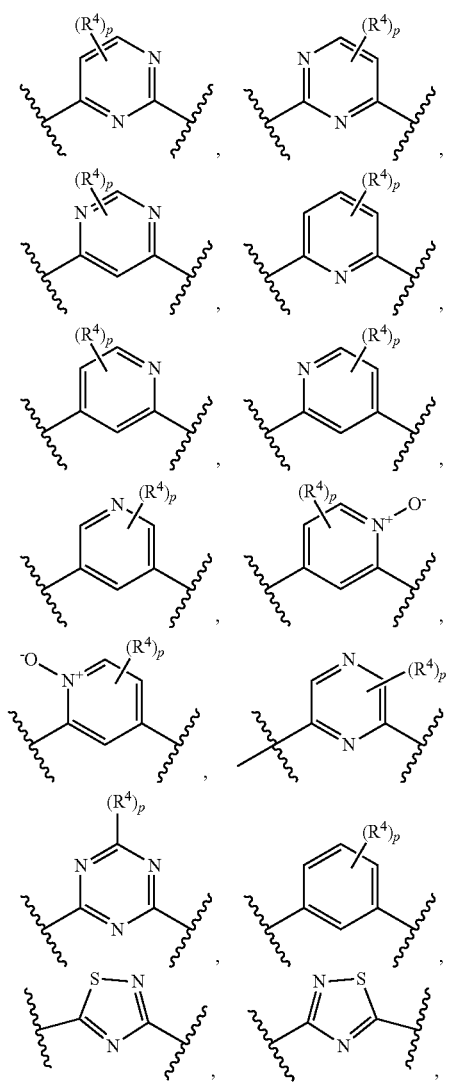

-continued

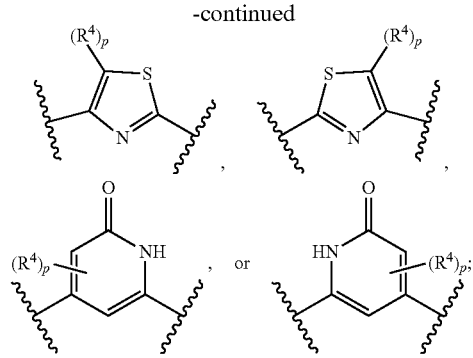

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent $C_{2-4}$ alkylene chain;

two R groups are optionally taken together with their intervening atoms to form an optionally substituted 3-7-membered saturated or partially unsaturated monocyclic ring having 0-4 heteroatoms independently selected from nitrogen, oxygen or sulfur;

each R' is independently hydrogen or a $C_{1-3}$ aliphatic group optionally substituted with halogen;

each of $R^1$ is independently hydrogen, halogen, —CN, —NO$_2$, —C(O)R, —C(O)OR, —C(O)NR$_2$, —C(O)NRS(O)$_2$R, —C(O)N=S(O)R$_2$, —NR$_2$, —NRC(O)R, —NRC(O)NR$_2$, —NRC(O)OR, —NRS(O)$_2$R, —NRS(O)$_2$NR$_2$, —OR, —ON(R)SO$_2$R, —P(O)R$_2$, —SR, —S(O)R, —S(O)$_2$R, —S(O)(NH)R, —S(O)$_2$N(R)$_2$, —S(NH$_2$)$_2$(O)OH, —N=S(O)R$_2$, —CH$_3$, —CH$_2$OH, —CH$_2$NHSO$_2$CH$_3$, —CD$_3$, —CD$_2$NRS(O)$_2$R, or R; or:

two $R^1$ groups are optionally taken together to form =O or =NH; or two $R^1$ groups are optionally taken together to form a bivalent $C_{2-4}$ alkylene chain;

each of $R^2$ is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from $C_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur;

$R^3$ is hydrogen, halogen, —CN, —OR', —N(R')$_2$, or an optionally substituted group selected from $C_{1-3}$ aliphatic, phenyl, or a 5-6 membered monocyclic heteroaromatic ring having 1-4 heteroatoms independently selected from nitrogen, oxygen, or sulfur;

$R^4$ is hydrogen, halogen, —CN, —OR, —N=S(O)R$_2$, —N(R)$_2$, or an optionally substituted group selected from $C_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur;

m is 0, 1, 2, 3, 4 or 5;
n is 0, 1, or 2;
p is 0 or 1; and
q is 0 or 1.

As defined above and described herein, Ring A is selected from a 3-8 membered saturated or partially unsaturated monocyclic carbocyclic ring, phenyl, an 8-10 membered bicyclic aromatic carbocyclic ring, a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur, a 7-12 membered partially unsaturated spirocyclic heterocyclic ring having 1-2 heteroatoms independently selected from nitrogen, oxygen, or sulfur, a 7-12 membered partially unsaturated bicyclic heterocyclic ring having 1-4 heteroatoms independently selected from nitrogen, oxygen, or sulfur, a 7-12 membered partially unsaturated bridged bicyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, an 8-10 membered bicyclic heteroaromatic ring having 1-5 heteroatoms independently selected from nitrogen, oxygen, or sulfur, or Het, wherein Het is a 4-8 membered saturated monocyclic heterocyclic ring having 1-2 heteroatoms independently selected from nitrogen, oxygen, or sulfur, a 7-12 membered saturated spirocyclic heterocyclic ring having 1-4 heteroatoms independently selected from nitrogen, oxygen, or sulfur, a 7-12 membered saturated bicyclic heterocyclic ring having 1-3 heteroatoms independently selected from nitrogen, oxygen, or sulfur, or a 7-12 membered saturated bridged bicyclic heterocyclic ring having 1-2 heteroatoms independently selected from nitrogen, oxygen, or sulfur.

In some embodiments, Ring A is 3-8 membered saturated or partially unsaturated monocyclic carbocyclic ring. In some embodiments, Ring A is phenyl. In some embodiments, Ring A is an 8-10 membered bicyclic aromatic carbocyclic ring. In some embodiments, Ring A is a 4-8 membered partially unsaturated monocyclic heterocyclic ring having 1-2 heteroatoms independently selected from nitrogen, oxygen, or sulfur optionally fused to a 5-6 membered aromatic ring having 0-4 heteroatoms independently selected from nitrogen, oxygen, or sulfur. In some embodiments, Ring A is a 7-12 membered partially unsaturated spirocyclic heterocyclic ring having 1-2 heteroatoms independently selected from nitrogen, oxygen, or sulfur. In some embodiments, Ring A is a 7-12 membered partially unsaturated bicyclic heterocyclic ring having 1-4 heteroatoms independently selected from nitrogen, oxygen, or sulfur. In some embodiments, Ring A is a 7-12 membered partially unsaturated bridged bicyclic heterocyclic ring having 1-2 heteroatoms independently selected from nitrogen, oxygen, or sulfur. In some embodiments, Ring A is a 5-6 membered monocyclic heteroaromatic ring having 1-4 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is Het. In some embodiments, Ring A is a 4-8 membered saturated monocyclic heterocyclic ring having 1-2 heteroatoms independently selected from nitrogen, oxygen, or sulfur. In some embodiments, Ring A is a 7-12 membered saturated spirocyclic heterocyclic ring having 1-4 heteroatoms independently selected from nitrogen, oxygen, or sulfur. In some embodiments, Ring A is a 7-12 membered saturated bicyclic heterocyclic ring having 1-3 heteroatoms independently selected from nitrogen, oxygen, or sulfur. In some embodiments, Ring A is a 7-12 membered saturated bridged bicyclic heterocyclic ring having 1-2 heteroatoms independently selected from nitrogen, oxygen, or sulfur.

In some embodiments, Ring A is

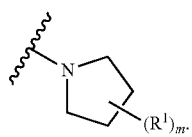

In some embodiments, Ring A is

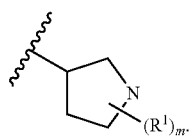

In some embodiments, Ring A is

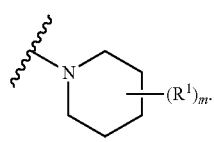

In some embodiments, Ring A is

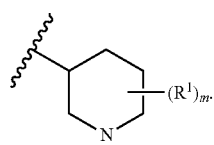

In some embodiments, Ring A is

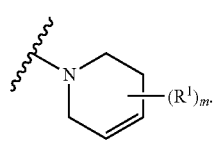

In some embodiments, Ring A is

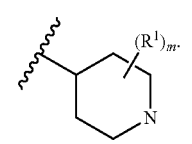

In some embodiments, Ring A is

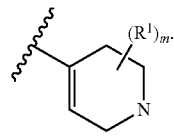

In some embodiments, Ring A is

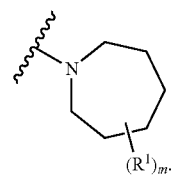

In some embodiments, Ring A is

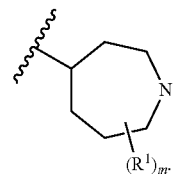

In some embodiments, Ring A is

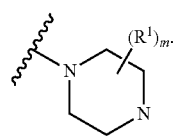

In some embodiments, Ring A is

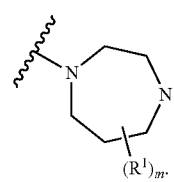

In some embodiments, Ring A is

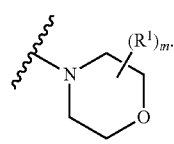

In some embodiments, Ring A is

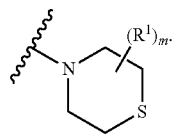

In some embodiments, Ring A is

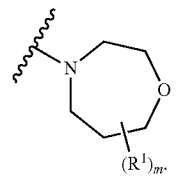

In some embodiments, Ring A is

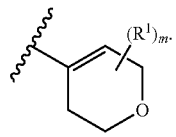

In some embodiments, Ring A is

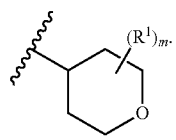

In some embodiments, Ring A is

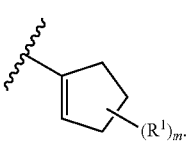

In some embodiments, Ring A is

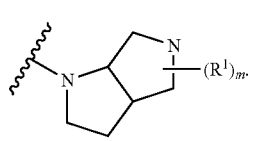

In some embodiments, Ring A is

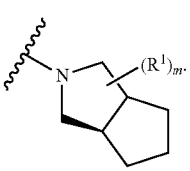

In some embodiments, Ring A is

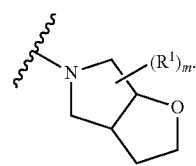

In some embodiments, Ring A is

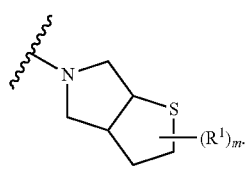

In some embodiments, Ring A is

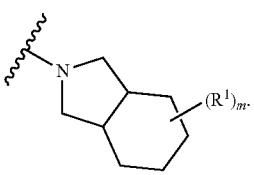

In some embodiments, Ring A is

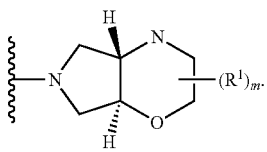

In some embodiments, Ring A is

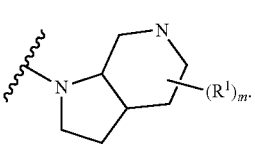

In some embodiments, Ring A is

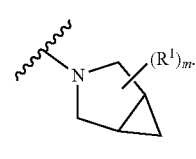

In some embodiments, Ring A is

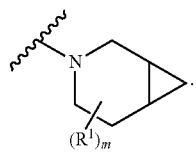

In some embodiments, Ring A is

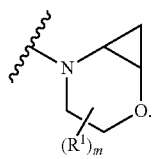

In some embodiments, Ring A is

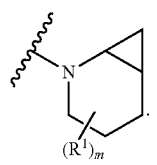

In some embodiments, Ring A is

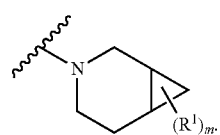

In some embodiments Ring A is

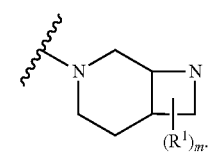

In some embodiments, Ring A is

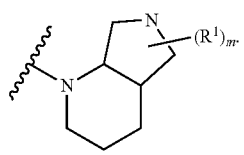

In some embodiments, Ring A is

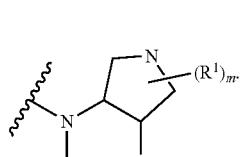

In some embodiments, Ring A is

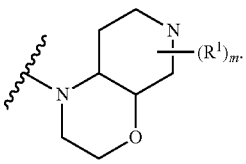

In some embodiments, Ring A is

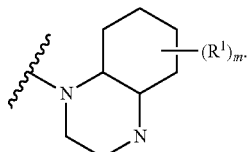

In some embodiments, Ring A is

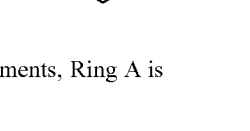

In some embodiments, Ring A is

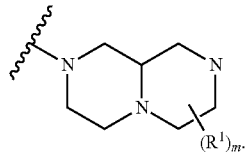

In some embodiments, Ring A is

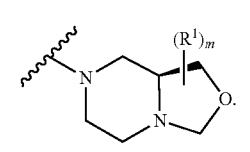

In some embodiments, Ring A is

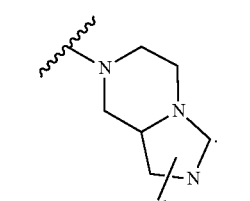

In some embodiments, Ring A is

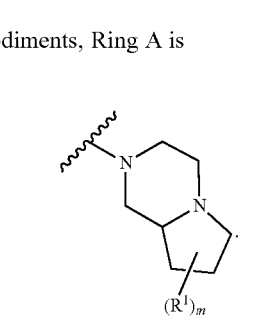

In some embodiments, Ring A is
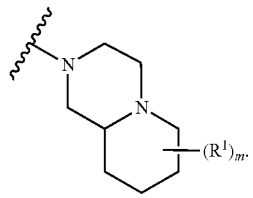
In some embodiments, Ring A is
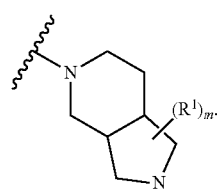
In some embodiments, Ring A is
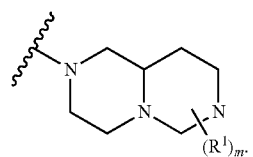
In some embodiments, Ring A is
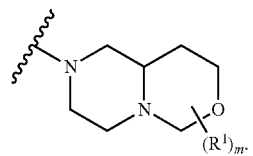
In some embodiments, Ring A is
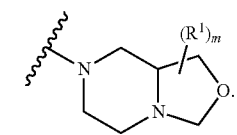
In some embodiments, Ring A is
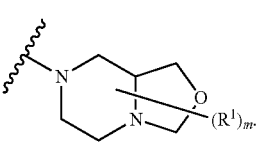
In some embodiments, Ring A is
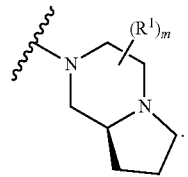
In some embodiments, Ring A is
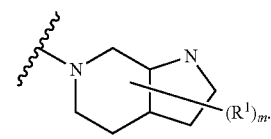
In some embodiments, Ring A is
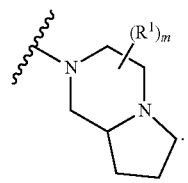
In some embodiments, Ring A is
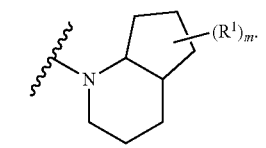
In some embodiments, Ring A is
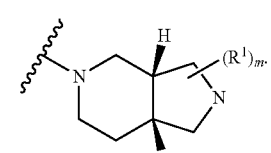
In some embodiments, Ring A is
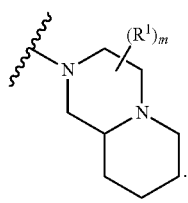

In some embodiments, Ring A is

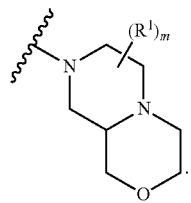

In some embodiments, Ring A is

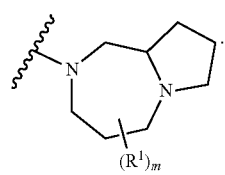

In some embodiments, Ring A is

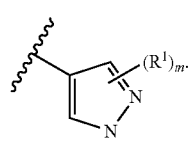

In some embodiments, Ring A is

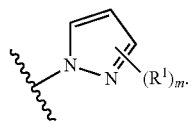

In some embodiments, Ring A is

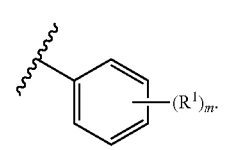

In some embodiments, Ring A is

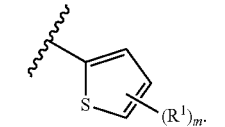

In some embodiments, Ring A is

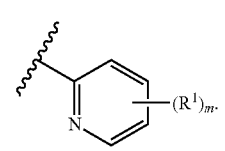

In some embodiments, Ring A is

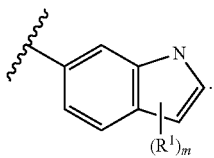

In some embodiments, Ring A is

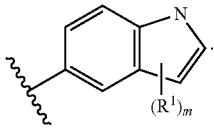

In some embodiments, Ring A is

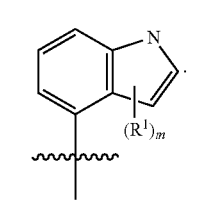

In some embodiments, Ring A is

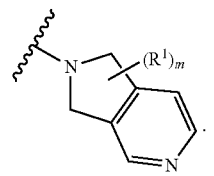

In some embodiments, Ring A is

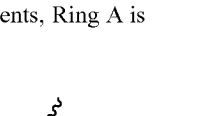

In some embodiments, Ring A is

In some embodiments, Ring A is
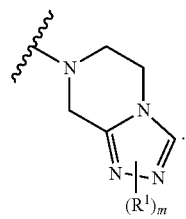
In some embodiments, Ring A is
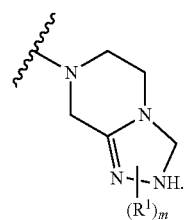
In some embodiments, Ring A is
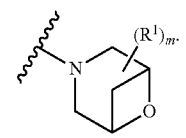
In some embodiments, Ring A is
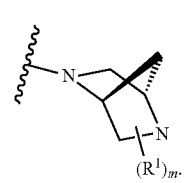
In some embodiments, Ring A is
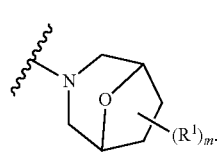
In some embodiments, Ring A is
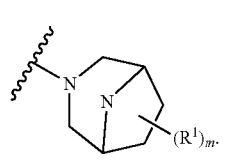
In some embodiments, Ring A is
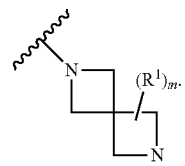
In some embodiments, Ring A is
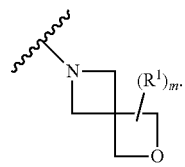
In some embodiments, Ring A is
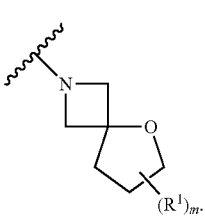
In some embodiments, Ring A is
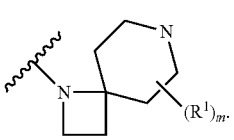
In some embodiments, Ring A is
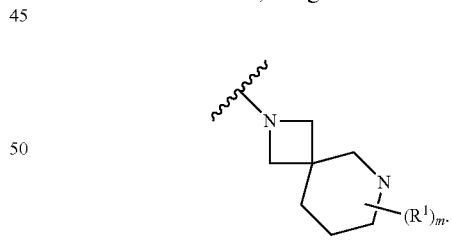
In some embodiments, Ring A is
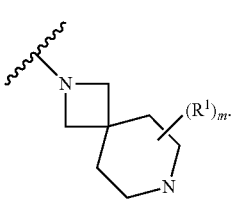

In some embodiments, Ring A is

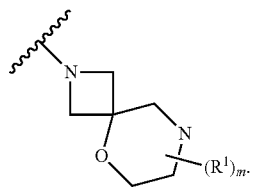

In some embodiments, Ring A is

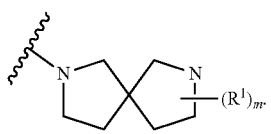

In some embodiments, Ring A is

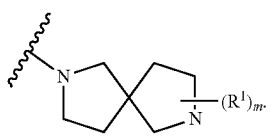

In some embodiments, Ring A is

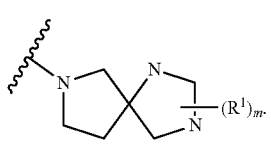

In some embodiments, Ring A is

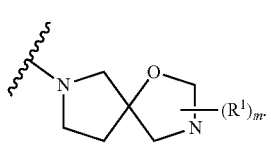

In some embodiments, Ring A is

In some embodiments, Ring A is

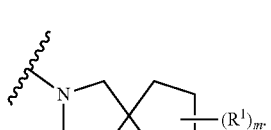

In some embodiments, Ring A is

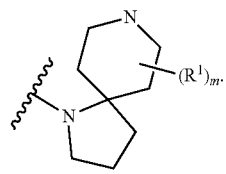

In some embodiments, Ring A is

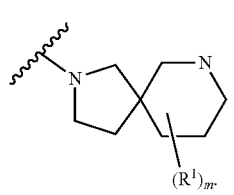

In some embodiments, Ring A is

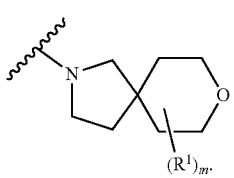

In some embodiments, Ring A is

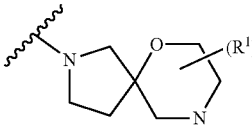

In some embodiments, Ring A is

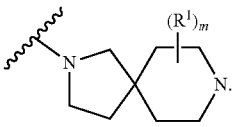

In some embodiments, Ring A is

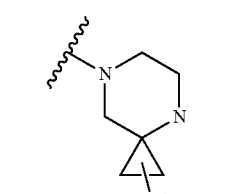

In some embodiments, Ring A is

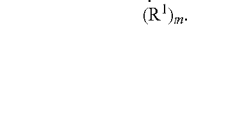

In some embodiments, Ring A is
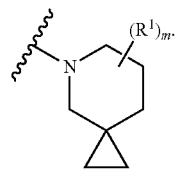
In some embodiments, Ring A is
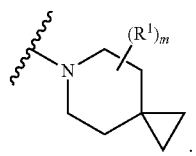
In some embodiments, Ring A is
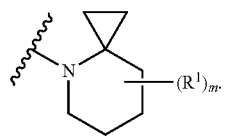
In some embodiments, Ring A is
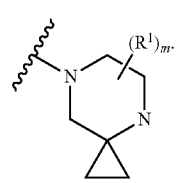
In some embodiments, Ring A is
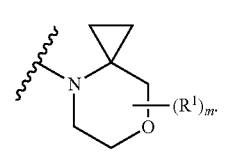
In some embodiments, Ring A is
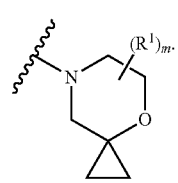
In some embodiments, Ring A is
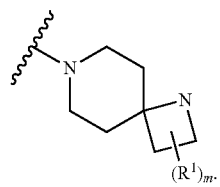
In some embodiments, Ring A is
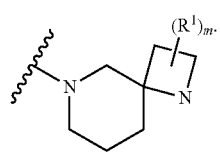
In some embodiments, Ring A is
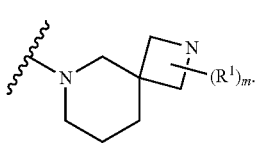
In some embodiments, Ring A is
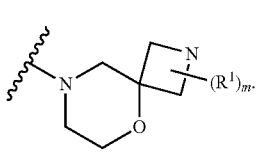
In some embodiments, Ring A is
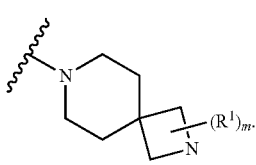
In some embodiments, Ring A is
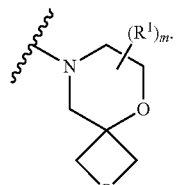

In some embodiments, Ring A is
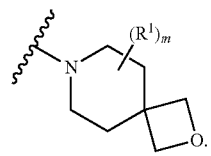
In some embodiments, Ring A is
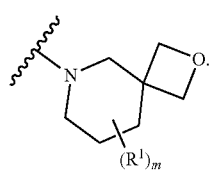
In some embodiments, Ring A is
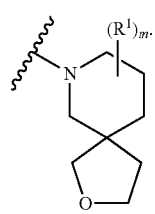
In some embodiments, Ring A is
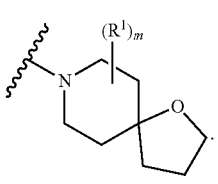
In some embodiments, Ring A is
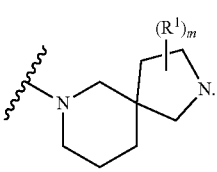
In some embodiments, Ring A is
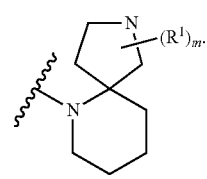
In some embodiments, Ring A is
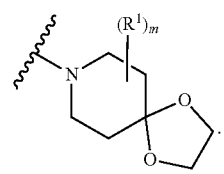
In some embodiments, Ring A is
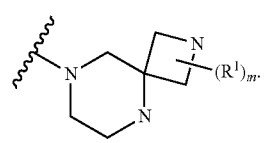
In some embodiments, Ring A is
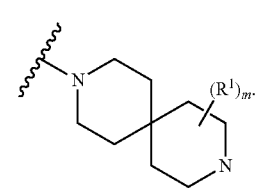
In some embodiments, Ring A is
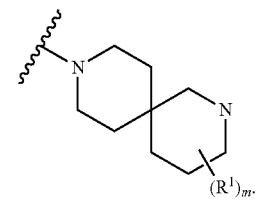
In some embodiments, Ring A is
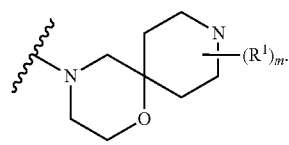
In some embodiments, Ring A is
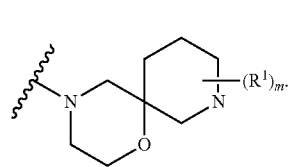

In some embodiments, Ring A is

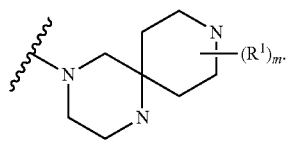

In some embodiments, Ring A is

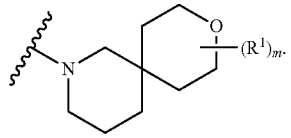

In some embodiments, Ring A is

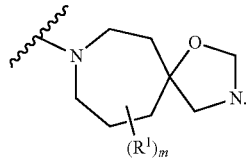

In some embodiments, Ring A is

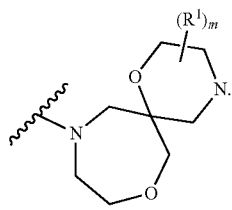

In some embodiments, Ring A is selected from those depicted in Table 1, below.

As defined above and described herein, Ring B is

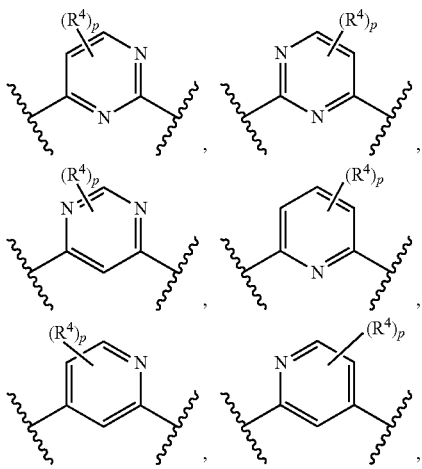

-continued

[structures with $(R^4)_p$ substituents including pyridines, pyridine N-oxides, pyrazine, triazine, benzene, thiadiazoles, thiazoles, and pyridinones]

, or .

In some embodiments, Ring B is

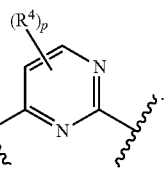

In some embodiments, Ring B is

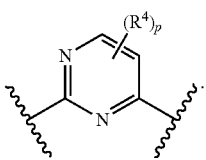

In some embodiments, Ring B is
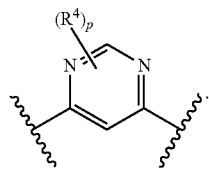
In some embodiments, Ring B is
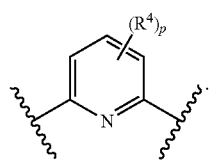
In some embodiments, Ring B is
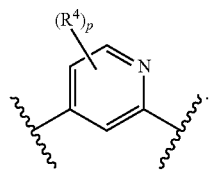
In some embodiments, Ring B is
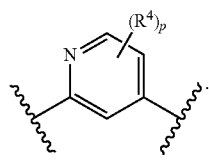
In some embodiments, Ring B is
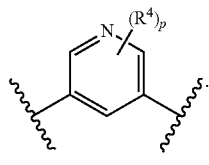
In some embodiments, Ring B is
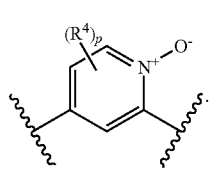
In some embodiments, Ring B is
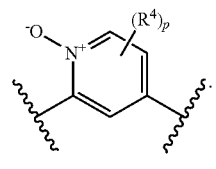
In some embodiments, Ring B is
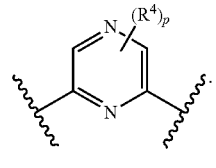
In some embodiments, Ring B is
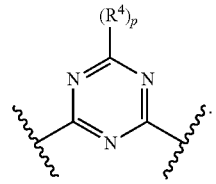
In some embodiments, Ring B is
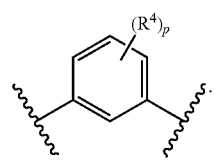
In some embodiments, Ring B is
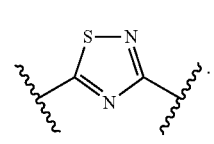
In some embodiments, Ring B is
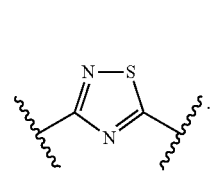

In some embodiments, Ring B is

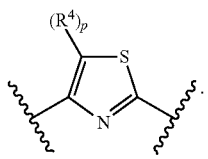

In some embodiments, Ring B is

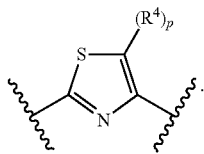

In some embodiments, Ring B is

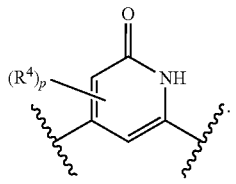

In some embodiments, Ring B is

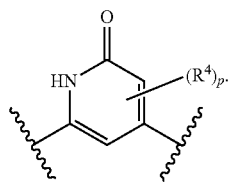

In some embodiments, Ring B is selected from those depicted in Table 1, below.

As defined above and described herein, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent $C_{2-4}$ alkylene chain; or two R groups are optionally taken together with their intervening atoms to form an optionally substituted 3-7-membered saturated or partially unsaturated monocyclic ring having 0-4 heteroatoms independently selected from nitrogen, oxygen or sulfur.

In some embodiments R is hydrogen. In some embodiments R is an optionally substituted $C_{1-6}$ aliphatic group. In some embodiments R is an optionally substituted 3-8 membered saturated or partially unsaturated monocyclic carbocyclic ring. In some embodiments R is an optionally substituted phenyl. In some embodiments R is an optionally substituted 8-10 membered bicyclic aromatic carbocyclic ring. In some embodiments R is an optionally substituted 4-8 membered saturated or partially unsaturated monocyclic heterocyclic ring having 1-2 heteroatoms independently selected from nitrogen, oxygen, or sulfur. In some embodiments R is an optionally substituted 5-6 membered monocyclic heteroaromatic ring having 1-4 heteroatoms independently selected from nitrogen, oxygen, or sulfur. In some embodiments R is an optionally substituted 8-10 membered bicyclic heteroaromatic ring having 1-5 heteroatoms independently selected from nitrogen, oxygen, or sulfur. In some embodiments two R groups are optionally taken together to form a bivalent $C_{2-4}$ alkylene chain. In some embodiments two R groups are optionally taken together with their intervening atoms to form an optionally substituted 3-7-membered saturated or partially unsaturated monocyclic ring having 0-4 heteroatoms independently selected from nitrogen, oxygen or sulfur.

In some embodiments, R is selected from those depicted in Table 1, below.

As defined above and described herein, each of $R^1$ is independently hydrogen or a $C_1$-3 aliphatic group optionally substituted with halogen.

In some embodiments, $R^1$ is hydrogen. In some embodiments, $R^1$ is a $C_{1-3}$ aliphatic group optionally substituted with halogen.

In some embodiments, R' is selected from those depicted in Table 1, below.

As defined above and described herein, each of $R^1$ is independently hydrogen, halogen, —CN, —NO$_2$, —C(O)R, —C(O)OR, —C(O)NR$_2$, —C(O)NRS(O)$_2$R, —C(O)N=S(O)R$_2$, —NR$_2$, —NRC(O)R, —NRC(O)NR$_2$, —NRC(O)OR, —NRS(O)$_2$R, —NRS(O)$_2$NR$_2$, —OR, —ON(R)SO$_2$R, —P(O)R$_2$, —SR, —S(O)R, —S(O)$_2$R, —S(O)(NH)R, —S(O)$_2$N(R)$_2$, —S(NH$_2$)$_2$(O)OH, —N=S(O)R$_2$, —CH$_3$, —CH$_2$OH, —CH$_2$NHSO$_2$CH$_3$, —CD$_3$, —CD$_2$NRS(O)$_2$R, or R; or: two $R^1$ groups are optionally taken together to form =O or =NH; or two $R^1$ groups are optionally taken together to form a bivalent $C_{2-4}$ alkylene chain.

In some embodiments, $R^1$ is hydrogen. In some embodiments, $R^1$ is halogen. In some embodiments, $R^1$ is —CN. In some embodiments, $R^1$ is —NO$_2$. In some embodiments, $R^1$ is —C(O)R. In some embodiments, $R^1$ is —C(O)OR. In some embodiments, $R^1$ is —C(O)NR$_2$. In some embodiments, $R^1$ is —C(O)NRS(O)$_2$R. In some embodiments, $R^1$ is —C(O)N=S(O)R$_2$. In some embodiments, $R^1$ is —NR$_2$. In some embodiments, $R^1$ is —NRC(O)R. In some embodiments, $R^1$ is —NRC(O)NR$_2$. In some embodiments, $R^1$ is —NRC(O)OR. In some embodiments, $R^1$ is —NRS(O)$_2$R. In some embodiments, $R^1$ is —NRS(O)$_2$NR$_2$. In some embodiments, $R^1$ is —OR. In some embodiments, $R^1$ is —ON(R)SO$_2$R. In some embodiments, $R^1$ is —P(O)R$_2$. In some embodiments, $R^1$ is —SR. In some embodiments, $R^1$ is —S(O)R. In some embodiments, $R^1$ is —S(O)$_2$R. In some embodiments, $R^1$ is —S(O)(NH)R. In some embodiments, $R^1$ is —S(O)$_2$N(R)$_2$. In some embodiments, $R^1$ is —S(NH$_2$)$_2$(O)OH. In some embodiments, $R^1$ is —N=S(O)R$_2$. In some embodiments, $R^1$ is —CD$_3$. In some embodiments, $R^1$ is —CD$_2$NRS(O)$_2$R. In some embodiments, $R^1$ is R. In some embodiments, two $R^1$ groups are optionally taken together to form =O or =NH. In some embodiments, two $R^1$ groups are optionally taken together to form a bivalent $C_{2-4}$ alkylene chain.

In some embodiments, $R^1$ is fluoro. In some embodiments, $R^1$ is chloro. In some embodiments, $R^1$ is methyl. In some embodiments, $R^1$ is ethyl. In some embodiments, $R^1$ is —OH. In some embodiments, R¹ is —OCH₃. In some embodiments, R¹ is —CH₂OH. In some embodiments, R¹ is —CH₂CN. In some embodiments, R¹ is —CF₃. In some embodiments, R¹ is —CH₂NH₂. In some embodiments, R¹ is —COOH. In some embodiments, R¹ is —NH₂.

In some embodiments, two R¹ groups form =O. In some embodiments, two R¹ groups form =NH. In some embodiments, two R¹ groups form

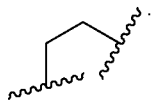

In some embodiments, R¹ is

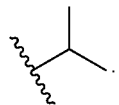

In some embodiments, R¹ is

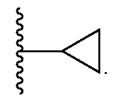

In some embodiments, R¹ is

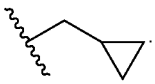

In some embodiments, R¹ is

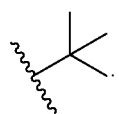

In some embodiments, R¹ is

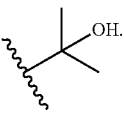

In some embodiments, R¹ is

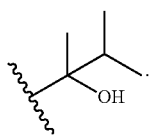

In some embodiments, R¹ is

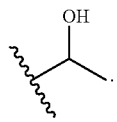

In some embodiments, R¹ is

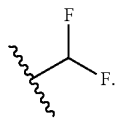

In some embodiments, R¹ is

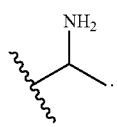

In some embodiments, R¹ is

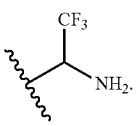

In some embodiments, R¹ is

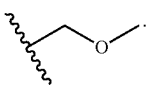

In some embodiments R¹ is

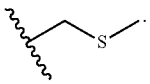

In some embodiments, R¹ is

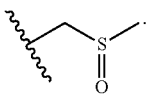

In some embodiments, R¹ is

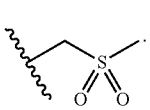

In some embodiments, R¹ is

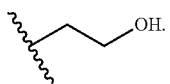

In embodiments, R¹ is

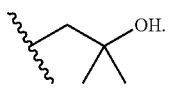

In some embodiments, R¹ is

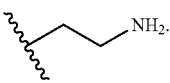

In some embodiments, R¹ is

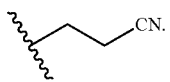

In some embodiments, R¹ is

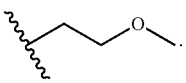

In some embodiments, R¹ is

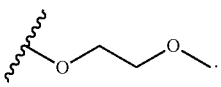

In some embodiments, R¹ is

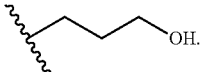

In some embodiments, R¹ is

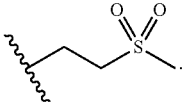

In some embodiments, R¹ is

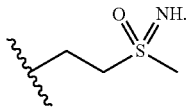

In some embodiments, R¹ is

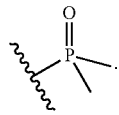

In some embodiments, R¹ is

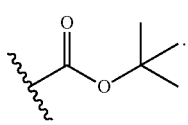

In some embodiments, R¹ is

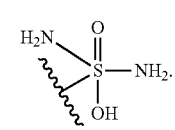

In some embodiments, R¹ is

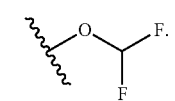

In some embodiments, R¹ is

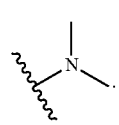

In some embodiments, R¹ is

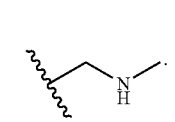

In some embodiments, R¹ is

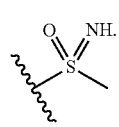

In some embodiments, R¹ is

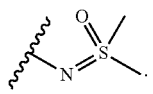

In some embodiments, R¹ is

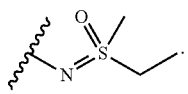

In some embodiments, R¹ is

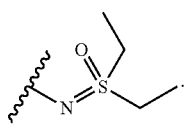

In some embodiments, R¹ is

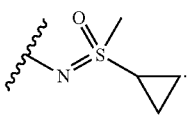

In some embodiments, R¹ is

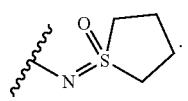

In some embodiments, R¹ is

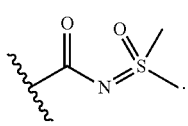

In some embodiments, R¹ is

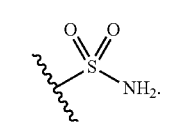

In some embodiments, R¹ is

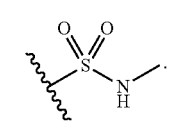

In some embodiments, R¹ is

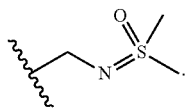

In some embodiments, R¹ is

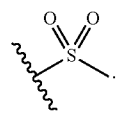

In some embodiments, R¹ is

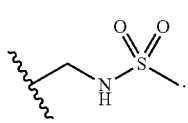

In some embodiments, R¹ is

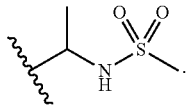

In some embodiments, R¹ is

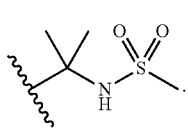

In some embodiments, R¹ is

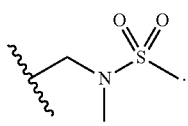

In some embodiments, R¹ is

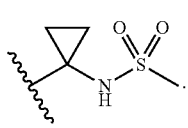

In some embodiments, R¹ is

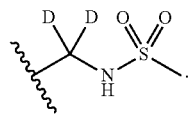

In some embodiments, R¹ is

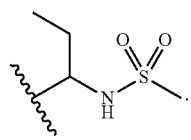

In some embodiments, R¹ is

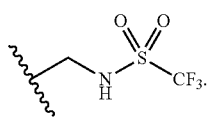

In some embodiments, R¹ is

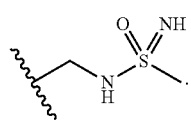

In some embodiments, R¹ is

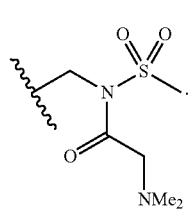

In some embodiments, R¹ is

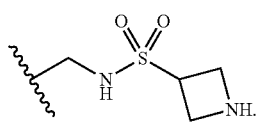

In some embodiments, R¹ is

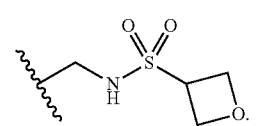

In some embodiments, R¹ is

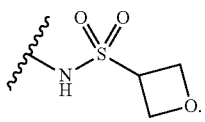

In some embodiments, R¹ is

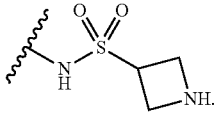

In some embodiments, R¹ is

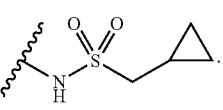

In some embodiments, R¹ is

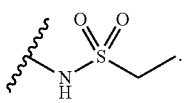

In some embodiments, R¹ is

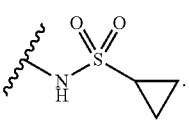

In some embodiments, R¹ is

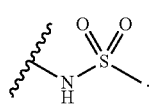

In some embodiments, R¹ is

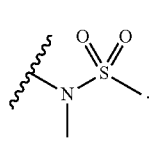

In some embodiments, R¹ is

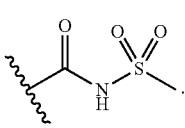

In some embodiments, R¹ is

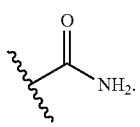

In some embodiments, R¹ is

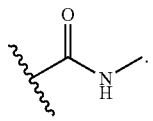

In some embodiments, R¹ is

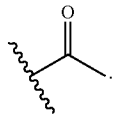

In some embodiments, R¹ is

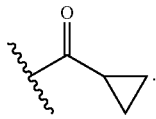

In some embodiments, R¹ is

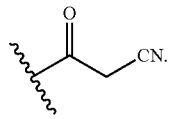

In some embodiments, R¹ is

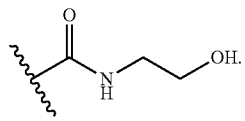

In some embodiments, R¹ is

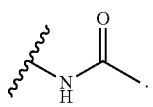

In some embodiments, R¹ is

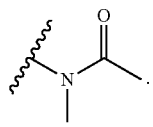

In some embodiments, R¹ is

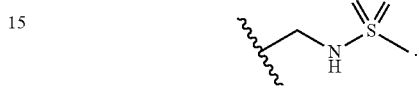

In some embodiments, R¹ is

In some embodiments, R¹ is

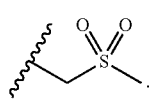

In some embodiments, R¹ is

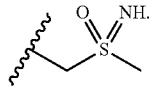

In some embodiments, R¹ is

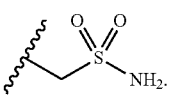

In some embodiments, R¹ is

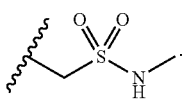

In some embodiments, R¹ is

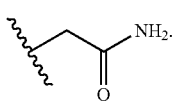

51

In some embodiments, R¹ is

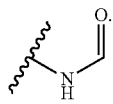

In some embodiments, R¹ is

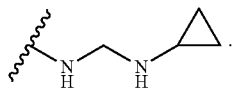

In some embodiments, R¹ is

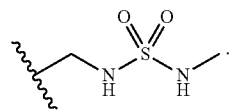

In some embodiments, R¹ is

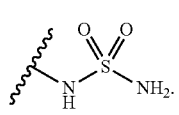

In some embodiments, R¹ is

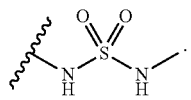

In some embodiments, R¹ is

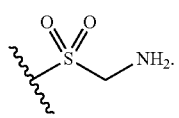

In some embodiments, R¹ is

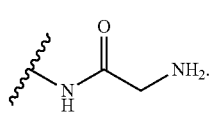

In some embodiments, R¹ is

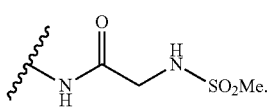

52

In some embodiments, R¹ is

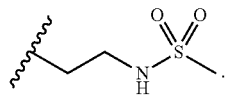

In some embodiments, R¹ is

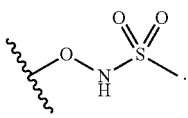

In some embodiments, R¹ is

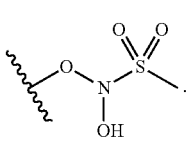

In some embodiments, R¹ is

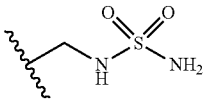

In some embodiments, R¹ is

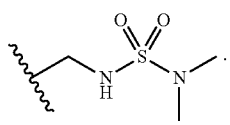

In some embodiments, R¹ is

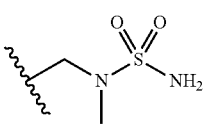

In some embodiments, R¹ is

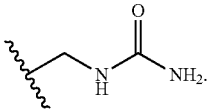

In some embodiments, R¹ is

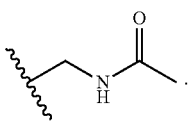

In some embodiments, R¹ is

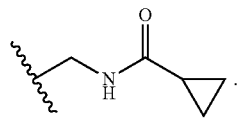

In some embodiments, R¹ is

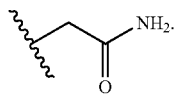

In some embodiments, R¹ is

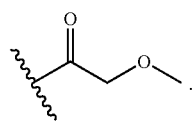

In some embodiments, R¹ is

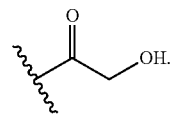

In some embodiments, R¹ is

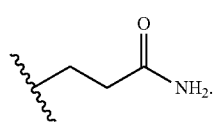

In some embodiments, R¹ is

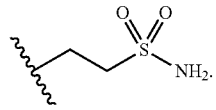

In some embodiments, R¹ is

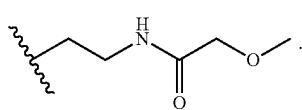

In some embodiments, R¹ is

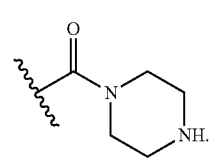

In some embodiments, R¹ is

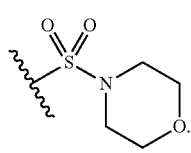

In some embodiments, R¹ is

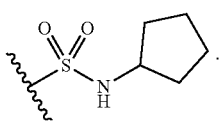

In some embodiments, R¹ is

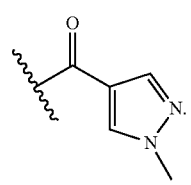

In some embodiments, R¹ is

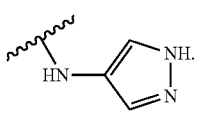

In some embodiments, R¹ is

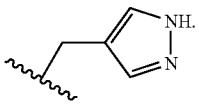

In some embodiments, R¹ is

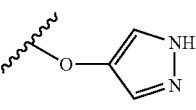

In some embodiments, R¹ is

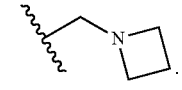

In some embodiments, R¹ is
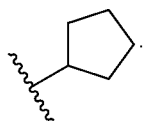
In some embodiments, R¹ is
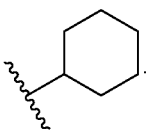
In some embodiments, R¹ is
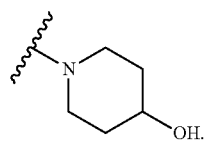
In some embodiments, R¹ is
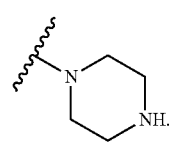
In some embodiments, R¹ is
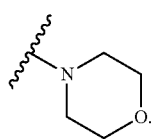
In some embodiments, R¹ is
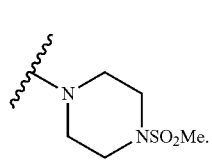
In some embodiments, R¹ is
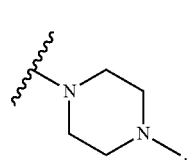
In some embodiments, R¹ is
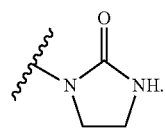
In some embodiments, R¹ is
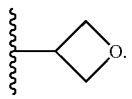
In some embodiments, R¹ is
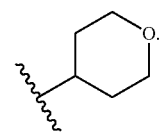
In some embodiments, R¹ is
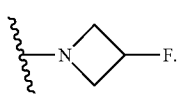
In some embodiments, R¹ is
In some embodiments, R¹ is
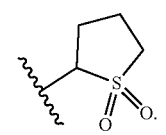
In some embodiments, R¹ is
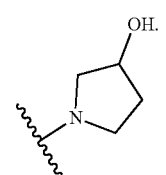

In some embodiments, R¹ is
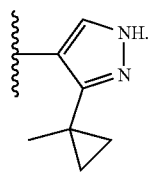
In some embodiments, R¹ is
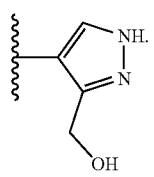
In some embodiments, R¹ is
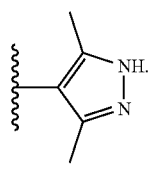
In some embodiments, R¹ is
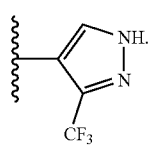
In some embodiments, R¹ is
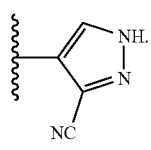
In some embodiments, R¹ is
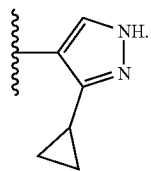
In some embodiments, R¹ is
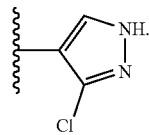
In some embodiments, R¹ is
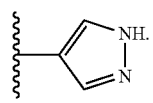
In some embodiments, R¹ is
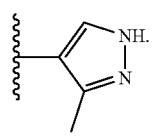
In some embodiments, R¹ is
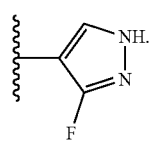
In some embodiments, R¹ is
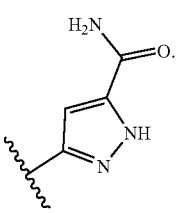
In some embodiments, R¹ is
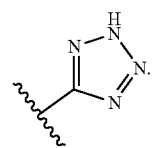
In some embodiments, R¹ is
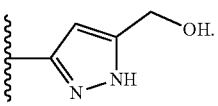

In some embodiments, R¹ is
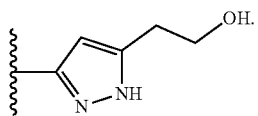
In some embodiments, R¹ is
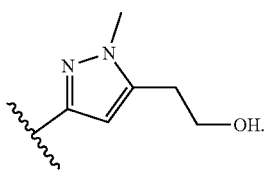
In some embodiments, R¹ is
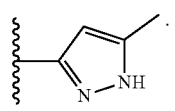
In some embodiments, R¹ is
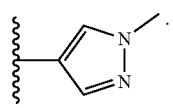
In some embodiments, R¹ is
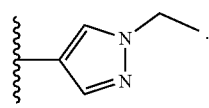
In some embodiments, R¹ is
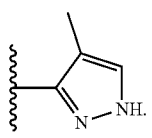
In some embodiments, R¹ is
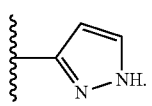
In some embodiments, R¹ is
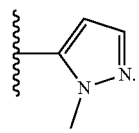
In some embodiments, R¹ is
In some embodiments, R¹ is
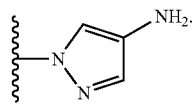
In some embodiments, R¹ is
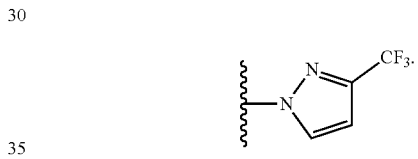
In some embodiments, R¹ is
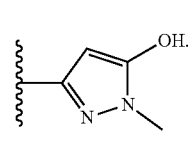
In some embodiments, R¹ is
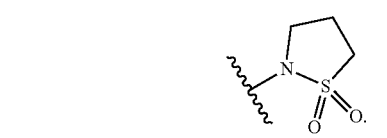
In some embodiments, R¹ is
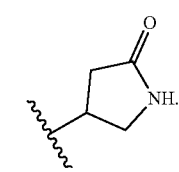

In some embodiments, $R^1$ is

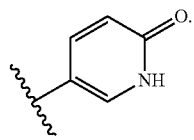

In some embodiments, $R^1$ is

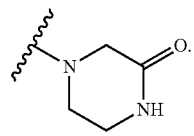

In some embodiments, $R^1$ is

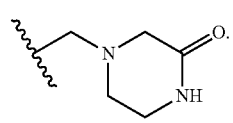

In some embodiments, $R^1$ is

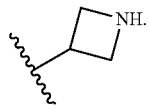

In some embodiments, $R^1$ is

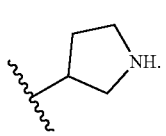

In some embodiments, $R^1$ is

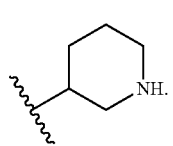

In some embodiments, $R^1$ is

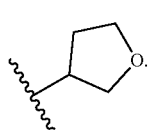

In some embodiments, $R^1$ is

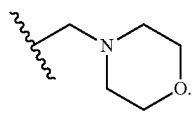

In some embodiments, $R^1$ is

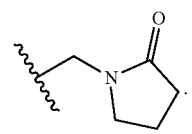

In some embodiments, $R^1$ is

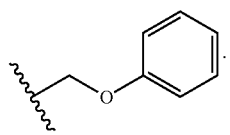

In some embodiments, $R^1$ is

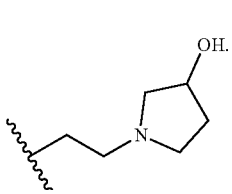

In some embodiments, $R^1$ is

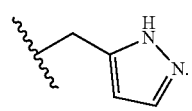

In some embodiments, $R^1$ is

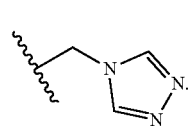

In some embodiments, $R^1$ is

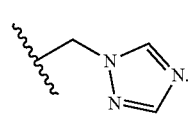

In some embodiments, R¹ is

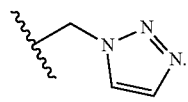

In some embodiments, R¹ is

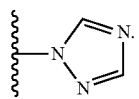

In some embodiments, R¹ is

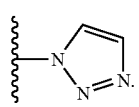

In some embodiments, R¹ is

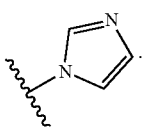

In some embodiments, R¹ is

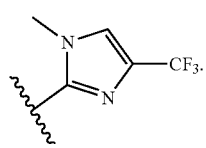

In some embodiments, R¹ is

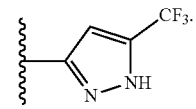

In some embodiments, R¹ is

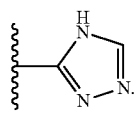

In some embodiments, R¹ is

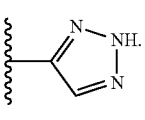

In some embodiments, R¹ is

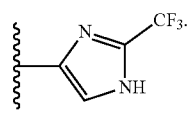

In some embodiments, R¹ is

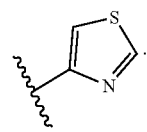

In some embodiments, R¹ is

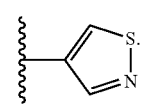

In some embodiments, R¹ is

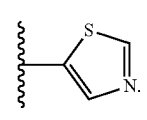

In some embodiments, R¹ is

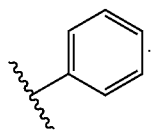

In some embodiments, R¹ is

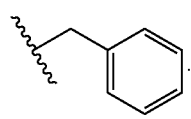

In some embodiments, R¹ is

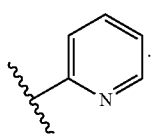

In some embodiments, R¹ is
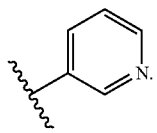
In some embodiments, R¹ is
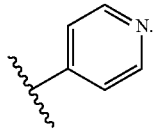
In some embodiments, R¹ is
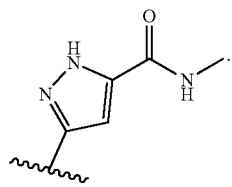
In some embodiments, R¹ is
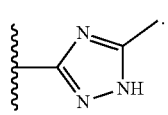
In some embodiments, R¹ is
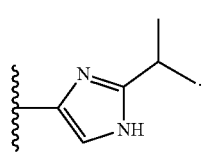
In some embodiments, R¹ is
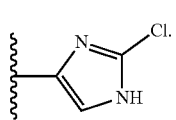
In some embodiments, R¹ is
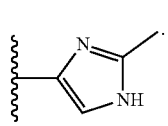
In some embodiments, R¹ is
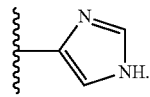
In some embodiments, R¹ is
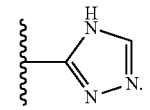
In some embodiments, R¹ is
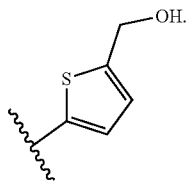
In some embodiments, R¹ is
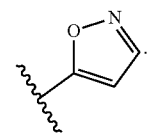
In some embodiments, R¹ is
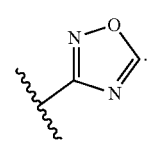
In some embodiments, R¹ is
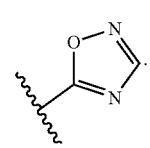
In some embodiments, R¹ is
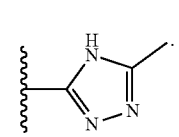

In some embodiments, R¹ is

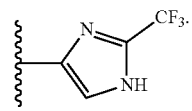

In some embodiments, R¹ is

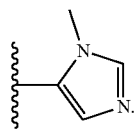

In some embodiments, R¹ is

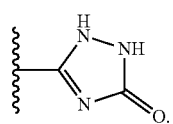

In some embodiments, R¹ is

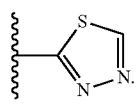

In some embodiments, R¹ is

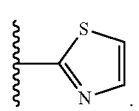

In some embodiments, R¹ is

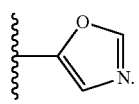

In some embodiments, R¹ is

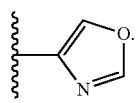

In some embodiments, R¹ is

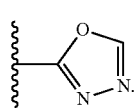

In some embodiments, R¹ is

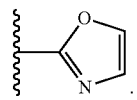

In some embodiments, R¹ is

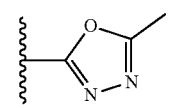

In some embodiments, R¹ is

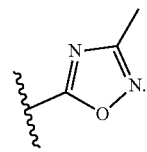

In some embodiments, R¹ is

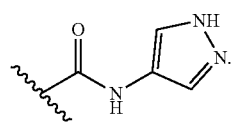

In some embodiments, R¹ is

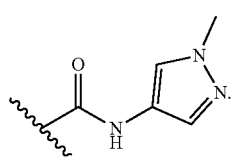

In some embodiments, R¹ is

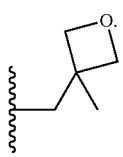

In some embodiments, R¹ is

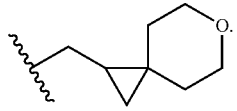

In some embodiments, R¹ is

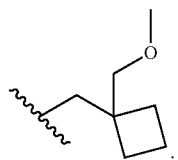

In some embodiments, R¹ is

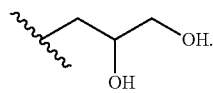

In some embodiments, R¹ is

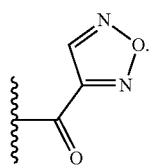

In some embodiments, R¹ is

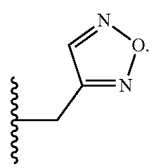

In some embodiments, R¹ is

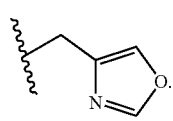

In some embodiments, R¹ is

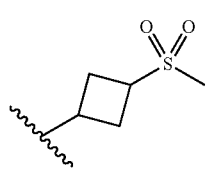

In some embodiments, R¹ is

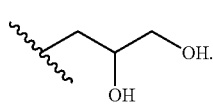

In some embodiments, R¹ is selected from those depicted in Table 1, below.

As defined above and described herein, each of R² is each of R² is independently hydrogen, halogen, —CN, —C(O)N(R')$_2$, —OR', —N(R')$_2$, —S(O)$_2$R, —S(O)$_2$N(R)$_2$, —O-phenyl, or an optionally substituted group selected from C$_{1-3}$ aliphatic, phenyl, 5-6 membered monocyclic heteroaromatic ring having 1-4 heteroatoms independently selected from nitrogen, oxygen, or sulfur, or 4-8 membered saturated monocyclic heterocycle having 1-4 heteroatoms independently selected from nitrogen, oxygen, or sulfur.

In some embodiments, R² is hydrogen. In some embodiments, R² is halogen. In some embodiments, R² is —CN. In some embodiments, R² is —C(O)N(R')$_2$. In some embodiments, R² is —OR'. In some embodiments, R² is —N(R')$_2$. In some embodiments, R² is —S(O)$_2$R. In some embodiments, R² is —S(O)$_2$N(R)$_2$. In some embodiments, R² is —O-phenyl. In some embodiments, R² is an optionally substituted C$_{1-3}$ aliphatic group. In some embodiments, R² is an optionally substituted phenyl. In some embodiments, R² is an optionally substituted 5-6 membered monocyclic heteroaromatic ring having 1-4 heteroatoms independently selected from nitrogen, oxygen, or sulfur. In some embodiments, R² is an optionally substituted 4-8 membered saturated monocyclic heterocycle having 1-4 heteroatoms independently selected from nitrogen, oxygen, or sulfur.

In some embodiments, R² is fluoro. In some embodiments, R² is chloro. In some embodiments, R² is bromo. In some embodiments, R² is methyl. In some embodiments, R² is ethyl. In some embodiments, R² is —CF$_3$. In some embodiments, R² is

In some embodiments, R² is

In some embodiments, R² is

In some embodiments, R² is

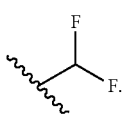

In some embodiments, R² is

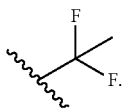

In some embodiments, R² is

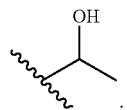

In some embodiments, R² is

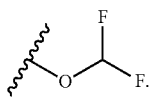

In some embodiments, R² is

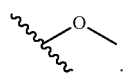

In some embodiments, R² is

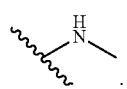

In some embodiments, R² is

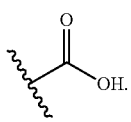

In some embodiments, R² is

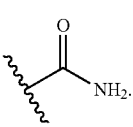

In some embodiments, R² is

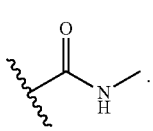

In some embodiments, R² is

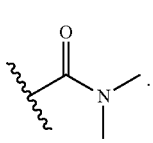

In some embodiments, R² is

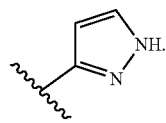

In some embodiments, R² is

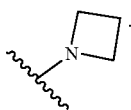

In some embodiments, R² is

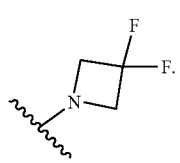

In some embodiments, R² is

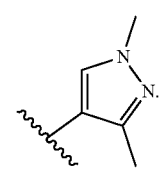

In some embodiments, R² is

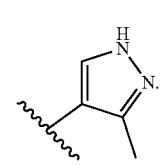

In some embodiments, R² is

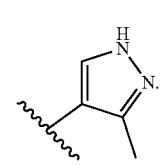

In some embodiments, R² is

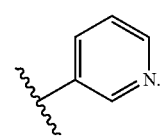

In some embodiments, $R^2$ is

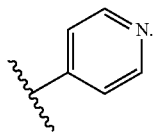

In some embodiments, $R^2$ is

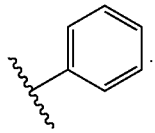

In some embodiments, $R^2$ is

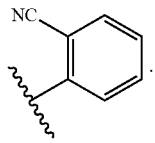

In some embodiments, $R^2$ is

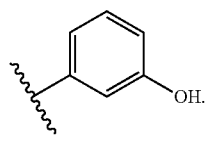

In some embodiments, $R^2$ is

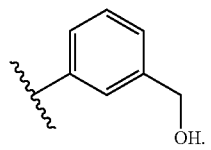

In some embodiments, $R^2$ is

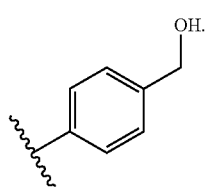

In some embodiments, $R^2$ is

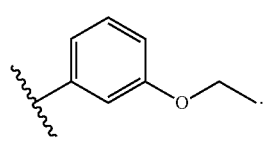

In some embodiments, $R^2$ is

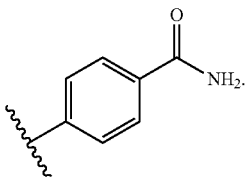

In some embodiments, $R^2$ is

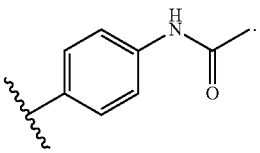

In some embodiments, $R^2$ is selected from those depicted in Table 1, below.

As defined above and described herein, $R^3$ is hydrogen, halogen, —CN, —OR', —N(R')$_2$, or an optionally substituted group selected from $C_{1-3}$ aliphatic, phenyl, or a 5-6 membered monocyclic heteroaromatic ring having 1-4 heteroatoms independently selected from nitrogen, oxygen, or sulfur.

In some embodiments, $R^3$ is hydrogen. In some embodiments, $R^3$ is halogen. In some embodiments, $R^3$ is —CN. In some embodiments, $R^3$ is —OR'. In some embodiments, $R^3$ is —N(R')$_2$. In some embodiments, $R^3$ is an optionally substituted $C_{1-3}$ aliphatic group. In some embodiments, $R^3$ is an optionally substituted phenyl. In some embodiments, $R^3$ is an optionally substituted 5-6 membered monocyclic heteroaromatic ring having 1-4 heteroatoms independently selected from nitrogen, oxygen, or sulfur.

In some embodiments, $R^3$ is selected from those depicted in Table 1, below.

As defined above and described herein, $R^4$ is hydrogen, halogen, —CN, —OR, —N=S(O)R$_2$, —N(R)$_2$, or an optionally substituted group selected from $C_{1-3}$ aliphatic, a 4-8 membered saturated or partially unsaturated monocyclic heterocyclic ring having 1-2 heteroatoms independently selected from nitrogen, oxygen, or sulfur, or a 7-12 membered saturated or partially unsaturated spirocyclic heterocyclic ring having 1-2 heteroatoms independently selected from nitrogen, oxygen, or sulfur.

In some embodiments, $R^4$ is hydrogen. In some embodiments, $R^4$ is halogen. In some embodiments, $R^4$ is —CN. In some embodiments, $R^4$ is —OR. In some embodiments, $R^4$ is —N=S(O)R$_2$. In some embodiments, $R^4$ is —N(R)$_2$. In some embodiments, $R^4$ is an optionally substituted $C_{1-3}$ aliphatic group. In some embodiments, $R^4$ is an optionally substituted 4-8 membered saturated or partially unsaturated monocyclic heterocyclic ring having 1-2 heteroatoms independently selected from nitrogen, oxygen, or sulfur. In some embodiments, $R^4$ is an optionally substituted 7-12 membered saturated or partially unsaturated spirocyclic heterocyclic ring having 1-2 heteroatoms independently selected from nitrogen, oxygen, or sulfur.

In some embodiments, $R^4$ is fluoro. In some embodiments, $R^4$ is chloro. In some embodiments, $R^4$ is methyl. In some embodiments, $R^4$ is —CF$_3$. In some embodiments, $R^4$ is —OH. In some embodiments, $R^4$ is

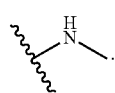

In some embodiments, R⁴ is

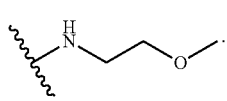

In some embodiments, R⁴ is

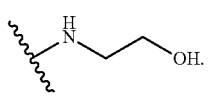

In some embodiments, R⁴ is

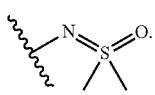

In some embodiments, R⁴ is

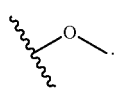

In some embodiments, R⁴ is

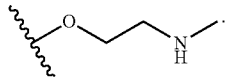

In some embodiments, R⁴ is

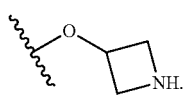

In some embodiments, R⁴ is

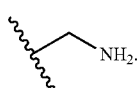

In some embodiments, R⁴ is

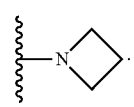

In some embodiments, R⁴ is

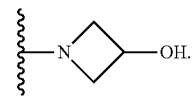

In some embodiments, R⁴ is

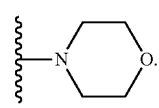

In some embodiments, R⁴ is

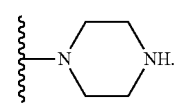

In some embodiments, R⁴ is

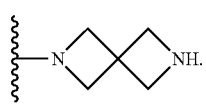

In some embodiments, R⁴ is

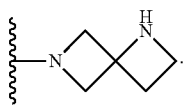

In some embodiments, R⁴ is

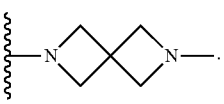

In some embodiments, R⁴ is

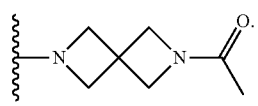

In some embodiments, R⁴ is

In some embodiments, R⁴ is

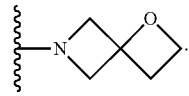

In some embodiments, R⁴ is selected from those depicted in Table 1, below.

As defined above and described herein, m is 0, 1, 2, 3, 4 or 5.

In some embodiments, m is 0. In some embodiments, m is 1. In some embodiments, m is 2. In some embodiments, m is 3. In some embodiments, m is 4. In some embodiments, m is 5.

In some embodiments, m is 1, 2 or 3.

In some embodiments, m is selected from those depicted in Table 1, below.

As defined above and described herein, n is 0, 1, or 2.

In some embodiments, n is 0. In some embodiments, n is 1. In some embodiments, n is 2.

In some embodiments, n is selected from those depicted in Table 1, below.

As defined above and described herein, p is 0 or 1.

In some embodiments, p is 0. In some embodiments, p is 1.

In some embodiments, p is selected from those depicted in Table 1, below.

As defined above and described herein, q is 0 or 1.

In some embodiments, q is 0. In some embodiments, q is 1.

In some embodiments, q is selected from those depicted in Table 1, below.

In certain embodiments, the present invention provides a compound of formula I, wherein Ring A is Het, thereby forming a compound of formula II:

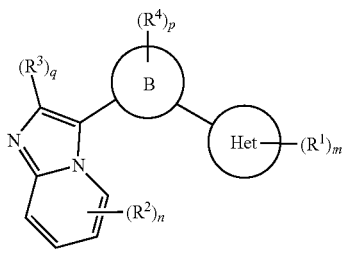

or a pharmaceutically acceptable salt thereof, wherein each of Ring B, R¹, R², R³, R⁴, m, n, p, and q is as defined above and described in embodiments herein, both singly and in combination.

In certain embodiments, the present invention provides a compound of formula I, wherein Ring A is Het and Ring B is

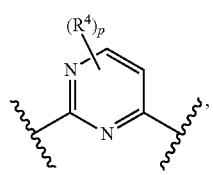

thereby forming a compound of formula

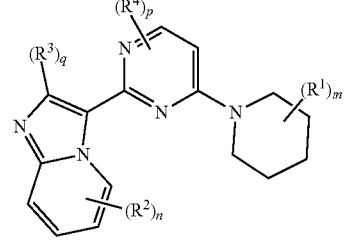

or a pharmaceutically acceptable salt thereof, wherein each of Het, R¹, R², R³, R⁴, m, n, p, and q is as defined above and described in embodiments herein, both singly and in combination.

In certain embodiments, the present invention provides a compound of formula I,

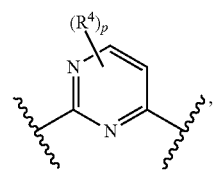

wherein Ring A is piperidinyl, piperazinyl, or morpholinyl, and Ring B is thereby forming a compound of formula IV-a, IV-b, or IV-c, respectively:

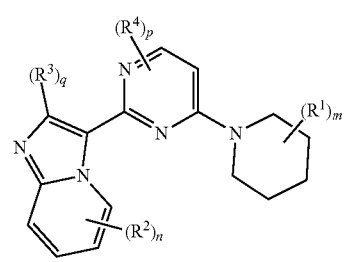

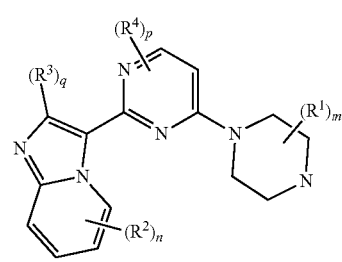

IV-c

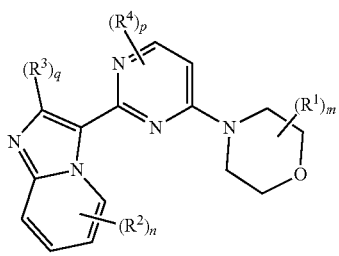

VI-a

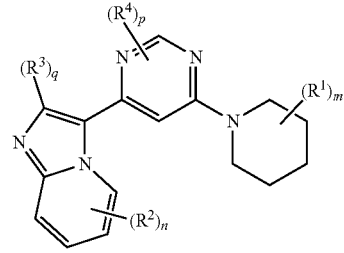

VI-b

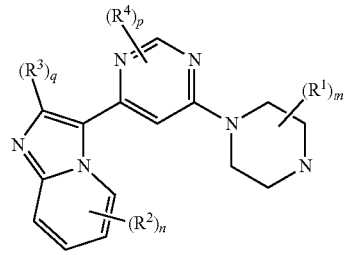

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of formula I, wherein Ring A is Het and Ring B is

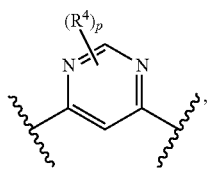

thereby forming a compound of formula V:

V

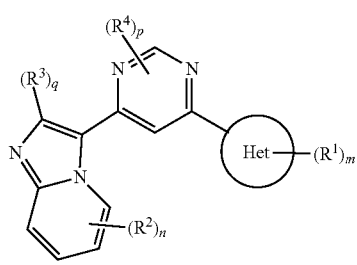

VI-c

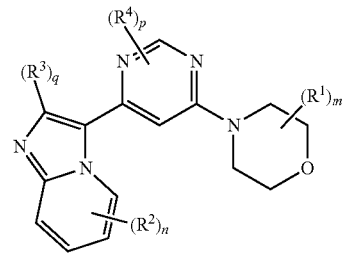

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of formula I, wherein Ring A is Het and Ring B is

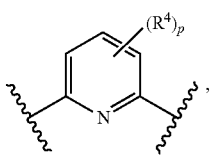

thereby forming a compound of formula VII:

VII

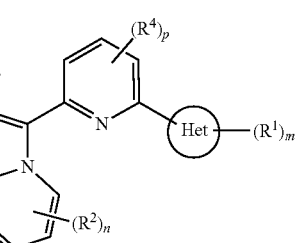

or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of formula I, wherein Ring A is piperidinyl, piperazinyl, or morpholinyl, and Ring B is

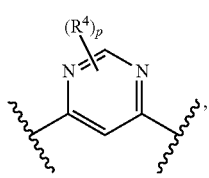

thereby forming a compound of formula VI-a, VI-b, or VI-c, respectively:

or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of formula I, wherein Ring A is piperidinyl, piperazinyl, or morpholinyl, and Ring B is

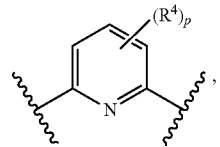

thereby forming a compound of formula VIII-a, VIII-b, or VIII-c, respectively:

VIII-a

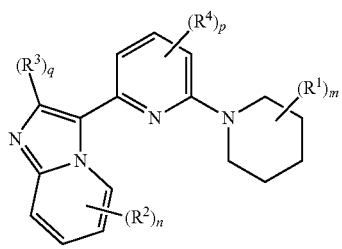

VIII-b

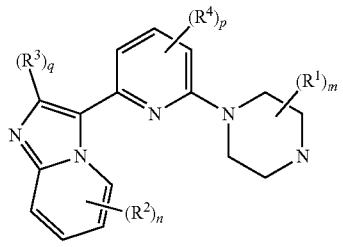

VIII-c

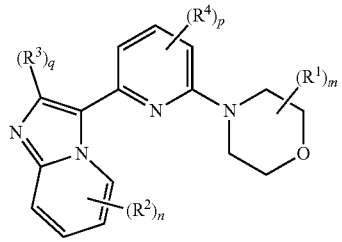

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of formula I, wherein Ring A is Het and Ring B is

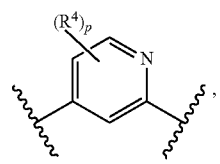

thereby forming a compound of formula IX:

IX

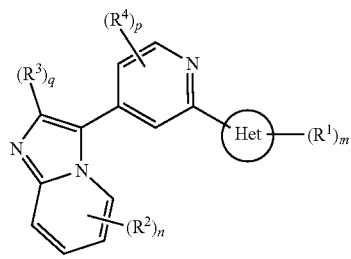

or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of formula I, wherein Ring A is piperidinyl, piperazinyl, or morpholinyl, and Ring B is

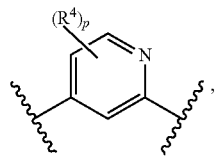

thereby forming a compound of formula X-a, X-b, or X-c, respectively:

X-a

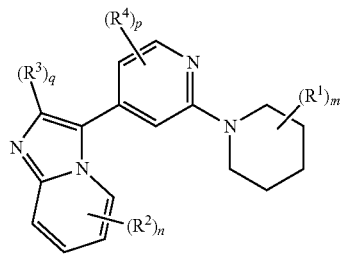

X-b

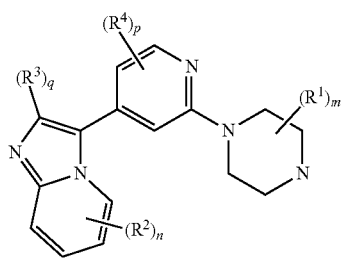

X-c

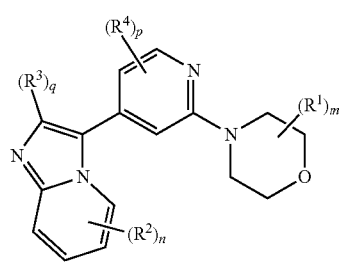

or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of formula I, wherein Ring A is Het and Ring B is

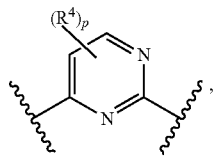

thereby forming a compound of formula XI:

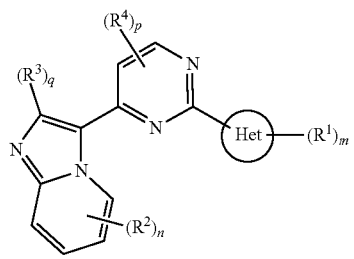

XI or a pharmaceutically acceptable salt thereof, wherein each of Het, $R^1$, $R^2$, $R^3$, $R^4$, m, n, p, and q is as defined above and described in embodiments herein, both singly and in combination.

In certain embodiments, the present invention provides a compound of formula I, wherein Ring A is piperidinyl, piperazinyl, or morpholinyl, and Ring B is

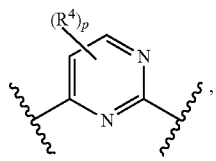

thereby forming a compound of formula XII-a, XII-b, or XII-c, respectively:

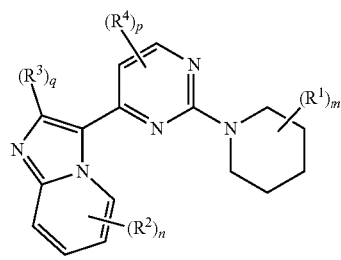

XII-a

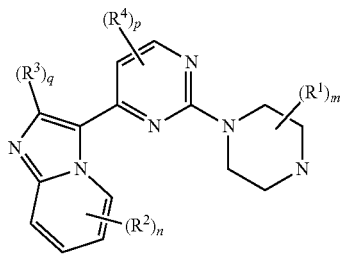

XII-b

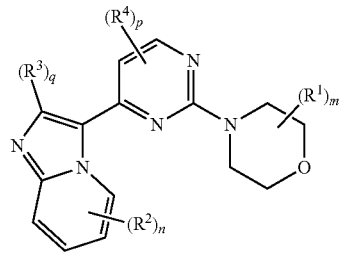

XII-c or a pharmaceutically acceptable salt thereof, wherein each of $R^1$, $R^2$, $R^3$, $R^4$, m, n, p, and q is as defined above and described in embodiments herein, both singly and in combination.

In certain embodiments, the present invention provides a compound of formula I, wherein n is 1, p is 1, q is 1, $R^2$ is —$CF_3$, $R^3$ is hydrogen, $R^4$ is hydrogen, Ring A is piperidinyl, piperazinyl, or morpholinyl, and Ring B is thereby forming a compound of formula XIII-a, XIII-b, or XIII-c, respectively:

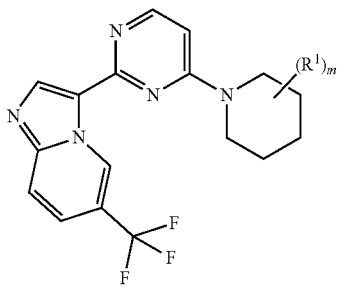

XIII-a

XIII-b

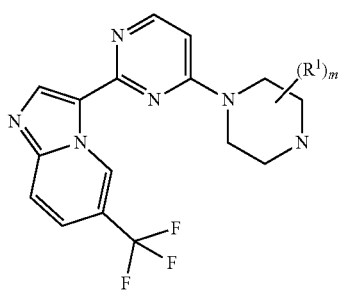

XIII-c

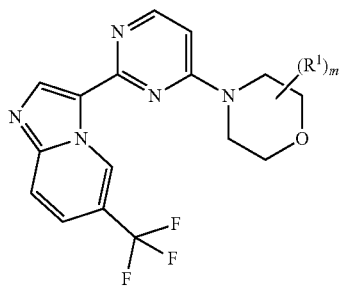

or a pharmaceutically acceptable salt thereof, wherein each of $R^1$ and m is as defined above and described in embodiments herein, both singly and in combination.

In certain embodiments, the present invention provides a compound of formula I, wherein n is 1, p is 1, q is 1, $R^2$ is chloro, $R^3$ is hydrogen, $R^4$ is hydrogen, Ring A is piperidinyl, piperazinyl, or morpholinyl, and Ring B is

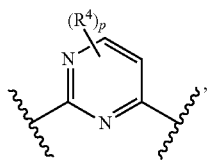

thereby forming a compound of formula XIV-a, XIV-b, or XIV-c, respectively:

XIV-a

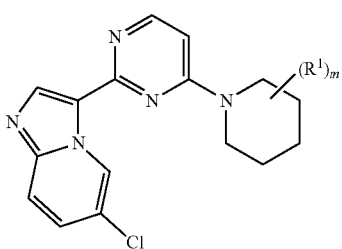

XIV-b

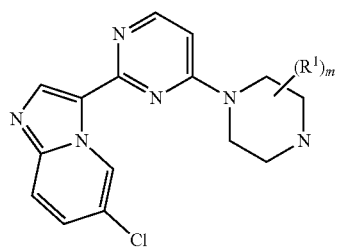

XIV-c

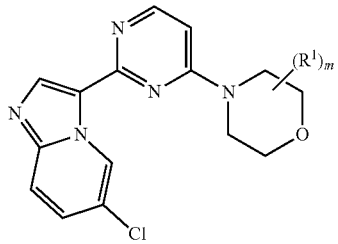

or a pharmaceutically acceptable salt thereof, wherein each of $R^1$ and m is as defined above and described in embodiments herein, both singly and in combination.

In certain embodiments, the present invention provides a compound of formula I, wherein n is 1, p is 1, q is 1, $R^2$ is —$CHF_2$, $R^3$ is hydrogen, $R^4$ is hydrogen, Ring A is piperidinyl, piperazinyl, or morpholinyl, and Ring B is

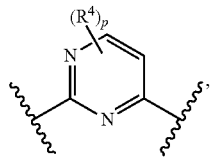

thereby forming a compound of formula XV-a, XV-b, or XV-c, respectively:

XV-a

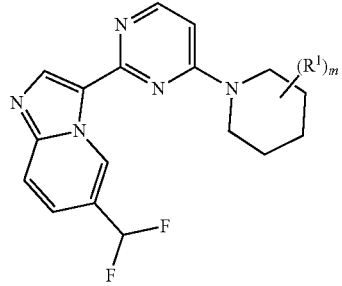

XV-b

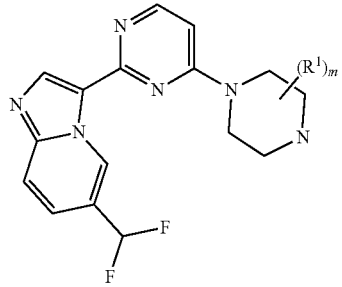

XV-c

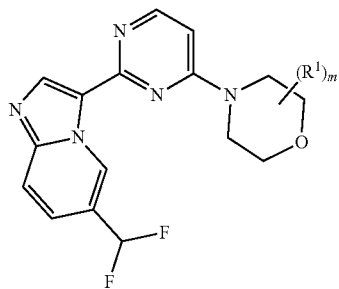

or a pharmaceutically acceptable salt thereof, wherein each of $R^1$ and m is as defined above and described in embodiments herein, both singly and in combination.

In certain embodiments, the present invention provides a compound of formula I, wherein n is 1, p is 1, q is 1, $R^2$ is —$CF_3$, $R^3$ is hydrogen, $R^4$ is hydrogen, Ring A is piperidinyl, piperazinyl, or morpholinyl, and Ring B is

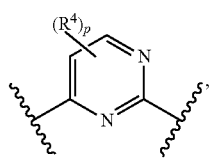

thereby forming a compound of formula XVI-a, XVI-b, or XVI-c, respectively:

XVI-a

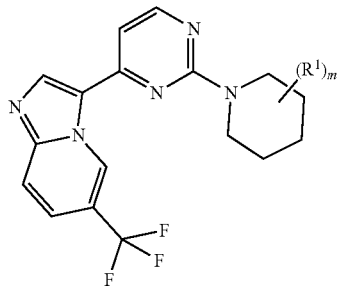

XVI-b

XVI-c

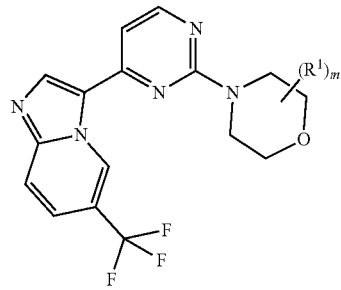

or a pharmaceutically acceptable salt thereof, wherein each of $R^1$ and m is as defined above and described in embodiments herein, both singly and in combination.

In certain embodiments, the present invention provides a compound of formula I, wherein n is 1, p is 1, q is 1, $R^2$ is chloro, $R^3$ is hydrogen, $R^4$ is hydrogen, Ring A is piperidinyl, piperazinyl, or morpholinyl, and Ring B is

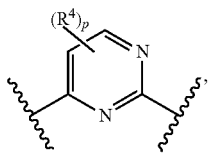

thereby forming a compound of formula XVII-a, XVII-b, or XVII-c, respectively:

XVII-a

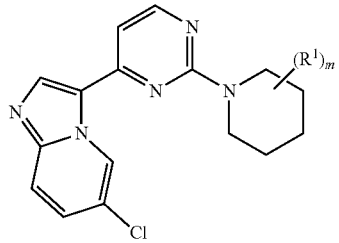

XVII-b

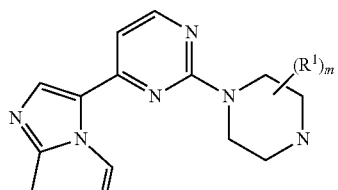

XVII-c

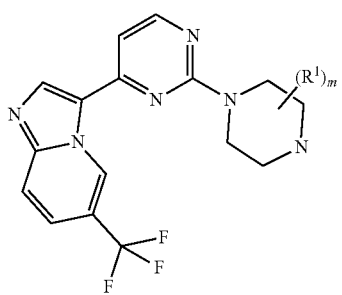

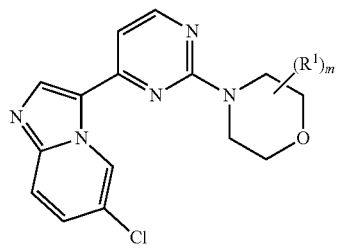

or a pharmaceutically acceptable salt thereof, wherein each of R¹ and m is as defined above and described in embodiments herein, both singly and in combination.

In certain embodiments, the present invention provides a compound of formula I, wherein n is 1, p is 1, q is 1, R² is —CHF₂, R³ is hydrogen, R⁴ is hydrogen, Ring A is piperidinyl, piperazinyl, or morpholinyl, and Ring B is

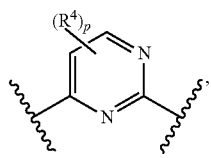

thereby forming a compound of formula XVIII-a, XVIII-b, or XVIII-c, respectively:

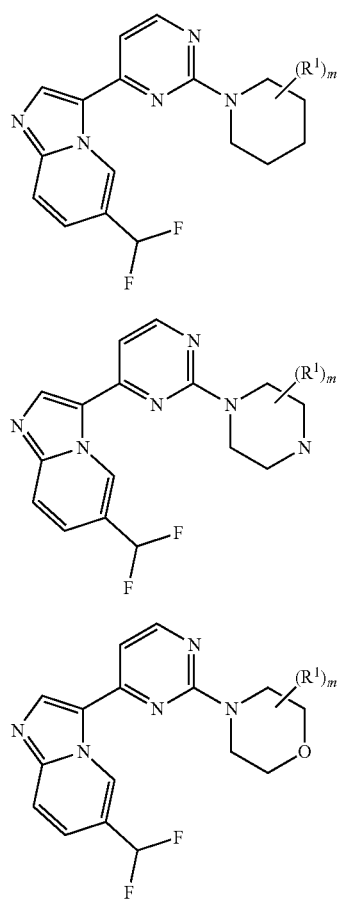

XVIII-a

XVIII-b

XVIII-c or a pharmaceutically acceptable salt thereof, wherein each of R¹ and m is as defined above and described in embodiments herein, both singly and in combination.

In certain embodiments, the present invention provides a compound of formula I, wherein n is 1, p is 1, q is 1, R² is cyclopropyl, R³ is hydrogen, R⁴ is hydrogen, Ring A is piperidinyl, piperazinyl, or morpholinyl, and Ring B is

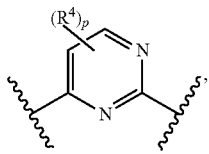

thereby forming a compound of formula XIX-a, XIX-b, or XIX-c, respectively:

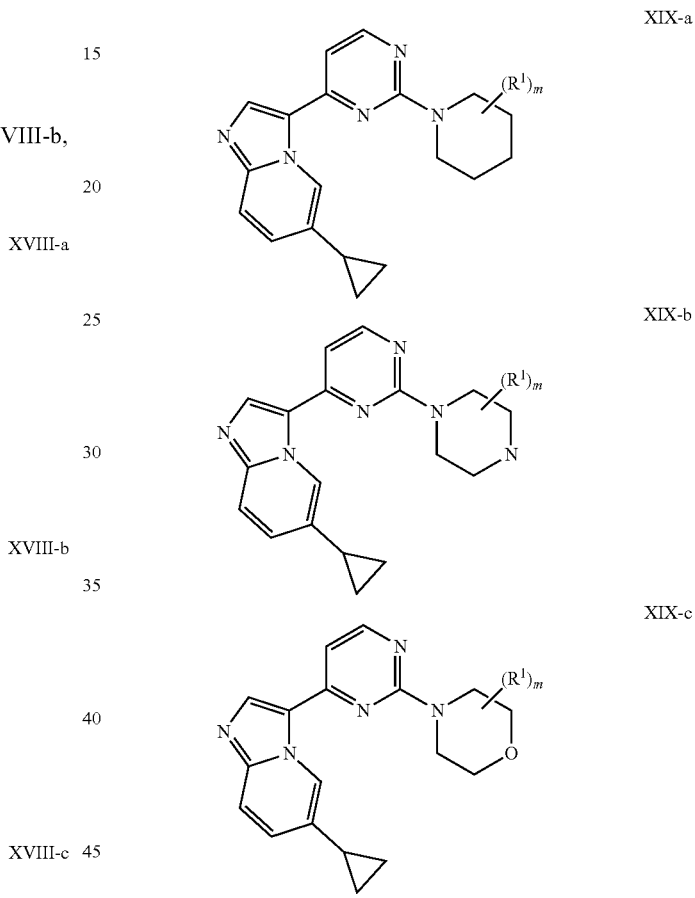

XIX-a

XIX-b

XIX-c or a pharmaceutically acceptable salt thereof, wherein each of R¹ and m is as defined above and described in embodiments herein, both singly and in combination.

In certain embodiments, the present invention provides a compound of formula I, wherein n is 1, p is 1, q is 1, R² is azetidinyl, R³ is hydrogen, R⁴ is hydrogen, Ring A is piperidinyl, piperazinyl, or morpholinyl, and Ring B is

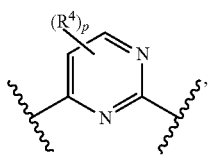

thereby forming a compound of formula XX-a, XX-b, or XX-c, respectively:

XX-a
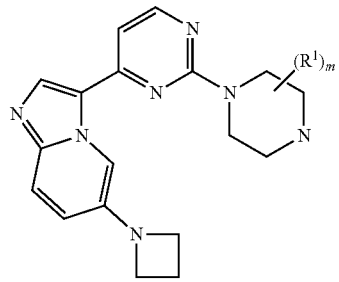

XX-b
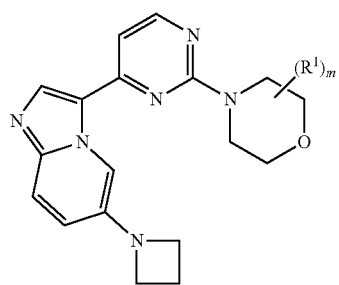

XX-c
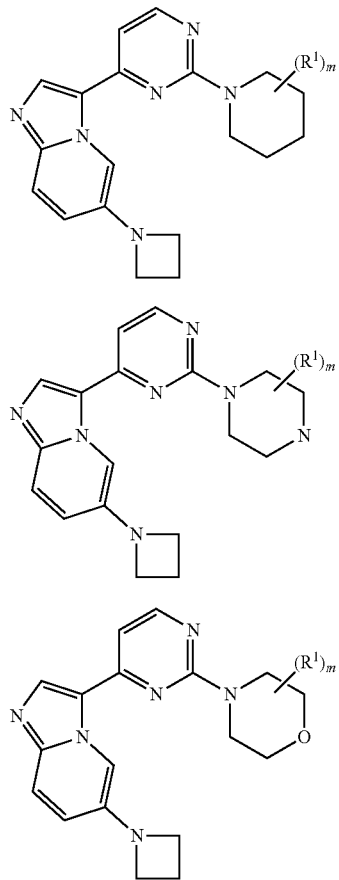

XXI-a
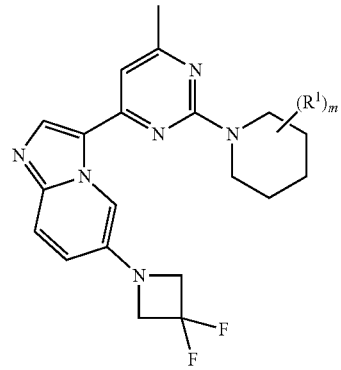

XXI-b
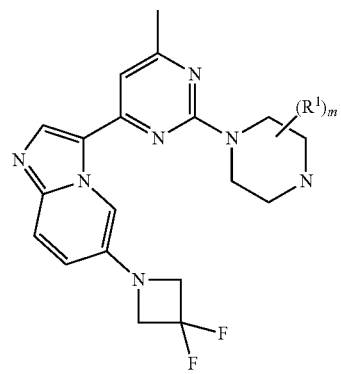

XXI-c
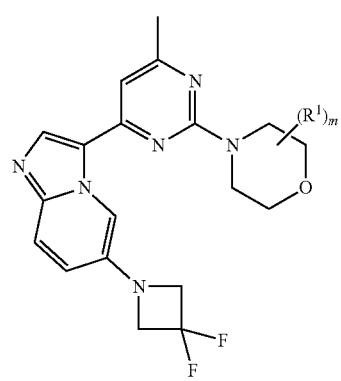

or a pharmaceutically acceptable salt thereof, wherein each of $R^1$ and m is as defined above and described in embodiments herein, both singly and in combination.

In certain embodiments, the present invention provides a compound of formula I, wherein n is 1, p is 1, q is 1, $R^2$ is

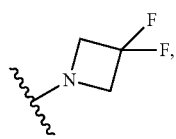

$R^3$ is hydrogen, $R^4$ is methyl, Ring A is piperidinyl, piperazinyl, or morpholinyl, and Ring B is

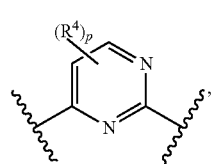

thereby forming a compound of formula XXI-a, XXI-b, or XXI-c, respectively:

or a pharmaceutically acceptable salt thereof, wherein each of $R^1$ and m is as defined above and described in embodiments herein, both singly and in combination.

Exemplary compounds of the invention are set forth in Table 1, below.

TABLE 1
Exemplary compounds of formula I
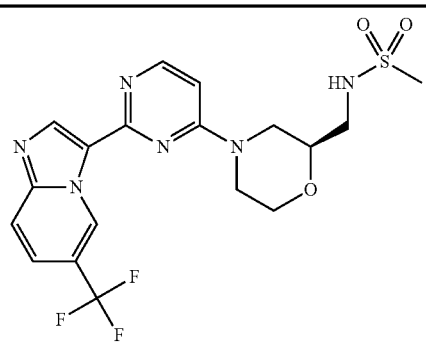
I-1
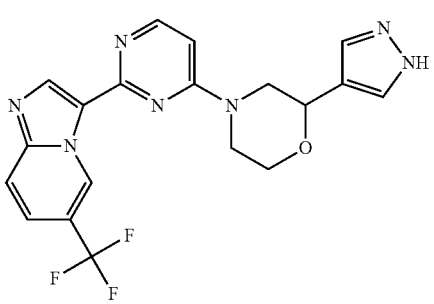
I-2
single stereoisomer
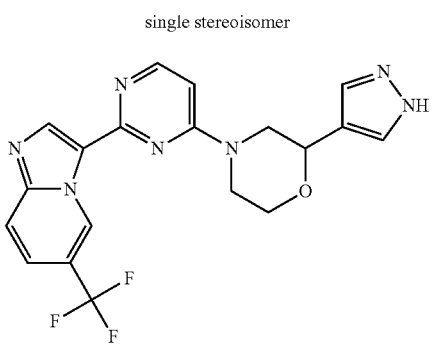
I-3
single stereoisomer
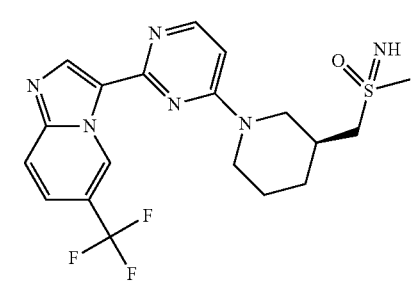
I-4
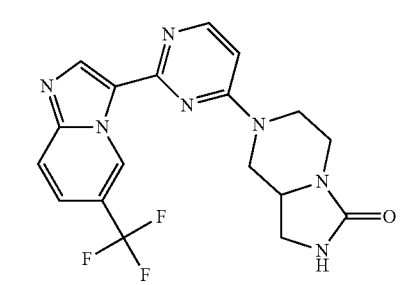
I-5
single stereoisomer
TABLE 1-continued
Exemplary compounds of formula I
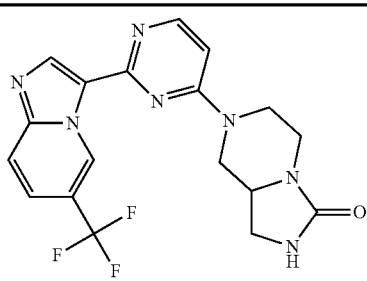
I-6
single stereoisomer
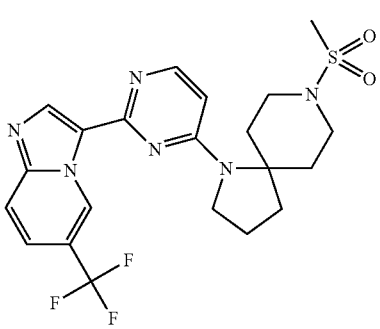
I-7
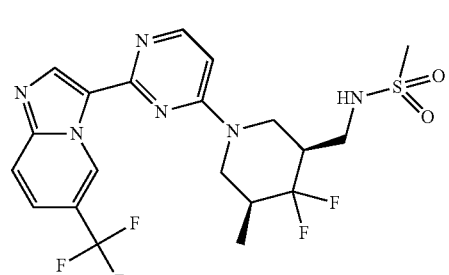
I-8
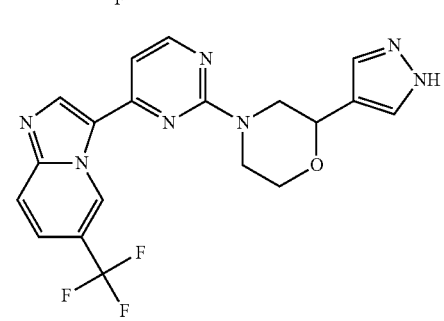
I-9
single stereoisomer
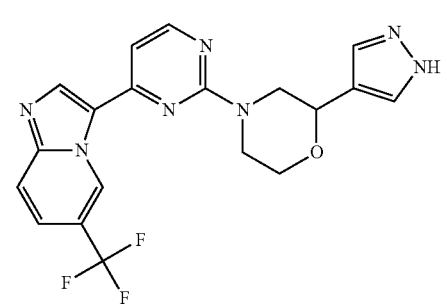
I-10
single stereoisomer TABLE 1-continued
Exemplary compounds of formula I
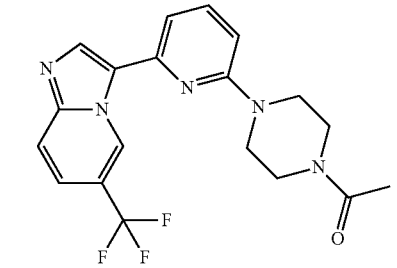 I-11
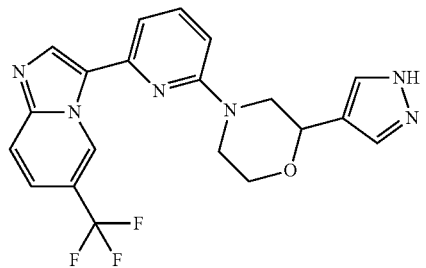 I-12
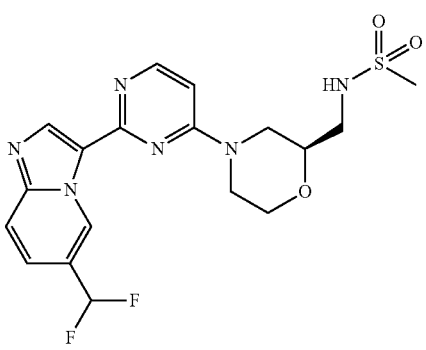 I-13
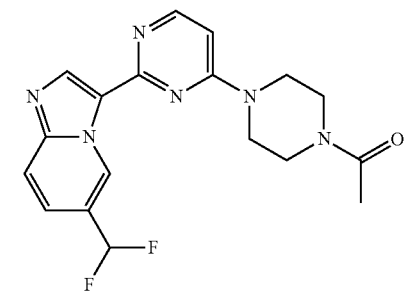 I-14
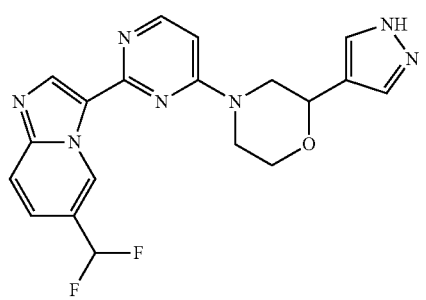 I-15
TABLE 1-continued
Exemplary compounds of formula I
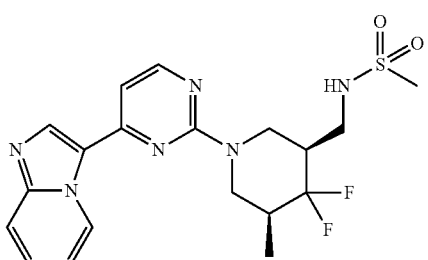 I-16
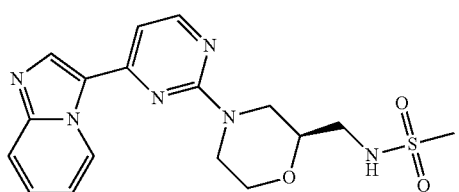 I-17
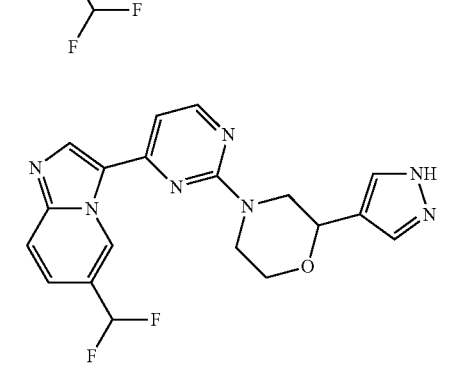 I-18
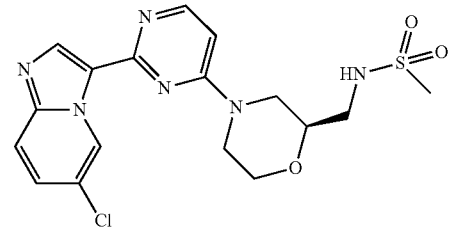 I-19
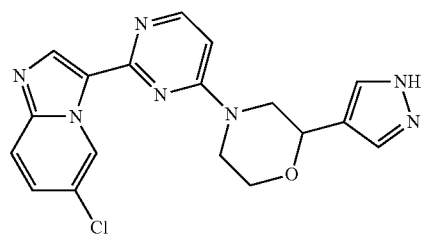 I-20

TABLE 1-continued
Exemplary compounds of formula I
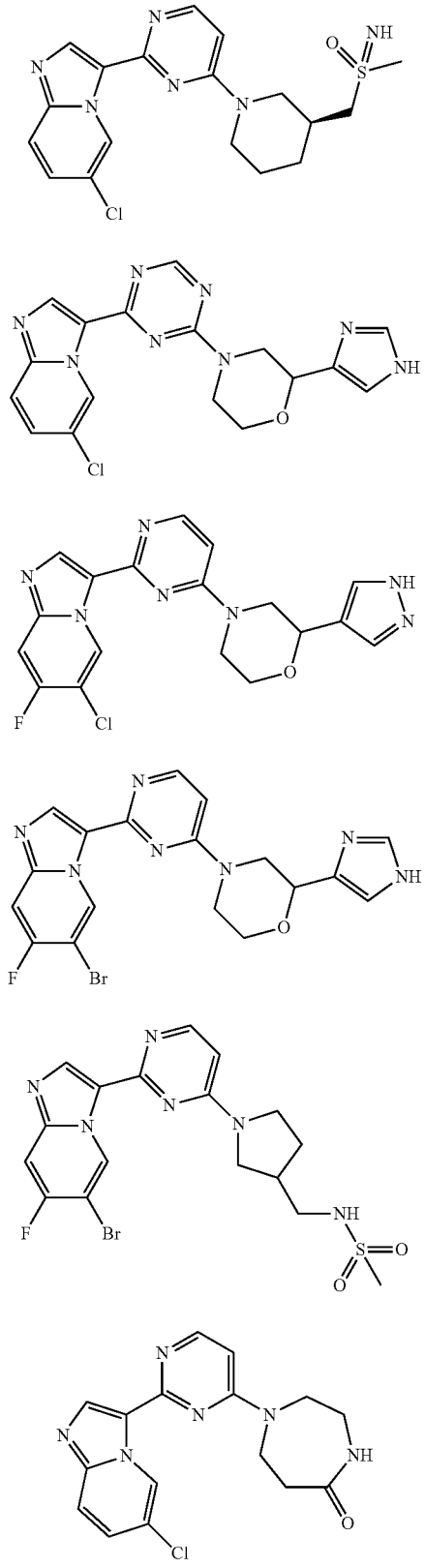
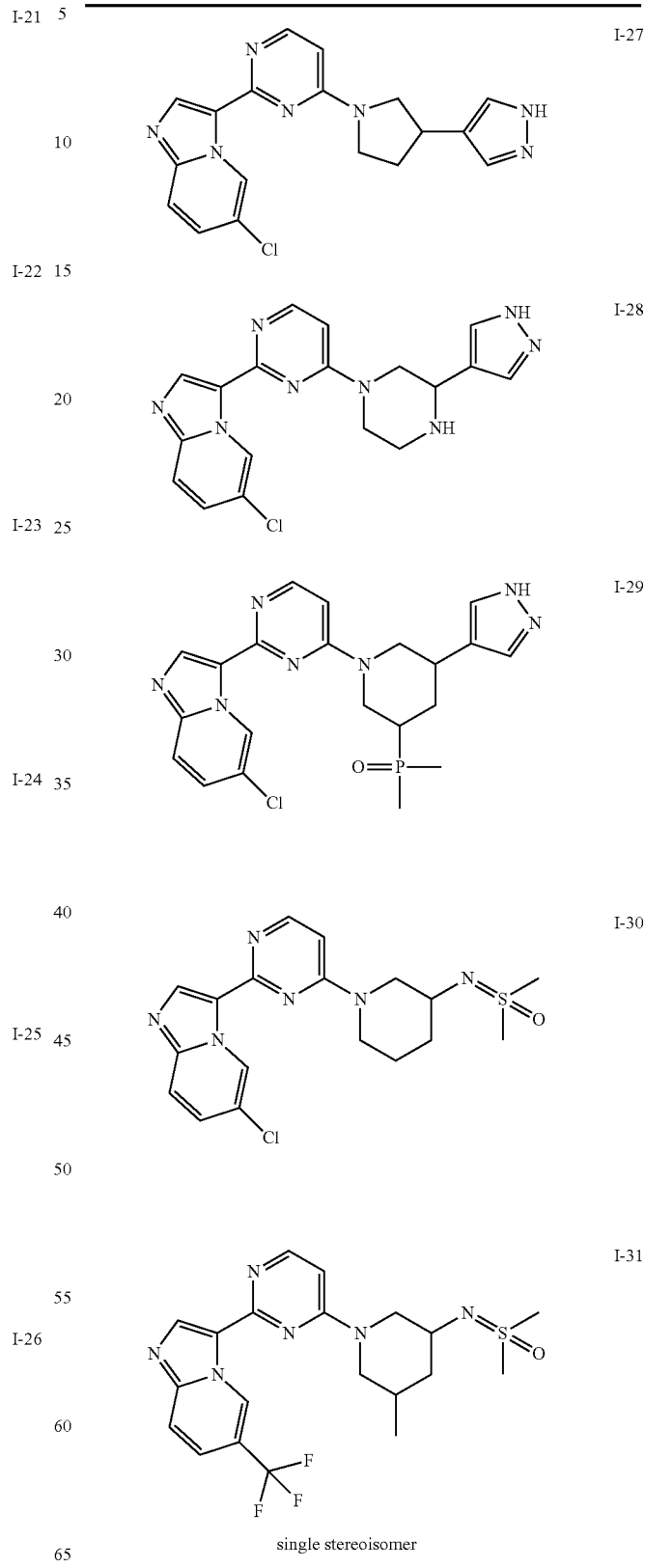

TABLE 1-continued
Exemplary compounds of formula I
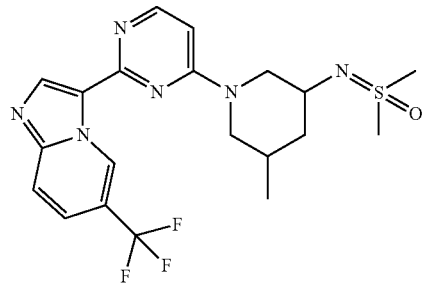
I-32
single stereoisomer
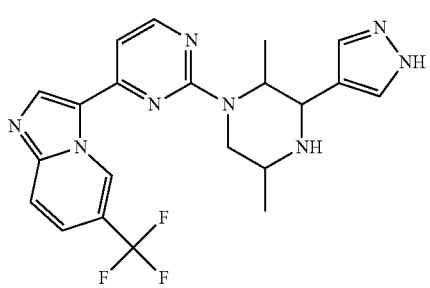
I-33
single stereoisomer
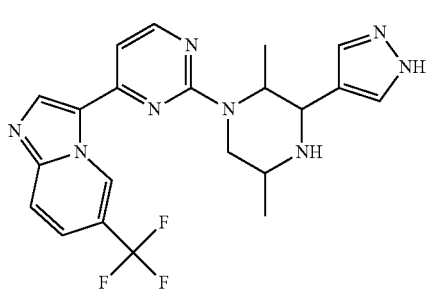
I-34
single stereoisomer
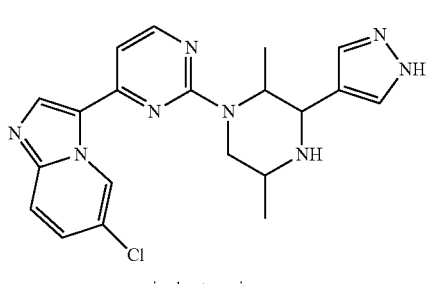
I-35
single stereoisomer
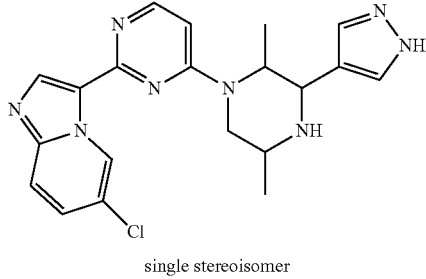
I-36
single stereoisomer
TABLE 1-continued
Exemplary compounds of formula I
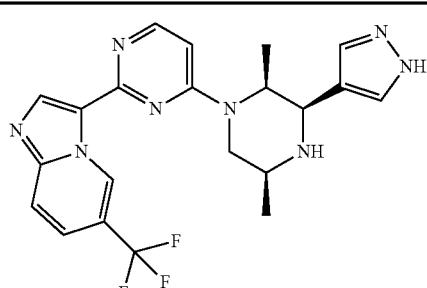
I-37
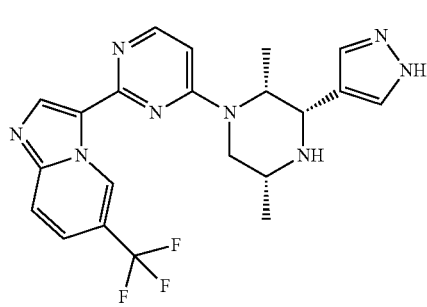
I-38
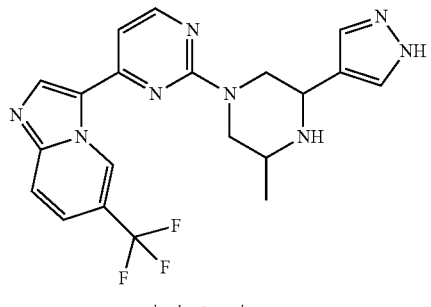
I-39
single stereoisomer
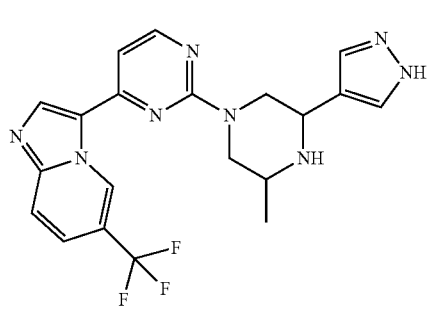
I-40
single stereoisomer
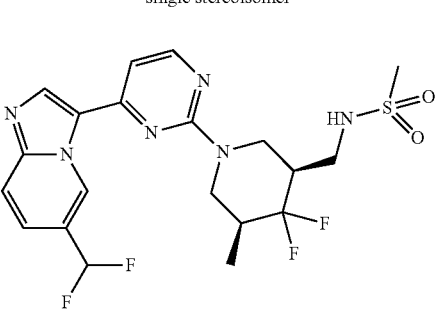
I-41

TABLE 1-continued
Exemplary compounds of formula I
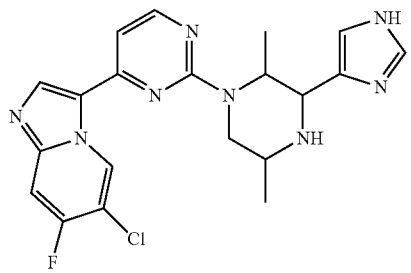
I-42
single diastereomer
(pair of enatiomers)
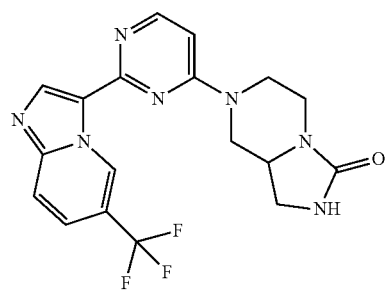
I-43
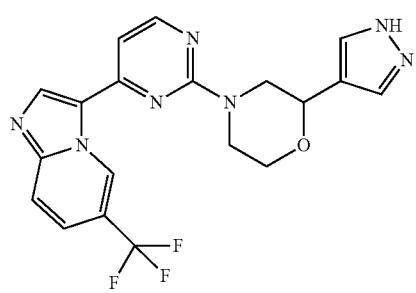
I-44
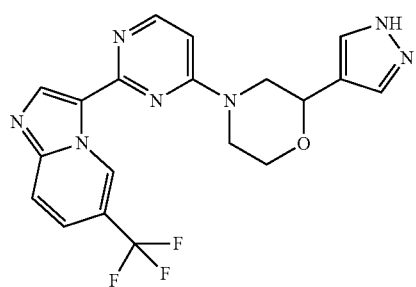
I-45
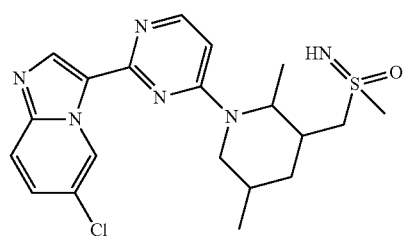
I-46
single diastereomer
(pair of enantiomers)
TABLE 1-continued
Exemplary compounds of formula I
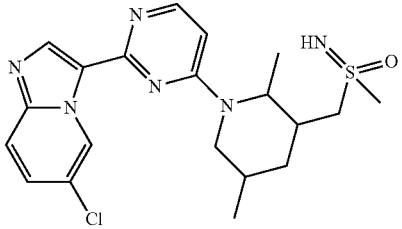
I-47
single diastereomer
(pair of enantiomers)
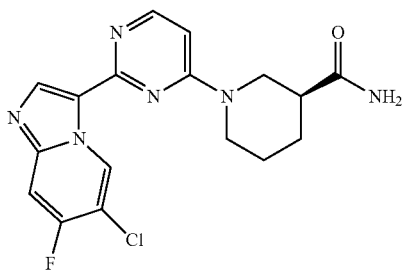
I-48
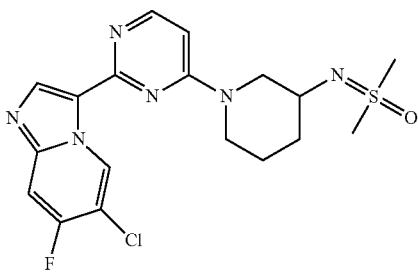
I-49
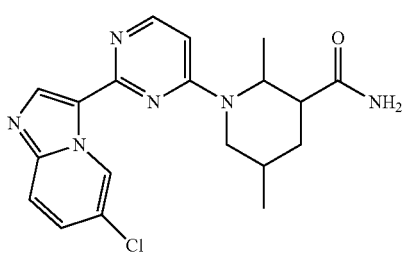
I-50
single diastereomer
(pair of enantiomers)
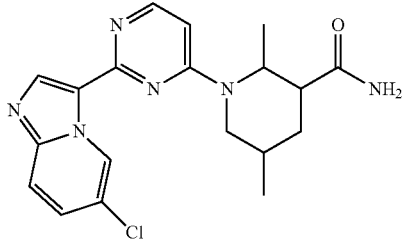
I-51
single diastereomer
(pair of enantiomers)

TABLE 1-continued

Exemplary compounds of formula I

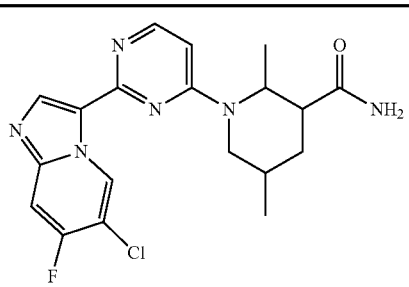

I-52 single diastereomer
(pair of enantiomers)

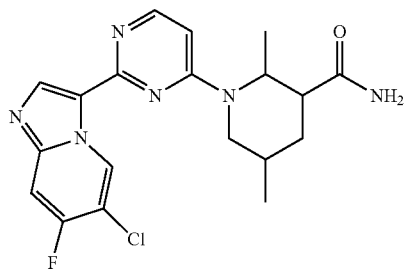

I-53 single diastereomer
(pair of enantiomers)

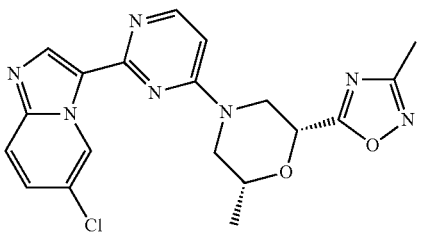

I-54 single diastereomer,
pair of enantiomers

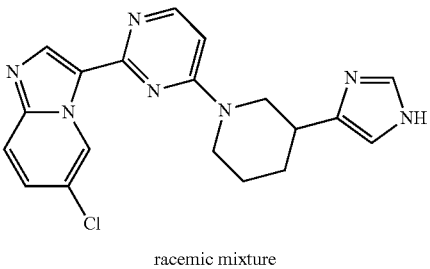

I-55 racemic mixture

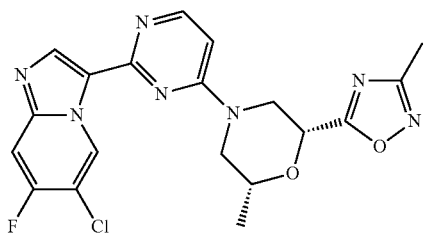

I-56 single diastereomer,
pair of enantiomers

TABLE 1-continued

Exemplary compounds of formula I

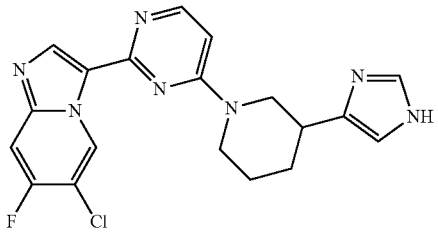

I-57 racemic mixture

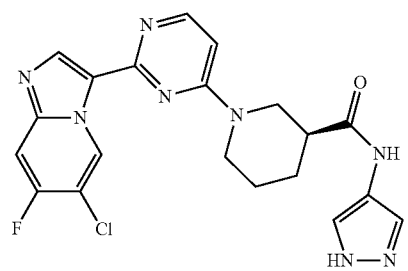

I-58 single enantiomer

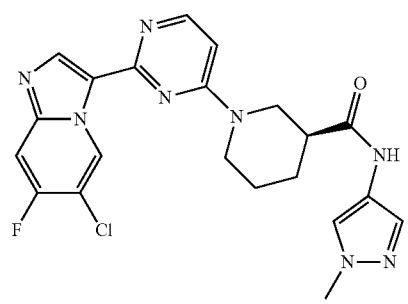

I-59 single enantiomer

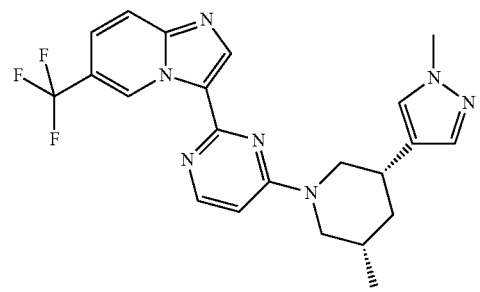

I-60 single diastereomer, pair of enantiomers

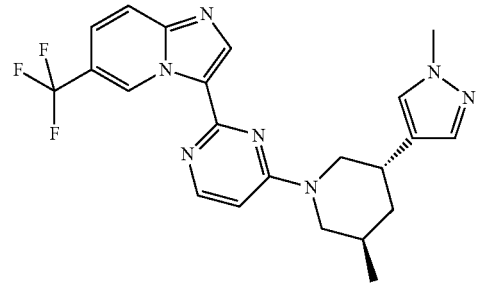

I-61 single diastereomer, pair of enantiomers

TABLE 1-continued
Exemplary compounds of formula I
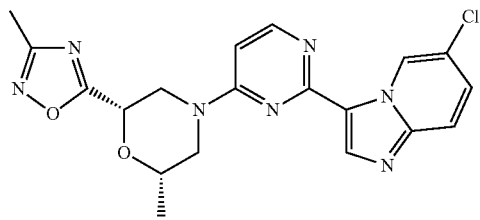
I-62
single enantiomer
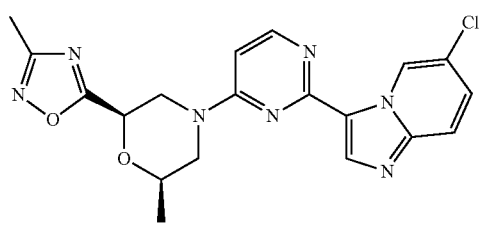
I-63
single enantiomer
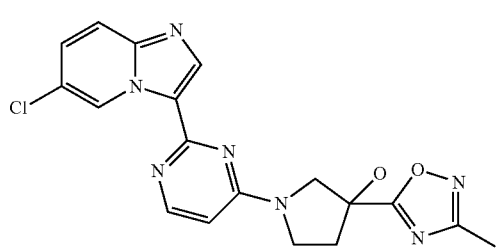
I-64
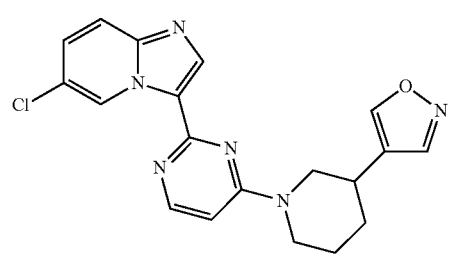
I-65
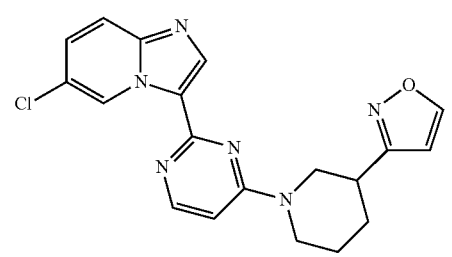
I-66
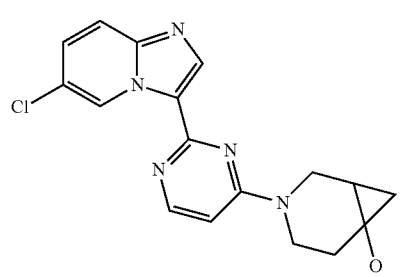
I-67
TABLE 1-continued
Exemplary compounds of formula I
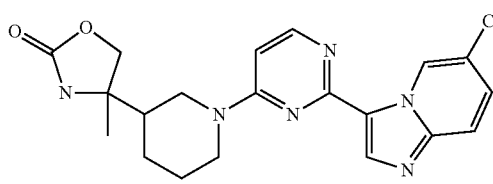
I-68
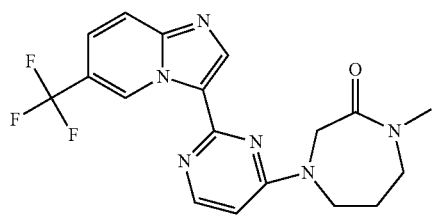
I-69
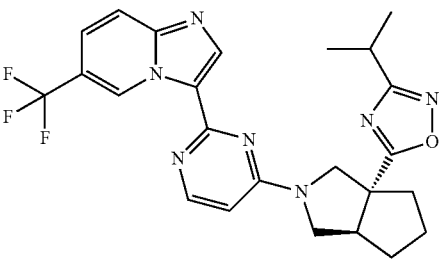
I-70
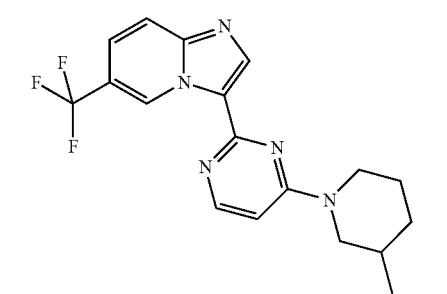
I-71
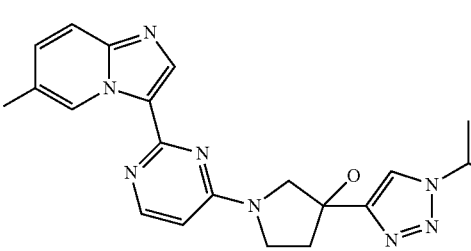
I-72
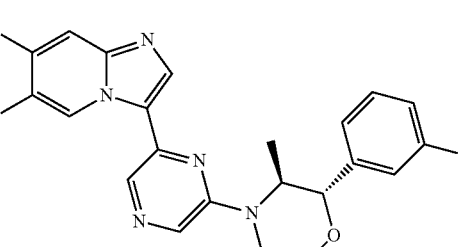
I-73

TABLE 1-continued

Exemplary compounds of formula I

| I-74 | (structure) |
| I-75 | (structure) |
| I-76 | (structure) |
| I-77 | (structure) |
| I-78 | (structure) |
| I-79 | (structure) |
| I-80 | (structure) |
| I-81 | (structure) |
| I-82 | (structure) |
| I-83 | (structure) |
| I-84 | (structure) |

TABLE 1-continued
Exemplary compounds of formula I
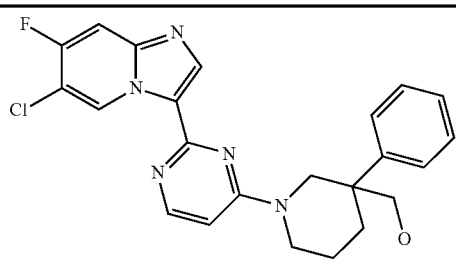
I-85
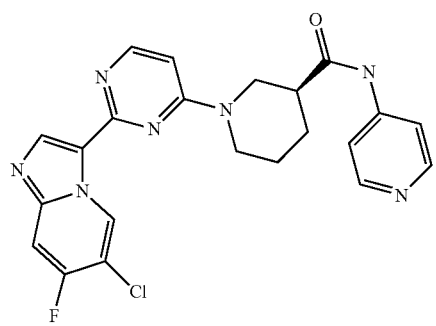
I-86
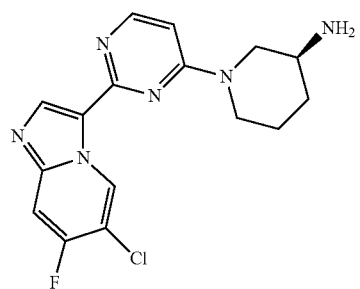
I-87
single enantiomer
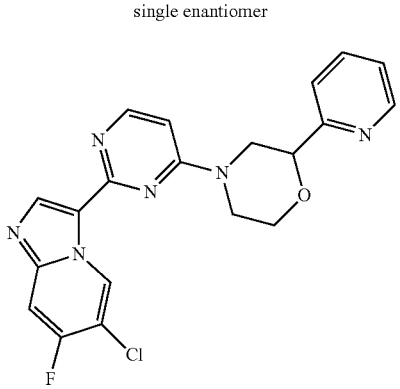
I-88
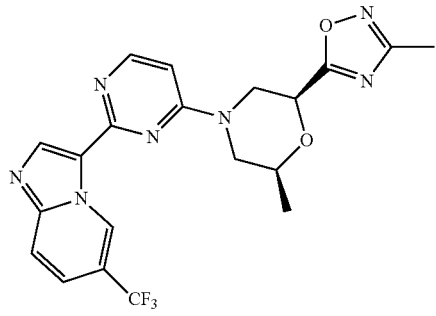
I-89
single enantiomer
TABLE 1-continued
Exemplary compounds of formula I
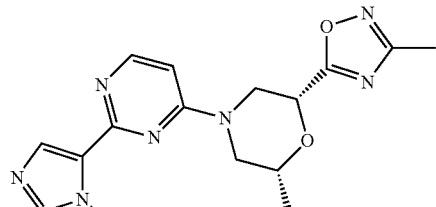
I-90
single enantiomer
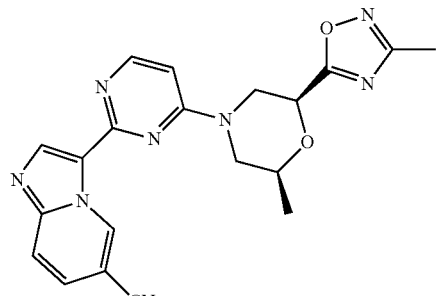
I-91
single enantiomer
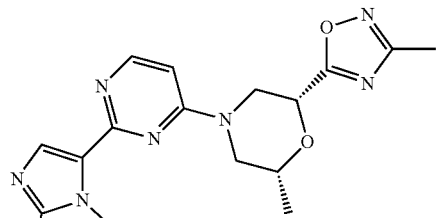
I-92
single enantiomer
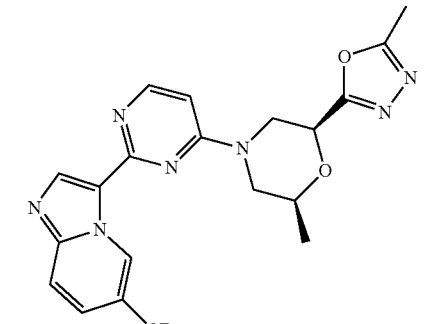
I-93
single diastereomer
(pair of enantiomers)

TABLE 1-continued
Exemplary compounds of formula I
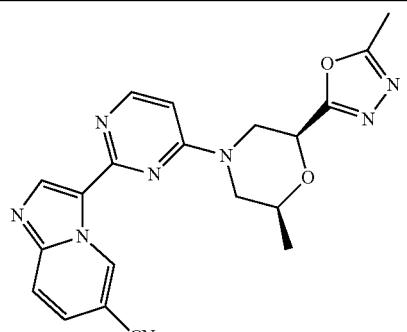
I-94
single diastereomer
(pair of enantiomers)
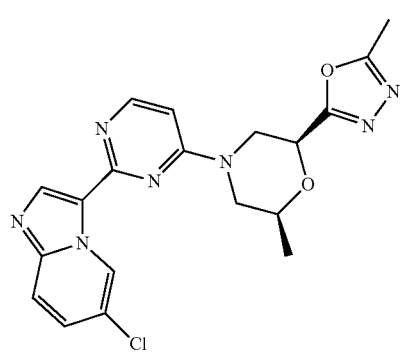
I-95
single diastereomer
(pair of enantiomers)
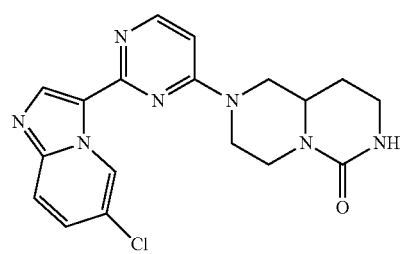
I-96
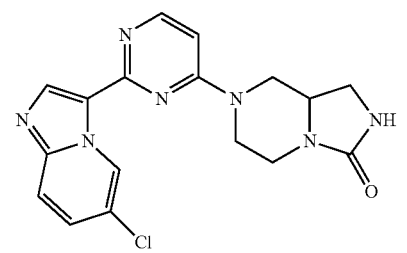
I-97
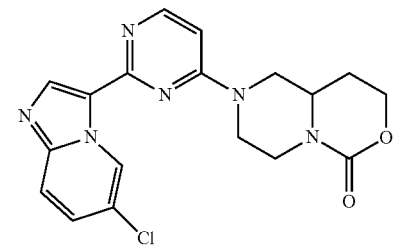
I-98
TABLE 1-continued
Exemplary compounds of formula I
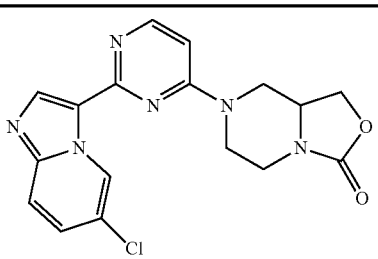
I-99
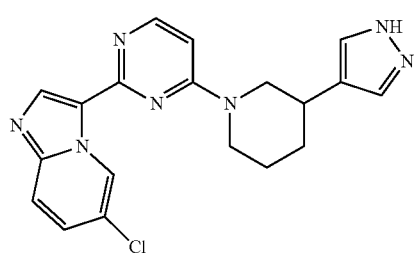
I-100
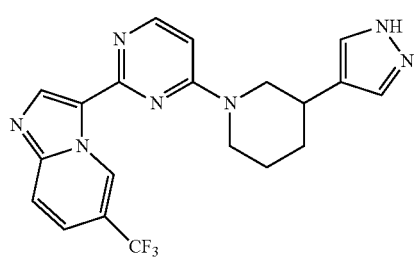
I-101
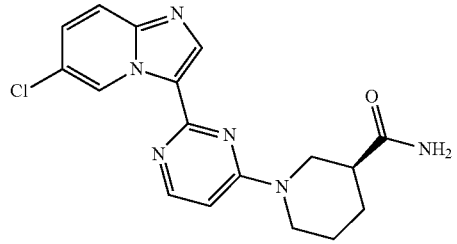
I-102
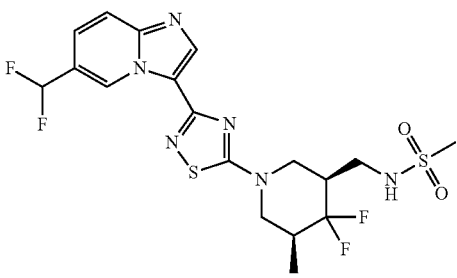
I-103
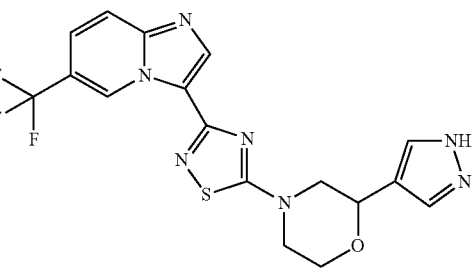
I-104

TABLE 1-continued
Exemplary compounds of formula I
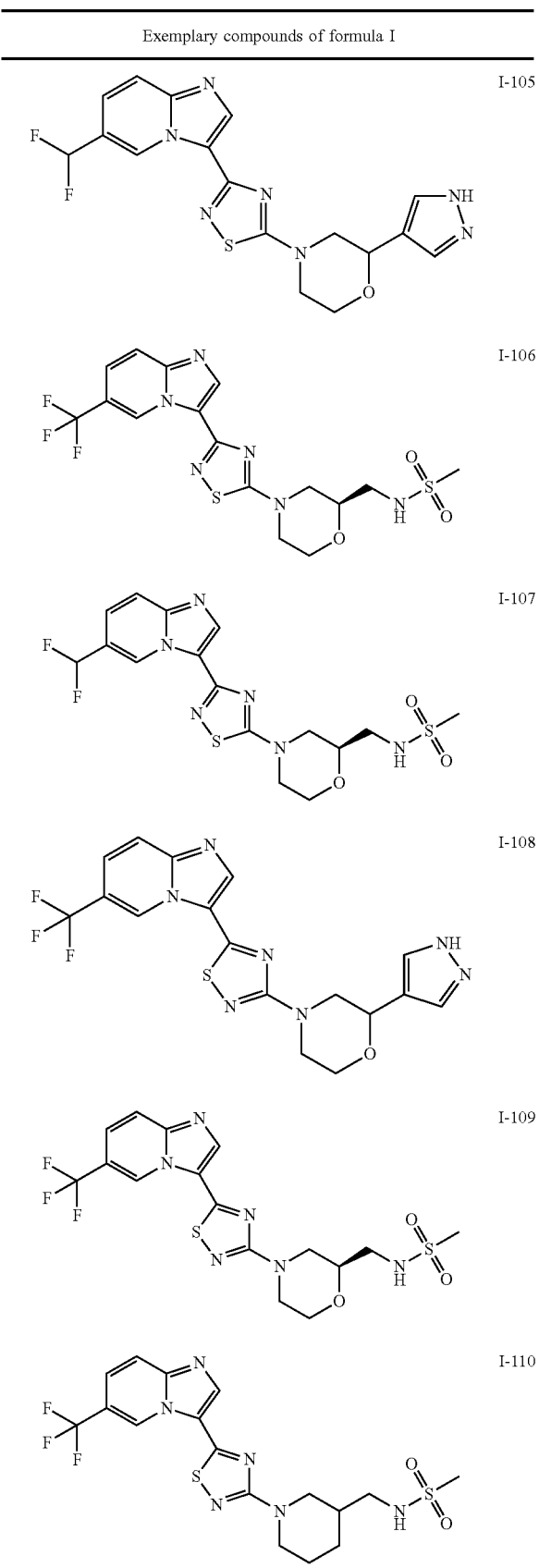
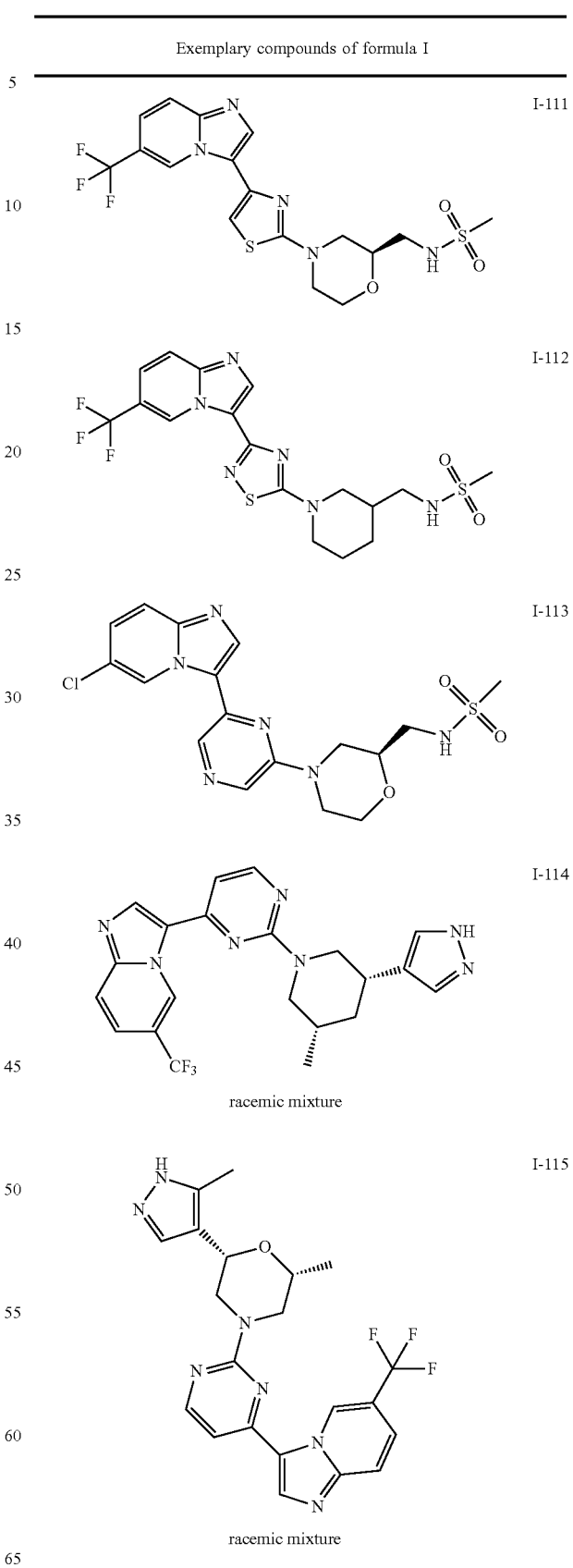

TABLE 1-continued
Exemplary compounds of formula I
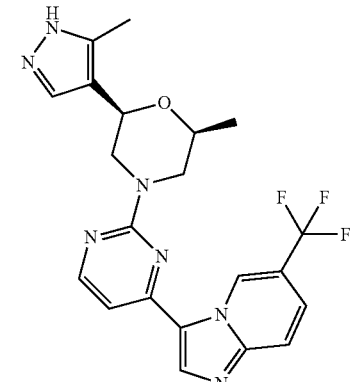
I-116
single diastereomer
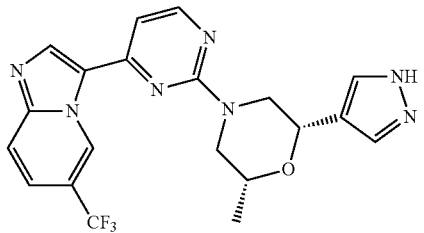
I-117
racemic mixture
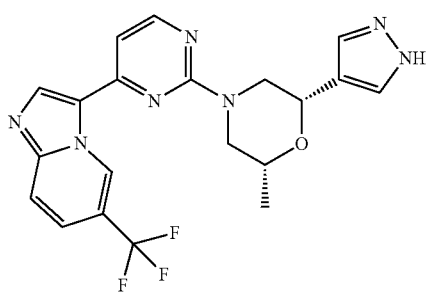
I-118
single diastereomer
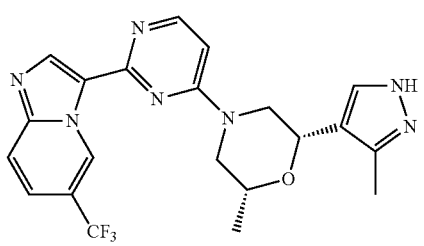
I-119
racemic mixture
TABLE 1-continued
Exemplary compounds of formula I
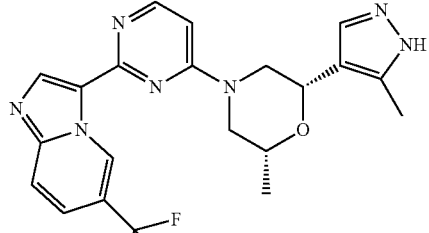
I-120
single diastereomer
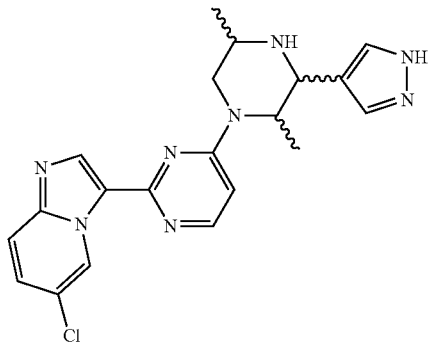
I-122
I-123
I-124
I-125

TABLE 1-continued
Exemplary compounds of formula I
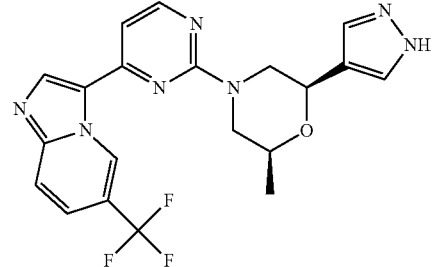 I-126
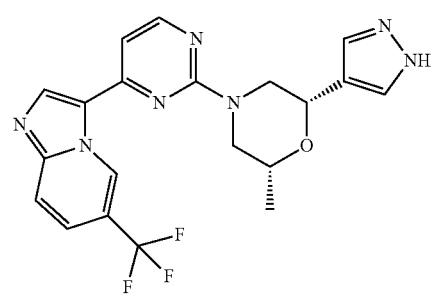 I-127
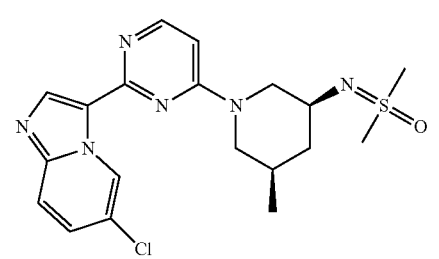 I-128
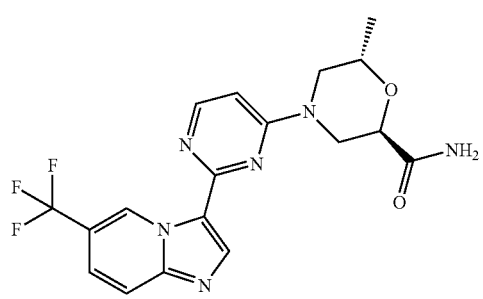 I-129
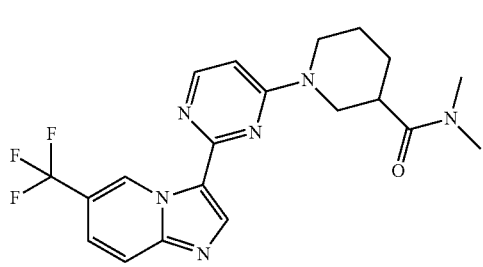 I-130
TABLE 1-continued
Exemplary compounds of formula I
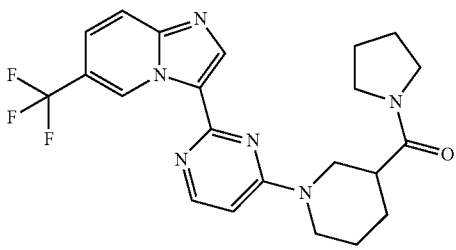 I-131
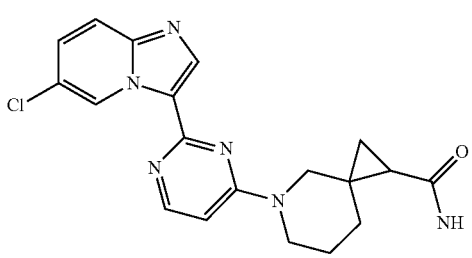 I-132
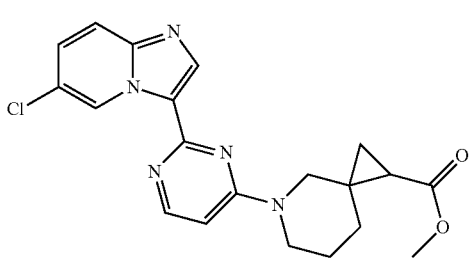 I-133
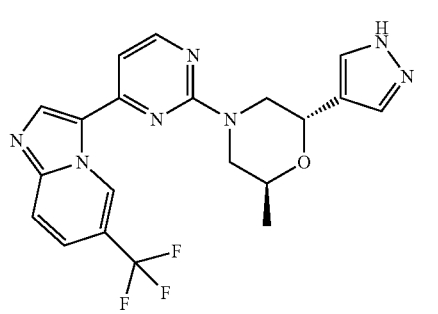 I-134
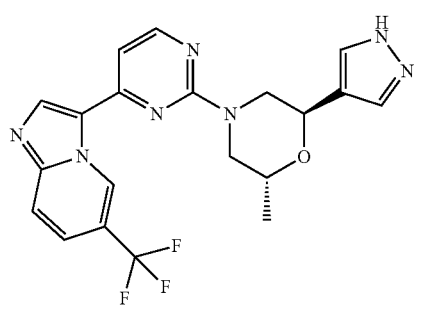 I-135

TABLE 1-continued
Exemplary compounds of formula I
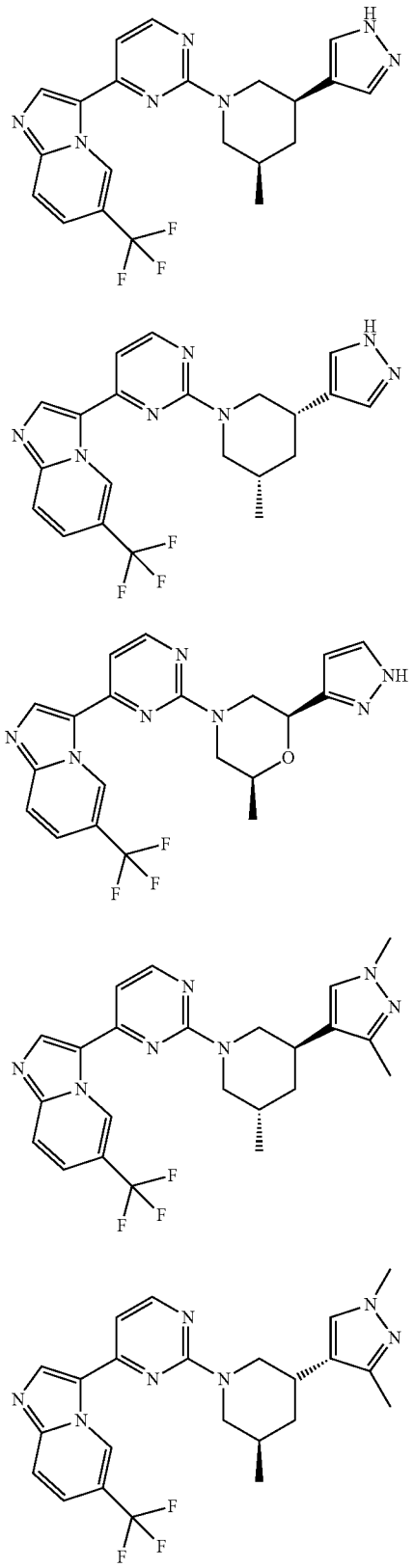
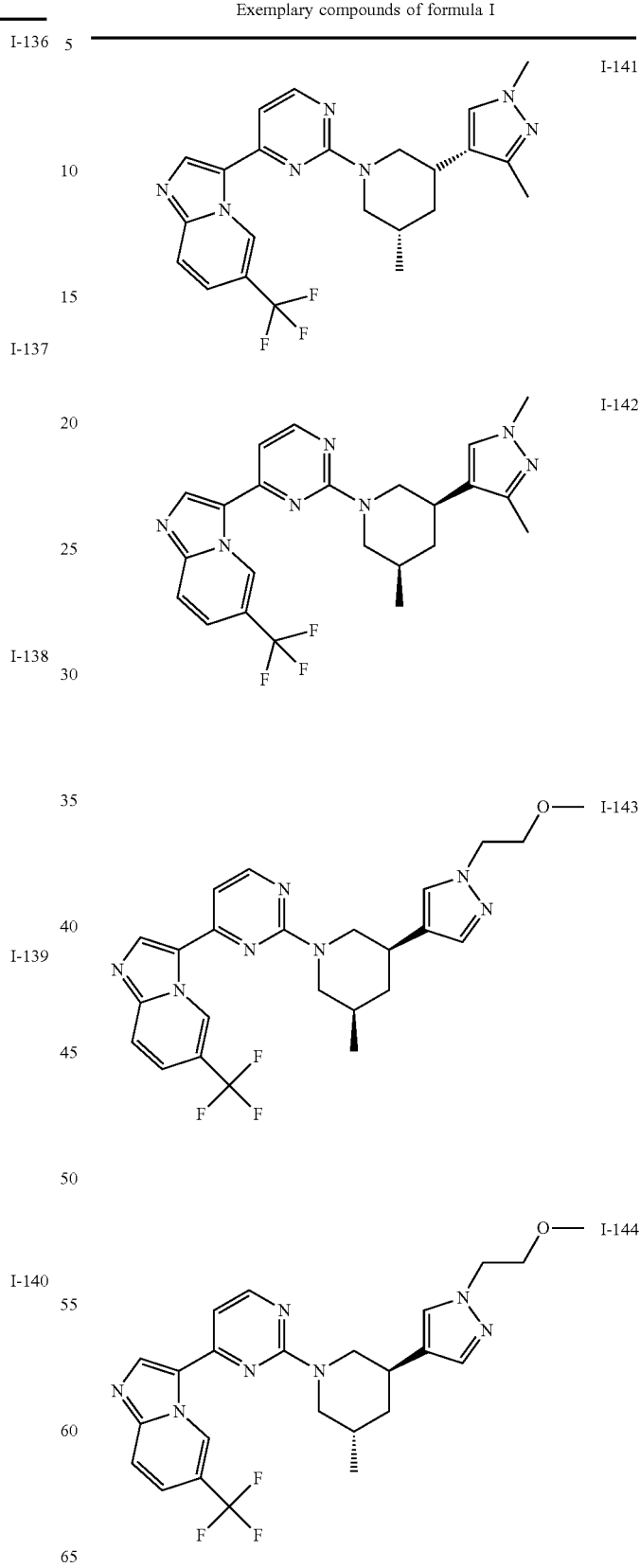

TABLE 1-continued

Exemplary compounds of formula I (Chemical structures shown for compounds I-145, I-146, I-147, I-148, I-149, I-150, I-151, I-152, I-153, I-154)

TABLE 1-continued

Exemplary compounds of formula I

TABLE 1-continued
Exemplary compounds of formula I
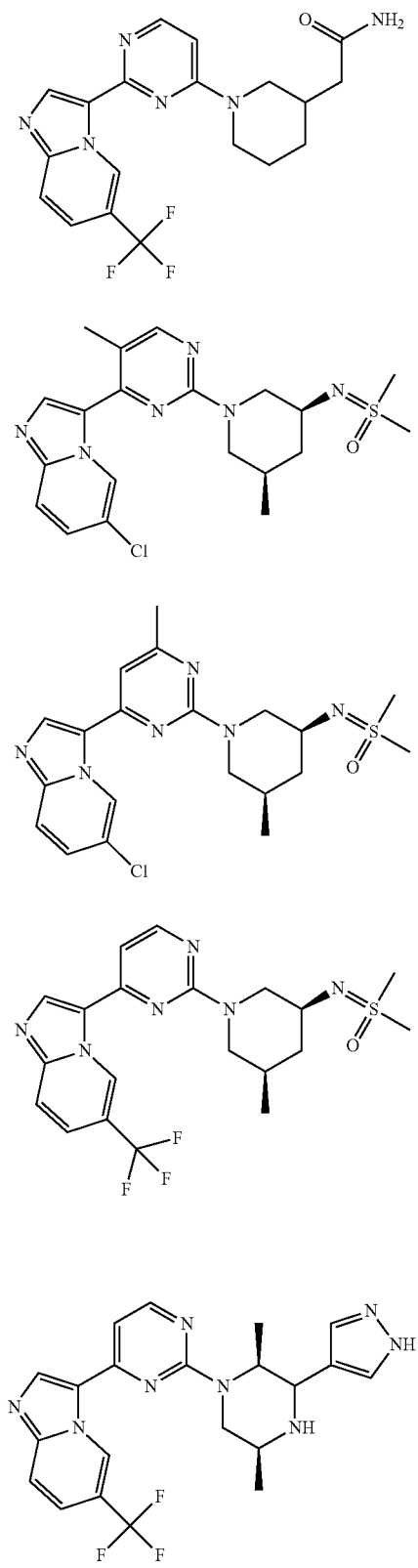
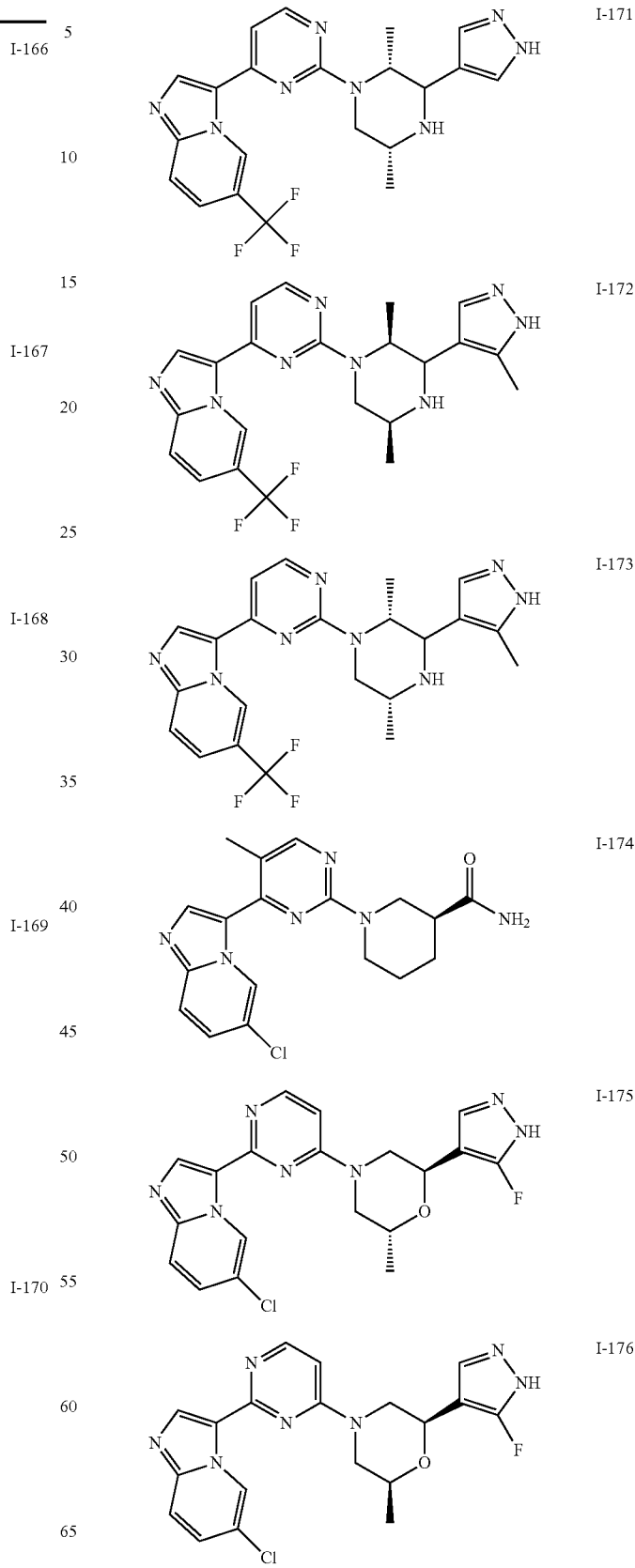

TABLE 1-continued
Exemplary compounds of formula I
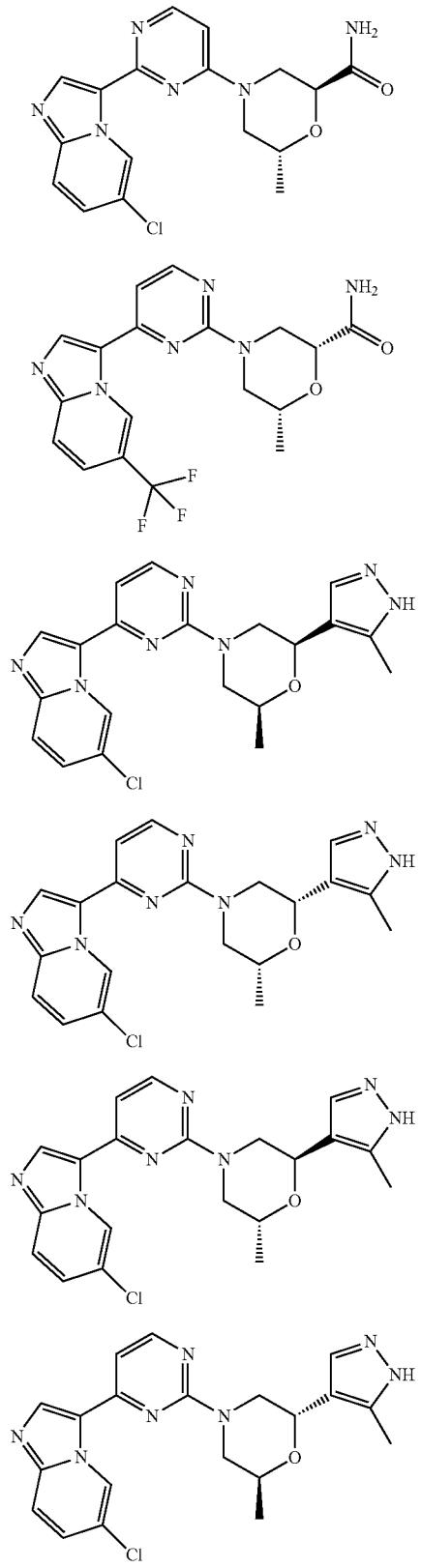
I-177
I-178
I-179
I-180
I-181
I-182
TABLE 1-continued
Exemplary compounds of formula I
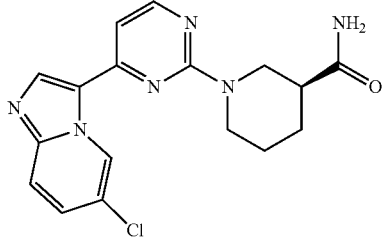
I-183
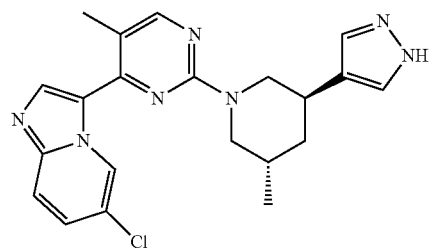
I-184
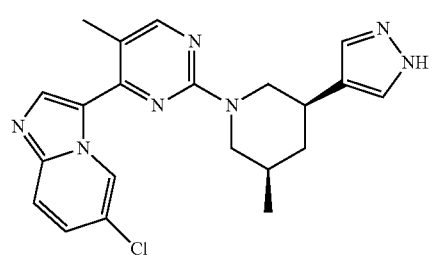
I-185
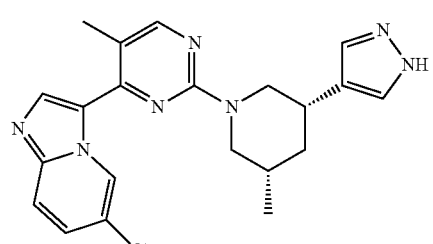
I-186
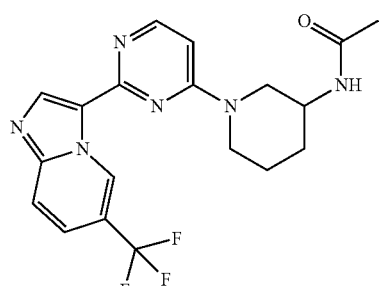
I-187
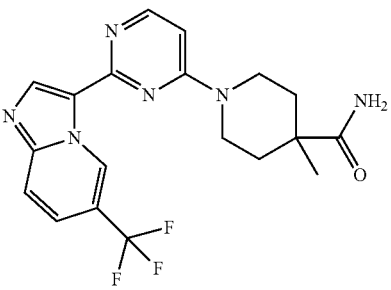
I-188

TABLE 1-continued
Exemplary compounds of formula I
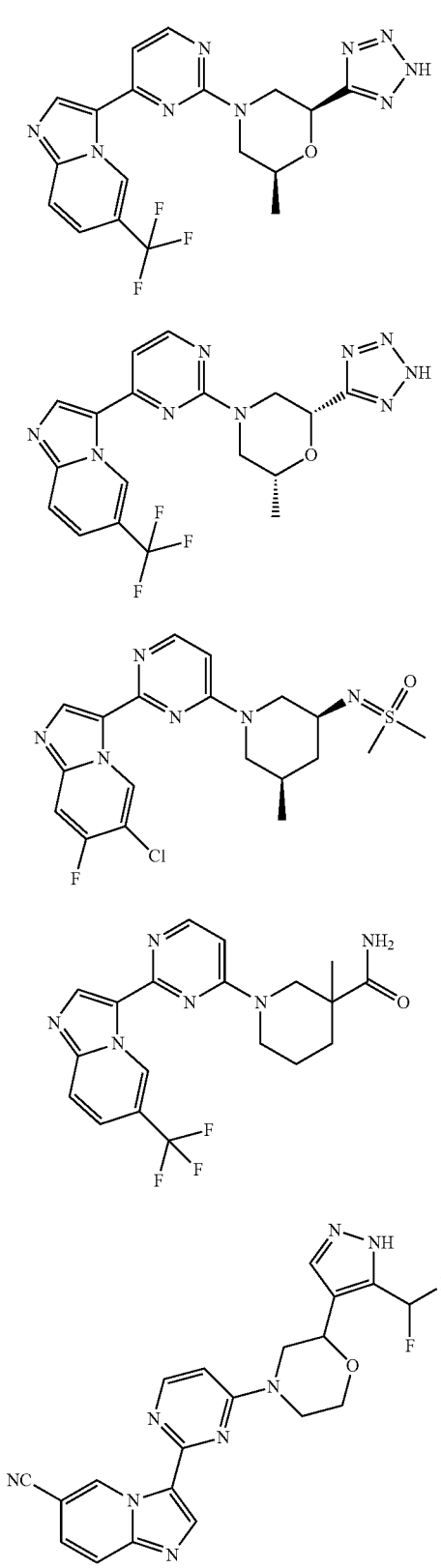
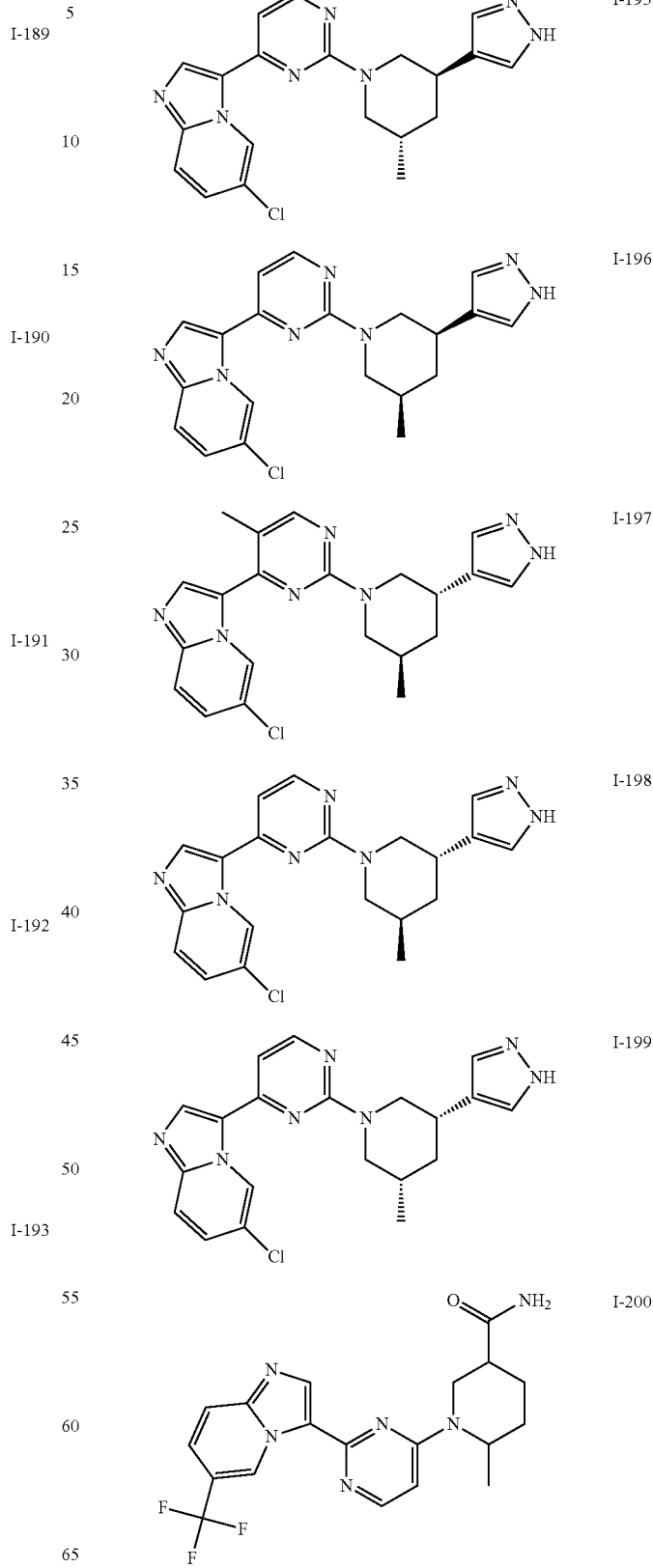

TABLE 1-continued
Exemplary compounds of formula I
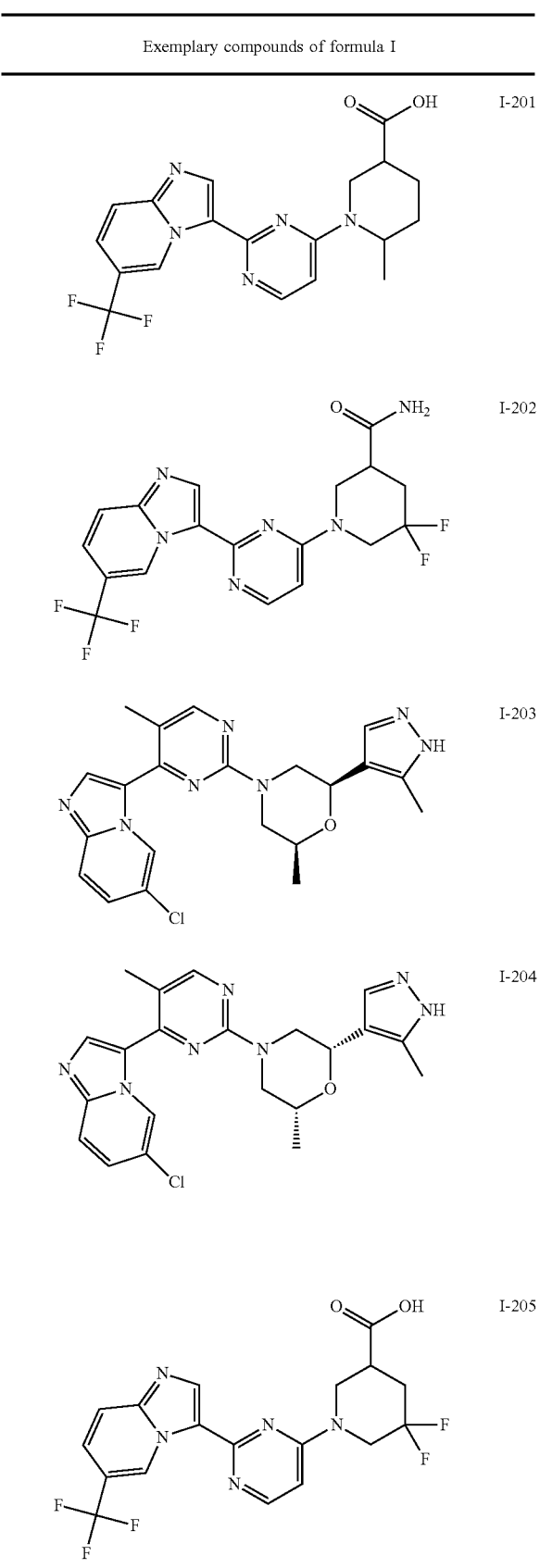
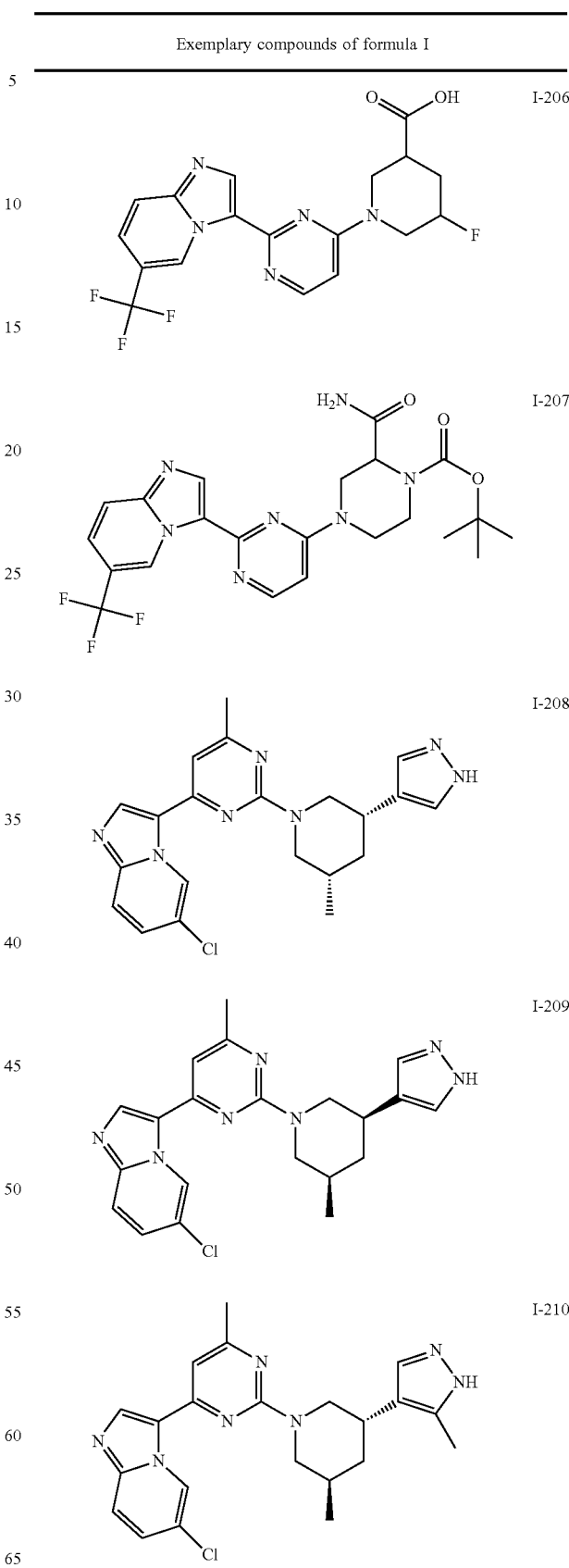

TABLE 1-continued
Exemplary compounds of formula I
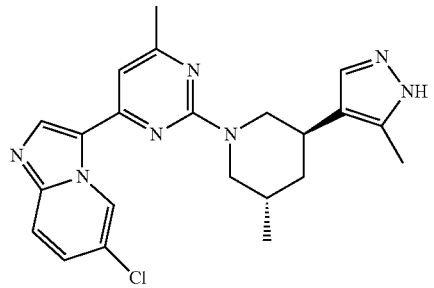 I-211
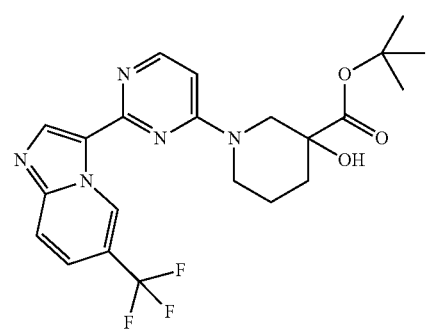 I-212
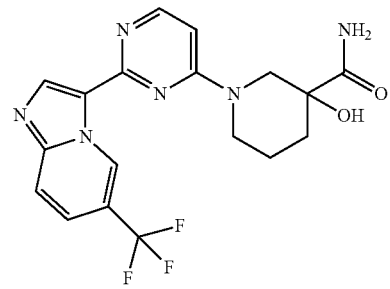 I-213
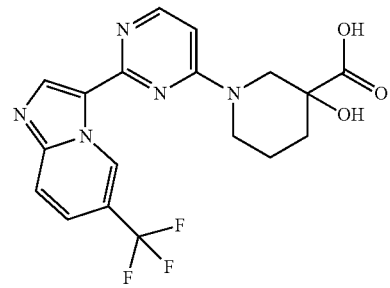 I-214
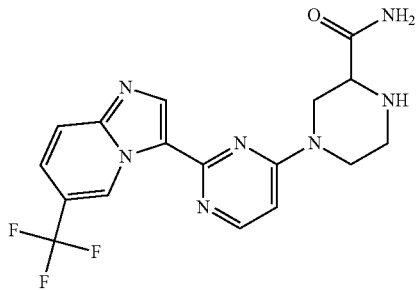 I-217
TABLE 1-continued
Exemplary compounds of formula I
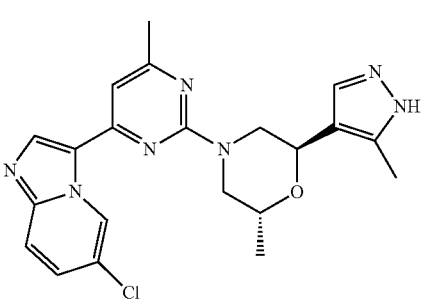 I-218
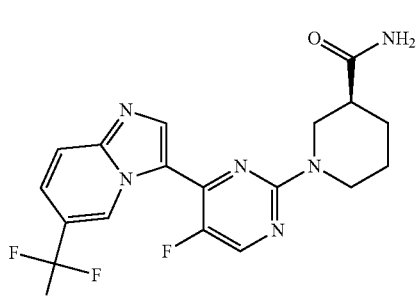 I-219
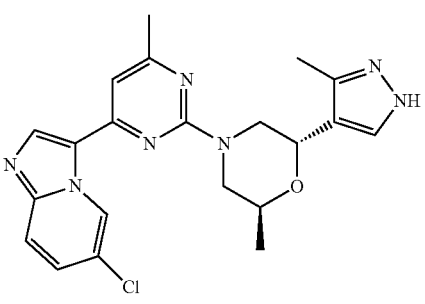 I-220
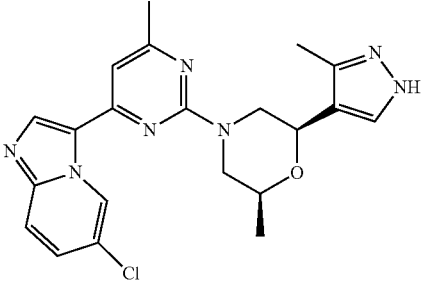 I-221
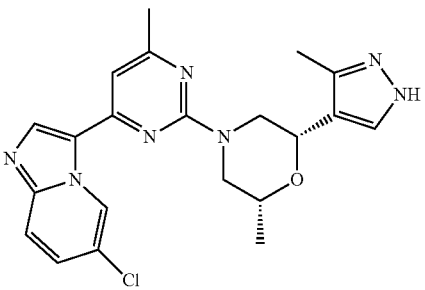 I-222

TABLE 1-continued
Exemplary compounds of formula I
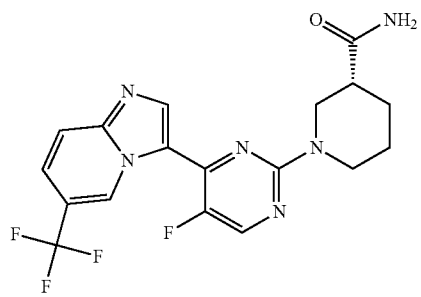 I-223
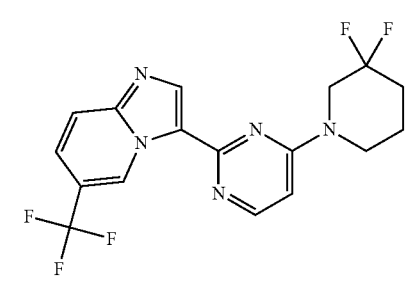 I-224
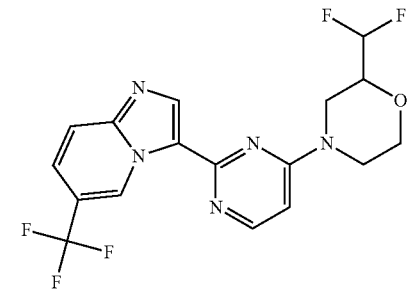 I-225
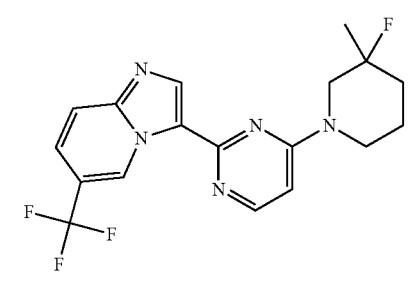 I-226
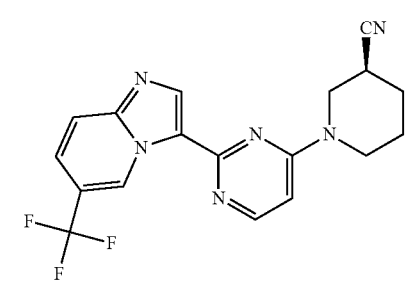 I-227
TABLE 1-continued
Exemplary compounds of formula I
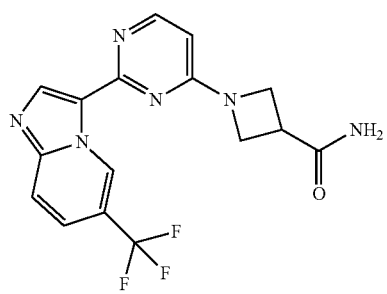 I-228
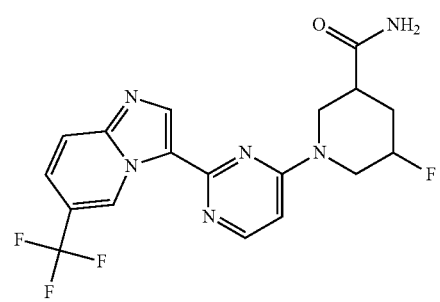 I-229
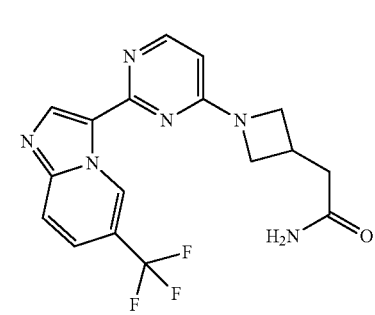 I-230
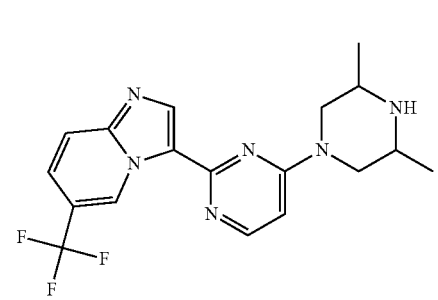 I-231
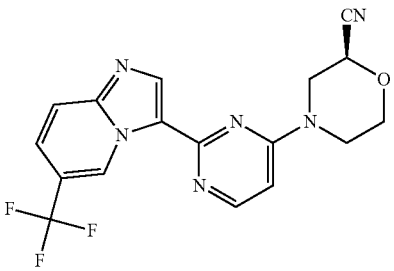 I-232

TABLE 1-continued

Exemplary compounds of formula I

| | |
|---|---|
| I-233 | I-238 |
| I-234 | I-239 |
| I-235 | I-240 |
| I-236 | I-241 |
| I-237 | I-242 |

TABLE 1-continued
Exemplary compounds of formula I
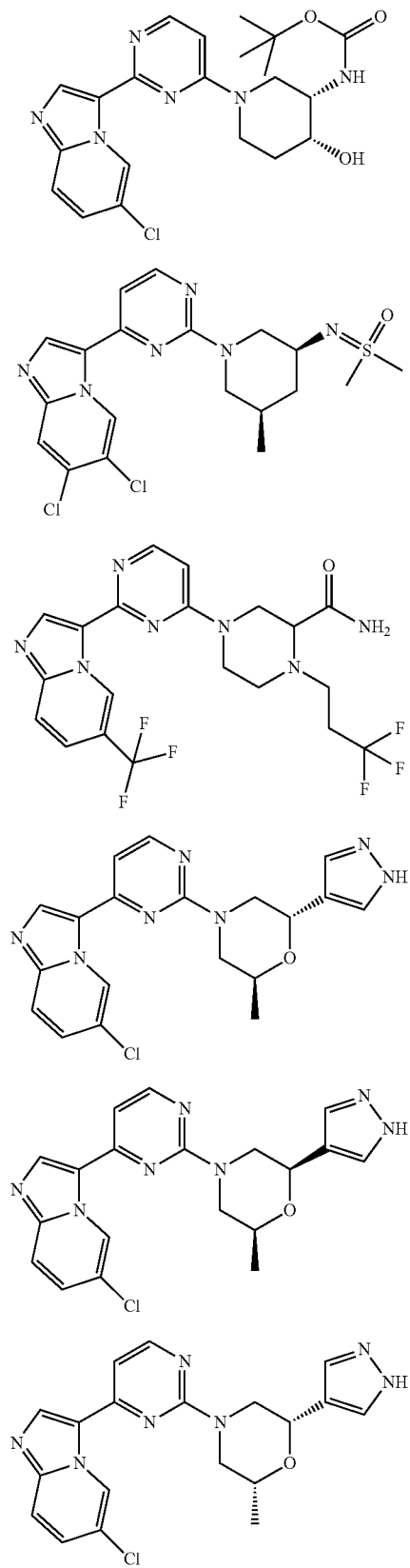
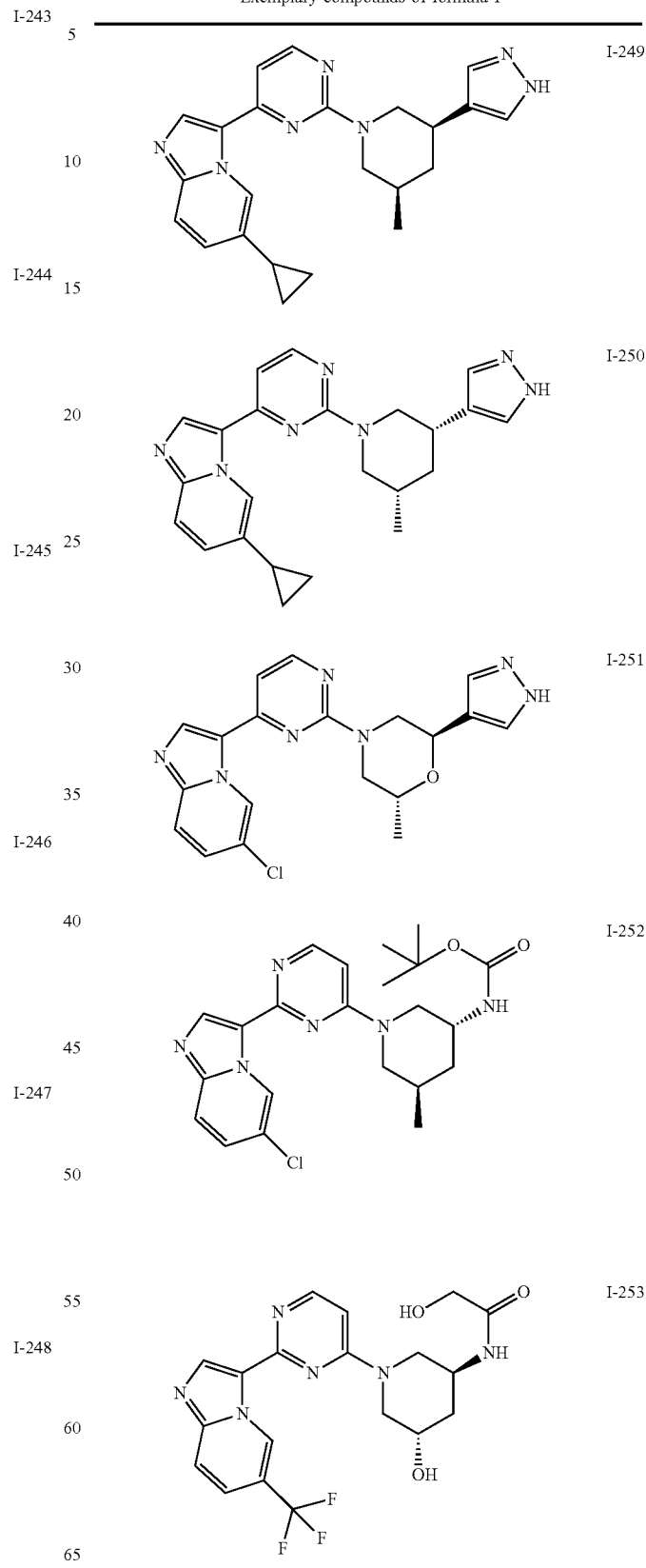

TABLE 1-continued
Exemplary compounds of formula I
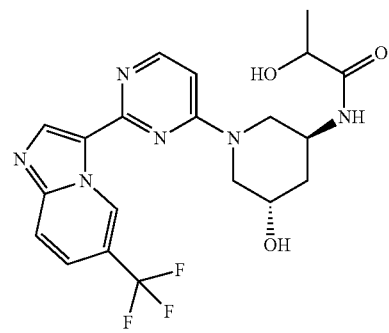 I-254
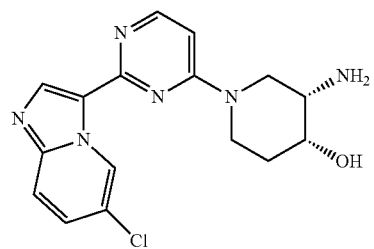 I-255
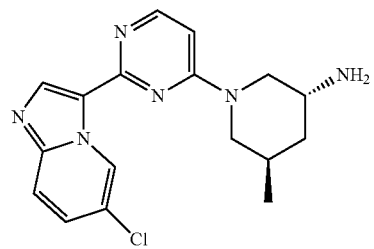 I-256
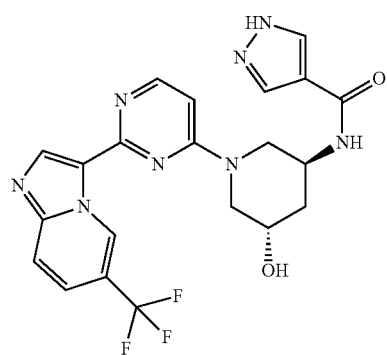 I-257
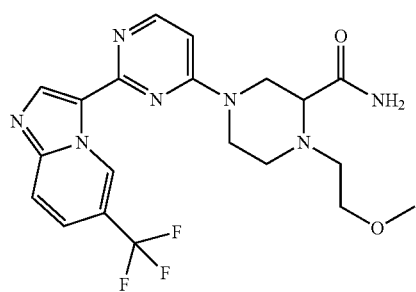 I-258
TABLE 1-continued
Exemplary compounds of formula I
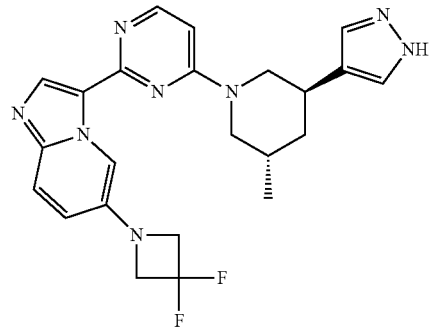 I-259
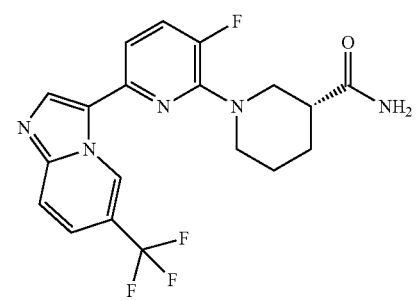 I-260
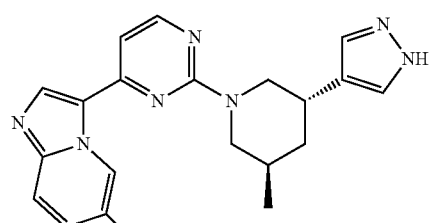 I-261
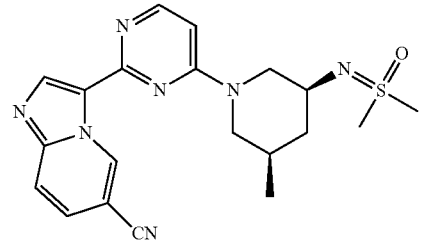 I-262
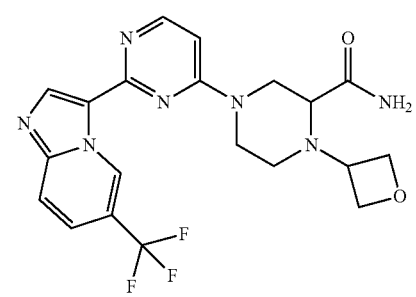 I-263

TABLE 1-continued
Exemplary compounds of formula I
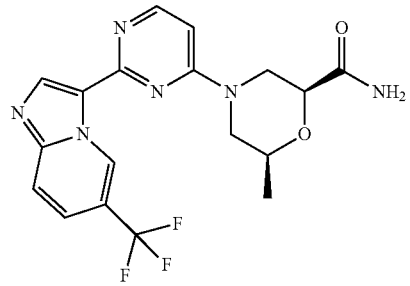 I-264
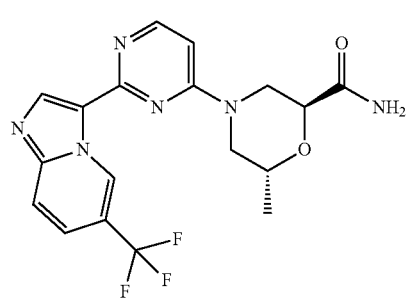 I-265
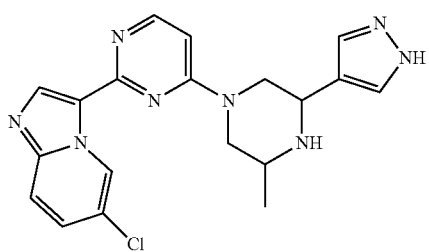 I-266
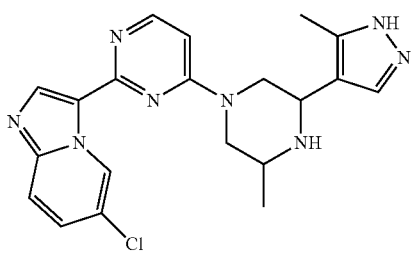 I-267
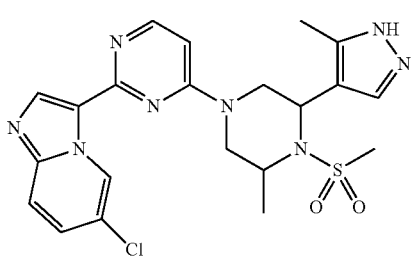 I-268
TABLE 1-continued
Exemplary compounds of formula I
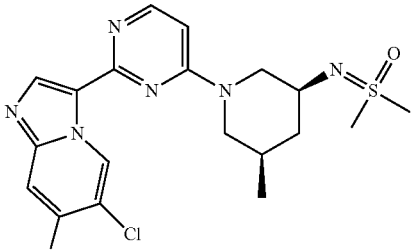 I-269
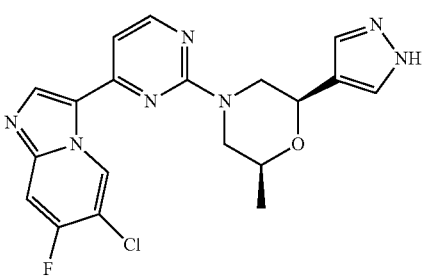 I-270
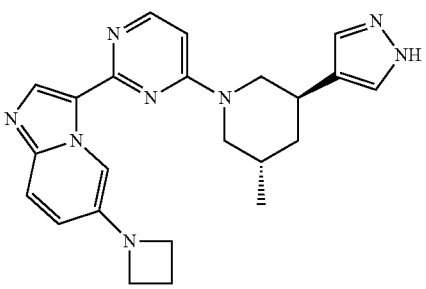 I-271
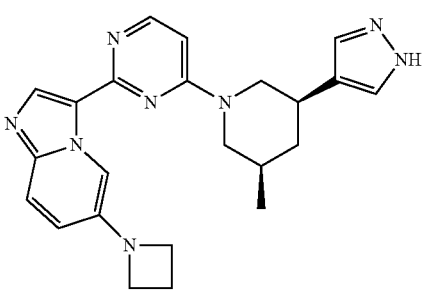 I-272
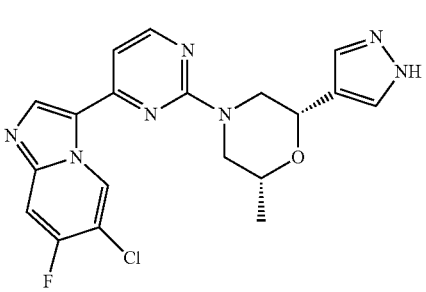 I-273

TABLE 1-continued
Exemplary compounds of formula I
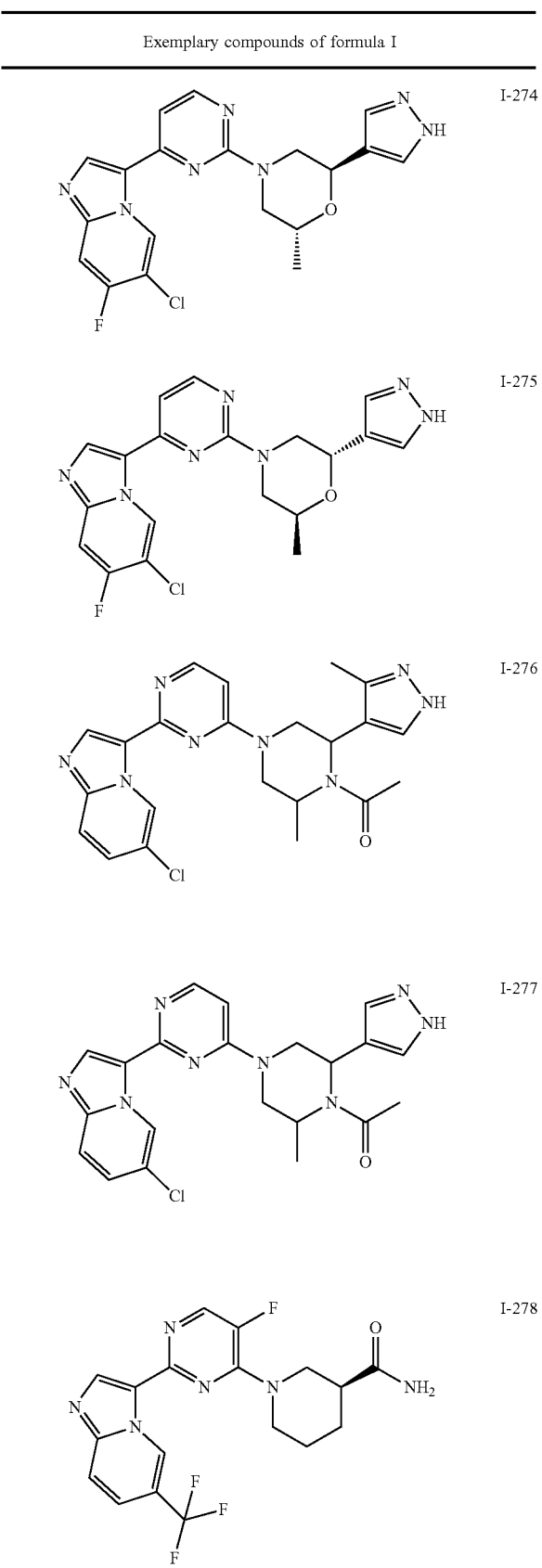
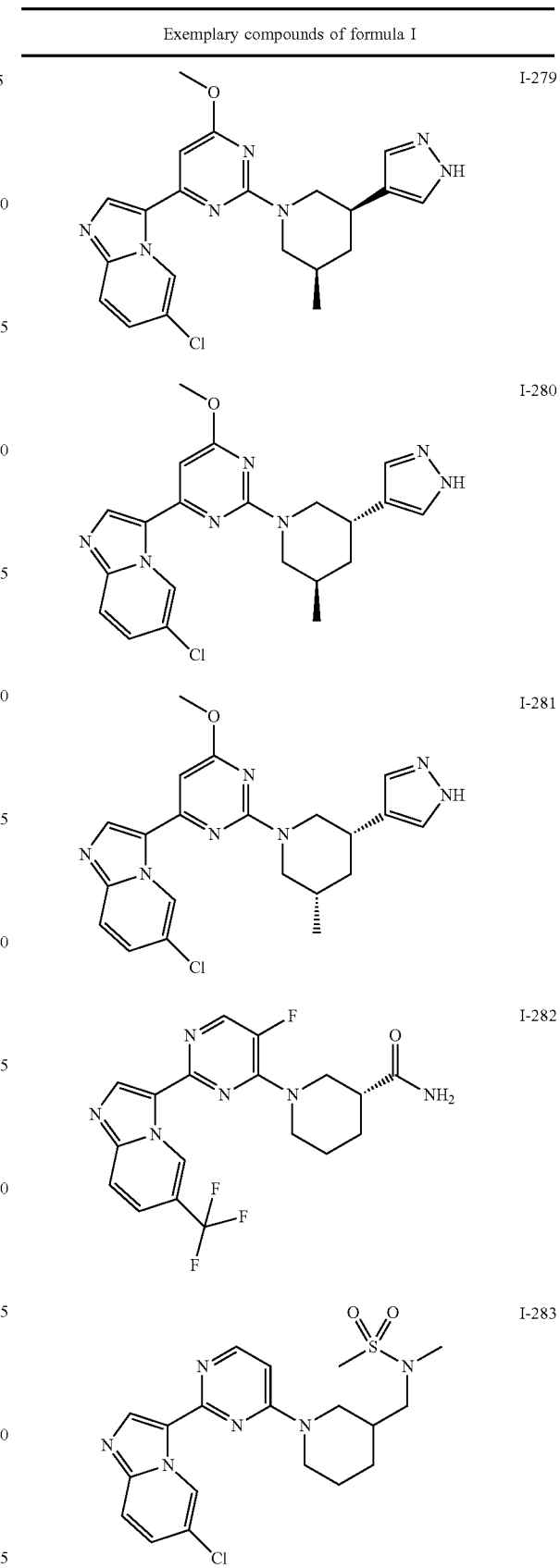

TABLE 1-continued
Exemplary compounds of formula I
| | |
|---|---|
| 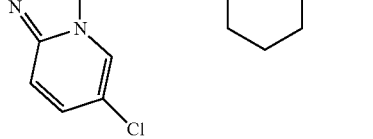 | I-284 |
| 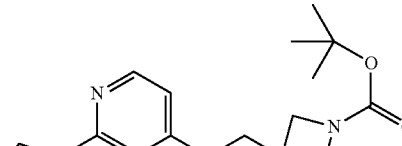 | I-285 |
| 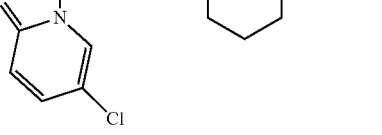 | I-286 |
| 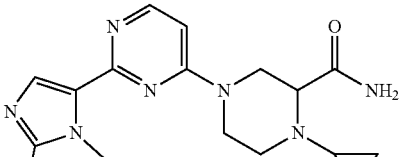 | I-287 |
| 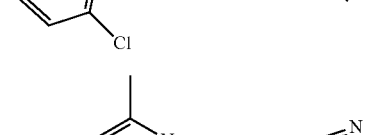 | I-288 |
TABLE 1-continued
Exemplary compounds of formula I
| | |
|---|---|
| I-289 | |
| I-290 | |
| I-291 | |
| I-292 | |
| I-293 | |

TABLE 1-continued
Exemplary compounds of formula I
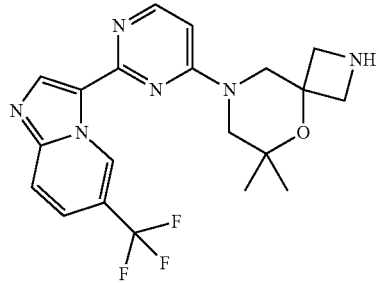 I-294
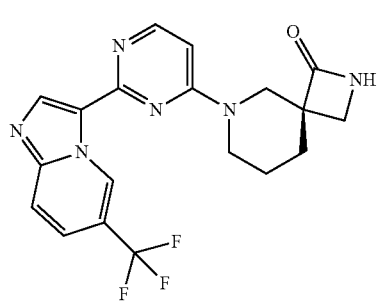 I-295
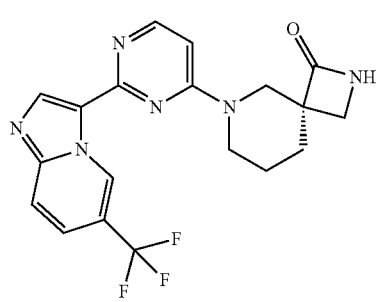 I-296
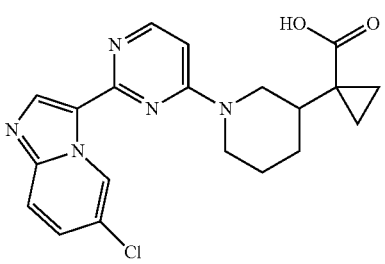 I-297
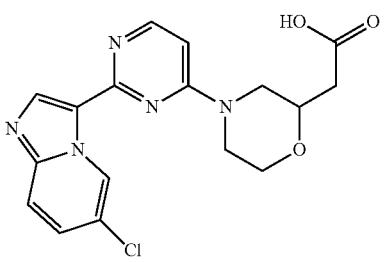 I-298
TABLE 1-continued
Exemplary compounds of formula I
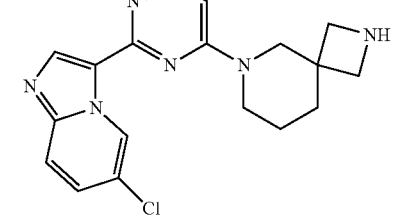 I-299
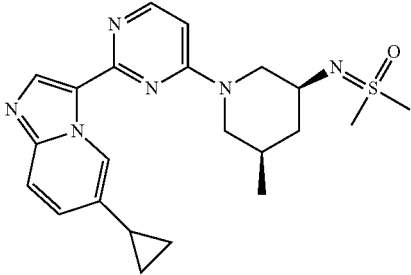 I-300
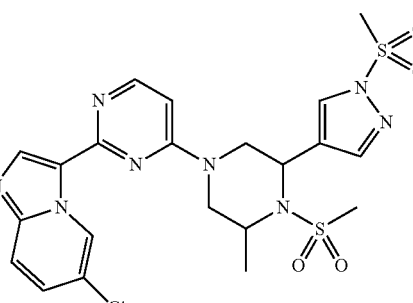 I-301
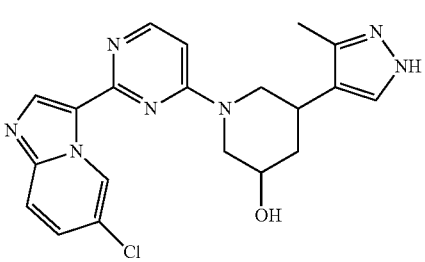 I-302
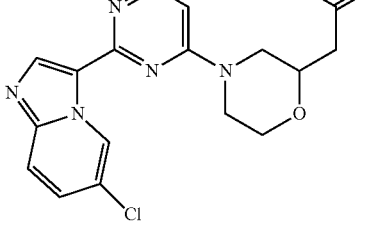 I-303

TABLE 1-continued
Exemplary compounds of formula I
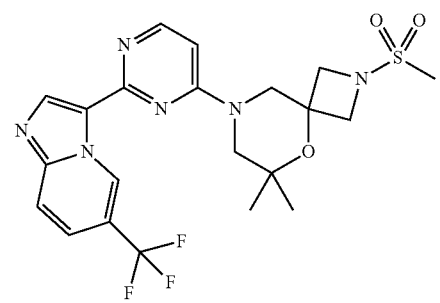
I-304
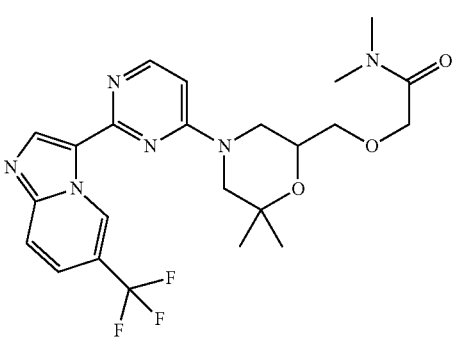
I-305
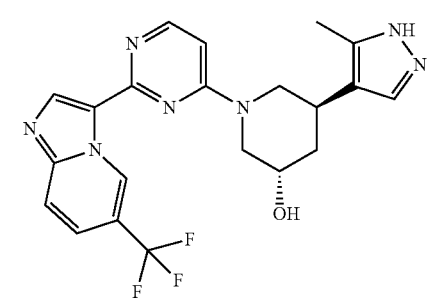
I-307
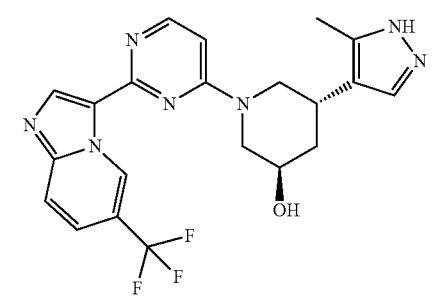
I-308
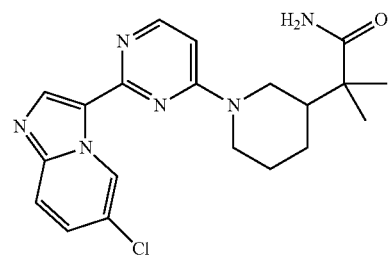
I-309
TABLE 1-continued
Exemplary compounds of formula I
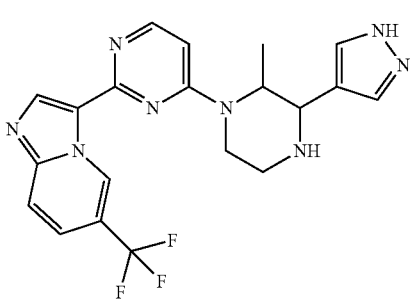
I-310
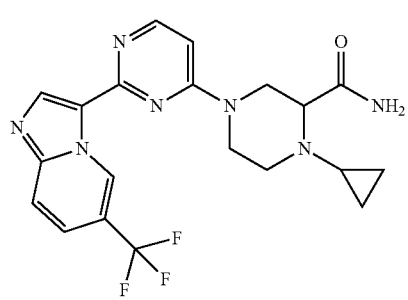
I-311
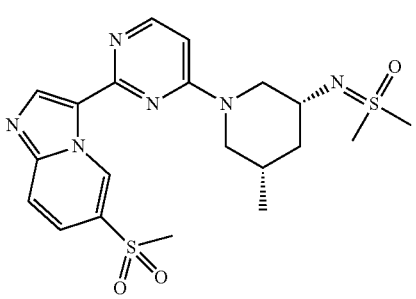
I-312
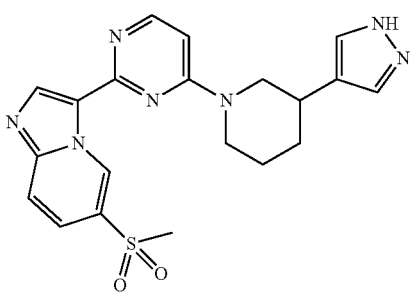
I-313
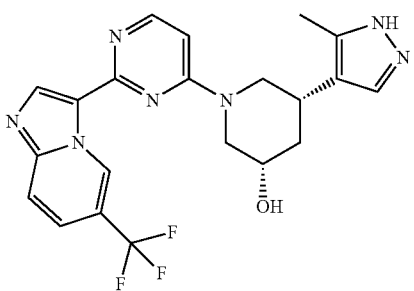
I-314

TABLE 1-continued
Exemplary compounds of formula I
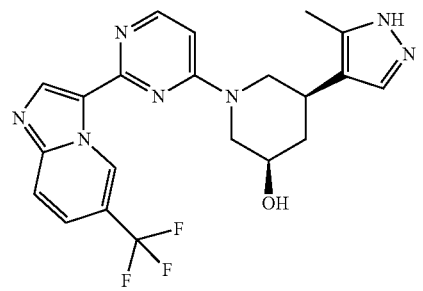 I-315
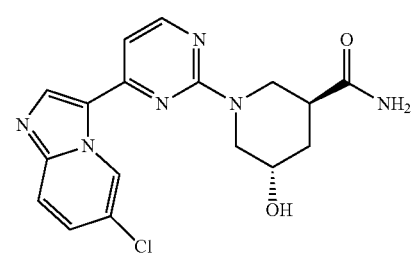 I-316
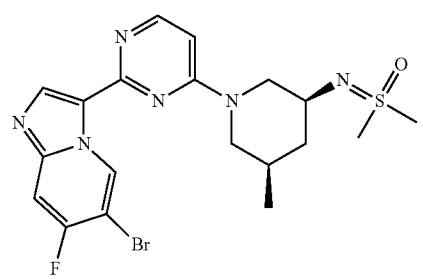 I-317
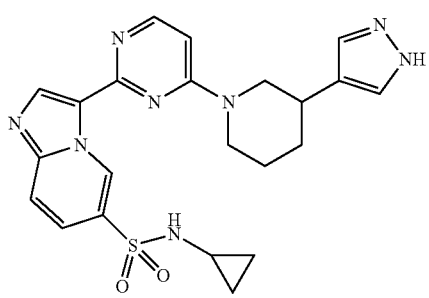 I-318
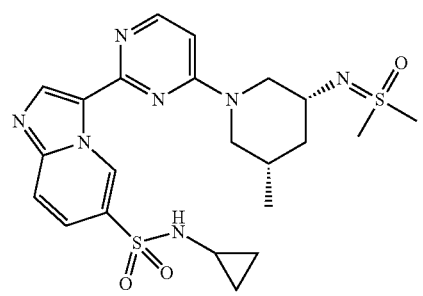 I-319
TABLE 1-continued
Exemplary compounds of formula I
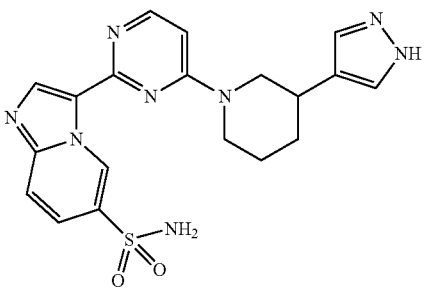 I-320
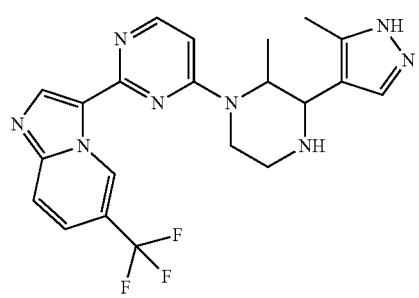 I-321
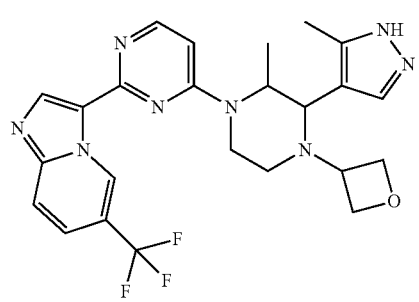 I-322
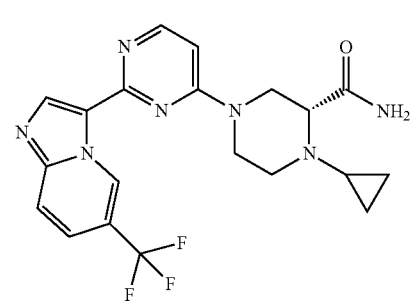 I-323
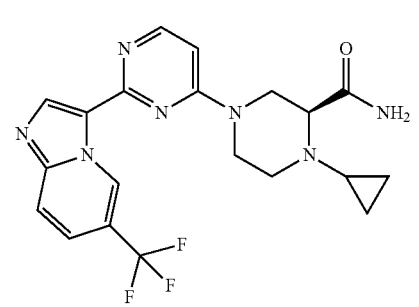 I-324

TABLE 1-continued
Exemplary compounds of formula I
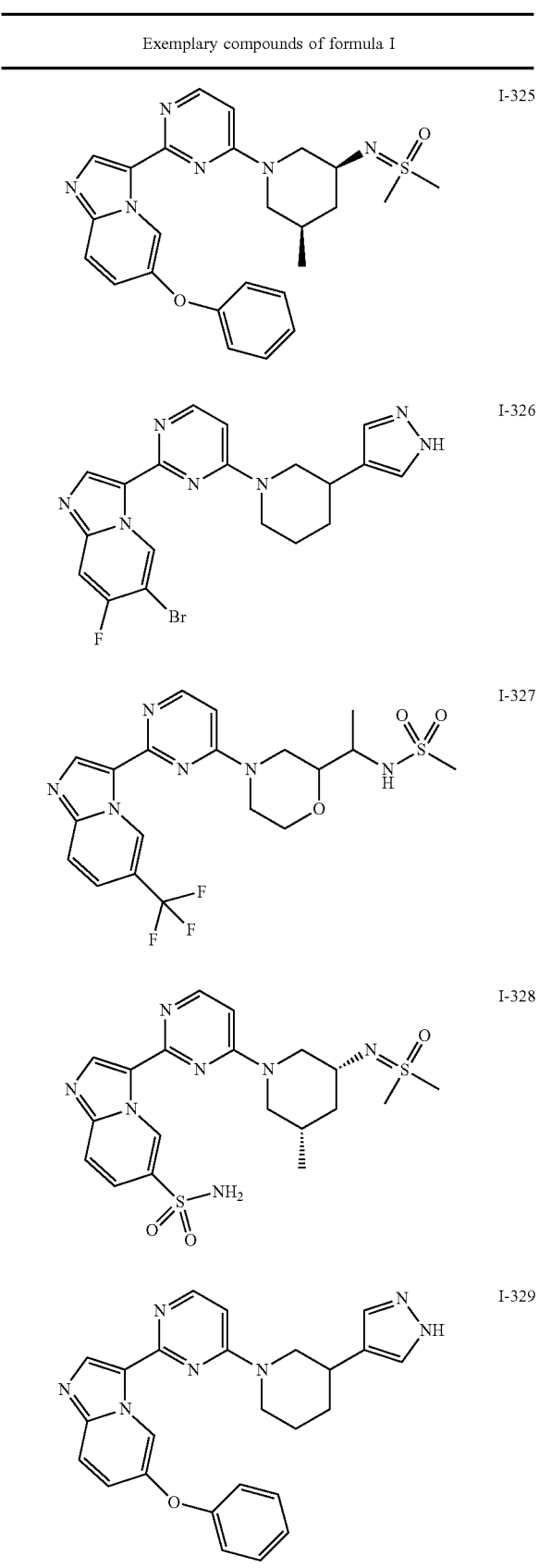
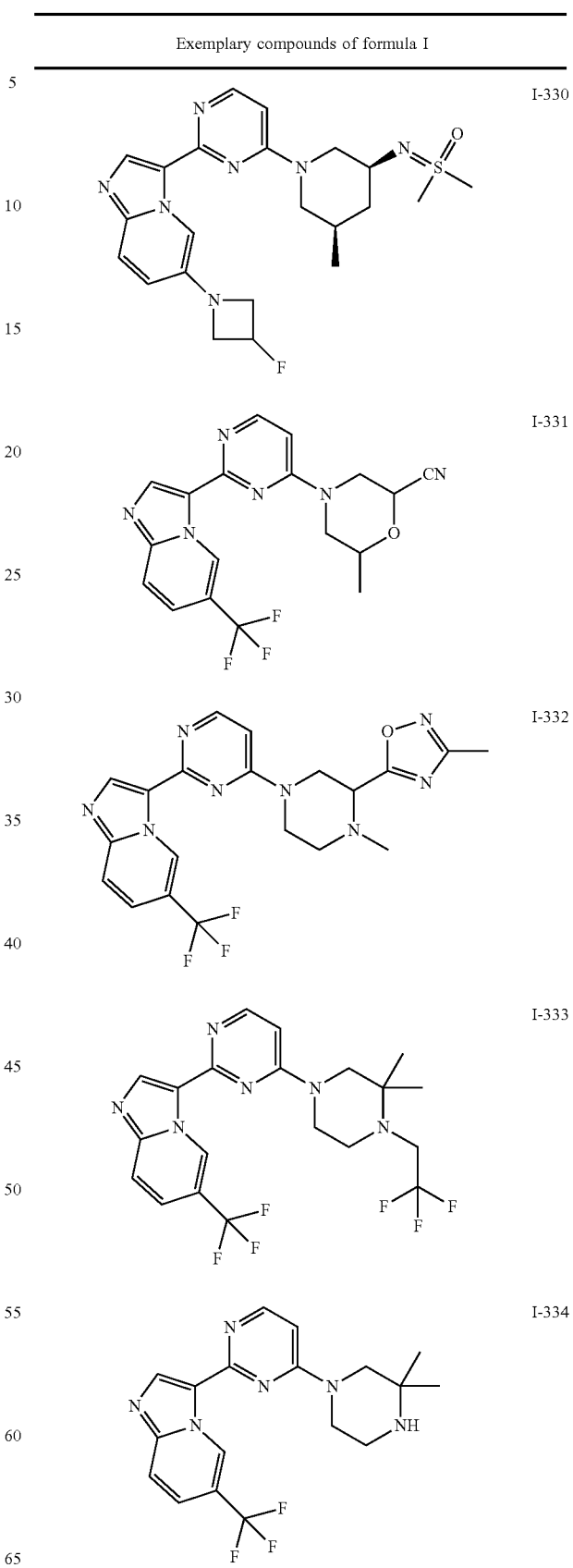

TABLE 1-continued
Exemplary compounds of formula I
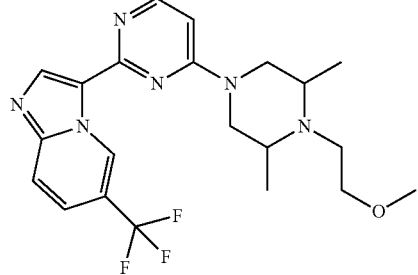 I-335
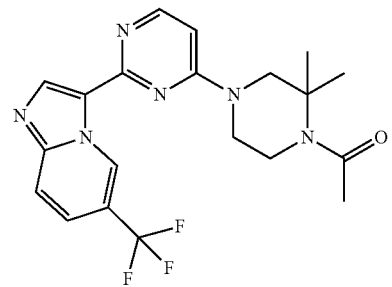 I-336
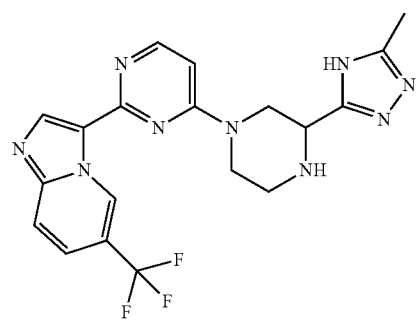 I-337
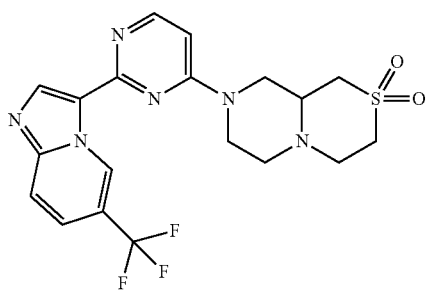 I-338
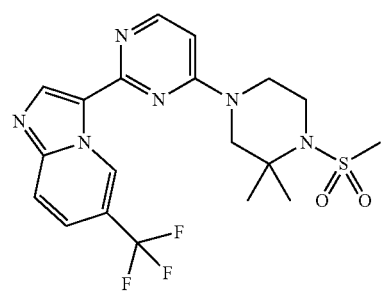 I-339
TABLE 1-continued
Exemplary compounds of formula I
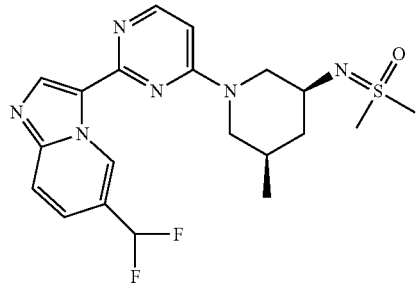 I-340
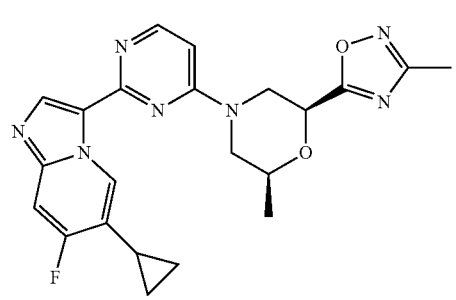 I-341
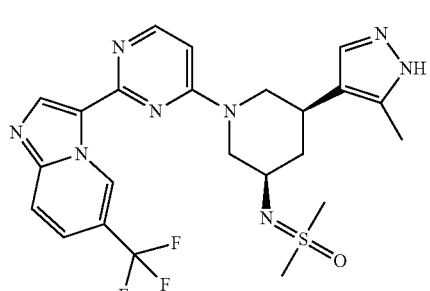 I-342
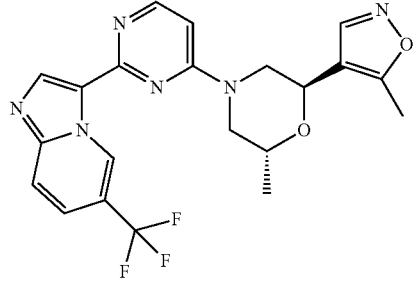 I-343
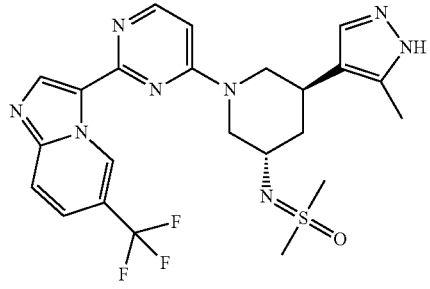 I-344

US 10,793,563 B2
TABLE 1-continued
Exemplary compounds of formula I
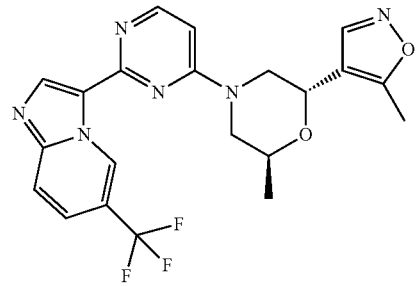 I-345
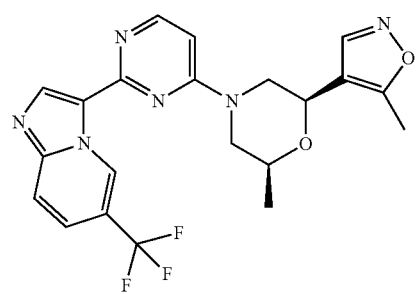 I-346
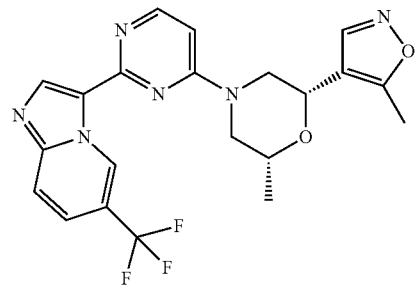 I-347
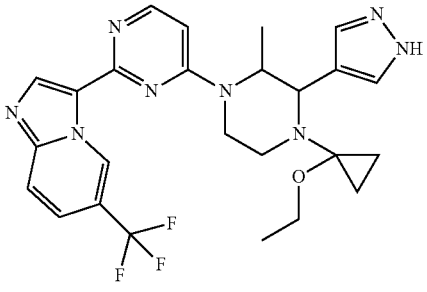 I-348
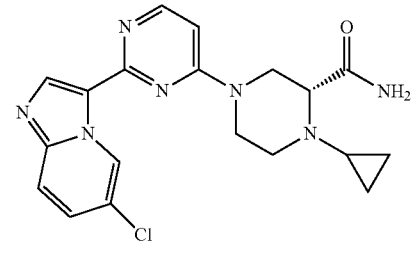 I-349
TABLE 1-continued
Exemplary compounds of formula I
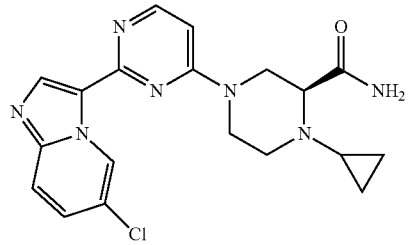 I-350
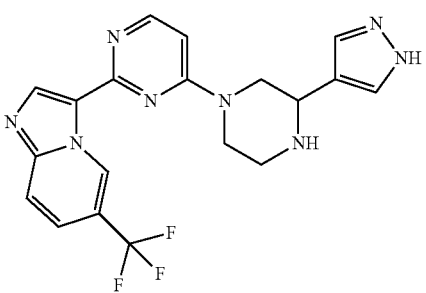 I-351
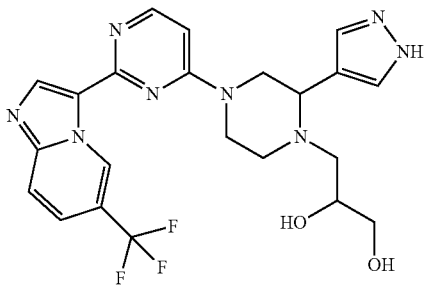 I-352
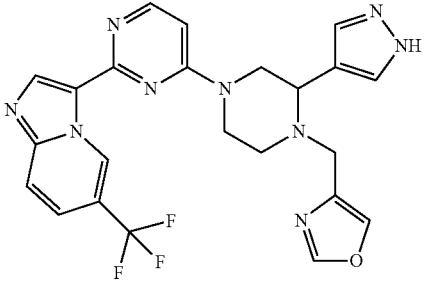 I-353
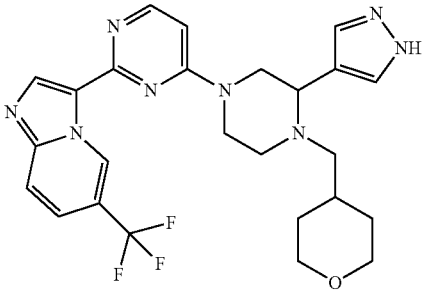 I-354

TABLE 1-continued
Exemplary compounds of formula I
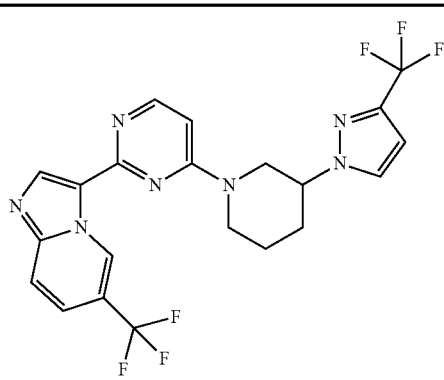 I-355
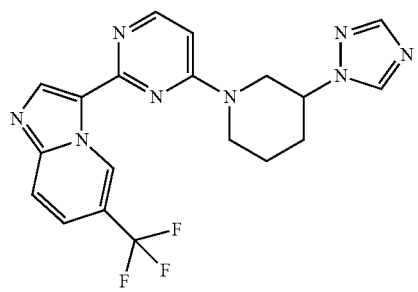 I-356
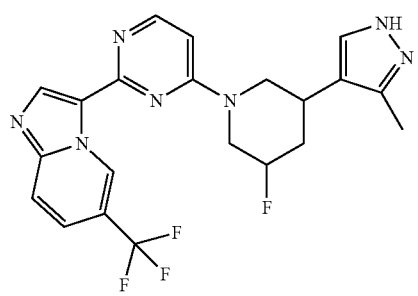 I-357
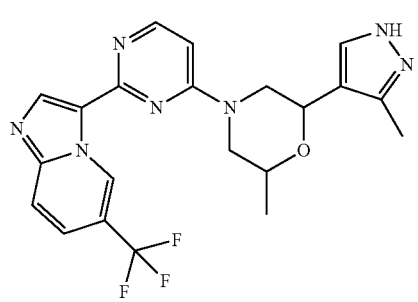 I-358
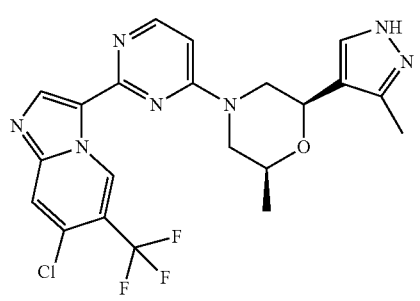 I-359
TABLE 1-continued
Exemplary compounds of formula I
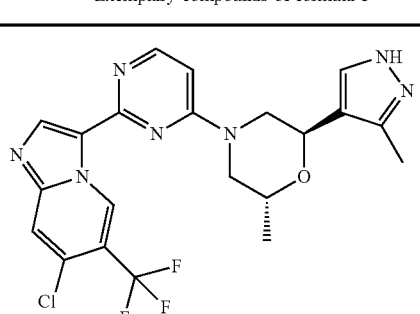 I-360
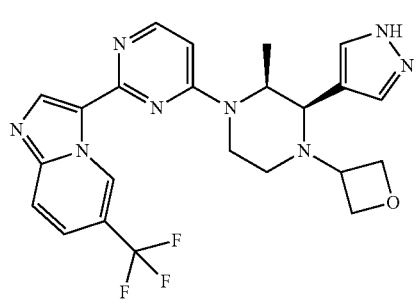 I-361
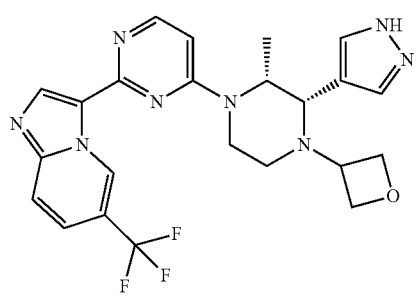 I-362
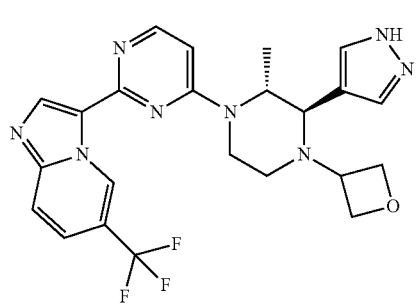 I-363
I-364

TABLE 1-continued
Exemplary compounds of formula I
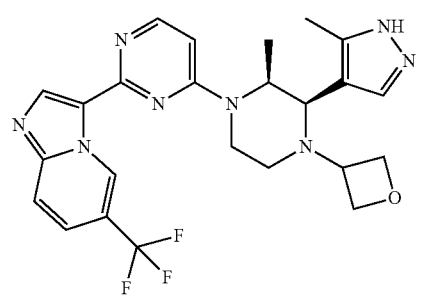 I-365
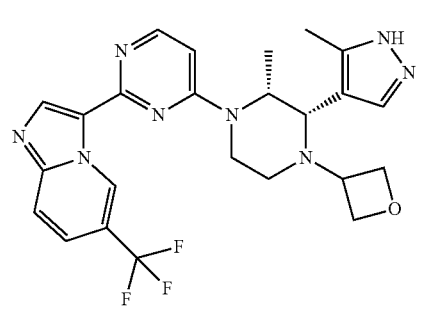 I-366
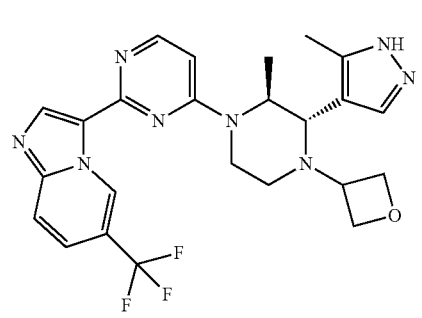 I-367
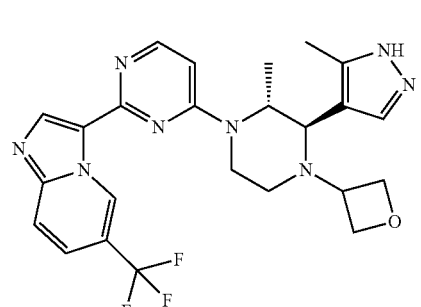 I-368
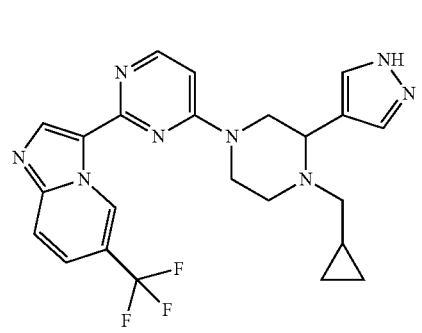 I-369
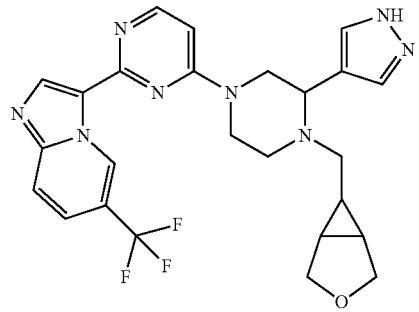 I-370
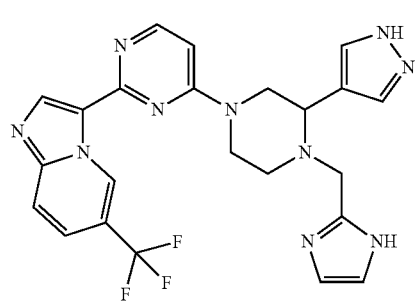 I-371
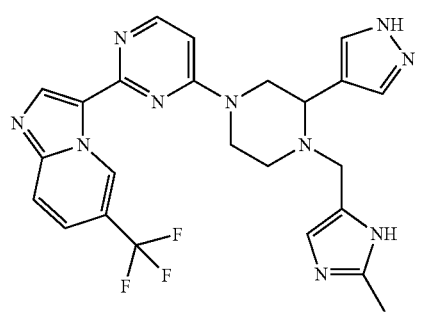 I-372
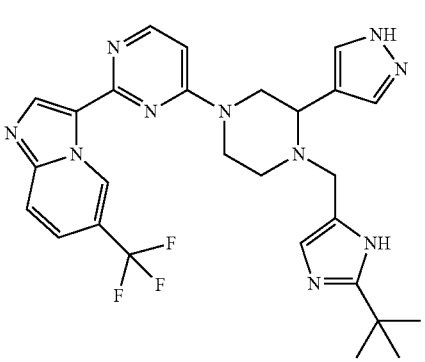 I-373
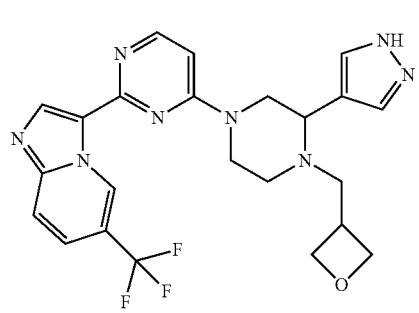 I-374

TABLE 1-continued
Exemplary compounds of formula I
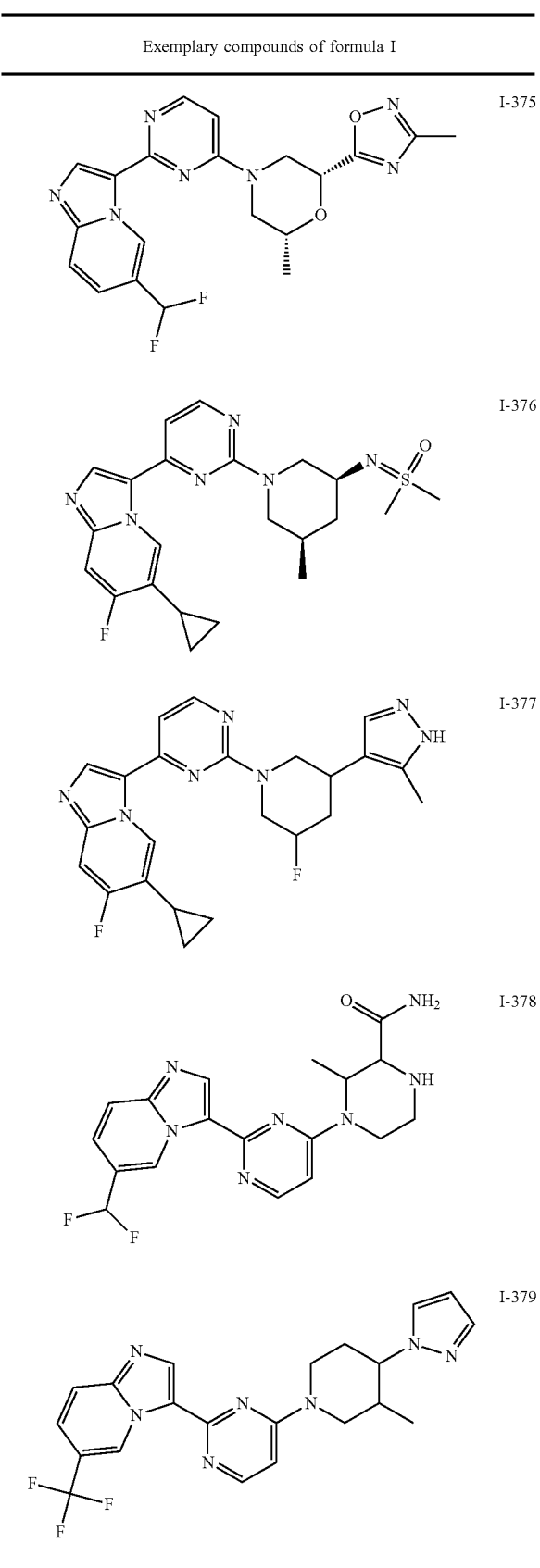
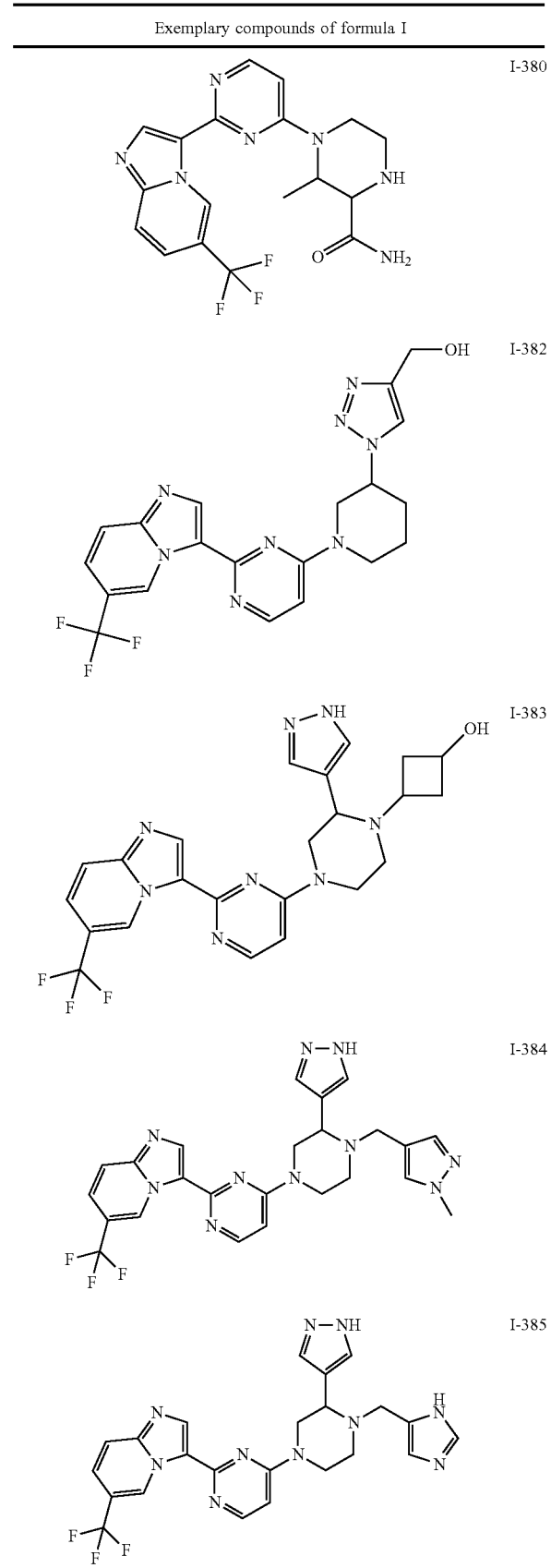

TABLE 1-continued

Exemplary compounds of formula I

| Compound | 
|---|
| I-386 |
| I-387 |
| I-388 |
| I-389 |
| I-390 |
| I-391 |
| I-392 |
| I-393 |
| I-394 |

TABLE 1-continued

Exemplary compounds of formula I

| I-395 | I-400 |
| I-396 | I-401 |
| I-397 | I-402 |
| I-398 | I-403 |
| I-399 | I-404 |

171
TABLE 1-continued
Exemplary compounds of formula I
I-405
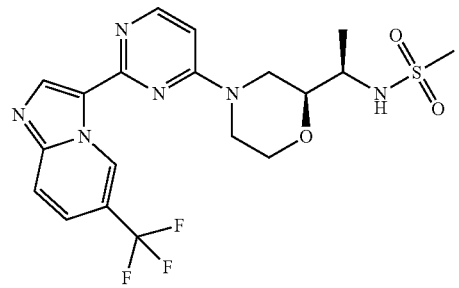
I-406
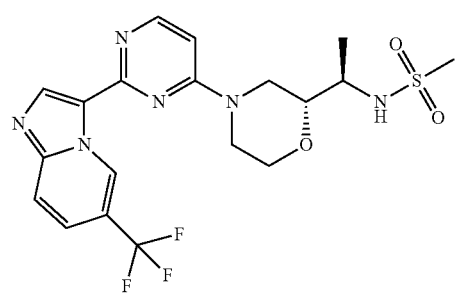
I-407
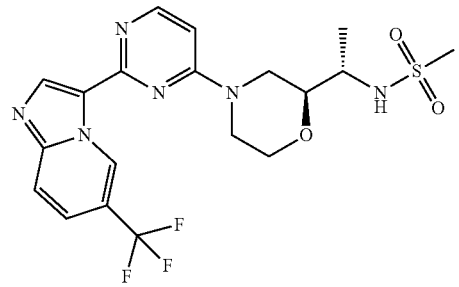
I-408
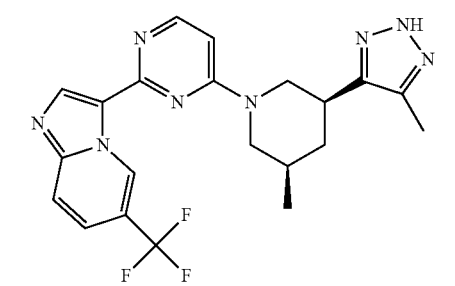
I-409
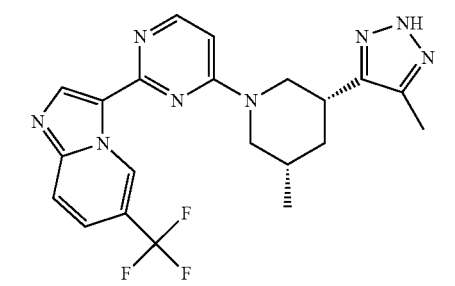
172
TABLE 1-continued
Exemplary compounds of formula I
I-410
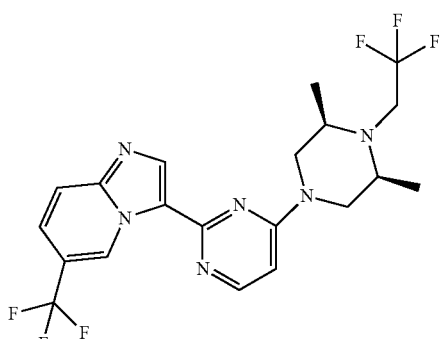
I-411
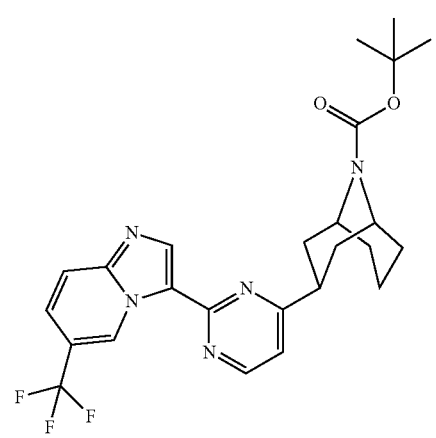
I-412
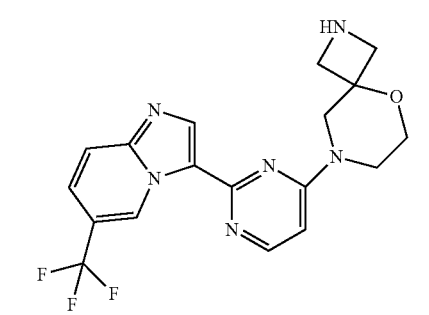
I-413
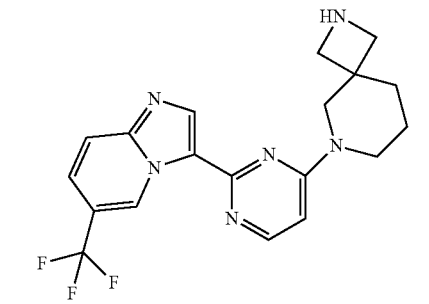

TABLE 1-continued
Exemplary compounds of formula I
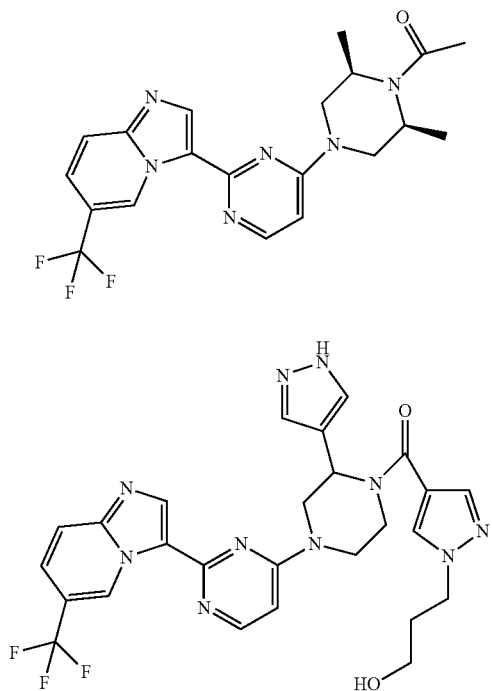
I-414
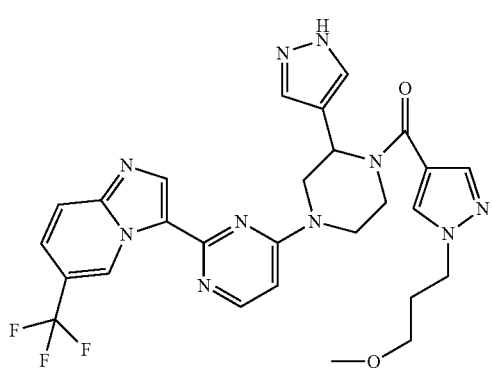
I-415
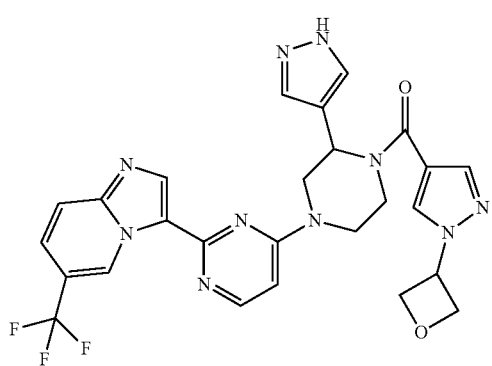
I-416
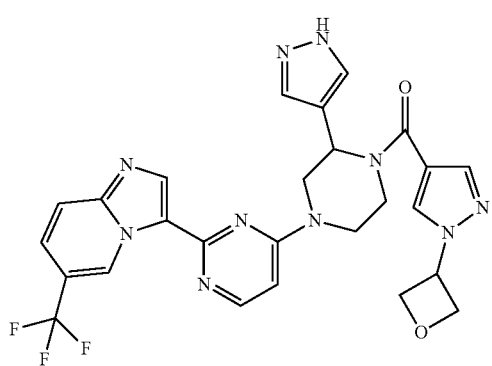
I-417
TABLE 1-continued
Exemplary compounds of formula I
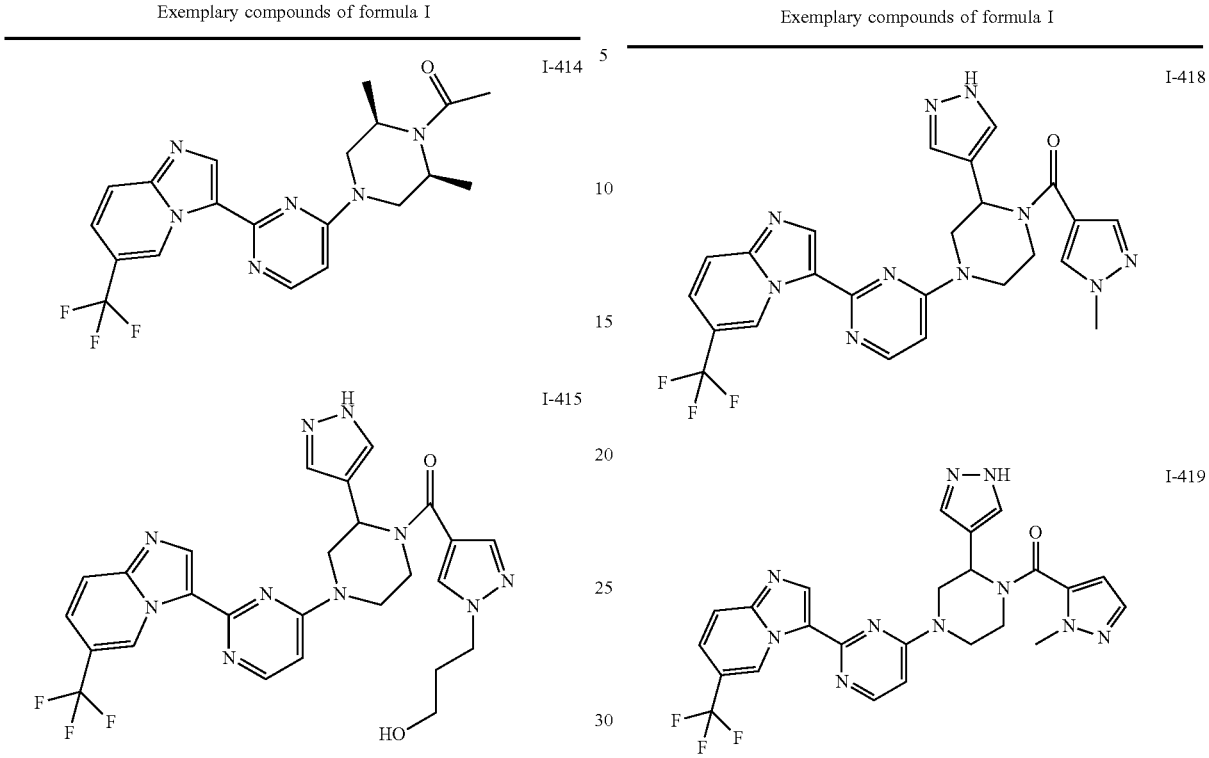
I-418
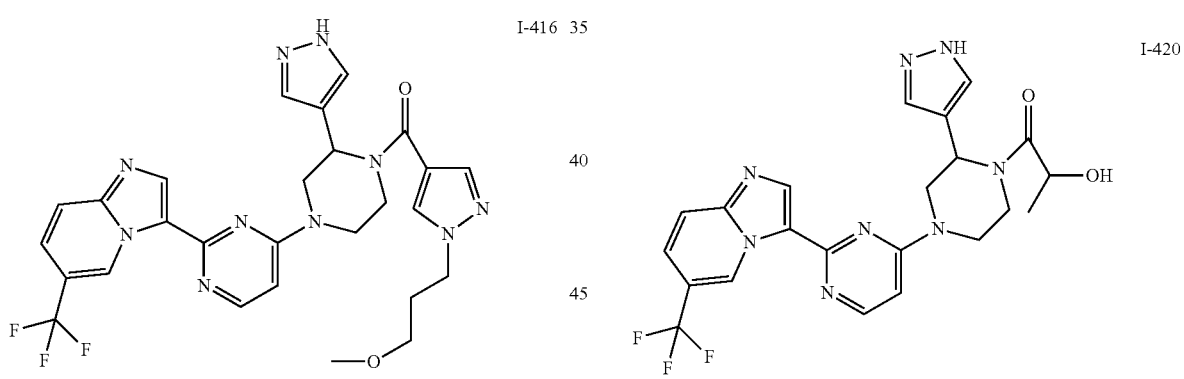
I-419
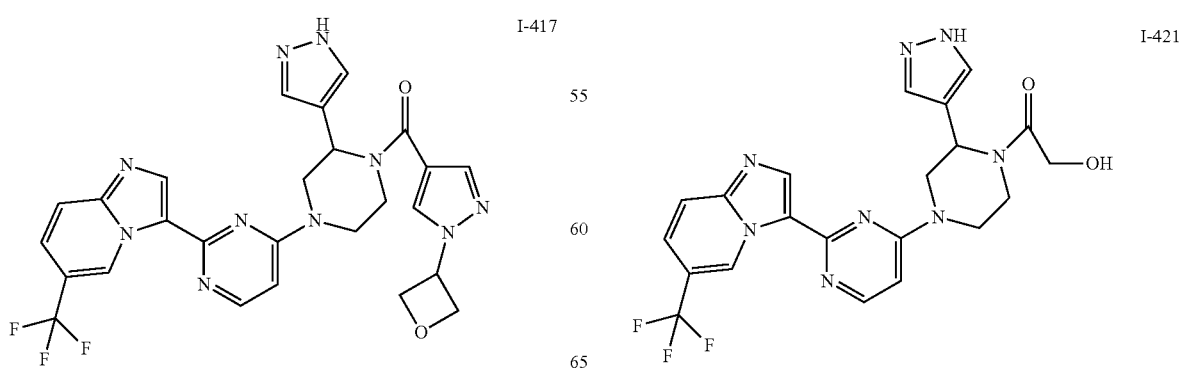
I-420
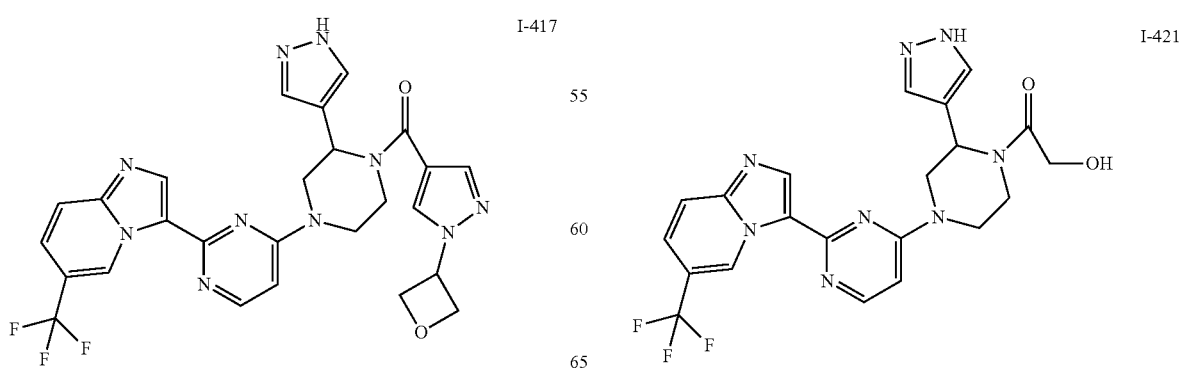
I-421

TABLE 1-continued
Exemplary compounds of formula I
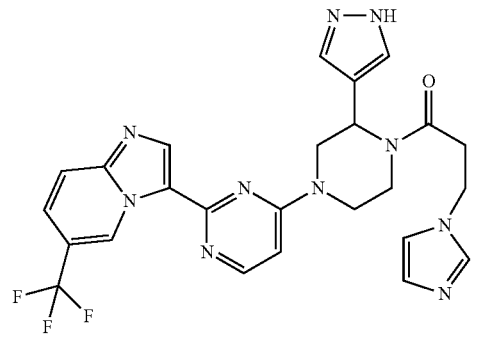
I-422
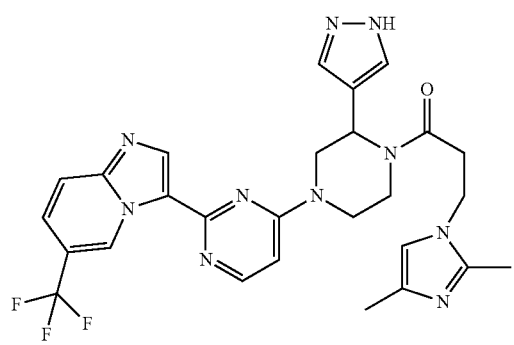
I-423
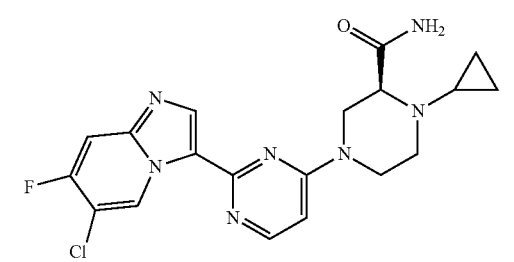
I-424
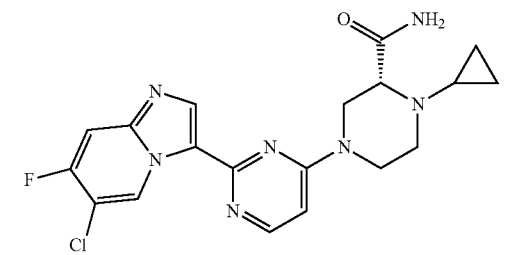
I-425
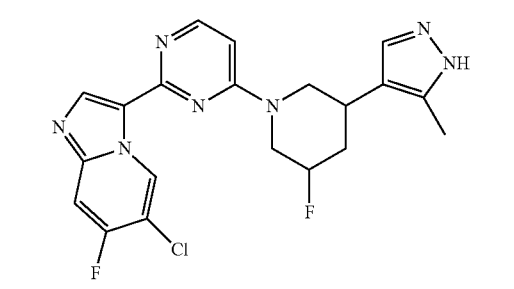
I-426
TABLE 1-continued
Exemplary compounds of formula I
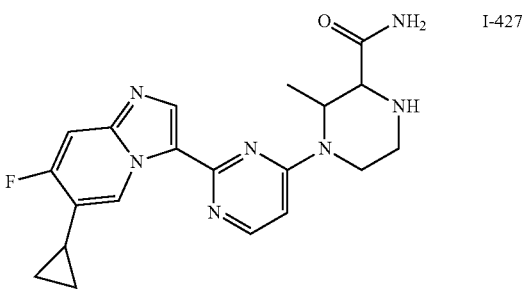
I-427
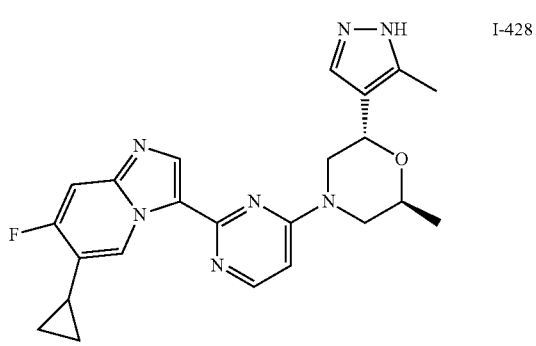
I-428
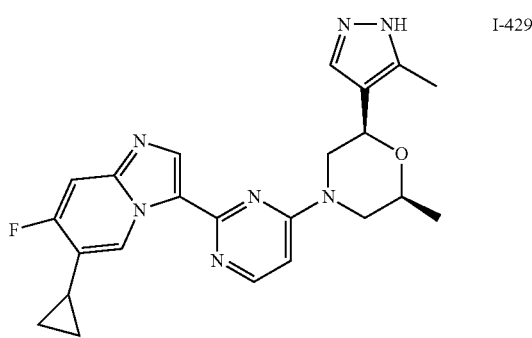
I-429
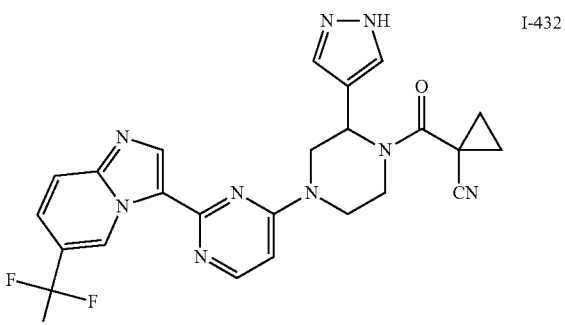
I-432

TABLE 1-continued
Exemplary compounds of formula I
I-433
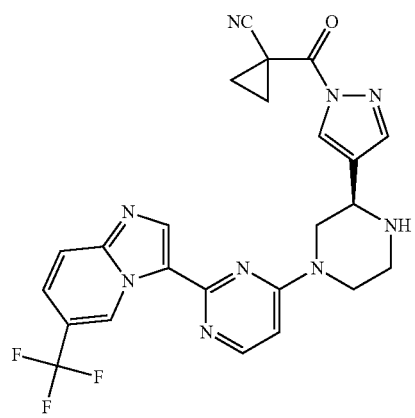
I-434
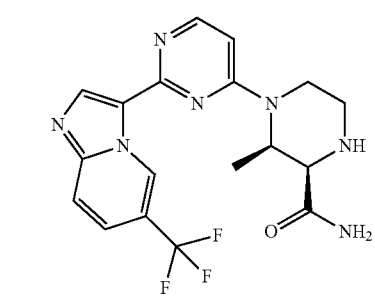
I-435
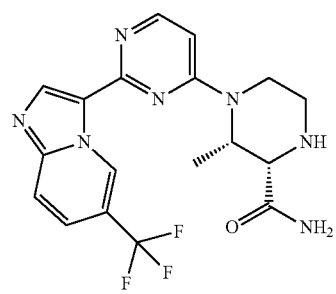
I-436
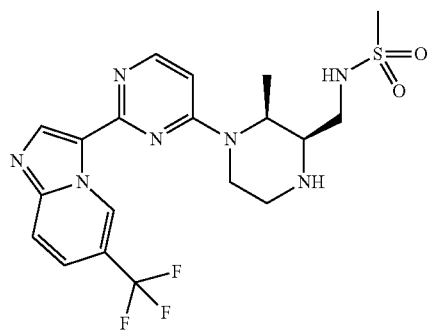
TABLE 1-continued
Exemplary compounds of formula I
I-437
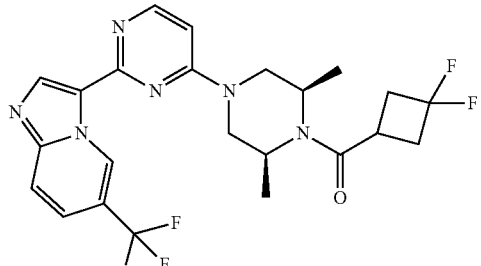
I-438
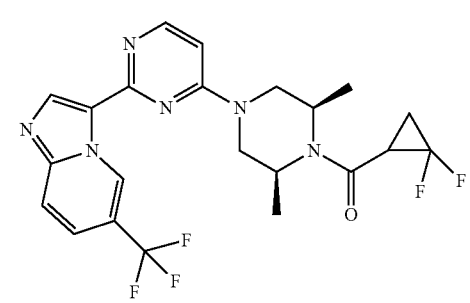
I-439
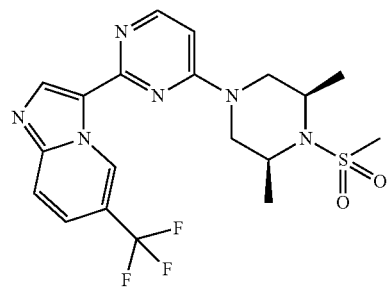
I-440
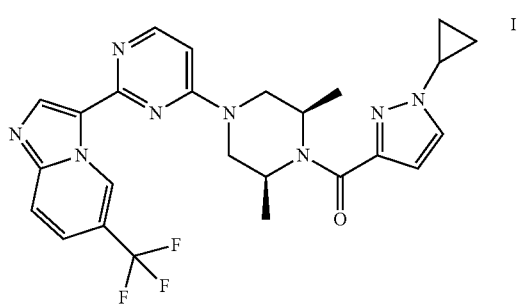
I-441
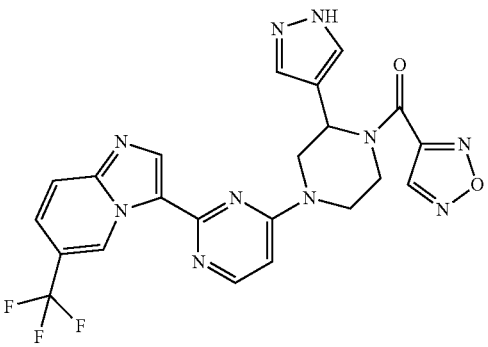

TABLE 1-continued
Exemplary compounds of formula I
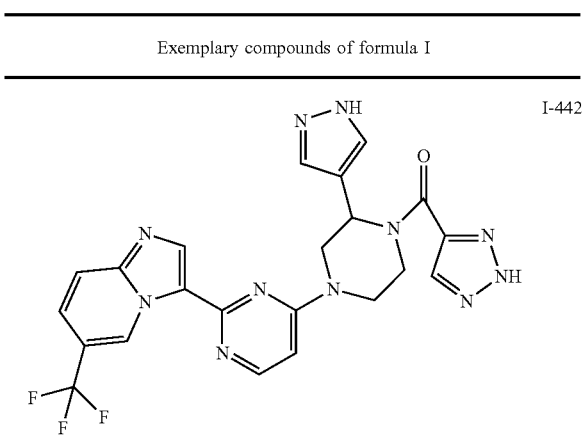
I-442
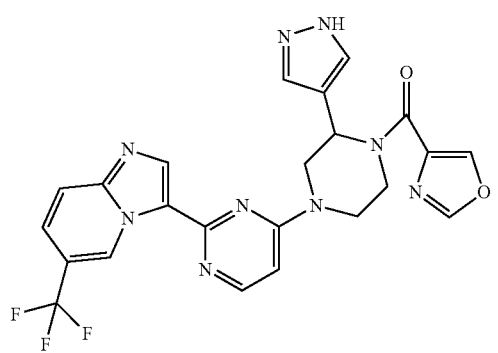
I-443
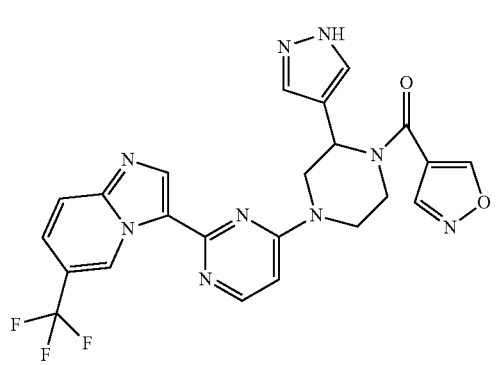
I-444
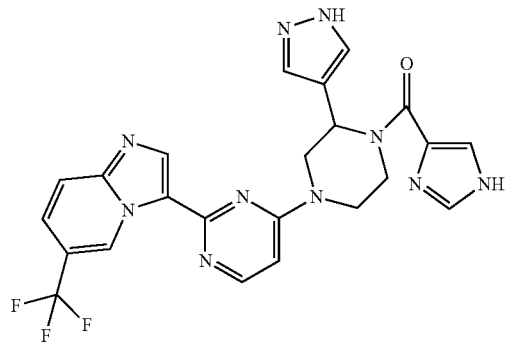
I-445
TABLE 1-continued
Exemplary compounds of formula I
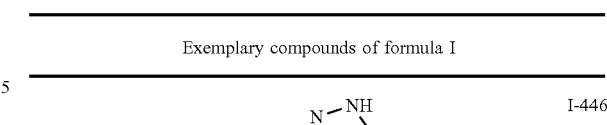
I-446
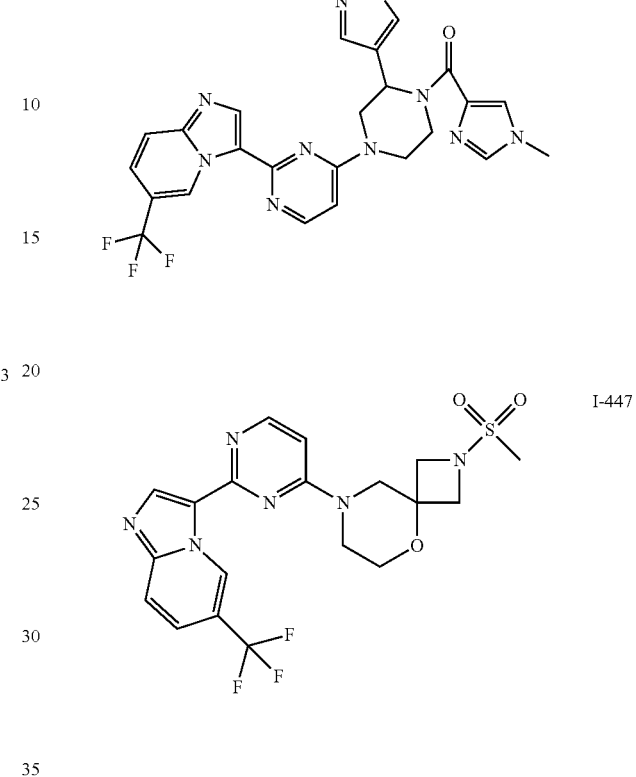
I-447
I-448
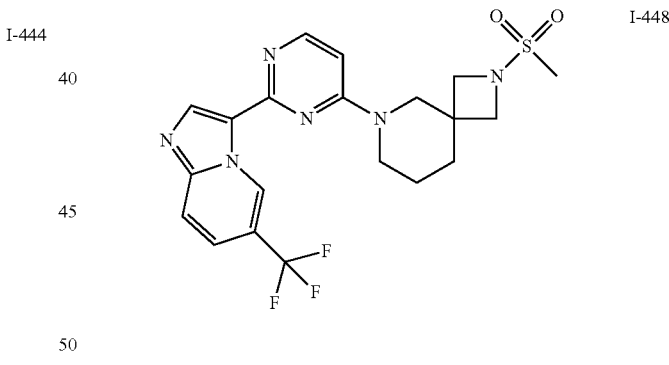
I-449
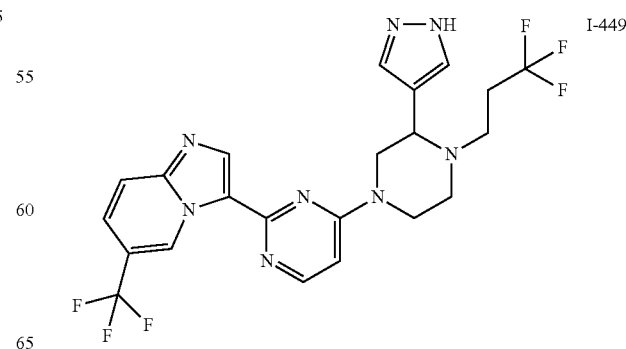

TABLE 1-continued
Exemplary compounds of formula I
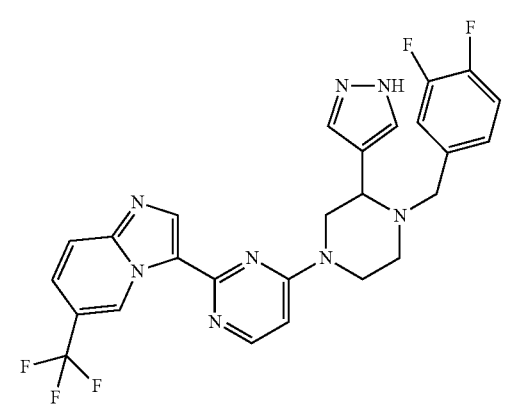 I-450
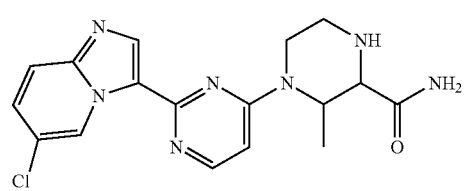 I-451
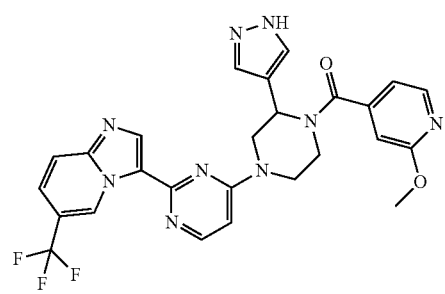 I-452
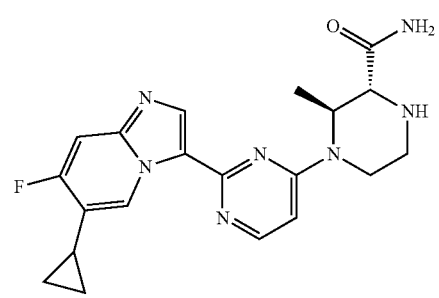 I-454
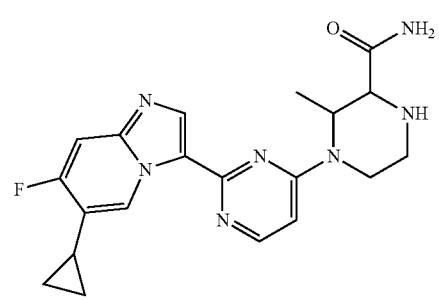 I-455
TABLE 1-continued
Exemplary compounds of formula I
I-456
I-457
I-458
I-459

TABLE 1-continued
Exemplary compounds of formula I
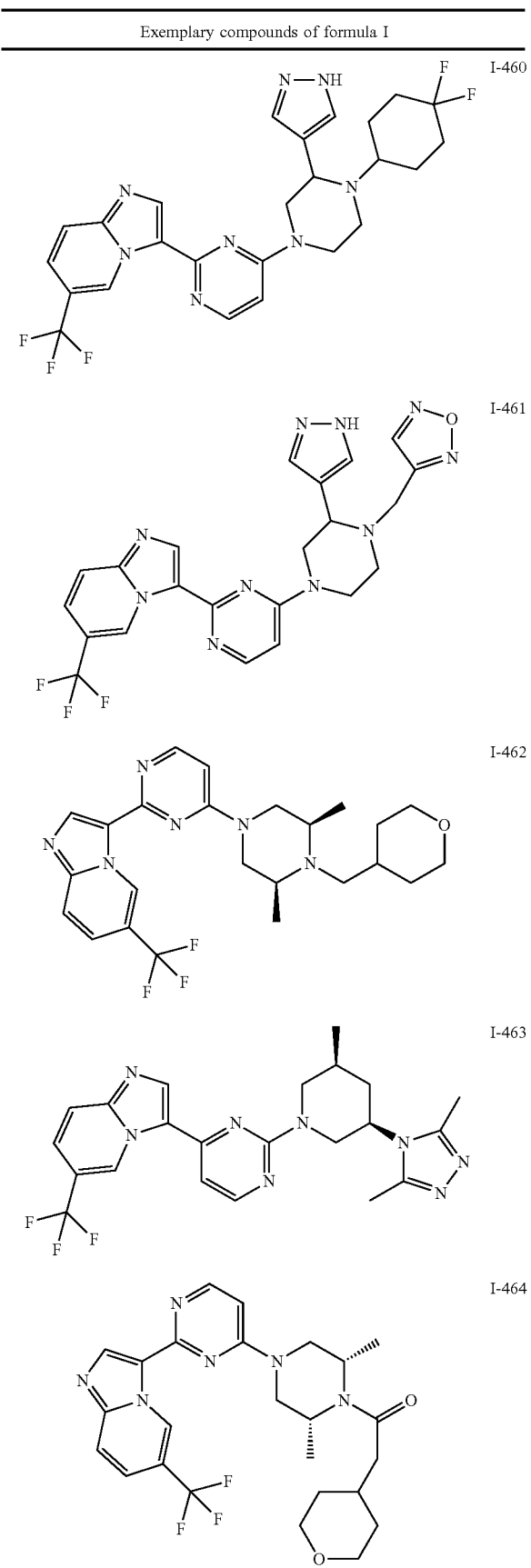
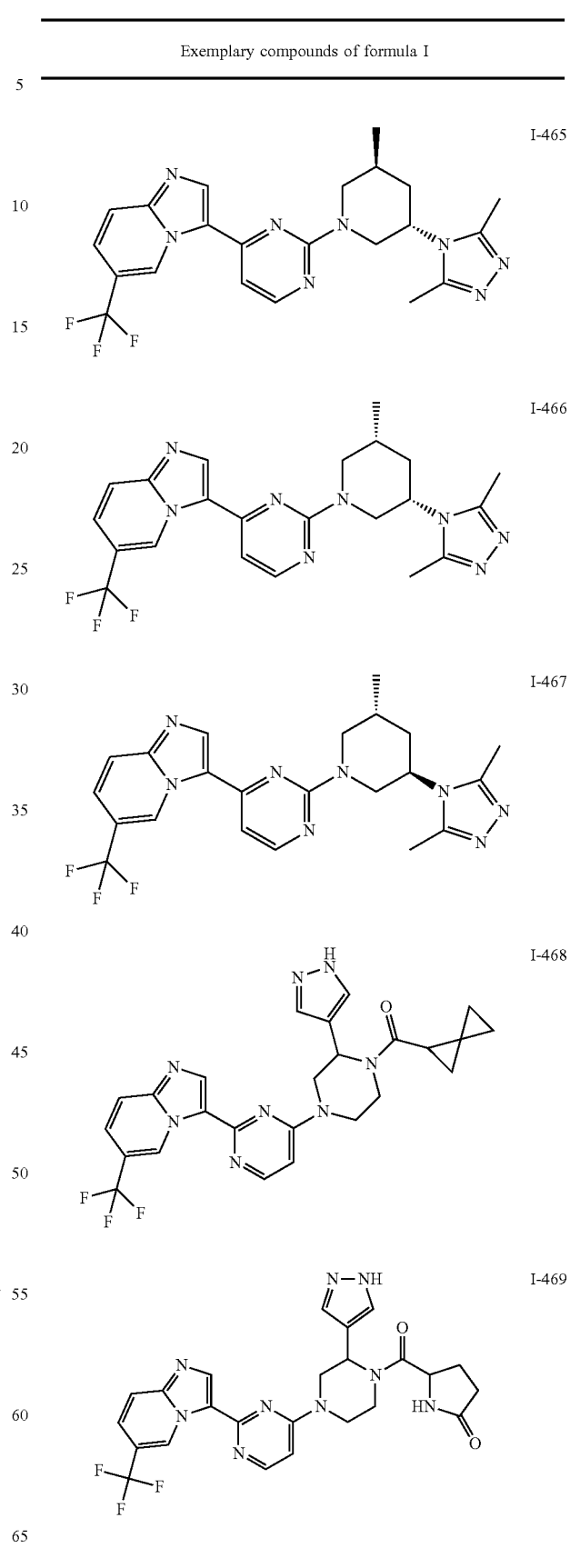

TABLE 1-continued
Exemplary compounds of formula I
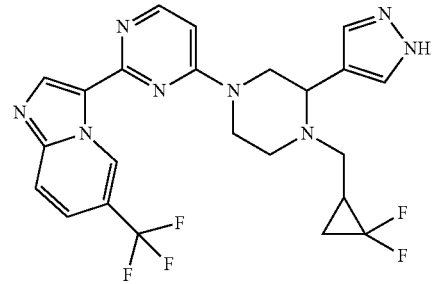 I-470
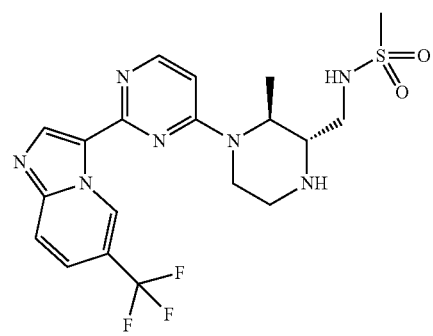 I-471
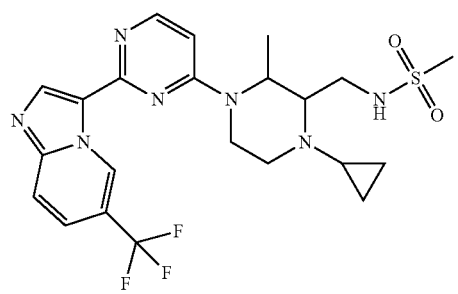 I-472
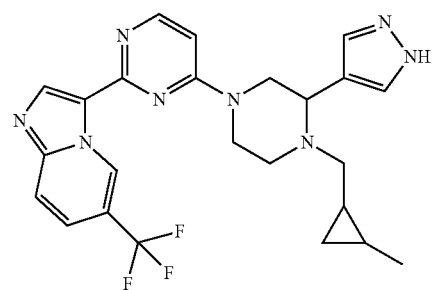 I-473
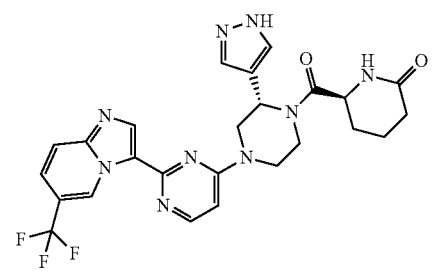 I-474
TABLE 1-continued
Exemplary compounds of formula I
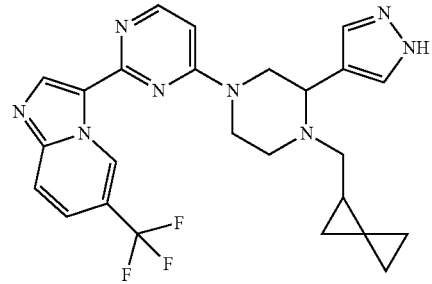 I-475
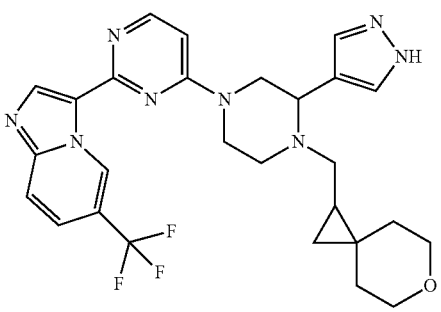 I-476
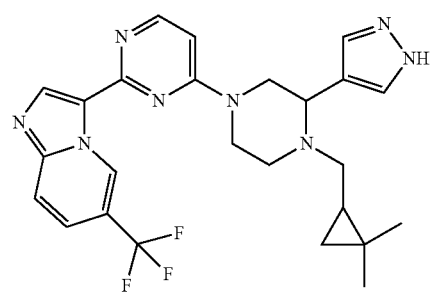 I-477
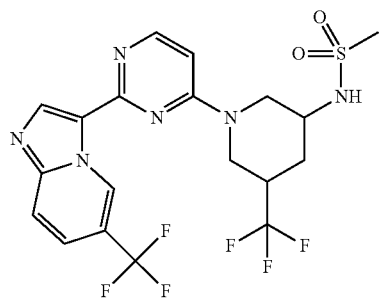 I-478
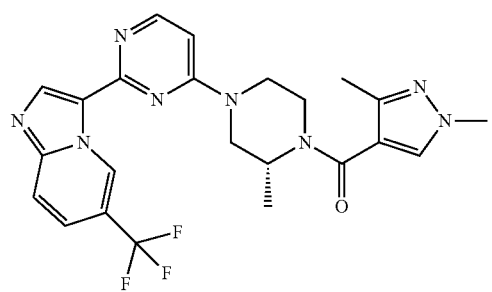 I-479

TABLE 1-continued
Exemplary compounds of formula I
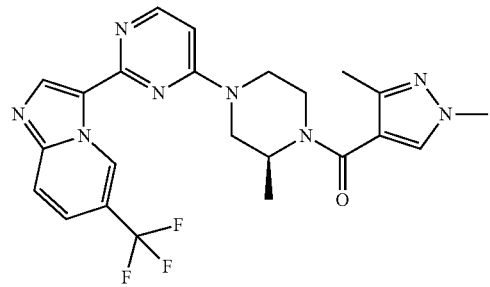 I-480
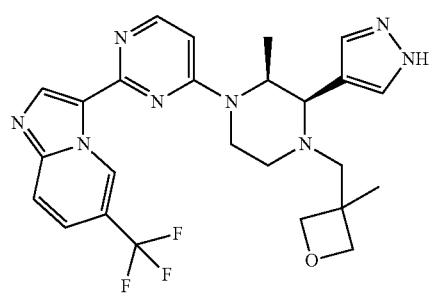 I-481
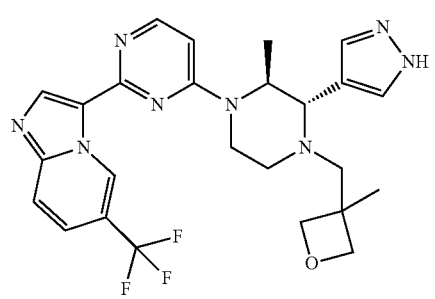 I-482
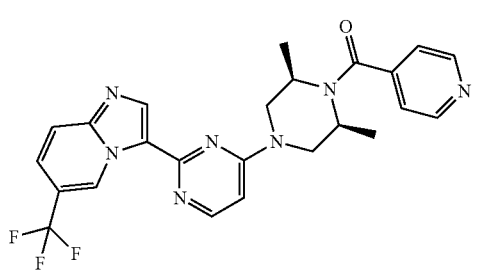 I-483
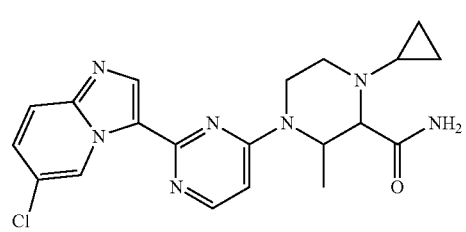 I-484
TABLE 1-continued
Exemplary compounds of formula I
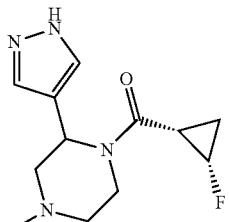 I-485
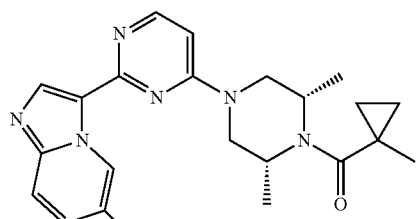 I-486
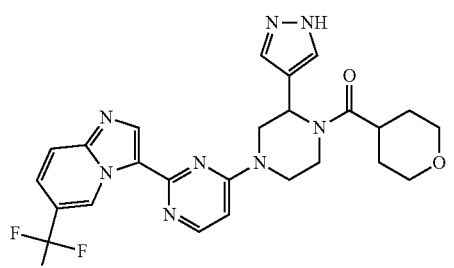 I-487
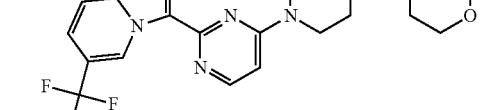 I-488

TABLE 1-continued

Exemplary compounds of formula I

I-489, I-490, I-491, I-492, I-493, I-494, I-495, I-496, I-497

TABLE 1-continued

Exemplary compounds of formula I

| Compound | Structure |
|---|---|
| I-498 | (structure) |
| I-499 | (structure) |
| I-500 | (structure) |
| I-501 | (structure) |
| I-502 | (structure) |
| I-503 | (structure) |
| I-504 | (structure) |
| I-505 | (structure) |
| I-506 | (structure) |
| I-507 | (structure) |

TABLE 1-continued
Exemplary compounds of formula I
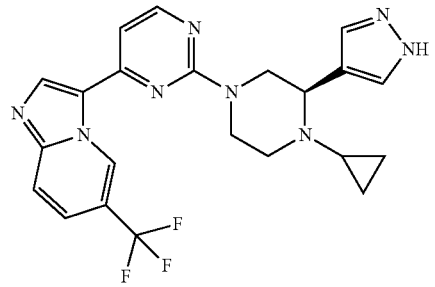 I-508
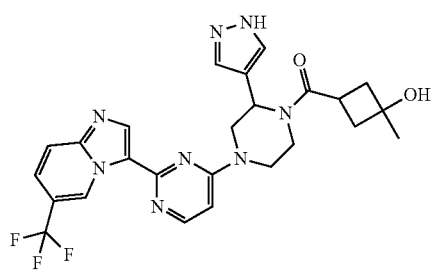 I-509
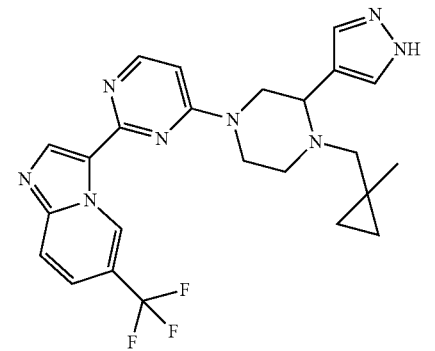 I-510
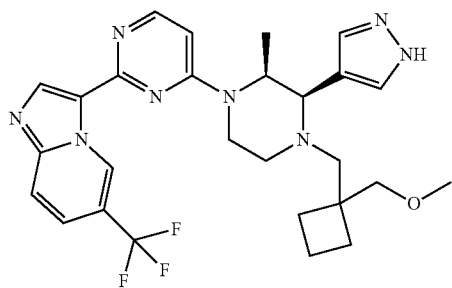 I-511
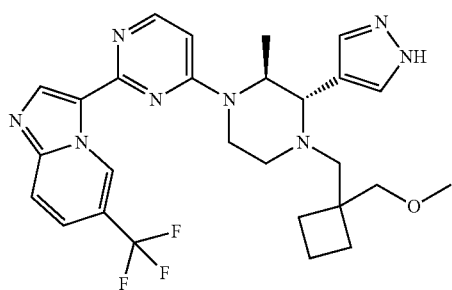 I-512
TABLE 1-continued
Exemplary compounds of formula I
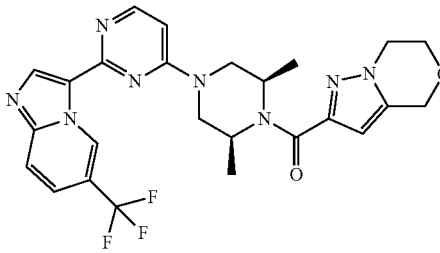 I-513
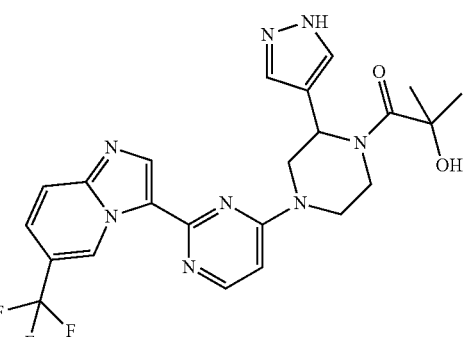 I-514
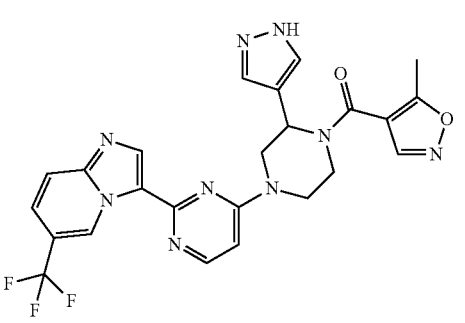 I-515
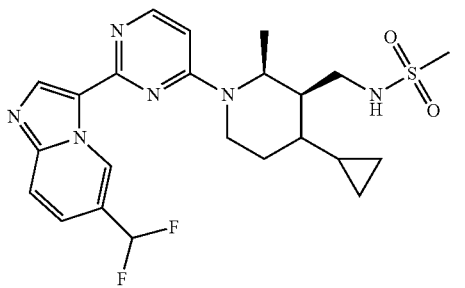 I-516
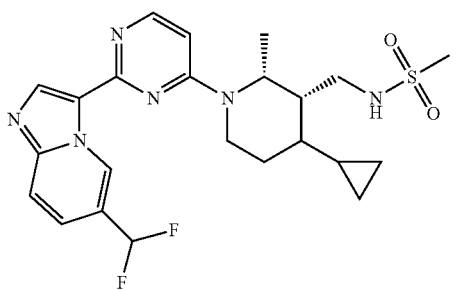 I-517

TABLE 1-continued
Exemplary compounds of formula I
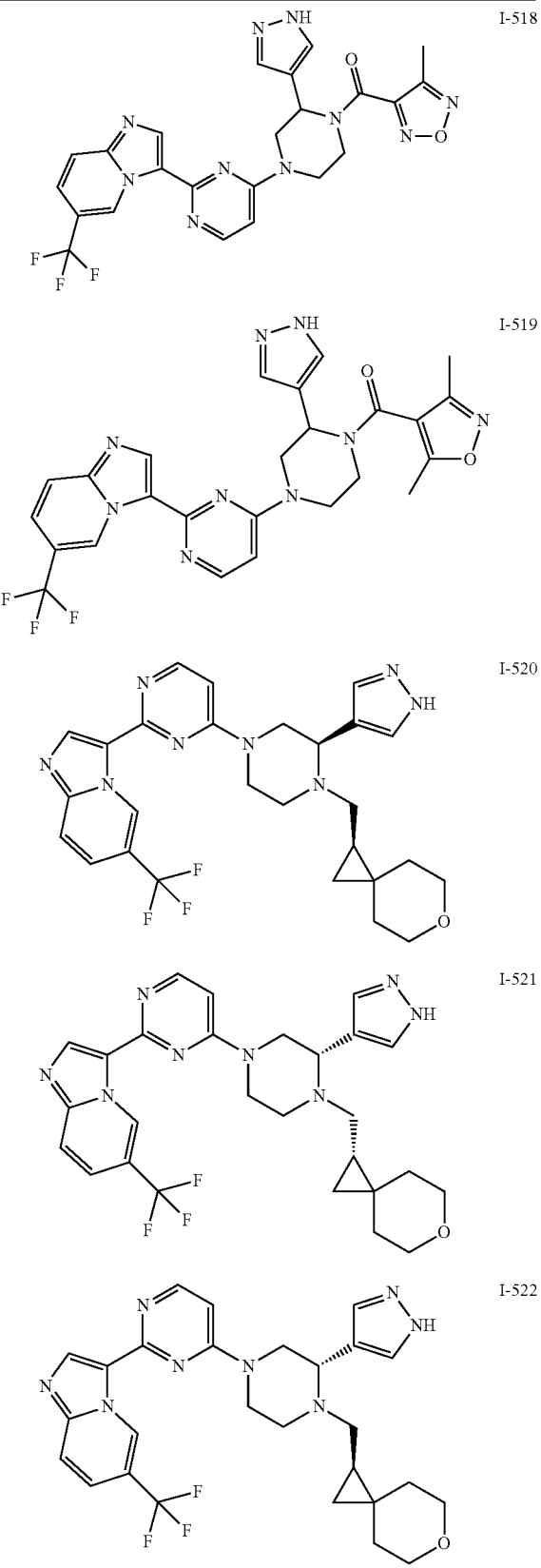
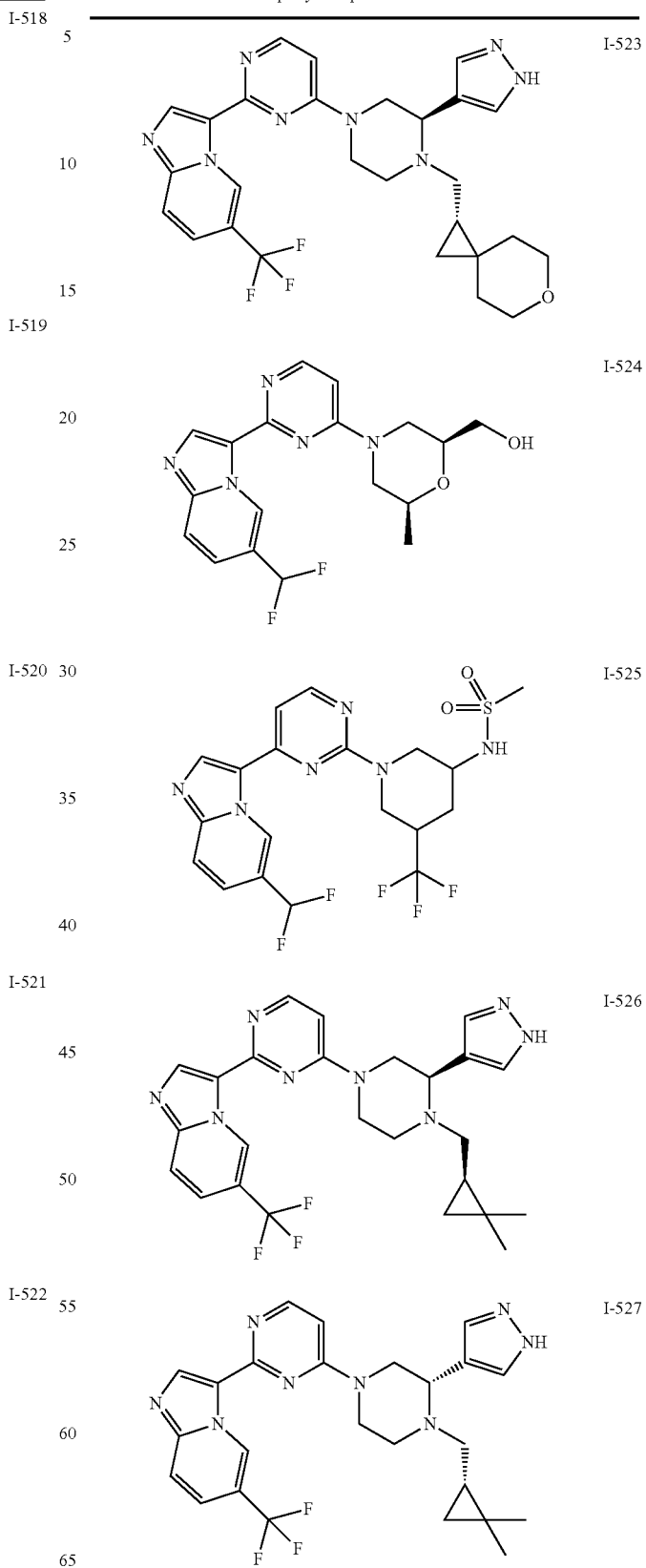

TABLE 1-continued
Exemplary compounds of formula I
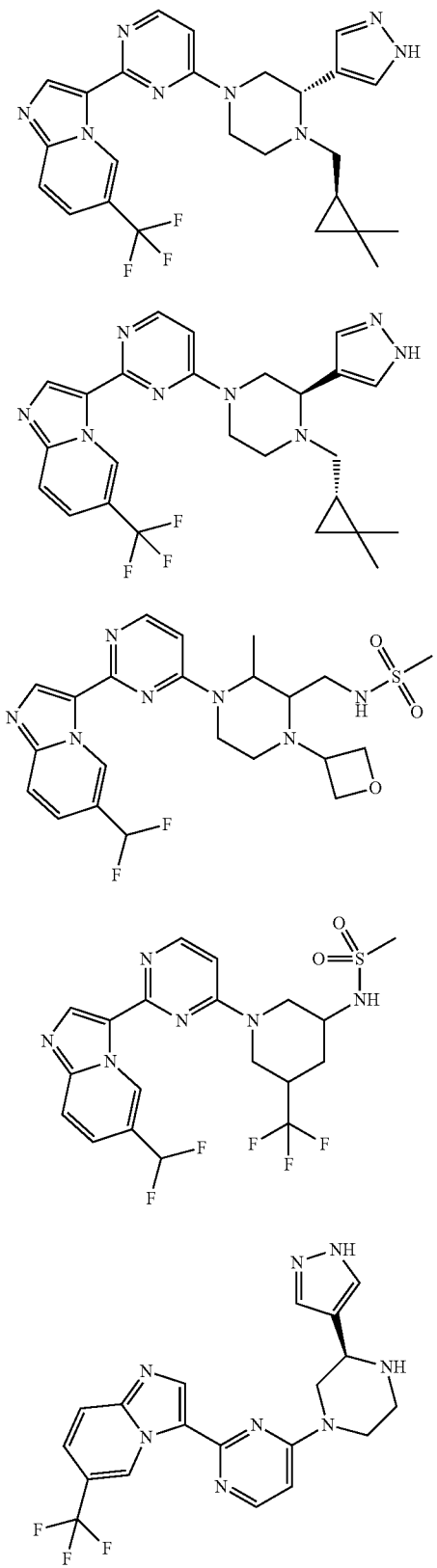
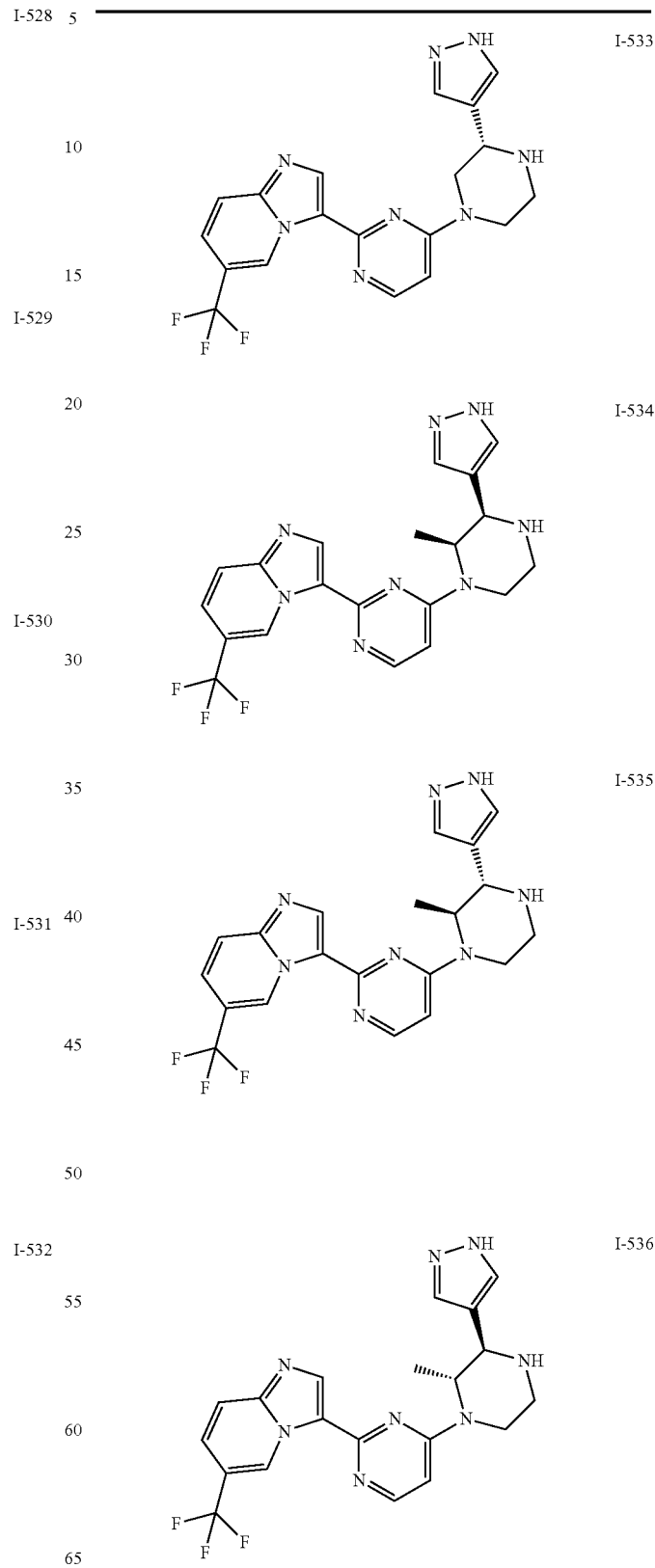

TABLE 1-continued
Exemplary compounds of formula I
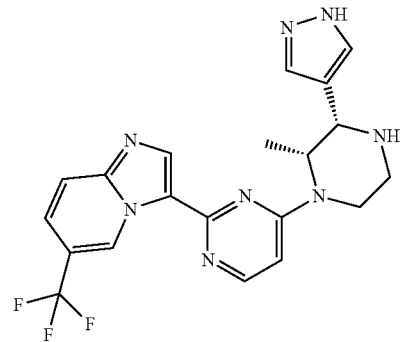 I-537
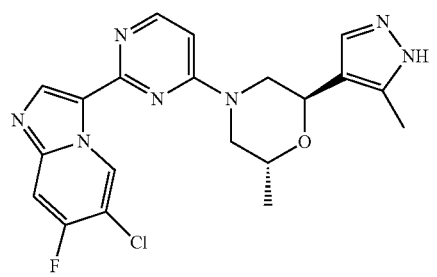 I-538
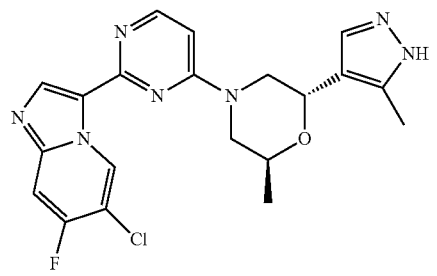 I-539
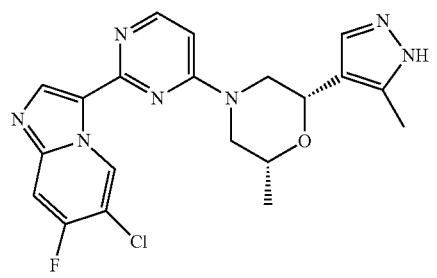 I-540
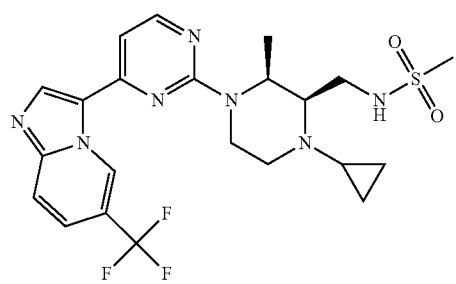 I-541
TABLE 1-continued
Exemplary compounds of formula I
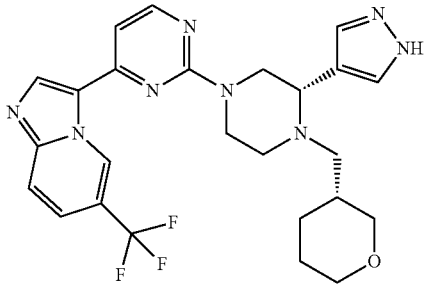 I-542
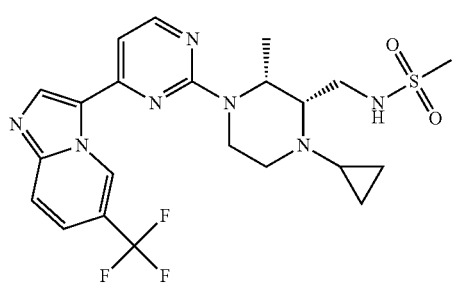 I-543
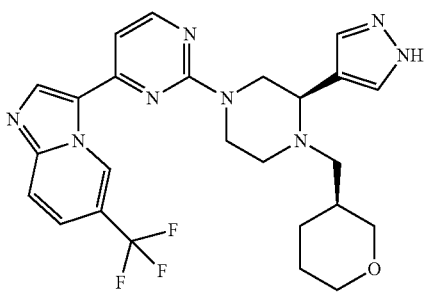 I-544
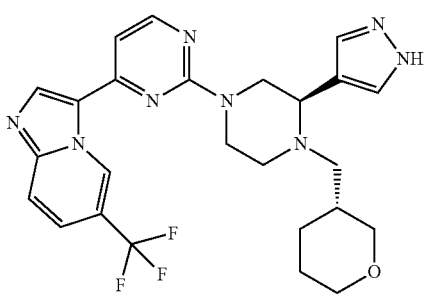 I-545
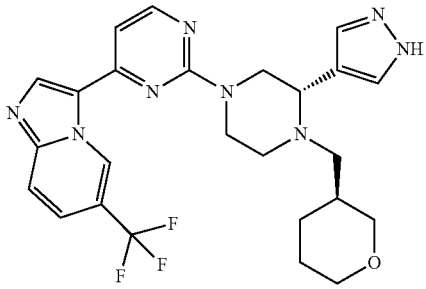 I-546

TABLE 1-continued
Exemplary compounds of formula I
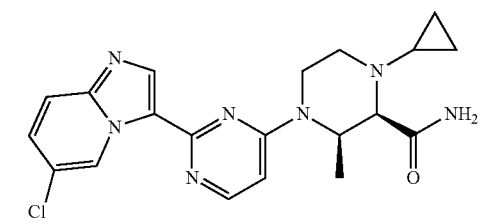 I-547
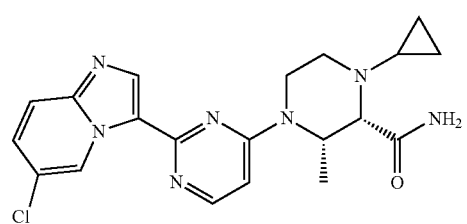 I-548
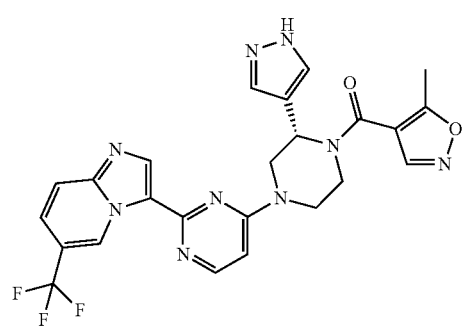 I-549
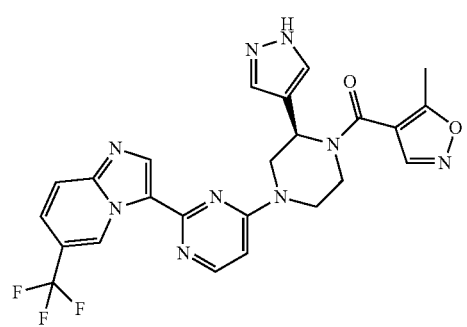 I-550
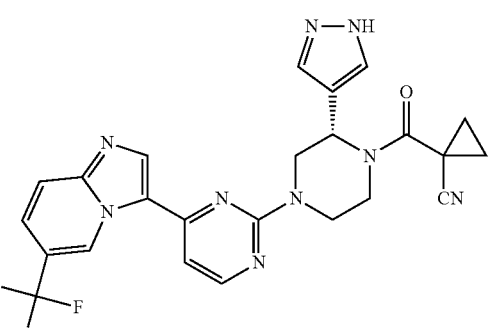 I-551
TABLE 1-continued
Exemplary compounds of formula I
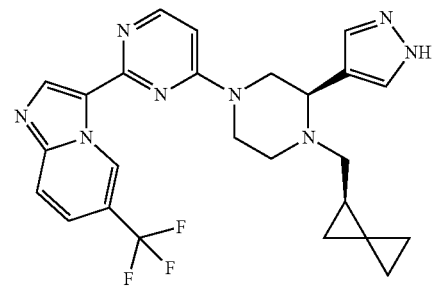 I-552
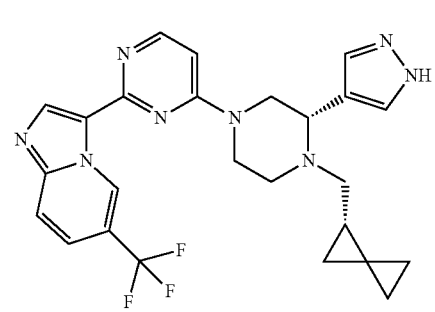 I-553
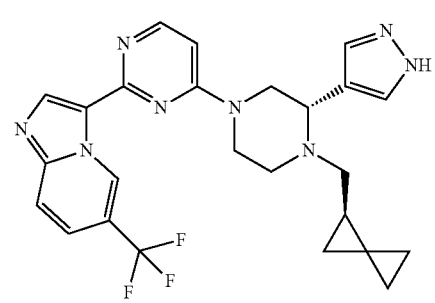 I-554
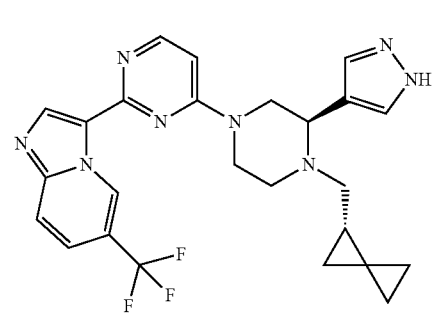 I-555
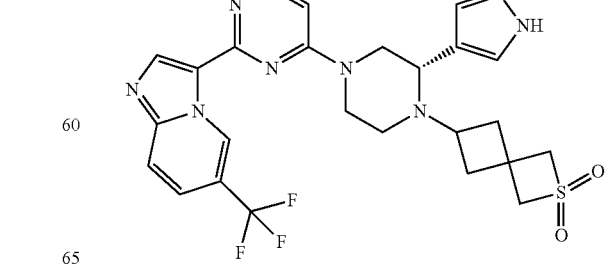 I-556

TABLE 1-continued
Exemplary compounds of formula I
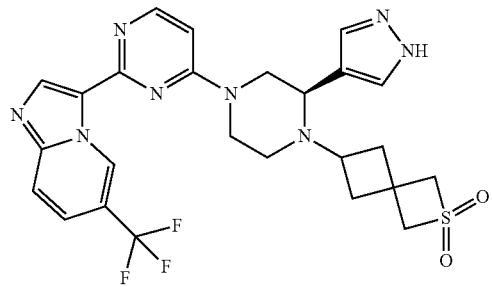 I-557
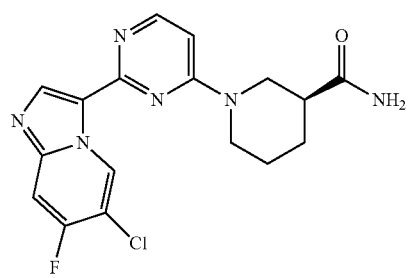 I-558
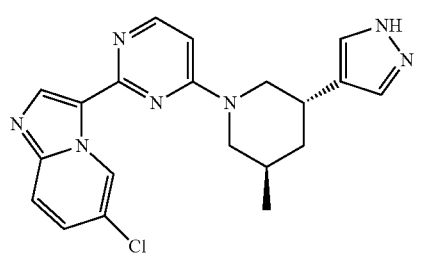 I-559
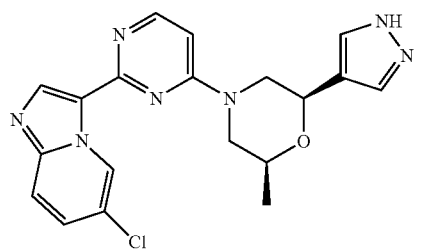 I-560
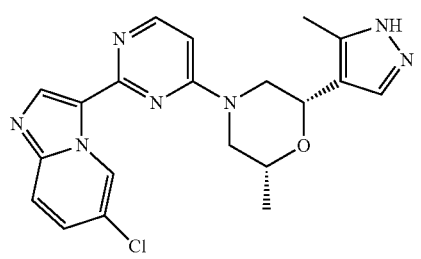 I-561
TABLE 1-continued
Exemplary compounds of formula I
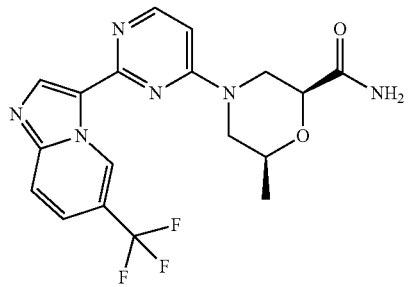 I-562
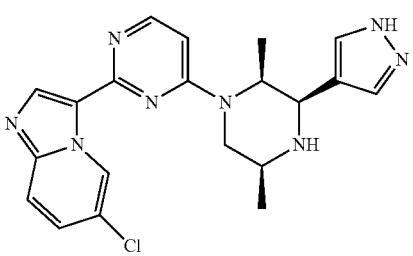 I-563
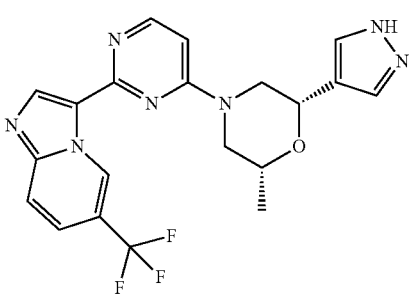 I-564
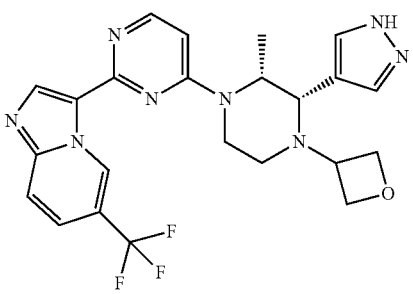 I-565
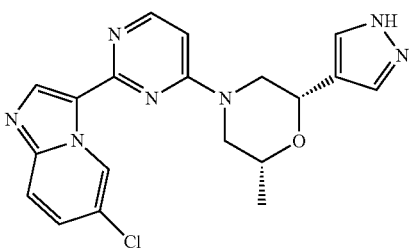 I-566

TABLE 1-continued

Exemplary compounds of formula I

I-567

I-568

I-569

I-570

In some embodiments, the present invention provides a compound set forth in Table 1, above, or a pharmaceutically acceptable salt thereof.

In certain embodiments, the present invention provides a complex comprising GCN2 and an inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

Scheme 1:

General scheme for the preparation of compounds of formula I where Ring B is a pyrimidine linked to the bicyclic core from position 2, $R^3$ is hydrogen, $R^4$ is hydrogen, p is 1, and q is 1.

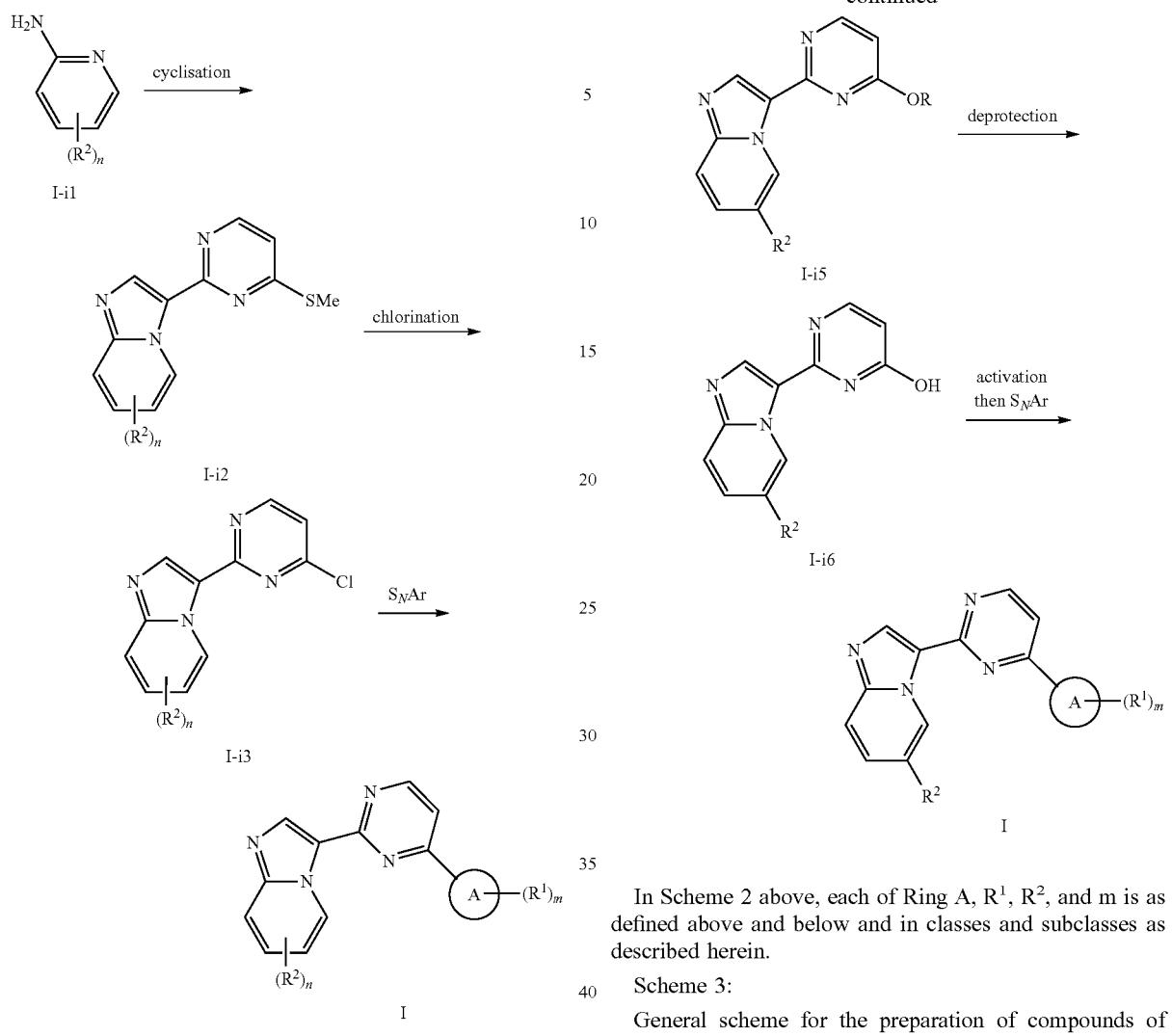

In Scheme 1 above, each of Ring A, R¹, R², m and n is as defined above and below and in classes and subclasses as described herein.

Scheme 2:

General scheme for the preparation of compounds of formula I where Ring B is a pyrimidine linked to the bicyclic core from position 2, R³ is hydrogen, R⁴ is hydrogen, n is 1, p is 1, and q is 1.

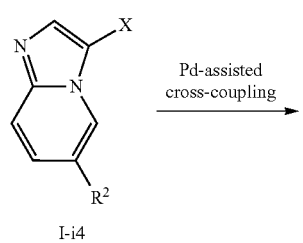

In Scheme 2 above, each of Ring A, R¹, R², and m is as defined above and below and in classes and subclasses as described herein.

Scheme 3:

General scheme for the preparation of compounds of formula I where Ring B is a pyrimidine linked to the bicyclic core from position 2, R³ is hydrogen, R⁴ is hydrogen, p is 1, and q is 1.

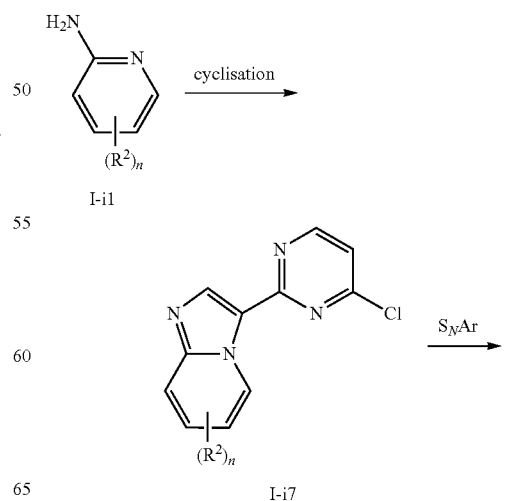

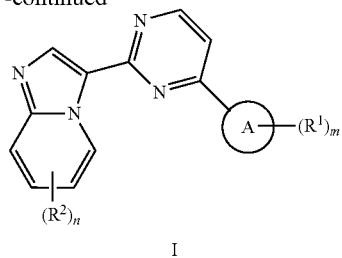

In Scheme 3 above, each of Ring A, $R^1$, $R^2$, m and n is as defined above and below and in classes and subclasses as described herein.

Scheme 4: General scheme for the preparation of compounds of formula I where Ring B is a pyrimidine linked to the bicyclic core from position 4, $R^3$ is hydrogen, $R^4$ is hydrogen, n is 1, p is 1, and q is 1.

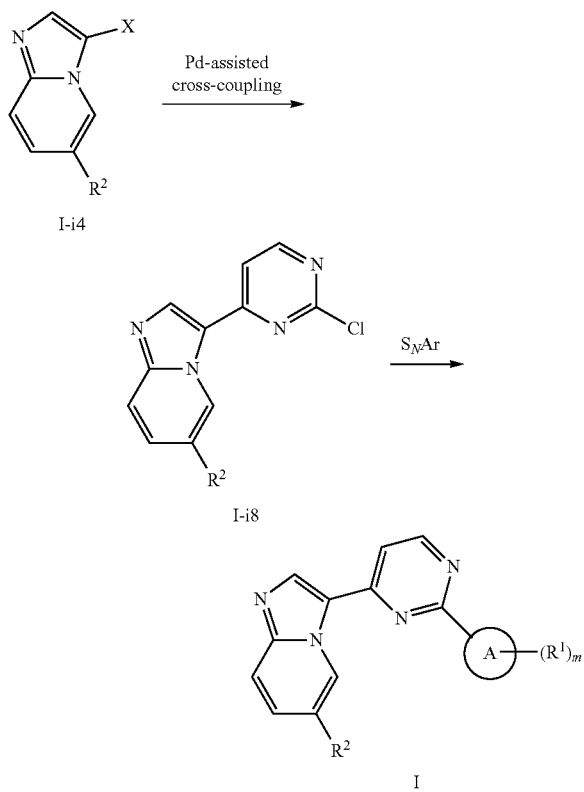

In Scheme 4 above, each of Ring A, $R^1$, $R^2$, and m is as defined above and below and in classes and subclasses as described herein.

One of skill in the art will appreciate that a compound of formula I may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration a. Pharmaceutically Acceptable Compositions According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit GCN2 protein kinase, or a mutant thereof, in a biological sample or in a patient. In certain embodiments, the amount of compound in compositions of this invention is such that is effective to measurably inhibit GCN2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of GCN2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

b. Uses of Compounds and Pharmaceutically Acceptable Compositions

Compounds and compositions described herein are generally useful for the inhibition of GCN2 kinase activity.

The activity of a compound utilized in this invention as an inhibitor of GCN2, or a mutant thereof, may be assayed in vitro, in vivo or in a cell line. In vitro assays include assays that determine inhibition of either the phosphorylation activity and/or the subsequent functional consequences, or ATPase activity of activated GCN2, or a mutant thereof. Alternate in vitro assays quantitate the ability of the inhibitor to bind to GCN2. Inhibitor binding may be measured by radiolabeling the inhibitor prior to binding, isolating the inhibitor/GCN2 complex and determining the amount of radiolabel bound. Alternatively, inhibitor binding may be determined by running a competition experiment where new inhibitors are incubated with GCN2 bound to known radioligands. Detailed conditions for assaying a compound utilized in this invention as an inhibitor of GCN2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of GCN2 and are therefore useful for treating one or more disorders associated with activity of GCN2. Thus, in certain embodiments, the present invention provides a method for treating a GCN2-mediated disorder comprising the step of administering to a patient in need thereof a compound of the present invention, or pharmaceutically acceptable composition thereof.

As used herein, the terms "GCN2-mediated" disorders, diseases, and/or conditions as used herein means any disease or other deleterious condition in which GCN2, or a mutant thereof, are known to play a role. Accordingly, another embodiment of the present invention relates to treating or lessening the severity of one or more diseases in which GCN2, or a mutant thereof, are known to play a role.

In some embodiments, the present invention provides a method for treating one or more disorders, diseases, and/or conditions wherein the disorder, disease, or condition is selected from the group consisting of inflammatory conditions, immunological conditions, autoimmune conditions, allergic conditions, rheumatic conditions, thrombotic conditions, cancer, infections, neurodegenerative diseases, degenerative diseases, neuroinflammatory diseases, cardiovascular diseases, and metabolic conditions.

In some embodiments, the cancer to be treated is a solid tumor or a tumor of the blood and immune system.

In some embodiments, the cancer is a solid tumor, wherein the solid tumor originates from the group of tumors of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondrosarcoma and Ewing sarcoma, germ cells, including embryonal tissue tumors, and/or the lung, from the group of monocytic leukemia, lung adenocarcinoma, small-cell lung carcinomas, pancreatic cancer, glioblastomas, neurofibroma, angiosarcoma, breast carcinoma and/or maligna melanoma.

In some embodiments, the autoimmune condition is rheumatoid arthritis, systemic lupus, multiple sclerosis, psoriasis, Sjögrens syndrome or transplant organ rejection.

In some embodiments, the metabolic condition is diabetes.

In some embodiments, the degenerative disease is osteoarthritis.

In some embodiments, the inflammatory condition is asthma, inflammatory bowel disease, or giant cell arteritis.

In some embodiments, the cardiovascular disease is an ischemic injury.

In some embodiments, the neurodegenerative disease is Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, or Parkinson's disease.

In some embodiments, the infection is caused by *leishmania*, mycobacteria, including *M. leprae, M. tuberculosis* and/or *M. avium, plasmodium*, human immunodeficiency virus, Epstein Barr virus, Herpes simplex virus, or hepatitis C virus.

Furthermore, the invention provides the use of a compound according to the definitions herein, or a pharmaceutically acceptable salt, or a hydrate or solvate thereof for the preparation of a medicament for the treatment of inflammatory conditions, immunological conditions, autoimmune conditions, allergic conditions, rheumatic conditions, thrombotic conditions, cancer, infections, neurodegenerative diseases, degenerative diseases, neuroinflammatory diseases, cardiovascular diseases, or metabolic conditions.

c. Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a compound of formula I and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis *nodosa* (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h)

absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting GCN2, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a GCN2 protein kinase, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting GCN2, or a mutant thereof, activity in a patient comprising the step of administering to said patient a compound of the present invention, or a composition comprising said compound. In other embodiments, the present invention provides a method for treating a disorder mediated by GCN2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (ParkeDavis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1 h68/GLV-h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodimens, a bispecific T cell engager (BiTE®) antibody construct is a CD19/CD3 bispecific antibody construct. In some embodimens, a bispecific T cell engager (BiTE®) antibody construct is an EGFR/CD3 bispecific antibody construct. In some embodimens, a bispecific T cell engager (BiTE®) antibody construct activates T cells. In some embodimens, a bispecific T cell engager (BiTE®) antibody construct activates T cells, which release cytokines inducing upregulation of intercellular adhesion molecule 1 (ICAM-1) and FAS on bystander cells. In some embodimens, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+(αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation 1: 3-(4-Methylsulfanylpyrimidin-2-yl)-6-(trifluoromethyl)imidazo[1,2-a]pyridine

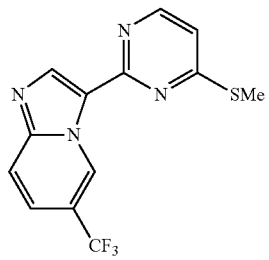

NBS (165.2 mg, 0.928 mmol) was added to a solution of 2-[(E)-2-ethoxyvinyl]-4-methylsulfanyl-pyrimidine (181.4 mg, 0.924 mmol) in 1,4-dioxane (5.5 mL) and water (2 mL) and the reaction mixture was stirred at ambient temperature for 15 min. 5-(Trifluoromethyl)pyridin-2-amine (150 mg, 0.925 mmol) was added and the reaction mixture heated at 65-75° C. for 7 hours. The mixture was cooled to ambient temperature and diluted with saturated aqueous NaHCO$_3$ and extracted with DCM. The combined organic extracts were dried (MgSO$_4$), filtered and concentrated in vacuo. The residue was purified by column chromatography (silica, EtOAc/petrol gradient) to give 3-(4-methyl sulfanylpyrimidin-2-yl)-6-(trifluoromethyl)imidazo[1,2-a]pyridine (165 mg, 58%); ESV-MS m/z 311.1 (M+H).

The following compounds were prepared using a methodology similar to the one described in Preparation 1:

6-Chloro-3-(4-methylsulfanylpyrimidin-2-yl)imidazo[1,2-a]pyridine using 5-chloropyridin-2-amine;

6-Chloro-7-fluoro-3-(4-methylsulfanylpyrimidin-2-yl)imidazo[1,2-a]pyridine using 5-chloro-4-fluoro-pyridin-2-amine;

6-Bromo-7-fluoro-3-(4-methyl sulfanylpyrimidin-2-yl)imidazo[1,2-a]pyridine using 5-bromo-4-fluoro-pyridin-2-amine;

6-Chloro-7-fluoro-3-(4-(methylthio)pyrimidin-2-yl)imidazo[1,2-a]pyridine using 5-chloro-4-fluoropyridin-2-amine.

Preparation 2: 3-(4-Chloropyrimidin-2-yl)-6-(trifluoromethyl)imidazo[1,2-a]pyridine

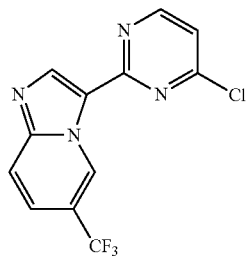

Sulfuryl chloride (174.9 µL, 2.160 mmol) was added to a solution of 3-(4-methylsulfanylpyrimidin-2-yl)-6-(trifluoromethyl)imidazo[1,2-a]pyridine (165 mg, 0.532 mmol) and conc. HCl (47.1 µL of 37% w/w, 0.860 mmol) in MeCN (13 mL) and the reaction mixture stirred for 5 minutes. Cooled saturated aqueous $NaHCO_3$ was added dropwise and the mixture stirred for 10 min. The resultant precipitate was isolated by filtration, washed with water and dried to give 3-(4-chloropyrimidin-2-yl)-6-(trifluoromethyl)imidazo[1,2-a]pyridine (125 mg, 79%).

The following compounds were prepared using a methodology similar to the one described in Preparation 2:

6-Chloro-3-(4-chloropyrimidin-2-yl)imidazo[1,2-a]pyridine using 6-chloro-3-(4-methyl sulfanylpyrimidin-2-yl)imidazo[1,2-a]pyridine;

6-Chloro-3-(4-chloropyrimidin-2-yl)-7-fluoro-imidazo[1,2-a]pyridine using 6-chloro-7-fluoro-3-(4-methyl sulfanylpyrimidin-2-yl)imidazo[1,2-a]pyridine;

6-Bromo-3-(4-chloropyrimidin-2-yl)-7-fluoro-imidazo[1,2-a]pyridine using 6-bromo-7-fluoro-3-(4-methylsulfanylpyrimidin-2-yl)imidazo[1,2-a]pyridine;

6-Chloro-3-(4-chloropyrimidin-2-yl)-7-fluoro-imidazo[1,2-a]pyridine using 6-chloro-7-fluoro-3-(4-(methylthio)pyrimidin-2-yl)imidazo[1,2-a]pyridine.

4-Chloro-2-{6-phenoxyimidazo[1,2-a]pyridin-3-yl}pyrimidine

4-Chloro-2-{6-methanesulfonylimidazo[1,2-a]pyridin-3-yl}pyrimidine 3-(4-Chloropyrimidin-2-yl)-N-cyclopropylimidazo[1,2-a]pyridine-6-sulfonamide 3-(4-Chloropyrimidin-2-yl)imidazo[1,2-a]pyridine-6-sulfonamide Preparation 3: 3-Bromo-6-(difluoromethyl)imidazo[1,2-a]pyridine

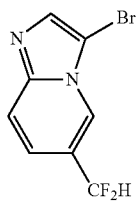

(Diethylamino)sulfur trifluoride (528.5 µL, 4.00 mmol) was added dropwise to 3-bromoimidazo[1,2-a]pyridine-6-carbaldehyde (450 mg, 2.00 mmol) in DCM (4.5 mL) at 0° C. After 2.5 hours, additional (diethylamino)sulfur trifluoride (150 µL, 1.135 mmol) was added and the reaction stirred at room temperature for 16 hours. The crude mixture was diluted with methanol and purified by means of an ion exchange SCX-2 cartridge to afford 3-bromo-6-(difluoromethyl)imidazo[1,2-a]pyridine (310 mg, 63%); ESV-MS m/z 247.0 (M+H).

Preparation 4: 2-[6-(Difluoromethyl)imidazo[1,2-a]pyridin-3-yl]pyrimidin-4-ol

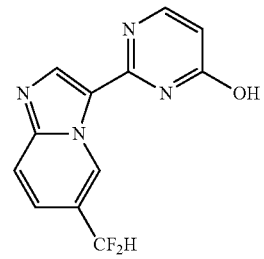

Step 1: 6-(Difluoromethyl)-3-(4-methoxypyrimidin-2-yl)imidazo[1,2-a]pyridine

3-Bromo-6-(difluoromethyl)imidazo[1,2-a]pyridine (120 mg, 0.486 mmol), tributyl-(4-methoxypyrimidin-2-yl)stannane (200 µL, 0.583 mmol) and $PdCl_2(PPh_3)_2$ (102.3 mg, 0.146 mmol) were combined in DMF (4 mL) and degassed with nitrogen and heated at 120° C. for 16 hours. The mixture was allowed to cool, filtered and then purified by reverse phase chromatography (C18; MeCN/water/0.05% TFA as eluent) to afford the trifluoroacetic acid salt of 6-(difluoromethyl)-3-(4-methoxypyrimidin-2-yl)imidazo[1,2-a]pyridine (97 mg, 72%); ESV-MS m/z 277.1 (M+H).

Step 2: 2-[6-(Difluoromethyl)imidazo[1,2-a]pyridin-3-yl]pyrimidin-4-ol

Chlorotrimethylsilane (267 µL, 2.107 mmol) was added to a solution of 6-(difluoromethyl)-3-(4-methoxypyrimidin-2-yl)imidazo[1,2-a]pyridine (97 mg, 0.351 mmol) and NaI (315.8 mg, 2.107 mmol) in MeCN (4 mL) and the mixture was heated at 80° C. for 16 hours. The reaction mixture was cooled to room temperature and the solvent removed under reduced pressure. The residue was suspended in water and washed with saturated aqueous sodium thiosulfate. The solid was filtered, washed with water, and dried under vacuum to afford 2-[6-(difluoromethyl)imidazo[1,2-a]pyridin-3-yl]pyrimidin-4-ol (75 mg, 81%); ESV-MS m/z 263.1 (M+H). The material was used without further purification.

249

Preparation 5: 3-(2-Chloropyrimidin-4-yl)-6-(trifluoromethyl)imidazo[1,2-a]pyridine

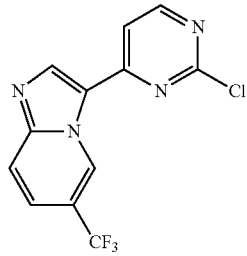

NBS (241 mg, 1.354 mmol) was added to a solution of 2-chloro-4-(2-ethoxyvinyl)pyrimidine (250 mg, 1.354 mmol) in 1,4-dioxane (8 mL)/water (3 mL) and the reaction mixture was stirred for 15 min. 5-(Trifluoromethyl)pyridin-2-amine (220 mg, 1.357 mmol) was added and the reaction mixture heated at 80° C. for 3 hours. The mixture was cooled to room temperature and diluted with saturated aqueous NaHCO₃ and extracted with DCM. The combined organic extracts were dried (MgSO₄), filtered and concentrated in vacuo. The residue was purified by flash column chromatography (silica, EtOAc/petrol gradient, then MeOH/DCM gradient) to afford 3-(2-chloropyrimidin-4-yl)-6-(trifluoromethyl)imidazo[1,2-a]pyridine (234.5 mg, 58%) as a beige solid; ¹H NMR (500 MHz, DMSO-d₆) δ 10.26 (s, 1H), 8.95 (s, 1H), 8.78 (d, 1H), 8.19 (d, 1H), 8.05 (d, 1H), 7.84 (dd, 1H); ¹⁹F NMR (471 MHz, DMSO-d₆) δ −60.86; ESV-MS m/z 299.1 (M+H).

Preparation 6: N-[[(2S)-Morpholin-2-yl]methyl]methanesulfonamide

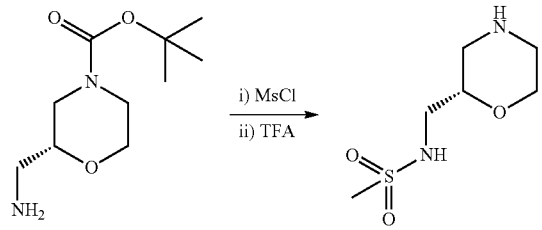

Step 1: tert-butyl (S)-2-(methylsulfonamidomethyl)morpholine-4-carboxylate

To a round bottom flask was added tert-butyl (2R)-2-(aminomethyl)morpholine-4-carboxylate (5 g, 23 mmol) and Et₃N (16.1 mL, 115 mmol) followed by THF (100 mL). DCM (50 mL) was added and the mixture was cooled to 0° C. Methanesulfonyl chloride (2.4 mL, 30.5 mmol) was added dropwise and the mixture stirred for 0.5 hours then left at ambient temperature for 16 hours under an atmosphere of N₂. The reaction was quenched with saturated aqueous NaHCO₃ solution (100 mL) and the majority of the volatiles were removed in vacuo. The aqueous layer was extracted with ethyl acetate (3×50 mL). The combined organics were dried over Na₂SO₄, filtered and concentrated in vacuo. The residue was purified by chromatography (silica; 70-100% EtOAc/Petroleum ether gradient elution).

250

The product fractions were combined and concentrated in vacuo. The residue was dried overnight under vacuum to give tert-butyl (S)-2-(methylsulfonamidomethyl)morpholine-4-carboxylate (3.61 g, 53%) as a white solid; ¹H NMR (500 MHz, Chloroform-d) δ 4.71-4.59 (m, 1H), 3.98-3.82 (m, 2H), 3.63-3.49 (m, 2H), 3.38-3.24 (m, 1H), 3.20-3.11 (m, 1H), 3.04-2.90 (m, 4H), 2.73 (s, 1H), 1.49 (s, 9H).

Step 2: N-[[(2S)-Morpholin-2-yl]methyl]methanesulfonamide

TFA (9 mL, 115 mmol) was added to a stirred solution of tert-butyl (2S)-2-(methanesulfonamidomethyl)morpholine-4-carboxylate (3.6 g, 12 mmol) in DCM (60 mL) and the reaction stirred at ambient temperature for 6 hours. The solvent was removed in vacuo and the residue azeotroped with DCM (×2) and diethyl ether (×2). The residue was taken up in methanol and passed through an ion-exchange cartridge, eluting with methanol (discarded) then a 2M methanolic ammonia solution. The filtrate was concentrated in vacuo to give N-[[(2S)-morpholin-2-yl]methyl]methanesulfonamide (2.3 g, 97%); ¹H NMR (500 MHz, Chloroform-d) δ 4.73 (s, 1H), 3.90-3.87 (m, 1H), 3.65-3.60 (m, 2H), 3.26 (dd, 1H), 3.09 (dd, 1H), 2.99 (s, 3H), 2.92-2.84 (m, 3H), 2.66 (dd, 1H); MS m/z: 195 (M+H)⁺.

Preparation 7: 2-(1H-Pyrazol-4-yl)morpholine

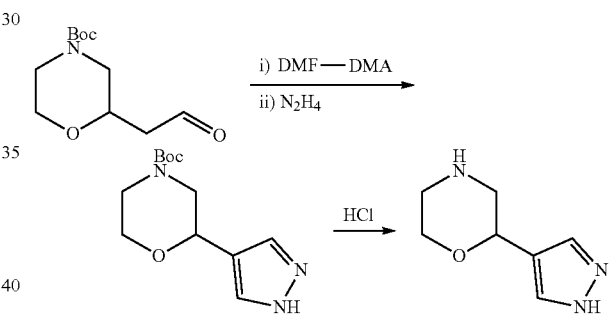

Step 1: tert-Butyl 2-(1H-pyrazol-4-yl)morpholine-4-carboxylate

A mixture of tert-butyl 2-(2-oxoethyl)morpholine-4-carboxylate (5.77 g, 25 mmol) and DMF-DMA (6.7 mL, 50 mmol) in DMF (50 mL) was stirred at 80° C. for 17 hours. The reaction mixture was cooled to ambient temperature and the solvent removed in vacuo. The residue was taken up in EtOH (100 mL) and hydrazine hydrate (1.3 mL, 26.5 mmol) was added with stirring at ambient temperature. After 3 hours, the solvent was removed in vacuo and the residue purified by chromatography (silica, PE/EtOAc gradient elution), to give tert-butyl 2-(1H-pyrazol-4-yl)morpholine-4-carboxylate (2.35 g, 37%) as a yellow solid. ¹H NMR (500 MHz, chloroform-d) δ 7.63 (s, 2H), 4.52 (dd, 1H), 4.12 (br s, 1H), 3.97-3.90 (m, 2H), 3.68 (td, 1H), 3.05 (d, 2H), 1.51 (s, 9H); MS m/z: 254.1 (M+H)⁺.

Step 2: 2-(1H-Pyrazol-4-yl)morpholine

3M HCl in methanol (45 mL of 3M, 135 mmol) was added to a stirred solution of tert-butyl 2-(1H-pyrazol-4-yl)morpholine-4-carboxylate (2.35 g, 9.3 mmol) in DCM (75 mL) and the reaction heated at reflux for 5 hours. The reaction was cooled to ambient temperature and the solvent removed in vacuo. The residue was dissolved in the minimum amount of DCM/MeOH and loaded on to an ion-exchange cartridge. The cartridge was washed with MeOH/DCM mixtures, which were discarded. The product was eluted by washing with 2M $NH_3$ in MeOH/DCM. The solvent was removed in vacuo to give 2-(1H-pyrazol-4-yl)morpholine (1.27 g, 89%) as an orange solid, which was taken on to the next reaction without further purification; $^1$H NMR (500 MHz, chloroform-d) δ 7.60 (s, 2H), 4.56 (dd, 1H), 3.98 (ddd, 1H), 3.77 (td, 1H), 3.11 (dd, 1H), 3.00 (td, 1H), 2x.93-2.88 (m, 2H); MS m/z: 154.2 $[M+H]^+$.

Preparation 8:
2-Methyl-6-(1H-pyrazol-4-yl)morpholine

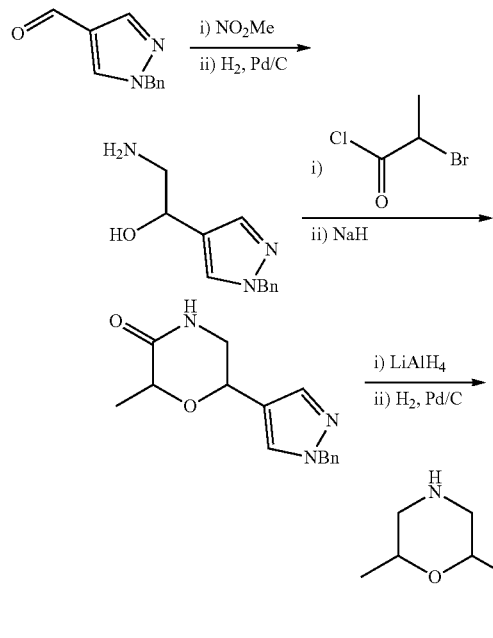

To a solution of 1-benzylpyrazole-4-carbaldehyde (2 g, 10.7 mmol) and nitromethane (7 mL, 129 mmol) cooled in an ice bath, was added $Et_3N$ (150 µL, 1.1 mmol). The mixture was stirred with cooling for 15 minutes, then at ambient temperature for 18 hours. The reaction mixture was concentrated in vacuo and the residue purified by chromatography (silica, EtOAc/Petroleum ether gradient elution). The relevant fractions were combined and concentrated in vacuo to give a colourless oil (1 g, 37%); MS m/z: 248 $(M+H)^+$. This material was taken directly onto the next reaction.

A mixture of 1-(1-benzylpyrazol-4-yl)-2-nitro-ethanol (100 mg, 0.4 mmol), Pd on C, wet, Degussa (20 mg, 0.2 mmol) in methanol (4 mL) was stirred at ambient temperature for 18 hours under $H_2$ at 1 atmosphere. The reaction mixture was filtered and the filtrate concentrated in vacuo to give a colourless gum (90 mg); MS m/z: 218 $(M+H)^+$. This material was taken directly onto next the reaction.

2-Bromopropanoyl bromide (114 mg, 0.5 mmol) was added to an ice-cold solution of 2-amino-1-(1-benzylpyrazol-4-yl)ethanol (100 mg, 0.5 mmol) and $Et_3N$ (83 µL, 0.6 mmol) in DCM (4 mL) under $N_2$. The reaction mixture was stirred at ambient temperature for 1 hour. The reaction mixture was diluted with DCM, washed with a 2M aqueous HCl solution, saturated aqueous $NaHCO_3$ solution and brine. The organic phase was dried over sodium sulfate, filtered and concentrated in vacuo to give a colourless oil. This material was taken up in THF (3 mL) and the solution cooled in an ice bath. Sodium hydride (37 mg of a 60% dispersion in mineral oil, 0.9 mmol) was added and the resulting suspension was stirred at ambient temperature for 2 hours. The reaction was quenched with methanol then diluted with EtOAc, washed with a saturated aqueous sodium bicarbonate solution and brine. The organic phase was dried over $MgSO_4$, filtered and concentrated in vacuo to give a pale yellow gum (100 mg), MS m/z: 272 $(M+H)^+$, that was taken directly on to next reaction without purification.

A mixture of 6-(1-benzylpyrazol-4-yl)-2-methyl-morpholin-3-one (100 mg, 0.4 mmol) and $LiAlH_4$ (184 µL of 2M, 0.4 mmol) in THF (3 mL) was stirred at 60° C. for 1 hour. The resulting suspension was quenched with $Na_2SO_4.10H_2O$ pellets and stirred for 30 minutes, then filtered. The filtrate was concentrated in vacuo and the residue taken up in methanol (2 mL). Three drops of concentrated HCl and Pd on C, wet, Degussa (20 mg, 0.02 mmol) were added to the solution. The reaction mixture was stirred at ambient temperature under $H_2$ at 1 atmosphere pressure for 18 hours. The reaction mixture was poured onto an ion-exchange cartridge and eluted with methanol (filtrate discarded), then a 2M methanolic $NH_3$ solution. The filtrate was concentrated in vacuo to give 2-methyl-6-(1H-pyrazol-4-yl)morpholine (23 mg), MS m/z: 168 $(M+H)^+$. This material was taken directly onto the next reaction.

Preparation 9: Imino(methyl)(piperidin-3-ylmethyl)-$λ^6$-sulfanone

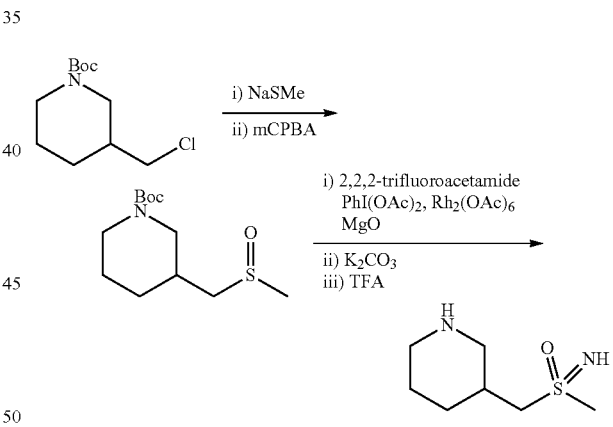

A mixture of tert-butyl 3-(chloromethyl)piperidine-1-carboxylate (500 mg, 2.14 mmol), NaSMe (3 mL of 20% w/v, 8.56 mmol), KI (355 mg, 2.14 mmol) in ethanol (10 mL) was stirred at 80° C. for 22 hours. The reaction mixture was cooled to ambient temperature then concentrated in vacuo. The residue was partitioned between EtOAc and saturated aqueous sodium bicarbonate solution. The organic phase was washed with brine, dried ($MgSO_4$), filtered and concentrated in vacuo to give the product as a pale brown oil (460 mg 88%), that was taken on to the next step without further purification or characterisation.

m-CPBA (324 mg, 1.88 mmol) was added to an ice cold solution of tert-butyl 3-(methylsulfanylmethyl)piperidine-1-carboxylate (460 mg, 1.88 mmol) in DCM (7 mL) under $N_2$. The reaction mixture was stirred for 20 hours, with the temperature rising to ambient. The reaction mixture was diluted with DCM, washed with saturated aqueous sodium bicarbonate solution and brine. The organic phase was dried over MgSO₄, filtered and concentrated in vacuo to give a pale brown oil (460 mg); MS m/z: 262 (M+H)⁺, that was used in the next step without further purification or characterisation. tert-Butyl 3-(methyl sulfinylmethyl)piperidine-1-carboxylate (5.5 g, 21.0 mmol), 2,2,2-trifluoroacetamide (5.2 g, 46.3 mmol), diacetoxyiodobenzene (10.2 g, 31.6 mmol) and MgO (3.39 g, 84.2 mmol) were combined in DCM (250 mL) under N₂. Rh₂(OAc)₆ (0.9 g, 2.0 mmol) was added and the reaction mixture mixture stirred at room temperature for 16 hours. The mixture was filtered through Celite, washing with methanol and DCM. The filtrate was concentrated in vacuo and the residue taken up in methanol (5 mL) and MeCN/water (3:1) (5 mL). K₂CO₃ (17.4 g, 126.0 mmol) was added and the mixture stirred at 90° C. for 2 hours. The mixture was diluted with EtOAc and washed with saturated aqueous sodium bicarbonate solution and brine. The organic phase was dried (Na₂SO₄), filtered and concentrated in vacuo to give tert-butyl 3-[(methylsulfonimidoyl)methyl]piperidine-1-carboxylate (5.96 g, quantitative yield) as an amber oil; MS m/z: 277 (M+H)⁺, that was taken directly on to the next reaction.

tert-Butyl 3-[(methylsulfonimidoyl)methyl]piperidine-1-carboxylate (600 mg, 2.17 mmol) in DCM (3 mL) was treated with TFA (1.7 mL, 21.7 mmol). The mixture was stirred at room temperature for 16 hours. The reaction mixture was concentrated in vacuo. The residue was taken up in methanol and loaded on to an ion-exchange cartridge. The cartridge was eluted MeOH/DCM (filtrate discarded) then with methanolic ammonia. The filtrate was concentrated in vacuo to give imino(methyl)(piperidin-3-ylmethyl)-λ⁶-sulfanone (250 mg, 65%); ¹H NMR (500 MHz, Methanol-d₄) δ 3.34-3.24 (m, 1H), 3.19-3.10 (m, 2H), 3.10-3.07 (m, 3H), 3.05-2.97 (m, 1H), 2.60 (ddd, 1H), 2.52-2.43 (m, 1H), 2.30-2.18 (m, 1H), 2.08 (ddtd, 1H), 1.75 (dq, 1H), 1.61 (dtq, 1H), 1.37 (dtd, 1H).

Preparation 10: Imino(methyl)(piperidin-3-ylmethyl)-λ⁶-sulfanone

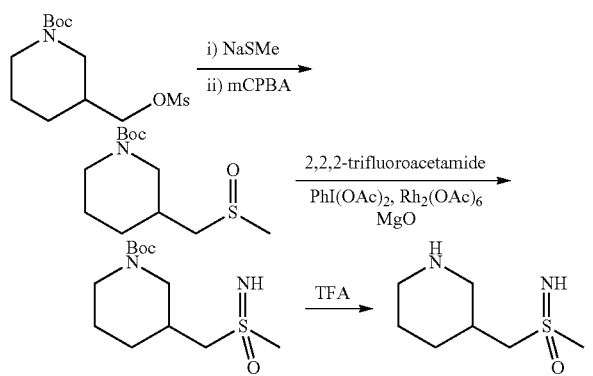

Sodium thiomethoxide (4.06 g, 58 mmol) was added to a solution of tert-butyl 3-(methylsulfonyloxymethyl)piperidine-1-carboxylate (8.5 g, 29 mmol) in ethanol (170 mL). The mixture was stirred at ambient temperature for 6 hours then concentrated in vacuo. The residue was partitioned between DCM and saturated aqueous NaHCO₃ solution. The organic phase was dried and concentrated in vacuo. The residue was purified by chromatography (silica, MeOH/ DCM gradient elution) to give a pale yellow oil (6.9 g). This material was dissolved in DCM (100 mL) and the solution cooled in an ice bath. m-CPBA (6.93 g of 70% pure w/w, 28 mmol) was added portionwise. After addition was complete the reaction mixture was stirred for 10 minutes then partitioned between DCM, saturated aqueous sodium bicarbonate solution and saturated aqueous sodium thiosulfate solution. The organic phase was dried and concentrated in vacuo. The residue was purified by chromatography (silica, DCM/ MeOH gradient elution) to give the product as a colourless oil.

tert-Butyl 3-((methylsulfinyl)methyl)piperidine-1-carboxylate (5.5 g, 21.0 mmol), 2,2,2-trifluoroacetamide (5.23 g, 46.3 mmol), (diacetoxyiodo)benzene (10.17 g, 31.6 mmol) and magnesium oxide (3.39 g, 84.2 mmol) were dissolved in DCM (250 mL) and diacetoxy(diacetoxyrhodio)rhodium (0.9 g, 2.04 mmol) was added. The mixture was stirred at ambient temperature overnight before being filtered through Celite and concentrated in vacuo. The residue was dissolved in methanol (50 mL) and water (10 mL) and K₂CO₃ (17.44 g, 126.2 mmol) was added. The mixture was stirred at ambient temperature for 3 hours before heating 50° C. for 3 days. The mixture was concentrated in vacuo and the residue dissolved in methanol (5 mL) and acetonitrile/water (3:1 mixture, 5 mL). After 1.5 hours at 90° C. the mixture was cooled, diluted in EtOAc and washed with brine and saturated aq. NaHCO₃ solution. The organic layer was dried (Na₂SO₄) and concentrated in vacuo to give tert-butyl 3-((S-methylsulfonimidoyl)methyl)piperidine-1-carboxylate (5.96 g) as an amber oil which was used without further purification.

A solution of tert-butyl 3-[(methylsulfonimidoyl)methyl] piperidine-1-carboxylate (600 mg, 2.17 mmol) and TFA (1.67 mL, 21.71 mmol) in DCM (3 mL) was stirred at ambient temperature for 16 hours before being concentrated in vacuo and the residue passed through an SCX-2 cartridge. The product was eluted with ammonia in methanol to give imino(methyl)(piperidin-3-ylmethyl)-λ⁶-sulfanone (250 mg, 65%); ¹H NMR (500 MHz, Methanol-d₄) δ 3.34-3.24 (m, 1H), 3.19-3.10 (m, 2H), 3.10-3.07 (m, 3H), 3.05-2.97 (m, 1H), 2.60 (ddd, J=12.4, 11.5, 3.1 Hz, 1H), 2.52-2.43 (m, 1H), 2.30-2.18 (m, 1H), 2.08 (ddtd, J=30.1, 10.9, 3.8, 1.8 Hz, 1H), 1.75 (dq, J=13.8, 3.3 Hz, 1H), 1.61 (dtq, J=13.6, 11.5, 3.8 Hz, 1H), 1.37 (dtd, J=12.8, 11.3, 3.9 Hz, 1H).

Preparation 11: 2,5-Dimethyl-3-((methylsulfinyl)methyl)piperidine

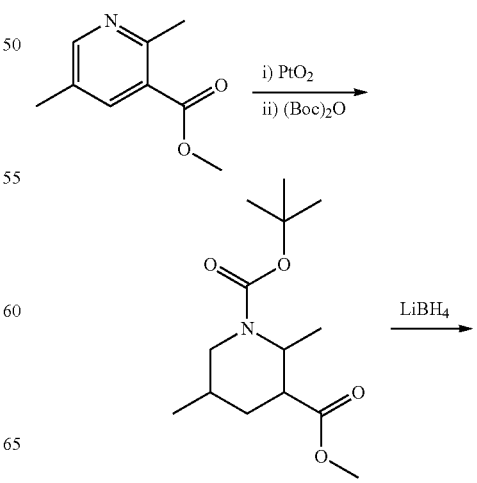

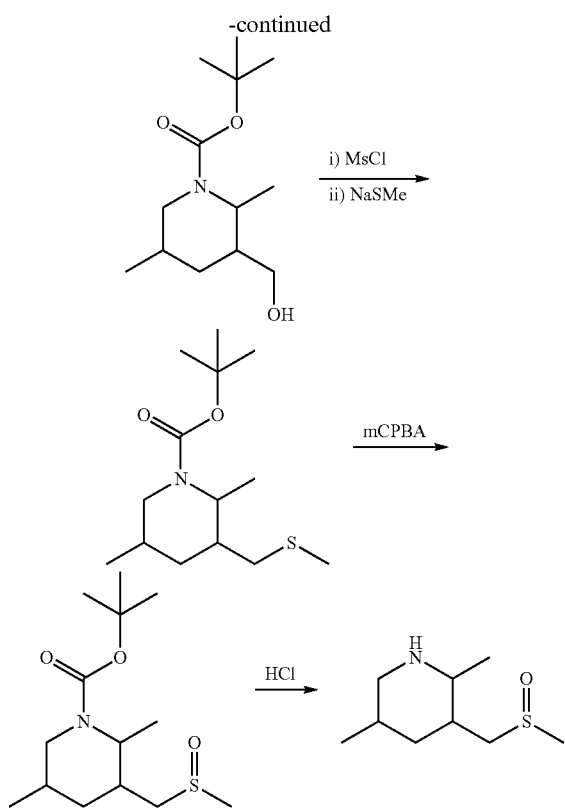

Step 1: 1-(tert-Butyl) 3-methyl 2,5-dimethylpiperidine-1,3-dicarboxylate

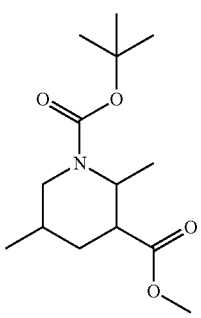

A mixture of methyl 2,5-dimethylpyridine-3-carboxylate (2.6 g, 15.74 mmol) and PtO$_2$ (713 mg, 3.14 mmol) in HCl (57 mL of a 3M solution in MeOH, 171.1 mmol) was stirred under a balloon of H$_2$. The reaction mixture was stirred for 16 hours at ambient temperature before being filtered through Celite and the filtrate concentrated in vacuo. The residue was dissolved in THF (27 mL) and triethylamine (6.6 mL, 47.3 mmol), DMAP (96 mg, 0.79 mmol) and di-tert-butyl dicarbonate (17.4 mL of a 1M solution in THF, 17.4 mmol) sequentially added. The reaction mixture was stirred for 16 hours, then partitioned between EtOAc and water. The organic layer was separated and washed with NH$_4$Cl solution, water (1×), brine (1×), then dried (MgSO$_4$), filtered and concentrated in vacuo. The residue was purified by chromatography (silica, 0-10% EtOAc/Petroleum ether gradient elution) to give 1-(tert-butyl) 3-methyl 2,5-dimethylpiperidine-1,3-dicarboxylate (1.4 g, 33%) as a colourless oil containing a mixture of diastereomers; $^1$H NMR (400 MHz, Methanol-d$_4$) δ 4.80-4.62 (m, 1H), 3.95-3.78 (m, 1H), 3.71 (d, 3H), 2.71 (dq, 1H), 2.46 (dt, 1H), 1.89-1.77 (m, 1H), 1.48 (q, 10H), 1.10-0.92 (m, 7H).

Step 2: tert-Butyl 3-(hydroxymethyl)-2,5-dimethyl-piperidine-1-carboxylate

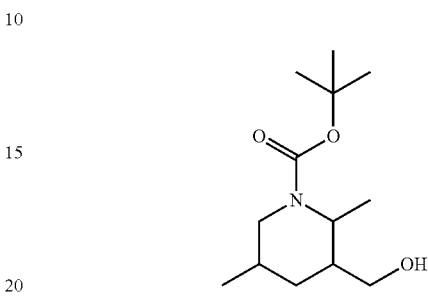

O1-tert-Butyl O3-methyl 2,5-dimethylpiperidine-1,3-dicarboxylate (1.40 g, 5.16 mmol) was dissolved in THF (42 mL) and cooled to 0° C. Lithium borohydride (10.3 mL of a 2M solution in THF, 20.6 mmol) was added and the reaction allowed to warm to ambient temperature. After 30 minutes the reaction mixture was warmed to 50° C. and stirred for 16 hours. The reaction was cooled to ambient temperature then quenched with water. The mixture was extracted with EtOAc (×3). The combined organics were dried and concentrated in vacuo to give tert-butyl 3-(hydroxymethyl)-2,5-dimethyl-piperidine-1-carboxylate (1.25 g, 100%) as a colourless oil that was taken directly on to the next reaction without further purification; $^1$H NMR (400 MHz, Methanol-d$_4$) δ 4.42-4.27 (m, 1H), 3.82-3.68 (m, 1H), 3.34-3.23 (m, 2H), 2.33 (dt, 1H), 1.91 (s, 1H), 1.82-1.68 (m, 1H), 1.54-1.37 (m, 2H), 1.35 (s, 9H), 0.95-0.87 (m, 3H), 0.86-0.76 (m, 4H).

Step 3: tert-Butyl 2,5-dimethyl-3-(((methylsulfonyl)oxy)methyl)piperidine-1-carboxylate

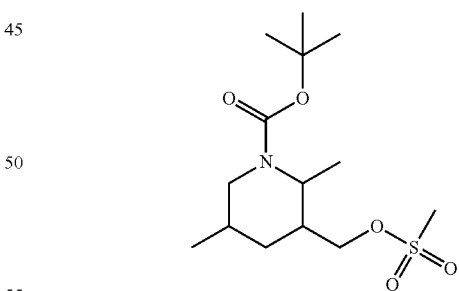

Methanesulfonyl chloride (2.77 mL, 35.7 mmol) was added to a solution of tert-butyl 3-(hydroxymethyl)-2,5-dimethylpiperidine-1-carboxylate (5.80 g, 23.8 mmol) and triethylamine (6.64 mL, 47.7 mmol) in DCM (116 mL) stirring at 0° C. After 30 mins the reaction was quenched with saturated aq. NaHCO$_3$, stirred for 5 mins and then the layers separated using a phase separator cartridge. The organic phase was evaporated in vacuo to give tert-butyl 2,5-dimethyl-3-(((methylsulfonyl)oxy)methyl)piperidine-1-carboxylate (7.6 g) which was used directly in the next step without further purification.

Step 4: tert-Butyl 2,5-dimethyl-3-((methylthio)methyl)piperidine-1-carboxylate

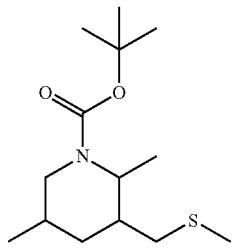

Sodium thiomethoxide (9.94 g, 141.8 mmol) was added to a solution of tert-butyl 2,5-dimethyl-3-(((methylsulfonyl)oxy)methyl)piperidine-1-carboxylate (7.6 g, 23.6 mmol) in EtOH (100 mL), stirring at 0° C. After addition, cooling was removed and the reaction heated at 60° C. for 16 hours. The reaction was cooled to ambient temperature, concentrated in vacuo and purified by column chromatography (silica, eluting with 0-12.5% MeOH in DCM gradient) to give tert-butyl 2,5-dimethyl-3-((methylthio)methyl)piperidine-1-carboxylate (3.4 g, 66%) as a colourless oil; $^1$H NMR (500 MHz, Methanol-$d_4$) δ 4.53-4.43 (m, 1H), 3.86 (td, J=13.3, 4.4 Hz, 1H), 2.53-2.31 (m, 3H), 2.10 (s, 3H), 1.91-1.81 (m, 1H), 1.74-1.63 (m, 1H), 1.61-1.50 (m, 1H), 1.48 (s, 9H), 1.10-0.99 (m, 4H), 0.93 (t, J=6.4 Hz, 3H).

Step 5: tert-Butyl 2,5-dimethyl-3-((methylsulfinyl)methyl)piperidine-1-carboxylate

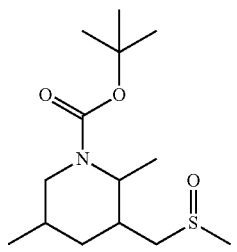

tert-Butyl 2,5-dimethyl-3-((methylthio)methyl)piperidine-1-carboxylate (2 g, 7.31 mmol) was dissolved in DCM (73 mL) and the solution cooled to 0° C. m-CPBA (1.80 g, 7.31 mmol) was added portionwise over 5 min and the reaction stirred for a further 5 min before being quenched by addition of saturated aqueous sodium thiosulphate (40 mL) and stirred for 5 min before extracting with DCM (3×50 mL). The combined organics were washed with with saturated aq. NaHCO$_3$ (2×40 mL), filtered through a phase separator cartridge and concentrated in vacuo to give tert-butyl 2,5-dimethyl-3-((methylsulfinyl)methyl)piperidine-1-carboxylate (2.1 g, 100%) as a colourless oil which was used without further purification.

Step 6: 2,5-Dimethyl-3-((methylsulfinyl)methyl)piperidine

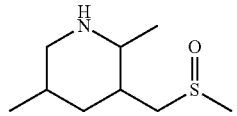

tert-Butyl 2,5-dimethyl-3-((methylsulfinyl)methyl)piperidine-1-carboxylate (2.1 g, 7.26 mmol) was dissolved in methanol (36 mL) and 4M HCl in dioxane (9.1 mL, 36.3 mmol) was added. The reaction was stirred for 16 hours at ambient temperature before being concentrated in vacuo to give 2,5-dimethyl-3-((methylsulfinyl)methyl)piperidine (1.85 g, 97%) as a white solid; MS m/z: 190.1 (M+H)$^+$.

Preparation 12: 2-(1H-Pyrazol-4-yl)piperazine

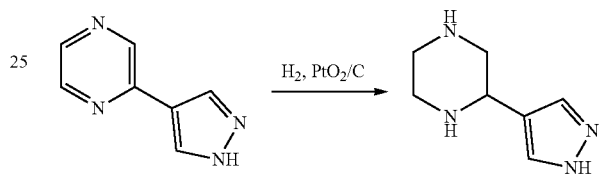

A mixture of 2-(1H-pyrazol-4-yl)pyrazine (400 mg, 2.7 mmol), PtO2 (100 mg, 0.4 mmol) in methanol (15 mL) was shaken at ambient temperature under a 60 psi H$_2$ pressure for 18 hours. The reaction mixture was filtered and the filtrate concentrated in vacuo to give 2-(1H-pyrazol-4-yl)piperazine as a colourless oil, which was taken directly on to the next reaction without purification; MS m/z: 153 (M+H)$^+$.

Preparation 13: 2,5-Dimethyl-3-(1H-pyrazol-4-yl)piperazine

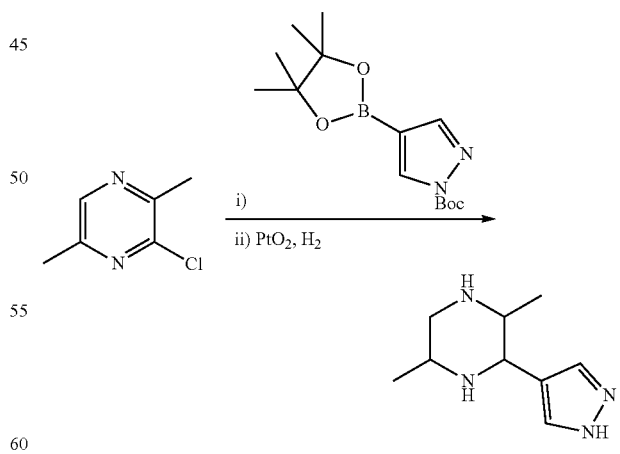

A 3-necked flask equipped with reflux condenser and thermometer was charged with 3-chloro-2,5-dimethyl-pyrazine (5 mL, 40 mmol), tert-butyl 4-(4,4,5,5-tetramethyl-1,3,2-dioxaborolan-2-yl)pyrazole-1-carboxylate (10 g, 34 mmol) in 1,4-dioxane (100 mL). Pd(PPh$_3$)$_4$(2 g, 2 mmol), and Na$_2$CO$_3$ (60 mL of 2M, 100 mmol) were added and the solution was evacuated and backfilled with $N_2$ (×2). The solution was heated at 100° C. and stirred overnight. The reaction mixture was cooled to ambient temperature and filtered, washing with diethyl ether. The filtrate was concentrated in vacuo and the residue purified by chromatography (silica, 0-100% [EtOAc+2% 2M methanolic ammonia]-Petroleum ether gradient elution). The product fractions were combined and concentrated in vacuo to give 2,5-dimethyl-3-(1H-pyrazol-4-yl)pyrazine as a white solid (4.5 g, 64%); MS m/z: 175 (M+H)$^+$.

A mixture of 2,5-dimethyl-3-(1H-pyrazol-4-yl)pyrazine (4.5 g, 26 mmol), $PtO_2$ (1 g, 4 mmol) and HCl (60 mL of a 3M solution in MeOH, 200 mmol) was shaken in a Parr hydrogenator for 24 hours under a pressure of 60 psi $H_2$. The reaction mixture was filtered and the filtrate concentrated in vacuo to give the product 2,5-dimethyl-3-(1H-pyrazol-4-yl)piperazine as an off-white solid (4.0 g, 61%); MS m/z: 181 (M+H)$^+$. This material was used in the next reaction assuming the dihydrochloride salt was isolated.

The following compounds were prepared using a methodology similar to the one described in Preparation 213:
2-Methyl-6-(1H-pyrazol-4-yl)piperazine;
3-(1H-Imidazol-4-yl)-2,5-dimethylpiperazine.

Preparation 14: Dimethyl((5-methylpiperidin-3-yl)imino)-$\lambda^6$-sulfanone

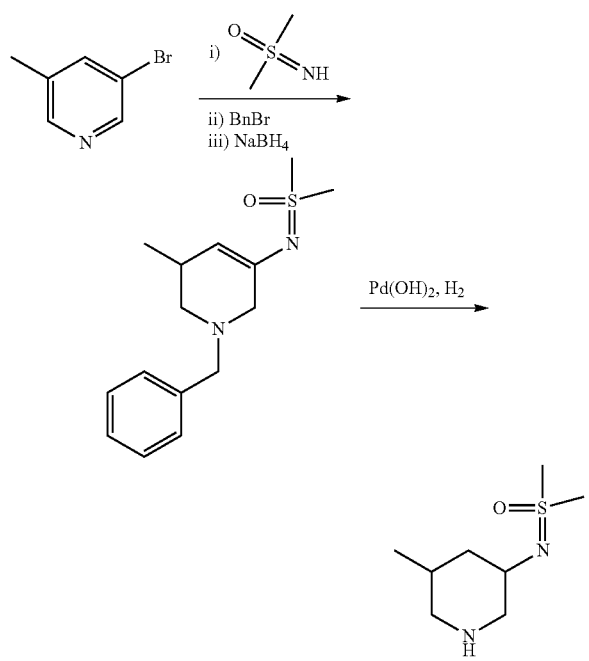

Step 1: Dimethyl((5-methyl-pyridin-3-yl)imino)-$\lambda^6$-sulfanone

3-Bromo-5-methyl-pyridine (250 g, 1.439 mol), iminodimethyl-$\lambda^6$-sulfane (142.6 g, 1.454 mol), Xantphos (24.976 g, 43.16 mmol), $K_2CO_3$ (218.8 g, 1.583 mol) and tris(benzylideneacetone)dipalladium(0) (19.76 g, 21.58 mmol) were suspended in 1,4-dioxane (2.4 L). The reaction mixture was degassed (vacuum/nitrogen 3 cycles) and stirred under reflux at 125° C. for 16 hours. The reaction mixture was allowed to cool to ambient temperature then filtered through Celite washing with EtOAc. The oil was diluted with a little MTBE (just enough to see hint of precipitation; ~150 ml), seeded with a few crystals of an authentic sample and stirred at ambient temperature for 2 hours. The solid was filtered and washed with a minimum of MTBE to give a light pink solid which was dried in the oven at 30° C. in vacuo to give the desired product (105.9 g, 40%). The mother liquors were concentrated in vacuo to give 247.4 g of a dark brown oil. 247.4 g of crude mixture was purified on column column chromatography (3 kg silica column; product adsorbed onto 350 g silica pad; 0 to 10% MeOH in EtOAc). Product-containing fractions were combined and concentrated in vacuo to give the product after trituration with diethyl ether (106.4 g 40%). Total yield 212.3 g (80%); $^1$H NMR (400 MHz, DMSO-$d_6$) δ 7.97 (d, J 2.4 Hz, 1H), 7.92 (dd, J 1.9, 0.9 Hz, 1H), 7.13 (dq, J 2.8, 0.9 Hz, 1H), 3.25 (s, 6H), 2.22 (d, J 0.8 Hz, 3H); ESV-MS m/z 185.0 (M+1)$^+$.

Step 2: 1-Benzyl-3-((dimethyl(oxo)-$\lambda^6$-sulfanylidene)amino)-5-methylpyridin-1-ium bromide To a solution of dimethyl((5-methyl-pyridin-3-yl)imino)-$\lambda^6$-sulfanone (105.9 g, 574.73 mmol) in MeCN (900 mL) was added BnBr (69 mL, 580 mmol). The mixture was stirred at 100° C. for 4 hours. The reaction mixture was allowed to cool to ambient temperature and the resulting precipitate collected by filtration, washing with cold MeCN. The product was obtained as an off-white solid (158.8 g, 78%); $^1$H NMR (400 MHz, DMSO-$d_6$) δ 8.55 (s, 1H), 8.48 (t, J 1.8 Hz, 1H), 7.87 (t, J=1.5 Hz, 1H), 7.58-7.49 (m, 2H), 7.49-7.37 (m, 3H), 5.67 (s, 2H), 3.44 (s, 6H), 2.41 (s, 3H). ESV-MS m/z 275.1 (M+1)$^+$.

Step 3: ((1-benzyl-, 5-methyl-1,2,5,6-tetrahydropyridin-3-yl)imino)dimethyl-$\lambda^6$-sulfanone A solution of $NaBH_4$ (43 g, 1.137 mol) in sodium hydroxide (1.6 L of 0.01 M 16.00 mmol) was added dropwise via syringe pump over 2 hours to a solution of 1-benzyl-3-((dimethyl(oxo)-$\lambda^6$-sulfanylidene)amino)-5-methylpyridin-1-ium bromide (200 g, 562.9 mmol) in ethanol (600 mL)/water (600 mL) at 0° C. under $N_2$. The mixture was extracted with MTBE (3×1.6 L), the organics combined and washed with brine (1×600 mL), dried ($MgSO_4$), filtered and concentrated in vacuo to give the desired product (142 g, 91%); 1H NMR (400 MHz, Chloroform-d) δ 7.40-7.17 (m, 5H), 5.18-5.10 (m, 1H), 3.58 (s, 2H), 3.08 (d, J=1.9 Hz, 6H), 3.04-2.93 (m, 1H), 2.86-2.68 (m, 3H), 2.55-2.40 (m, 1H), 1.92 (dd, J=11.0, 8.2 Hz, 1H), 0.95 (d, J=6.9 Hz, 3H). ESV-MS m/z 279.1 (M+1)$^+$.

Step 4: Dimethyl((5-methylpiperidin-3-yl)imino)-$\lambda^6$-sulfanone

Pd(OH)$_2$, (59 g, 20% w/w, Degussa, 84.03 mmol) was transferred to a nitrogen-filled bottle and the vessel evacuated and re-filled with nitrogen. A solution of ((1-benzyl-, 5-methyl-1,2,5,6-tetrahydropyridin-3-yl)imino)dimethyl-$\lambda^6$-sulfanone (117 g, 420.2 mmol) in methanol (700 mL) was then added and the resulting solution degassed by vacuum/nitrogen cycles (×3). The atmosphere was exchanged by vacuum/hydrogen cycles and the reaction mixture was shaken on a Parr hydrogenator for 16 hours. The reaction mixture was cooled to ambient temperature then was filtered through Celite and concentrated in vacuo to leave an orange oil which was analysed and showed incomplete reaction. The product was redissolved in methanol (700 mL) and added to the Parr bottle containing dihydroxypalladium (59 g of 20% w/w, 84.03 mmol). The mixture was then shaken at 50° C. and 30 psi of molecular hydrogen overnight. The reaction mixture was cooled to ambient temperature then filtered through Celite and the filtrate concentrated in vacuo to leave an orange oil which was analysed by UPLC-MS—showing incomplete reaction. The mixture was again redissolved in methanol (700 mL) and added to a Parr bottle containing dihydroxypalladium (59 g of 20% w/w, 84.03 mmol). The mixture was shaken at 50° C. and under a 30 psi atmosphere of molecular hydrogen on a Parr hydrogenator overnight. The mixture was cooled to ambient temperature then filtered through Celite before concentrating in vacuo to give dimethyl((5-methylpiperidin-3-yl)imino)-$\lambda^6$-sulfanone (56.7 g, 71%); 1H NMR (500 MHz, DMSO-$d_6$) δ 3.54 (masked signal, 1H), 3.09 (tt, J=10.8, 4.4 Hz, 1H), 2.95 (s, 6H), 2.89-2.74 (m, 2H), 2.11 (dd, J=12.0, 10.3 Hz, 1H), 1.92 (dd, J=12.1, 11.0 Hz, 1H), 1.84-1.73 (m, 1H), 1.58-1.44 (m, 1H), 0.89 (d, J=12.4 Hz, 1H), 0.77 (d, J=6.6 Hz, 3H).

The following compound was prepared using a methodology similar to the one described in Preparation 214:

Dimethyl((piperidin-3-yl)imino)-$\lambda^6$-sulfanone

Preparation 15:
2,5-Dimethylpiperidine-3-carboxamide

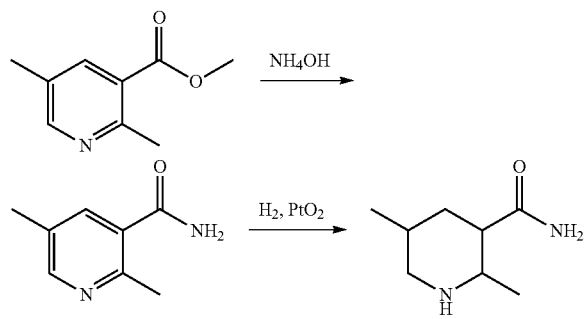

Step 1: 2,5-Dimethylnicotinamide

Methyl 2,5-dimethylpyridine-3-carboxylate (100 mg, 0.61 mmol) was dissolved in ammonium hydroxide (480 µL, 12.3 mmol) and the mixture heated to 70° C. in a sealed tube. After 16 hours the reaction was diluted in water and the mixture concentrated in vacuo to give 2,5-dimethylpyridine-3-carboxamide (91 mg, 100%) as a white solid; MS m/z: 151.0 (M+H)$^+$.

Step 2: 2,5-Dimethylpiperidine-3-carboxamide 2,5-dimethylnicotinamide (99 mg, 0.66 mmol) and PtO$_2$ (30.4 mg, 0.13 mmol) were dissolved in methanol (3 mL) and 3M HCl (1.1 mL, 3.30 mmol). The mixture was degassed and stirred under a balloon of H$_2$ for 90 min before being passed through Celite and the filtrate concentrated in vacuo to give 2,5-dimethylpiperidine-3-carboxamide (dihydrochloride salt) (150 mg, 99%); MS m/z: 157.0 (M+H)$^+$.

Preparation 16: N-(((3S,5S)-4,4-Difluoro-5-methyl-piperidin-3-yl)methyl)methanesulfonamide

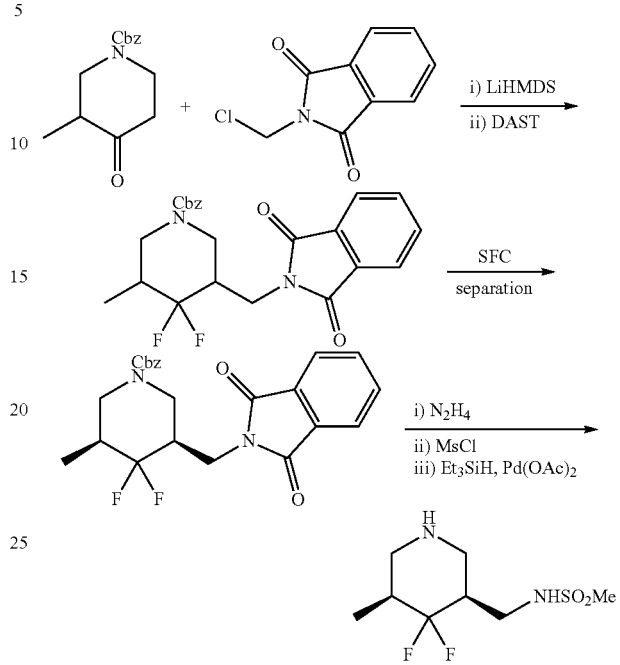

Step 1: Benzyl 3-((1,3-dioxoisoindolin-2-yl)methyl)-5-methyl-4-oxopiperidine-1-carboxylate Benzyl 3-methyl-4-oxo-piperidine-1-carboxylate (20 g, 0.08 mol) was dissolved in THF (300 mL) under N$_2$. The solution was cooled to −78° C. and LiHMDS (1M in THF, 101.1 mL, 0.1 mol) was added dropwise over 20 minutes, keeping the temperature below −70° C. After stirring at −78° C. for 90 minutes, a solution of 2-(chloromethyl)isoindoline-1,3-dione (23.7 g, 0.12 mol) in THF (200 mL) was added dropwise over 25 minutes, keeping the temperature below −70° C. The reaction was stirred at −78° C. for 1 hour then quenched at −78° C. by the addition of saturated aqueous ammonium chloride solution (65 mL) and the mixture allowed to warm to ambient temperature. The reaction was repeated and the two mixtures obtained were combined and extracted with EtOAc (300 mL). The organic phase was washed with saturated aqueous sodium bicarbonate solution (300 mL) and brine (300 mL), dried (Na$_2$SO$_4$), filtered and concentrated in vacuo. The residue was purified by chromatography (silica, EtOAc/Petroleum ether elution). Product fractions were combined and concentrated in vacuo and the residue recrystallized from EtOAc to give the product as a white solid (7.56 g, 23%).

Step 2: Benzyl (3R,5S)-3-[(1,3-Dioxoisoindolin-2-yl)methyl]-4,4-difluoro-5-methyl-piperidine-1-carboxylate A flask was charged with benzyl 3-((1,3-dioxoisoindolin-2-yl)methyl)-5-methyl-4-oxopiperidine-1-carboxylate (60 g, 0.15 mol) and cooled in an ice/water bath. DAST (325 mL, 2.5 mol) was added in one portion and the mixture stirred at ambient temperature for 3 days. The resulting yellow solution was diluted with DCM (1 L) and slowly added to a mixture of ice/water and solid sodium bicarbonate with overhead stirring. The temperature remained below 0° C. and additional sodium bicarbonate was added to maintain a pH of 7-8. The mixture was warmed to ambient temperature and the layers separated. The aqueous phase was extracted with DCM (2 L). The combined organics were washed with brine, dried (Na$_2$SO$_4$), filtered and concentrated in vacuo. The residue was purified by chromatography (silica, EtOAc/Petroleum ether elution). Product fractions were combined and concentrated in vacuo. The product benzyl 3-((1,3-dioxoisoindolin-2-yl)methyl)-4,4-difluoro-5-methylpiperidine-1-carboxylate, was obtained as a glass (32.5 g, 51%); $^1$H NMR (400 MHz, chloroform-d) δ 7.89-7.64 (4H, m), 7.42-7.11 (5H, m), 5.15-5.03 (2H, m), 4.39-4.07 (3H, m), 3.83-3.66 (1H, m), 2.97-2.60 (2H, m), 2.56-2.31 (1H, m), 2.08-1.89 (1H, m), 1.05 (3H, d) as a mixture of isomers.

Preparative chiral supercritical fluid chromatography (conditions: Chiralpak® IC 5 µm, CO$_2$/iPrOH 90/10, 230 nm) was used to isolate the single enantiomer benzyl (3R,5S)-3-[(1,3-dioxoisoindolin-2-yl)methyl]-4,4-difluoro-5-methyl-piperidine-1-carboxylate, (98.7% ee).

Step 3: Benzyl (3R,5S)-3-(aminomethyl)-4,4-difluoro-5-methyl-piperidine-1-carboxylate To a suspension of benzyl (3R,5S)-3-[(1,3-dioxoisoindolin-2-yl)methyl]-4,4-difluoro-5-methyl-piperidine-1-carboxylate (9.6 g, 22.4 mmol) in ethanol (144 mL) was added hydrazine hydrate (8.5 mL, 112 mmol). The reaction mixture was heated to reflux for 5 hours then allowed to cool to ambient temperature overnight. The resulting suspension was filtered and the precipitate washed with EtOH (×2). The filtrate was loaded onto ion-exchange cartridges (50 g×10). The cartridges were washed with MeOH/DCM mixtures (filtrates discarded), then with 2M methanolic ammonia solution. The filtrates were combined and concentrated in vacuo. The residue was taken up in methanol and concentrated in vacuo (×2), then treated with heptane and concentrated in vacuo. The resulting yellow oil was dried under vacuum overnight to give the product as a solid (6.77 g), which was taken directly on to the next reaction; $^1$H NMR (400 MHz, DMSO-d$_6$) δ 7.48-7.17 (m, 5H), 5.11 (s, 2H), 4.41 (ddt, 1H), 4.02 (d, 1H), 2.98 (dd, 1H), 2.64 (s, 2H), 2.41 (dd, 1H), 2.15-1.78 (m, 2H), 1.50 (s, 2H), 0.93 (d, 3H); MS m/z: 299 (M+H)$^+$.

Step 4: Benzyl (3S,5S)-4,4-difluoro-3-(methanesulfonamidomethyl)-5-methyl-piperidine-1-carboxylate Benzyl (3R,5S)-3-(aminomethyl)-4,4-difluoro-5-methyl-piperidine-1-carboxylate (6.6 g, 22 mmol) was dissolved in DCM (66 mL) and cooled in an ice bath. The internal temperature reached was 3° C. Et$_3$N (3.4 mL, 24 mmol) was added with stirring. Methanesulfonyl chloride (1.88 mL, 24 mmol) was added over 5 minutes, at such a rate to keep the internal temperature below 10° C. After 30 minutes, the ice bath was removed. The solution was warmed up to ambient temperature and quenched with a saturated aqueous NaHCO$_3$ solution (66 mL). The layers were separated and the aqueous phase extracted with DCM (33 mL). The combined organics were dried over MgSO$_4$, filtered and concentrated in vacuo. The residue was purified by chromatography (silica; 0 to 100% EtOAc/Petroleum ether gradient elution). The product fractions were combined and concentrated in vacuo. The residue was dried overnight under vacuum to give a white solid (7.92 g; 95%); $^1$H NMR (400 MHz, DMSO-d$_6$) δ 7.45-7.31 (m, 5H), 7.31-7.19 (m, 1H), 5.12 (s, 2H), 4.37 (d, 1H), 4.18-3.94 (m, 1H), 3.38 (ddd, 1H), 3.00-2.80 (m, 4H), 2.68 (s, 2H), 2.15 (s, 2H), 0.95 (d, 3H); MS m/z: 377 (M+H)$^+$.

Step 5: N-(((3S,5S)-4,4-Difluoro-5-methylpiperidin-3-yl)methyl)methanesulfonamide To a solution of benzyl (3S,5S)-4,4-difluoro-3-(methanesulfonamidomethyl)-5-methyl-piperidine-1-carboxylate (7.54 g, 20 mmol) in DCM (113 mL) was added Et$_3$N (8.38 mL, 60 mmol), followed by Pd(OAc)$_2$ (1.799 g, 8 mmol). Et$_3$SiH (19.20 mL, 120 mmol) was added over 5 minutes. The solution was stirred at ambient temperature for 1 hour then separated into 6 equal portions and loaded onto ion-exchange cartridges (50 g). The cartridges were washed with DCM, 1:1 MeOH:DCM and methanol. The filtrates were discarded. The cartridges were washed with 2M methanolic ammonia solution. The filtrates were combined and concentrated in vacuo. The residue was azeotroped with DCM then taken up in methanol (45 mL) and stirred with SPM32 (3-mercaptopropyl ethyl sulfide silica) for 2 hours at ambient temperature, then at 50° C. for 1 hour. The mixture was cooled and filtered through Celite and the filtrate concentrated in vacuo. The residue was taken up in DCM and concentrated in vacuo. The residue was dried overnight under vacuum to give N-(((3S,5S)-4,4-difluoro-5-methylpiperidin-3-yl)methyl)methanesulfonamide as a white solid (4.40 g, 91%); $^1$H NMR (400 MHz, DMSO-d$_6$) δ 7.10 (t, 1H), 3.43-3.33 (m, 1H), 3.26-3.10 (m, 1H), 2.93-2.88 (m, 4H), 2.79 (dtd, 1H), 2.38-2.20 (m, 2H), 2.13-1.78 (m, 2H), 0.89 (d, 3H); MS m/z: 243.0 (M+H)$^+$.

Preparation 17:
N-(Pyrrolidin-3-ylmethyl)methanesulfonamide

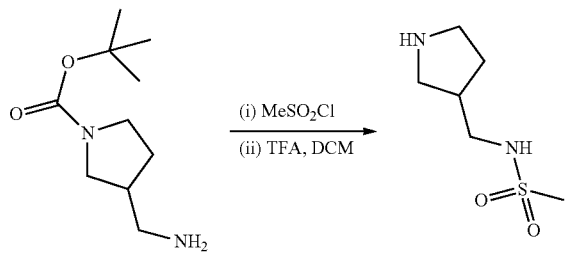

Step 1: tert-Butyl 3-(methanesulfonamidomethyl)pyrrolidine-1-carboxylate

Methanesulfonyl chloride (222 mg, 150 µL, 1.938 mmol) was added to a stirred solution of tert-butyl 3-(aminomethyl) pyrrolidine-1-carboxylate (300 mg, 1.498 mmol) and triethylamine (232.3 mg, 320 µL, 2.296 mmol) in THF (10 mL) under an atmosphere of nitrogen and the reaction was stirred at ambient temperature for 1.5 hours. The reaction was diluted with DCM and saturated aqueous NaHCO$_3$ and the mixture was stirred for 10 minutes. The layers were separated and the aqueous layer extracted with DCM (×2). The combined organic extracts were dried (MgSO$_4$), filtered and concentrated in vacuo to give tert-butyl 3-(methanesulfonamidomethyl)pyrrolidine-1-carboxylate as a pale yellow oil that was deprotected assuming 100% yield and purity; $^1$H NMR (500 MHz, DMSO-d$_6$) δ 7.11 (t, J=6.2 Hz, 1H), 3.40-3.35 (m, 1H), 3.32-3.28 (m, 1H), 3.23-3.15 (m, 1H), 2.95-2.93 (m, 3H), 2.89 (s, 3H), 2.31-2.26 (m, 1H), 1.93-1.88 (m, 1H), 1.65-1.52 (m, 1H), 1.40 (s, 9H); ESV-MS m/z calc. 278.13004, found 223.1 (M+1)⁺.

Step 2:
N-(Pyrrolidin-3-ylmethyl)methanesulfonamide

TFA (2.960 g, 2 mL, 25.96 mmol) was added to a stirred solution of tert-butyl 3-(methanesulfonamidomethyl)pyrrolidine-1-carboxylate (417 mg, 1.498 mmol) in DCM (20 mL) and the reaction mixture was stirred at ambient temperature for 15 hours. The solvent was removed in vacuo and the residue azeotroped with DCM (×2) and diethyl ether (×2). The residue was passed through a 10 g SCX-2 cartridge and washed with MeOH/DCM mixtures. The product was eluted by washing the cartridge with 2M NH₃ in MeOH/DCM mixtures. The solvent was removed in vacuo to give N-(pyrrolidin-3-ylmethyl)methanesulfonamide (227.4 mg, 85%) as a pale yellow solid; ¹H NMR (500 MHz, chloroform-d) δ 3.16 (qd, J=12.3, 6.5 Hz, 2H), 3.09-3.03 (m, 2H), 2.98 (s, 3H), 2.94-2.89 (m, 1H), 2.75 (dd, J=10.7, 5.0 Hz, 1H), 2.40-2.32 (m, 1H), 2.04-1.96 (m, 1H), 1.55-1.48 (m, 1H). ESV-MS m/z 179.2 (M+1)⁺.

Preparation 18: 4-Pyrrolidin-3-yl-1H-pyrazole

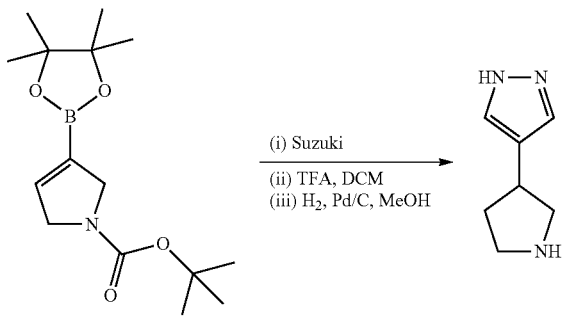

Step 1: tert-Butyl 3-(1H-pyrazol-4-yl)-2,5-dihydropyrrole-1-carboxylate tert-Butyl 4-bromopyrazole-1-carboxylate (230 mg, 0.931 mmol), tert-butyl 3-(4,4,5,5-tetramethyl-1,3,2-dioxaborolan-2-yl)-2,5-dihydropyrrole-1-carboxylate (250 mg, 0.847 mmol) and potassium carbonate (1.3 mL of 2M, 2.60 mmol) were combined in dioxane (3 mL) and the mixture de-gassed (×2 vacuum cycles). Pd(dppf)Cl₂.DCM (70 mg, 0.086 mmol) was added and the mixture de-gassed (×2 vacuum cycles) then heated at 90° C. overnight. The reaction mixture was partitioned between EtOAc and water. The organic phase was dried (Na₂SO₄), filtered and concentrated in vacuo. The residue was purified by chromatography (silica, 0-100% EtOAc/Petroleum ether gradient elution). Product fractions were combined and concentrated to give the product as a pale yellow film (65 mg, 33%) that was taken on to the next reaction. ESV-MS m/z 236.0 (M+1)⁺.

Steps 2 and 3: 4-Pyrrolidin-3-yl-1H-pyrazole tert-Butyl 3-(1H-pyrazol-4-yl)-2,5-dihydropyrrole-1-carboxylate (550 mg, 2.338 mmol) was dissolved in DCM (10 mL) and TFA added. After 1 hour the reaction mixture was concentrated in vacuo and the residue azeotroped with DCM (×2). The residue was taken up in methanol (10 mL) and the solution degassed (×3 vacuum—N₂ cycles). Pd on C, wet, Degussa (200 mg of 10% w/w, 0.188 mmol) was added and the mixture degassed (×3 cycles). The N₂ atmosphere was replaced with hydrogen (×3 cycles) and the mixture stirred at ambient temperature. After 90 minutes the reaction mixture was filtered over Celite, washing with methanol. The filtrate was concentrated in vacuo (cold water bath) to give crude 4-pyrrolidin-3-yl-1H-pyrazole (trifluoroacetate salt) (600 mg, quantitative yield); ESV-MS m/z 136.0 (M+1)⁺

Preparation 19: (E)-2-(2-Ethoxyvinyl)-4-(methylthio)pyrimidine

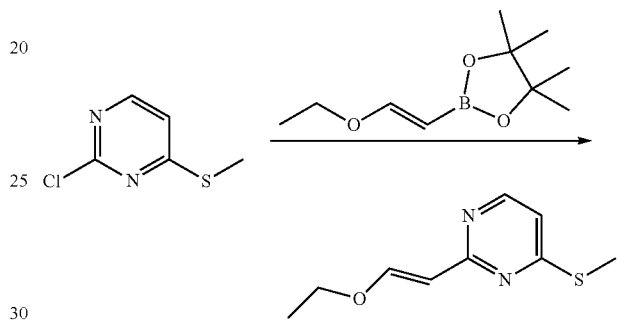

To a suspension of 2-chloro-4-(methylthio)pyrimidine (56.1 g, 349.3 mmol) and 2 M aq. Na₂CO₃ (524 mL, 1.05 mol) in 1,2-dimethoxyethane (730 mL) was added 2-[(E)-2-ethoxyvinyl]-4,4,5,5-tetramethyl-1,3,2-dioxaborolane (76.1 g, 384 mmol). Pd(PPh₃)₄ (20.2 g, 17.5 mmol) was added and the mixture degassed. The reaction was placed under a nitrogen atmosphere and heated at reflux for 4 hours. The mixture was cooled to ambient temperature and partitioned between EtOAc (1.1 L) and water (560 mL). The organic layer was washed with water (2×560 mL), the combined organic layers were re-extracted with EtOAc (280 mL) and the combined organic phases were washed with brine (×1), dried (MgSO₄), filtered and concentrated in vacuo. The residue was purified by column chromatography (silica, eluting with 0 to 25% EtOAc/petroleum ether) to give (E)-2-(2-ethoxyvinyl)-4-(methylthio)pyrimidine as a pale yellow, crystalline solid (62.4 g, 91%); ¹H NMR (500 MHz, Chloroform-d) δ 8.18 (d, J=5.5 Hz, 1H), 7.95 (d, J=12.6 Hz, 1H), 6.85 (d, J=5.5 Hz, 1H), 5.91 (d, J=12.6 Hz, 1H), 4.02 (q, J=7.0 Hz, 2H), 2.56 (s, 3H), 1.40 (t, J=7.0 Hz, 3H); ES+[M+H]=197.1.

Preparation 20: 2-chloro-4-{6-cyclopropylimidazo[1,2-a]pyridin-3-yl}pyrimidine

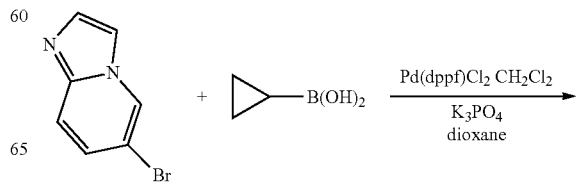

-continued

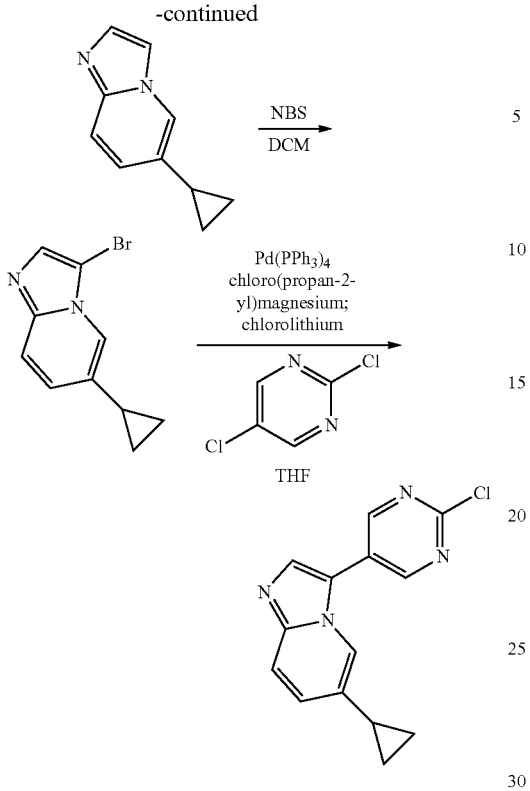

Step 1: 6-Cyclopropylimidazo[1,2-a]pyridine. Into a 150-mL round-bottom flask, was placed 6-bromoimidazo[1,2-a]pyridine (5 g, 22.84 mmol, 1 equiv, 90%), cyclopropylboronic acid (3.1 g, 34.26 mmol, 1.50 equiv, 95%), Pd(dppf)Cl$_2$.CH$_2$Cl$_2$ (2.0 g, 2.33 mmol, 0.10 equiv, 95%), dioxane (20 mL, 224.28 mmol, 9.82 equiv, 95%), K$_3$PO$_4$ (10.2 g, 45.68 mmol, 2.00 equiv, 95%). The resulting solution was stirred for overnight at 100 degrees C. in an oil bath. The resulting mixture was concentrated. The residue was applied onto a silica gel column with ethyl acetate/petroleum ether (1/5). This resulted in 3.6 g (89.67%) of 6-cyclopropylimidazo[1,2-a]pyridine as a white solid.

Step 2: 3-Bromo-6-cyclopropylimidazo[1,2-a]pyridine. Into a 150-mL round-bottom flask, was placed 6-cyclopropylimidazo[1,2-a]pyridine (3.6 g, 20.48 mmol, 1 equiv, 90%), NBS (3.8 g, 20.28 mmol, 0.99 equiv, 95%), DCM (20 mL, 298.87 mmol, 14.59 equiv, 95%). The resulting solution was stirred for 3 hr at 25 degrees C. The resulting mixture was concentrated. The residue was applied onto a silica gel column with ethyl acetate/petroleum ether (1/5). This resulted in 4.3 g (79.70%) of 3-bromo-6-cyclopropylimidazo[1,2-a]pyridine as a white solid.

Step 3: 2-Chloro-4-{6-cyclopropylimidazo[1,2-a]pyridin-3-yl}pyrimidine. To a stirred solution of 3-bromo-6-cyclopropylimidazo[1,2-a]pyridine (1.5 g, 5.694 mmol, 1 equiv, 90%) in THF (10 mL, 117.259 mmol, 21.0 equiv, 95%) was added iPrMgCl.LiCl (1.74 g, 11.388 mmol, 2 equiv, 95%) dropwise at −10 degrees Celsius under nitrogen atmosphere. The resulting mixture was stirred for 2 h at 0 degrees Celsius under nitrogen atmosphere. The above mixture was added into a stirred mixture of 2,4-dichloropyrimidine (1.07 g, 6.824 mmol, 1.20 equiv, 95%) and Pd(PPh$_3$)$_4$(0.35 g, 0.285 mmol, 0.05 equiv, 95%) in THF (10 mL, 117.259 mmol, 21.0 equiv, 95%) at room temperature. The resulting mixture was stirred for additional 4 h at 70 degrees Celsius. The resulting mixture was concentrated. The residue was applied onto a silica gel column with ethyl acetate/petroleum ether (1/10). This resulted in 1 g (58.39%) of 2-chloro-4-[6-cyclopropylimidazo[1,2-a]pyridin-3-yl]pyrimidine as a white solid.

The following compounds were prepared using a methodology similar to the one described in Preparation 20:

2-Chloro-4-{6-chloroimidazo[1,2-a]pyridin-3-yl}pyrimidine

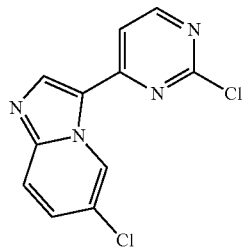

Preparation 21: 2-chloro-4-[(E)-2-ethoxyethenyl]-6-methylpyrimidine

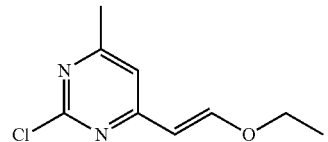

To a stirred solution of 2,4-dichloro-6-methylpyrimidine (246.88 mg, 1.439 mmol, 1.20 equiv, 95%), 2-[(E)-2-ethoxyethenyl]-4,4,5,5-tetramethyl-1,3,2-dioxaborolane (250 mg, 1.199 mmol, 1 equiv, 95%) and K$_3$PO$_4$ (535.84 mg, 2.398 mmol, 2.00 equiv, 95%) in MeCN (12.45 mL, 303.230 mmol, 187.63 equiv, 95%) and H2O (4 mL, 210.932 mmol, 364.96 equiv, 95%) were added SPhos (36.27 mg, 0.084 mmol, 0.07 equiv, 95%) and Pd(AcO)2 (8.50 mg, 0.036 mmol, 0.03 equiv, 95%) at room temperature under nitrogen atmosphere. The resulting mixture was stirred for overnight at room temperature under nitrogen atmosphere. The resulting mixture was concentrated to a small volume. The resulting mixture was diluted with brine (20 mL). The resulting mixture was extracted with EtOAc (3×50 mL). The combined organic layers were washed with brine (2×20 mL), dried over anhydrous MgSO4. After filtration, the filtrate was concentrated under reduced pressure. The residue was purified by silica gel column chromatography, eluted with PE/EtOAc (5:1) to afford 2-chloro-4-[(E)-2-ethoxyethenyl]-6-methylpyrimidine (100 mg, 37.78%) as a light yellow oil.

Preparation 22: 2-chloro-4-[6-(3,3-difluoroazetidin-1-yl)imidazo[1,2-a]pyridin-3-yl]-6-methylpyrimidine

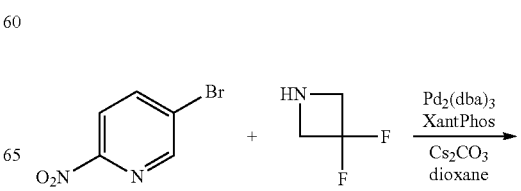

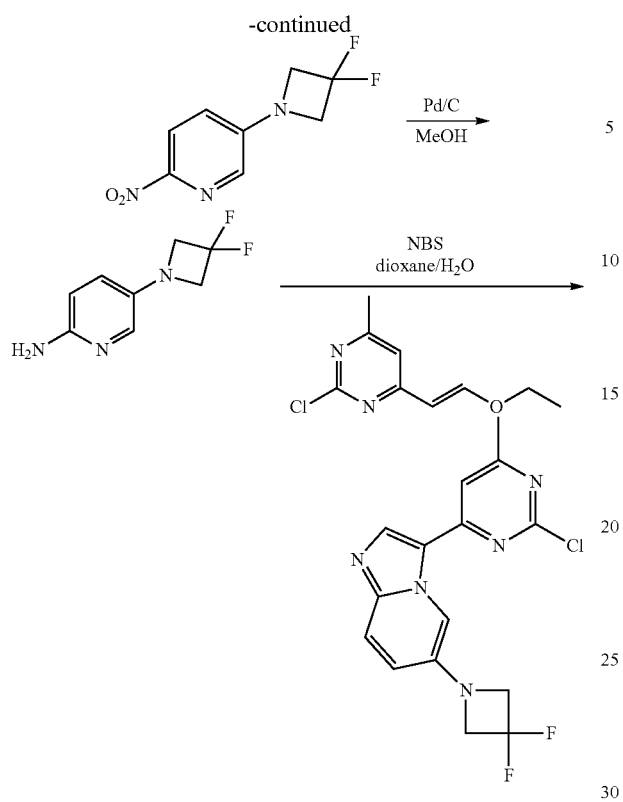

Step 1: 5-(3,3-difluoroazetidin-1-yl)-2-nitropyridine. To a stirred solution of 5-bromo-2-nitropyridine (500 mg, 2.340 mmol, 1 equiv, 95%), 3,3-difluoroazetidine hydrochloride (350.95 mg, 2.574 mmol, 1.1 equiv, 95%) and Cs2CO3 (4012.66 mg, 11.700 mmol, 5.00 equiv, 95%) in dioxane (37.50 mL, 425.622 mmol, 179.71 equiv, 95%) was added Pd2(dba)3 (112.78 mg, 0.117 mmol, 0.05 equiv, 95%) and XantPhos (142.52 mg, 0.234 mmol, 0.10 equiv, 95%) at room temperature under nitrogen atmosphere. The resulting mixture was stirred for 3 h at 100 degrees C. under nitrogen atmosphere. The resulting mixture was concentrated under reduced pressure. The residue was purified by silica gel column chromatography, eluted with PE/EtOAc (1:1) to afford 5-(3,3-difluoroazetidin-1-yl)-2-nitropyridine (200 mg, 27.81%) as a light yellow solid.

Step 2: 5-(3,3-difluoroazetidin-1-yl)pyridin-2-amine. To a stirred solution of 543,3-difluoroazetidin-1-yl)-2-nitropyridine (175 mg, 0.569 mmol, 1 equiv, 70%) in MeOH (56.00 mL, 1747.713 mmol, 2307.89 equiv, 95%) was added Pd/C (318.89 mg, 2.847 mmol, 5 equiv, 95%) in portions at room temperature under nitrogen atmosphere. The resulting mixture was stirred for overnight at room temperature under hydrogen atmosphere. The resulting mixture was filtered, the filter cake was washed with MeOH (3×30 mL). The filtrate was concentrated under reduced pressure. The crude product/resulting mixture was used in the next step directly without further purification.

Step 3: 2-chloro-4-[6-(3,3-difluoroazetidin-1-yl)imidazo[1,2-a]pyridin-3-yl]-6-methylpyrimidine. To a stirred solution of 2-chloro-4-[(E)-2-ethoxyethenyl]-6-methylpyrimidine (550 mg, 2.630 mmol, 1 equiv, 95%) in H2O (18 mL, 999.151 mmol, 379.87 equiv, 9%) and H2O (18 mL, 999.151 mmol, 379.87 equiv, 9%) was added NBS (492.78 mg, 2.630 mmol, 1 equiv, 95%) at room temperature. The resulting mixture was stirred for 1 h at room temperature. To the above mixture was added 5-(3,3-difluoroazetidin-1-yl)pyri-din-2-amine (666.51 mg, 3.419 mmol, 1.3 equiv, 95%). The resulting mixture was stirred for additional 2.5 h at 85 degrees C. The resulting mixture was diluted with EtOAc (20 mL). The mixture was neutralized to pH 7 with saturated Na2CO3 (aq.). The resulting mixture was extracted with EtOAc (3×30 mL). The combined organic layers were washed with brine (2×50 mL), dried over anhydrous MgSO4. After filtration, the filtrate was concentrated under reduced pressure. The residue was purified by silica gel column chromatography, eluted with CH2Cl2/MeOH (20:1). This resulted in 2-chloro-4-[6-(3,3-difluoroazetidin-1-yl)imidazo[1,2-a]pyridin-3-yl]-6-methylpyrimidine (290 mg, 31.85%) as a light yellow solid.

The following compounds were prepared using a methodology similar to the one described in Preparation 22:

2-Chloro-4-[6-(3-fluoroazetidin-1-yl)imidazo[1,2-a]pyridin-3-yl]pyrimidine

Preparation 23: 5-[6-(azetidin-1-yl)imidazo[1,2-a]pyridin-3-yl]-2-chloropyrimidine

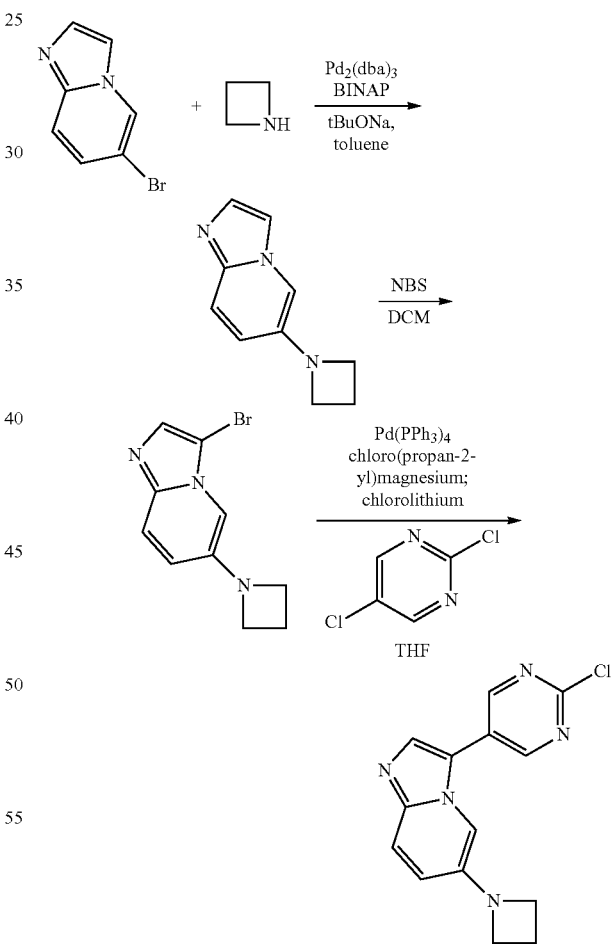

Step 1: 1-{imidazo[1,2-a]pyridin-6-yl}azetidine. Into a 500 mL round-bottom flask were added 6-bromoimidazo[1,2-a]pyridine (3.5 g, 15.99 mmol, 1 equiv, 90%), azetidine (1441.3 mg, 23.98 mmol, 1.50 equiv, 95%), toluene (300 mL, 2678.69 mmol, 167.55 equiv, 95%), BINAP (1047.9 mg, 1.60 mmol, 0.10 equiv, 95%) and t-BuONa (3234.5 mg, 31.97 mmol, 2.00 equiv, 95%) at room temperature. The resulting mixture was stirred for overnight at 100 degrees C. under nitrogen atmosphere. The resulting mixture was concentrated under vacuum. The residue was purified by silica gel column chromatography, eluted with PE/EtOAc (5:1) to afford 1-[imidazo[1,2-a]pyridin-6-yl]azetidine (2.5 g, 78.72%) as a green solid.

Step 2: 1-{3-bromoimidazo[1,2-a]pyridin-6-yl}azetidine. Into a 25 mL round-bottom flask were added 1-[imidazo[1,2-a]pyridin-6-yl]azetidine (1 g, 5.03 mmol, 1 equiv, 87.2%), NBS (896.0 mg, 4.78 mmol, 0.95 equiv, 95%) and DCM (60 mL, 896.61 mmol, 178.11 equiv, 95%) at room temperature. The resulting mixture was stirred for overnight at room temperature under nitrogen atmosphere. The resulting mixture was concentrated under reduced pressure. The residue was purified by silica gel column chromatography, eluted with PE/EtOAc (5:1) to afford 1-[3-bromoimidazo[1,2-a]pyridin-6-yl]azetidine (1.1 g, 56.25%) as a green solid.

Step 3: 5-[6-(azetidin-1-yl)imidazo[1,2-a]pyridin-3-yl]-2-chloropyrimidine. To a stirred solution of 1-[3-bromoimidazo[1,2-a]pyridin-6-yl]azetidine (200 mg, 0.777 mmol, 1 equiv, 98%) in THF (20 mL, 234.517 mmol, 301.66 equiv, 95%) was added dropwise at −10 degrees C. under N2 atmosphere. Chloro(propan-2-yl)magnesium chlorolithium (1 mL, 1.084 mmol, 1.39 equiv, 17.5%) was added. The resulting mixture was stirred for 2 h at 0 degrees C. under N2 atmosphere. The above mixture was added into a stirred mixture of 2,4-dichloropyrimidine (182.86 mg, 1.166 mmol, 1.50 equiv, 95%) and Pd(PPh₃)₄(47.28 mg, 0.039 mmol, 0.05 equiv, 95%) in THF at room temperature. The resulting mixture was stirred for additional 4 h at 80 degrees C. The reaction was quenched with sat. NH₄Cl (aq.) at room temperature. The aqueous layer was extracted with EtOAc (3×20 mL). The resulting mixture was concentrated under reduced pressure. The residue was purified by silica gel column chromatography, eluted with EA:PE (1:1) to afford 4-[6-(azetidin-1-yl)imidazo[1,2-a]pyridin-3-yl]-2-chloropyrimidine (120 mg, 19.61%) as a green solid.

Preparation 24:
5-(3-methyl-1H-pyrazol-4-yl)piperidin-3-ol

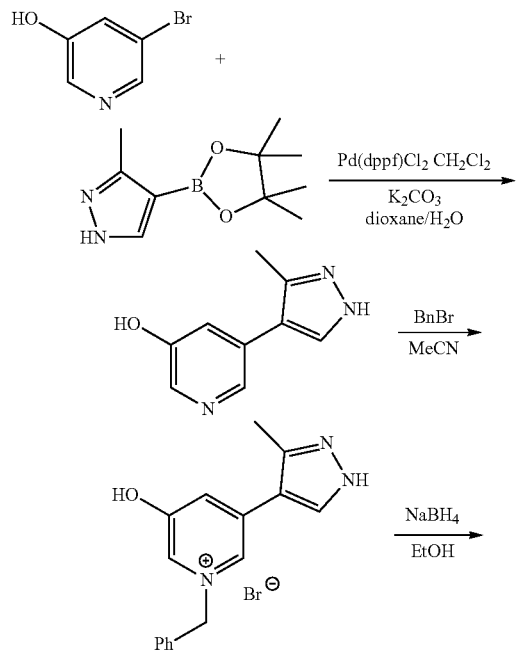

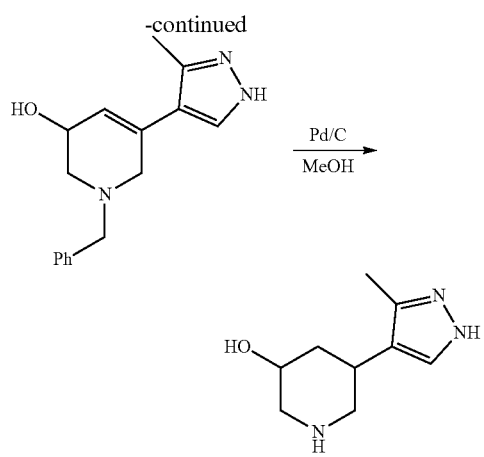

Step 1: 5-(3-Methyl-1H-pyrazol-4-yl)pyridin-3-ol. A mixture of 5-bromopyridin-3-ol (10 g, 54.599 mmol, 1 equiv, 95%), Pd(dppf)Cl₂.CH₂Cl₂ (2.35 g, 2.730 mmol, 0.05 equiv, 95%), K₂CO₃ (11.91 g, 81.898 mmol, 1.50 equiv, 95%) and 3-methyl-4-(4,4,5,5-tetramethyl-1,3,2-dioxaborolan-2-yl)-1H-pyrazole (14.35 g, 65.518 mmol, 1.2 equiv, 95%) in dioxane (150.01 mL, 1682.194 mmol, 30.81 equiv, 95%) and H2O (29.99 mL, 1664.971 mmol, 28.97 equiv, 95%) was stirred for overnight at 100 degrees C. under nitrogen atmosphere. The resulting mixture was concentrated under reduced pressure. The residue was purified by silica gel column chromatography, eluted with CH₂Cl₂/MeOH (10:1) to afford 5-(3-methyl-1H-pyrazol-4-yl)pyridin-3-ol (6.5 g, 61.16%) as a brown solid.

Step 2: 1-Benzyl-3-hydroxy-5-(3-methyl-1H-pyrazol-4-yl)pyridin-1-ium bromide. A mixture of 5-(3-methyl-1H-pyrazol-4-yl)pyridin-3-ol (6.2 g, 31.851 mmol, 1 equiv, 90%) and BnBr (6.88 g, 0.038 mmol, 1.2 equiv, 95%) in MeCN (300.00 mL, 6942.365 mmol, 170.23 equiv, 95%) was stirred for overnight at 60 degrees C. under hydrogen atmosphere. The resulting mixture was concentrated under reduced pressure. The residue was purified by silica gel column chromatography, eluted with CH₂Cl₂/MeOH (85:15) to afford 1-benzyl-3-hydroxy-5-(3-methyl-1H-pyrazol-4-yl)pyridin-1-ium bromide (9 g, 73.45%) as a brown solid.

Step 3: 1-Benzyl-5-(3-methyl-1H-pyrazol-4-yl)-1,2,3,6-tetrahydropyridin-3-ol. A mixture of 1-benzyl-3-hydroxy-5-(3-methyl-1H-pyrazol-4-yl)pyridin-1-ium bromide (6.5 g, 16.896 mmol, 1 equiv, 90%) and NaBH4 (2.68 g, 67.296 mmol, 3.98 equiv, 95%) in EtOH (260.00 mL, 5643.864 mmol, 251.64 equiv, 95%) was stirred for overnight at room temperature under nitrogen atmosphere. The reaction was quenched with sat. NH4Cl (aq.) at room temperature. The resulting mixture was concentrated under reduced pressure. The residue was purified by silica gel column chromatography, eluted with CH2Cl2/MeOH (10:1) to afford 1-benzyl-5-(3-methyl-1H-pyrazol-4-yl)-1,2,3,6-tetrahydropyridin-3-ol (5 g, 98.88%) as a yellow oil.

Step 4: 5-(3-Methyl-1H-pyrazol-4-yl)piperidin-3-ol. A mixture of 1-benzyl-5-(3-methyl-1H-pyrazol-4-yl)-1,2,3,6-tetrahydropyridin-3-ol (3.2 g, 10.692 mmol, 1 equiv, 90%) and Pd/C (1137.89 mg, 1.069 mmol, 0.10 equiv, 10%) in MeOH (200.00 mL, 5929.777 mmol, 438.89 equiv, 95%) was stirred for 4 h at room temperature under hydrogen atmosphere. The resulting mixture was filtered, the filter cake was washed with MeOH (3×5 mL). The filtrate was concentrated under reduced pressure to afford 5-(3-methyl-1H-pyrazol-4-yl)piperidin-3-ol (2 g, 92.88%) as a colorless semi-solid.

The following compounds were prepared using a methodology similar to the one described in Preparation 24:

3-(3-Fluoro-1H-pyrazol-4-yl)-5-methylpiperidine

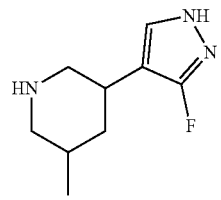

Example 1: 3-(4-(3-((S-Methylsulfonimidoyl)methyl)piperidin-1-yl)pyrimidin-2-yl)-6-(trifluoromethyl)imidazo[1,2-a]pyridine, I-4

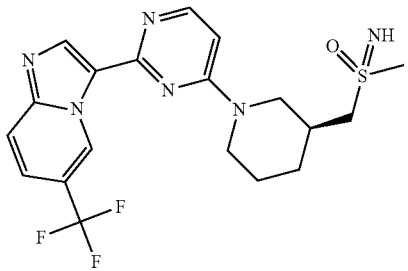

3-(4-Chloropyrimidin-2-yl)-6-(trifluoromethyl)imidazo [1,2-a]pyridine (13.2 mg, 0.05 mmol), 3-((S-methylsulfonimidoyl)methyl)piperidine (8 mg, 0.045 mmol), diisopropylethylamine (8 μL, 0.045 mmol) in DMF were heated at 80° C. After 20 mins the reaction was cooled to room temperature and the mixture was filtered and purified by reverse phase chromatography (C18; MeCN/water/0.05% TFA as eluent) to afford the trifluoroacetic acid salt of 3-(4-(3-((S-methylsulfonimidoyl)methyl)piperidin-1-yl)pyrimidin-2-yl)-6-(trifluoromethyl)imidazo[1,2-a]pyridine (12.7 mg, 40%).

The following compounds were prepared using a methodology similar to the one described in Example 1:
8-Methylsulfonyl-1-[2-[6-(trifluoromethyl)imidazo[1,2-a]pyridin-3-yl]pyrimidin-4-yl]-1,8-diazaspiro[4.5]decane, I-7
N-[[-4,4-Difluoro-5-methyl-1-[2-[6-(trifluoromethyl)imidazo[1,2-a]pyridin-3-yl]pyrimidin-4-yl]-3-piperidyl]methyl]methanesulfonamide, I-8
N-[[(2S)-4-[2-(6-Chloroimidazo[1,2-a]pyridin-3-yl)pyrimidin-4-yl]morpholin-2-yl]methyl]methanesulfonamide, I-19 (using 6-chloro-3-(4-chloropyrimidin-2-yl)imidazo [1,2-a]pyridine)
4-[2-(6-Chloroimidazo[1,2-a]pyridin-3-yl)pyrimidin-4-yl]-2-(1H-pyrazol-4-yl)morpholine, I-20 (using 6-chloro-3-(4-chloropyrimidin-2-yl)imidazo[1,2-a]pyridine)
6-Chloro-3-(4-(3-((methylsulfonimidoyl)methyl)piperidin-1-yl)pyrimidin-2-yl)imidazo[1,2-a]pyridine, I-21 (using 6-chloro-3-(4-chloropyrimidin-2-yl)imidazo[1,2-a]pyridine)
4-[2-(6-Chloro-7-fluoro-imidazo[1,2-a]pyridin-3-yl)pyrimidin-4-yl]-2-(1H-pyrazol-4-yl)morpholine, I-23 (using 6-chloro-3-(4-chloropyrimidin-2-yl)-7-fluoro-imidazo[1,2-a]pyridine)
4-[2-(6-Bromo-7-fluoro-imidazo[1,2-a]pyridin-3-yl)pyrimidin-4-yl]-2-(1H-pyrazol-4-yl)morpholine, I-24 (using 6-bromo-7-fluoro-3-(4-methylsulfanylpyrimidin-2-yl)imidazo[1,2-a]pyridine)
N-[[1-[2-(6-Bromo-7-fluoro-imidazo[1,2-a]pyridin-3-yl)pyrimidin-4-yl]pyrrolidin-3-yl]methyl]methanesulfonamide I-25 (using 6-bromo-7-fluoro-3-(4-methyl sulfanylpyrimidin-2-yl)imidazo[1,2-a]pyridine)
1-[2-(6-Chloroimidazo[1,2-a]pyridin-3-yl)pyrimidin-4-yl]-1,4-diazepan-5-one I-26 (using 6-chloro-3-(4-chloropyrimidin-2-yl)imidazo[1,2-a]pyridine);
6-Chloro-3-[4-[3-(1H-pyrazol-4-yl)pyrrolidin-1-yl]pyrimidin-2-yl]imidazo[1,2-a]pyridine I-27 (using 6-chloro-3-(4-chloropyrimidin-2-yl)imidazo[1,2-a]pyridine)
6-Chloro-3-[4-[3-(1H-pyrazol-4-yl)piperazin-1-yl]pyrimidin-2-yl]imidazo[1,2-a]pyridine I-28 (using 6-chloro-3-(4-chloropyrimidin-2-yl)imidazo[1,2-a]pyridine)
6-Chloro-3-[4-[3-dimethylphosphoryl-5-(1H-pyrazol-4-yl)-1-piperidyl]pyrimidin-2-yl]imidazo[1,2-a]pyridine I-29 (using 6-chloro-3-(4-chloropyrimidin-2-yl)imidazo[1,2-a]pyridine)
((1-(2-(6-Chloroimidazo[1,2-a]pyridin-3-yl)pyrimidin-4-yl)piperidin-3-yl)imino)dimethyl-$\lambda^6$-sulfanone I-30 (using 6-chloro-3-(4-chloropyrimidin-2-yl)imidazo[1,2-a]pyridine)
N-[[-1-[4-[6-(Difluoromethyl)imidazo[1,2-a]pyridin-3-yl]pyrimidin-2-yl]-4,4-difluoro-5-methyl-3-piperidyl]methyl]methanesulfonamide, I-41 (using 3-(2-chloropyrimidin-4-yl)-6-(difluoromethyl)imidazo[1,2-a]pyridine);
6-Chloro-7-fluoro-3-[4-[3-(1H-imidazol-4-yl)-2,5-dimethyl-piperazin-1-yl]pyrimidin-2-yl]imidazo[1,2-a]pyridine I-42 (using 6-chloro-3-(4-chloropyrimidin-2-yl)-7-fluoro-imidazo[1,2-a]pyridine)
7-[2-[6-(Trifluoromethyl)imidazo[1,2-a]pyridin-3-yl]pyrimidin-4-yl]-1,2,5,6,8,8a-hexahydroimidazo[1,5-a]pyrazin-3-one I-43 (using 3-(4-chloropyrimidin-2-yl)-6-(trifluoromethyl)imidazo[1,2-a]pyridine)
2-(1H-Pyrazol-4-yl)-4-[4-[6-(trifluoromethyl)imidazo[1,2-a]pyridin-3-yl]pyrimidin-2-yl]morpholine I-44 (using 3-(2-chloropyrimidin-4-yl)-6-(trifluoromethyl)imidazo [1,2-a]pyridine)
(3S)-1-[2-(6-Chloro-7-fluoro-imidazo[1,2-a]pyridin-3-yl)pyrimidin-4-yl]piperidine-3-carboxamide I-48 (using 6-chloro-3-(4-chloropyrimidin-2-yl)-7-fluoro-imidazo[1,2-a]pyridine)
((1-(2-(6-Chloro-7-fluoroimidazo[1,2-a]pyridin-3-yl)pyrimidin-4-yl)piperidin-3-yl)imino)dimethyl-$\lambda^6$-sulfanone I-49 (using (using 6-chloro-3-(4-chloropyrimidin-2-yl)-7-fluoro-imidazo[1,2-a]pyridine)
1-[2-(6-Chloroimidazo[1,2-a]pyridin-3-yl)pyrimidin-4-yl]-2,5-dimethyl-piperidine-3-carboxamide I-50 (using 6-chloro-3-(4-chloropyrimidin-2-yl)imidazo[1,2-a]pyridine);
1-[2-(6-Chloroimidazo[1,2-a]pyridin-3-yl)pyrimidin-4-yl]-2,5-dimethyl-piperidine-3-carboxamide I-51 (using 6-chloro-3-(4-chloropyrimidin-2-yl)imidazo[1,2-a]pyridine)
1-[2-(6-Chloro-7-fluoro-imidazo[1,2-a]pyridin-3-yl)pyrimidin-4-yl]-2,5-dimethyl-piperidine-3-carboxamide I-52 and 1-[2-(6-chloro-7-fluoro-imidazo[1,2-a]pyridin-3-yl)pyrimidin-4-yl]-2,5-dimethyl-piperidine-3-carboxamide I-53

Example 2: 1H-Pyrazol-4-yl-4-[2-[6-(trifluoromethyl)imidazo[1,2-a]pyridin-3-yl]pyrimidin-4-yl]morpholine and 1H-pyrazol-4-yl-4-[2-[6-(trifluoromethyl)imidazo[1,2-a]pyridin-3-yl]pyrimidin-4-yl]morpholine, I-2 and I-3

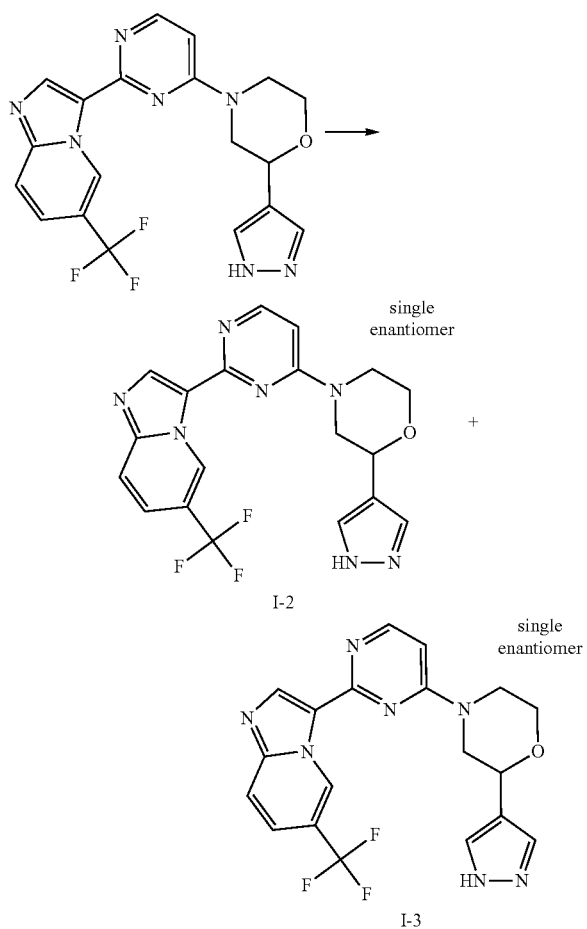

I-2 single enantiomer

I-3 single enantiomer

The racemic mixture of 2-(1H-pyrazol-4-yl)-4-[2-[6-(trifluoromethyl)imidazo[1,2-a]pyridin-3-yl]pyrimidin-4-yl]morpholine (prepared using a methodology similar to the one described in Example 107) was separated by chiral supercritical fluid chromatography (conditions: OD-H, 45% MeOH, 20 mM NH3, 290 nm). The first species to be eluted was compound I-2 (99.3% ee); ESV-MS m/z 416.8 (M+H). The second species to be eluted was compound I-3 (98.2% ee); ESV-MS m/z 416.4 (M+H).

The following compounds were prepared using a similar methodology to the one described in Example 2:

7-(2-(6-(Trifluoromethyl)imidazo[1,2-a]pyridin-3-yl)pyrimidin-4-yl)hexahydroimidazo[1,5-a]pyrazin-3(2H)-one I-5

7-(2-(6-(trifluoromethyl)imidazo[1,2-a]pyridin-3-yl)pyrimidin-4-yl)hexahydroimidazo[1,5-a]pyrazin-3(2H)-one, I-6

2-(1H-Pyrazol-4-yl)-4-(4-(6-(trifluoromethyl)imidazo[1,2-a]pyridin-3-yl)pyrimidin-2-yl)morpholine, I-9

2-(1H-pyrazol-4-yl)-4-(4-(6-(trifluoromethyl)imidazo[1,2-a]pyridin-3-yl)pyrimidin-2-yl)morpholine, I-10

Dimethyl((5-methyl-1-(2-(6-(trifluoromethyl)imidazo[1,2-a]pyridin-3-yl)pyrimidin-4-yl)piperidin-3-yl)imino)-λ⁶-sulfanone I-31 and dimethyl((5-methyl-1-(2-(6-(trifluoromethyl)imidazo[1,2-a]pyridin-3-yl)pyrimidin-4-yl)piperidin-3-yl)imino)-$\lambda^6$-sulfanone I-32

3-[2-[2,5-Dimethyl-3-(1H-pyrazol-4-yl)piperazin-1-yl]pyrimidin-4-yl]-6-(trifluoromethyl)imidazo[1,2-a]pyridine I-33 and 3-[2-[2,5-dimethyl-3-(1H-pyrazol-4-yl)piperazin-1-yl]pyrimidin-4-yl]-6-(trifluoromethyl)imidazo[1,2-a]pyridine I-34

6-Chloro-3-[4-[2,5-dimethyl-3-(1H-pyrazol-4-yl)piperazin-1-yl]pyrimidin-2-yl]imidazo[12-a]pyridine I-35 and 6-chloro-3-[4-[2,5-dimethyl-3-(1H-pyrazol-4-yl)piperazin-1-yl]pyrimidin-2-yl]imidazo[1,2-a]pyridine I-36

3-[4-[2,5-Dimethyl-3-(1H-pyrazol-4-yl)piperazin-1-yl]pyrimidin-2-yl]-6-(trifluoromethyl)imidazo[1,2-a]pyridine I-37 and 3-[4-[2,5-dimethyl-3-(1H-pyrazol-4-yl)piperazin-1-yl]pyrimidin-2-yl]-6-(trifluoromethyl)imidazo[1,2-a]pyridine I-38

3-[4-[3-Methyl-5-(1H-pyrazol-4-yl)piperazin-1-yl]pyrimidin-2-yl]-6-(trifluoromethyl)imidazo[1,2-a]pyridine I-39 and 3-[4-[3-methyl-5-(1H-pyrazol-4-yl)piperazin-1-yl]pyrimidin-2-yl]-6-(trifluoromethyl)imidazo[1,2-a]pyridine I-40

Example 3: N-[[(2S)-4-[2-[6-(Difluoromethyl)imidazo[1,2-a]pyridin-3-yl]pyrimidin-4-yl]morpholin-2-yl]methyl]methanesulfonamide, I-13

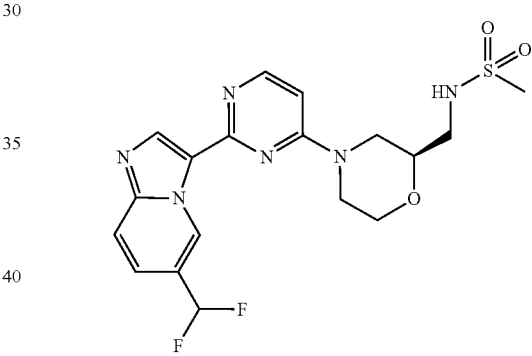

DBU (79.8 µL, 0.534 mmol) and PyBroP (124.5 mg, 0.267 mmol) were added to a solution of 2-[6-(difluoromethyl)imidazo[1,2-a]pyridin-3-yl]pyrimidin-4-ol (35 mg, 0.134 mmol) in MeCN (700 µL). After 5 min N-[[(2S)-morpholin-2-yl]methyl]methanesulfonamide (31.1 mg, 0.160 mmol) was added and the mixture heated at 40° C. After 2 hours the reaction was cooled to room temperature and the mixture was filtered and purified by reverse phase chromatography (C18; MeCN/water/0.05% TFA as eluent) to afford the trifluoroacetic acid salt of N-[[(2S)-4-[2-[6-(difluoromethyl)imidazo[1,2-a]pyridin-3-yl]pyrimidin-4-yl]morpholin-2-yl]methyl]methanesulfonamide (28.2 mg, 45%).

The following compounds were prepared using a methodology similar to the one described in Example 3:

N-[[(2S)-4-[2-[6-(Trifluoromethyl)imidazo[1,2-a]pyridin-3-yl]pyrimidin-4-yl]morpholin-2-yl]methyl]methanesulfonamide, I-1 (using 2-[6-(trifluoromethyl)imidazo[1,2-a]pyridin-3-yl]-1H-pyrimidin-6-one)

1-[4-[2-[6-(Difluoromethyl)imidazo[1,2-a]pyridin-3-yl]pyrimidin-4-yl]piperazin-1-yl]ethanone, I-14

4-[2-[6-(Difluoromethyl)imidazo[1,2-a]pyridin-3-yl]pyrimidin-4-yl]-2-(1H-pyrazol-4-yl)morpholine, I-15

N-(((3 S,5S)-1-(2-(6-(Difluoromethyl)imidazo[1,2-a]pyridin-3-yl)pyrimidin-4-yl)-4,4-difluoro-5-methylpiperidin-3-yl)methyl)methanesulfonamide, I-16

2-(1H-Pyrazol-4-yl)-4-(2-(6-(trifluoromethyl)imidazo[1,2-a]pyridin-3-yl)pyrimidin-4-yl)morpholine, I-45

Example 4: N-[[(2S)-4-[4-[6-(Difluoromethyl)imidazo[1,2-a]pyridin-3-yl]pyrimidin-2-yl]morpholin-2-yl]methyl]methanesulfonamide, I-17

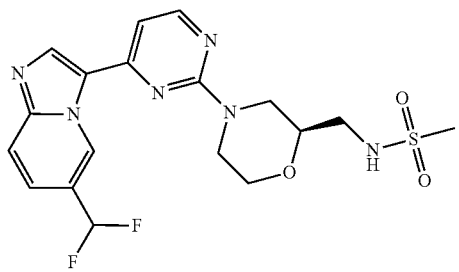

3-Bromo-6-(difluoromethyl)imidazo[1,2-a]pyridine (70 mg, 0.283 mmol), tributyl-(2-chloropyrimidin-4-yl)stannane (137.3 mg, 0.340 mmol) and PdCl$_2$(PPh$_3$)$_2$(59.7 mg, 0.085 mmol) were combined in DMF (2.1 mL) and degassed with nitrogen before heating at 120° C. To the mixture was added N-[[(2S)-morpholin-2-yl]methyl]methanesulfonamide (27.7 mg, 0.143 mmol) and diisopropylethylamine (49.6 µL, 0.285 mmol) and the reaction was heated at 150° C. After 16 hours the reaction was cooled to room temperature and the mixture was filtered and purified by reverse phase chromatography (C18; MeCN/water/0.05% TFA as eluent) to afford the trifluoroacetic acid salt of N-[[(2S)-4-[4-[6-(difluoromethyl)imidazo[1,2-a]pyridin-3-yl]pyrimidin-2-yl]morpholin-2-yl]methyl]methanesulfonamide (6.5 mg, 5%).

The following compound was prepared using a methodology similar to the one described in Example 4:

4-[4-[6-(Difluoromethyl)imidazo[1,2-a]pyridin-3-yl]pyrimidin-2-yl]-2-(1H-pyrazol-4-yl)morpholine, I-18

Example 5: 1-[4-[6-[6-(Trifluoromethyl)imidazo[1,2-a]pyridin-3-yl]-2-pyridyl]piperazin-1-yl]ethanone, I-11

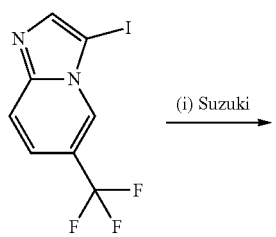

(i) Suzuki

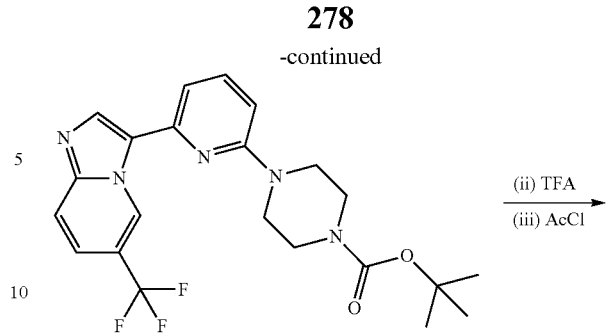

(ii) TFA
(iii) AcCl

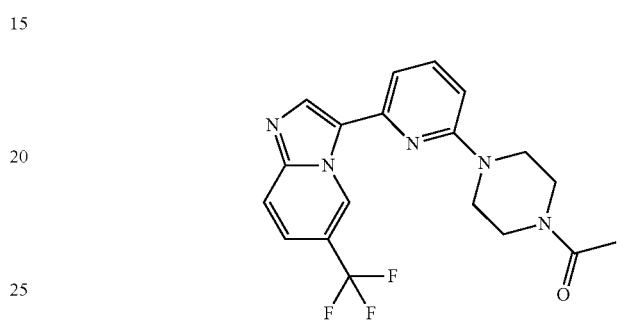

Step 1: tert-Butyl 4-[6-[6-(trifluoromethyl)imidazo[1,2-a]pyridin-3-yl]-2-pyridyl]piperazine-1-carboxylate

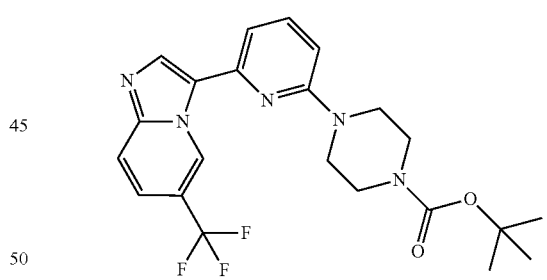

A mixture of 3-iodo-6-(trifluoromethyl)imidazo[1,2-a]pyridine (50 mg, 0.160 mmol), tert-butyl-4-[6-(4,4,5,5-tetramethyl-1,3,2-dioxaborolan-2-yl)-2-pyridyl]piperazine-1-carboxylate (62.4 mg, 0.160 mmol), dppf (8.8 mg, 0.016 mmol), Pd(OAc)$_2$ (1.8 mg, 0.008 mmol), CuCl (15.9 mg, 0.160 mmol) and Cs$_2$CO$_3$ (156.6 mg, 0.481 mmol) in DMF (1 mL) was degassed with nitrogen and heated to 90° C. for 16 hours. The reaction was cooled to ambient temperature, filtered through a silica gel pad and concentrated under reduced pressure to afford tert-butyl 4-[6-[6-(trifluoromethyl)imidazo[1,2-a]pyridin-3-yl]-2-pyridyl]piperazine-1-carboxylate; ESV-MS m/z 448.2 (M+H). The material was used without further purification.

Step 2: 3-(6-Piperazin-1-yl-2-pyridyl)-6-(trifluoromethyl)imidazo[1,2-a]pyridine

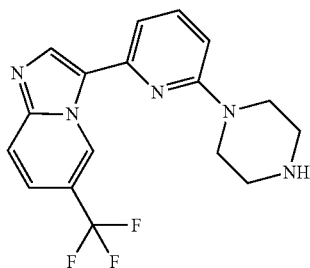

tert-Butyl-4-[6-[6-(trifluoromethyl)imidazo[1,2-a]pyridin-3-yl]-2-pyridyl]piperazine-1-carboxylate was dissolved in DCM (2 mL) and TFA (1 mL, 12.98 mmol) was added. The mixture was stirred for 1 hour and then concentrated under reduced pressure. The residue was dissolved in methanol and purified by means of an ion exchange SCX-2 cartridge to afford 3-(6-piperazin-1-yl-2-pyridyl)-6-(trifluoromethyl)imidazo[1,2-a]pyridine; ESV-MS m/z 348.1 (M+H).

Step 3: 1-[4-[6-[6-(Trifluoromethyl)imidazo[1,2-a]pyridin-3-yl]-2-pyridyl]piperazin-1-yl]ethanone

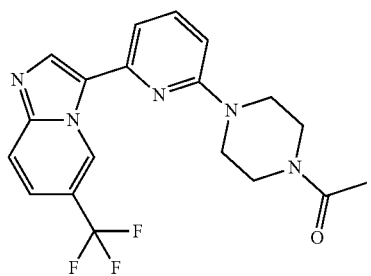

Acetyl chloride (15 μL, 0.208 mmol) and triethylamine (67 μL, 0.481 mmol) were added to a solution of 3-(6-piperazin-1-yl-2-pyridyl)-6-(trifluoromethyl)imidazo[1,2-a]pyridine in CH$_2$Cl$_2$ (1 mL) and stirred for 20 mins. The mixture was concentrated and purified by reverse phase chromatography (C18; MeCN/water/0.05% TFA as eluent) to afford the trifluoroacetic acid salt of 1-[4-[6-[6-(trifluoromethyl)imidazo[1,2-a]pyridin-3-yl]-2-pyridyl]piperazin-1-yl]ethanone (5.5 mg, 5%).

Example 6: 2-(1H-Pyrazol-4-yl)-4-[6-[6-(trifluoromethyl)imidazo[1,2-a]pyridin-3-yl]-2-pyridyl]morpholine, I-12

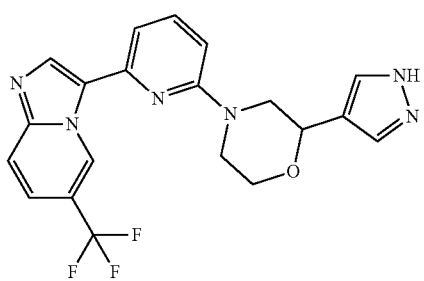

3-Bromo-6-(trifluoromethyl)imidazo[1,2-a]pyridine (100 mg, 0.377 mmol), 2-fluoro-6-(4,4,5,5-tetramethyl-1,3,2-dioxaborolan-2-yl)pyridine (84.2 mg, 0.377 mmol), dppf (20.6 mg, 0.038 mmol), Pd(OAc)$_2$ (4.2 mg, 0.0189 mmol), CuCl (37.4 mg, 0.377 mmol) and Cs$_2$CO$_3$ (368.8 mg, 1.132 mmol) in DMF (2 mL) were degassed with nitrogen and heated to 90° C. for 16 hours. The reaction was cooled to ambient temperature and filtered through a silica gel pad. Diisopropylethylamine (48.8 mg, 66 μL, 0.377 mmol) and 2-(1H-pyrazol-4-yl)morpholine (57.8 mg, 0.377 mmol) were added directly to the filtrate and the mixture was heated at 120° C. for 16 hours. The reaction mixture was cooled to ambient temperature, filtered and purified by reverse phase chromatography (C18; MeCN/water/0.05% TFA as eluent) to afford the trifluoroacetic acid salt of 2-(1H-pyrazol-4-yl)-4-[6-[6-(trifluoromethyl)imidazo[1,2-a]pyridin-3-yl]-2-pyridyl]morpholine (3.1 mg, 2%).

Example 7: 4-[4-(6-Chloroimidazo[1,2-a]pyridin-3-yl)-1,3,5-triazin-2-yl]-2-(1H-pyrazol-4-yl)morpholine, I-22

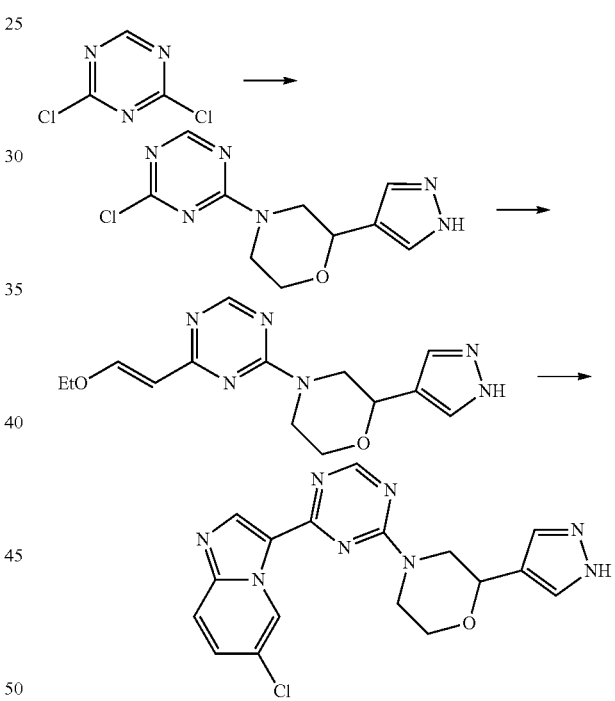

Step 1: 4-(4-Chloro-1,3,5-triazin-2-yl)-2-(1H-pyrazol-4-yl)morpholine

To a solution of 2,4-dichloro-1,3,5-triazine (50 mg, 0.333 mmol) and diisopropylethylamine (128 μL, 0.734 mmol) in 1,4-dioxane (500 µL) was added 2-(1H-pyrazol-4-yl)morpholine (51.1 mg, 0.333 mmol). The reaction mixture was stirred for 90 mins and then was partitioned between DCM and water, the organics extracted, dried (MgSO₄), filtered and concentrated to afford 4-(4-chloro-1,3,5-triazin-2-yl)-2-(1H-pyrazol-4-yl)morpholine; ESV-MS m/z 267.1 (M+H). The material was used without further purification.

Step 2: 4-[4-[(E)-2-Ethoxyvinyl]-1,3,5-triazin-2-yl]-2-(1H-pyrazol-4-yl)morpholine

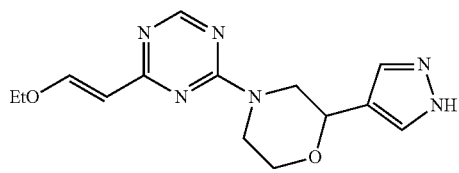

4-(4-Chloro-1,3,5-triazin-2-yl)-2-(1H-pyrazol-4-yl)morpholine was dissolved in DME (750 µL) and 2-(2-ethoxyvinyl)-4,4,5,5-tetramethyl-1,3,2-dioxaborolane (99 mg, 0.5 mmol) and Na₂CO₃ (500 µL of 2M, 1 mmol) were added. The mixture was degassed via vacuum/nitrogen cycles (×3), then Pd(PPh₃)₄ (38.5 mg, 0.033 mmol) was added and the mixture again degassed via vacuum/nitrogen cycles (×3). The mixture was heated at 40° C. for 2 hours. The reaction was purified by column chromatography (silica, EtOAc/Petroleum ether gradient) to afford 4-[4-[(E)-2-ethoxyvinyl]-1,3,5-triazin-2-yl]-2-(1H-pyrazol-4-yl)morpholine; ESV-MS m/z 303.2 (M+H).

Step 3: 4-[4-(6-Chloroimidazo[1,2-a]pyridin-3-yl)-1,3,5-triazin-2-yl]-2-(1H-pyrazol-4-yl)morpholine

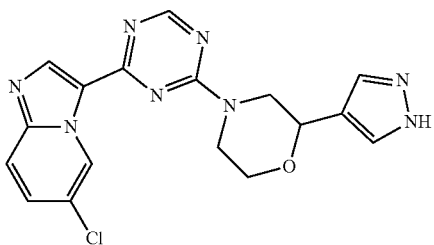

NBS (5.9 mg, 0.033 mmol) was added to a solution of 4-[4-[(E)-2-ethoxyvinyl]-1,3,5-triazin-2-yl]-2-(1H-pyrazol-4-yl)morpholine (10 mg, 0.033 mmol) in 1,4-dioxane (300 µL)/water (100 µL) and the reaction mixture stirred for 15 minutes. 5-Chloropyridin-2-amine (5.1 mg, 0.040 mmol) was then added and the reaction mixture heated at 65° C. After 16 hours the reaction mixture was cooled to ambient temperature, filtered and purified by reverse phase chromatography (C18; MeCN/water/0.05% TFA as eluent) to afford the trifluoroacetic acid salt of 4-[4-(6-chloroimidazo[1,2-a]pyridin-3-yl)-1,3,5-triazin-2-yl]-2-(1H-pyrazol-4-yl)morpholine (4.9 mg, 26%).

Example 8: ((1-(2-(6-Chloroimidazo[1,2-a]pyridin-3-yl)pyrimidin-4-yl)-2,5-dimethylpiperidin-3-yl)methyl)(imino)(methyl)-λ⁶-sulfanone (trans diastereomer), I-46

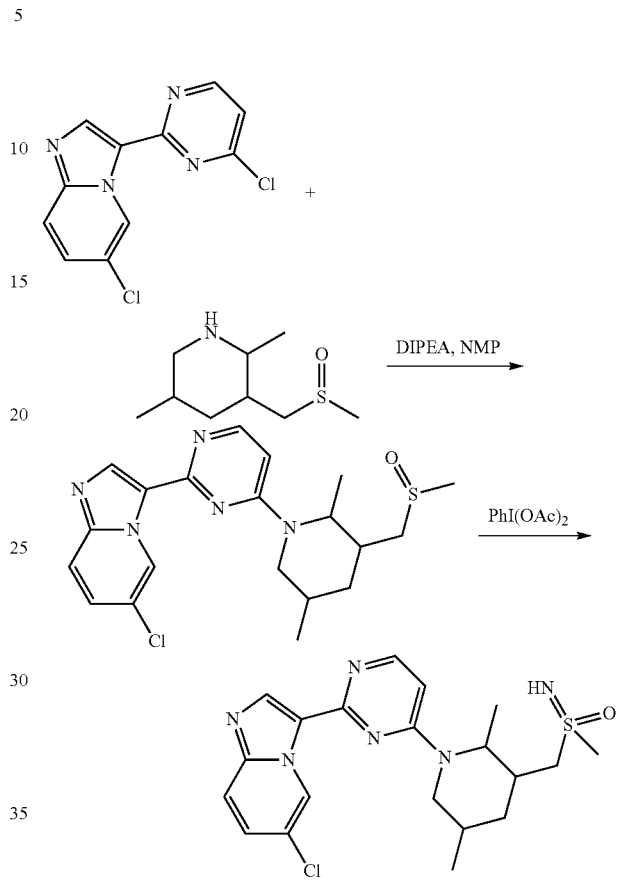

Step 1: 6-Chloro-3-[4-[2,5-dimethyl-3-(methylsulfinylmethyl)-1-piperidyl]pyrimidin-2-yl]imidazo[1,2-a]pyridine (trans diastereomer)

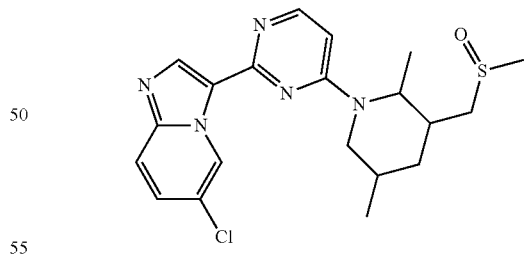

A microwave vial was charged with 6-chloro-3-(4-chloropyrimidin-2-yl)imidazo[1,2-a]pyridine (30 mg, 0.113 mmol), 2,5-dimethyl-3-(methylsulfinylmethyl)piperidine (dihydrochloride salt) (42 mg, 0.160 mmol), DIPEA (60 µL, 0.345 mmol) and NMP (900 µL) before sealing and heating at 100° C. for 16 hours. The reaction was allowed to cool before purifying by reverse phase chromatography (C18; MeCN/water—0.1% ammonium hydroxide as eluent) to provide 6-chloro-3-[4-[2,5-dimethyl-3-(methylsulfinylmethyl)-1-piperidyl]pyrimidin-2-yl]imidazo[1,2-a]pyridine (11 mg, 45%).

Step 2: ((1-(2-(6-Chloroimidazo[1,2-a]pyridin-3-yl)pyrimidin-4-yl)-2,5-dimethylpiperidin-3-yl)methyl)(imino)(methyl)-λ⁶-sulfanone (trans diastereomer)

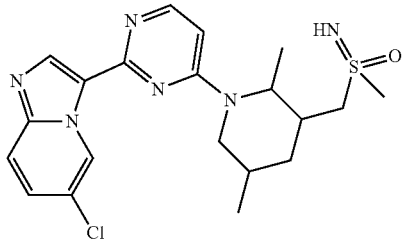

Methanol (375 μL) was added to a mixture of 6-chloro-3-[4-[2,5-dimethyl-3-(methylsulfinylmethyl)-1-piperidyl]pyrimidin-2-yl]imidazo[1,2-a]pyridine (11.2 mg, 0.144 mmol) and (diacetoxyiodo)benzene (34.7 mg, 0.108 mmol) followed by DCM (375 μL). The reaction was stirred at ambient temperature for 3 hours. The crude reaction mixture was filtered then purified by reverse phase chromatography (C18; MeCN/water—0.1% ammonium hydroxide as eluent) to give ((1-(2-(6-chloroimidazo[1,2-a]pyridin-3-yl)pyrimidin-4-yl)-2,5-dimethylpiperidin-3-yl)methyl)(imino)(methyl)-λ⁶-sulfanone (3 mg, 19%, trans diastereomer) I-46.

The following compound was prepared using a methodology similar to the one described in Example 8:

((1-(2-(6-Chloroimidazo[1,2-a]pyridin-3-yl)pyrimidin-4-yl)-2,5-dimethylpiperidin-3-yl)methyl)(imino)(methyl)-λ⁶-sulfanone (cis diastereomer), I-47

Example 9: 6-chloro-3-{4-cis-2-methyl-6-(3-methyl-[1,2,4]oxadiazol-5-yl)-morpholin-4-yl]-pyrimidin-2-yl}-imidazo[1,2-a]pyridine, I-54

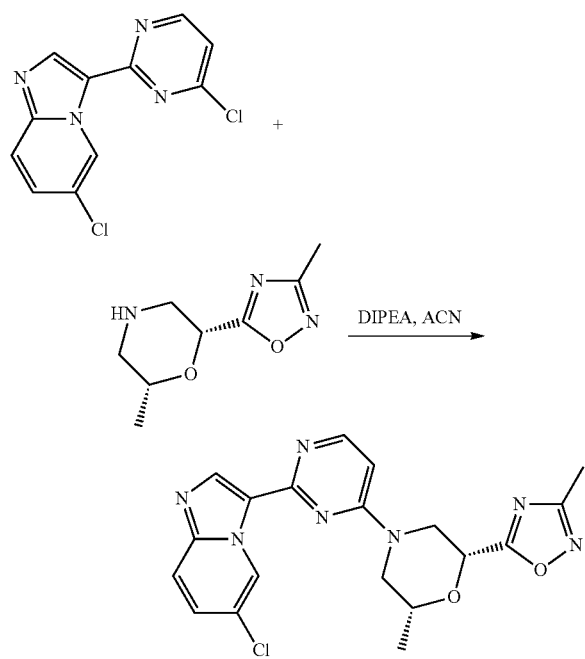

To a microwave vial containing 6-chloro-3-(4-chloro-pyrimidin-2-yl)-imidazo[1,2-a]pyridine (50.00 mg; 0.19 mmol; 1.00 eq.) and rac-(2r,6r)-2-methyl-6-(3-methyl-1,2,4-oxadiazol-5-yl)morpholine hydrochloride (41.43 mg; 0.19 mmol; 1.00 eq.) was added DIPEA (0.11 ml; 0.66 mmol; 3.50 eq.) and acetonitrile (2.00 ml). The reaction was stirred at 85° C. for 2 h before the mixture was diluted in 5 mL DMSO (partially dissolved), filtered and purified with basic pre-HPLC (C18, 10-90% ACN/H₂O/0.1% NH₄OH as eluent) to afford the 6-chloro-3-{4-cis-2-methyl-6-(3-methyl-[1,2,4]oxadiazol-5-yl)-morpholin-4-yl]-pyrimidin-2-yl}-imidazo[1,2-a]pyridine (5.0 mg, 6.4%)

The following compounds were prepared using a methodology similar to the one described in Example 9:

6-Chloro-3-{4-[3-(1H-imidazol-4-yl)-piperidin-1-yl]-pyrimidin-2-yl}-imidazo[1,2-a]pyridine, I-55

3-(2-((3R,5R)-3-Methyl-5-(1H-pyrazol-4-yl)piperidin-1-yl)pyrimidin-4-yl)-6-(trifluoromethyl)imidazo[1,2-a]pyridine, I-136 (after chiral separation)

3-(2-((3S,5S)-3-Methyl-5-(1H-pyrazol-4-yl)piperidin-1-yl)pyrimidin-4-yl)-6-(trifluoromethyl)imidazo[1,2-a]pyridine, I-137 (after chiral separation)

5-Methyl-1-[2-(6-trifluoromethyl-imidazo[1,2-a]pyridin-3-yl)-pyrimidin-4-yl]-piperidine-3-carboxylic acid amide, I-149

(S)-1-[2-(6-Trifluoromethyl-imidazo[1,2-a]pyridin-3-yl)-pyrimidin-4-yl]-piperidine-3-carboxylic acid amide, I-154

5,5-Difluoro-1-[2-(6-trifluoromethyl-imidazo[1,2-a]pyridin-3-yl)-pyrimidin-4-yl]-piperidine-3-carboxylic acid methyl ester, I-570

2-[(3R,5R)-3-methyl-5-(1H-pyrazol-4-yl)piperidin-1-yl]-4-[6-(trifluoromethyl)imidazo[1,2-a]pyridin-3-yl]pyrimidine I-136 and 3-(2-((3S,5S)-3-Methyl-5-(1H-pyrazol-4-yl)piperidin-1-yl)pyrimidin-4-yl)-6-(trifluoromethyl)imidazo[1,2-a]pyridine, I-137 were purified by Prep-Chiral-HPLC at follows:

(2-[(3R,5R)-3-methyl-5-(1H-pyrazol-4-yl)piperidin-1-yl]-4-[6-(trifluoromethyl)imidazo[1,2-a]pyridin-3-yl]pyrimidine (200 mg, 0.42 mmol, 1 equiv, 90%) was purified by Prep-Chiral-HPLC with the following conditions (Column: Chiralpak IA, 2*25 cm, 5 um; Mobile Phase A:Hex (8 mmol/L NH3.MeOH)—HPLC, Mobile Phase B: IPA-HPLC; Flow rate: 20 mL/min; Gradient: 20 B to 20 B in 25 min; 254/220 nm; RT1:11.829). This resulted in 116.2 mg (63.86%) of 2-[(3R,5R)-3-methyl-5-(1H-pyrazol-4-yl)piperidin-1-yl]-4-[6-(trifluoromethyl)imidazo[1,2-a]pyridin-3-yl]pyrimidine I-136 as a white solid.

2-[(3 S,5S)-3-methyl-5-(1H-pyrazol-4-yl)piperidin-1-yl]-4-[6-(trifluoromethyl)imidazo[1,2-a]pyridin-3-yl]pyrimidine 200 mg, 0.42 mmol, 1 equiv, 90%) was purified by Prep-Chiral-HPLC with the following conditions (Column: Chiralpak IA, 2*25 cm, 5 um; Mobile Phase A:Hex (8 mmol/L NH3.MeOH)—HPLC, Mobile Phase B: IPA-HPLC; Flow rate: 20 mL/min; Gradient: 20 B to 20 B in 25 min; 254/220 nm; RT2:19.149). This resulted in 117.8 mg of 2-[(3 S,5S)-3-methyl-5-(1H-pyrazol-4-yl)piperidin-1-yl]-4-[6-(trifluoromethyl)imidazo[1,2-a]pyridin-3-yl]pyrimidine I-137 as a white solid Example 10: 6-Chloro-7-fluoro-3-{4-[cis-2-methyl-6-(3-methyl-[1,2,4]oxadiazol-5-yl)-morpholin-4-yl]-pyrimidin-2-yl}-imidazo[1,2-a]pyridine, I-56

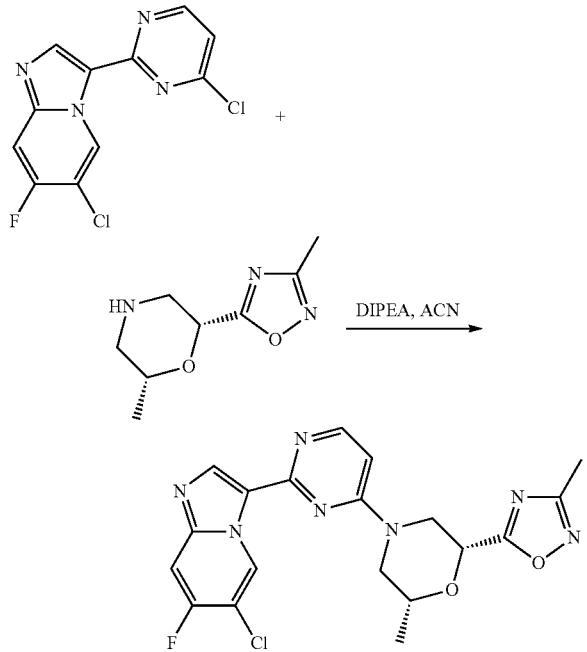

To a microwave vial containing 6-chloro-3-(4-chloro-pyrimidin-2-yl)-7-fluoro-imidazo[1,2-a]pyridine (50.00 mg; 0.18 mmol; 1.00 eq.) and rac-(2r,6r)-2-methyl-6-(3-methyl-1,2,4-oxadiazol-5-yl) morpholine hydrochloride (38.80 mg; 0.18 mmol; 1.00 eq.) was added DIPEA (0.10 ml; 0.62 mmol; 3.50 eq.) and acetonitrile (2.00 ml). The reaction was stirred at 85° C. for 2 h. The white precipitate was filtered, wash with H$_2$O (2 mL×2), dried to afford 6-chloro-7-fluoro-3-{4-[cis-2-methyl-6-(3-methyl-[1,2,4]oxadiazol-5-yl)-morpholin-4-yl]-pyrimidin-2-yl}-imidazo[1,2-a]pyridine (75.9 mg, 79.2%).

The following compounds were prepared using a methodology similar to the one described in Example 10:
6-Chloro-7-fluoro-3-{4-[3-(1H-imidazol-4-yl)-piperidin-1-yl]-pyrimidin-2-yl}-imidazo[1,2-a]pyridine, I-57
3-{4-[(3 S,5S)-3-Methyl-5-(1-methyl-1H-pyrazol-4-yl)-piperidin-1-yl]-pyrimidin-2-yl}-6-trifluoromethyl-imidazo[1,2-a]pyridine (racemic mixture), I-60
3-{4-[(3R,5S)-3-Methyl-5-(1-methyl-1H-pyrazol-4-yl)-piperidin-1-yl]-pyrimidin-2-yl}-6-trifluoromethyl-imidazo[1,2-a]pyridine (racemic mixture), I-61
1-[2-(6-Chloro-imidazo[1,2-a]pyridin-3-yl)-pyrimidin-4-yl]-3-(3-methyl-[1,2,4]oxadiazol-5-yl)-pyrrolidin-3-ol, I-64
6-Chloro-3-[4-(3-isoxazol-4-yl-piperidin-1-yl)-pyrimidin-2-yl]-imidazo[1,2-a]pyridine, I-65
6-Chloro-3-[4-(3-isoxazol-3-yl-piperidin-1-yl)-pyrimidin-2-yl]-imidazo[1,2-a]pyridine, I-66
3-[2-(6-Chloro-imidazo[1,2-a]pyridin-3-yl)-pyrimidin-4-yl]-3-aza-bicyclo[4.1.0]heptan-6-ol, I-67
4-{1-[2-(6-Chloro-imidazo[1,2-a]pyridin-3-yl)-pyrimidin-4-yl]-piperidin-3-yl}-4-methyl-oxazolidin-2-one, I-68
1-Methyl-4-[2-(6-trifluoromethyl-imidazo[1,2-a]pyridin-3-yl)-pyrimidin-4-yl]-[1,4]diazepan-2-one, I-69
3-{4-[(3aR,6aR)-3a-(3-Isopropyl-[1,2,4]oxadiazol-5-yl)-hexahydro-cyclopenta[c]pyrrol-2-yl]-pyrimidin-2-yl}-6-trifluoromethyl-imidazo[1,2-a]pyridine, I-70
3-[4-(3-Methyl-piperidin-1-yl)-pyrimidin-2-yl]-6-trifluoromethyl-imidazo[1,2-a]pyridine, I-71
1-[2-(6-Chloro-imidazo[1,2-a]pyridin-3-yl)-pyrimidin-4-yl]-3-(1-isopropyl-1H-[1,2,3]triazol-4-yl)-pyrrolidin-3-ol, I-72
6-Chloro-3-{4-[(2S,3 S)-2-(3-chloro-phenyl)-3-methyl-morpholin-4-yl]-pyrimidin-2-yl}-7-fluoro-imidazo[1,2-a]pyridine (racemic mixture), I-73
3-[2-(6-Trifluoromethyl-imidazo[1,2-a]pyridin-3-yl)-pyrimidin-4-yl]-3-aza-bicyclo[4.1.0]heptan-1-ol, I-74
6-Chloro-3-{4-[(3 aR,6aR)-3a-(3-isopropyl-[1,2,4]oxadiazol-5-yl)-hexahydro-cyclopenta[c]pyrrol-2-yl]-pyrimidin-2-yl}-imidazo[1,2-a]pyridine (racemic mixture), I-75
1-[2-(6-Chloro-imidazo[1,2-a]pyridin-3-yl)-pyrimidin-4-yl]-3-(1-isopropyl-1H-[1,2,3]triazol-4-yl)-piperidin-3-ol, I-76
(S)-1-[2-(6-Chloro-7-fluoro-imidazo[1,2-a]pyridin-3-yl)-pyrimidin-4-yl]-piperidine-3-carboxylic acid (1-methyl-1H-pyrazol-4-yl)-amide, I-77
5-[2-(6-Chloro-imidazo[1,2-a]pyridin-3-yl)-pyrimidin-4-yl]-5-aza-spiro[2.5]octane-1-carboxylic acid, I-78
6-Chloro-3-[4-(7,7-difluoro-6-methyl-3-aza-bicyclo[4.1.0]hept-3-yl)-pyrimidin-2-yl]-imidazo[1,2-a]pyridine, I-79
4-[2-(6-Trifluoromethyl-imidazo[1,2-a]pyridin-3-yl)-pyrimidin-4-yl]-[1,4]diazepan-2-one, I-80
1-[2-(6-Chloro-7-fluoro-imidazo[1,2-a]pyridin-3-yl)-pyrimidin-4-yl]-3-phenyl-piperidin-3-ol, I-81
1-{1-[2-(6-Chloro-imidazo[1,2-a]pyridin-3-yl)-pyrimidin-4-yl]-3-hydroxy-piperidin-3-yl}-cyclobutanecarboxylic acid methyl ester, I-82
{1-[2-(6-Chloro-7-fluoro-imidazo[1,2-a]pyridin-3-yl)-pyrimidin-4-yl]-3-phenyl-piperidin-4-yl}-methanol, I-83
6-Chloro-3-[4-(1-phenyl-3-aza-bicyclo[3.1.0]hex-3-yl)-pyrimidin-2-yl]-imidazo[1,2-a]pyridine, I-84
{1-[2-(6-Chloro-7-fluoro-imidazo[1,2-a]pyridin-3-yl)-pyrimidin-4-yl]-3-phenyl-piperidin-3-yl}-methanol, I-85

Example 11: (S)-1-[2-(6-Chloro-7-fluoro-imidazo[1,2-a]pyridine-3-yl)-pyrimidin-4-yl]-piperidine-3-carboxylic acid, I-58

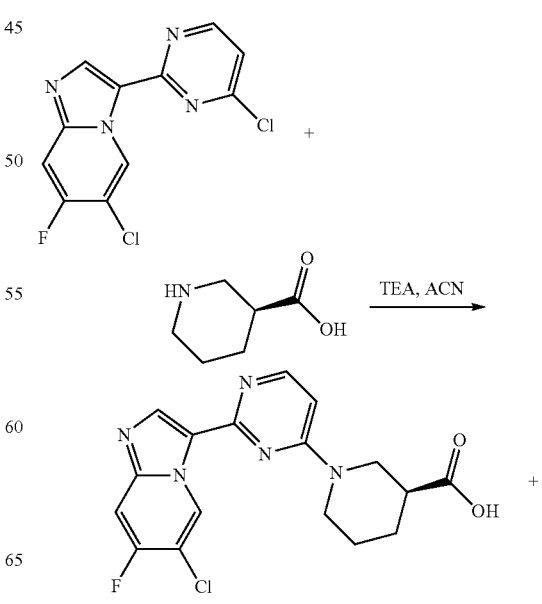

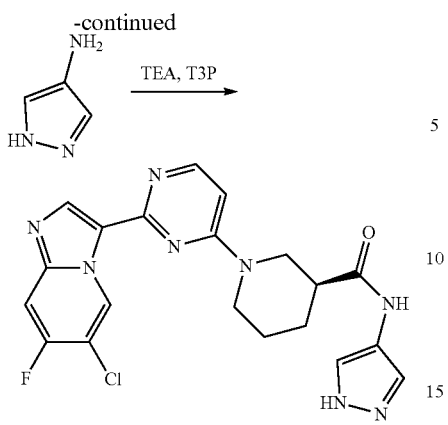

Step 1: (S)-1-[2-(6-Chloro-7-fluoro-imidazo[1,2-a]pyridine-3-yl)-pyrimidin-4-yl]-piperidine-3-carboxylic acid

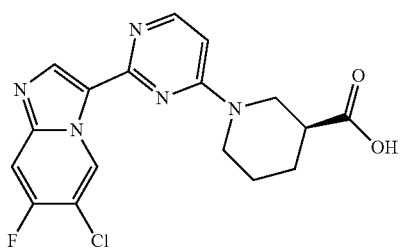

To a solution of 6-Chloro-3-(4-chloro-pyrimidin-2-yl)-7-fluoro-imidazo[1,2-a]pyridine (120.00 mg; 0.42 mmol; 1.00 eq.) and (R)-(−)-nipecotic acid (54.75 mg; 0.42 mmol; 1.00 eq.) in acetonitrile (2.00 ml) was added TEA (0.15 ml; 1.06 mmol; 2.50 eq.) and allowed to stir at 85° C. for 3 h. The white precipitate was dried and used in the next step.

Step 2: (S)-1-[2-(6-Chloro-7-fluoro-imidazo[1,2-a]pyridine-3-yl)-pyrimidin-4-yl]-piperidine-3-carboxylic acid (1H-pyrazol-4-yl)-amide

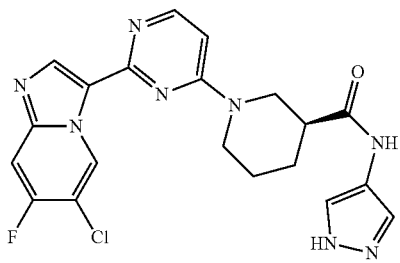

To a rbf containing (S)-1-[2-(6-Chloro-7-fluoro-imidazo[1,2-a]pyridine-3-yl)-pyrimidin-4-yl]-piperidine-3-carboxylic acid (50.00 mg; 0.10 mmol; 1.00 eq.) and 1H-Pyrazol-4-ylamine (8.27 mg; 0.10 mmol; 1.00 eq.) in DCM (2.00 ml) was added TEA (0.03 ml; 0.22 mmol; 2.20 eq.). After stirring at rt for 2 min, 1-propanephosphonic anhydride (63.37 mg; 0.20 mmol; 2.00 eq.) was added in two portions. The reaction was stirred at rt for 15 min before it was concentrated, diluted with 2 mL MeOH/1 mL DMSO, filtered and purified with basic pre-HPLC (10-90% I/H$_2$O/0.1% NH$_4$OH as eluent) to afford (S)-1-[2-(6-Chloro-7-fluoro-imidazo[1,2-a]pyridine-3-yl)-pyrimidin-4-yl]-piperidine-3-carboxylic acid (1H-pyrazol-4-yl)-amide (43.9 mg, 15.6%).

The following compounds were prepared using a methodology similar to the one described in Example 11:

(S)-1-[2-(6-Chloro-7-fluoro-imidazo[1,2-a]pyridine-3-yl)-pyrimidin-4-yl]-piperidine-3-carboxylic acid (1-methyl-1H-pyrazol-4-yl)-amide, I-59

(S)-1-[2-(6-Chloro-7-fluoro-imidazo[1,2-a]pyridine-3-yl)-pyrimidin-4-yl]-piperidine-3-carboxylic acid pyridine-4-ylamide, I-86

Example 12: (3S)-1-(2-{6-chloroimidazo[1,2-a]pyridine-3-yl}pyrimidin-4-yl)piperidin-3-amine, I-87

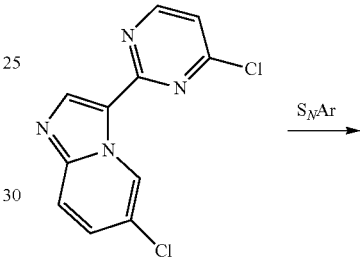

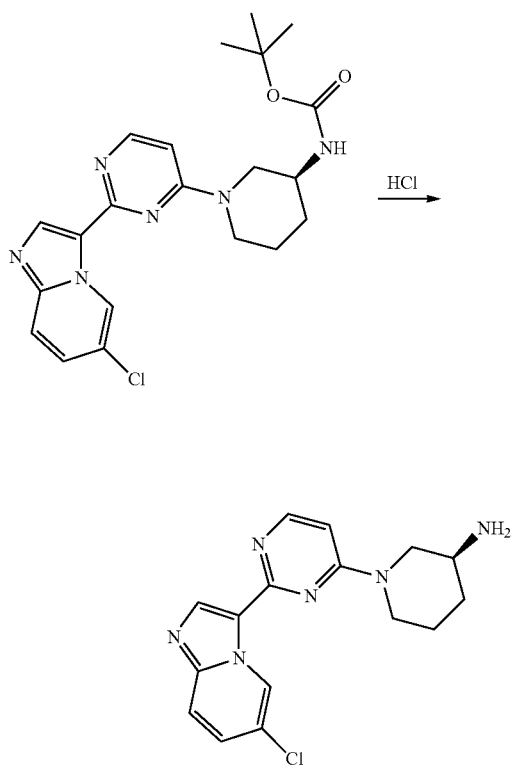

Step 1: tert-butyl N-[(3S)-1-(2-{6-chloroimidazo[1,2-a]pyridine-3-yl}pyrimidin-4-yl)piperidin-3-yl] carbamate

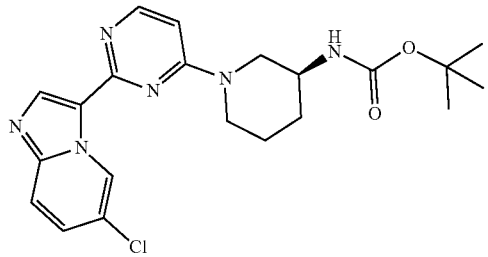

A mixture of tert-butyl N-[(3S)-piperidin-3-yl]carbamate (195.3 mg, 0.98 mmol) and 6-chloro-3-(4-chloro-pyrimidin-2-yl)imidazo[1,2-a]pyridine (198.8 mg, 0.75 mmol) in DCM (3.75 mL) was added triethylamine (0.21 mL, 1.50 mmol). After stirring overnight at room temperature reaction quenched with water (3 mL) and extracted with DCM (2×5 mL). The combined organic layers were dried over anhydrous sodium sulfate, filtered and solvent removed in vacuo to afford tert-butyl N-[(3S)-1-(2-{6-chloroimidazo[1,2-a]pyridine-3-yl}pyrimidin-4-yl)piperidin-3-yl]carbamate; ESI-MS m/z 429.2 (M+H). The material was used with our further purification.

Step 2: (3S)-1-(2-{6-chloroimidazo[1,2-a]pyridine-3-yl}pyrimidin-4-yl)piperidin-3-amine

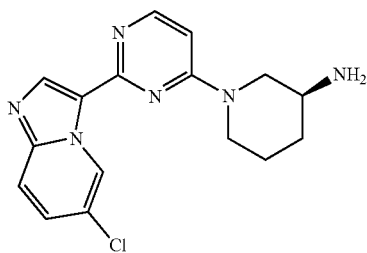

N-[(3S)-1-(2-{6-chloroimidazo[1,2-a]pyridine-3-yl}pyrimidin-4-yl)piperidin-3-yl]carbamate was dissolved in 1,4-dioxane (3 mL) and 4H HCl in 1,4-dioxane (3 mL, 35.2 mmol) was added. The mixture was stirred for 1 hour at 40° C. and then concentrated under reduced pressure. The residue was dissolved in DMSO and purified by reverse phase chromatography (C18; MeCN/water/0.01% NH$_4$OH as eluent) to afford (3S)-1-(2-{6-chloroimidazo[1,2-a]pyridine-3-4-}pyrimidin-4-yl)piperidin-3-amine (72.7 mg, 29%).

Example 13: 6-Chloro-7-fluoro-3-[4-(2-pyridin-2-yl-morpholin-4-yl)-pyrimidin-2-yl]-imidazo[1,2-a]pyridine, I-88

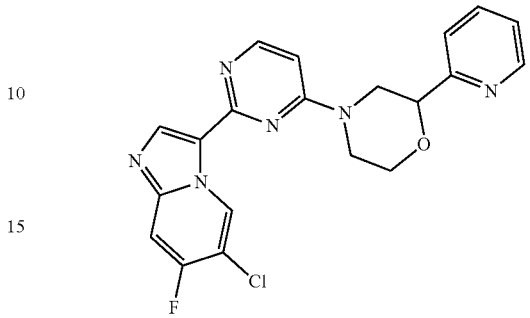

6-chloro-4-(4-chloro-pyrimidin-2-yl)-7-fluoro-imidazo [1,2-a]pyridine (50.0 mg, 0.18 mmol), 2-(pyridine-2-yl) morpholine (35.0 mg, 0.21 mmol), triethylamine (20 μL, 0.18 mmol) in DMF (1.0 mL) were heated at 80° C. After 14 hrs the reaction was cooled to room temperature and the mixture was filtered and purified by reverse phase chromatography (C18; MeCN/water/0.01% NH$_4$OH as eluent) to afford 6-chloro-7-fluoro-3-[4-(2-pyridin-2-yl-morpholin-4-yl)-pyrimidin-2-yl]-imidazo[1,2-a]pyridine (11.1 mg, 16%).

The following compounds were prepared using a methodology similar to the one described in Example 13:

cis-2-methyl-6-(5-methyl-1,3,4-oxadiazol-2-yl)-4-{2-[6-(trifluoromethyl)imidazo[1,2-a]pyridin-3-yl]pyrimidin-4-yl}morpholine, I-93 (using 3-(4-Chloropyrimidin-2-yl)-6-(trifluoromethyl)imidazo[1,2-a]pyridine)

3-{4-[cis-2-methyl-6-(5-methyl-1,3,4-oxadiazol-2-yl)morpholin-4-yl]pyrimidin-2-yl}imidazo[1,2-a]pyridine-6-carbonitrile, I-94 (using 3-(4-chloropyrimidin-2-yl)imidazo[1,2-a]pyridine-6-carbonitrile)

cis-4-(2-{6-chloroimidazo[1,2-a]pyridin-3-yl}pyrimidin-4-yl)-2-methyl-6-(5-methyl-1,3,4-oxadiazol-2-yl)morpholine, I-95 (using 4-chloro-2-{6-chloroimidazo[1,2-a]pyridin-3-yl}pyrimidine)

2-(2-{6-chloroimidazo[1,2-a]pyridin-3-yl}pyrimidin-4-yl)-octahydro-1H-pyrazino[1,2-c]pyrimidin-6-one, I-96 (using 4-chloro-2-{6-chloroimidazo[1,2-a]pyridin-3-yl}pyrimidine)

7-(2-{6-chloroimidazo[1,2-a]pyridin-3-yl}pyrimidin-4-yl)-octahydroimidazo[1,5-a]pyrazin-3-one, I-97 (using 4-chloro-2-{6-chloroimidazo[1,2-a]pyridin-3-yl}pyrimidine)

2-(2-{6-chloroimidazo[1,2-a]pyridin-3-yl}pyrimidin-4-yl)-octahydropyrazino[1,2-c][1,3]oxazin-6-one, I-98 (using 4-chloro-2-{6-chloroimidazo[1,2-a]pyridin-3-yl}pyrimidine)

7-(2-{6-chloroimidazo[1,2-a]pyridin-3-yl}pyrimidin-4-yl)-hexahydro-1H-[1,3]oxazolo[3,4-a]pyrazin-3-one, I-99 (using 4-chloro-2-{6-chloroimidazo[1,2-a]pyridin-3-yl}pyrimidine)

2-{6-chloroimidazo[1,2-a]pyridin-3-yl}-4-[3-(1H-pyrazol-4-yl)piperidin-1-yl]pyrimidine, I-100 (using 4-chloro-2-{6-chloroimidazo[1,2-a]pyridin-3-yl}pyrimidine)

4-[3-(1H-pyrazol-4-yl)piperidin-1-yl]-2-[6-(trifluoromethyl)imidazo[1,2-a]pyridin-3-yl]pyrimidine, I-101 (using 3-(4-Chloropyrimidin-2-yl)-6-(trifluoromethyl)imidazo[1,2-a]pyridine)

Example 14: 2-methyl-6-(3-methyl-1,2,4-oxadiazol-5-yl)-4-{2-[6-(trifluoromethyl)imidazo[1,2-a]pyridin-3-yl]pyrimidin-4-yl}morpholine, I-89 and I-90

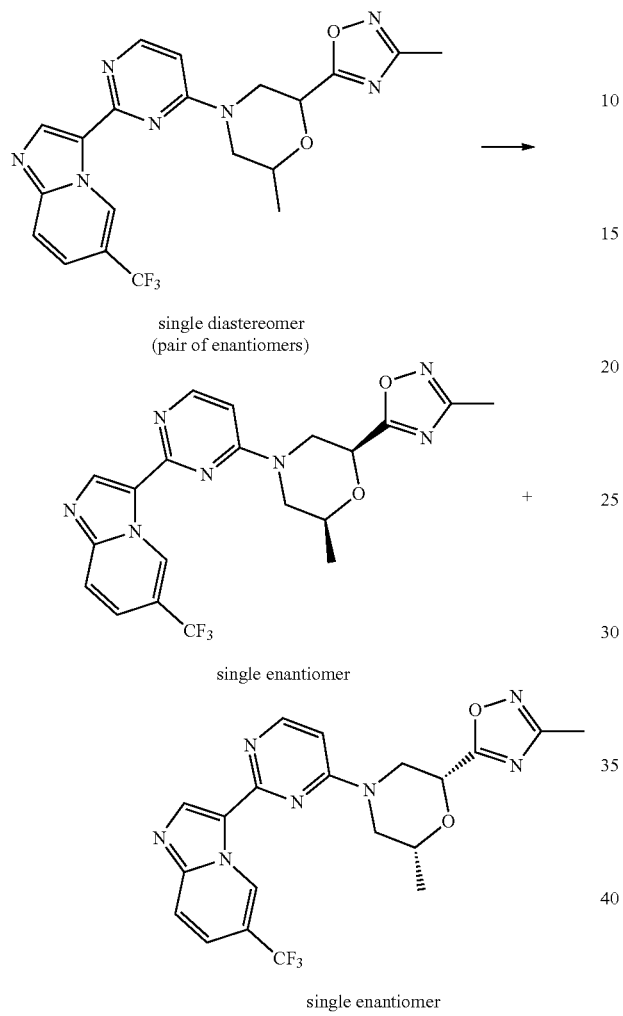

The racemic mixture of cis-(2-methyl-6-(3-methyl-1,2,4-oxadiazol-5-yl)-4-{2-[6-(trifluoromethyl)imidazo[1,2-a]pyridin-3-yl]pyrimidin-4-yl}morpholine (prepared using a methodology similar to the one described in Example 1) was separated by chrial supercritical fluid chromatography (conditions: IA-H, MeOH+0.5% DMEA, 2 mL/min, 220 nm). The first species to be eluted was compound I-89 (98% ee); ESI-MS m/z 446.2 (M+H). The second species to be eluted was compound I-90 (98% ee); ESI-MS m/z 446.2 (M+H).

The following compounds were prepared using a similar methodology to the one described in Example 14:
3-{4-[(2S,6S)-2-methyl-6-(3-methyl-1,2,4-oxadiazol-5-yl)morpholin-4-yl]pyrimidin-2-yl}imidazo[1,2-a]pyridine-6-carbonitrile, I-91 and 3-{4-[(2R,6R)-2-methyl-6-(3-methyl-1,2,4-oxadiazol-5-yl)morpholin-4-yl]pyrimidin-2-yl}imidazo[1,2-a]pyridine-6-carbonitrile, I-92

Example 15: Exemplary Compounds I-102 to I-113

Additional compounds were prepared using similar methodologies to those described in examples I-14 above:

(S)-1-(2-(6-chloroimidazo[1,2-a]pyridin-3-yl)pyrimidin-4-yl)piperidine-3-carboxamide, I-102
N-(((3S,5S)-1-(3-(6-(difluoromethyl)imidazo[1,2-a]pyridin-3-yl)-1,2,4-thiadiazol-5-yl)-4,4-difluoro-5-methylpiperidin-3-yl)methyl)methanesulfonamide, I-103
2-(1H-pyrazol-4-yl)-4-(3-(6-(trifluoromethyl)imidazo[1,2-a]pyridin-3-yl)-1,2,4-thiadiazol-5-yl)morpholine, I-104
4-(3-(6-(difluoromethyl)imidazo[1,2-a]pyridin-3-yl)-1,2,4-thiadiazol-5-yl)-2-(1H-pyrazol-4-yl)morpholine, I-105
(S)—N-((4-(3-(6-(trifluoromethyl)imidazo[1,2-a]pyridin-3-yl)-1,2,4-thiadiazol-5-yl)morpholin-2-yl)methyl)methanesulfonamide, I-106
(S)—N-((4-(3-(6-(difluoromethyl)imidazo[1,2-a]pyridin-3-yl)-1,2,4-thiadiazol-5-yl)morpholin-2-yl)methyl)methanesulfonamide, I-107
2-(1H-pyrazol-4-yl)-4-(5-(6-(trifluoromethyl)imidazo[1,2-a]pyridin-3-yl)-1,2,4-thiadiazol-3-yl)morpholine, I-108
(S)—N-((4-(5-(6-(trifluoromethyl)imidazo[1,2-a]pyridin-3-yl)-1,2,4-thiadiazol-3-yl)morpholin-2-yl)methyl)methanesulfonamide, I-109
N-((1-(5-(6-(trifluoromethyl)imidazo[1,2-a]pyridin-3-yl)-1,2,4-thiadiazol-3-yl)piperidin-3-yl)methyl)methanesulfonamide, I-110
(S)—N-((4-(4-(6-(trifluoromethyl)imidazo[1,2-a]pyridin-3-yl)thiazol-2-yl)morpholin-2-yl)methyl)methanesulfonamide, I-111
N-((1-(3-(6-(trifluoromethyl)imidazo[1,2-a]pyridin-3-yl)-1,2,4-thiadiazol-5-yl)piperidin-3-yl)methyl)methanesulfonamide, I-112
(S)—N-((4-(6-(6-chloroimidazo[1,2-a]pyridin-3-yl)pyrazin-2-yl)morpholin-2-yl)methyl)methanesulfonamide, I-113

Example 16: 6-chloro-3-{4-cis-2-methyl-6-(3-methyl-[1,2,4]oxadiazol-5-yl)-morpholin-4-yl]-pyrimidin-2-yl}-imidazo[1,2-a]pyridine, I-114

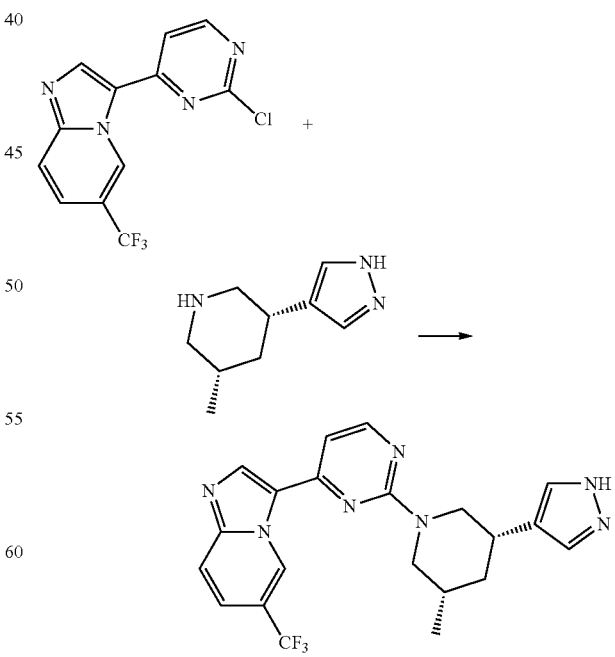

To a 25-mL sealed tube, was placed 2-chloro-4-[6-(trifluoromethyl)imidazo[1,2-a]pyridin-3-yl]pyrimidine (200.000 mg, 0.60 mmol, 1.00 equiv, 90%), 3-methyl-5-(1H-pyrazol-4-yl)piperidine (110.658 mg, 0.60 mmol, 1.00 equiv, 90%), DIEA (163.993 mg, 1.21 mmol, 2.00 equiv, 95%), i-propanol (10.000 mL, 124.30 mmol, 206.24 equiv, 95%). The resulting solution was stirred for overnight at 100° C. The resulting mixture was concentrated under vacuum. The crude product (300 mg) was purified by Prep-HPLC with the following conditions (Prep-HPLC-015): Column, XBridge Shield RP18 OBD Column, 30*150 mm, 5 um; mobile phase, Water (10 MMOL/L $NH_4HCO_3$+ 0.1% $NH_3.H_2O$) and ACN (43.0% ACN up to 47.0% in 9 min); Detector, uv 254 nm. This resulted in 23.9 mg (9%) of 2-[3-methyl-5-(1H-pyrazol-4-yl)piperidin-1-yl]-4-[6-(trifluoromethyl)imidazo[1,2-a]pyridin-3-yl]pyrimidine I-114 as a white solid.

The following compounds were prepared using a methodology similar to the one described in Example 16:

cis-2-Methyl-6-(3-methyl-1H-pyrazol-4-yl)-4-{4-[6-(trifluoromethyl)imidazo[1,2-a]pyridin-3-yl]pyrimidin-2-yl}morpholine, I-115 cis-2-Methyl-6-(1H-pyrazol-4-yl)-4-{4-[6-(trifluoromethyl)imidazo[1,2-a]pyridin-3-yl]pyrimidin-2-yl}morpholine, I-117

3-{4-[cis-2-Methyl-6-(3-methyl-1H-pyrazol-4-yl)-morpholin-4-yl]-pyrimidin-2-yl}-6-trifluoromethyl-imidazo[1,2-a]pyridine, I-119

TABLE 2

Analytical data for compounds of formula I

| Cmpd No. | LCMS (ES+) | LCMS (rt, min) | $^1$H NMR |
|---|---|---|---|
| I-1 | 457.2 | 2.46 | (500 MHz, Methanol-d4) δ 10.40 (s, 1H), 8.71 (s, 1H), 8.34 (d, 1H), 8.03 (d, 1H), 7.93 (dd, 1H), 6.91 (d, 1H), 4.58-4.34 (m, 1H), 4.13 (ddd, 1H), 3.80-3.68 (m, 2H), 3.22-3.12 (m, 1H), 2.99 (s, 3H) |
| I-2 | 416.8 | 2.37 | (500 MHz, DMSO-d6) δ 10.33 (s, 1H), 8.65 (s, 1H), 8.42 (d, 1H), 7.99 (d, 1H), 7.75 (dd, 1H), 7.69 (s, 2H), 6.95 (d, 1H), 4.60 (dd, 1H), 4.08-4.01 (m, 1H), 3.23 (dd, 2H) |
| I-3 | 416.4 | 2.37 | (500 MHz, DMSO-d6) δ 10.33 (s, 1H), 8.65 (s, 1H), 8.42 (d, 1H), 7.99 (d, 1H), 7.75 (dd, 1H), 7.69 (s, 2H), 6.95 (d, 1H), 4.60 (dd, 1H), 4.08-4.01 (m, 1H), 3.23 (dd, J = 13.1, 10.6 Hz, 2H) |
| I-4 | 439.2 | 2.41 | (500 MHz, DMSO-d6) δ 10.43-10.36 (m, 1H), 8.61 (d, 1H), 8.40 (dd, 1H), 7.97 (dt, 1H), 7.72 (dd, 1H), 6.79 (d, 1H), 3.90-3.66 (m, 2H), 3.62 (d, 3H), 3.37-3.08 (m, 2H), 2.36 (d, 1H), 2.02 (s, 1H), 1.79 (s, 1H), 1.68-1.47 (m, 2H) |
| I-5 | 404.5 | 2.24 | (500 MHz, Methanol-d4) δ 10.38-10.32 (m, 1H), 8.75 (s, 1H), 8.34 (d, 1H), 8.04 (d, 1H), 7.94 (dd, 1H), 6.99 (d, 1H), 4.79-4.65 (m, 1H), 4.65-4.47 (m, 1H), 4.01-3.88 (m, 2H), 3.65 (dd, 1H), 3.29-3.17 (m, 3H), 3.12 (ddd, 1H) |
| I-6 | 404.4 | 2.24 | (500 MHz, Methanol-d4) δ 10.38-10.32 (m, 1H), 8.75 (s, 1H), 8.34 (d, 1H), 8.04 (d, 1H), 7.94 (dd, 1H), 6.99 (d, 1H), 4.79-4.65 (m, 1H), 4.65-4.47 (m, 1H), 4.01-3.88 (m, 2H), 3.65 (dd, 1H), 3.29-3.17 (m, 3H), 3.12 (ddd, 1H) |
| I-7 | 481.2 | 3.13 | (500 MHz, DMSO-d6) δ 10.47 (d, 1H), 8.47 (s, 1H), 8.36 (d, 1H), 7.96 (d, 1H), 7.70 (dd, 1H), 6.48 (s, 2H), 3.72-3.65 (m, 6H), 2.95 (s, 3H), 2.88 (dd, 2H), 2.16-2.08 (m, 2H), 1.96 (p, 2H), 1.51 (d, 2H) |
| I-8 | 398.1 | 1.47 | (400 MHz, d4-MeOH) δ 8.81 (d, 1H), 7.16 (d, 1H), 3.98 (dd, 1H), 3.76 (dt, 1H), 3.50 (dd, 1H), 3.35 (ddd, 1H), 2.68 (tt, 1H), 2.05 (dt, 1H), 1.88-1.58 (m, 3H) |
| I-9 | 416.1 | 2.39 | (500 MHz, Methanol-d4) δ 10.50 (s, 1H), 8.56 (s, 1H), 8.44 (d, 1H), 7.89 (d, 1H), 7.73 (br s, 2H), 7.70 (dd, 1H), 7.26 (d, 1H), 4.74-4.70 (m, 2H), 4.58 (d, 1H), 4.13 (ddd, 1H), 3.87 (td, 1H), 3.37-3.28 (m, 2H) |
| I-10 | 416.3 | 2.38 | (500 MHz, Methanol-d4) δ 10.50 (s, 1H), 8.56 (s, 1H), 8.44 (d, 1H), 7.89 (d, 1H), 7.74 (br s, 2H), 7.70 (dd, 1H), 7.26 (d, 1H), 4.74-4.70 (m, 2H), 4.58 (d, 1H), 4.13 (ddd, 1H), 3.87 (td, 1H), 3.37-3.28 (m, 2H) |
| I-11 | 390.1 | 2.65 | (500 MHz, Methanol-d4) δ 10.66 (s, 1H), 8.58 (s, 1H), 8.02 (d, 1H), 7.94 (d, 1H), 7.77 (dd, 1H), 7.37 (d, 1H), 6.94 (d, 1H), 3.84-3.68 (m, 8H), 2.20 (s, 3H) |
| I-12 | 415.2 | 2.6 | (500 MHz, DMSO-d6) δ 10.35 (dt, 1H), 8.47 (s, 1H), 7.89 (dt, 1H), 7.76 (s, 1H), 7.72 (dd, 1H), 7.58 (dd, 1H), 7.53 (s, 1H), 7.39 (d, 1H), 6.92 (d, 1H), 4.63 (dd, 1H), 4.30-4.22 (m, 1H), 4.13-4.00 (m, 2H), 3.78 (td, 1H), 3.10 (td, 1H), 3.05 (dd, 1H) |
| I-13 | 439.1 | 2.18 | (500 MHz, Methanol-d4) δ 10.18 (tt, 1H), 8.45 (s, 1H), 8.30 (d, 1H), 7.78 (dd, 1H), 7.60 (dd, 1H), 7.03 (t, 1H), 6.65 (d, 1H), 4.41 (s, 1H), 4.27 (d, 1H), 4.12 (ddd, 1H), 3.78-3.66 (m, 2H), 3.30 (dd, 1H), 3.22-3.14 (m, 2H), 3.05 (s, 3H), 2.95 (dd, 1H) |
| I-14 | 373.1 | 2.12 | (500 MHz, DMSO-d6) δ 10.17 (d, 1H), 8.65 (s, 1H), 8.40 (d, 1H), 7.96 (dd, 1H), 7.72 (dd, 1H), 7.31 (t, 1H), 6.87 (d, 1H), 3.88-3.81 (m, 2H), 3.81-3.74 (m, 2H), 3.65-3.60 (m, 4H), 2.08 (s, 3H) |

TABLE 2-continued

Analytical data for compounds of formula I

| Cmpd No. | LCMS (ES+) | LCMS (rt, min) | ¹H NMR |
|---|---|---|---|
| I-15 | 398.1 | 2.16 | (500 MHz, DMSO-d6) δ 10.18 (d, 1H), 8.64 (s, 1H), 8.40 (d, 1H), 7.94 (d, 1H), 7.75-7.64 (m, 3H), 7.24 (t, 1H), 6.93 (d, 1H), 4.60 (dd, 1H), 4.09-4.00 (m, 1H), 3.72 (td, 1H), 3.26-3.16 (m, 1H) |
| I-16 | 487.2 | 2.71 | — |
| I-17 | 439.1 | 2.25 | (500 MHz, Methanol-d4) δ 10.38 (dd, 1H), 8.83 (s, 1H), 8.47 (d, 1H), 8.11-7.99 (m, 2H), 7.27 (d, 1H), 7.15 (td, 1H), 4.60 (ddd, 1H), 4.50 (dt, 1H), 4.10 (ddd, 1H), 3.77-3.64 (m, 2H), 3.30-3.22 (m, 2H), 3.05 (dd, 1H), 2.99 (s, 3H) |
| I-18 | 398.1 | 2.2 | (500 MHz, Methanol-d4) δ 10.38 (d, 1H), 8.86 (s, 1H), 8.50 (d, 1H), 8.13-7.98 (m, 2H), 7.76 (s, 2H), 7.29 (d, 1H), 7.01 (t, 1H), 4.71 (dt, 2H), 4.59-4.51 (m, 1H), 4.14 (ddd, 1H), 3.86 (td, 1H), 3.43-3.32 (m, −2H) |
| I-19 | 423.1 | 2.3 | (500 MHz, Methanol-d4) δ 10.13 (dd, 1H), 8.73 (s, 1H), 8.33 (d, 1H), 7.95 (dd, 1H), 7.92 (dd, 1H), 6.91 (d, 1H), 4.54 (s, 1H), 4.36 (s, 1H), 4.19-4.08 (m, 1H), 3.79-3.66 (m, 2H), 3.34 (d, 3H), 3.13 (dd, 1H), 2.99 (s, 3H) |
| I-20 | 382.1 | 2.24 | (500 MHz, DMSO-d6) δ 10.02 (d, 1H), 8.60 (s, 1H), 8.41 (d, 1H), 7.87 (d, 1H), 7.70 (s, 2H), 7.63 (dd, 1H), 6.92 (d, 1H), 4.60 (dd, 1H), 4.05 (dd, 1H), 3.71 (td, 1H), 3.22 (td, 2H) |
| I-21 | 405.1 | 2.26 | (500 MHz, DMSO-d6) δ 10.03 (dd, 1H), 8.56 (d, 1H), 8.38 (dd, 1H), 7.86 (d, 1H), 7.61 (dd, 1H), 6.80 (dd1H), 3.94-3.68 (m, 2H), 3.64 (d, 3H), 3.23 (dd, 2H), 2.44-2.32 (m, 1H), 2.02 (d, 1H), 1.85-1.73 (m, 1H), 1.67-1.45 (m, 2H) |
| I-22 | 383.1 | 2.23 | (500 MHz, DMSO-d6) δ 9.92 (s, 1H), 8.74 (s, 1H), 8.66 (d, 1H), 7.87 (d, 1H), 7.69 (d, 2H), 7.63 (d, 1H), 4.80-4.65 (m, 1H), 4.65-4.48 (m, 2H), 4.11-3.96 (m, 1H), 3.68 (d, 1H) |
| I-23 | 400.1 | 2.36 | (500 MHz, DMSO-d6) δ 12.81 (s, 1H), 10.14 (d, 1H), 8.45 (d, 1H), 8.38 (dd, 1H), 7.91 (d, 1H), 7.70 (s, 2H), 6.86 (d, 1H), 4.59 (dd, 1H), 4.56-4.15 (m, 2H), 4.12-4.01 (m, 1H), 3.71 (td, 1H), 3.24-3.09 (m, 2H) |
| I-24 | 446 | 2.35 | (500 MHz, DMSO-d6) δ 10.20 (d, 1H), 8.51 (s, 1H), 8.40 (d, 1H), 7.92 (d, 1H), 7.70 (s, 2H), 6.90 (d, 1H), 4.59 (dd, 1H), 4.09-4.00 (m, 1H), 3.70 (dd, 1H), 3.28-3.12 (m, 2H) |
| I-25 | 469.1 | 2.5 | (500 MHz, DMSO-d6) δ 10.35 (d, 1H), 8.39 (s, 1H), 8.29 (d, 1H), 7.88 (d, 1H), 7.22 (d, 1H), 6.43 (s, 1H), 3.81-3.42 (m, 5H), 3.10-3.02 (m, 2H), 2.93 (s, 3H), 2.17 (s, 1H), 1.84 (s, 1H) |
| I-26 | 343.1 | 2.0 | (400 MHz, DMSO-d6) δ 10.04-9.98 (m, 1H), 8.47 (s, 1H), 8.37 (d, J = 6.2 Hz, 1H), 7.85-7.77 (m, 1H), 7.69 (t, J = 5.6 Hz, 1H), 7.52 (dd, J = 9.5, 2.1 Hz, 1H), 6.80 (d, J = 6.3 Hz, 1H), 3.91 (s, 4H), 3.30 (s, 3H), 2.62 (d, J = 6.8 Hz, 2H). |
| I-27 | 366.1 | 2.42 | (400 MHz, DMSO-d6) δ 12.68 (s, 1H), 10.13 (dd, J = 2.2, 0.9 Hz, 1H), 8.42 (s, 1H), 8.28 (d, J = 5.9 Hz, 1H), 7.79 (dd, J = 9.5, 0.9 Hz, 1H), 7.69 (s, 1H), 7.49 (dd, J = 9.6, 2.1 Hz, 2H), 6.43 (d, J = 6.1 Hz, 1H), 3.85 (d, J = 30.4 Hz, 1H), 3.63 (d, J = 35.1 Hz, 1H), 3.49 (d, J = 8.0 Hz, 2H), 2.42 (d, J = 18.1 Hz, 1H), 2.05 (s, 1H), 0.99-0.90 (m, 1H). |
| I-28 | 381.1 | 2.0 | — |
| I-29 | 456.1 | 1.89 | — |
| I-30 | 405.1 | 2.25 | (400 MHz, DMSO-d6) δ 10.04 (dd, J = 2.1, 0.8 Hz, 1H), 8.42 (s, 1H), 8.31 (d, J = 6.3 Hz, 1H), 7.79 (dd, J = 9.5, 0.8 Hz, 1H), 7.49 (dd, J = 9.5, 2.2 Hz, 1H), 6.71 (d, J = 6.3 Hz, 1H), 3.30 (s, 2H), 3.05 (d, J = 0.9 Hz, 3H), 3.02 (d, J = 1.0 Hz, 3H), 2.97 (d, J = 3.4 Hz, 1H), 2.86 (s, 2H), 1.91 (dd, J = 9.1, 4.9 Hz, 1H), 1.77 (d, J = 11.5 Hz, 1H), 1.50 (t, J = 9.4 Hz, 2H). |
| I-31 | 453.1 | 2.55 | (500 MHz, Methanol-d4) δ 10.33 (s, 1H), 8.39 (s, 1H), 8.15 (d, 1H), 7.74 (d, 1H), 7.54 (dd, 1H), 6.56 (d, 1H), 4.40 (br s, 2H), 3.22 (masked, 1H), 3.04 (d, 6H), 2.98 (s, 1H), 2.60 (m, 1H), 2.43 (m, 1H), 1.93 (m, 1H), 1.67 (m, 1H), 1.27 (d, 1H), 1.18 (qd, 1H), 0.93 (d, 3H). |
| I-32 | 453.1 | 2.55 | (500 MHz, Methanol-d4) δ 10.33 (s, 1H), 8.39 (s, 1H), 8.15 (d, 1H), 7.74 (d, 1H), 7.54 (dd, 1H), 6.56 (d, 1H), 4.40 (br s, 2H), 3.22 (masked, 1H), 3.04 (d, 6H), 2.98 (s, 1H), 2.60 (m, 1H), 2.43 (m, 1H), 1.93 (m, 1H), 1.67 (m, 1H), 1.27 (d, 1H), 1.18 (qd, 1H), 0.93 (d, 3H). |
| I-33 | 443.1 | 2.37 | — |
| I-34 | 443.1 | 2.37 | (500 MHz, Methanol-d4) δ 10.60-10.22 (m, 1H), 8.53 (s, 1H), 8.41 (d, J = 5.2 Hz, 1H), 7.86 (d, J = 9.5 Hz, 1H), 7.73 (s, 2H), 7.68 (d, J = 9.3 Hz, 1H), 7.22 (d, J = 5.2 Hz, 1H), 5.05 (s, 1H), 4.64 (s, 1H), 4.50 (s, 1H), 3.29-3.19 (m, 1H), 2.99 (s, 1H), 1.38 (d, J = 6.3 Hz, 3H), 1.32-0.97 (m, 3H). |

TABLE 2-continued

Analytical data for compounds of formula I

| Cmpd No. | LCMS (ES+) | LCMS (rt, min) | ¹H NMR |
|---|---|---|---|
| I-35 | 409.1 | 2.29 | (500 MHz, DMSO-d6) δ 12.59 (s, 1H), 10.05 (m, 1H), 8.45 (m, 1H), 8.36 (m, 1H), 7.95 (d, 1H), 7.80 (d, 1H), 7.61 (d, 1H), 6.79 (m, 1H), 5.03-4.60 (m, 1H), 4.23-3.83 (m, 2H), 2.92 (m, 1H), 2.76 (m, 1H), 2.51 (m, 1H), 1.19 (m, 3H), 0.99 (m, 3H). |
| I-36 | 409.3 | 2.48 | (500 MHz, DMSO-d6) δ 12.59 (s, 1H), 10.05 (m, 1H), 8.45 (m, 1H), 8.36 (m, 1H), 7.95 (d, 1H), 7.80 (d, 1H), 7.61 (d, 1H), 6.79 (m, 1H), 5.03-4.60 (m, 1H), 4.23-3.83 (m, 2H), 2.92 (m, 1H), 2.76 (m, 1H), 2.51 (m, 1H), 1.19 (m, 3H), 0.99 (m, 3H). |
| I-37 | 443.4 | 2.45 | (500 MHz, DMSO-d6) δ 10.41 (m, 1H), 8.54 (s, 1H), 8.35 (d, 1H), 7.96 (d, 1H), 7.66-7.61 (m, 3H), 6.85 (m, 1H), 5.92-5.45 (m, 1H), 4.06 (m, 1H), 2.89 (m, 1H), 2.80-2.65 (m, 1H), 2.55 (m, 1H), 1.18 (m, 3H), 0.98 (m, 3H). |
| I-38 | 443.4 | 2.45 | — |
| I-39 | 429.4 | 2.35 | (500 MHz, Methanol-d4) δ 10.37 (s, 1H), 8.47 (s, 1H), 8.27 (d, 1H), 7.82 (d, 1H), 7.76 (s, 1H), 7.64 (d, 1H), 6.72 (d, 1H), 4.47 (s, 2H), 4.00 (d, 1H), 3.07-2.97 (m, 2H), 1.26 (d, 3H). |
| I-40 | 429.4 | 2.35 | — |
| I-41 | 487.3 | 2.79 | (500 MHz, DMSO-d6) δ 10.11 (s, 1H), 8.67 (s, 1H), 8.48 (d, J = 5.3 Hz, 1H), 7.92 (d, J = 9.6 Hz, 1H), 7.62 (dd, J = 9.3, 1.7 Hz, 1H), 7.33 (d, J = 5.3 Hz, 1H), 7.25 (t, J = 55.8 Hz, 1H), 7.25 (s, 1H), 5.12 (d, J = 15.6 Hz, 1H), 4.73 (d, J = 15.0 Hz, 1H), 3.47-3.42 (m, 1H), 3.01-2.84 (m, 3H), 2.96 (s, 3H), 2.23 (s, 2H), 1.07 (d, J = 6.6 Hz, 3H). |
| I-42 | 427.8 | 2.2 | (500 MHz, Methanol-d4) δ 10.39-10.32 (m, 1H), 8.72 (d, J = 7.0 Hz, 1H), 8.53-8.38 (m, 2H), 7.84-7.78 (m, 1H), 7.59 (d, J = 18.5 Hz, 1H), 6.94 (dd, J = 18.3, 6.5 Hz, 1H), 5.33 (s, 1H), 5.14 (d, J = 4.4 Hz, 1H), 4.89 (d, J = 4.1 Hz, 1H), 4.45 (d, J = 14.7 Hz, 1H), 4.09 (dq, J = 6.7, 3.8 Hz, 1H), 3.80 (dd, J = 14.8, 3.4 Hz, 1H), 3.65-3.54 (m, 1H), 3.29 (d, J = 14.1 Hz, 1H), 1.56 (dd, J = 6.7, 2.1 Hz, 3H), 1.31 (dd, J = 12.3, 7.0 Hz, 3H). |
| I-43 | 404.1 | 2.24 | (500 MHz, Methanol-d4) δ 10.38-10.32 (m, 1H), 8.75 (s, 1H), 8.34 (d, J = 6.9 Hz, 1H), 8.04 (d, J = 9.4 Hz, 1H), 7.94 (dd, J = 9.4, 1.8 Hz, 1H), 6.99 (d, J = 6.9 Hz, 1H), 4.79-4.65 (m, 1H), 4.65-4.47 (m, 1H), 4.01-3.88 (m, 2H), 3.65 (dd, J = 9.5, 8.4 Hz, 1H), 3.29-3.17 (m, 3H), 3.12 (ddd, J = 13.3, 12.0, 3.4 Hz, 1H). |
| I-44 | 416.1 | 2.37 | (500 MHz, DMSO-d6) δ 10.35 (s, 1H), 8.73 (s, 1H), 8.47 (d, J = 5.2 Hz, 1H), 7.96 (d, J = 9.4 Hz, 1H), 7.74-7.68 (m, 1H), 7.65 (s, 2H), 7.34 (d, J = 5.3 Hz, 1H), 4.63-4.54 (m, 2H), 4.46 (d, J = 13.3 Hz, 1H), 4.07-3.99 (m, 1H), 3.72 (td, J = 11.6, 2.9 Hz, 1H), 3.22 (d, J = 11.8 Hz, 1H). |
| I-45 | 416.2 | 2.33 | (500 MHz, Methanol-d4) δ 10.29 (s, 1H), 8.77 (s, 1H), 8.33 (d, J = 7.2 Hz, 1H), 8.06 (dt, J = 9.5, 0.8 Hz, 1H), 7.97 (dd, J = 9.4, 1.8 Hz, 1H), 7.76 (s, 2H), 7.05 (d, J = 7.2 Hz, 1H), 4.76 (dd, J = 10.6, 2.7 Hz, 1H), 4.19 (ddd, J = 11.8, 3.8, 1.6 Hz, 1H), 3.88 (td, J = 11.8, 2.8 Hz, 1H), 3.59-3.41 (m, 2H). |
| I-46 | 433.3 | 2.53 | — |
| I-47 | 433.2 | 2.53 | — |
| I-48 | 377.1 | 2.19 | (500 MHz, Methanol-d4) δ 10.01 (d, J = 7.0 Hz, 1H), 8.62 (s, 1H), 8.22 (d, J = 7.3 Hz, 1H), 7.82 (dd, J = 8.7, 0.6 Hz, 1H), 7.02 (d, J = 7.3 Hz, 1H), 4.58 (s, 1H), 4.30 (s, 1H), 3.76 (dd, J = 13.5, 9.4 Hz, 1H), 3.60 (t, J = 11.7 Hz, 1H), 2.71 (tt, J = 9.4, 4.1 Hz, 1H), 2.21-2.12 (m, 1H), 2.08-1.94 (m, 2H), 1.83-1.71 (m, 1H). |
| I-49 | 423.0 | 2.29 | (500 MHz, Methanol-d4) δ 10.12 (d, J = 6.9 Hz, 1H), 8.63 (s, 1H), 8.29 (dd, J = 7.0, 0.6 Hz, 1H), 7.84 (d, J = 8.7 Hz, 1H), 6.96 (d, J = 7.1 Hz, 1H), 4.50 (s, 1H), 4.19 (s, 1H), 3.89 (tt, J = 8.5, 3.9 Hz, 1H), 3.61-3.59 (m, 7H), 3.55 (dd, J = 13.2, 8.6 Hz, 1H), 2.25-2.16 (m, 1H), 2.05 (ddq, J = 13.4, 6.9, 3.9, 3.4 Hz, 1H), 1.90-1.76 (m, 2H). |
| I-50 | 385.1 | 2.32 | (500 MHz, Methanol-d4) δ 10.05 (dd, J = 2.0, 0.9 Hz, 1H), 8.70 (s, 1H), 8.27 (d, J = 7.2 Hz, 1H), 7.93 (dd, J = 9.5, 0.8 Hz, 1H), 7.85 (dd, J = 9.5, 2.0 Hz, 1H), 7.00 (d, J = 7.2 Hz, 1H), 5.37 (s, 1H), 4.06 (s, 1H), 3.59 (dd, J = 13.9, 3.2 Hz, 1H), 3.04 (dt, J = 12.7, 4.5 Hz, 1H), 2.40-2.29 (m, 2H), 1.68-1.61 (m, 1H), 1.39 (d, J = 6.9 Hz, 3H), 1.14 (d, J = 6.8 Hz, 3H). |
| I-51 | 385.1 | 2.38 | (500 MHz, Methanol-d4) δ 10.04 (s, 1H), 8.71 (s, 1H), 8.29 (d, J = 7.1 Hz, 1H), 7.94 (dd, J = 9.7, 0.9 Hz, 1H), 7.87 (dd, J = 9.5, 2.0 Hz, 1H), 7.03 (d, J = 7.2 Hz, 1H), 2.96 (s, 1H), 2.80 (d, J = 11.6 Hz, 1H), 1.89 (s, 1H), 1.77 (t, J = 11.9 Hz, 2H), 1.35 (d, J = 6.9 Hz, 3H), 1.17 (s, 3H). |
| I-52 | 403.1 | 2.41 | (500 MHz, Methanol-d4) δ 10.06 (d, J = 7.0 Hz, 1H), 8.65 (s, 1H), 8.25 (d, J = 7.3 Hz, 1H), 7.84 (dd, J = 8.7, 0.6 Hz, 1H), 7.02 (d, J = 7.3 Hz, 1H), 5.39 (s, 1H), 4.07 (s, 1H), 3.62 (dd, J = 13.7, |

TABLE 2-continued

Analytical data for compounds of formula I

| Cmpd No. | LCMS (ES+) | LCMS (rt, min) | $^1$H NMR |
|---|---|---|---|
| | | | 3.3 Hz, 1H), 3.04 (dt, J = 12.8, 4.7 Hz, 1H), 2.43-2.27 (m, 2H), 1.71-1.61 (m, 1H), 1.40 (d, J = 7.0 Hz, 3H), 1.14 (d, J = 6.8 Hz, 3H). |
| I-53 | 403.1 | 2.47 | 1H NMR (500 MHz, Methanol-d4) δ 10.06 (d, J = 7.0 Hz, 1H), 8.66 (s, 1H), 8.26 (d, J = 7.2 Hz, 1H), 7.84 (dd, J = 8.8, 0.6 Hz, 1H), 7.05 (d, J = 7.3 Hz, 1H), 5.66 (s, 1H), 4.06 (s, 1H), 2.99 (s, 2H), 2.87-2.77 (m, 1H), 1.89 (s, 1H), 1.77 (q, J = 12.0 Hz, 2H), 1.36 (s, 3H), 1.17 (s, 3H). |
| I-54 | 412 | 1.92 | (400 MHz, DMSO-d6) δ 10.02 (s, 1H), 8.61-8.37 (m, 2H), 7.81 (d, 1H), 7.52 (d, 1H), 6.89 (d, 1H), 5.08 (dd, 1H), 3.92 (t, 2H), 2.86 (t, 1H), 2.41 (s, 3H), 1.44 (s, 1H), 1.28 (d, 3H). |
| I-55 | 380 | 0.89 | (400 MHz, DMSO-d6) δ 11.76 (s, 1H), 10.0 (s, 1H), 8.43 (m, 2H), 7.76 (d, 1H), 7.51 (m, 2H), 6.88 (m, 2H), 3.07 (m, 2H), 2.76 (s, 1H), 2.03 (m, 1H), 1.55 (m, 3H). |
| I-56 | 430 | 2.22 | (400 MHz, DMSO-d6) δ 8.48 (s, 1H), 8.41 (d, 1H), 7.92 (d, 1H), 6.89 (d, 1H), 5.07 (dd, 1H), 4.01-3.70 (m, 1H), 2.84 (dd, 1H), 2.41 (s, 3H), 2.08 (s, 1H), 1.28 (d, 3H). |
| I-57 | 398 | 0.98 | (400 MHz, DMSO-d6) δ 11.90 (s, 1H), 10.12 (d, 1H), 8.50-8.16 (m, 2H), 7.89 (d, 1H), 7.58 (s, 1H), 6.96-6.59 (m, 2H), 3.11 (dd, 2H), 2.77 (dq, 1H), 2.15-2.01 (m, 1H), 1.89-1.67 (m, 2H), 1.60 (dd, 1H). |
| I-58 | 441 | 1.27 | (400 MHz, DMSO-d6) δ 12.53 (s, 1H), 10.02 (s, 1H), 8.52-8.11 (m, 2H), 7.90 (d, 1H), 7.68 (s, 2H), 6.83 (d, 1H), 3.22 (dd, 1H), 3.07 (t, 1H), 2.63-2.52 (m, 1H), 1.99 (d, 1H), 1.92-1.65 (m, 2H), 1.50 (d, 1H). |
| I-59 | 455 | 1.40 | (400 MHz, DMSO-d6) δ 10.14 (d, 1H), 10.01 (s, 1H), 8.41 (s, 1H), 8.32 (d, 1H), 7.97-7.72 (m, 2H), 7.39 (s, 1H), 6.83 (d, 1H), 3.78 (s, 3H), 3.22 (dd, 1H), 3.08 (t, 1H), 1.98 (d, 1H), 1.82 (s, 2H), 1.51 (t, 1H). |
| I-60 | 442 | 1.84 | 1H NMR (400 MHz, DMSO-d6) δ 10.40 (s, 1H), 8.53 (s, 1H), 8.30 (d, J = 6.2 Hz, 1H), 7.95 (d, J = 9.4 Hz, 1H), 7.67 (d, J = 9.4 Hz, 1H), 7.49 (d, J = 39.5 Hz, 1H), 7.39-7.19 (m, 2H), 6.82 (d, J = 6.1 Hz, 1H), 3.74 (s, 4H), 3.47 (s, 1H), 3.05 (s, 1H), 2.05-1.87 (m, 2H), 1.72 (d, J = 10.6 Hz, 1H), 0.99 (d, J = 6.7 Hz, 3H). |
| I-61 | 442 | 1.91 | 1H NMR (400 MHz, DMSO-d6) δ 10.37 (s, 1H), 8.52 (s, 1H), 8.32 (d, J = 6.2 Hz, 1H), 7.94 (d, J = 9.4 Hz, 1H), 7.82-7.54 (m, 2H), 7.40 (s, 1H), 6.87 (d, J = 6.3 Hz, 1H), 3.80 (s, 3H), 2.79 (t, J = 12.1 Hz, 1H), 2.68 (t, J = 13.1 Hz, 1H), 2.58 (t, J = 12.3 Hz, 1H), 2.05 (d, J = 12.8 Hz, 1H), 1.71 (s, 1H), 1.31 (q, J = 11.9 Hz, 1H), 1.00 (d, J = 6.4 Hz, 3H). |
| I-62 | 412 | | |
| I-63 | 412 | | |
| I-64 | 398 | 1.65 | 1H NMR (400 MHz, DMSO-d6) δ 10.10 (s, 1H), 8.43 (s, 1H), 8.34 (s, 1H), 7.80 (d, J = 9.9 Hz, 1H), 7.51 (d, J = 9.5 Hz, 1H), 6.64 (s, 1H), 6.50 (s, 1H), 4.27-3.56 (m, 5H), 2.56 (s, 1H), 2.39 (s, 3H). |
| I-65 | 381 | 1.59 | 1H NMR (400 MHz, DMSO-d6) δ 10.00 (s, 1H), 8.42 (d, J = 5.9 Hz, 1H), 8.33 (d, J = 6.2 Hz, 1H), 7.79 (d, J = 9.5 Hz, 1H), 7.49 (d, J = 10.1 Hz, 2H), 6.78 (dd, J = 16.5, 6.3 Hz, 1H), 4.43 (s, 2H), 3.00 (q, J = 16.5, 14.9 Hz, 1H), 2.94-2.76 (m, 1H), 1.82 (d, J = 12.5 Hz, 2H), 1.68-1.42 (m, 2H). |
| I-66 | 381 | 1.65 | 1H NMR (400 MHz, DMSO-d6) δ 9.98 (dd, J = 2.2, 0.9 Hz, 1H), 8.86 (d, J = 1.6 Hz, 1H), 8.41 (s, 1H), 8.33 (d, J = 6.3 Hz, 1H), 7.78 (dd, J = 9.5, 0.8 Hz, 1H), 7.48 (dd, J = 9.5, 2.2 Hz, 1H), 6.83 (d, J = 6.3 Hz, 1H), 6.68 (d, J = 1.7 Hz, 1H), 4.58 (s, 1H), 4.34 (s, 1H), 3.22 (ddd, J = 13.6, 11.4, 2.8 Hz, 1H), 3.03 (tt, J = 10.4, 3.9 Hz, 1H), 2.12 (d, J = 10.0 Hz, 1H), 1.84 (dtd, J = 13.9, 10.3, 9.3, 4.2 Hz, 2H), 1.63 (q, J = 12.9 Hz, 1H). |
| I-67 | 342 | 1.22 | 1H NMR (400 MHz, DMSO-d6) δ 10.13-9.94 (m, 1H), 8.41 (d, J = 3.0 Hz, 1H), 8.31 (d, J = 6.2 Hz, 1H), 7.79 (d, J = 9.9 Hz, 1H), 7.50 (d, J = 9.2 Hz, 1H), 6.63 (d, J = 6.3 Hz, 1H), 5.70 (d, J = 2.5 Hz, 1H), 4.37 (s, 1H), 3.68 (d, J = 13.1 Hz, 2H), 2.13 (s, 1H), 1.68 (d, J = 10.3 Hz, 1H), 1.21 (s, 1H), 0.75 (d, J = 9.4 Hz, 1H), 0.36 (d, J = 5.0 Hz, 1H). |
| I-68 | 413 | 1.38 | 1H NMR (400 MHz, DMSO-d6) δ 10.04 (d, J = 8.7 Hz, 1H), 8.52 (s, 1H), 8.35 (d, J = 6.3 Hz, 1H), 8.06 (s, 1H), 7.80 (d, J = 9.4 Hz, 1H), 7.55-7.43 (m, 1H), 6.77 (d, J = 6.4 Hz, 1H), 4.45 (s, 2H), 4.25 (d, J = 8.7 Hz, 1H), 3.98 (t, J = 9.9 Hz, 1H), 2.92 (t, J = 12.3 Hz, 1H), 2.74 (t, J = 12.5 Hz, 1H), 1.79 (dd, J = 21.9, 11.6 Hz, 2H), 1.58 (d, J = 11.5 Hz, 1H), 1.39 (dt, J = 23.5, 14.1 Hz, 2H), 1.29 (d, J = 11.8 Hz, 3H). |
| I-69 | 390 | 1.57 | 1H NMR (400 MHz, DMSO-d6) δ 10.41 (s, 1H), 8.55 (d, J = 2.9 Hz, 1H), 8.38 (d, J = 5.9 Hz, 1H), 7.95 (d, J = 9.5 Hz, 1H), |

TABLE 2-continued

Analytical data for compounds of formula I

| Cmpd No. | LCMS (ES+) | LCMS (rt, min) | ¹H NMR |
|---|---|---|---|
| | | | 7.68 (d, J = 9.5 Hz, 1H), 6.72 (s, 1H), 4.41 (s, 2H), 3.94 (dd, J = 47.0, 23.2 Hz, 2H), 3.57 (s, 2H), 2.81 (s, 3H), 1.85 (s, 2H). |
| I-70 | 484 | 2.65 | ¹H NMR (400 MHz, DMSO-d₆) δ 10.50 (s, 1H), 8.52 (d, J = 1.5 Hz, 1H), 8.34 (dd, J = 6.1, 1.5 Hz, 1H), 7.94 (d, J = 9.4 Hz, 1H), 7.67 (d, J = 9.5 Hz, 1H), 6.52 (d, J = 6.1 Hz, 1H), 4.25 (s, 1H), 3.89 (s, 2H), 3.19 (s, 1H), 3.12-2.94 (m, 1H), 2.30 (dt, J = 14.3, 7.7 Hz, 1H), 2.12 (dq, J = 16.2, 8.8, 7.9 Hz, 2H), 1.92 (ddp, J = 34.3, 13.4, 7.0, 6.5 Hz, 2H), 1.72 (dt, J = 13.0, 6.4 Hz, 1H), 1.26 (s, 6H). |
| I-71 | 362 | 2.43 | 1H NMR (400 MHz, DMSO-d6) δ 10.40 (s, 1H), 8.51 (d, J = 1.3 Hz, 1H), 8.30 (dd, J = 6.4, 1.4 Hz, 1H), 7.94 (d, J = 9.4 Hz, 1H), 7.67 (d, J = 9.3 Hz, 1H), 6.78 (d, J = 6.3 Hz, 1H), 4.33 (s, 1H), 3.02 (t, J = 12.0 Hz, 1H), 1.79 (dd, J = 33.2, 13.3 Hz, 2H), 1.70-1.41 (m, 2H), 1.41-1.17 (m, 1H), 0.95 (d, J = 6.5 Hz, 3H). |
| I-72 | 425 | 1.6 | 1H NMR (400 MHz, DMSO-d6) δ 10.14 (d, J = 19.7 Hz, 1H), 8.43 (d, J = 8.7 Hz, 1H), 8.31 (dd, J = 16.7, 6.1 Hz, 1H), 8.17 (d, J = 1.5 Hz, 1H), 7.79 (s, 1H), 7.50 (s, 1H), 6.46 (dd, J = 19.6, 6.0 Hz, 1H), 5.80 (d, J = 20.5 Hz, 1H), 4.84 (p, J = 6.9 Hz, 1H), 3.89 (dt, J = 45.7, 12.7 Hz, 3H), 3.66 (d, J = 10.1 Hz, 2H), 2.31 (s, 1H), 1.51 (d, J = 6.7 Hz, 7H). |
| I-73 | 459 | 2.8 | 1H NMR (400 MHz, DMSO-d6) δ 10.14 (d, J = 7.5 Hz, 1H), 8.47 (s, 1H), 8.40 (d, J = 6.2 Hz, 1H), 7.90 (d, J = 9.8 Hz, 1H), 7.48 (s, 1H), 7.44-7.25 (m, 3H), 6.84 (d, J = 6.3 Hz, 1H), 5.14 (d, J = 7.1 Hz, 1H), 4.85 (d, J = 2.2 Hz, 1H), 4.21-3.97 (m, 1H), 3.78 (dd, J = 11.2, 4.1 Hz, 1H), 3.55 (td, J = 11.5, 3.7 Hz, 1H), 3.42 (td, J = 12.6, 4.3 Hz, 1H), 1.41 (d, J = 6.6 Hz, 3H). |
| I-74 | 376 | 1.44 | 1H NMR (400 MHz, DMSO-d6) δ 10.42 (s, 1H), 8.51 (s, 1H), 8.31 (d, J = 6.1 Hz, 1H), 7.94 (d, J = 9.4 Hz, 1H), 7.67 (d, J = 9.5 Hz, 1H), 6.66 (d, J = 6.2 Hz, 1H), 5.69 (d, J = 2.6 Hz, 1H), 4.34 (s, 1H), 3.68 (d, J = 13.1 Hz, 2H), 2.22-2.04 (m, 1H), 1.76-1.50 (m, 1H), 1.22 (s, 1H), 0.76 (dd, J = 10.3, 5.1 Hz, 1H), 0.36 (t, J = 5.1 Hz, 1H). |
| I-75 | 450 | 2.29 | 1H NMR (400 MHz, DMSO-d6) δ 10.03 (d, J = 4.9 Hz, 1H), 8.40 (d, J = 5.2 Hz, 1H), 7.77 (d, J = 9.4 Hz, 1H), 7.61-7.31 (m, 1H), 6.48 (d, J = 6.0 Hz, 1H), 4.18 (d, J = 35.3 Hz, 1H), 3.86 (s, 2H), 3.17 (d, J = 8.8 Hz, 1H), 3.04 (p, J = 7.1 Hz, 1H), 2.30 (dt, J = 14.7, 7.7 Hz, 1H), 2.12 (dp, J = 16.1, 8.0, 7.5 Hz, 2H), 2.04-1.76 (m, 2H), 1.72 (dt, J = 13.1, 6.6 Hz, 1H), 1.36-1.13 (m, 6H). |
| I-76 | 439 | 1.3 | 1H NMR (400 MHz, DMSO-d6) δ 10.0 (s, 1H), 8.4 (s, 1H), 8.25 (d, 1H), 8.16 (s, 1H), 7.76 (d, 1H), 7.51 (d, 1H), 6.77 (d, 1H), 5.25 (s, 1H), 4.75 (m, 1H), 3.70 (m, 1H), 2.22 (m, 1H), 1,92 (m, 2H), 1.61 (m, 1H), 1.46 (m, 6H). |
| I-77 | 455 | 1.4 | 1H NMR (400 MHz, DMSO-d6) δ 10.14 (d, J = 7.6 Hz, 1H), 10.01 (s, 1H), 8.41 (s, 1H), 8.32 (d, J = 6.3 Hz, 1H), 7.97-7.72 (m, 2H), 7.39 (s, 1H), 6.83 (d, J = 6.3 Hz, 1H), 3.78 (s, 3H), 3.22 (dd, J = 13.2, 10.9 Hz, 1H), 3.08 (t, J = 12.4 Hz, 1H), 1.98 (d, J = 11.8 Hz, 1H), 1.82 (s, 2H), 1.51 (t, J = 12.9 Hz, 1H). |
| I-78 | 384 | 1.39 | 1H NMR (400 MHz, DMSO-d6) δ 10.03 (d, J = 13.8 Hz, 1H), 8.45 (s, 1H), 8.29 (t, J = 6.5 Hz, 1H), 7.78 (dd, J = 9.8, 5.5 Hz, 1H), 7.49 (d, J = 9.6 Hz, 1H), 6.84-6.47 (m, 1H), 1.93-1.46 (m, 5H), 1.22-0.98 (m, 1H), 0.91 (dt, J = 13.2, 4.6 Hz, 1H). Several peaks overlap with solvent peak. |
| I-79 | 376 | 2.0 | 1H NMR (400 MHz, DMSO-d6) δ 10.02 (s, 1H), 8.51-8.16 (m, 2H), 7.78 (d, J = 9.5 Hz, 1H), 7.64-7.36 (m, 1H), 6.67 (d, J = 6.3 Hz, 1H), 4.40-4.06 (m, 1H), 3.80-3.54 (m, 2H), 2.01-1.64 (m, 3H), 1.26 (s, 3H). |
| I-80 | 377 | 1.46 | 1H NMR (400 MHz, DMSO-d6) δ 10.42 (s, 1H), 8.55 (s, 1H), 8.40 (d, J = 6.1 Hz, 1H), 7.95 (d, J = 9.4 Hz, 1H), 7.68 (d, J = 9.5 Hz, 2H), 6.72 (s, 1H), 4.31 (s, 2H), 4.19-3.63 (m, 2H), 1.77 (d, J = 6.6 Hz, 2H). |
| I-81 | 424 | 1.79 | 1H NMR (400 MHz, DMSO-d6) δ 10.15 (d, J = 7.6 Hz, 1H), 8.46-8.16 (m, 2H), 7.90 (d, J = 9.9 Hz, 1H), 7.63 (d, J = 7.7 Hz, 2H), 7.33 (dt, J = 40.4, 7.4 Hz, 2H), 6.76 (d, J = 6.3 Hz, 1H), 5.06 (s, 1H), 3.44 (d, J = 13.4 Hz, 1H), 3.15 (t, J = 12.2 Hz, 1H), 2.16 (td, J = 12.6, 4.1 Hz, 1H), 1.84 (d, J = 13.1 Hz, 1H), 1.65 (d, J = 12.9 Hz, 1H). |
| I-82 | 442 | 1.9 | 1H NMR (400 MHz, DMSO-d6) δ 10.01 (s, 1H), 8.38 (s, 1H), 8.26 (d, J = 6.3 Hz, 1H), 7.79 (d, J = 9.5 Hz, 1H), 7.49 (d, J = 9.2 Hz, 1H), 6.69 (d, J = 6.4 Hz, 1H), 4.73 (s, 1H), 2.96 (d, J = 12.9 Hz, 1H), 2.84 (t, J = 13.5 Hz, 1H), 2.61 (d, J = 9.3 Hz, 1H), 2.43 (t, J = 9.9 Hz, 1H), 2.36-2.15 (m, 2H), 1.87 (d, J = 12.6 Hz, 1H), 1.72 (dt, J = 24.0, 11.6 Hz, 3H), 1.55 (q, J = 13.0, 12.2 Hz, 2H). |

TABLE 2-continued

Analytical data for compounds of formula I

| Cmpd No. | LCMS (ES+) | LCMS (rt, min) | $^1$H NMR |
|---|---|---|---|
| I-83 | 438 | 1.7 | 1H NMR (400 MHz, DMSO-d6) δ 10.06 (s, 1H), 8.44-8.21 (m, 2H), 7.87 (d, J = 9.9 Hz, 1H), 7.44-7.13 (m, 5H), 6.79 (d, J = 6.1 Hz, 1H), 4.46 (s, 1H), 4.17 (s, 1H), 3.90 (s, 1H), 3.65 (s, 1H), 2.14 (s, 1H), 1.75 (s, 2H). |
| I-84 | 388 | 2.2 | 1H NMR (400 MHz, DMSO-d6) δ 10.16 (m, 1H), 8.47 (s, 1H), 8.25 (d, 1H), 7.79 (d, 1H), 7.50 (d, 1H), 7.31 (m, 4H), 7.24 (m, 1H), 6.5 (m, 1H), 4.07 (m, 1H), 2.22 (m, 1H), 1.25 (m, 1H), 1.0 (m, 1H). Several peaks overlap with solvent peak. |
| I-85 | 438 | 1.95 | 1H NMR (400 MHz, DMSO-d6) δ 10.20 (d, J = 7.5 Hz, 1H), 8.45 (s, 1H), 8.28 (d, J = 6.2 Hz, 1H), 7.91 (d, J = 9.8 Hz, 1H), 7.49 (d, J = 7.8 Hz, 2H), 7.27 (t, J = 7.6 Hz, 2H), 7.15 (t, J = 7.3 Hz, 1H), 6.80 (s, 1H), 4.69 (s, 1H), 3.78 (d, J = 13.5 Hz, 2H), 3.51 (s, 3H), 2.07 (s, 2H), 1.70 (s, 1H). |
| I-86 | 452 | 1.0 | 1H NMR (400 MHz, DMSO-d6) δ 10.40 (s, 1H), 10.12 (d, J = 7.5 Hz, 1H), 8.48-8.22 (m, 4H), 7.89 (d, J = 9.9 Hz, 1H), 7.65-7.44 (m, 2H), 6.85 (d, J = 6.3 Hz, 1H), 3.12 (t, J = 12.5 Hz, 1H), 2.66 (d, J = 5.6 Hz, 1H), 2.06 (d, J = 12.3 Hz, 1H), 1.84 (t, J = 12.4 Hz, 2H), 1.53 (t, J = 12.4 Hz, 1H). |
| I-87 | 329.1 | 0.80 | (500 MHz, Methanol-d4) δ 10.17-10.04 (m, 1H), 8.44 (s, 1H), 8.28 (d, 1H), 7.70 (d, 1H), 7.49 (d, 1H), 6.69 (d, 1H), 4.43 (s, 1H), 4.31 (s, 1H), 3.18 (t, 1H), 3.04-2.92 (m, 1H), 2.92-2.81 (m, 1H), 2.16-2.02 (m, 1H), 1.95-1.84 (m, 1H), 1.64 (q, 1H), 1.59-1.40 (m, 1H). |
| I-88 | 411.1 | 1.49 | (400 MHz, DMSO-d6) δ 10.11 (d, 1H), 8.66-8.55 (m, 1H), 8.46-8.33 (m, 2H), 7.95-7.80 (m, 2H), 7.56 (d, 1H), 7.38 (dd, 1H), 6.83 (d, 1H), 4.74 (s, 1H), 4.66 (dd, 1H), 4.35 (s, 1H), 4.26-4.13 (m, 1H), 3.81 (td, 1H), 3.28-3.16 (m, 1H), 3.16-3.06 (m, 1H). |
| I-89 | 446.2 | 1.46 | $^1$H NMR (400 MHz, DMSO-d$_6$) δ 10.37 (s, 1H), 8.60 (s, 1H), 8.44 (d, J = 6.2 Hz, 1H), 7.96 (d, J = 9.4 Hz, 1H), 7.68 (dd, J = 9.4, 2.0 Hz, 1H), 6.92 (d, J = 6.3 Hz, 1H), 5.09 (dd, J = 11.0, 2.8 Hz, 1H), 4.80 (s, 1H), 4.49 (s, 1H), 3.92 (s, 1H), 2.92-2.81 (m, 1H), 2.41 (s, 3H), 1.28 (d, J = 6.2 Hz, 3H). |
| I-90 | 446.2 | 1.46 | $^1$H NMR (400 MHz, DMSO-d$_6$) δ 10.37 (s, 1H), 8.60 (s, 1H), 8.44 (d, J = 6.2 Hz, 1H), 7.96 (d, J = 9.4 Hz, 1H), 7.68 (dd, J = 9.4, 2.0 Hz, 1H), 6.92 (d, J = 6.3 Hz, 1H), 5.09 (dd, J = 11.0, 2.8 Hz, 1H), 4.80 (s, 1H), 4.49 (s, 1H), 3.92 (s, 1H), 2.92-2.81 (m, 1H), 2.41 (s, 3H), 1.28 (d, J = 6.2 Hz, 3H). |
| I-91 | 403.2 | 1.24 | $^1$H NMR (400 MHz, DMSO-d$_6$) δ 10.40 (d, J = 1.4 Hz, 1H), 8.61 (s, 1H), 8.44 (d, J = 6.2 Hz, 1H), 7.92 (dd, J = 9.3, 1.0 Hz, 1H), 7.70 (dd, J = 9.3, 1.8 Hz, 1H), 6.92 (d, J = 6.3 Hz, 1H), 5.07 (dd, J = 11.0, 2.8 Hz, 1H), 4.50 (s, 1H), 3.92 (ddd, J = 10.9, 6.3, 2.7 Hz, 1H), 2.91-2.80 (m, 1H), 2.41 (s, 3H), 1.28 (d, J = 6.2 Hz, 3H). |
| I-92 | 403.2 | 1.26 | 1H NMR (400 MHz, DMSO-d$_6$) δ 10.40 (d, J = 1.4 Hz, 1H), 8.61 (s, 1H), 8.44 (d, J = 6.2 Hz, 1H), 7.92 (dd, J = 9.3, 1.0 Hz, 1H), 7.70 (dd, J = 9.3, 1.8 Hz, 1H), 6.92 (d, J = 6.3 Hz, 1H), 5.07 (dd, J = 11.0, 2.8 Hz, 1H), 4.50 (s, 1H), 3.92 (ddd, J = 10.9, 6.3, 2.7 Hz, 1H), 2.91-2.80 (m, 1H), 2.41 (s, 3H), 1.28 (d, J = 6.2 Hz, 3H). |
| I-93 | 446.3 | 1.28 | $^1$H NMR (400 MHz, DMSO-d$_6$) δ 10.36 (s, 1H), 8.58 (s, 1H), 8.42 (d, J = 6.1 Hz, 1H), 7.95 (d, J = 9.4 Hz, 1H), 7.67 (dd, J = 9.4, 1.9 Hz, 1H), 6.89 (d, J = 6.3 Hz, 1H), 5.01 (dd, J = 11.1, 2.7 Hz, 1H), 4.61 (d, J = 103.5 Hz, 2H), 4.07-3.83 (m, 1H), 2.85 (dd, J = 13.2, 10.8 Hz, 1H), 1.26 (d, J = 6.2 Hz, 3H). |
| I-94 | 403.2 | 1.07 | $^1$H NMR (400 MHz, DMSO-d$_6$) δ 10.42 (s, 1H), 8.61 (s, 1H), 8.44 (d, J = 6.3 Hz, 1H), 7.91 (d, J = 9.3 Hz, 1H), 7.70 (d, J = 9.3, 1.8 Hz, 1H), 6.92 (d, J = 6.3 Hz, 1H), 4.99 (dd, J = 11.1, 2.7 Hz, 1H), 4.66 (d, J = 106.3 Hz, 2H), 3.98-3.83 (m, 1H), 2.94-2.76 (m, 1H), 1.27 (d, J = 6.2 Hz, 3H). |
| I-95 | 412.2 | 1.11 | $^1$H NMR (400 MHz, DMSO-d$_6$) δ 10.00 (s, 1H), 8.49 (d, J = 2.3 Hz, 1H), 8.44-8.37 (m, 1H), 7.79 (dd, J = 9.6, 2.2 Hz, 1H), 7.49 (dd, J = 9.5, 2.5 Hz, 1H), 6.90-6.83 (m, 1H), 4.99 (dd, J = 11.1, 2.7 Hz, 1H), 4.78 (s, 1H), 4.48 (s, 1H), 3.90 (t, J = 8.4 Hz, 1H), 2.84 (t, J = 12.0 Hz, 1H), 2.53 (d, J = 23.2 Hz, 3H), 1.26 (d, J = 5.9 Hz, 3H). |
| I-96 | 384.1 | 1.29 | $^1$H NMR (400 MHz, DMSO-d$_6$) δ 9.98 (d, J = 2.6 Hz, 1H), 8.49 (d, J = 2.2 Hz, 1H), 8.36 (dd, J = 6.4, 2.2 Hz, 1H), 7.78 (dd, J = 9.5, 2.2 Hz, 1H), 7.57-7.43 (m, 1H), 6.79 (dd, J = 6.5, 2.1 Hz, 1H), 4.48 (d, J = 40.8 Hz, 2H), 4.33-4.07 (m, 4H), 3.60 (d, J = 7.8 Hz, 1H), 3.10 (t, J = 12.3 Hz, 1H), 2.92 (dt, J = 37.3, 12.3 Hz, 2H), 2.20 (d, J = 14.0 Hz, 1H), 1.82 (q, J = 11.5 Hz, 1H). |
| I-97 | 370.1 | 0.82 | $^1$H NMR (400 MHz, DMSO-d$_6$) δ 10.04 (s, 1H), 8.51 (d, J = 2.9 Hz, 1H), 8.43-8.31 (m, 1H), 7.81 (d, J = 9.6 Hz, 1H), 7.52 (d, J = 9.6 Hz, |

TABLE 2-continued

Analytical data for compounds of formula I

| Cmpd No. | LCMS (ES+) | LCMS (rt, min) | ¹H NMR |
|---|---|---|---|
| | | | 1H), 6.83 (d, J = 6.3 Hz, 1H), 6.59 (s, 1H), 4.55 (d, J = 55.4 Hz, 2H), 3.71 (d, J = 11.1 Hz, 2H), 3.47 (t, J = 9.0 Hz, 1H), 3.15-2.79 (m, 4H). |
| I-98 | 385.1 | 1.35 | ¹H NMR (400 MHz, DMSO-d₆) δ 10.00 (s, 1H), 8.51 (d, J = 2.1 Hz, 1H), 8.35 (dd, J = 6.3, 2.2 Hz, 1H), 7.80 (dd, J = 9.7, 2.3 Hz, 1H), 7.52 (d, J = 9.3 Hz, 1H), 7.34-6.97 (m, 2H), 6.80 (d, J = 6.4 Hz, 1H), 6.44 (s, 1H), 4.46 (d, J = 44.9 Hz, 2H), 4.26-4.12 (m, 1H), 3.22-2.90 (m, 4H), 2.77 (dt, J = 23.4, 12.1 Hz, 2H), 2.05 (d, J = 12.3 Hz, 1H), 1.69 (d, J = 11.9 Hz, 1H). |
| I-99 | 371.1 | 0.91 | ¹H NMR (400 MHz, DMSO-d₆) δ 10.04 (s, 1H), 8.54 (d, J = 1.7 Hz, 1H), 8.48-8.37 (m, 1H), 7.83 (d, J = 9.6 Hz, 1H), 7.53 (d, J = 9.8 Hz, 1H), 6.85 (d, J = 6.3 Hz, 1H), 4.79 (s, 1H), 4.56 (s, 1H), 4.48 (t, J = 8.6 Hz, 1H), 4.12-4.05 (m, 1H), 3.96 (dd, J = 11.5, 8.3 Hz, 1H), 3.71 (d, J = 11.3 Hz, 1H), 3.05 (dt, J = 40.0, 12.6 Hz, 3H). |
| I-100 | 380.2 | 0.97 | ¹H NMR (400 MHz, DMSO-d₆) δ 12.65 (s, 1H), 10.03 (d, J = 2.1 Hz, 1H), 8.44 (d, J = 1.8 Hz, 1H), 8.33 (dd, J = 6.3, 1.9 Hz, 1H), 7.80 (dd, J = 9.7, 1.8 Hz, 1H), 7.74-7.39 (m, 3H), 6.84 (dd, J = 6.4, 1.9 Hz, 1H), 4.53 (s, 2H), 3.18-2.98 (m, 2H), 2.76 (t, J = 10.9 Hz, 1H), 2.10 (d, J = 12.4 Hz, 1H), 1.84 (d, J = 13.0 Hz, 1H), 1.77-1.50 (m, 2H). |
| I-101 | 414.2 | 1.05 | ¹H NMR (400 MHz, DMSO-d₆) δ 10.36 (s, 1H), 8.51 (d, J = 1.8 Hz, 1H), 8.31 (dd, J = 6.4, 1.8 Hz, 1H), 7.93 (d, J = 9.4 Hz, 1H), 7.65 (d, J = 9.4 Hz, 1H), 7.56 (s, 2H), 6.84 (d, J = 6.3 Hz, 1H), 4.45 (s, 2H), 3.09 (q, J = 11.9 Hz, 3H), 2.85-2.60 (m, 1H), 2.12-1.96 (m, 1H), 1.81 (d, J = 12.7 Hz, 1H), 1.65 (tq, J = 24.5, 12.3, 11.5 Hz, 2H), 1.20 (t, J = 7.4 Hz, 1H). |
| I-102 | 357.1 | 1.1 | 1H NMR (400 MHz, DMSO-d6) δ 10.02 (s, 1H), 8.43 (d, J = 2.2 Hz, 1H), 8.33 (d, J = 6.2 Hz, 1H), 7.80 (d, J = 9.3 Hz, 1H), 7.50 (d, J = 9.6 Hz, 1H), 7.41 (s, 1H), 6.91 (s, 1H), 6.80 (d, J = 6.4 Hz, 1H), 4.42 (s, 2H), 3.09 (dt, J = 32.0, 12.4 Hz, 2H), 2.37 (s, 1H), 1.93 (d, J = 13.4 Hz, 1H), 1.74 (dt, J = 24.2, 13.3 Hz, 2H), 1.48 (t, J = 13.1 Hz, 1H). |
| I-114 | 441 | 1.1 | 1H NMR (300 MHz, DMSO-d6) δ 12.39 (s, 1H), 10.41 (s, 1H), 8.53 (s, 1H), 8.36 (s, 1H), 7.98 (d, J = 9.0 Hz, 1H), 7.71 (s, 1H), 7.47 (s, 1H), 6.87 (s, 1H), 2.73 (d, J = 50.4 Hz, 4H), 2.16 (d, J = 31.7 Hz, 3H), 1.98 (s, 1H), 1.75 (s, 1H), 1.43 (s, 1H), 1.26 (s, 1H), 1.02 (d, J = 6.3 Hz, 3H). |
| I-115 | 443 | 1.2 | 1H NMR (300 MHz, DMSO-d6) δ 12.49 (d, J = 28.6 Hz, 1H), 10.36 (s, 1H), 8.73 (s, 1H), 8.44 (d, J = 5.3 Hz, 1H), 7.96 (d, J = 9.4 Hz, 1H), 7.70 (d, J = 9.4 Hz, 1H), 7.60-7.16 (m, 2H), 4.55 (d, J = 10.1 Hz, 3H), 3.80 (s, 1H), 3.09 (t, 1H), 2.78 (t, 1H), 2.37-2.05 (m, 3H), 1.23 (d, J = 6.1 Hz, 3H).1.2 min, 443). |
| I-116 | 443 | 1.2 | 1H NMR (300 MHz, DMSO-d6) δ 12.49 (d, J = 28.6 Hz, 1H), 10.36 (s, 1H), 8.73 (s, 1H), 8.44 (d, J = 5.3 Hz, 1H), 7.96 (d, J = 9.4 Hz, 1H), 7.70 (d, J = 9.4 Hz, 1H), 7.60-7.16 (m, 2H), 4.55 (d, J = 10.1 Hz, 3H), 3.80 (s, 1H), 3.09 (t, 1H), 2.78 (t, 1H), 2.37-2.05 (m, 3H), 1.23 (d, J = 6.1 Hz, 3H).1.2 min, 443). |
| I-117 | 429 | 1.4 | 1H NMR (300 MHz, DMSO-d6) δ 12.84 (s, 1H), 10.37 (s, 1H), 8.73 (s, 1H), 8.45 (d, J = 5.3 Hz, 1H), 7.96 (d, J = 9.4 Hz, 1H), 7.79 (s, 1H), 7.74-7.65 (m, 1H), 7.55 (s, 1H), 7.33 (d, J = 5.3 Hz, 1H), 4.57 (dd, J = 25.6, 12.1 Hz, 3H), 3.79 (d, J = 7.2 Hz, 1H), 3.06 (t, J = 12.3 Hz, 1H), 2.79 (t, J = 11.8 Hz, 1H), 1.24 (d, J = 6.2 Hz, 3H). |
| I-118 | 429 | 1.4 | 1H NMR (300 MHz, DMSO-d6) δ 12.84 (s, 1H), 10.37 (s, 1H), 8.73 (s, 1H), 8.45 (d, J = 5.3 Hz, 1H), 7.96 (d, J = 9.4 Hz, 1H), 7.79 (s, 1H), 7.74-7.65 (m, 1H), 7.55 (s, 1H), 7.33 (d, J = 5.3 Hz, 1H), 4.57 (dd, J = 25.6, 12.1 Hz, 3H), 3.79 (d, J = 7.2 Hz, 1H), 3.06 (t, J = 12.3 Hz, 1H), 2.79 (t, J = 11.8 Hz, 1H), 1.24 (d, J = 6.2 Hz, 3H). |
| I-119 | 443 | 1.1 | 1H NMR (300 MHz, DMSO-d6) δ 12.52 (s, 1H), 10.38 (s, 1H), 8.56 (s, 1H), 8.38 (d, J = 6.2 Hz, 1H), 7.96 (d, J = 9.4 Hz, 1H), 7.76-7.49 (m, 2H), 6.89 (d, J = 6.3 Hz, 1H), 4.63-4.22 (m, 3H), 3.79 (s, 1H), 3.10 (t, J = 12.0 Hz, 1H), 2.84-2.69 (m, 1H), 2.25 (s, 3H), 1.25 (d, J = 6.2 Hz, 3H). |
| I-120 | 443 | 1.1 | 1H NMR (300 MHz, DMSO-d6) δ 12.52 (s, 1H), 10.38 (s, 1H), 8.56 (s, 1H), 8.38 (d, J = 6.2 Hz, 1H), 7.96 (d, J = 9.4 Hz, 1H), 7.76-7.49 (m, 2H), 6.89 (d, J = 6.3 Hz, 1H), 4.63-4.22 (m, 3H), 3.79 (s, 1H), 3.10 (t, J = 12.0 Hz, 1H), 2.84-2.69 (m, 1H), 2.25 (s, 3H), 1.25 (d, J = 6.2 Hz, 3H). |

TABLE 2-continued

Analytical data for compounds of formula I

| Cmpd No. | LCMS (ES+) | LCMS (rt, min) | ¹H NMR |
|---|---|---|---|
| I-123 | 452.90 | 1.825 | 1H NMR (400 MHz, DMSO-d6) d 10.41 (s, 1H), 8.53 (s, 1H), 8.33 (d, J = 6.2 Hz, 1H), 7.95 (d, J = 9.5 Hz, 1H), 7.72-7.62 (m, 1H), 6.75 (d, J = 6.4 Hz, 1H), 3.03 (d, J = 11.1 Hz, 6H), 2.34-2.26 (m, 1H), 2.01-1.82 (m, 2H), 1.28-1.08 (m, 2H), 0.96 (d, J = 6.6 Hz, 3H). |
| I-126 | 430.1 | 1.47 | (300 MHz, DMSO, ppm): 12.84 (s, 1H), 10.37 (s, 1H), 8.73 (s, 1H), 8.45 (d, J = 5.3 Hz, 1H), 7.96 (d, J = 9.4 Hz, 1H), 7.79 (s, 1H), 7.74-7.65 (m, 1H), 7.55 (s, 1H), 7.33 (d, J = 5.3 Hz, 1H), 4.57 (dd, J = 25.6, 12.1 Hz, 3H), 3.79 (d, J = 7.2 Hz, 1H), 3.06 (t, J = 12.3 Hz, 1H), 2.79 (t, J = 11.8 Hz, 1H), 1.24 (d, J = 6.2 Hz, 3H). |
| I-127 | 430.1 | 1.47 | (300 MHz, DMSO, ppm): 12.84 (s, 1H), 10.37 (s, 1H), 8.73 (s, 1H), 8.45 (d, J = 5.3 Hz, 1H), 7.96 (d, J = 9.4 Hz, 1H), 7.79 (s, 1H), 7.74-7.65 (m, 1H), 7.55 (s, 1H), 7.33 (d, J = 5.3 Hz, 1H), 4.57 (dd, J = 25.6, 12.1 Hz, 3H), 3.79 (d, J = 7.2 Hz, 1H), 3.06 (t, J = 12.3 Hz, 1H), 2.79 (t, J = 11.8 Hz, 1H), 1.24 (d, J = 6.2 Hz, 3H). |
| I-136 | 407.1 | 1.59 | (300 MHz, DMSO, ppm): 12.65 (s, 1H), 10.35 (s, 1H), 8.70 (s, 1H), 8.40 (d, J = 5.3 Hz, 1H), 7.96 (d, J = 9.4 Hz, 1H), 7.82-7.67 (m, 1H), 7.61 (s, 1H), 7.43 (s, 1H), 7.23 (d, J = 5.3 Hz, 1H), 4.86 (d, J = 10.2 Hz, 1H), 4.68 (d, J = 12.8 Hz, 1H), 2.72 (d, J = 9.4 Hz, 2H), 2.59 (d, J = 12.0 Hz, 1H), 2.15-1.90 (m, 1H), 1.71 (s, 1H), 1.31 (q, J = 12.0 Hz, 1H), 0.98 (d, J = 6.5 Hz, 3H). |
| I-137 | 407.1 | 1.46 | (300 MHz, DMSO, ppm): 12.64 (s, 1H), 10.36 (s, 1H), 8.70 (s, 1H), 8.41 (d, J = 5.2 Hz, 1H), 7.96 (d, J = 9.4 Hz, 1H), 7.70 (dd, J = 9.4, 1.9 Hz, 1H), 7.61 (s, 1H), 7.43 (s, 1H), 7.24 (d, J = 5.4 Hz, 1H), 4.86 (d, J = 9.1 Hz, 1H), 4.69 (d, J = 12.7 Hz, 1H), 2.73 (d, J = 9.4 Hz, 2H), 2.59 (d, J = 12.1 Hz, 1H), 2.06 (d, J = 12.9 Hz, 1H), 1.73 (s, 1H), 1.31 (q, J = 11.9 Hz, 1H), 0.99 (d, J = 6.5 Hz, 3H). |
| I-149 | 405.2 | 1.38 | 1H NMR (400 MHz, DMSO-d6) δ 10.39 (d, J = 15.2 Hz, 1H), 8.53 (d, J = 2.3 Hz, 1H), 8.31 (ddd, J = 15.4, 6.3, 2.1 Hz, 1H), 7.95 (d, J = 9.5 Hz, 1H), 7.84-7.54 (m, 1H), 7.40 (s, 1H), 7.03-6.73 (m, 2H), 3.78-3.50 (m, 2H), 2.93 (m, 1H), 2.45-2.0 (m, 2H), 1.58-1.35 (m, 2H), 1.02-0.74 (m, 3H). |
| I-154 | 391.2 | 1.31 | 1H NMR (400 MHz, DMSO-d6) δ 10.40 (s, 1H), 8.53 (s, 1H), 8.34 (dd, J = 6.3, 2.3 Hz, 1H), 7.96 (d, J = 9.4 Hz, 1H), 7.68 (d, J = 9.5 Hz, 1H), 7.40 (s, 1H), 7.00-6.74 (m, 2H), 4.50 (m, 2H), 3.11 (dt, J = 35.7, 12.4 Hz, 2H), 2.42-2.25 (m, 2H), 1.94 (d, J = 12.9 Hz, 1H), 1.76 (dd, J = 24.5, 13.2 Hz, 2H), 1.48 (d, J = 12.7 Hz, 1H). |
| I-202 | 427.1 | 1.76 | 1H NMR (400 MHz, DMSO-d6) δ 10.36 (s, 1H), 8.59 (s, 1H), 8.44 (d, J = 6.2 Hz, 1H), 7.97 (d, J = 9.4 Hz, 1H), 7.73-7.61 (m, 2H), 7.15 (s, 1H), 7.01 (d, J = 6.3 Hz, 1H), 2.75-2.64 (m, 3H). |
| I-214 | 444.1 | 1.67 | (400 MHz, DMSO-d6) δ 12.48 (d, J = 37.9 Hz, 1H), 10.38 (s, 1H), 8.55 (s, 1H), 8.38 (d, J = 6.2 Hz, 1H), 7.95 (d, J = 9.4 Hz, 1H), 7.67 (dd, J = 9.4, 2.0 Hz, 1H), 7.45 (s, 1H), 6.87 (d, J = 6.3 Hz, 1H), 4.55 (dd, J = 11.0, 2.7 Hz, 1H), 4.49-4.19 (m, 2H), 3.85-3.67 (m, 1H), 3.09 (t, J = 12.1 Hz, 1H), 2.85-2.69 (m, 1H), 2.25 (s, 3H), 1.24 (d, J = 6.2 Hz, 3H). |
| I-247 | 396.0 | 1.11 | (300 MHz, DMSO, ppm): 12.84 (s, 1H), 9.94 (s, 1H), 8.73-8.54 (m, 1H), 8.40 (d, J = 3.8 Hz, 1H), 7.91-7.70 (m, 2H), 7.53 (d, J = 10.5 Hz, 2H), 7.26 (d, J = 4.9 Hz, 1H), 4.57 (d, J = 32.9 Hz, 3H), 3.80 (d, J = 10.8 Hz, 1H), 3.17-2.63 (m, 2H), 1.26 (d, J = 6.4 Hz, 3H). |
| I-248 | 396.0 | 1.10 | (300 MHz, DMSO, ppm): 12.84 (s, 1H), 9.96 (s, 1H), 8.62 (s, 1H), 8.42 (s, 1H), 7.82 (d, J = 8.6 Hz, 2H), 7.54 (d, J = 10.6 Hz, 2H), 7.28 (s, 1H), 4.63 (d, J = 11.5 Hz, 3H), 3.81 (s, 1H), 3.23-2.68 (m, 2H), 1.26 (d, J = 6.0 Hz, 3H). |
| I-249 | 400.1 | 1.71 | (300 MHz, DMSO, ppm): 12.64 (s, 1H), 9.62 (s, 1H), 8.46 (s, 1H), 8.32 (d, J = 5.3 Hz, 1H), 7.87-7.36 (m, 3H), 7.14 (t, J = 7.2 Hz, 2H), 4.80 (dd, J = 37.2, 11.9 Hz, 2H), 3.45 (qd, J = 7.0, 5.1 Hz, 1H), 2.89-2.66 (m, 2H), 2.03 (d, J = 12.7 Hz, 1H), 1.71 (s, 2H), 1.26 (dd, J = 20.9, 8.9 Hz, 1H), 1.09-0.85 (m, 5H), 0.64 (s, 2H). |
| I-259 | 451.1 | 2.11 | 1H NMR (400 MHz, DMSO-d6, ppm) 12.66 (s, 1H), 9.05 (s, 1H), 8.44 (s, 1H), 8.33 (d, J = 5.3 Hz, 1H), 7.69 (d, J = 9.5 Hz, 1H), 7.64 (s, 1H), 7.45 (s, 1H), 7.15 (d, J = 5.3 Hz, 1H), 7.04 (d, J = 9.5 Hz, 1H), 4.80-4.77 (m, 2H), 4.14-3.71 (m, 4H), 2.87-2.83 (m, 1H), 2.78-2.73 (m, 1H), 2.59-2.55 (m, 1H), 2.00-1.98 (m, 1H), 1.72-1.70 (m, 1H), 1.34-1.30 (m, 1H), 0.98 (d, J = 6.5 Hz, 3H). |
| I-261 | 451.2 | 1.19 | 1H NMR (300 MHz, DMSO-d6, ppm) 12.53 (s, 1H), 9.10 (s, 1H), 8.43 (s, 1H), 8.31 (d, J = 5.3 Hz, 1H), 7.68 (d, J = 9.6 Hz, |

TABLE 2-continued

Analytical data for compounds of formula I

| Cmpd No. | LCMS (ES+) | LCMS (rt, min) | 1H NMR |
|---|---|---|---|
| | | | 1H), 7.53 (s, 1H), 7.39 (s, 1H), 7.12 (d, J = 5.3 Hz, 1H), 7.08-7.04 (m, 1H), 4.32-4.08 (m, 4H), 4.02-3.90 (m, 3H), 3.59-3.56 (m, 1H), 3.15-3.10 (m, 1H), 1.94-1.90 (m, 2H), 1.72-1.62 (m, 1H), 0.96 (d, J = 6.6 Hz, 3H). |
| I-271 | 415.0 | 1.15 | 1H NMR (300 MHz, DMSO-d6, ppm) 12.62 (s, 1H), 8.86 (s, 1H), 8.37 (s, 1H), 8.28 (d, J = 5.3 Hz, 1H), 7.57 (d, J = 9.5 Hz, 3H), 7.10 (d, J = 5.3 Hz, 1H), 6.88 (dd, J = 9.5, 2.1 Hz, 1H), 4.76 (d, J = 11.7 Hz, 2H), 3.56 (br s, 4H), 2.76 (t, J = 12.7 Hz, 2H), 2.44 (s, 1H), 2.12 (s, 2H), 1.95 (d, J = 12.7 Hz, 1H), 1.67 (s, 1H), 1.26 (q, J = 11.7 Hz, 1H), 0.94 (d, J = 6.5 Hz, 3H). |
| I-287 | 465.1 | 1.24 | 1H NMR (400 MHz, DMSO-d6, ppm) 12.55 (s, 1H), 9.13 (s, 1H), 8.40 (s, 1H), 7.68 (d, J = 9.5 Hz, 1H), 7.56 (s, 1H), 7.40 (s, 1H), 7.10-7.01 (m, 2H), 4.14 (s, 4H), 4.02 (s, 1H), 3.98 (d, J = 12.8 Hz, 2H), 3.52 (s, 1H), 3.11 (s, 1H), 2.32 (s, 3H), 1.89 (d, J = 9.3 Hz, 2H), 1.67 (s, 1H), 0.97 (d, J = 6.5 Hz, 3H). |
| I-288 | 465.1 | 1.23 | (400 MHz, DMSO-d6. ppm) 12.67 (s, 1H), 9.06 (s, 1H), 8.39 (s, 1H), 7.67 (d, J = 9.6 Hz, 2H), 7.45 (s, 1H), 7.08 (s, 1H), 7.02 (d, J = 9.5 Hz, 1H), 4.82 (d, J = 10.4 Hz, 2H), 4.07 (s, 4H), 2.77 (d, J = 11.5 Hz, 2H), 2.55 (d, J = 17.2 Hz, 1H), 2.32 (s, 3H), 1.98 (d, J = 12.7 Hz, 1H), 1.71 (s, 1H), 1.28 (q, J = 12.1 Hz, 1H), 0.98 (d, J = 6.5 Hz, 3H). |
| I-272 | 415.0 | 1.16 | (300 MHz, DMSO-d6, ppm) 12.62 (s, 1H), 8.86 (s, 1H), 8.37 (s, 1H), 8.28 (d, J = 5.3 Hz, 1H), 7.65-7.33 (m, 3H), 7.10 (d, J = 5.3 Hz, 1H), 6.88 (dd, J = 9.5, 2.1 Hz, 1H), 4.85-4.72 (m, 2H), 3.72-3.35 (m, 4H), 2.87-2.73 (m, 2H), 2.57-2.43 (m, 1H), 2.20-2.03 (m, 2H), 2.01-1.90 (m, 1H), 1.80-1.63 (m, 1H), 1.32-1.09 (m, 1H), 0.94 (d, J = 6.5 Hz, 3H). |
| I-310 | 429 | 1.392 | 12.70 (1H), 10.06 (1H), 8.46 (1H), 8.31 (1H), 7.80 (2H), 7.57 (1H), 7.46 (1H), 6.84 (1H), 3.82 (1H), 2.83 (2H), 2.58 (2H), 2.42 (1H), 1.13 (3H) |
| I-312 | 463.1 | 1.08 | 1H NMR (400 MHz, DMSO-d6) d 10.50 (dd, J = 1.9, 0.9 Hz, 1H), 8.54 (s, 1H), 8.33 (d, J = 6.3 Hz, 1H), 7.95 (dd, J = 9.4, 0.9 Hz, 1H), 7.81 (dd, J = 9.4, 1.9 Hz, 1H), 6.73 (d, J = 6.4 Hz, 1H), 5.14-3.91 (m, 3H), 3.37 (s, 3H), 3.22 (td, J = 10.4, 9.8, 5.1 Hz, 1H), 3.06 (d, J = 0.9 Hz, 3H), 3.02 (d, J = 0.9 Hz, 3H), 2.55 (s, 1H), 1.93 (d, J = 12.8 Hz, 1H), 1.76-1.58 (m, 1H), 1.17 (q, J = 11.9 Hz, 1H), 0.97 (d, J = 6.5 Hz, 3H). |
| I-313 | 424.2 | 1.19 | 1H NMR (400 MHz, DMSO-d6) d 12.61 (s, 1H), 10.54 (dd, J = 2.0, 0.9 Hz, 1H), 8.54 (s, 1H), 8.34 (d, J = 6.3 Hz, 1H), 7.95 (dd, J = 9.4, 0.9 Hz, 1H), 7.81 (dd, J = 9.4, 1.9 Hz, 1H), 7.68 (s, 1H), 7.49 (s, 1H), 6.87 (d, J = 6.3 Hz, 1H), 4.49 (d, J = 54.0 Hz, 4H), 3.11 (d, J = 23.8 Hz, 2H), 2.71 (d, J = 24.5 Hz, 2H), 2.16-2.03 (m, 1H), 1.85 (d, J = 5.6 Hz, 1H), 1.79-1.55 (m, 2H). |
| I-314 | 444.0 | 0.93 | (300 MHz, DMSO, ppm) 12.34 (d, J = 35.0 Hz, 1H), 10.35 (s, 1H), 8.48 (s, 1H), 8.33 (d, J = 6.3 Hz, 1H), 7.92 (d, J = 9.4 Hz, 1H), 7.65 (m, 1H), 7.36 (s, 1H), 6.79 (d, J = 6.4 Hz, 1H), 5.12 (d, J = 4.6 Hz, 1H), 4.46 (s, 1H), 3.31 (m, 1H), 3.56 (d, J = 4.9 Hz, 1H), 2.67 (d, J = 26.7 Hz, 3H), 2.16 (s, 4H), 1.60 (s, 1H). |
| I-315 | 444.0 | 0.93 | (300 MHz, DMSO, ppm) 12.33 (d, J = 36.2 Hz, 1H), 10.35 (s, 1H), 8.48 (s, 1H), 8.33 (d, J = 6.3 Hz, 1H), 7.92 (d, J = 9.4 Hz, 1H), 7.78-7.25 (m, 2H), 6.79 (d, J = 6.4 Hz, 1H), 5.12 (d, J = 4.5 Hz, 1H), 4.82-4.01 (s, 1H), 3.56 (s, 1H), 3.31 (m, 1H), 2.87-2.54 (m, 3H), 2.17 (m, 4H), 1.59 (s, 1H). |
| I-318 | 465.5 | 1.29 | 1H NMR (400 MHz, DMSO-d6) d 12.61 (s, 1H), 10.50 (dd, J = 2.0, 0.9 Hz, 1H), 8.52 (s, 1H), 8.33 (d, J = 6.3 Hz, 1H), 8.17 (s, 1H), 7.94 (dd, J = 9.4, 0.8 Hz, 1H), 7.64 (dd, J = 9.4, 1.9 Hz, 2H), 7.53 (s, 1H), 6.86 (d, J = 6.3 Hz, 1H), 4.47 (d, J = 66.6 Hz, 2H), 3.20-3.04 (m, 2H), 2.75 (dd, J = 9.7, 5.1 Hz, 1H), 2.21 (dt, J = 6.7, 3.4 Hz, 1H), 2.09 (dd, J = 11.2, 3.5 Hz, 1H), 1.89-1.78 (m, 1H), 1.79-1.67 (m, 1H), 1.67-1.56 (m, 1H), 0.60-0.45 (m, 2H), 0.41 (qd, J = 5.4, 2.4 Hz, 2H). |
| I-319 | 504.2 | 1.23 | 1H NMR (400 MHz, DMSO-d6) d 10.46 (dd, J = 2.0, 0.9 Hz, 1H), 8.52 (s, 1H), 8.33 (d, J = 6.3 Hz, 1H), 8.19 (s, 1H), 7.94 (dd, J = 9.5, 0.9 Hz, 1H), 7.65 (dd, J = 9.4, 1.9 Hz, 1H), 6.73 (d, J = 6.4 Hz, 1H), 4.94-4.07 (m, 3H), 3.23 (s, 1H), 3.05 (dd, J = 13.6, 0.9 Hz, 6H), 2.70-2.59 (m, 1H), 2.26 (dt, J = 6.8, 3.4 Hz, 1H), 1.94 (d, J = 12.8 Hz, 1H), 1.75-1.57 (m, 1H), 1.17 (q, J = 12.0 Hz, 1H), 0.98 (d, J = 6.5 Hz, 3H), 0.60-0.46 (m, 2H), 0.47-0.34 (m, 2H). |
| I-320 | 425.1 | 1.09 | 1H NMR (400 MHz, DMSO-d6) δ 12.62 (s, 1H), 10.49 (dd, J = 1.9, 0.9 Hz, 1H), 8.51 (s, 1H), 8.32 (d, J = 6.3 Hz, 1H), 7.93 (dd, J = 9.4, 0.9 Hz, 1H), 7.72 (dd, J = 9.4, 1.9 Hz, 1H), 7.70-7.41 (m, 4H), 6.86 (d, J = 6.4 Hz, 1H), 4.48 (d, J = 59.9 Hz, 2H), 3.11 (tt, J = 10.6, 4.5 Hz, 2H), 2.73 (dd, J = 9.1, 5.0 Hz, 1H), |

TABLE 2-continued

Analytical data for compounds of formula I

| Cmpd No. | LCMS (ES+) | LCMS (rt, min) | $^1$H NMR |
|---|---|---|---|
| | | | 2.14-2.05 (m, 1H), 1.83 (d, J = 13.4 Hz, 1H), 1.70 (ddd, J = 22.7, 11.5, 2.9 Hz, 1H), 1.65-1.55 (m, 1H). |
| I-322 | 485 | 2.037 | 12.70 (1H), 10.06 (1H), 8.46 (1H), 8.31 (1H), 7.80 (2H), 7.57 (1H), 7.46 (1H), 6.84 (1H), 4.72 (1H), 4.47 (4H), 3.82 (1H), 2.83 (2H), 2.58 (2H), 2.42 (1H), 1.13 (3H) |
| I-325 | 477.25 | 1.392 | $^1$H NMR (400 MHz, Chloroform-d) δ 9.90 (d, J = 2.3 Hz, 1H), 8.54 (s, 1H), 8.24 (d, J = 6.2 Hz, 1H), 7.73 (d, J = 9.7 Hz, 1H), 7.40-7.34 (m, 2H), 7.23-7.09 (m, 2H), 7.09-7.01 (m, 2H), 6.41 (d, J = 6.2 Hz, 1H), 4.51 (s, 2H), 3.29 (dq, J = 10.5, 5.3, 4.4 Hz, 1H), 3.05 (d, J = 13.3 Hz, 7H), 2.73 (t, J = 11.9 Hz, 1H), 2.47 (t, J = 12.4 Hz, 1H), 2.07 (d, J = 13.1 Hz, 1H), 1.31 (q, J = 12.0 Hz, 1H), 0.97 (d, J = 6.6 Hz, 3H). |
| I-328 | 464.2 | 1.00 | 1H NMR (400 MHz, DMSO-d6) δ 10.45 (dd, J = 2.0, 0.9 Hz, 1H), 8.51 (s, 1H), 8.31 (d, J = 6.3 Hz, 1H), 7.92 (dd, J = 9.4, 0.9 Hz, 1H), 7.72 (dd, J = 9.4, 1.9 Hz, 1H), 7.63 (s, 2H), 6.73 (d, J = 6.4 Hz, 1H), 4.51 (s, 3H), 3.29-3.16 (m, 1H), 3.06 (d, J = 0.9 Hz, 3H), 3.03 (d, J = 0.9 Hz, 3H), 2.68-2.56 (m, 1H), 1.93 (d, J = 12.6 Hz, 1H), 1.76-1.59 (m, 1H), 1.17 (q, J = 11.9 Hz, 1H), 0.97 (d, J = 6.5 Hz, 3H). |
| I-329 | 437.90 | 1.857 | 1H NMR (400 MHz, Chloroform-d) d 9.88 (dd, J = 2.4, 0.8 Hz, 1H), 8.56 (s, 1H), 8.26 (d, J = 6.2 Hz, 1H), 7.74 (dd, J = 9.7, 0.8 Hz, 1H), 7.50 (s, 2H), 7.41-7.33 (m, 2H), 7.20 (dd, J = 9.6, 2.3 Hz, 1H), 7.18-7.12 (m, 1H), 7.09-7.04 (m, 2H), 6.40 (d, J = 6.2 Hz, 1H), 4.25 (s, 1H), 3.20-2.93 (m, 2H), 1.91-1.79 (m, 2H), 1.78-1.63 (m, 2H), 1.60-1.40 (m, 2H). Spectra |
| I-330 | 458.2 | 1.16 | $^1$H NMR (400 MHz, DMSO-d6) δ 9.11 (s, 1H), 8.41 (s, 1H), 8.30 (d, J = 5.3 Hz, 1H), 7.66 (d, J = 9.5 Hz, 1H), 7.13 (d, J = 5.3 Hz, 1H), 7.03 (dd, J = 9.5, 2.1 Hz, 1H), 5.55 (d, J = 57.5 Hz, 1H), 4.70 (d, J = 12.6 Hz, 2H), 4.26 (d, J = 6.7 Hz, 2H), 4.03 (ddd, J = 34.5, 23.2, 9.1 Hz, 2H), 3.01 (d, J = 6.1 Hz, 7H), 2.65 (d, J = 14.6 Hz, 1H), 1.99 (d, J = 12.7 Hz, 1H), 1.68 (s, 1H), 1.13 (q, J = 11.9 Hz, 1H), 0.94 (d, J = 6.5 Hz, 3H). |
| I-340 | 434.90 | 1.546 | $^1$H NMR (400 MHz, Chloroform-d) δ 10.22 (dd, J = 2.5, 1.5 Hz, 1H), 8.59 (s, 1H), 8.29 (d, J = 6.3 Hz, 1H), 7.85-7.75 (m, 1H), 7.45 (dd, J = 9.3, 1.8 Hz, 1H), 6.45 (d, J = 6.3 Hz, 1H), 3.33 (tt, J = 10.9, 4.4 Hz, 1H), 3.10 (d, J = 0.9 Hz, 3H), 3.07 (d, J = 0.9 Hz, 3H), 2.76 (t, J = 13.0, 10.7 Hz, 1H), 2.53 (t, J = 12.3 Hz, 1H), 2.09 (ddt, J = 12.7, 4.0, 2.1 Hz, 1H), 1.79 (d, J = 12.8 Hz, 3H), 1.42-1.28 (m, 1H), 1.04 (d, J = 6.6 Hz, 3H). |
| I-352 | 489 | 0.979 | 12.7 (1H), 10.36 (1H), 8.56 (1H), 8.36 (1H), 7.90 (2H), 7.42 (1H), 6.84 (1H), 4.42 (1H), 4.25 (1H), 3.52 (1H), 3.43 (1H), 3.11 (1H), 2.32 (1H), 1.83 (1H) |
| I-353 | 496 | 1.255 | 12.84 (1H), 10.36 (1H), 8.56 (1H), 8.36 (1H), 8.27 (1H), 7.90 (2H), 7.71 (1H), 7.63 (1H), 7.01 (1H), 6.84 (1H), 4.27 (2H), 3.72 (2H), 3.43 (2H), 2.98 (2H), 2.30 (1H) |
| I-362 | 485 | 1.671 | 12.70 (1H), 10.06 (1H), 8.46 (1H), 8.31 (1H), 7.80 (2H), 7.57 (1H), 7.46 (1H), 6.84 (1H), 4.72 (1H), 4.47 (4H), 3.82 (1H), 2.83 (2H), 2.58 (2H), 2.42 (1H), 1.13 (3H) |
| I-369 | 469 | 1.059 | 12.70 (1H), 10.06 (1H), 8.46 (1H), 8.31 (1H), 7.80 (2H), 7.57 (1H), 7.46 (1H), 6.84 (1H), 4.32 (2H), 3.39 (2H), 3.22 (2H), 2.39 (2H), 1.95 (1H), 0.85 (1H), 0.45 (2H), 0.04 (2H) |
| I-380 | 406.1 | 1.0 | 1H NMR (400 MHz, DMSO-d6) δ 10.42 (d, J = 38.1 Hz, 1H), 8.53 (s, 1H), 8.38 (dd, J = 15.5, 6.2 Hz, 1H), 7.95 (d, J = 9.4 Hz, 1H), 7.67 (dd, J = 9.4, 2.0 Hz, 1H), 7.27 (d, J = 43.5 Hz, 2H), 6.76 (d, J = 6.3 Hz, 1H), 3.08 (d, J = 12.7 Hz, 2H), 2.88-2.62 (m, 1H), 1.12 (d, J = 6.7 Hz, 3H). |
| I-398 | 437.95 | 1.398 | 1H NMR (400 MHz, Chloroform-d) d 9.87 (s, 1H), 8.54 (s, 1H), 8.23 (d, J = 6.0 Hz, 1H), 7.65 (d, J = 38.3 Hz, 2H), 7.37 (t, J = 7.8 Hz, 2H), 7.15 (q, J = 9.0, 7.5 Hz, 2H), 7.05 (d, J = 8.0 Hz, 2H), 6.87 (s, 1H), 6.43 (d, J = 6.2 Hz, 1H), 4.49 (d, J = 12.8 Hz, 1H), 4.22 (s, 1H), 3.28 (t, J = 11.6 Hz, 1H), 3.11 (t, J = 12.2 Hz, 1H), 2.95 (s, 1H), 2.20 (d, J = 12.8 Hz, 1H), 1.95-1.78 (m, 2H), 1.65 (d, J = 12.4 Hz, 1H). Spectra |
| I-399 | 437.95 | 1.419 | 1H NMR (400 MHz, DMSO-d6) d 9.77-9.66 (m, 1H), 8.42 (d, J = 21.7 Hz, 1H), 8.24 (dd, J = 12.9, 6.3 Hz, 1H), 7.80 (d, J = 9.6 Hz, 1H), 7.54 (d, J = 5.2 Hz, 1H), 7.47-7.29 (m, 2H), 7.21-7.13 (m, 2H), 7.13-7.07 (m, 2H), 6.91 (s, 1H), 6.82-6.65 (m, 1H), 4.35 (d, J = 73.8 Hz, 2H), 3.01 (dt, J = 32.7, 12.0 Hz, 2H), 2.83-2.61 (m, 1H), 2.05 (t, J = 10.5 Hz, 1H), 1.72 (q, J = 11.7 Hz, 2H), 1.49 (d, J = 12.4 Hz, 1H). Spectra |

TABLE 2-continued

Analytical data for compounds of formula I

| Cmpd No. | LCMS (ES+) | LCMS (rt, min) | $^1$H NMR |
|---|---|---|---|
| I-461 | 497 | 2.101 | 12.84 (1H), 10.36 (1H), 8.56 (1H), 8.36 (1H), 8.27 (1H), 7.90 (2H), 7.71 (1H), 7.63 (1H), 6.84 (1H), 4.27 (2H), 3.72 (2H), 3.43 (2H), 2.98 (2H), 2.30 (1H) |
| I-476 | 538.85 | 1.469 | 1H NMR (400 MHz, Chloroform-d) d 10.40 (s, 1H), 8.59 (s, 1H), 8.35 (dd, J = 6.2, 1.5 Hz, 1H), 7.83 (d, J = 9.4 Hz, 1H), 7.64 (s, 2H), 7.46 (dd, J = 9.4, 1.9 Hz, 1H), 6.44 (dd, J = 6.3, 1.7 Hz, 1H), 4.29 (s, 2H), 3.79 (ddd, J = 20.2, 10.4, 4.4 Hz, 1H), 3.60 (tq, J = 21.0, 11.1, 9.7 Hz, 1H), 2.76-2.37 (m, 2H), 2.17 (d, J = 54.3 Hz, 1H), 1.84-1.53 (m, 1H), 1.22-0.96 (m, 2H), 0.78 (s, 1H), 0.62 (s, 1H). |
| I-481 | 512.80 | 1.832 | 1H NMR (400 MHz, Chloroform-d) d 10.35 (s, 1H), 8.73 (s, 1H), 8.35 (s, 1H), 7.90 (d, J = 9.9 Hz, 1H), 7.64-7.47 (m, 3H), 6.42 (s, 1H), 4.62 (s, 1H), 4.40 (d, J = 5.5 Hz, 1H), 4.29 (d, J = 22.7 Hz, 3H), 3.66 (s, 1H), 3.43 (s, 2H), 2.26 (s, 2H), 1.54 (s, 3H), 1.34 (s, 3H). |
| I-484 | 411.9 | 1.38 | No NMR was obtained due to the limited amount. |
| I-490 | 547.2 | 0.085 | (300 MHz, DMSO) 12.74 (s, 1H), 10.33 (s, 1H), 8.49 (s, 1H), 8.34 (d, J = 6.2 Hz, 1H), 7.93 (d, J = 9.4 Hz, 1H), 7.65 (d, J = 9.4 Hz, 2H), 7.44 (br, 1H), 6.80 (d, J = 6.4 Hz, 1H), 3.94 (br, 2H), 3.81-3.44 (m, 5H), 2.81 (s, 3H), 2.80-2.73 (m, 1H), 2.38-2.16 (m, 3H), 2.05-1.93 (m, 1H), 1.83-1.72 (m, 1H). |
| I-495 | 547.2 | 1.65 | (300 MHz, DMSO) 12.74 (s, 1H), 10.32 (s, 1H), 8.49 (s, 1H), 8.33 (d, J = 6.3 Hz, 1H), 7.93 (d, J = 9.4 Hz, 1H), 7.65 (d, J = 9.5 Hz, 2H), 7.46 (br, 1H), 6.80 (d, J = 6.2 Hz, 1H), 3.93 (br, 2H), 3.71 (br, 2H), 3.63-3.51 (m, 2H), 2.81 (s, 3H), 2.80-2.73 (m, 1H), 2.38-2.16 (m, 3H), 2.05-1.93 (m, 1H), 1.83-1.72 (m, 1H). |
| I-499 | 434.90 | 1.847 | $^1$H NMR (400 MHz, Chloroform-d) δ 10.28-10.15 (m, 1H), 8.37-8.29 (m, 2H), 7.81 (d, J = 9.3 Hz, 1H), 7.49 (dd, J = 9.2, 1.8 Hz, 1H), 6.91 (d, J = 5.3 Hz, 1H), 4.92-4.82 (m, 1H), 4.82-4.70 (m, 1H), 3.37 (tt, J = 10.9, 4.5 Hz, 1H), 3.18-2.99 (m, 6H), 2.78 (dd, J = 12.8, 10.7 Hz, 1H), 2.50 (t, J = 12.2 Hz, 1H), 2.15-2.04 (m, 1H), 1.80 (dq, J = 10.6, 6.9 Hz, 1H), 1.34 (q, J = 12.0 Hz, 1H), 1.04 (d, J = 6.6 Hz, 3H). |
| I-508 | 455.1 | 0.98 | (300 MHz, Chloroform-d, ppm) 10.36 (s, 1H), 8.41-8.29 (m, 2H), 7.80 (d, J = 9.4 Hz, 1H), 7.59 (s, 2H), 7.45 (dd, J = 9.4, 1.9 Hz, 1H), 6.93 (d, J = 5.3 Hz, 1H), 4.22-4.01 (m, 2H), 4.01-3.74 (m, 3H), 3.02 (br, 1H), 2.67 (br, 1H), 1.56 (br, 1H), 0.52-0.18 (m, 4H).; |
| I-511 | 540.90 | 1.849 | $^1$H NMIR (400 MHz, Chloroform-d) δ 12.34 (s, 1H), 10.39 (s, 1H), 8.65 (d, J = 48.3 Hz, 1H), 8.40 (d, J = 23.0 Hz, 1H), 8.04 (dd, J = 51.1, 38.0 Hz, 2H), 7.81-7.49 (m, 1H), 6.54 (s, 1H), 4.75 (s, 1H), 4.03-3.11 (m, 5H), 3.03 (s, 1H), 1.97 (s, 7H), 1.27 (s, 4H), 0.88 (d, J = 20.3 Hz, 2H), 0.10 (s, 3H). |
| I-537 | 429 | 1.416 | 12.70 (1H), 10.06 (1H), 8.46 (1H), 8.31 (1H), 7.80 (2H), 7.57 (1H), 7.46 (1H), 6.84 (1H), 3.82 (1H), 2.83 (2H), 2.58 (2H), 2.42 (1H), 1.13 (3H) |
| I-543 | 510.2 | 1.67 | (400 MHz, DMSO-d6): 10.39 (s, 1H), 8.71 (s, 1H), 8.48 (d, J = 5.2 Hz, 1H), 7.97 (d, J = 9.4 Hz, 1H), 7.72 (dd, J = 9.4, 1.9 Hz, 1H), 7.29 (d, J = 5.3 Hz, 1H), 7.17 (br, 1H), 5.00 (br, 1H), 4.36 (br, 1H), 3.71 (br, 1H), 3.26-3.17 (m, 1H), 3.06 (d, J = 11.4 Hz, 1H), 2.95 (s, 3H), 2.92-2.81 (m, 1H), 2.67-2.57 (m, 1H), 2.39 (t, J = 11.6 Hz, 1H), 1.62 (br, 1H), 1.08 (d, J = 6.6 Hz, 3H), 0.70 (q, J = 5.9 Hz, 1H), 0.50 (p, J = 4.6, 4.2 Hz, 2H), 0.42-0.31 (m, 1H).; |

Purity and retention time of the compounds from this invention were measured by HPLC.

HPLC method: analytical reverse phase UPLC-MS was carried out on a waters Acquity UPLC-MS system equipped with a waters BEH 1.7 mm C-18 reverse phase column (2.1 mm×50 mm, 1.7 μm). The mobile phases were acetonitrile and water/acetonitrile (95:5 with 10 mM ammonium formate, pH 9). Run time 5 min Example 17: GCN2 Enzyme Inhibition Assay Compounds were screened for their ability to inhibit GCN2 kinase activity using a Transcreener® ADP$^2$ fluorescence polarization assay that detects ADP levels (BellBrook Labs, WI). Assays were carried out in a buffer consisting of 25 mM Tris-HCl (pH 7.5), 50 mM NaCl, 10 mM MgCl$_2$ and 1 mM DTT. Final substrate concentrations were 280 μM ATP and 200 μM peptidic substrate (H-Gly-Arg-Ser-Arg-Ser-Arg-Ser-Arg-Ser-Arg-Ser-Arg-Ser-Arg-Ser-Arg-OH [(RS)$_7$], Bachem, Switzerland). Assays were carried out at 25° C. in the presence of a (typical) final concentration of 4 nM GCN2 kinase.

An assay buffer containing GCN2 kinase and (RS)$_7$ was prepared. 4.7 μL of this stock solution was placed per well of a black, low volume, 384-well microtitre plate (e.g. catalogue number 3676, Corning Inc., NY). To this was added 0.65 μM of DMSO containing serial dilutions of the test compound (typical final concentrations of test compound were 0 to 8 μM). The plate was incubated for 10 minutes at 25° C. prior to the addition of 4.7 μL of ATP stock buffer to initiate the enzyme reaction. The reaction was allowed to proceed for 1 hour at 25° C., prior to the addition of 10 µL detection buffer (consisting of appropriate concentrations of ADP$^2$ antibody and ADP Alexa633 tracer in 1× stop and detect buffer as supplied by BellBrook Labs). The reaction was left to incubate for 1 hour at 25° C., prior to measuring the fluorescence polarisation signal (mP) in each well using a PHERAstar FS reader (BMG Labtech, Germany).

Fluorescence polarization values were normalized to an in plate standard curve consisting of various ratios of ATP to ADP in assay buffer to a final total concentration of 280 µM. 9.4 µL of each ATP:ADP ratio buffer was added to the plate along with 0.65 µL DMSO, prior to addition of detection buffer, to mimic assay volumes and conditions. The standard curve was used to convert mP values obtained from test wells into percentage ATP converted to ADP. Percentage inhibition of enzyme activity was then calculated at each compound dose. $IC_{50}$ and $Ki_{(app)}$ (using known assay and kinetic parameters) values were calculated from percentage inhibition data using a non-linear, tight-binding algorithm. All data analysis was undertaken using the Screener® software package (Genedata, Switzerland).

TABLE 3

Enzyme activity for compounds of formula I

| Compound | GCN2 (Ki) |
| --- | --- |
| I-1 | ++ |
| I-2 | +++ |
| I-3 | +++ |
| I-4 | ++ |
| I-5 | ++ |
| I-6 | ++ |
| I-7 | + |
| I-8 | ++ |
| I-9 | +++ |
| I-10 | +++ |
| I-11 | ++ |
| I-12 | +++ |
| I-13 | +++ |
| I-14 | ++ |
| I-15 | +++ |
| I-16 | +++ |
| I-17 | +++ |
| I-18 | +++ |
| I-19 | ++ |
| I-20 | +++ |
| I-21 | ++ |
| I-22 | +++ |
| I-23 | +++ |
| I-24 | +++ |
| I-25 | +++ |
| I-26 | + |
| I-27 | +++ |
| I-28 | +++ |
| I-29 | +++ |
| I-30 | + |
| I-31 | ++ |
| I-32 | ++ |
| I-33 | ++ |
| I-34 | +++ |
| I-35 | ++ |
| I-36 | +++ |
| I-37 | +++ |
| I-38 | ++ |
| I-39 | +++ |
| I-40 | +++ |
| I-41 | +++ |
| I-42 | +++ |
| I-43 | +++ |
| I-44 | +++ |
| I-45 | +++ |
| I-46 | ++ |
| I-47 | +++ |
| I-48 | +++ |
| I-49 | ++ |
| I-50 | +++ |
| I-51 | +++ |
| I-52 | +++ |
| I-53 | +++ |
| I-54 | ++ |
| I-55 | ++ |
| I-56 | ++ |
| I-57 | ++ |
| I-58 | ++ |
| I-59 | + |
| I-62 | ++ |
| I-63 | +++ |
| I-65 | ++ |
| I-66 | ++ |
| I-76 | + |
| I-77 | + |
| I-81 | ++ |
| I-83 | ++ |
| I-84 | + |
| I-85 | + |
| I-86 | ++ |
| I-87 | + |
| I-88 | + |
| I-89 | ++ |
| I-90 | +++ |
| I-91 | ++ |
| I-92 | +++ |
| I-93 | ++ |
| I-94 | + |
| I-95 | ++ |
| I-96 | +++ |
| I-97 | ++ |
| I-98 | ++ |
| I-99 | ++ |
| I-100 | +++ |
| I-101 | +++ |
| I-102 | +++ |
| I-103 | +++ |
| I-104 | ++ |
| I-105 | ++ |
| I-106 | ++ |
| I-107 | +++ |
| I-108 | +++ |
| I-109 | ++ |
| I-110 | +++ |
| I-111 | ++ |
| I-112 | +++ |
| I-113 | +++ |
| I-114 | +++ |
| I-115 | +++ |
| I-116 | +++ |
| I-117 | +++ |
| I-118 | +++ |
| I-119 | +++ |
| I-120 | +++ |
| I-137 | +++ |
| I-154 | +++ |
| I-137 | +++ |
| I-149 | +++ |
| I-202 | +++ |
| I-380 | +++ |
| I-484 | +++ |

+++ for Ki < 10 nM;
++ for Ki in 10 nM-100 nM range; and
+ for Ki 100 nM-1 µM.

TABLE 4

Enzyme activity for compounds of formula I

| Compound | GCN2 (IC$_{50}$) |
|---|---|
| I-122 | +++ |
| I-123 | ++ |
| I-124 | +++ |
| I-125 | +++ |
| I-126 | +++ |
| I-127 | +++ |
| I-128 | ++ |
| I-129 | ++ |
| I-130 | ++ |
| I-131 | + |
| I-132 | ++ |
| I-133 | + |
| I-134 | ++ |
| I-135 | +++ |
| I-136 | +++ |
| I-137 | +++ |
| I-138 | ++ |
| I-139 | + |
| I-140 | + |
| I-141 | + |
| I-142 | + |
| I-143 | ++ |
| I-144 | + |
| I-145 | + |
| I-146 | + |
| I-147 | ++ |
| I-148 | +++ |
| I-149 | +++ |
| I-150 | ++ |
| I-151 | + |
| I-152 | ++ |
| I-153 | +++ |
| I-154 | +++ |
| I-155 | + |
| I-156 | + |
| I-157 | + |
| I-158 | ++ |
| I-159 | ++ |
| I-160 | +++ |
| I-161 | ++ |
| I-162 | ++ |
| I-163 | ++ |
| I-164 | ++ |
| I-165 | ++ |
| I-166 | ++ |
| I-167 | + |
| I-168 | ++ |
| I-169 | ++ |
| I-170 | ++ |
| I-171 | ++ |
| I-172 | ++ |
| I-173 | + |
| I-174 | ++ |
| I-175 | +++ |
| I-176 | +++ |
| I-177 | ++ |
| I-178 | + |
| I-179 | +++ |
| I-180 | +++ |
| I-181 | ++ |
| I-182 | ++ |
| I-183 | ++ |
| I-184 | ++ |
| I-185 | ++ |
| I-186 | +++ |
| I-187 | ++ |
| I-188 | ++ |
| I-189 | ++ |
| I-190 | + |
| I-191 | ++ |
| I-192 | ++ |
| I-193 | +++ |
| I-195 | ++ |
| I-196 | +++ |
| I-197 | ++ |
| I-198 | +++ |
| I-199 | +++ |
| I-200 | +++ |
| I-201 | ++ |
| I-202 | +++ |
| I-203 | ++ |
| I-204 | ++ |
| I-205 | ++ |
| I-206 | ++ |
| I-207 | + |
| I-208 | ++ |
| I-209 | ++ |
| I-210 | + |
| I-211 | + |
| I-212 | + |
| I-213 | ++ |
| I-214 | + |
| I-217 | ++ |
| I-218 | ++ |
| I-219 | ++ |
| I-220 | ++ |
| I-221 | +++ |
| I-222 | ++ |
| I-223 | +++ |
| I-224 | + |
| I-225 | + |
| I-226 | + |
| I-227 | ++ |
| I-228 | + |
| I-229 | +++ |
| I-230 | ++ |
| I-231 | + |
| I-232 | + |
| I-233 | + |
| I-234 | ++ |
| I-235 | ++ |
| I-236 | ++ |
| I-238 | ++ |
| I-239 | + |
| I-240 | + |
| I-241 | ++ |
| I-242 | ++ |
| I-243 | + |
| I-244 | ++ |
| I-245 | ++ |
| I-246 | ++ |
| I-247 | +++ |
| I-248 | +++ |
| I-249 | +++ |
| I-250 | ++ |
| I-251 | ++ |
| I-252 | + |
| I-253 | + |
| I-254 | + |
| I-255 | + |
| I-256 | + |
| I-257 | + |
| I-258 | ++ |
| I-259 | +++ |
| I-260 | +++ |
| I-261 | +++ |
| I-262 | ++ |
| I-263 | ++ |
| I-264 | +++ |
| I-265 | ++ |
| I-266 | +++ |
| I-267 | ++ |
| I-268 | +++ |
| I-269 | ++ |
| I-270 | +++ |
| I-271 | ++ |
| I-272 | +++ |
| I-273 | +++ |
| I-274 | ++ |
| I-275 | +++ |
| I-276 | + |
| I-277 | ++ |

TABLE 4-continued

Enzyme activity for compounds of formula I

| Compound | GCN2 (IC$_{50}$) |
|---|---|
| I-278 | +++ |
| I-279 | ++ |
| I-280 | ++ |
| I-281 | ++ |
| I-282 | + |
| I-283 | ++ |
| I-284 | ++ |
| I-285 | + |
| I-286 | +++ |
| I-287 | ++ |
| I-288 | +++ |
| I-289 | ++ |
| I-290 | ++ |
| I-291 | ++ |
| I-292 | + |
| I-293 | +++ |
| I-294 | + |
| I-295 | ++ |
| I-296 | + |
| I-297 | ++ |
| I-298 | + |
| I-299 | + |
| I-300 | ++ |
| I-301 | + |
| I-302 | +++ |
| I-303 | ++ |
| I-304 | ++ |
| I-305 | + |
| I-307 | ++ |
| I-308 | ++ |
| I-309 | + |
| I-310 | +++ |
| I-311 | ++ |
| I-312 | + |
| I-313 | ++ |
| I-314 | +++ |
| I-315 | +++ |
| I-316 | +++ |
| I-317 | ++ |
| I-318 | + |
| I-319 | + |
| I-320 | ++ |
| I-321 | ++ |
| I-322 | ++ |
| I-323 | +++ |
| I-324 | + |
| I-325 | + |
| I-326 | +++ |
| I-327 | ++ |
| I-328 | + |
| I-329 | ++ |
| I-330 | + |
| I-331 | + |
| I-332 | + |
| I-333 | + |
| I-334 | + |
| I-335 | + |
| I-336 | ++ |
| I-337 | + |
| I-338 | + |
| I-339 | ++ |
| I-340 | +++ |
| I-341 | + |
| I-342 | ++ |
| I-343 | + |
| I-344 | + |
| I-345 | + |
| I-346 | ++ |
| I-347 | + |
| I-348 | ++ |
| I-349 | ++ |
| I-350 | + |
| I-351 | +++ |
| I-352 | +++ |
| I-353 | +++ |
| I-354 | +++ |
| I-355 | + |
| I-356 | ++ |
| I-357 | ++ |
| I-358 | +++ |
| I-359 | +++ |
| I-360 | +++ |
| I-361 | ++ |
| I-362 | +++ |
| I-363 | + |
| I-364 | + |
| I-365 | + |
| I-366 | +++ |
| I-367 | + |
| I-368 | + |
| I-369 | +++ |
| I-370 | +++ |
| I-371 | +++ |
| I-372 | +++ |
| I-373 | +++ |
| I-374 | +++ |
| I-375 | ++ |
| I-376 | ++ |
| I-377 | ++ |
| I-378 | ++ |
| I-379 | ++ |
| I-380 | +++ |
| I-382 | + |
| I-383 | +++ |
| I-384 | +++ |
| I-385 | +++ |
| I-386 | + |
| I-387 | + |
| I-388 | + |
| I-389 | ++ |
| I-390 | +++ |
| I-391 | + |
| I-392 | + |
| I-393 | + |
| I-394 | + |
| I-395 | + |
| I-396 | ++ |
| I-397 | ++ |
| I-398 | + |
| I-399 | ++ |
| I-400 | ++ |
| I-401 | + |
| I-402 | + |
| I-403 | + |
| I-404 | ++ |
| I-405 | ++ |
| I-406 | ++ |
| I-407 | ++ |
| I-408 | ++ |
| I-409 | ++ |
| I-410 | + |
| I-411 | + |
| I-412 | + |
| I-413 | + |
| I-414 | ++ |
| I-415 | + |
| I-416 | ++ |
| I-417 | + |
| I-418 | ++ |
| I-419 | ++ |
| I-420 | ++ |
| I-421 | ++ |
| I-422 | ++ |
| I-423 | + |
| I-424 | ++ |
| I-425 | + |
| I-426 | ++ |
| I-427 | ++ |
| I-428 | ++ |
| I-429 | +++ |
| I-432 | ++ |
| I-433 | ++ |

TABLE 4-continued

Enzyme activity for compounds of formula I

| Compound | GCN2 (IC$_{50}$) |
|---|---|
| I-434 | + |
| I-435 | +++ |
| I-436 | ++ |
| I-437 | + |
| I-438 | ++ |
| I-439 | + |
| I-440 | + |
| I-441 | ++ |
| I-442 | ++ |
| I-443 | ++ |
| I-444 | ++ |
| I-445 | ++ |
| I-446 | ++ |
| I-447 | ++ |
| I-448 | ++ |
| I-449 | +++ |
| I-450 | ++ |
| I-451 | ++ |
| I-452 | + |
| I-454 | ++ |
| I-455 | ++ |
| I-456 | ++ |
| I-457 | ++ |
| I-458 | ++ |
| I-459 | +++ |
| I-460 | ++ |
| I-461 | +++ |
| I-462 | + |
| I-463 | ++ |
| I-464 | + |
| I-465 | + |
| I-466 | ++ |
| I-467 | ++ |
| I-468 | + |
| I-469 | ++ |
| I-470 | +++ |
| I-471 | + |
| I-472 | ++ |
| I-473 | +++ |
| I-474 | + |
| I-475 | ++ |
| I-476 | +++ |
| I-477 | ++ |
| I-478 | ++ |
| I-479 | + |
| I-480 | + |
| I-481 | +++ |
| I-482 | ++ |
| I-483 | + |
| I-484 | +++ |
| I-485 | ++ |
| I-486 | + |
| I-487 | + |
| I-488 | ++ |
| I-489 | ++ |
| I-490 | +++ |
| I-491 | ++ |
| I-492 | ++ |
| I-493 | ++ |
| I-494 | + |
| I-495 | +++ |
| I-496 | + |
| I-497 | + |
| I-498 | ++ |
| I-499 | +++ |
| I-500 | + |
| I-501 | + |
| I-502 | ++ |
| I-503 | ++ |
| I-504 | +++ |
| I-505 | + |
| I-506 | ++ |
| I-507 | + |
| I-508 | +++ |
| I-509 | + |
| I-510 | +++ |
| I-511 | +++ |
| I-512 | + |
| I-513 | + |
| I-514 | + |
| I-515 | + |
| I-516 | +++ |
| I-517 | + |
| I-518 | ++ |
| I-519 | + |
| I-520 | ++ |
| I-521 | +++ |
| I-522 | +++ |
| I-523 | ++ |
| I-524 | ++ |
| I-525 | ++ |
| I-526 | ++ |
| I-527 | ++ |
| I-528 | ++ |
| I-529 | +++ |
| I-530 | ++ |
| I-531 | ++ |
| I-532 | ++ |
| I-533 | +++ |
| I-534 | + |
| I-535 | + |
| I-536 | + |
| I-537 | +++ |
| I-538 | ++ |
| I-539 | ++ |
| I-540 | +++ |
| I-541 | + |
| I-542 | +++ |
| I-543 | +++ |
| I-544 | +++ |
| I-545 | +++ |
| I-546 | +++ |
| I-547 | +++ |
| I-548 | ++ |
| I-549 | + |
| I-550 | + |
| I-551 | ++ |

+++ for IC$_{50}$ < 10 nM;
++ for IC$_{50}$ in 10 nM-100 nM range;
+ for IC$_{50}$ 100 nM-1 μM.

Example 18: GCN2 Cellular Inhibition Assay

Compounds can be screened for their ability to inhibit intracellular GCN2 using an AlphaScreen assay (Perkin Elmer) to detect phosphorylation of the GCN2 substrate eIF2α in borrelidin-treated cells. U2OS cells are plated at 5,000 cells per well in 384-well white polystyrene plates (Corning 3570) in McCoy's 5A media (GIBCO 26600-023) supplemented with 10% foetal bovine serum (SAFC 12103C), Penicillin/Streptomycin solution diluted 1:100 (Sigma P0781), and 2 mM L-glutamine (Sigma G7513), and allowed to adhere overnight at 37° C. in 5% CO$_2$. Compounds are then added to the cell media from a final concentration of 40 μM in 4-fold serial dilutions. Borrelidin (FluoroChem M01440) is immediately added to the wells to a final concentration of 10 μM and the cells are incubated for 1 h at 37° C. in 5% CO$_2$. After 1 h of treatment with borrelidin, the media is removed, and the cells are lysed with lysis buffer (TGR BioSceinces TGRLB) at ambient temperature.

An AlphaScreen SureFire P-eIF2α (Ser51) assay kit (Perkin Elmer TGREIF2S) was used to measure levels of eIF2α phosphorylated on Serine 51. Anti-phosphorylated eIF2α Ser51 antibody-linked acceptor beads (TGR BioScience 6760617) are added to the cell homogenate (diluted 1:250 into a mixture of activation (TGR BioScience TGRAB) and reaction buffer (TGR BioScience TGREIF2S) prepared immediately before use). The plate is then incubated for 2 h at ambient temperature in the dark. Anti-eIF2α antibody-linked donor beads (TGR BioScience 6760617) were then added (diluted 1:100 in dilution buffer (TGR BioScience TGRDB) prepared immediately before use). The plate is then incubated overnight at ambient temperature in the dark.

Plates are analyzed on an Alpha Technology-compatible PHERAstar FS plate reader (BMG Labtech Version 1.14) to quantify phosphorylated eIF2α Ser51 levels. The percentage inhibition of phosphorylated eIF2α is calculated by comparison to control wells stimulated with borrelidin alone. These data are plotted against concentration of compound and $IC_{50}$ are determined using Genedata Analyzer (Genedata AG Version 12.0.3).

TABLE 5

Cellular activity for compounds of formula I (biomarker assay)

| Compound | GCN2 Biomarker ($IC_{50}$) |
|---|---|
| I-1 | ++ |
| I-2 | +++ |
| I-3 | +++ |
| I-4 | ++ |
| I-5 | ++ |
| I-6 | ++ |
| I-8 | ++ |
| I-9 | +++ |
| I-10 | +++ |
| I-11 | + |
| I-12 | +++ |
| I-13 | ++ |
| I-14 | ++ |
| I-15 | +++ |
| I-16 | ++ |
| I-17 | +++ |
| I-18 | +++ |
| I-19 | ++ |
| I-20 | +++ |
| I-21 | ++ |
| I-22 | +++ |
| I-23 | +++ |
| I-24 | +++ |
| I-25 | ++ |
| I-27 | +++ |
| I-28 | ++ |
| I-29 | + |
| I-31 | ++ |
| I-32 | ++ |
| I-33 | + |
| I-34 | +++ |
| I-35 | ++ |
| I-36 | +++ |
| I-37 | +++ |
| I-39 | +++ |
| I-41 | ++ |
| I-42 | ++ |
| I-43 | ++ |
| I-44 | +++ |
| I-45 | +++ |
| I-46 | ++ |
| I-47 | ++ |
| I-48 | +++ |
| I-49 | + |
| I-50 | ++ |
| I-54 | ++ |
| I-55 | ++ |
| I-56 | ++ |
| I-57 | ++ |
| I-58 | ++ |
| I-59 | + |
| I-62 | ++ |
| I-63 | +++ |
| I-65 | ++ |
| I-66 | ++ |
| I-76 | + |
| I-77 | + |
| I-81 | ++ |
| I-83 | ++ |
| I-84 | + |
| I-85 | + |
| I-86 | ++ |
| I-88 | +++ |
| I-90 | +++ |
| I-92 | ++ |
| I-102 | +++ |
| I-103 | +++ |
| I-104 | ++ |
| I-105 | + |
| I-106 | + |
| I-107 | +++ |
| I-108 | +++ |
| I-109 | ++ |
| I-110 | ++ |
| I-111 | ++ |
| I-112 | ++ |
| I-113 | ++ |
| I-114 | +++ |
| I-115 | +++ |
| I-116 | ++ |
| I-117 | +++ |
| I-118 | +++ |
| I-120 | +++ |
| I-123 | +++ |
| I-124 | +++ |
| I-125 | +++ |
| I-126 | +++ |
| I-127 | +++ |
| I-128 | +++ |
| I-130 | ++ |
| I-134 | +++ |
| I-135 | +++ |
| I-136 | +++ |
| I-137 | +++ |
| I-138 | +++ |
| I-143 | +++ |
| I-144 | +++ |
| I-145 | +++ |
| I-146 | ++ |
| I-147 | +++ |
| I-148 | +++ |
| I-149 | +++ |
| I-150 | +++ |
| I-153 | +++ |
| I-154 | +++ |
| I-157 | +++ |
| I-159 | +++ |
| I-169 | ++ |
| I-170 | +++ |
| I-171 | +++ |
| I-172 | +++ |
| I-175 | +++ |
| I-176 | +++ |
| I-177 | +++ |
| I-179 | +++ |
| I-180 | +++ |
| I-181 | ++ |
| I-182 | +++ |
| I-183 | +++ |
| I-184 | +++ |
| I-185 | +++ |
| I-186 | +++ |
| I-191 | +++ |
| I-193 | +++ |
| I-196 | +++ |
| I-197 | +++ |
| I-198 | ++ |

TABLE 5-continued

Cellular activity for compounds of formula I (biomarker assay)

| Compound | GCN2 Biomarker (IC$_{50}$) |
|---|---|
| I-199 | +++ |
| I-200 | +++ |
| I-201 | ++ |
| I-202 | +++ |
| I-203 | ++ |
| I-204 | ++ |
| I-208 | +++ |
| I-209 | +++ |
| I-213 | ++ |
| I-217 | ++ |
| I-218 | ++ |
| I-219 | ++ |
| I-220 | ++ |
| I-221 | +++ |
| I-222 | +++ |
| I-223 | +++ |
| I-224 | +++ |
| I-225 | ++ |
| I-226 | ++ |
| I-227 | ++ |
| I-232 | ++ |
| I-233 | ++ |
| I-235 | +++ |
| I-236 | +++ |
| I-238 | ++ |
| I-240 | ++ |
| I-241 | ++ |
| I-242 | + |
| I-244 | ++ |
| I-245 | ++ |
| I-246 | ++ |
| I-247 | +++ |
| I-248 | +++ |
| I-249 | +++ |
| I-250 | +++ |
| I-251 | ++ |
| I-252 | ++ |
| I-259 | +++ |
| I-260 | +++ |
| I-261 | +++ |
| I-262 | + |
| I-263 | ++ |
| I-266 | +++ |
| I-267 | ++ |
| I-268 | ++ |
| I-269 | ++ |
| I-270 | +++ |
| I-271 | +++ |
| I-272 | +++ |
| I-273 | +++ |
| I-274 | ++ |
| I-275 | ++ |
| I-277 | ++ |
| I-278 | +++ |
| I-279 | ++ |
| I-280 | +++ |
| I-281 | +++ |
| I-283 | ++ |
| I-284 | + |
| I-285 | ++ |
| I-286 | ++ |
| I-287 | +++ |
| I-288 | +++ |
| I-289 | ++ |
| I-290 | ++ |
| I-291 | ++ |
| I-293 | +++ |
| I-294 | + |
| I-295 | ++ |
| I-297 | ++ |
| I-298 | + |
| I-300 | ++ |
| I-301 | ++ |
| I-302 | +++ |
| I-303 | ++ |
| I-304 | ++ |
| I-307 | ++ |
| I-308 | ++ |
| I-310 | +++ |
| I-311 | ++ |
| I-313 | ++ |
| I-314 | +++ |
| I-315 | +++ |
| I-316 | +++ |
| I-317 | ++ |
| I-318 | + |
| I-320 | ++ |
| I-321 | ++ |
| I-322 | +++ |
| I-323 | ++ |
| I-324 | + |
| I-325 | ++ |
| I-326 | +++ |
| I-327 | ++ |
| I-329 | +++ |
| I-339 | ++ |
| I-340 | +++ |
| I-342 | +++ |
| I-343 | ++ |
| I-344 | ++ |
| I-345 | ++ |
| I-346 | +++ |
| I-347 | ++ |
| I-348 | +++ |
| I-349 | ++ |
| I-351 | +++ |
| I-352 | ++ |
| I-353 | +++ |
| I-354 | +++ |
| I-355 | ++ |
| I-356 | ++ |
| I-357 | +++ |
| I-358 | +++ |
| I-359 | +++ |
| I-360 | +++ |
| I-361 | ++ |
| I-362 | +++ |
| I-363 | ++ |
| I-363 | ++ |
| I-364 | + |
| I-365 | ++ |
| I-366 | +++ |
| I-368 | ++ |
| I-369 | +++ |
| I-370 | +++ |
| I-371 | ++ |
| I-372 | ++ |
| I-373 | +++ |
| I-383 | ++ |
| I-384 | +++ |
| I-385 | ++ |
| I-386 | ++ |
| I-387 | ++ |
| I-388 | + |
| I-389 | ++ |
| I-390 | +++ |
| I-391 | ++ |
| I-392 | ++ |
| I-393 | ++ |
| I-395 | ++ |
| I-396 | + |
| I-397 | ++ |
| I-398 | ++ |
| I-399 | ++ |
| I-400 | ++ |
| I-401 | ++ |
| I-402 | ++ |
| I-403 | ++ |
| I-404 | ++ |
| I-405 | ++ |

TABLE 5-continued

Cellular activity for compounds of formula I (biomarker assay)

| Compound | GCN2 Biomarker (IC$_{50}$) |
|---|---|
| I-406 | ++ |
| I-407 | ++ |
| I-408 | ++ |
| I-409 | +++ |
| I-413 | + |
| I-414 | ++ |
| I-416 | ++ |
| I-417 | + |
| I-418 | ++ |
| I-419 | ++ |
| I-420 | ++ |
| I-421 | + |
| I-422 | + |
| I-423 | + |
| I-424 | ++ |
| I-426 | ++ |
| I-440 | + |
| I-441 | + |
| I-442 | ++ |
| I-443 | ++ |
| I-444 | ++ |
| I-445 | ++ |
| I-446 | ++ |
| I-447 | ++ |
| I-448 | ++ |
| I-449 | +++ |
| I-450 | +++ |
| I-461 | +++ |
| I-464 | ++ |
| I-470 | +++ |
| I-472 | +++ |
| I-473 | +++ |
| I-476 | +++ |
| I-477 | +++ |
| I-478 | +++ |
| I-481 | +++ |
| I-490 | +++ |
| I-491 | +++ |
| I-492 | ++ |
| I-493 | +++ |
| I-494 | ++ |
| I-495 | +++ |
| I-499 | +++ |
| I-500 | ++ |
| I-501 | ++ |
| I-502 | +++ |
| I-503 | +++ |
| I-504 | +++ |
| I-505 | + |
| I-506 | ++ |
| I-507 | ++ |
| I-508 | +++ |
| I-510 | +++ |
| I-511 | +++ |
| I-512 | ++ |
| I-516 | +++ |
| I-517 | ++ |
| I-520 | +++ |
| I-521 | +++ |
| I-522 | +++ |
| I-523 | +++ |
| I-524 | ++ |
| I-525 | ++ |
| I-526 | +++ |
| I-527 | ++ |
| I-528 | +++ |
| I-529 | +++ |
| I-530 | ++ |
| I-531 | +++ |
| I-532 | ++ |
| I-533 | +++ |
| I-536 | ++ |
| I-537 | +++ |
| I-538 | ++ |
| I-540 | +++ |
| I-541 | ++ |
| I-543 | +++ |
| I-544 | +++ |
| I-545 | +++ |
| I-546 | +++ |
| I-552 | +++ |
| I-553 | +++ |
| I-554 | +++ |
| I-556 | ++ |

+++ for IC$_{50}$ < 0.5 µM;
++ for IC$_{50}$ in 0.5 µM-5 µM range; and
+ for IC$_{50}$ > 5 µM.

Example 19: 4-(2-{6-chloroimidazo[1,2-a]pyridin-3-yl}pyrimidin-4-yl)-3-methylpiperazine-2-carboxamide, I-484

To a solution of 4-(2-{6-chloroimidazo[1,2-a]pyridin-3-yl}pyrimidin-4-yl)-3-methylpiperazine-2-carboxamide I-451 (49.00 mg; 0.13 µmmol; 1.00 eq.) and 1-ethoxycyclopropoxy)trimethylsilane (0.13 ml; 0.66 mmol; 5.00 eq.) in methanol (2.50 ml; 61.72 mmol; 468.32 eq.) was added acetic acid (0.06 ml; 1.05 mmol; 8.00 eq.) and then sodium cyanoborohydride (66.25 mg; 1.05 mmol; 8.00 eq.). Reaction was allowed to stir overnight at 70° C. and purified with pre-HPLC (10-90% ACN/NH$_4$OH—H$_2$O in 12 min) to afford 4-(2-{6-chloroimidazo[1,2-a]pyridin-3-yl}pyrimidin-4-yl)-3-methylpiperazine-2-carboxamide (17.6 mg, 31%) as a white solid.

Example 20: 5,5-Difluoro-1-[2-(6-trifluoromethyl-imidazo[1,2-a]pyridin-3-yl)-pyrimidin-4-yl]-piperidine-3-carboxylic acid amide, I-202

Example 21: 3-{2-[(2R,6S)-2-Methyl-6-(1H-pyrazol-4-yl)-morpholin-4-yl]-pyrimidin-4-yl}-6-trifluoromethyl-imidazo[1,2-a]pyridine I-127 and (2S,6R)-2-methyl-6-(1H-pyrazol-4-yl)-4-{4-[6-(trifluoromethyl)imidazo[1,2-a]pyridin-3-yl]pyrimidin-2-yl}morpholine I-126

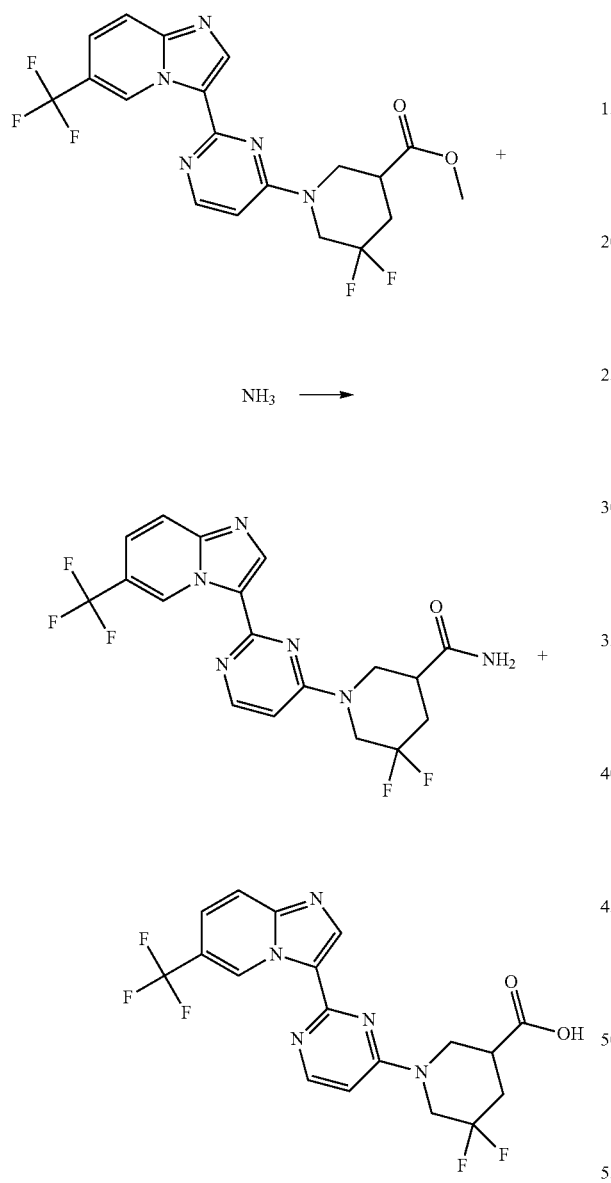

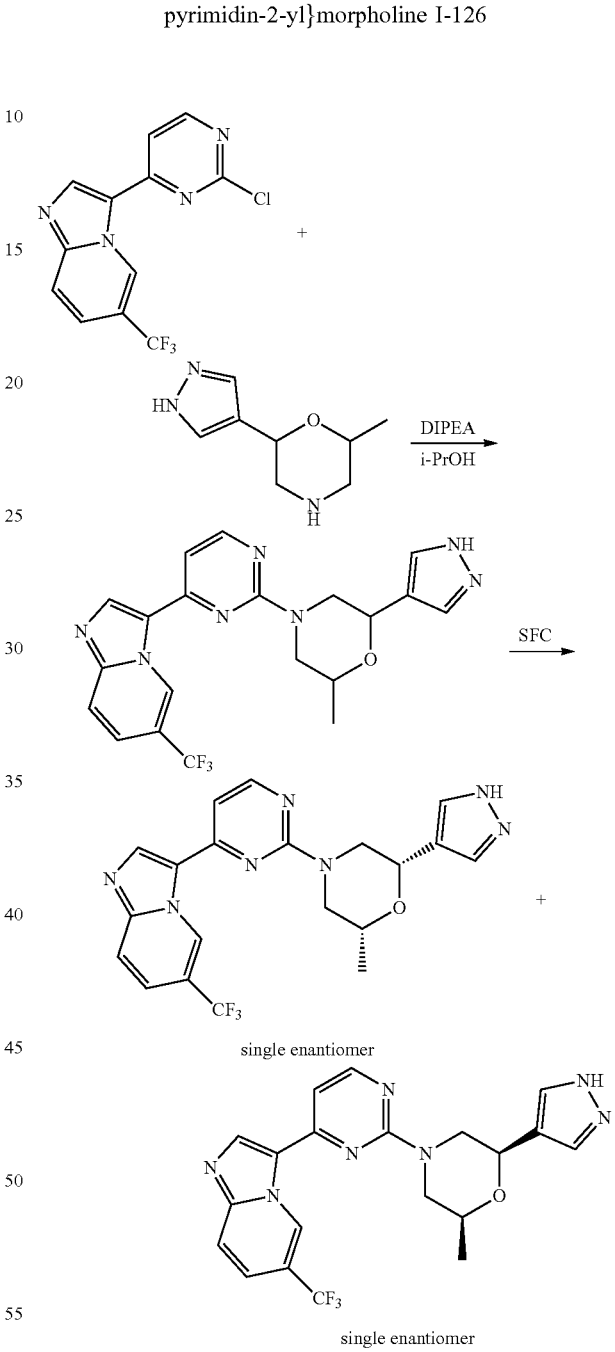

In a microwave vial containing 5,5-Difluoro-1-[2-(6-trifluoromethyl-imidazo[1,2-a]pyridin-3-yl)-pyrimidin-4-yl]-piperidine-3-carboxylic acid methyl ester (118.23 mg; 0.27 mmol; 1.00 eq.) was added ammonia 7N in MeOH (2.00 ml). The reaction was stirred at 100° C. for 72 h before it was purified with pre-HPLC (10-90% ACN/0.10% NH4OH—H2O in 12 min) to afford 5,5-Difluoro-1-[2-(6-trifluoromethyl-imidazo[1,2-a]pyridin-3-yl)-pyrimidin-4-yl]-piperidine-3-carboxylic acid amide (2.2 mg, 1.9%) as a white solid.

Step 1: 2-Methyl-6-(1H-pyrazol-4-yl)-4-{4-[6-(trifluoromethyl)imidazo[1,2-a]pyridin-3-yl]pyrimidin-2-yl}morpholine. A solution of 2-chloro-4-[6-(trifluoromethyl)imidazo[1,2-a]pyridin-3-yl]pyrimidine (200 mg, 0.60 mmol, 1 equiv, 90%), 2-methyl-6-(1H-pyrazol-4-yl)morpholine (112.0 mg, 0.60 mmol, 1 equiv, 90%) and DIPEA (155.8 mg, 1.21 mmol, 2 equiv, 95%) in i-PrOH (10 mL, 124.30 mmol, 206.24 equiv, 95%) was stirred for 16 h at 100 degrees Celsius under nitrogen atmosphere. The resulting mixture was concentrated under vacuum. The residue was purified by silica gel column chromatography, eluted with hexane/EtOAc (1:1) to afford 2-methyl-6-(1H-pyrazol-4-yl)-4-[4-[6-(trifluoromethyl)imidazo[1,2-a]pyridin-3-yl]pyrimidin-2-yl]morpholine (100 mg, 34.77%) as a white solid.

Step 2: 3-{2-[(2R,6S)-2-Methyl-6-(1H-pyrazol-4-yl)-morpholin-4-yl]-pyrimidin-4-yl}-6-trifluoromethyl-imidazo[1,2-a]pyridine and (2S,6R)-2-methyl-6-(1H-pyrazol-4-yl)-4-{4-[6-(trifluoromethyl)imidazo[1,2-a]pyridin-3-yl]pyrimidin-2-yl}morpholine. The racemic mixture of 2-methyl-6-(1H-pyrazol-4-yl)-4-[4-[6-(trifluoromethyl)imidazo[1,2-a]pyridin-3-yl]pyrimidin-2-yl]morpholine was purified by Chiral-Prep-HPLC with the following conditions (Prep-HPLC-032): Column, Chiralpak IA, 2*25 cm, 20 um; mobile phase, Hex (8 mmol/L NH3.MeOH)—HPLC and IPA-HPLC (hold 15% IPA-HPLC in 29 min); Detector, UV 254/220 nm. Two pure compounds were obtained: Peak 1 3-{2-[(2R,6S)-2-Methyl-6-(1H-pyrazol-4-yl)-morpholin-4-yl]-pyrimidin-4-yl}-6-trifluoromethyl-imidazo[1,2-a]pyridine I-127, retention time=18.029 min, 10.6 mg (22%), white solid; Peak 2 (2S,6R)-2-methyl-6-(1H-pyrazol-4-yl)-4-{4-[6-(trifluoromethyl)imidazo[1,2-a]pyridin-3-yl]pyrimidin-2-yl}morpholine I-126, retention time=25.76 min, 12.3 mg (25%), white solid.

Example 22: 3-{4-[(S)-4-(3-Methanesulfonyl-cyclobutyl)-3-(1H-pyrazol-4-yl)-piperazin-1-yl]-pyrimidin-2-yl}-6-trifluoromethyl-imidazo[1,2-a]pyridine I-495 and 3-{4-[(R)-4-(3-Methanesulfonyl-cyclobutyl)-3-(1H-pyrazol-4-yl)-piperazin-1-yl]-pyrimidin-2-yl}-6-trifluoromethyl-imidazo[1,2-a]pyridine I-490

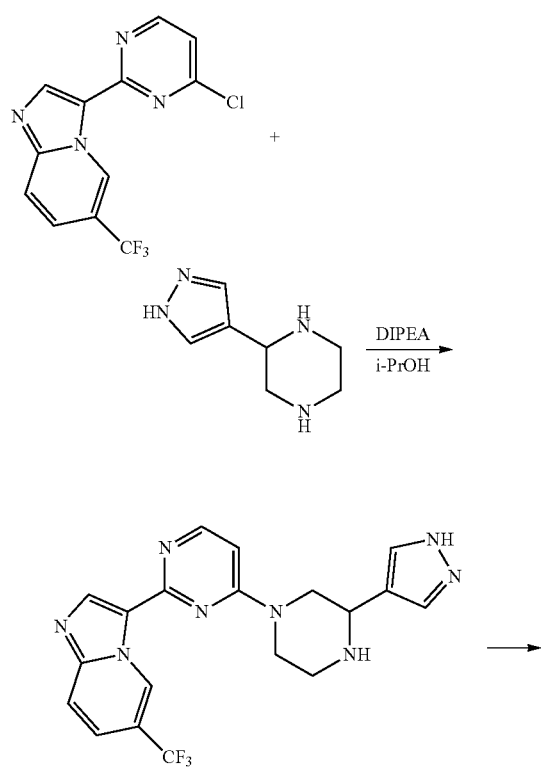

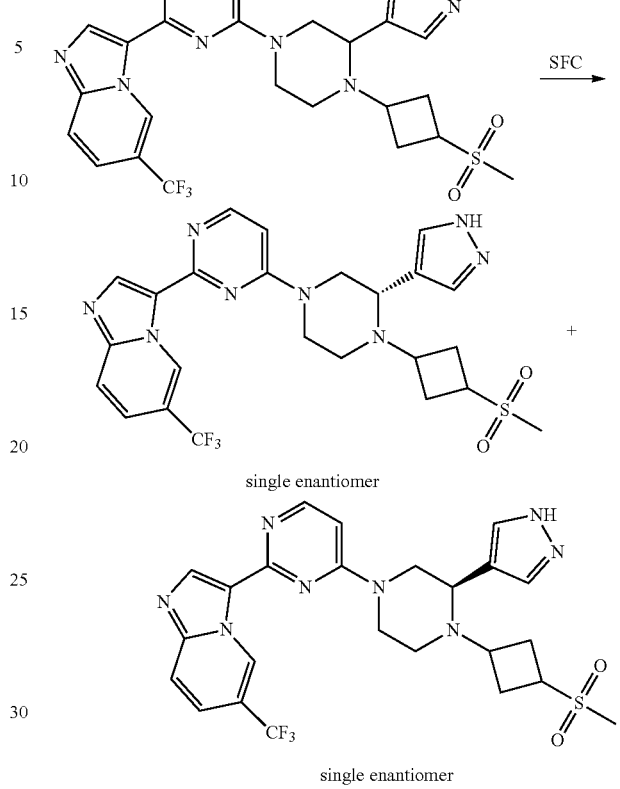

Step 1: 4-[3-(1H-pyrazol-4-yl)piperazin-1-yl]-2-[6-(trifluoromethyl)imidazo[1,2-a]pyridin-3-yl]pyrimidine. To a stirred mixture of 4-chloro-2-[6-(trifluoromethyl)imidazo[1,2-a]pyridin-3-yl]pyrimidine (600.00 mg, 1.808 mmol, 1.00 equiv, 90%) and 2-(1H-pyrazol-4-yl)piperazine (458.67 mg, 2.712 mmol, 1.50 equiv, 90%) in i-PrOH (15.00 mL, 245.293 mmol, 271.32 equiv, 95%) were added DIEA (491.98 mg, 3.616 mmol, 2.00 equiv, 95%) dropwise at room temperature under nitrogen atmosphere. The resulting mixture was stirred for 3 h at 100° C. under nitrogen atmosphere. Desired product could be detected by LCMS. The resulting mixture was concentrated under reduced pressure. The residue was purified by silica gel column chromatography, eluted with CH2Cl2/MeOH (8:1) to afford 4-[3-(1H-pyrazol-4-yl)piperazin-1-yl]-2-[6-(trifluoromethyl)imidazo[1,2-a]pyridin-3-yl]pyrimidine (510 mg, 61.26%) as a light yellow oil.

Step 2: 4-[4-(3-methanesulfonylcyclobutyl)-3-(1H-pyrazol-4-yl)piperazin-1-yl]-2-[6-(trifluoromethyl)imidazo[1,2-a]pyridine-3-yl]pyrimidine. To a stirred mixture of 4-[3-(1H-pyrazol-4-yl)piperazin-1-yl]-2-[6-(trifluoromethyl)imidazo[1,2-a]pyridin-3-yl]pyrimidine (100.00 mg, 0.217 mmol, 1.00 equiv, 90%) and 3-methanesulfonylcyclobutan-1-one (169.38 mg, 1.086 mmol, 5.00 equiv, 95%) in MeOH (2.50 mL, 74.121 mmol, 270.09 equiv, 95%) were added CH₃COOH (109.83 mg, 1.737 mmol, 8.00 equiv, 95%) and NaBH₃CN (57.47 mg, 0.869 mmol, 4.00 equiv, 95%) in portions at room temperature under nitrogen atmosphere. The resulting mixture was stirred for 3 h at 70° C. under nitrogen atmosphere. Desired product could be detected by LCMS. The crude product (110 mg) was purified by Prep-HPLC with the following conditions (2# SHIMADZU (HPLC-01)): Column, XBridge Shield RP18 OBD Column, 30*150 mm, 5 um; mobile phase, Water (10 MMOL/L NH4HCO3+0.1% NH3.H2O) and ACN (30% PhaseB up to 35% in 8 min); Detector, UV 254 nm. 80 mg racemic product was obtained. The racemic product (80) mg was resolved by Chiral-Prep-HPLC with the following conditions (Prep-HPLC-032): Column, CHIRAL ART Cellulose-SB, 2*25 cm, 5 um; mobile phase, Hex (8 mmol/L NH3.MeOH)- and EtOH— (hold 50% EtOH— in 17 min); Detector, UV 254 nm. This resulted in Peak 1: of 4-[(3 S)-4-(3-methanesulfonylcyclobutyl)-3-(1H-pyrazol-4-yl) piperazin-1-yl]-2-[6-(trifluoromethyl)imidazo[1,2-a]pyridin-3-yl]pyrimidine (11.0 mg 9.08%) as a white solid, retention time=4.501 min, ee: 99; Peak 2: 4-[(3R)-4-(3-methanesulfonylcyclobutyl)-3-(1H-pyrazol-4-yl)piperazin-1-yl]-2-[6-(trifluoromethyl)imidazo[1,2-a]pyridin-3-yl]pyrimidine (12.1 mg, 9.17%) as a white solid, retention time=5.529 min, ee: 98.

Example 23: 4-[4-({6-oxaspiro[2.5]octan-1-yl}methyl)-3-(1H-pyrazol-4-yl)piperazin-1-yl]-2-[6-(trifluoromethyl)imidazo[1,2-a]pyridin-3-yl]pyrimidine I-476

To a microwave vial containing a solution of 4-[3-(1H-pyrazol-4-yl)piperazin-1-yl]-2-[6-(trifluoromethyl)imidazo [1,2-a]pyridin-3-yl]pyrimidine (50.00 mg; 0.12 mmol; 1.00 eq.) and 6-oxaspiro[2.5]octane-1-carbaldehyde (84.57 mg; 0.60 mmol; 5.00 eq.) in methanol (2.50 ml; 61.72 mmol; 640.56 eq.), was added acetic acid (0.01 ml; 0.24 mmol; 2.00 eq.) and then sodium cyanoborohydride (30.33 mg; 0.48 mmol; 4.00 eq.). Reaction allowed to stir overnight at 70 C. LCMS-3 showed desired product mass with full conversion. Reaction was allowed to cool, then diluted with DCM. The reaction was then added drop wise to sat. NaHCO₃ and washed 3 times with NaHCO₃ and twice with brine. The organic layer was dried with anhydrous Na₂SO₄, filtered, and concentrated in vacuo. The crude was dissolved in DMSO then purified PuriFlash PF-C18HP 15 uL 10-90% MeCN in water (0.1% Formic Acid) 14 min gradient, then 90% for 3 min. The pure fractions were combined and lyophilized to afford the product: 4-[4-({6-oxaspiro[2.5] octan-1-yl}methyl)-3-(1H-pyrazol-4-yl)piperazin-1-yl]-2-[6-(trifluoromethyl)imidazo[1,2-a]pyridin-3-yl]pyrimidine (46.60 mg; 0.09 mmol)

Example 24: 4-[2-methyl-4-(oxetan-3-yl)-3-(1H-pyrazol-4-yl)piperazin-1-yl]-2-[6-(trifluoromethyl) imidazo[1,2-a]pyridin-3-yl]pyrimidine, I-322

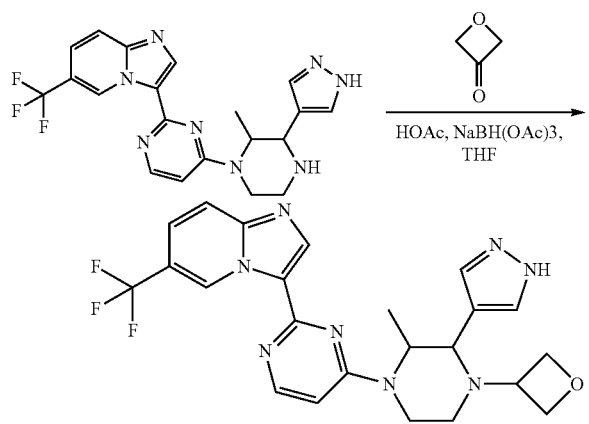

To a solution of 4-[2-methyl-3-(1H-pyrazol-4-yl)piperazin-1-yl]-2-[6-(trifluoromethyl)imidazo[1,2-a]pyridin-3-yl]pyrimidine (150.00 mg; 0.35 mmol; 1.00 eq.), oxetan-3-one (30.28 mg; 0.42 mmol; 1.20 eq.) and acetic acid (210.26 mg; 3.50 mmol; 10.00 eq.) in THF (3 ml) was treated with sodium triacetoxyborohydride (742.07 mg; 3.50 mmol; 10.00 eq.) and the mixture was stirred at room temperature for overnight. LCMS-3 showed that the desired product was observed. The crude product was loaded at reverse phase HPLC and purified with 20% ACN in Water containing 0.1% NH₄OH to 100% ACN in 10 minutes at the flow rate of 60 mL/minute to provide the product 4-[2-methyl-4-(oxetan-3-yl)-3-(1H-pyrazol-4-yl)piperazin-1-yl]-2-[6-(trifluoromethyl) imidazo[1,2-a]pyridin-3-yl]pyrimidine in 16% yield. M/z (M+H): 485; H NMR (DMSO-d6): 12.70 (1H), 10.06 (1H), 8.46 (1H), 8.31 (1H), 7.80 (2H), 7.57 (1H), 7.46 (1H), 6.84 (1H), 3.82 (1H), 2.83 (2H), 2.58 (2H), 2.42 (1H), 1.13 (3H)

Example 25: Exemplary Compounds I-122 to I-563

Additional compounds were prepared using similar methodologies to those described in the examples above:
6-Chloro-3-(4-(2,5-dimethyl-3-(1H-pyrazol-4-yl)piperazin-1-yl)pyrimidin-2-yl)imidazo[1,2-a]pyridine, I-122
Dimethyl(((3R,5S)-5-methyl-1-(2-(6-(trifluoromethyl)imidazo[1,2-a]pyridin-3-yl)pyrimidin-4-yl)piperidin-3-yl) imino)-λ6-sulfanone, I-123
3-{4-[(2S,6R)-2-Methyl-6-(3-methyl-1H-pyrazol-4-yl)-morpholin-4-yl]-pyrimidin-2-yl}-6-trifluoromethyl-imidazo[1,2-a]pyridine, I-124
(2R,6S)-2-methyl-6-(5-methyl-1H-pyrazol-4-yl)-4-(2-(6-(trifluoromethyl)imidazo[1,2-a]pyridin-3-yl)pyrimidin-4-yl)morpholine, I-125
(((3R,5S)-1-(2-(6-chloroimidazo[1,2-a]pyridin-3-yl)pyrimidin-4-yl)-5-methylpiperidin-3-yl)imino)dimethyl-λ6-sulfanone, I-128
(2R,6 S)-6-methyl-4-(2-(6-(trifluoromethyl)imidazo[1,2-a]pyridin-3-yl)pyrimidin-4-yl)morpholine-2-carboxamide, I-129
N,N-dimethyl-1-(2-(6-(trifluoromethyl)imidazo[1,2-a]pyridin-3-yl)pyrimidin-4-yl)piperidine-3-carboxamide, I-130
pyrrolidin-1-yl(1-(2-(6-(trifluoromethyl)imidazo[1,2-a] pyridin-3-yl)pyrimidin-4-yl)piperidin-3-yl)methanone, I-131
5-(2-(6-chloroimidazo[1,2-a]pyridin-3-yl)pyrimidin-4-yl)-5-azaspiro[2.5]octane-1-carboxamide, I-132
methyl 5-(2-(6-chloroimidazo[1,2-a]pyridin-3-yl)pyrimidin-4-yl)-5-azaspiro[2.5]octane-1-carboxylate, I-133
(2S,6S)-2-methyl-6-(1H-pyrazol-4-yl)-4-(4-(6-(trifluoromethyl)imidazo[1,2-a]pyridin-3-yl)pyrimidin-2-yl)morpholine, I-134
(2R,6R)-2-methyl-6-(1H-pyrazol-4-yl)-4-(4-(6-(trifluoromethyl)imidazo[1,2-a]pyridin-3-yl)pyrimidin-2-yl)morpholine, I-135
3-(2-((3R,5R)-3-Methyl-5-(1H-pyrazol-4-yl)piperidin-1-yl) pyrimidin-4-yl)-6-(trifluoromethyl)imidazo[1,2-a]pyridine, I-136 (after chiral separation).
3-(2-((3S,5S)-3-Methyl-5-(1H-pyrazol-4-yl)piperidin-1-yl) pyrimidin-4-yl)-6-(trifluoromethyl)imidazo[1,2-a]pyridine, I-137 (after chiral separation).
(2S,6R)-2-methyl-6-(1H-pyrazol-3-yl)-4-(4-(6-(trifluoromethyl)imidazo[1,2-a]pyridin-3-yl)pyrimidin-2-yl)morpholine, I-138
3-(2-((3R,5S)-3-(1,3-dimethyl-1H-pyrazol-4-yl)-5-methylpiperidin-1-yl)pyrimidin-4-yl)-6-(trifluoromethyl)imidazo[1,2-a]pyridine, I-139

3-(2-((3S,5R)-3-(1,3-dimethyl-1H-pyrazol-4-yl)-5-methyl-piperidin-1-yl)pyrimidin-4-yl)-6-(trifluoromethyl)imidazo[1,2-a]pyridine, I-140

3-(2-((3S,5S)-3-(1,3-dimethyl-1H-pyrazol-4-yl)-5-methyl-piperidin-1-yl)pyrimidin-4-yl)-6-(trifluoromethyl)imidazo[1,2-a]pyridine, I-141

3-(2-((3R,5R)-3-(1,3-dimethyl-1H-pyrazol-4-yl)-5-methyl-piperidin-1-yl)pyrimidin-4-yl)-6-(trifluoromethyl)imidazo[1,2-a]pyridine, I-142

3-(2-((3R,5R)-3-(1-(2-methoxyethyl)-1H-pyrazol-4-yl)-5-methylpiperidin-1-yl)pyrimidin-4-yl)-6-(trifluoromethyl)imidazo[1,2-a]pyridine, I-143

3-(2-((3R,5S)-3-(1-(2-methoxyethyl)-1H-pyrazol-4-yl)-5-methylpiperidin-1-yl)pyrimidin-4-yl)-6-(trifluoromethyl)imidazo[1,2-a]pyridine, I-144

3-(2-((3S,5R)-3-(1-(2-methoxyethyl)-1H-pyrazol-4-yl)-5-methylpiperidin-1-yl)pyrimidin-4-yl)-6-(trifluoromethyl)imidazo[1,2-a]pyridine, I-145

3-(2-((3S,5S)-3-(1-(2-methoxyethyl)-1H-pyrazol-4-yl)-5-methylpiperidin-1-yl)pyrimidin-4-yl)-6-(trifluoromethyl)imidazo[1,2-a]pyridine, I-146

(2 S,6 S)-2-methyl-6-(5-methyl-1H-pyrazol-4-yl)-4-(2-(6-(trifluoromethyl)imidazo[1,2-a]pyridin-3-yl)pyrimidin-4-yl)morpholine, I-147

(3R,5S)-5-methyl-1-(2-(6-(trifluoromethyl)imidazo[1,2-a]pyridin-3-yl)pyrimidin-4-yl)piperidine-3-carboxamide, I-148

5-Methyl-1-[2-(6-trifluoromethyl-imidazo[1,2-a]pyridin-3-yl)-pyrimidin-4-yl]-piperidine-3-carboxylic acid amide, I-149

(S)-4-(2-(6-(trifluoromethyl)imidazo[1,2-a]pyridin-3-yl)pyrimidin-4-yl)morpholine-2-carboxamide, I-150

(R)-4-(2-(6-(trifluoromethyl)imidazo[1,2-a]pyridin-3-yl)pyrimidin-4-yl)morpholine-2-carboxamide, I-151

(R)-1-(4-(6-(trifluoromethyl)imidazo[1,2-a]pyridin-3-yl)pyrimidin-2-yl)piperidine-3-carboxamide, I-152

(S)-1-(4-(6-(trifluoromethyl)imidazo[1,2-a]pyridin-3-yl)pyrimidin-2-yl)piperidine-3-carboxamide, I-153

(S)-1-[2-(6-Trifluoromethyl-imidazo[1,2-a]pyridin-3-yl)-pyrimidin-4-yl]-piperidine-3-carboxylic acid amide, I-154

(2R,6R)-2-(1,3-dimethyl-1H-pyrazol-4-yl)-6-methyl-4-(4-(6-(trifuoromethyl)imidazo[1,2-a]pyridin-3-yl)pyrimidin-2-yl)morpholine, I-155

(2S,6S)-2-(1,3-dimethyl-1H-pyrazol-4-yl)-6-methyl-4-(4-(6-(trifluoromethyl)imidazo[1,2-a]pyridin-3-yl)pyrimidin-2-yl)morpholine, I-156

(2R,6S)-2-(1,3-dimethyl-1H-pyrazol-4-yl)-6-methyl-4-(4-(6-(trifluoromethyl)imidazo[1,2-a]pyridin-3-yl)pyrimidin-2-yl)morpholine, I-157

(2S,6R)-2-(1,3-dimethyl-1H-pyrazol-4-yl)-6-methyl-4-(4-(6-(trifluoromethyl)imidazo[1,2-a]pyridin-3-yl)pyrimidin-2-yl)morpholine, I-158

(((3R,5S)-1-(4-(6-chloroimidazo[1,2-a]pyridin-3-yl)pyrimidin-2-yl)-5-methylpiperidin-3-yl)imino)dimethyl-λ6-sulfanone, I-159

4-(4-(6-chloroimidazo[1,2-a]pyridin-3-yl)pyrimidin-2-yl)-2-methyl-6-(3-methyl-1H-pyrazol-4-yl)morpholine, I-160

2-(1-(2-(6-chloroimidazo[1,2-a]pyridin-3-yl)pyrimidin-4-yl)piperidin-3-yl)acetic acid, I-161

2-(1-(2-(6-chloroimidazo[1,2-a]pyridin-3-yl)pyrimidin-4-yl)piperidin-3-yl)acetamide, I-162

4-(2-(6-chloroimidazo[1,2-a]pyridin-3-yl)pyrimidin-4-yl)morpholine-2-carboxamide, I-163

(R)-1-(2-(6-chloroimidazo[1,2-a]pyridin-3-yl)pyrimidin-4-yl)piperidine-3-carboxamide, I-164

2-(1-(2-(6-(trifluoromethyl)imidazo[1,2-a]pyridin-3-yl)pyrimidin-4-yl)piperidin-3-yl)acetic acid, I-165

2-(1-(2-(6-(trifluoromethyl)imidazo[1,2-a]pyridin-3-yl)pyrimidin-4-yl)piperidin-3-yl)acetamide, I-166

(((3 S,5R)-1-(4-(6-chloroimidazo[1,2-a]pyridin-3-yl)-5-methylpyrimidin-2-yl)-5-methylpiperidin-3-yl)imino)dimethyl-λ6-sulfanone, I-167

(((3 S,5R)-1-(4-(6-chloroimidazo[1,2-a]pyridin-3-yl)-6-methylpyrimidin-2-yl)-5-methylpiperidin-3-yl)imino)dimethyl-λ6-sulfanone, I-168 dimethyl(((3 S,5R)-5-methyl-1-(4-(6-(trifluoromethyl)imidazo[1,2-a]pyridin-3-yl)pyrimidin-2-yl)piperidin-3-yl)imino)-λ6-sulfanone, I-169

3-(2-((2S,5S)-2,5-dimethyl-3-(1H-pyrazol-4-yl)piperazin-1-yl)pyrimidin-4-yl)-6-(trifluoromethyl)imidazo[1,2-a]pyridine, I-170

3-(2-((2R,5R)-2,5-dimethyl-3-(1H-pyrazol-4-yl)piperazin-1-yl)pyrimidin-4-yl)-6-(trifluoromethyl)imidazo[1,2-a]pyridine, I-171

3-(2-((2S,5S)-2,5-dimethyl-3-(5-methyl-1H-pyrazol-4-yl)piperazin-1-yl)pyrimidin-4-yl)-6-(trifluoromethyl)imidazo[1,2-a]pyridine, I-172

3-(2-((2R,5R)-2,5-dimethyl-3-(5-methyl-1H-pyrazol-4-yl)piperazin-1-yl)pyrimidin-4-yl)-6-(trifluoromethyl)imidazo[1,2-a]pyridine, I-173

(S)-1-(4-(6-chloroimidazo[1,2-a]pyridin-3-yl)-5-methylpyrimidin-2-yl)piperidine-3-carboxamide, I-174

(2S,6S)-4-(2-(6-chloroimidazo[1,2-a]pyridin-3-yl)pyrimidin-4-yl)-2-(5-fluoro-1H-pyrazol-4-yl)-6-methylmorpholine, I-175

(2R,6S)-4-(2-(6-chloroimidazo[1,2-a]pyridin-3-yl)pyrimidin-4-yl)-2-(5-fluoro-1H-pyrazol-4-yl)-6-methylmorpholine, I-176

(2S,6R)-4-(2-(6-chloroimidazo[1,2-a]pyridin-3-yl)pyrimidin-4-yl)-6-methylmorpholine-2-carboxamide, I-177

(2R,6R)-4-(2-(6-chloroimidazo[1,2-a]pyridin-3-yl)pyrimidin-4-yl)-6-methylmorpholine-2-carboxamide, I-178

(2S,6R)-4-(4-(6-chloroimidazo[1,2-a]pyridin-3-yl)pyrimidin-2-yl)-2-methyl-6-(5-methyl-1H-pyrazol-4-yl)morpholine, I-179

(2R,6S)-4-(4-(6-chloroimidazo[1,2-a]pyridin-3-yl)pyrimidin-2-yl)-2-methyl-6-(5-methyl-1H-pyrazol-4-yl)morpholine, I-180

(2S,6S)-4-(4-(6-chloroimidazo[1,2-a]pyridin-3-yl)pyrimidin-2-yl)-2-methyl-6-(5-methyl-1H-pyrazol-4-yl)morpholine, I-181

(2R,6R)-4-(4-(6-chloroimidazo[1,2-a]pyridin-3-yl)pyrimidin-2-yl)-2-methyl-6-(5-methyl-1H-pyrazol-4-yl)morpholine, I-182

(S)-1-(4-(6-chloroimidazo[1,2-a]pyridin-3-yl)pyrimidin-2-yl)piperidine-3-carboxamide, I-183

6-chloro-3-(5-methyl-2-((3R,5S)-3-methyl-5-(1H-pyrazol-4-yl)piperidin-1-yl)pyrimidin-4-yl)imidazo[1,2-a]pyridine, I-184

6-chloro-3-(5-methyl-2-((3R,5R)-3-methyl-5-(1H-pyrazol-4-yl)piperidin-1-yl)pyrimidin-4-yl)imidazo[1,2-a]pyridine, I-185

6-chloro-3-(5-methyl-2-((3S,5S)-3-methyl-5-(1H-pyrazol-4-yl)piperidin-1-yl)pyrimidin-4-yl)imidazo[1,2-a]pyridine, I-186

N-(1-(2-(6-(trifluoromethyl)imidazo[1,2-a]pyrimidin-4-yl)piperidin-3-yl)acetamide, I-187

4-methyl-1-(2-(6-(trifluoromethyl)imidazo[1,2-a]pyridin-3-yl)pyrimidin-4-yl)piperidine-4-carboxamide, I-188

(2S,6S)-2-methyl-6-(2H-tetrazol-5-yl)-4-(4-(6-(trifluoromethyl)imidazo[1,2-a]pyridin-3-yl)pyrimidin-2-yl)morpholine, I-189

(2R,6R)-2-methyl-6-(2H-tetrazol-5-yl)-4-(4-(6-(trifluoromethyl)imidazo[1,2-a]pyridin-3-yl)pyrimidin-2-yl)morpholine, I-190

(((3S,5R)-1-(2-(6-chloro-7-fluoroimidazo[1,2-a]pyridin-3-yl)pyrimidin-4-yl)-5-methylpiperidin-3-yl)imino)dimethyl-λ6-sulfanone, I-191

3-methyl-1-(2-(6-(trifluoromethyl)imidazo[1,2-a]pyridin-3-yl)pyrimidin-4-yl)piperidine-3-carboxamide, I-192

3-(4-(2-(5-(difluoromethyl)-1H-pyrazol-4-yl)morpholino)pyrimidin-2-yl)imidazo[1,2-a]pyridine-6-carbonitrile, I-193

6-chloro-3-(2-((3R,5S)-3-methyl-5-(1H-pyrazol-4-yl)piperidin-1-yl)pyrimidin-4-yl)imidazo[1,2-a]pyridine, I-195

6-chloro-3-(2-((3R,5R)-3-methyl-5-(1H-pyrazol-4-yl)piperidin-1-yl)pyrimidin-4-yl)imidazo[1,2-a]pyridine, I-196

6-chloro-3-(5-methyl-2-((3S,5R)-3-methyl-5-(1H-pyrazol-4-yl)piperidin-1-yl)pyrimidin-4-yl)imidazo[1,2-a]pyridine, I-197

6-chloro-3-(2-((3S,5R)-3-methyl-5-(1H-pyrazol-4-yl)piperidin-1-yl)pyrimidin-4-yl)imidazo[1,2-a]pyridine, I-198

6-chloro-3-(2-((3S,5S)-3-methyl-5-(1H-pyrazol-4-yl)piperidin-1-yl)pyrimidin-4-yl)imidazo[1,2-a]pyridine, I-199

6-methyl-1-(2-(6-(trifluoromethyl)imidazo[1,2-a]pyridin-3-yl)pyrimidin-4-yl)piperidine-3-carboxamide, I-200

6-methyl-1-(2-(6-(trifluoromethyl)imidazo[1,2-a]pyridin-3-yl)pyrimidin-4-yl)piperidine-3-carboxylic acid, I-201

(2S,6R)-4-(4-(6-chloroimidazo[1,2-a]pyridin-3-yl)-5-methylpyrimidin-2-yl)-2-methyl-6-(5-methyl-1H-pyrazol-4-yl)morpholine, I-203

(2R,6S)-4-(4-(6-chloroimidazo[1,2-a]pyridin-3-yl)-5-methylpyrimidin-2-yl)-2-methyl-6-(5-methyl-1H-pyrazol-4-yl)morpholine, I-204

5,5-Difluoro-1-[2-(6-trifluoromethyl-imidazo[1,2-a]pyridin-3-yl)-pyrimidin-4-yl]-piperidine-3-carboxylic acid, I-205

5-fluoro-1-[2-(6-trifluoromethyl-imidazo[1,2-a]pyridin-3-yl)-pyrimidin-4-yl]-piperidine-3-carboxylic acid, I-206 tert-butyl 2-carbamoyl-4-(2-(6-(trifluoromethyl)imidazo[1,2-a]pyridin-3-yl)pyrimidin-4-yl)piperazine-1-carboxylate, I-207

6-chloro-3-(6-methyl-2-((3S,5S)-3-methyl-5-(1H-pyrazol-4-yl)piperidin-1-yl)pyrimidin-4-yl)imidazo[1,2-a]pyridine, I-208

6-chloro-3-(6-methyl-2-((3R,5R)-3-methyl-5-(1H-pyrazol-4-yl)piperidin-1-yl)pyrimidin-4-yl)imidazo[1,2-a]pyridine, I-209

6-chloro-3-(6-methyl-2-((3S,5R)-3-methyl-5-(1H-pyrazol-4-yl)piperidin-1-yl)pyrimidin-4-yl)imidazo[1,2-a]pyridine, I-210

6-chloro-3-(6-methyl-2-((3R,5S)-3-methyl-5-(1H-pyrazol-4-yl)piperidin-1-yl)pyrimidin-4-yl)imidazo[1,2-a]pyridine, I-211 tert-butyl 3-hydroxy-1-(2-(6-(trifluoromethyl)imidazo[1,2-a]pyridin-3-yl)pyrimidin-4-yl)piperidine-3-carboxylate, I-212

3-hydroxy-1-(2-(6-(trifluoromethyl)imidazo[1,2-a]pyridin-3-yl)pyrimidin-4-yl)piperidine-3-carboxamide, I-213

3-hydroxy-1-(2-(6-(trifluoromethyl)imidazo[1,2-a]pyridin-3-yl)pyrimidin-4-yl)piperidine-3-carboxylic acid, I-214

4-(2-(6-(trifluoromethyl)imidazo[1,2-a]pyridin-3-yl)pyrimidin-4-yl)piperazine-2-carboxamide, I-217

(2R,6R)-4-(4-(6-chloroimidazo[1,2-a]pyridin-3-yl)-6-methylpyrimidin-2-yl)-2-methyl-6-(5-methyl-1H-pyrazol-4-yl)morpholine, I-218

(S)-1-(5-fluoro-4-(6-(trifluoromethyl)imidazo[1,2-a]pyridin-3-yl)pyrimidin-2-yl)piperidine-3-carboxamide, I-219

(2S,6S)-4-(4-(6-chloroimidazo[1,2-a]pyridin-3-yl)-6-methylpyrimidin-2-yl)-2-methyl-6-(5-methyl-1H-pyrazol-4-yl)morpholine, I-220

(2S,6R)-4-(4-(6-chloroimidazo[1,2-a]pyridin-3-yl)-6-methylpyrimidin-2-yl)-2-methyl-6-(5-methyl-1H-pyrazol-4-yl)morpholine, I-221

(2R,6S)-4-(4-(6-chloroimidazo[1,2-a]pyridin-3-yl)-6-methylpyrimidin-2-yl)-2-methyl-6-(5-methyl-1H-pyrazol-4-yl)morpholine, I-222

(R)-1-(5-fluoro-4-(6-(trifluoromethyl)imidazo[1,2-a]pyridin-3-yl)pyrimidin-2-yl)piperidine-3-carboxamide, I-223

3-(4-(3,3-difluoropiperidin-1-yl)pyrimidin-2-yl)-6-(trifluoromethyl)imidazo[1,2-a]pyridine, I-224

2-(difluoromethyl)-4-(2-(6-(trifluoromethyl)imidazo[12-a]pyridin-3-yl)pyrimidin-4-yl)morpholine, I-225

3-(4-(3-fluoro-3-methylpiperidin-1-yl)pyrimidin-2-yl)-6-(trifluoromethyl)imidazo[1,2-a]pyridine, I-226

(S)-1-(2-(6-(trifluoromethyl)imidazo[1,2-a]pyridin-3-yl)pyrimidin-4-yl)piperidine-3-carbonitrile, I-227

1-(2-(6-(trifluoromethyl)imidazo[1,2-a]pyridin-3-yl)pyrimidin-4-yl)azetidine-3-carboxamide, I-228

5-fluoro-1-(2-(6-(trifluoromethyl)imidazo[1,2-a]pyridin-3-yl)pyrimidin-4-yl)piperidine-3-carboxamide, I-229

2-(1-(2-(6-(trifluoromethyl)imidazo[1,2-a]pyridin-3-yl)pyrimidin-4-yl)azetidin-3-yl)acetamide, I-230

3-(4-(3,5-dimethylpiperazin-1-yl)pyrimidin-2-yl)-6-(trifluoromethyl)imidazo[1,2-a]pyridine, I-231

(S)-4-(2-(6-(trifluoromethyl)imidazo[1,2-a]pyridin-3-yl)pyrimidin-4-yl)morpholine-2-carbonitrile, I-232

(S)-6-(trifluoromethyl)-3-(4-(3-(trifluoromethyl)piperidin-1-yl)pyrimidin-2-yl)imidazo[1,2-a]pyridine, I-233

3-(4-(3,5-dimethyl-4-(oxetan-3-yl)piperazin-1-yl)pyrimidin-2-yl)-6-(trifluoromethyl)imidazo[1,2-a]pyridine, I-234

6-cyclopropyl-3-(2-((3S,5R)-3-methyl-5-(1H-pyrazol-4-yl)piperidin-1-yl)pyrimidin-4-yl)imidazo[1,2-a]pyridine, I-235

6-cyclopropyl-3-(2-((3R,5S)-3-methyl-5-(1H-pyrazol-4-yl)piperidin-1-yl)pyrimidin-4-yl)imidazo[1,2-a]pyridine, I-236 tert-butyl ((3S,5S)-5-hydroxy-1-(2-(6-(trifluoromethyl)imidazo[1,2-a]pyridin-3-yl)pyrimidin-4-yl)piperidin-3-yl)carbamate, I-237

(3R,5S)-1-(2-(6-(trifluoromethyl)imidazo[1,2-a]pyridin-3-yl)pyrimidin-4-yl)piperidine-3,5-diol, I-238

(3S,5S)-5-amino-1-(2-(6-(trifluoromethyl)imidazo[1,2-a]pyridin-3-yl)pyrimidin-4-yl)piperidin-3-ol, I-239

3-(4-((3R,4R)-3-fluoro-4-methylpiperidin-1-yl)pyrimidin-2-yl)-6-(trifluoromethyl)imidazo[1,2-a]pyridine, I-240

3-(hydroxymethyl)-1-(2-(6-(trifluoromethyl)imidazo[1,2-a]pyridin-3-yl)pyrimidin-4-yl)piperidin-4-ol, I-241

1-(2-(6-(trifluoromethyl)imidazo[1,2-a]pyridin-3-yl)pyrimidin-4-yl)piperidine-3-sulfonamide, I-242 tert-butyl ((3R,4R)-1-(2-(6-chloroimidazo[1,2-a]pyridin-3-yl)pyrimidin-4-yl)-4-hydroxypiperidin-3-yl)carbamate, I-243

(((3S,5R)-1-(4-(6,7-dichloroimidazo[1,2-a]pyridin-3-yl)pyrimidin-2-yl)-5-methylpiperidin-3-yl)imino)dimethyl-λ6-sulfanone, I-244

4-(2-(6-(trifluoromethyl)imidazo[1,2-a]pyridin-3-yl)pyrimidin-4-yl)-1-(3,3,3-trifluoropropyl)piperazine-2-carboxamide, I-245

(2S,6S)-4-(4-(6-chloroimidazo[1,2-a]pyridin-3-yl)pyrimidin-2-yl)-2-methyl-6-(1H-pyrazol-4-yl)morpholine, I-246

6-Chloro-3-{2-[(2S,6R)-2-methyl-6-(1H-pyrazol-4-yl)-morpholin-4-yl]-pyrimidin-4-yl}-imidazo[1,2-a]pyridine, I-247

6-Chloro-3-{2-[(2R,6S)-2-methyl-6-(1H-pyrazol-4-yl)-morpholin-4-yl]-pyrimidin-4-yl}-imidazo[1,2-a]pyridine, I-248

6-Cyclopropyl-3-{2-[(3R,5R)-3-methyl-5-(1H-pyrazol-4-yl)-piperidin-1-yl]-pyrimidin-4-yl}-imidazo[1,2-a]pyridine, I-249

6-Cyclopropyl-3-{2-[(3 S,5S)-3-methyl-5-(1H-pyrazol-4-yl)-piperidin-1-yl]-pyrimidin-4-yl}-imidazo[1,2-a]pyridine, I-250

(2R,6R)-4-(4-(6-chloroimidazo[1,2-a]pyridin-3-yl)pyrimidin-2-yl)-2-methyl-6-(1H-pyrazol-4-yl)morpholine, I-251 tert-butyl ((3R,5R)-1-(2-(6-chloroimidazo[1,2-a]pyridin-3-yl)pyrimidin-4-yl)-5-methylpiperidin-3-yl)carbamate, I-252

2-hydroxy-N-((3S,5S)-5-hydroxy-1-(2-(6-(trifluoromethyl)imidazo[1,2-a]pyridin-3-yl)pyrimidin-4-yl)piperidin-3-yl)acetamide, I-253

2-hydroxy-N-((3S,5S)-5-hydroxy-1-(2-(6-(trifluoromethyl)imidazo[1,2-a]pyridin-3-yl)pyrimidin-4-yl)piperidin-3-yl)propanamide, I-254

(3R,4R)-3-amino-1-(2-(6-chloroimidazo[1,2-a]pyridin-3-yl)pyrimidin-4-yl)piperidin-4-ol, I-255

(3R,5R)-1-(2-(6-chloroimidazo[1,2-a]pyridin-3-yl)pyrimidin-4-yl)-5-methylpiperidin-3-amine, I-256

N-((3S,5S)-5-hydroxy-1-(2-(6-(trifluoromethyl)imidazo[1,2-a]pyridin-3-yl)pyrimidin-4-yl)piperidin-3-yl)-1H-pyrazole-4-carboxamide, I-257

1-(2-methoxyethyl)-4-(2-(6-(trifluoromethyl)imidazo[1,2-a]pyridin-3-yl)pyrimidin-4-yl)piperazine-2-carboxamide, I-258

6-(3,3-difluoroazetidin-1-yl)-3-(2-((3S,5R)-3-methyl-5-(1H-pyrazol-4-yl)piperidin-1-yl)pyrimidin-4-yl)imidazo[1,2-a]pyridine, I-259

(R)-1-(3-fluoro-6-(6-(trifluoromethyl)imidazo[1,2-a]pyridin-3-yl)pyridin-2-yl)piperidine-3-carboxamide, I-260

6-(3,3-difluoroazetidin-1-yl)-3-(2-((3R,5S)-3-methyl-5-(1H-pyrazol-4-yl)piperidin-1-yl)pyrimidin-4-yl)imidazo[1,2-a]pyridine, I-261

3-(4-((3S,5R)-3-((dimethyl(oxo)-λ6-sulfaneylidene)amino)-5-methylpiperidin-1-yl)pyrimidin-2-yl)imidazo[1,2-a]pyridine-6-carbonitrile, I-262

1-(oxetan-3-yl)-4-(2-(6-(trifluoromethyl)imidazo[1,2-a]pyridin-3-yl)pyrimidin-4-yl)piperazine-2-carboxamide, I-263

(2S,6S)-6-methyl-4-(2-(6-(trifluoromethyl)imidazo[1,2-a]pyridin-3-yl)pyrimidin-4-yl)morpholine-2-carboxamide, I-264

(2S,6R)-6-methyl-4-(2-(6-(trifluoromethyl)imidazo[1,2-a]pyridin-3-yl)pyrimidin-4-yl)morpholine-2-carboxamide, I-265

6-chloro-3-(4-(3-methyl-5-(1H-pyrazol-4-yl)piperazin-1-yl)pyrimidin-2-yl)imidazo[1,2-a]pyridine, I-266

6-chloro-3-(4-(3-methyl-5-(5-methyl-1H-pyrazol-4-yl)piperazin-1-yl)pyrimidin-2-yl)imidazo[1,2-a]pyridine, I-267

6-chloro-3-(4-(3-methyl-5-(5-methyl-1H-pyrazol-4-yl)-4-(methylsulfonyl)piperazin-1-yl)pyrimidin-2-yl)imidazo[1,2-a]pyridine, I-268

(((3 S,5R)-1-(2-(6,7-dichloroimidazo[1,2-a]pyridin-3-yl)pyrimidin-4-yl)-5-methylpiperidin-3-yl)imino)dimethyl-λ6-sulfanone, I-269

(2S,6R)-4-(4-(6-chloro-7-fluoroimidazo[1,2-a]pyridin-3-yl)pyrimidin-2-yl)-2-methyl-6-(1H-pyrazol-4-yl)morpholine, I-270

6-(azetidin-1-yl)-3-(2-((3S,5R)-3-methyl-5-(1H-pyrazol-4-yl)piperidin-1-yl)pyrimidin-4-yl)imidazo[1,2-a]pyridine, I-271

6-(azetidin-1-yl)-3-(2-((3R,5R)-3-methyl-5-(1H-pyrazol-4-yl)piperidin-1-yl)pyrimidin-4-yl)imidazo[1,2-a]pyridine, I-272

(2R,6S)-4-(4-(6-chloro-7-fluoroimidazo[1,2-a]pyridin-3-yl)pyrimidin-2-yl)-2-methyl-6-(1H-pyrazol-4-yl)morpholine, I-273

(2R,6R)-4-(4-(6-chloro-7-fluoroimidazo[1,2-a]pyridin-3-yl)pyrimidin-2-yl)-2-methyl-6-(1H-pyrazol-4-yl)morpholine, I-274

(2S,6S)-4-(4-(6-chloro-7-fluoroimidazo[1,2-a]pyridin-3-yl)pyrimidin-2-yl)-2-methyl-6-(1H-pyrazol-4-yl)morpholine, I-275

1-(4-(2-(6-chloroimidazo[1,2-a]pyridin-3-yl)pyrimidin-4-yl)-2-methyl-6-(3-methyl-1H-pyrazol-4-yl)piperazin-1-yl)ethan-1-one, I-276

1-(4-(2-(6-chloroimidazo[1,2-a]pyridin-3-yl)pyrimidin-4-yl)-2-methyl-6-(1H-pyrazol-4-yl)piperazin-1-yl)ethan-1-one, I-277

(S)-1-(5-fluoro-2-(6-(trifluoromethyl)imidazo[1,2-a]pyridin-3-yl)pyrimidin-4-yl)piperidine-3-carboxamide, I-278

6-chloro-3-(6-methoxy-2-((3R,5R)-3-methyl-5-(1H-pyrazol-4-yl)piperidin-1-yl)pyrimidin-4-yl)imidazo[1,2-a]pyridine, I-279

6-chloro-3-(6-methoxy-2-((3R,5S)-3-methyl-5-(1H-pyrazol-4-yl)piperidin-1-yl)pyrimidin-4-yl)imidazo[1,2-a]pyridine, I-280

6-chloro-3-(6-methoxy-2-((3S,5S)-3-methyl-5-(1H-pyrazol-4-yl)piperidin-1-yl)pyrimidin-4-yl)imidazo[1,2-a]pyridine, I-281

(S)-1-(5-fluoro-2-(6-(trifluoromethyl)imidazo[1,2-a]pyridin-3-yl)pyrimidin-4-yl)piperidine-3-carboxamide, I-282

N-((1-(2-(6-chloroimidazo[1,2-a]pyridin-3-yl)pyrimidin-4-yl)piperidin-3-yl)methyl)-N-methylmethanesulfonamide, I-283

2-(1-(2-(6-chloroimidazo[1,2-a]pyridin-3-yl)pyrimidin-4-yl)piperidin-3-yl)-2-methylpropanoic acid, I-284 tert-butyl 6-(2-(6-chloroimidazo[1,2-a]pyridin-3-yl)pyrimidin-4-yl)-2,6-diazaspiro[3.5]nonane-2-carboxylate, I-285

4-(2-(6-chloroimidazo[1,2-a]pyridin-3-yl)pyrimidin-4-yl)-1-cyclopropylpiperazine-2-carboxamide, I-286

6-(3,3-difluoroazetidin-1-yl)-3-(6-methyl-2-((3 S, 5R)-3-methyl-5-(1H-pyrazol-4-yl)piperidin-1-yl)pyrimidin-4-yl)imidazo[1,2-a]pyridine, I-287

6-(3,3-difluoroazetidin-1-yl)-3-(6-methyl-2-((3R,5R)-3-methyl-5-(1H-pyrazol-4-yl)piperidin-1-yl)pyrimidin-4-yl)imidazo[1,2-a]pyridine, I-288

(((3 S,5R)-1-(2-(6-bromoimidazo[1,2-a]pyridin-3-yl)pyrimidin-4-yl)-5-methylpiperidin-3-yl)imino)dimethyl-λ6-sulfanone, I-289 dimethyl(((3 S,5R)-5-methyl-1-(2-(6-(trifluoromethoxy)imidazo[1,2-a]pyridin-3-yl)pyrimidin-4-yl)piperidin-3-yl)imino)-λ6-sulfanone, I-290 dimethyl(((3 S,5R)-5-methyl-1-(2-(6-(difluoromethoxy)imidazo[1,2-a]pyridin-3-yl)pyrimidin-4-yl)piperidin-3-yl)imino)-λ6-sulfanone, I-291 tert-butyl 6,6-dimethyl-8-(2-(6-(trifluoromethyl)imidazo[1,2-a]pyridin-3-yl)pyrimidin-4-yl)-5-oxa-2,8-diazaspiro[3.5]nonane-2-carboxylate, I-292

(2R,6 S)-2-methyl-6-(1H-pyrazol-4-yl)-4-(2-(6-(trifluoromethoxy)imidazo[1,2-a]pyridin-3-yl)pyrimidin-4-yl)morpholine, I-293

6,6-dimethyl-8-(2-(6-(trifluoromethyl)imidazo[1,2-a]pyridin-3-yl)pyrimidin-4-yl)-5-oxa-2,8-diazaspiro[3.5]nonane, I-294

(R)-6-(2-(6-(trifluoromethyl)imidazo[1,2-a]pyridin-3-yl)pyrimidin-4-yl)-2,6-diazaspiro[3.5]nonan-1-one, I-295

(S)-6-(2-(6-(trifluoromethyl)imidazo[1,2-a]pyridin-3-yl)pyrimidin-4-yl)-2,6-diazaspiro[3.5]nonan-1-one, I-296

1-(1-(2-(6-chloroimidazo[1,2-a]pyridin-3-yl)pyrimidin-4-yl)piperidin-3-yl)cyclopropane-1-carboxylic acid, I-297

2-(4-(2-(6-chloroimidazo[1,2-a]pyridin-3-yl)pyrimidin-4-yl)morpholin-2-yl)acetic acid, I-298

6-(2-(6-chloroimidazo[1,2-a]pyridin-3-yl)pyrimidin-4-yl)-2,6-diazaspiro[3.5]nonane, I-299

(((3 S,5R)-1-(2-(6-cyclopropylimidazo[1,2-a]pyridin-3-yl)pyrimidin-4-yl)-5-methylpiperidin-3-yl)imino)dimethyl-λ6-sulfanone, I-300

6-chloro-3-(4-(3-methyl-4-(methyl sulfonyl)-5-(1-(methyl sulfonyl)-1H-pyrazol-4-yl)piperazin-1-yl)pyrimidin-2-yl)imidazo[1,2-a]pyridine, I-301

1-(2-(6-chloroimidazo[1,2-a]pyridin-3-yl)pyrimidin-4-yl)-5-(3-methyl-1H-pyrazol-4-yl)piperidin-3-ol, I-302

1-(1-(2-(6-chloroimidazo[1,2-a]pyridin-3-yl)pyrimidin-4-yl)piperidin-3-yl)cyclopropane-1-carboxamide, I-303

6,6-dimethyl-2-(methylsulfonyl)-8-(2-(6-(trifluoromethyl)imidazo[1,2-a]pyridin-3-yl)pyrimidin-4-yl)-5-oxa-2,8-diazaspiro[3.5]nonane, I-304

2-((6,6-dimethyl-4-(2-(6-(trifluoromethyl)imidazo[1,2-a]pyridin-3-yl)pyrimidin-4-yl)morpholin-2-yl)methoxy)-N,N-dimethylacetamide, I-305

(3 S, 5R)-5-(5-methyl-1H-pyrazol-4-yl)-1-(2-(6-(trifluoromethyl)imidazo[1,2-a]pyridin-3-yl)pyrimidin-4-yl)piperidin-3-ol, I-307

(3R,5S)-5-(5-methyl-1H-pyrazol-4-yl)-1-(2-(6-(trifluoromethyl)imidazo[1,2-a]pyridin-3-yl)pyrimidin-4-yl)piperidin-3-ol, I-308

2-(1-(2-(6-chloroimidazo[1,2-a]pyridin-3-yl)pyrimidin-4-yl)piperidin-3-yl)-2-methylpropanamide, I-309

3-(4-((3R)-2-methyl-3-(1H-pyrazol-4-yl)piperazin-1-yl)pyrimidin-2-yl)-6-(trifluoromethyl)imidazo[1,2-a]pyridine, I-310

1-cyclopropyl-4-(2-(6-(trifluoromethyl)imidazo[1,2-a]pyridin-3-yl)pyrimidin-4-yl)piperazine-2-carboxamide, I-311 dimethyl(((3R,5S)-5-methyl-1-(2-(6-(methyl sulfonyl)imidazo[1,2-a]pyridin-3-yl)pyrimidin-4-yl)piperidin-3-yl)imino)-λ6-sulfanone, I-312

3-(4-(3-(1H-pyrazol-4-yl)piperidin-1-yl)pyrimidin-2-yl)-6-(methylsulfonyl)imidazo[1,2-a]pyridine, I-313

(3 S,5S)-5-(3-Methyl-1H-pyrazol-4-yl)-1-[2-(6-trifluoromethyl-imidazo[1,2-a]pyridin-3-yl)-pyrimidin-4-yl]-piperidin-3-ol I-314.

(3R,5R)-5-(3-Methyl-1H-pyrazol-4-yl)-1-[2-(6-trifluoromethyl-imidazo[1,2-a]pyridin-3-yl)-pyrimidin-4-yl]-piperidin-3-ol I-315

(3 S,5S)-1-(4-(6-chloroimidazo[1,2-a]pyridin-3-yl)pyrimidin-2-yl)-5-hydroxypiperidine-3-carboxamide, I-316

(((3 S,5R)-1-(2-(6-bromo-7-fluoroimidazo[1,2-a]pyridin-3-yl)pyrimidin-4-yl)-5-methylpiperidin-3-yl)imino)dimethyl-λ6-sulfanone, I-317

3-(4-(3-(1H-pyrazol-4-yl)piperidin-1-yl)pyrimidin-2-yl)-N-cyclopropylimidazo[1,2-a]pyridine-6-sulfonamide, I-318

N-cyclopropyl-3-(4-((3R,5S)-3-((dimethyl(oxo)-λ6-sulfaneylidene)amino)-5-methylpiperidin-1-yl)pyrimidin-2-yl)imidazo[1,2-a]pyridine-6-sulfonamide, I-319, 3-(4-(3-(1H-pyrazol-4-yl)piperidin-1-yl)pyrimidin-2-yl)imidazo[1,2-a]pyridine-6-sulfonamide, I-320

3-(4-(2-methyl-3-(5-methyl-1H-pyrazol-4-yl)piperazin-1-yl)pyrimidin-2-yl)-6-(trifluoromethyl)imidazo[1,2-a]pyridine, I-321

(R)-1-cyclopropyl-4-(2-(6-(trifluoromethyl)imidazo[1,2-a]pyridin-3-yl)pyrimidin-4-yl)piperazine-2-carboxamide, I-323

(S)-1-cyclopropyl-4-(2-(6-(trifluoromethyl)imidazzo[1,2-a]pyridin-3-yl)pyrimidin-4-yl)piperazine-2-carboxamide, I-324 dimethyl({[(3 S,5R)-5-methyl-1-(2-{6-phenoxyimidazo[1,2-a]pyridin-3-yl}pyrimidin-4-yl)piperidin-3-yl]imino})-λ6-sulfanone I-325

3-(4-(3-(1H-pyrazol-4-yl)piperidin-1-yl)pyrimidin-2-yl)-6-bromo-7-fluoroimidazo[1,2-a]pyridine, I-326

N-(1-(4-(2-(6-(trifluoromethyl)imidazo[1,2-a]pyridin-3-yl)pyrimidin-4-yl)morpholin-2-yl)ethyl)methanesulfonamide, I-327

3-(4-((3R,5S)-3-((dimethyl(oxo)-λ6-sulfaneylidene)amino)-5-methylpiperidin-1-yl)pyrimidin-2-yl)imidazo[1,2-a]pyridine-6-sulfonamide, I-328

2-{6-phenoxyimidazo[1,2-a]pyridin-3-yl}-4-[3-(1H-pyrazol-4-yl)piperidin-1-yl]pyrimidine I-329

(((3 S,5R)-1-(2-(6-(3-fluoroazetidin-1-yl)imidazo[1,2-a]pyridin-3-yl)pyrimidin-4-yl)-5-methylpiperidin-3-yl)imino)dimethyl-λ6-sulfanone, I-330

6-methyl-4-(2-(6-(trifluoromethyl)imidazo[1,2-a]pyridin-3-yl)pyrimidin-4-yl)morpholine-2-carbonitrile, I-331

3-methyl-5-(1-methyl-4-(2-(6-(trifluoromethyl)imidazo[1,2-a]pyridin-3-yl)pyrimidin-4-yl)piperazin-2-yl)-1,2,4-oxadiazole, I-332

3-(4-(3,3-dimethyl-4-(2,2,2-trifluoroethyl)piperazin-1-yl)pyrimidin-2-yl)-6-(trifluoromethyl)imidazo[1,2-a]pyridine, I-333

3-(4-(3,3-dimethylpiperazin-1-yl)pyrimidin-2-yl)-6-(trifluoromethyl)imidazo[1,2-a]pyridine, I-334

3-(4-(4-(2-methoxyethyl)-3,5-dimethylpiperazin-1-yl)pyrimidin-2-yl)-6-(trifluoromethyl)imidazo[1,2-a]pyridine, I-335

1-(2,2-dimethyl-4-(2-(6-(trifluoromethyl)imidazo[1,2-a]pyridin-3-yl)pyrimidin-4-yl)piperazin-1-yl)ethan-1-one, I-336

3-(4-(3-(5-methyl-4H-1,2,4-triazol-3-yl)piperazin-1-yl)pyrimidin-2-yl)-6-(trifluoromethyl)imidazo[1,2-a]pyridine, I-337

8-(2-(6-(trifluoromethyl)imidazo[1,2-a]pyridin-3-yl)pyrimidin-4-yl)octahydropyrazino[2,1-c][1,4]thiazine 2,2-dioxide, I-338

3-(4-(3,3-dimethyl-4-(methylsulfonyl)piperazin-1-yl)pyrimidin-2-yl)-6-(trifluoromethyl)imidazo[1,2-a]pyridine, I-339

(((3 S, 5R)-1-(2-(6-(difluoromethyl)imidazo[1,2-a]pyridin-3-yl)pyrimidin-4-yl)-5-methylpiperidin-3-yl)imino)dimethyl-λ6-sulfanone, I-340

(2S,6S)-4-(2-(6-cyclopropyl-7-fluoroimidazo[1,2-a]pyridin-3-yl)pyrimidin-4-yl)-2-methyl-6-(3-methyl-1,2,4-oxadiazol-5-yl)morpholine, I-341 dimethyl(((3R,5R)-5-(5-methyl-1H-pyrazol-4-yl)-1-(2-(6-(trifluoromethyl)imidazo[1,2-a]pyridin-3-yl)pyrimidin-4-yl)piperidin-3-yl)imino)-λ6-sulfanone, I-342

(2R,6R)-2-methyl-6-(5-methylisoxazol-4-yl)-4-(2-(6-(trifluoromethyl)imidazo[1,2-a]pyridin-3-yl)pyrimidin-4-yl)morpholine, I-343 dimethyl(((3 S,5R)-5-(5-methyl-1H-pyrazol-4-yl)-1-(2-(6-(trifluoromethyl)imidazo[1,2-a]pyridin-3-yl)pyrimidin-4-yl)piperidin-3-yl)imino)-λ6-sulfanone, I-344

(2S,6S)-2-methyl-6-(5-methylisoxazol-4-yl)-4-(2-(6-(trifluoromethyl)imidazo[1,2-a]pyridin-3-yl)pyrimidin-4-yl)morpholine, I-345

(2S,6R)-2-methyl-6-(5-methylisoxazol-4-yl)-4-(2-(6-(trifluoromethyl)imidazo[1,2-a]pyridin-3-yl)pyrimidin-4-yl)morpholine, I-346

(2R,6S)-2-methyl-6-(5-methylisoxazol-4-yl)-4-(2-(6-(trifluoromethyl)imidazo[1,2-a]pyridin-3-yl)pyrimidin-4-yl)morpholine, I-347

3-(4-(4-(1-ethoxycyclopropyl)-2-methyl-3-(1H-pyrazol-4-yl)piperazin-1-yl)pyrimidin-2-yl)-6-(trifluoromethyl)imidazo[1,2-a]pyridine, I-348

(R)-4-(2-(6-chloroimidazo[1,2-a]pyridin-3-yl)pyrimidin-4-yl)-1-cyclopropylpiperazine-2-carboxamide, I-349

(s)-4-(2-(6-chloroimidazo[1,2-a]pyridin-3-yl)pyrimidin-4-yl)-1-cyclopropylpiperazine-2-carboxamide, I-350

3-(4-(3-(1H-pyrazol-4-yl)piperazin-1-yl)pyrimidin-2-yl)-6-(trifluoromethyl)imidazo[1,2-a]pyridine, I-351

3-(2-(1H-pyrazol-4-yl)-4-(2-(6-(trifluoromethyl)imidazo[1,2-a]pyridin-3-yl)pyrimidin-4-yl)piperazin-1-yl)propane-1,2-diol, I-352

4-((2-(1H-pyrazol-4-yl)-4-(2-(6-(trifluoromethyl)imidazo[1,2-a]pyridin-3-yl)pyrimidin-4-yl)piperazin-1-yl)methyl)oxazole, I-353

3-(4-(3-(1H-pyrazol-4-yl)-4-((tetrahydro-2H-pyran-4-yl)methyl)piperazin-1-yl)pyrimidin-2-yl)-6-(trifluoromethyl)imidazo[1,2-a]pyridine, I-354

6-(trifluoromethyl)-3-(4-(3-(3-(trifluoromethyl)-1H-pyrazol-1-yl)piperidin-1-yl)pyrimidin-2-yl)imidazo[1,2-a]pyridine, I-355

3-(4-(3-(1H-1,2,4-triazol-1-yl)piperidin-1-yl)pyrimidin-2-yl)-6-(trifluoromethyl)imidazo[1,2-a]pyridine, I-356

3-(4-(3-fluoro-5-(3-methyl-1H-pyrazol-4-yl)piperidin-1-yl)pyrimidin-2-yl)-6-(trifluoromethyl)imidazo[1,2-a]pyridine, I-357

2-methyl-6-(3-methyl-1H-pyrazol-4-yl)-4-(2-(6-(trifluoromethyl)imidazo[1,2-a]pyridin-3-yl)pyrimidin-4-yl)morpholine, I-358

(2S,6R)-4-(2-(7-chloro-6-(trifluoromethyl)imidazo[1,2-a]pyridin-3-yl)pyrimidin-4-yl)-2-methyl-6-(3-methyl-1H-pyrazol-4-yl)morpholine, I-359

(2R,6R)-4-(2-(7-chloro-6-(trifluoromethyl)imidazo[1,2-a]pyridin-3-yl)pyrimidin-4-yl)-2-methyl-6-(3-methyl-1H-pyrazol-4-yl)morpholine, I-360

3-(4-((2S,3R)-2-methyl-4-(oxetan-3-yl)-3-(1H-pyrazol-4-yl)piperazin-1-yl)pyrimidin-2-yl)-6-(trifluoromethyl)imidazo[1,2-a]pyridine, I-361

4-[(2R,3 S)-2-methyl-4-(oxetan-3-yl)-3-(1H-pyrazol-4-yl)piperazin-1-yl]-2-[6-(trifluoromethyl)imidazo[1,2-a]pyridin-3-yl]pyrimidine, I-362

3-(4-((2R,3R)-2-methyl-4-(oxetan-3-yl)-3-(1H-pyrazol-4-yl)piperazin-1-yl)pyrimidin-2-yl)-6-(trifluoromethyl)imidazo[1,2-a]pyridine, I-363

3-(4-((2S,3 S)-2-methyl-4-(oxetan-3-yl)-3-(1H-pyrazol-4-yl)piperazin-1-yl)pyrimidin-2-yl)-6-(trifluoromethyl)imidazo[1,2-a]pyridine, I-364

3-(4-(2 S,3R)-2-methyl-3-(5-methyl-1H-pyrazol-4-yl)-4-(oxetan-3-yl)piperazin-1-yl)pyrimidin-2-yl)-6-(trifluoromethyl)imidazo[1,2-a]pyridine, I-365

3-(4-(2R,3 S)-2-methyl-3-(5-methyl-1H-pyrazol-4-yl)-4-(oxetan-3-yl)piperazin-1-yl)pyrimidin-2-yl)-6-(trifluoromethyl)imidazo[1,2-a]pyridine, I-366

3-(4-(2 S,3 S)-2-methyl-3-(5-methyl-1H-pyrazol-4-yl)-4-(oxetan-3-yl)piperazin-1-yl)pyrimidin-2-yl)-6-(trifluoromethyl)imidazo[1,2-a]pyridine, I-367

3-(4-(2R,3R)-2-methyl-3-(5-methyl-1H-pyrazol-4-yl)-4-(oxetan-3-yl)piperazin-1-yl)pyrimidin-2-yl)-6-(trifluoromethyl)imidazo[1,2-a]pyridine, I-368

4-[4-(cyclopropylmethyl)-3-(1H-pyrazol-4-yl)piperazin-1-yl]-2-[6-(trifluoromethyl)imidazo[1,2-a]pyridin-3-yl]pyrimidine, I-369

3-(4-(4-((3-oxabicyclo[3.1.0]hexan-6-yl)methyl)-3-(1H-pyrazol-4-yl)piperazin-1-yl)pyrimidin-2-yl)-6-(trifluoromethyl)imidazo[1,2-a]pyridine, I-370

3-(4-(4-((1H-imidazol-2-yl)methyl)-3-(1H-pyrazol-4-yl)piperazin-1-yl)pyrimidin-2-yl)-6-(trifluoromethyl)imidazo[1,2-a]pyridine, I-371

3-(4-(4-((2-methyl-1H-imidazol-5-yl)methyl)-3-(1H-pyrazol-4-yl)piperazin-1-yl)pyrimidin-2-yl)-6-(trifluoromethyl)imidazo[1,2-a]pyridine, I-372

3-(4-(4-((2-(tert-butyl)-1H-imidazol-5-yl)methyl)-3-(1H-pyrazol-4-yl)piperazin-1-yl)pyrimidin-2-yl)-6-(trifluoromethyl)imidazo[1,2-a]pyridine, I-373

3-(4-(4-(oxetan-3-ylmethyl)-3-(1H-pyrazol-4-yl)piperazin-1-yl)pyrimidin-2-yl)-6-(trifluoromethyl)imidazo[1,2-a]pyridine, I-374

(2R,6R)-4-(2-(6-(difluoromethyl)imidazo[1,2-a]pyridin-3-yl)pyrimidin-4-yl)-2-methyl-6-(3-methyl-1,2,4-oxadiazol-5-yl)morpholine, I-375

(((3 S, 5R)-1-(2-(6-cyclopropyl-7-fluoroimidazo[1,2-a]pyridin-3-yl)pyrimidin-4-yl)-5-methylpiperidin-3-yl)imino)dimethyl-λ6-sulfanone, I-376

6-cyclopropyl-7-fluoro-3-(4-(3-fluoro-5-(5-methyl-1H-pyrazol-4-yl)piperidin-1-yl)pyrimidin-2-yl)imidazo[1,2-a]pyridine, I-377

4-(2-(6-(difluoromethyl)imidazo[1,2-a]pyridin-3-yl)pyrimidin-4-yl)-3-methylpiperazine-2-carboxamide, I-378

3-(4-(3-methyl-4-(1H-pyrazol-1-yl)piperidin-1-yl)pyrimidin-2-yl)-6-(trifluoromethyl)imidazo[1,2-a]pyridine, I-379

3-methyl-4-{2-[6-(trifluoromethyl)imidazo[1,2-a]pyridin-3-yl]pyrimidin-4-yl}piperazine-2-carboxamide, I-380

(1-(1-(2-(6-(trifluoromethyl)imidazo[1,2-a]pyridin-3-yl)pyrimidin-4-yl)piperidin-3-yl)-1H-1,2,3-triazol-4-yl)methanol, I-382

3-(2-(1H-pyrazol-4-yl)-4-(2-(6-(trifluoromethyl)imidazo[1,2-a]pyridin-3-yl)pyrimidin-4-yl)piperazin-1-yl)cyclobutan-1-ol, I-383

3-(4-(4-((1-methyl-1H-pyrazol-4-yl)methyl)-3-(1H-pyrazol-4-yl)piperazin-1-yl)pyrimidin-2-yl)-6-(trifluoromethyl)imidazo[1,2-a]pyridine, I-384

3-(4-(4-((1H-imidazol-5-yl)methyl)-3-(1H-pyrazol-4-yl)piperazin-1-yl)pyrimidin-2-yl)-6-(trifluoromethyl)imidazo[1,2-a]pyridine, I-385 tert-butyl 8-(2-(6-(trifluoromethyl)imidazo[1,2-a]pyridin-3-yl)pyrimidin-4-yl)-5-oxa-2,8-diazaspiro[3.5]nonane-2-carboxylate, I-386 tert-butyl 6-(2-(6-(trifluoromethyl)imidazo[1,2-a]pyridin-3-yl)pyrimidin-4-yl)-2,6-diazaspiro[3.5]nonane-2-carboxylate, I-387 tert-butyl 9,9-dimethyl-8-(2-(6-(trifluoromethyl)imidazo[1,2-a]pyridin-3-yl)pyrimidin-4-yl)-5-oxa-2,8-diazaspiro[3.5]nonane-2-carboxylate, I-388

4-(2-(6-chloro-7-fluoroimidazo[1,2-a]pyridin-3-yl)pyrimidin-4-yl)-1-cyclopropylpiperazine-2-carboxamide, I-389

(3-(2-(1H-pyrazol-4-yl)-4-(2-(6-(trifluoromethyl)imidazo[1,2-a]pyridin-3-yl)pyrimidin-4-yl)piperazin-1-yl)cyclobutyl)methanol, I-390

(2-(1H-pyrazol-4-yl)-4-(2-(6-(trifluoromethyl)imidazo[1,2-a]pyridin-3-yl)pyrimidin-4-yl)piperazin-1-yl)(1-isopropyl-1H-pyrazol-4-yl)methanone, I-391

3-(4-(4-cyclopropyl-3,5-dimethylpiperazin-1-yl)pyrimidin-2-yl)-6-(trifluoromethyl)imidazo[1,2-a]pyridine, I-392

2-(2,6-dimethyl-4-(2-(6-(trifluoromethyl)imidazo[1,2-a]pyridin-3-yl)pyrimidin-4-yl)piperazin-1-yl)acetonitrile, I-393

N-(((1R,4S)-2-(2-(6-(difluoromethyl)imidazo[1,2-a]pyridin-3-yl)pyrimidin-4-yl)-2-azabicyclo[2.2.2]octan-6-yl)methyl)methanesulfonamide, I-394

6-(2-(6-(difluoromethyl)imidazo[1,2-a]pyridin-3-yl)pyrimidin-4-yl)-2-(methylsulfonyl)-2,6-diazaspiro[3.5]nonane, I-395

8-(2-(6-(difluoromethyl)imidazo[1,2-a]pyridin-3-yl)pyrimidin-4-yl)-6,6-dimethyl-2-(methyl sulfonyl)-5-oxa-2,8-diazaspiro[3.5]nonane, I-396

(2-(1H-pyrazol-4-yl)-4-(2-(6-(trifluoromethyl)imidazo[1,2-a]pyridin-3-yl)pyrimidin-4-yl)piperazin-1-yl)(cyclopropyl)methanone, I-397

2-{6-phenoxyimidazo[1,2-a]pyridin-3-yl}-4-[(3R)-3-(1H-pyrazol-4-yl)piperidin-1-yl]pyrimidine I-398

2-{6-phenoxyimidazo[1,2-a]pyridin-3-yl)}-4-[(3 S)-3-(1H-pyrazol-4-yl)piperidin-1-yl]pyrimidine I-399

(2-(1H-pyrazol-4-yl)-4-(2-(6-(trifluoromethyl)imidazo[1,2-a]pyridin-3-yl)pyrimidin-4-yl)piperazin-1-yl)(2,2-difluorocyclopropyl)methanone, I-400

(cis-2,6-dimethyl-4-(2-(6-(trifluoromethyl)imidazo[12-a]pyridin-3-yl)pyrimidin-4-yl)piperazin-1-yl)(1-isopropyl-1H-pyrazol-3-yl)methanone, I-401

(2-(1H-pyrazol-4-yl)-4-(2-(6-(trifluoromethyl)imidazo[1,2-a]pyridin-3-yl)pyrimidin-4-yl)piperazin-1-yl)(3,3-difluorocyclobutyl)methanone, I-402 cyclopropyl(cis-2,6-dimethyl-4-(2-(6-(trifluoromethyl)imidazo[1,2-a]pyridin-3-yl)pyrimidin-4-yl)piperazin-1-yl)methanone, I-403

N—((R)-1-((S)-4-(2-(6-(trifluoromethyl)imidazo[1,2-a]pyridin-3-yl)pyrimidin-4-yl)morpholin-2-yl)ethyl)methanesulfonamide, I-404

N—((S)-1-((R)-4-(2-(6-(trifluoromethyl)imidazo[1,2-a]pyridin-3-yl)pyrimidin-4-yl)morpholin-2-yl)ethyl)methanesulfonamide, I-405

N—((R)-1-((R)-4-(2-(6-(trifluoromethyl)imidazo[1,2-a]pyridin-3-yl)pyrimidin-4-yl)morpholin-2-yl)ethyl)methanesulfonamide, I-406

N—((S)-1-((S)-4-(2-(6-(trifluoromethyl)imidazo[1,2-a]pyridin-3-yl)pyrimidin-4-yl)morpholin-2-yl)ethyl)methanesulfonamide, I-407

3-(4-((3R,5S)-3-methyl-5-(5-methyl-2H-1,2,3-triazol-4-yl)piperidin-1-yl)pyrimidin-2-yl)-6-(trifluoromethyl)imidazo[1,2-a]pyridine, I-408

3-(4-((3S,5R)-3-methyl-5-(5-methyl-2H-1,2,3-triazol-4-yl)piperidin-1-yl)pyrimidin-2-yl)-6-(trifluoromethyl)imidazo[1,2-a]pyridine, I-409

3-(4-(cis-3,5-dimethyl-4-(2,2,2-trifluoroethyl)piperazin-1-yl)pyrimidin-2-yl)-6-(trifluoromethyl)imidazo[1,2-a]pyridine, I-410 tert-butyl 3-(2-(6-(trifluoromethyl)imidazo[1,2-a]pyridin-3-yl)pyrimidin-4-yl)-3,9-diazabicyclo[3.3.1]nonane-9-carboxylate, I-411

8-(2-(6-(trifluoromethyl)imidazo[1,2-a]pyridin-3-yl)pyrimidin-4-yl)-5-oxa-2,8-diazaspiro[3.5]nonane, I-412

6-(2-(6-(trifluoromethyl)imidazo[1,2-a]pyridin-3-yl)pyrimidin-4-yl)-2,6-diazaspiro[3.5]nonane, I-413

1-(cis-2,6-dimethyl-4-(2-(6-(trifluoromethyl)imidazo[1,2-a]pyridin-3-yl)pyrimidin-4-yl)piperazin-1-yl)ethan-1-one, I-414

(2-(1H-pyrazol-4-yl)-4-(2-(6-(trifluoromethyl)imidazo[1,2-a]pyridin-3-yl)pyrimidin-4-yl)piperazin-1-yl)(1-(2-hydroxyethyl)-1H-pyrazol-4-yl)methanone, I-415

(2-(1H-pyrazol-4-yl)-4-(2-(6-(trifluoromethyl)imidazo[1,2-a]pyridin-3-yl)pyrimidin-4-yl)piperazin-1-yl)(1-(2-methoxyethyl)-1H-pyrazol-4-yl)methanone, I-416

(2-(1H-pyrazol-4-yl)-4-(2-(6-(trifluoromethyl)imidazo[1,2-a]pyridin-3-yl)pyrimidin-4-yl)piperazin-1-yl)(1-(oxetan-3-yl)-1H-pyrazol-4-yl)methanone, I-417

(2-(1H-pyrazol-4-yl)-4-(2-(6-(trifluoromethyl)imidazo[1,2-a]pyridin-3-yl)pyrimidin-4-yl)piperazin-1-yl)(1-methyl-1H-pyrazol-4-yl)methanone, I-418

(2-(1H-pyrazol-4-yl)-4-(2-(6-(trifluoromethyl)imidazo[1,2-a]pyridin-3-yl)pyrimidin-4-yl)piperazin-1-yl)(1-methyl-1H-pyrazol-5-yl)methanone, I-419

1-(2-(1H-pyrazol-4-yl)-4-(2-(6-(trifluoromethyl)imidazo[1,2-a]pyridin-3-yl)pyrimidin-4-yl)piperazin-1-yl)-2-hydroxypropan-1-one, I-420

1-(2-(1H-pyrazol-4-yl)-4-(2-(6-(trifluoromethyl)imidazo[1,2-a]pyridin-3-yl)pyrimidin-4-yl)piperazin-1-yl)-2-hydroxyethan-1-one, I-421

1-(2-(1H-pyrazol-4-yl)-4-(2-(6-(trifluoromethyl)imidazo[1,2-a]pyridin-3-yl)pyrimidin-4-yl)piperazin-1-yl)-3-(1H-imidazol-1-yl)propan-1-one, I-422

1-(2-(1H-pyrazol-4-yl)-4-(2-(6-(trifluoromethyl)imidazo[1,2-a]pyridin-3-yl)pyrimidin-4-yl)piperazin-1-yl)-3-(3,5-dimethyl-1H-pyrazol-1-yl)propan-1-one, I-423

(S)-4-(2-(6-chloro-7-fluoroimidazo[1,2-a]pyridin-3-yl)pyrimidin-4-yl)-1-cyclopropylpiperazine-2-carboxamide, I-424

(R)-4-(2-(6-chloro-7-fluoroimidazo[1,2-a]pyridin-3-yl)pyrimidin-4-yl)-1-cyclopropylpiperazine-2-carboxamide, I-425

6-chloro-7-fluoro-3-(4-(3-fluoro-5-(5-methyl-1H-pyrazol-4-yl)piperidin-1-yl)pyrimidin-2-yl)imidazo[1,2-a]pyridine, I-426

4-(2-(6-cyclopropyl-7-fluoroimidazo[1,2-a]pyridin-3-yl)pyrimidin-4-yl)-3-methylpiperazine-2-carboxamide, I-427

(2S,6S)-4-(2-(6-cyclopropyl-7-fluoroimidazo[1,2-a]pyridin-3-yl)pyrimidin-4-yl)-2-methyl-6-(5-methyl-1H-pyrazol-4-yl)morpholine, I-428

(2S,6R)-4-(2-(6-cyclopropyl-7-fluoroimidazo[1,2-a]pyridin-3-yl)pyrimidin-4-yl)-2-methyl-6-(5-methyl-1H-pyrazol-4-yl)morpholine, I-429

1-(2-(1H-pyrazol-4-yl)-4-(2-(6-(trifluoromethyl)imidazo[1,2-a]pyridin-3-yl)pyrimidin-4-yl)piperazine-1-carbonyl)cyclopropane-1-carbonitrile, I-432

(R)-1-(4-(4-(2-(6-(trifluoromethyl)imidazo[1,2-a]pyridin-3-yl)pyrimidin-4-yl)piperazin-2-yl)-1H-pyrazole-1-carbonyl)cyclopropane-1-carbonitrile, I-433

(2R,3R)-3-methyl-4-(2-(6-(trifluoromethyl)imidazo[1,2-a]pyridin-3-yl)pyrimidin-4-yl)piperazine-2-carboxamide, I-434

(2S,3 S)-3-methyl-4-(2-(6-(trifluoromethyl)imidazo[1,2-a]pyridin-3-yl)pyrimidin-4-yl)piperazine-2-carboxamide, I-435

N-(((2R,3 S)-3-methyl-4-(2-(6-(trifluoromethyl)imidazo[1,2-a]pyridin-3-yl)pyrimidin-4-yl)piperazin-2-yl)methyl)methanesulfonamide, I-436

(3,3-difluorocyclobutyl)(cis-2,6-dimethyl-4-(2-(6-(trifluoromethyl)imidazo[1,2-a]pyridin-3-yl)pyrimidin-4-yl)piperazin-1-yl)methanone, I-437

(2,2-difluorocyclopropyl)(cis-2,6-dimethyl-4-(2-(6-(trifluoromethyl)imidazo[1,2-a]pyridin-3-yl)pyrimidin-4-yl)piperazin-1-yl)methanone, I-438

3-(4-(cis-3,5-dimethyl-4-(methylsulfonyl)piperazin-1-yl)pyrimidin-2-yl)-6-(trifluoromethyl)imidazo[1,2-a]pyridine, I-439

(1-cyclopropyl-1H-pyrazol-3-yl)(cis-2,6-dimethyl-4-(2-(6-(trifluoromethyl)imidazo[1,2-a]pyridin-3-yl)pyrimidin-4-yl)piperazin-1-yl)methanone, I-440

(2-(1H-pyrazol-4-yl)-4-(2-(6-(trifluoromethyl)imidazo[1,2-a]pyridin-3-yl)pyrimidin-4-yl)piperazin-1-yl)(1,2,5-oxadiazol-3-yl)methanone, I-441

(2-(1H-pyrazol-4-yl)-4-(2-(6-(trifluoromethyl)imidazo[1,2-a]pyridin-3-yl)pyrimidin-4-yl)piperazin-1-yl)(2H-1,2,3-triazol-4-yl)methanone, I-442

(2-(1H-pyrazol-4-yl)-4-(2-(6-(trifluoromethyl)imidazo[1,2-a]pyridin-3-yl)pyrimidin-4-yl)piperazin-1-yl)(oxazol-4-yl)methanone, I-443

(2-(1H-pyrazol-4-yl)-4-(2-(6-(trifluoromethyl)imidazo[1,2-a]pyridin-3-yl)pyrimidin-4-yl)piperazin-1-yl)(isoxazol-4-yl)methanone, I-444

(2-(1H-pyrazol-4-yl)-4-(2-(6-(trifluoromethyl)imidazo[1,2-a]pyridin-3-yl)pyrimidin-4-yl)piperazin-1-yl)(1H-imidazol-4-yl)methanone, I-445

(2-(1H-pyrazol-4-yl)-4-(2-(6-(trifluoromethyl)imidazo[1,2-a]pyridin-3-yl)pyrimidin-4-yl)piperazin-1-yl)(1-methyl-1H-imidazol-4-yl)methanone, I-446

2-(methylsulfonyl)-8-(2-(6-(trifluoromethyl)imidazo[1,2-a]pyridin-3-yl)pyrimidin-4-yl)-5-oxa-2,8-diazaspiro[3.5]nonane, I-447

2-(methylsulfonyl)-6-(2-(6-(trifluoromethyl)imidazo[1,2-a]pyridin-3-yl)pyrimidin-4-yl)-2,6-diazaspiro[3.5]nonane, I-448

3-(4-(3-(1H-pyrazol-4-yl)-4-(3,3,3-trifluoropropyl)piperazin-1-yl)pyrimidin-2-yl)-6-(trifluoromethyl)imidazo[1,2-a]pyridine, I-449

3-(4-(4-(3,4-difluorobenzyl)-3-(1H-pyrazol-4-yl)piperazin-1-yl)pyrimidin-2-yl)-6-(trifluoromethyl)imidazo[1,2-a]pyridine, I-450

4-(2-{6-chloroimidazo[1,2-a]pyridin-3-yl}pyrimidin-4-yl)-3-methylpiperazine-2-carboxamide, I-451

(2-(1H-pyrazol-4-yl)-4-(2-(6-(trifluoromethyl)imidazo[1,2-a]pyridin-3-yl)pyrimidin-4-yl)piperazin-1-yl)(2-methoxypyridin-4-yl)methanone, I-452

(2R,3 S)-4-(2-(6-cyclopropyl-7-fluoroimidazo[1,2-a]pyridin-3-yl)pyrimidin-4-yl)-3-methylpiperazine-2-carboxamide, I-454

4-(2-(6-cyclopropyl-7-fluoroimidazo[1,2-a]pyridin-3-yl)pyrimidin-4-yl)-3-methylpiperazine-2-carboxamide, I-455

3-(4-(3-(1H-pyrazol-4-yl)-4-(tetrahydro-2H-pyran-4-yl)piperazin-1-yl)pyrimidin-2-yl)-6-(trifluoromethyl)imidazo[1,2-a]pyridine, I-456

3-(4-(4-(4-fluorobenzyl)-3-(1H-pyrazol-4-yl)piperazin-1-yl)pyrimidin-2-yl)-6-(trifluoromethyl)imidazo[1,2-a]pyridine, I-457

3-(4-(4-(3-fluorobenzyl)-3-(1H-pyrazol-4-yl)piperazin-1-yl)pyrimidin-2-yl)-6-(trifluoromethyl)imidazo[1,2-a]pyridine, I-458

3-(4-(4-(2-fluorobenzyl)-3-(1H-pyrazol-4-yl)piperazin-1-yl)pyrimidin-2-yl)-6-(trifluoromethyl)imidazo[1,2-a]pyridine, I-459

3-(4-(4-(4,4-difluorocyclohexyl)-3-(1H-pyrazol-4-yl)piperazin-1-yl)pyrimidin-2-yl)-6-(trifluoromethyl)imidazo[1,2-a]pyridine, I-460

4-{4-[(1,2,5-oxadiazol-3-yl)methyl]-3-(1H-pyrazol-4-yl)piperazin-1-yl}-2-[6-(trifluoromethyl)imidazo[1,2-a]pyridin-3-yl]pyrimidine, I-461

3-(4-(cis-3,5-dimethyl-4-((tetrahydro-2H-pyran-4-yl)methyl)piperazin-1-yl)pyrimidin-2-yl)-6-(trifluoromethyl)imidazo[1,2-a]pyridine, I-462

3-(2-((3R,5S)-3-(3,5-dimethyl-4H-1,2,4-triazol-4-yl)-5-methylpiperidin-1-yl)pyrimidin-4-yl)-6-(trifluoromethyl)imidazo[1,2-a]pyridine, I-463

1-(cis-2,6-dimethyl-4-(2-(6-(trifluoromethyl)imidazo[1,2-a]pyridin-3-yl)pyrimidin-4-yl)piperazin-1-yl)-2-(tetrahydro-2H-pyran-4-yl)ethan-1-one, I-464

3-(2-((3S,5S)-3-(3,5-dimethyl-4H-1,2,4-triazol-4-yl)-5-methylpiperidin-1-yl)pyrimidin-4-yl)-6-(trifluoromethyl)imidazo[1,2-a]pyridine, I-465

3-(2-((3S,5R)-3-(3,5-dimethyl-4H-1,2,4-triazol-4-yl)-5-methylpiperidin-1-yl)pyrimidin-4-yl)-6-(trifluoromethyl)imidazo[1,2-a]pyridine, I-466

3-(2-((3R,5R)-3-(3,5-dimethyl-4H-1,2,4-triazol-4-yl)-5-methylpiperidin-1-yl)pyrimidin-4-yl)-6-(trifluoromethyl)imidazo[1,2-a]pyridine, I-467

(2-(1H-pyrazol-4-yl)-4-(2-(6-(trifluoromethyl)imidazo[1,2-a]pyridin-3-yl)pyrimidin-4-yl)piperazin-1-yl)(spiro[2.2]pentan-1-yl)methanone, I-468

5-(2-(1H-pyrazol-4-yl)-4-(2-(6-(trifluoromethyl)imidazo[1,2-a]pyridin-3-yl)pyrimidin-4-yl)piperazine-1-carbonyl)pyrrolidin-2-one, I-469

3-(4-(4-((2,2-difluorocyclopropyl)methyl)-3-(1H-pyrazol-4-yl)piperazin-1-yl)pyrimidin-2-yl)-6-(trifluoromethyl)imidazo[1,2-a]pyridine, I-470

N-(((2 S,3 S)-3-methyl-4-(2-(6-(trifluoromethyl)imidazo[1,2-a]pyridin-3-yl)pyrimidin-4-yl)piperazin-2-yl)methyl)methanesulfonamide, I-471

N-((1-cyclopropyl-4-(2-(6-(difluoromethyl)imidazo[1,2-a]pyridin-3-yl)pyrimidin-4-yl)-3-methylpiperazin-2-yl)methyl)methanesulfonamide, I-472

3-(4-(4-((2-methyl cyclopropyl)methyl)-3-(1H-pyrazol-4-yl)piperazin-1-yl)pyrimidin-2-yl)-6-(trifluoromethyl)imidazo[1,2-a]pyridine, I-473

(S)-6-((S)-2-(1H-pyrazol-4-yl)-4-(2-(6-(trifluoromethyl)imidazo[1,2-a]pyridin-3-yl)pyrimidin-4-yl)piperazine-1-carbonyl)piperidin-2-one, I-474

3-(4-(3-(1H-pyrazol-4-yl)-4-(spiro[2.2]pentan-1-ylmethyl)piperazin-1-yl)pyrimidin-2-yl)-6-(trifluoromethyl)imidazo[1,2-a]pyridine, I-475

3-(4-(4-((2,2-dimethylcyclopropyl)methyl)-3-(1H-pyrazol-4-yl)piperazin-1-yl)pyrimidin-2-yl)-6-(trifluoromethyl)imidazo[1,2-a]pyridine, I-477

N-(5-(trifluoromethyl)-1-(2-(6-(trifluoromethyl)imidazo[1,2-a]pyridin-3-yl)pyrimidin-4-yl)piperidin-3-yl)methanesulfonamide, I-478

(R)-(1,3-dimethyl-1H-pyrazol-4-yl)(2-methyl-4-(2-(6-(trifluoromethyl)imidazo[1,2-a]pyridin-3-yl)pyrimidin-4-yl)piperazin-1-yl)methanone, I-479

(S)-(1,3-dimethyl-1H-pyrazol-4-yl)(2-methyl-4-(2-(6-(trifluoromethyl)imidazo[1,2-a]pyridin-3-yl)pyrimidin-4-yl)piperazin-1-yl)methanone, I-480

3-(4-((2 S,3R)-2-methyl-4-((3-methyloxetan-3-yl)methyl)-3-(1H-pyrazol-4-yl)piperazin-1-yl)pyrimidin-2-yl)-6-(trifluoromethyl)imidazo[1,2-a]pyridine, I-481

3-(4-((2 S,3 S)-2-methyl-4-((3-methyloxetan-3-yl)methyl)-3-(1H-pyrazol-4-yl)piperazin-1-yl)pyrimidin-2-yl)-6-(trifluoromethyl)imidazo[1,2-a]pyridine, I-482

(cis-2,6-dimethyl-4-(2-(6-(trifluoromethyl)imidazo[1,2-a]pyridin-3-yl)pyrimidin-4-yl)piperazin-1-yl)(pyridin-4-yl)methanone, I-483

(2-(1H-pyrazol-4-yl)-4-(2-(6-(trifluoromethyl)imidazo[1,2-a]pyridin-3-yl)pyrimidin-4-yl)piperazin-1-yl)((1R,2R)-2-fluorocyclopropyl)methanone, I-485

(cis-2,6-dimethyl-4-(2-(6-(trifluoromethyl)imidazo[1,2-a]pyridin-3-yl)pyrimidin-4-yl)piperazin-1-yl)(1-methylcyclopropyl)methanone, I-486

(2-(1H-pyrazol-4-yl)-4-(2-(6-(trifluoromethyl)imidazo[1,2-a]pyridin-3-yl)pyrimidin-4-yl)piperazin-1-yl)(tetrahydro-2H-pyran-4-yl)methanone, I-487

(2-(1H-pyrazol-4-yl)-4-(2-(6-(trifluoromethyl)imidazo[1,2-a]pyridin-3-yl)pyrimidin-4-yl)piperazin-1-yl)(1-(difluoromethyl)cyclopropyl)methanone, I-488

(2-(1H-pyrazol-4-yl)-4-(2-(6-(trifluoromethyl)imidazo[1,2-a]pyridin-3-yl)pyrimidin-4-yl)piperazin-1-yl)((1R,2R)-2-fluorocyclopropyl)methanone, I-489

N-(((2R,3 S,6S)-1-cyclopropyl-3,6-dimethyl-4-(2-(6-(trifluoromethyl)imidazo[1,2-a]pyridin-3-yl)pyrimidin-4-yl)piperazin-2-yl)methyl)methanesulfonamide, I-491

4-(2,2-dimethyl-4-(2-(6-(trifluoromethyl)imidazo[1,2-a]pyridin-3-yl)pyrimidin-4-yl)piperazine-1-carbonyl)cyclohexan-1-one, I-492

N-(((2R,3R,6R)-1-cyclopropyl-3,6-dimethyl-4-(2-(6-(trifluoromethyl)imidazo[1,2-a]pyridin-3-yl)pyrimidin-4-yl)piperazin-2-yl)methyl)methanesulfonamide, I-493

N-(((2S,3R,6R)-1-cyclopropyl-3,6-dimethyl-4-(2-(6-(trifluoromethyl)imidazo[1,2-a]pyridin-3-yl)pyrimidin-4-yl)piperazin-2-yl)methyl)methanesulfonamide, I-494

N-((4-(2-(6-(difluoromethyl)imidazo[1,2-a]pyridin-3-yl)pyrimidin-4-yl)-3-(trifluoromethyl)piperazin-2-yl)methyl)methanesulfonamide, I-496

(2R,6R)-4-(2-(6-(difluoromethyl)imidazo[1,2-a]pyridin-3-yl)pyrimidin-4-yl)-2-methyl-6-(3-methyl-1,2,4-oxadiazol-5-yl)morpholine, I-497

(2S,6S)-4-(2-(6-(difluoromethyl)imidazo[1,2-a]pyridin-3-yl)pyrimidin-4-yl)-2-methyl-6-(3-methyl-1,2,4-oxadiazol-5-yl)morpholine, I-498

(((3 S,5R)-1-(4-(6-(difluoromethyl)imidazo[1,2-a]pyridin-3-yl)pyrimidin-2-yl)-5-methylpiperidin-3-yl)imino)dimethyl-λ6-sulfanone, I-499

N—(S)-1-((2S,3 S)-1-cyclopropyl-3-methyl-4-(2-(6-(trifluoromethyl)imidazo[1,2-a]pyridin-3-yl)pyrimidin-4-yl)piperazin-2-yl)ethyl)methanesulfonamide, I-500

1-(cis-2,6-dimethyl-4-(2-(6-(trifluoromethyl)imidazo[1,2-a]pyridin-3-yl)pyrimidin-4-yl)piperazin-1-yl)-2-(oxetan-3-yl)ethan-1-one, I-501

(S)-3-(4-(3-(1H-pyrazol-4-yl)-4-(2-oxaspiro[3.3]heptan-6-yl)piperazin-1-yl)pyrimidin-2-yl)-6-(trifluoromethyl)imidazo[1,2-a]pyridine, I-502

(R)-3-(4-(4-cyclopropyl-3-(1H-pyrazol-4-yl)piperazin-1-yl)pyrimidin-2-yl)-6-(trifluoromethyl)imidazo[1,2-a]pyridine, I-503

(R)-3-(4-(3-(1H-pyrazol-4-yl)-4-(2-oxaspiro[3.3]heptan-6-yl)piperazin-1-yl)pyrimidin-2-yl)-6-(trifluoromethyl)imidazo[1,2-a]pyridine, I-504

N—((R)-1-((2R,3R)-1-cyclopropyl-3-methyl-4-(2-(6-(trifluoromethyl)imidazo[1,2-a]pyridin-3-yl)pyrimidin-4-yl)piperazin-2-yl)ethyl)methanesulfonamide, I-505

N—((R)-1-((2 S,3 S)-1-cyclopropyl-3-methyl-4-(2-(6-(trifluoromethyl)imidazo[1,2-a]pyridin-3-yl)pyrimidin-4-yl)piperazin-2-yl)ethyl)methanesulfonamide, I-506

N—((S)-1-((2R,3R)-1-cyclopropyl-3-methyl-4-(2-(6-(trifluoromethyl)imidazo[1,2-a]pyridin-3-yl)pyrimidin-4-yl)piperazin-2-yl)ethyl)methanesulfonamide, I-507

3-{2-[(R)-4-Cyclopropyl-3-(1H-pyrazol-4-yl)-piperazin-1-yl]-pyrimidin-4-yl}-6-trifluoromethyl-imidazo[1,2-a]pyridine, I-508, (2-(1H-pyrazol-4-yl)-4-(2-(6-(trifluoromethyl)imidazo[1,2-a]pyridin-3-yl)pyrimidin-4-yl)piperazin-1-yl)(3-hydroxy-3-methylcyclobutyl)methanone, I-509

3-(4-(4-((1-methyl cyclopropyl)methyl)-3-(1H-pyrazol-4-yl)piperazin-1-yl)pyrimidin-2-yl)-6-(trifluoromethyl)imidazo[1,2-a]pyridine, I-510

4-[(2R,3 S)-4-{[1-(methoxymethyl)cyclobutyl]methyl}-2-methyl-3-(1H-pyrazol-4-yl)piperazin-1-yl]-2-[6-(trifluoromethyl)imidazo[1,2-a]pyridin-3-yl]pyrimidine, I-511

4-[(2S,3 S)-4-{[1-(methoxymethyl)cyclobutyl]methyl}-2-methyl-3-(1H-pyrazol-4-yl)piperazin-1-yl]-2-[6-(trifluoromethyl)imidazo[1,2-a]pyridin-3-yl]pyrimidine, I-512

(6,7-dihydro-4H-pyrazolo[5,1-c][1,4]oxazin-2-yl)(cis-2,6-dimethyl-4-(2-(6-(trifluoromethyl)imidazo[1,2-a]pyridin-3-yl)pyrimidin-4-yl)piperazin-1-yl)methanone, I-513

1-(2-(1H-pyrazol-4-yl)-4-(2-(6-(trifluoromethyl)imidazo[1,2-a]pyridin-3-yl)pyrimidin-4-yl)piperazin-1-yl)-2-hydroxy-2-methylpropan-1-one, I-514

(2-(1H-pyrazol-4-yl)-4-(2-(6-(trifluoromethyl)imidazo[1,2-a]pyridin-3-yl)pyrimidin-4-yl)piperazin-1-yl)(5-methylisoxazol-4-yl)methanone, I-515

N-(((2R,3 S)-1-cyclopropyl-4-(2-(6-(difluoromethyl)imidazo[1,2-a]pyridin-3-yl)pyrimidin-4-yl)-3-methylpiperazin-2-yl)methyl)methanesulfonamide, I-516

N-(((2 S,3R)-1-cyclopropyl-4-(2-(6-(difluoromethyl)imidazo[1,2-a]pyridin-3-yl)pyrimidin-4-yl)-3-methylpiperazin-2-yl)methyl)methanesulfonamide, I-517

(2-(1H-pyrazol-4-yl)-4-(2-(6-(trifluoromethyl)imidazo[1,2-a]pyridin-3-yl)pyrimidin-4-yl)piperazin-1-yl)(4-methyl-1,2,5-oxadiazol-3-yl)methanone, I-518

(2-(1H-pyrazol-4-yl)-4-(2-(6-(trifluoromethyl)imidazo[1,2-a]pyridin-3-yl)pyrimidin-4-yl)piperazin-1-yl)(3,5-dimethylisoxazol-4-yl)methanone, I-519

3-(4-((R)-4-(((R)-6-oxaspiro[2.5]octan-1-yl)methyl)-3-(1H-pyrazol-4-yl)piperazin-1-yl)pyrimidin-2-yl)-6-(trifluoromethyl)imidazo[1,2-a]pyridine, I-520

3-(4-((S)-4-(((S)-6-oxaspiro[2.5]octan-1-yl)methyl)-3-(1H-pyrazol-4-yl)piperazin-1-yl)pyrimidin-2-yl)-6-(trifluoromethyl)imidazo[1,2-a]pyridine, I-521

3-(4-((S)-4-(((R)-6-oxaspiro[2.5]octan-1-yl)methyl)-3-(1H-pyrazol-4-yl)piperazin-1-yl)pyrimidin-2-yl)-6-(trifluoromethyl)imidazo[1,2-a]pyridine, I-522

3-(4-((R)-4-(((S)-6-oxaspiro[2.5]octan-1-yl)methyl)-3-(1H-pyrazol-4-yl)piperazin-1-yl)pyrimidin-2-yl)-6-(trifluoromethyl)imidazo[1,2-a]pyridine, I-523

((2S,6S)-4-(2-(6-(difluoromethyl)imidazo[1,2-a]pyridin-3-yl)pyrimidin-4-yl)-6-methylmorpholin-2-yl)methanol, I-524

N-(1-(4-(6-(difluoromethyl)imidazo[1,2-a]pyridin-3-yl)pyrimidin-2-yl)-5-(trifluoromethyl)piperidin-3-yl)methanesulfonamide, I-525

3-(4-((R)-4-(((R)-2,2-dimethylcyclopropyl)methyl)-3-(1H-pyrazol-4-yl)piperazin-1-yl)pyrimidin-2-yl)-6-(trifluoromethyl)imidazo[1,2-a]pyridine, I-526

3-(4-((S)-4-(((S)-2,2-dimethylcyclopropyl)methyl)-3-(1H-pyrazol-4-yl)piperazin-1-yl)pyrimidin-2-yl)-6-(trifluoromethyl)imidazo[1,2-a]pyridine, I-527

3-(4-((S)-4-(((R)-2,2-dimethylcyclopropyl)methyl)-3-(1H-pyrazol-4-yl)piperazin-1-yl)pyrimidin-2-yl)-6-(trifluoromethyl)imidazo[1,2-a]pyridine, I-528

3-(4-((R)-4-(((S)-2,2-dimethylcyclopropyl)methyl)-3-(1H-pyrazol-4-yl)piperazin-1-yl)pyrimidin-2-yl)-6-(trifluoromethyl)imidazo[1,2-a]pyridine, I-529

N-((4-(2-(6-(difluoromethyl)imidazo[1,2-a]pyridin-3-yl)pyrimidin-4-yl)-3-methyl-1-(oxetan-3-yl)piperazin-2-yl)methyl)methanesulfonamide, I-530

N-(1-(2-(6-(difluoromethyl)imidazo[1,2-a]pyridin-3-yl)pyrimidin-4-yl)-5-(trifluoromethyl)piperidin-3-yl)methanesulfonamide, I-531

(R)-3-(4-(3-(1H-pyrazol-4-yl)piperazin-1-yl)pyrimidin-2-yl)-6-(trifluoromethyl)imidazo[1,2-a]pyridine, I-532

(S)-3-(4-(3-(1H-pyrazol-4-yl)piperazin-1-yl)pyrimidin-2-yl)-6-(trifluoromethyl)imidazo[1,2-a]pyridine, I-533

3-(4-((2 S,3R)-2-methyl-3-(1H-pyrazol-4-yl)piperazin-1-yl)pyrimidin-2-yl)-6-(trifluoromethyl)imidazo[1,2-a]pyridine, I-534

3-(4-((2S,3 S)-2-methyl-3-(1H-pyrazol-4-yl)piperazin-1-yl)pyrimidin-2-yl)-6-(trifluoromethyl)imidazo[1,2-a]pyridine, I-535

3-(4-((2R,3R)-2-methyl-3-(1H-pyrazol-4-yl)piperazin-1-yl)pyrimidin-2-yl)-6-(trifluoromethyl)imidazo[1,2-a]pyridine, I-536

4-[(2R,3 S)-2-methyl-3-(1H-pyrazol-4-yl)piperazin-1-yl]-2-[6-(trifluoromethyl)imidazo[1,2-a]pyridin-3-yl]pyrimidine, I-537

(2R,6R)-4-(2-(6-chloro-7-fluoroimidazo[1,2-a]pyridin-3-yl)pyrimidin-4-yl)-2-methyl-6-(5-methyl-1H-pyrazol-4-yl)morpholine, I-538

(2S,6S)-4-(2-(6-chloro-7-fluoroimidazo[1,2-a]pyridin-3-yl)pyrimidin-4-yl)-2-methyl-6-(5-methyl-1H-pyrazol-4-yl)morpholine, I-539

(2R,6S)-4-(2-(6-chloro-7-fluoroimidazo[1,2-a]pyridin-3-yl)pyrimidin-4-yl)-2-methyl-6-(5-methyl-1H-pyrazol-4-yl)morpholine, I-540

N-(((2R,3 S)-1-cyclopropyl-3-methyl-4-(4-(6-(trifluoromethyl)imidazo[1,2-a]pyridin-3-yl)pyrimidin-2-yl)piperazin-2-yl)methyl)methanesulfonamide, I-541

3-(2-((S)-3-(1H-pyrazol-4-yl)-4-(((R)-tetrahydro-2H-pyran-3-yl)methyl)piperazin-1-yl)pyrimidin-4-yl)-6-(trifluoromethyl)imidazo[1,2-a]pyridine, I-542

N-{(2S,3R)-1-Cyclopropyl-3-methyl-4-[4-(6-trifluoromethyl-imidazo[1,2-a]pyridin-3-yl)-pyrimidin-2-yl]-piperazin-2-ylmethyl}-methanesulfonamide, I-543

3-(2-((R)-3-(1H-pyrazol-4-yl)-4-(((S)-tetrahydro-2H-pyran-3-yl)methyl)piperazin-1-yl)pyrimidin-4-yl)-6-(trifluoromethyl)imidazo[1,2-a]pyridine, I-544

3-(2-((R)-3-(1H-pyrazol-4-yl)-4-(((R)-tetrahydro-2H-pyran-3-yl)methyl)piperazin-1-yl)pyrimidin-4-yl)-6-(trifluoromethyl)imidazo[1,2-a]pyridine, I-545

3-(2-((S)-3-(1H-pyrazol-4-yl)-4-(((S)-tetrahydro-2H-pyran-3-yl)methyl)piperazin-1-yl)pyrimidin-4-yl)-6-(trifluoromethyl)imidazo[1,2-a]pyridine, I-546

(2R,3R)-4-(2-(6-chloroimidazo[1,2-a]pyridin-3-yl)pyrimidin-4-yl)-1-cyclopropyl-3-methylpiperazine-2-carboxamide, I-547

(2S,3 S)-4-(2-(6-chloroimidazo[1,2-a]pyridin-3-yl)pyrimidin-4-yl)-1-cyclopropyl-3-methylpiperazine-2-carboxamide, I-548

(S)-(2-(1H-pyrazol-4-yl)-4-(2-(6-(trifluoromethyl)imidazo[1,2-a]pyridin-3-yl)pyrimidin-4-yl)piperazin-1-yl)(5-methylisoxazol-4-yl)methanone, I-549

(R)-(2-(1H-pyrazol-4-yl)-4-(2-(6-(trifluoromethyl)imidazo[1,2-a]pyridin-3-yl)pyrimidin-4-yl)piperazin-1-yl)(5-methylisoxazol-4-yl)methanone, I-550

1-(2-(1H-pyrazol-4-yl)-4-(4-(6-(trifluoromethyl)imidazo[1,2-a]pyridin-3-yl)pyrimidin-2-yl)piperazine-1-carbonyl)cyclopropane-1-carbonitrile, I-551

3-(4-((R)-3-(1H-pyrazol-4-yl)-4-(((R)-spiro[2.2]pentan-1-yl)methyl)piperazin-1-yl)pyrimidin-2-yl)-6-(trifluoromethyl)imidazo[1,2-a]pyridine, I-552

3-(4-((S)-3-(1H-pyrazol-4-yl)-4-(((S)-spiro[2.2]pentan-1-yl)methyl)piperazin-1-yl)pyrimidin-2-yl)-6-(trifluoromethyl)imidazo[1,2-a]pyridine, I-553

3-(4-((S)-3-(1H-pyrazol-4-yl)-4-(((R)-spiro[2.2]pentan-1-yl)methyl)piperazin-1-yl)pyrimidin-2-yl)-6-(trifluoromethyl)imidazo[1,2-a]pyridine, I-554

3-(4-((R)-3-(1H-pyrazol-4-yl)-4-(((S)-spiro[2.2]pentan-1-yl)methyl)piperazin-1-yl)pyrimidin-2-yl)-6-(trifluoromethyl)imidazo[1,2-a]pyridine, I-555

(S)-6-(2-(1H-pyrazol-4-yl)-4-(2-(6-(trifluoromethyl)imidazo[1,2-a]pyridin-3-yl)pyrimidin-4-yl)piperazin-1-yl)-2-thiaspiro[3.3]heptane 2,2-dioxide, I-556

(R)-6-(2-(1H-pyrazol-4-yl)-4-(2-(6-(trifluoromethyl)imidazo[1,2-a]pyridin-3-yl)pyrimidin-4-yl)piperazin-1-yl)-2-thiaspiro[3.3]heptane 2,2-dioxide, I-557

(S)-1-(2-(6-chloro-7-fluoroimidazo[1,2-a]pyridin-3-yl)pyrimidin-4-yl)piperidine-3-carboxamide, I-558

6-chloro-3-(4-((3R,5S)-3-methyl-5-(1H-pyrazol-4-yl)piperidin-1-yl)pyrimidin-2-yl)imidazo[1,2-a]pyridine, I-559

(2S,6R)-2-methyl-6-(1H-pyrazol-4-yl)-4-(2-(6-(trifluoromethyl)imidazo[1,2-a]pyridin-3-yl)pyrimidin-4-yl)morpholine, I-560

(2R,6S)-4-(2-(6-chloroimidazo[1,2-a]pyridin-3-yl)pyrimidin-4-yl)-2-methyl-6-(5-methyl-1H-pyrazol-4-yl)morpholine, I-561

(2S,6S)-6-methyl-4-(2-(6-(trifluoromethyl)imidazo[1,2-a]pyridin-3-yl)pyrimidin-4-yl)morpholine-2-carboxamide, I-562

6-chloro-3-(4-((2S,3R,5S)-2,5-dimethyl-3-(1H-pyrazol-4-yl)piperazin-1-yl)pyrimidin-2-yl)imidazo[1,2-a]pyridine, I-563

(2R,6S)-2-methyl-6-(1H-pyrazol-4-yl)-4-(2-(6-(trifluoromethyl)imidazo[1,2-a]pyridin-3-yl)pyrimidin-4-yl)morpholine, I-564

3-(4-((2R,3 S)-2-methyl-4-(oxetan-3-yl)-3-(1H-pyrazol-4-yl)piperazin-1-yl)pyrimidin-2-yl)-6-(trifluoromethyl)imidazo[1,2-a]pyridine, I-565

(2R,6S)-4-(2-(6-chloroimidazo[1,2-a]pyridin-3-yl)pyrimidin-4-yl)-2-methyl-6-(1H-pyrazol-4-yl)morpholine, I-566

3-(4-((3R,5S)-3-methyl-5-(1H-pyrazol-4-yl)piperidin-1-yl)pyrimidin-2-yl)-6-(trifluoromethyl)imidazo[1,2-a]pyridine, I-567

(2S,6R)-4-(2-(6-chloro-7-fluoroimidazo[1,2-a]pyridin-3-yl)pyrimidin-4-yl)-2-methyl-6-(1H-pyrazol-4-yl)morpholine, I-568

(((3R,5R)-1-(2-(6-(difluoromethyl)imidazo[1,2-a]pyridin-3-yl)pyrimidin-4-yl)-5-methylpiperidin-3-yl)imino)dimethyl-$\lambda$6-sulfanone, I-569

Example 26: Human IL-2 Assay for GCN2 Inhibition

Tumor microenvironment is profoundly immuno-suppressive. This may be attributed to the depletion of amino acids (like arginine and tryptophan) which triggers the activation of GCN2 in immune cells, including T cell and myeloid cells. In T cells, activation of GCN2 leads to reduce effector functions of CD8 T cells and induction and/or maintenance of immuno-suppressive T-regs. Inhibition of that immuno-suppressive response by GCN2 inhibitors enables an anti-cancer immune response by activating effector T-cells. Herein we describe an in-vitro system we established using human T-cells stimulated in low amino acid condition in order to engage the GCN2 biology. The method described involves the modulation of IL-2 levels secreted by human T cells in responses to the GCN2 inhibitors disclosed herein.

Amino acid-free RPMI was reconstituted with all but one of the amino acids found in standard RMPI (e.g. Arginine, Tryptophan), 10% charcoal-stripped fetal bovine serum, 100 Units/mL penicillin and 0.1 mg/mL streptomycin. Primary human pan T-cells were isolated using Pan T Cell Isolation Kit, human (MACS Miltenyi biotech Cat # Order no. 130-096-535) from apheresis cones and 5×104 pan T-cells per well. The purified T cells are seeded in Nunc™ 96-Well Polystyrene Round Bottom Microwell Plates (the cells are rested in No TRP media in a 15 ml falcon tube in the incubator for 30-45 minutes while titrations for tryptophan and the GCN2 inhibitor compound are made) A plate matrix was developed to titrate both a GCN2 inhibitor and the amino acid of interest ranging from "No Amino Acid" condition, up to the concentration found in the regular RPMI media (20 μM for TRP and 950 μM for Arginine). The cells were incubated for 30 min at 37° C. with the GCN2 inhibitor and then stimulated with 5×104 anti-CD3/CD28 Dynabeads® per well. After 96 hours of incubation the IL-2 level in the supernatant were measured using ELISA (R&D systems Cat # DY202 (Human IL-2 DuoSet ELISA). Data were plotted in GraphPad Prism software and $EC_{50}$ is calculated.

TABLE 6

$EC_{50}$ values based on IL-2 secretion from T cells

| Compound I# | IL2/T-cell $EC_{50}$ (nM) |
| --- | --- |
| I-102 | ++ |
| I-116 | +++ |
| I-123 | +, − |
| I-124 | ++, +++ |
| I-125 | +++, ++, + |
| I-126 | ++ |
| I-127 | +++ |
| I-128 | + |
| I-134 | + |
| I-135 | ++ |
| I-136 | +++, ++ |
| I-137 | ++ |
| I-148 | ++ |
| I-154 | +++ |
| I-160 | ++ |
| I-170 | ++ |
| I-176 | +++ |
| I-179 | ++ |
| I-185 | − |
| I-191 | − |
| I-200 | ++ |
| I-209 | ++ |
| I-223 | ++ |
| I-247 | +++ |
| I-248 | ++ |
| I-249 | ++ |
| I-250 | − |
| I-259 | +++ |
| I-293 | +++ |
| I-314 | − |
| I-315 | ++ |
| I-323 | + |
| I-354 | ++ |
| I-359 | ++ |
| I-366 | +++ |
| I-409 | + |
| I-473 | ++ |
| I-481 | +++ |
| I-482 | + |
| I-495 | + |
| I-499 | + |
| I-504 | ++ |
| I-547 | ++ |
| I-558 | ++ |
| I-559 | +++ |
| I-560 | +++ |
| I-561 | ++ |
| I-562 | ++ |
| I-563 | ++ |
| I-564 | +++ |
| I-565 | +++ |
| I-566 | +++ |

TABLE 6-continued $EC_{50}$ values based on IL-2 secretion from T cells

| Compound I# | IL2/T-cell $EC_{50}$ (nM) |
| --- | --- |
| I-567 | +++ |
| I-568 | ++ |
| I-569 | ++ |
| I-562 | ++ |

+++ for $EC_{50}$ < 100 nM;
++ for $EC_{50}$ in the 100-500 nM range;
+ for $EC_{50}$ > 500 nM; and
"−" for not active While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of one of formula XV-a, XV-a, or XV-c:

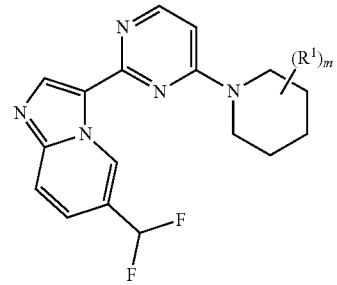

XV-a

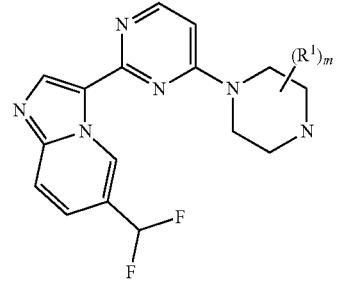

XV-b

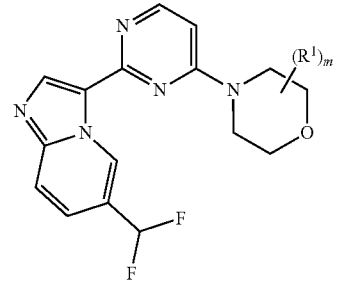

XV-c or a pharmaceutically acceptable salt thereof, wherein:
each of $R^1$ is independently hydrogen, halogen, —CN, —NO$_2$, —C(O)R, —C(O)OR, —C(O)NR$_2$, —C(O)NRS(O)$_2$R, —C(O)N=S(O)R$_2$, —NR$_2$, —NRC(O)R, —NRC(O)NR$_2$, —NRC(O)OR, —NRS(O)$_2$R, —NRS(O)$_2$NR$_2$, —OR, —ON(R)SO$_2$R, —P(O)R$_2$, —SR, —S(O)R, —S(O)₂R, —S(O)(NH)R, —S(O)₂N(R)₂, —S(NH₂)₂(O)OH, —N=S(O)R₂, —CH₃, —CH₂OH, —CH₂NHSO₂CH₃, —CD₃, —CD₂NRS(O)₂R, or R; or two R¹ groups are optionally taken together to form =O or =NH; or two R¹ groups are optionally taken together to form a bivalent C₂₋₄ alkylene chain;

each R is independently hydrogen or an optionally substituted group selected from C₁₋₆ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or two R groups are optionally taken together to form a bivalent C₂₋₄ alkylene chain; or two R groups are optionally taken together with their intervening atoms to form an optionally substituted 3-7 membered saturated or partially unsaturated monocyclic ring having 0-4 heteroatoms independently selected from nitrogen, oxygen or sulfur;

m is 0, 1, 2, 3, 4 or 5.

2. The compound of claim 1, wherein m is 1, 2 or 3.

3. A compound selected from the group consisting of:

I-1

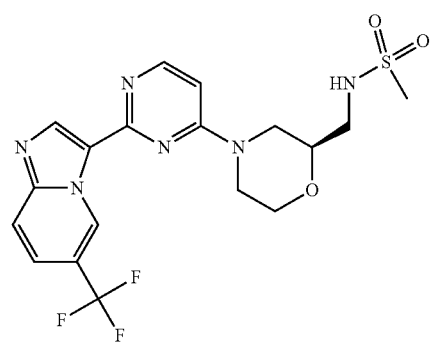

I-2

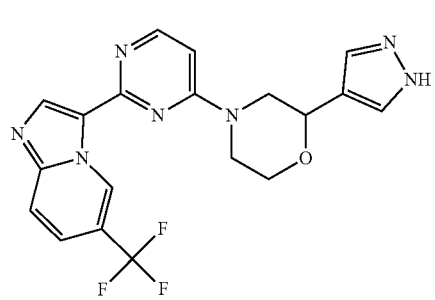

I-4

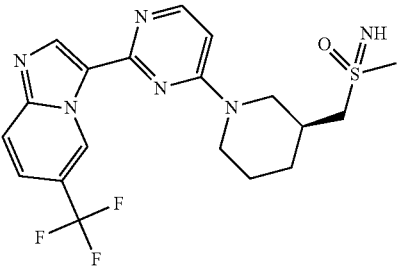

I-5

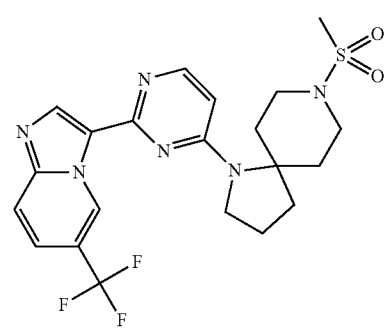

I-7

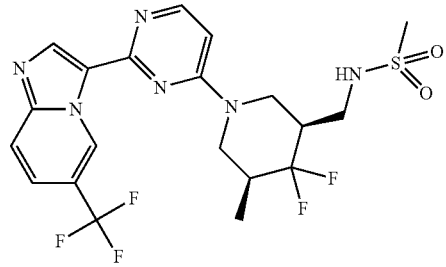

I-8

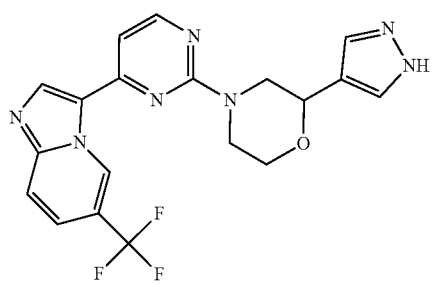

I-9

-continued
I-11
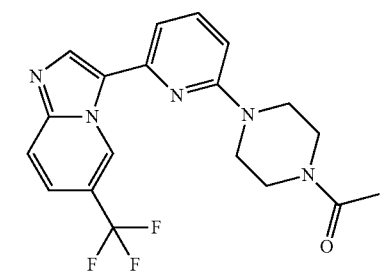
I-12
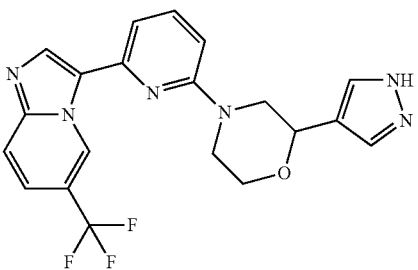
I-13
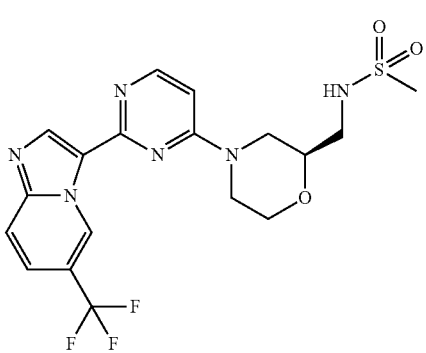
I-14
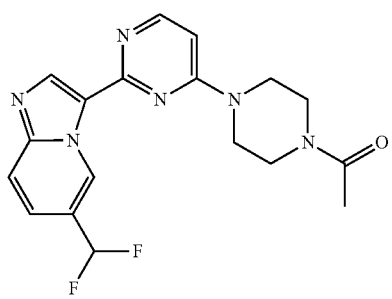
I-15
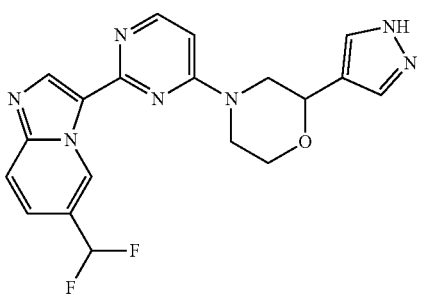
-continued
I-16
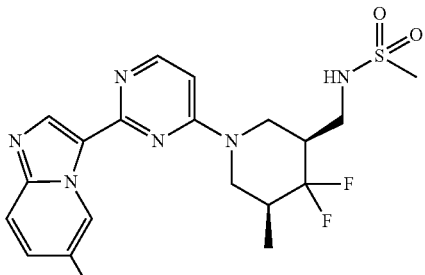
I-17
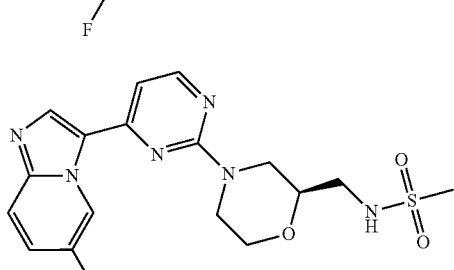
I-18
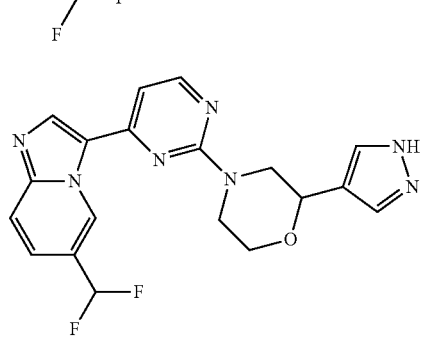
I-19
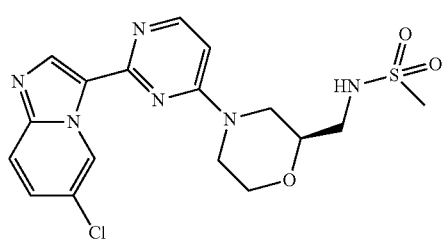
I-20
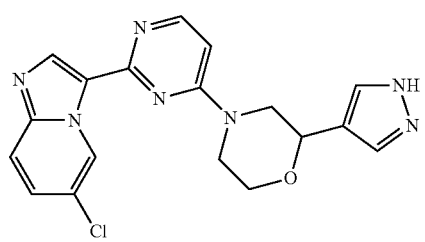
I-21
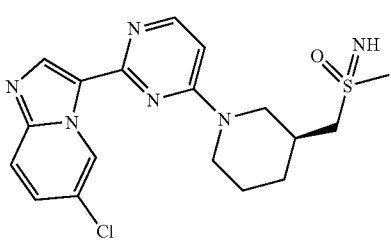

I-22
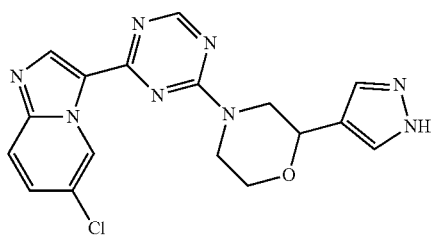
I-23
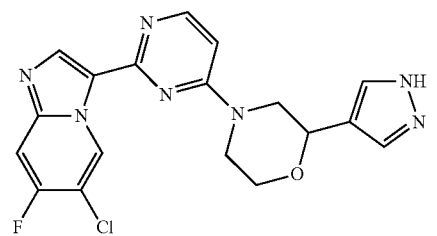
I-24
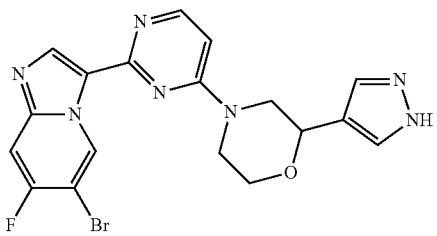
I-25
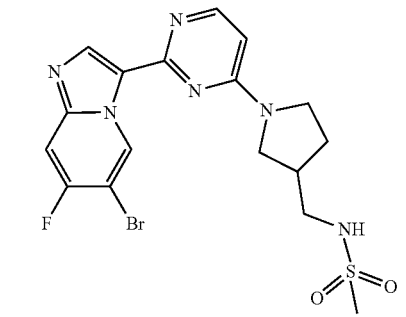
I-26
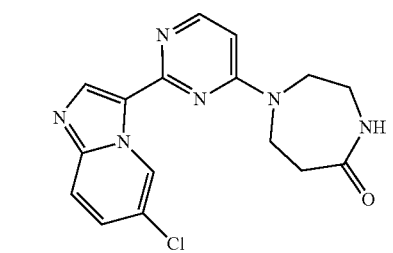
I-27
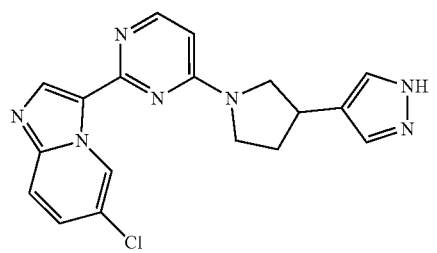
I-28
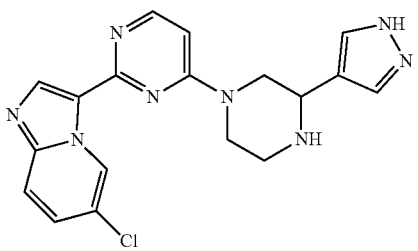
I-29
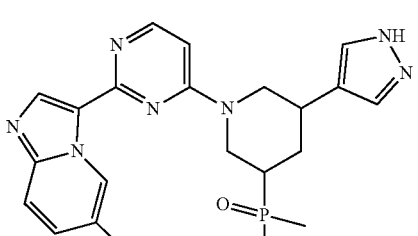
I-30
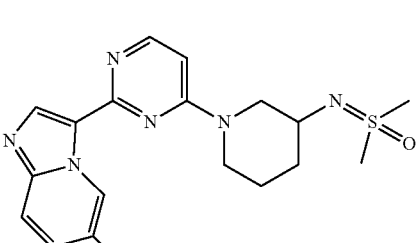
I-31
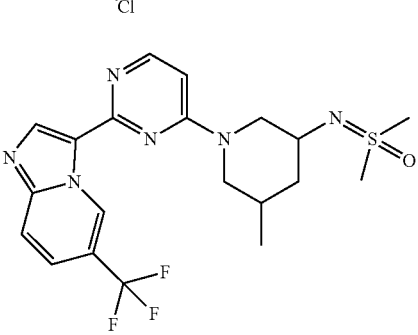
I-33
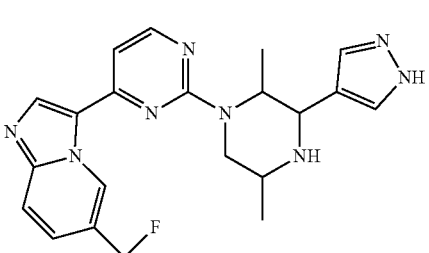
I-35
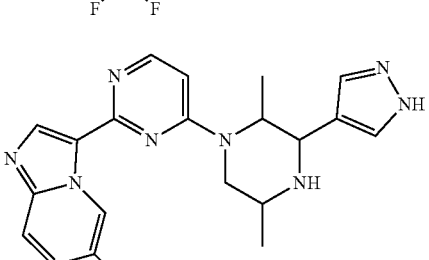

I-37
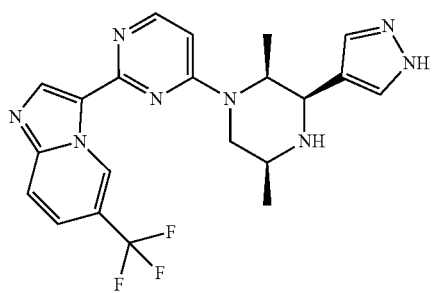
I-38
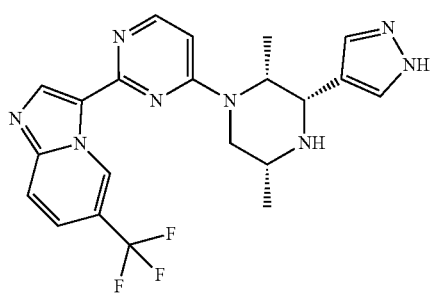
I-39
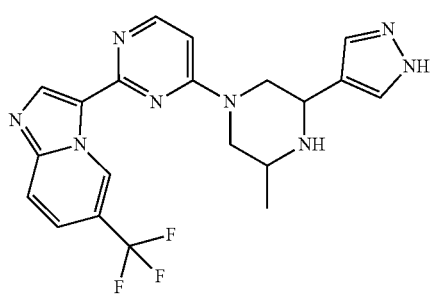
I-41
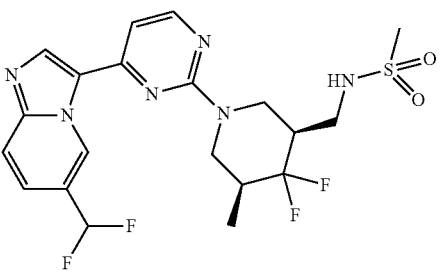
I-42
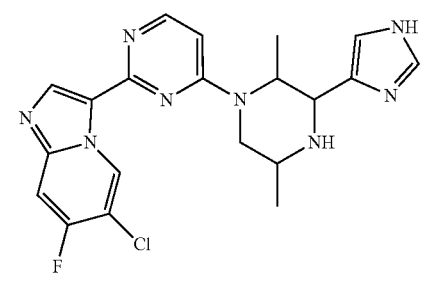
I-43
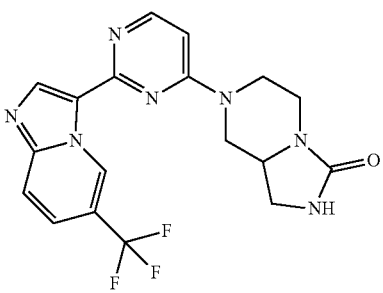
I-44
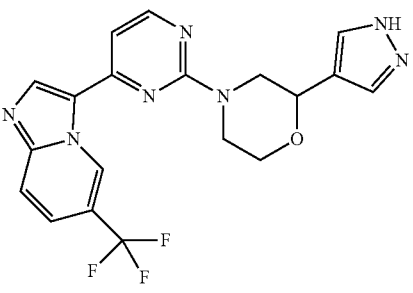
I-45
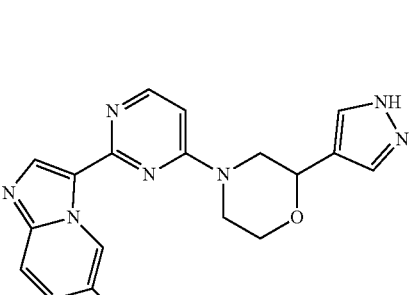
I-46
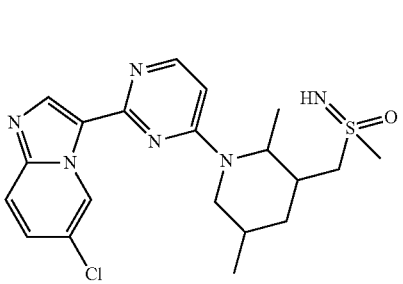
I-48
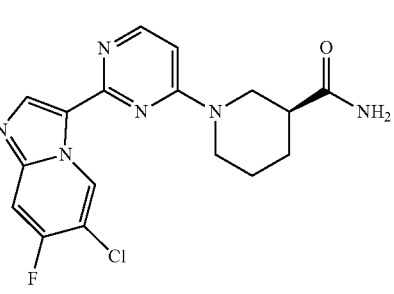

I-49
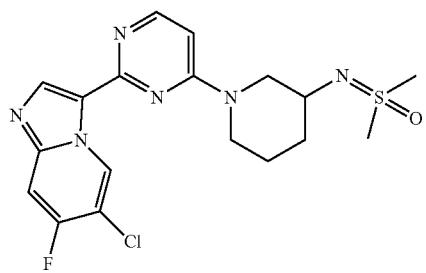
I-50
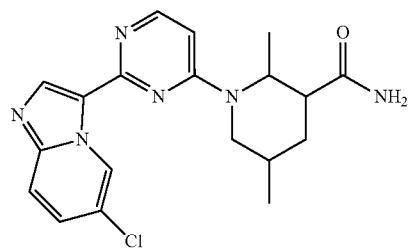
I-52
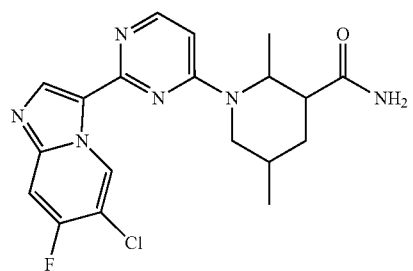
I-54
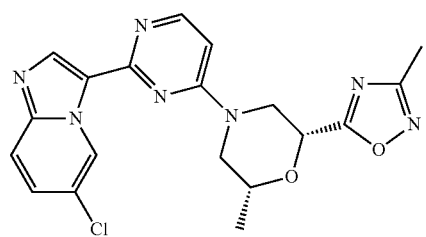
I-55
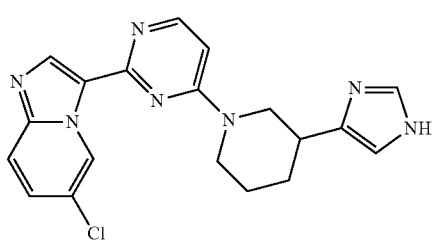
I-56
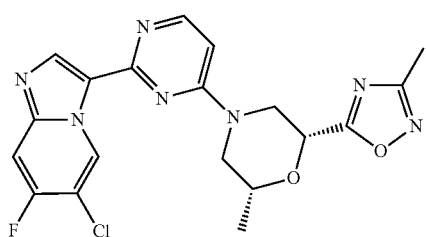
I-57
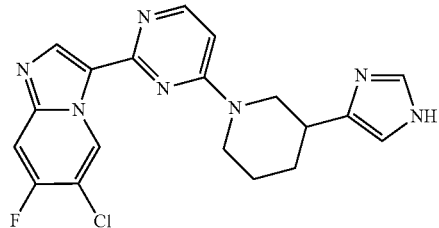
I-58
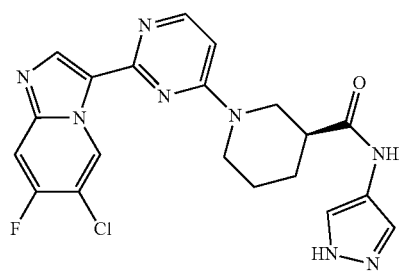
I-59
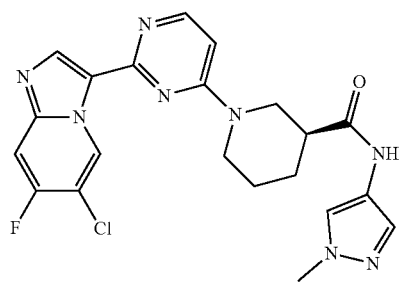
I-60
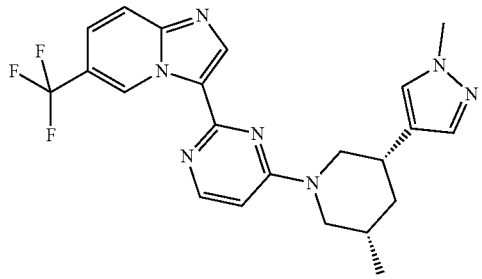
I-61
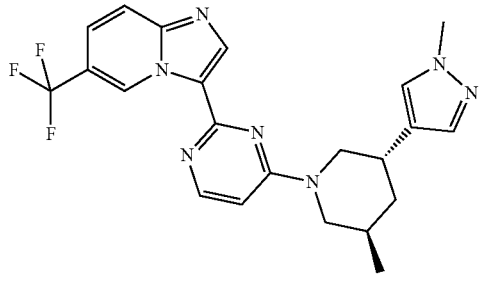
I-62
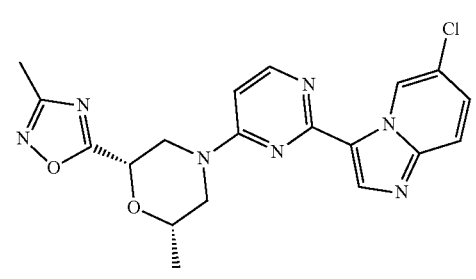

I-63
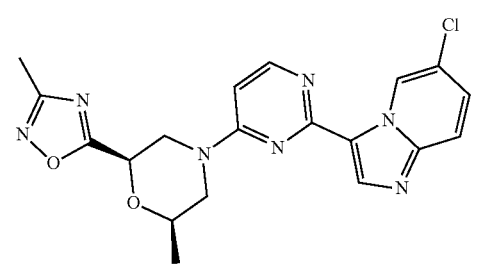
I-64
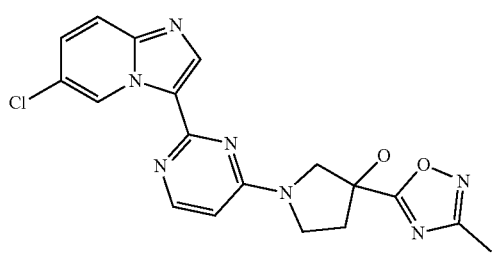
I-65
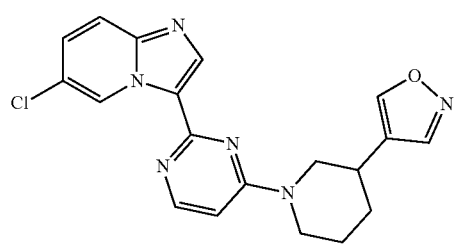
I-66
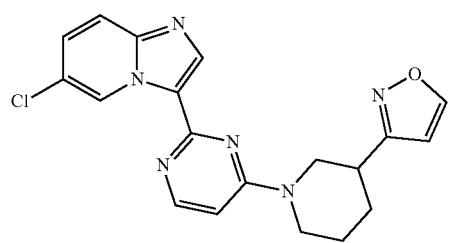
I-67
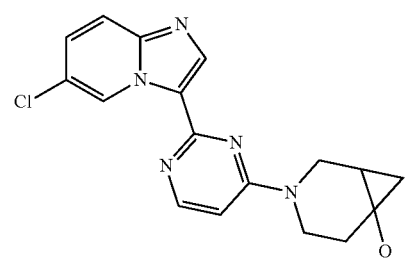
I-68
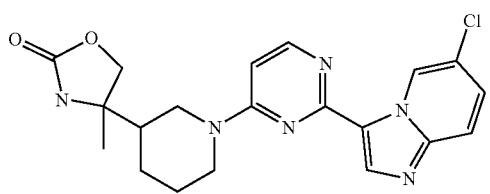
I-69
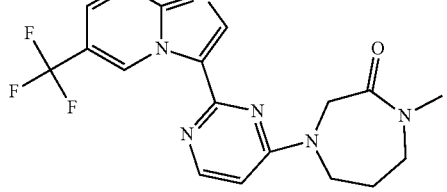
I-70
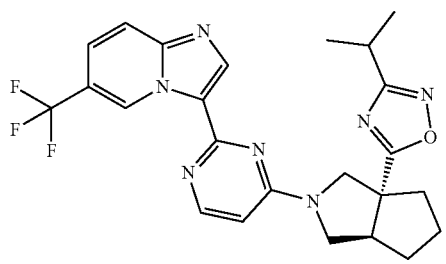
I-71
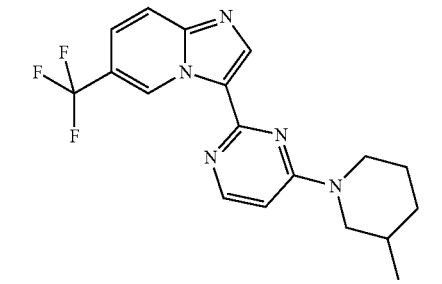
I-72
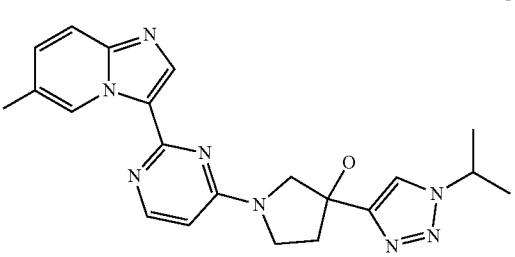
I-73
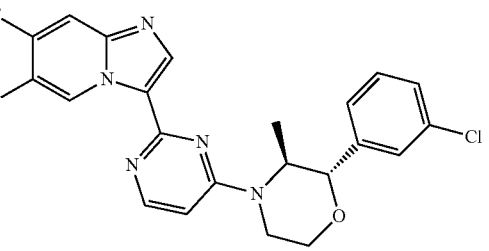
I-74
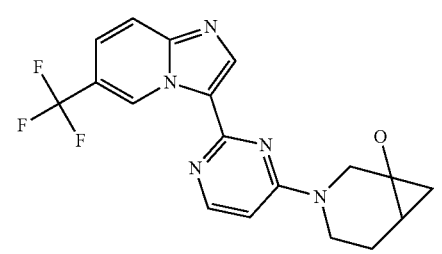

I-75 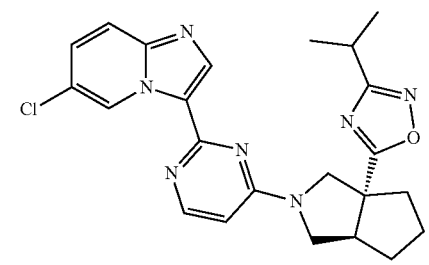
I-76 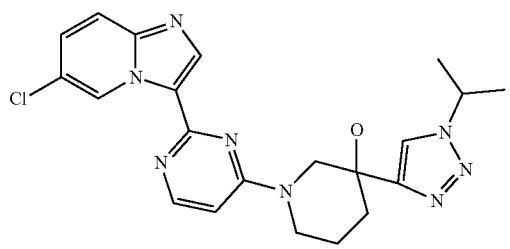
I-77 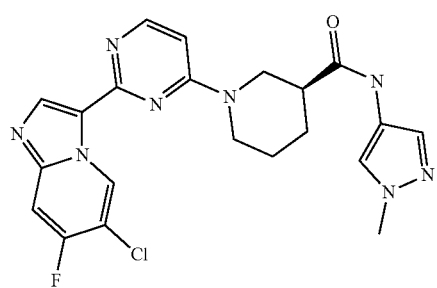
I-78 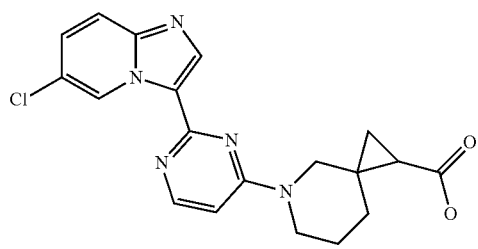
I-79 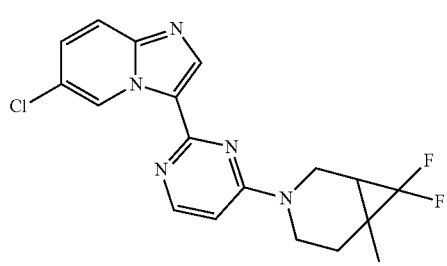
I-80 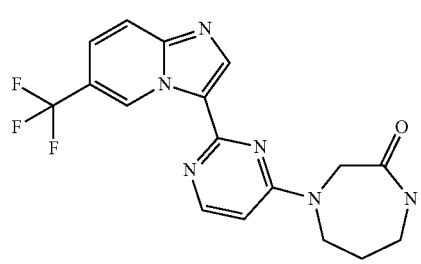
I-81 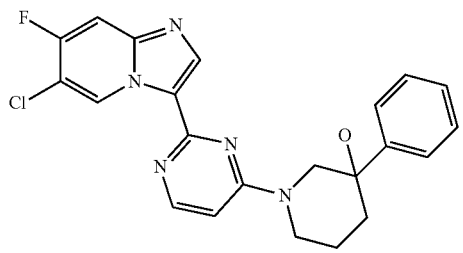
I-82 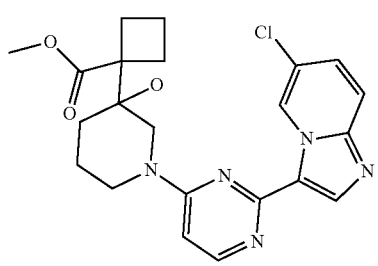
I-83 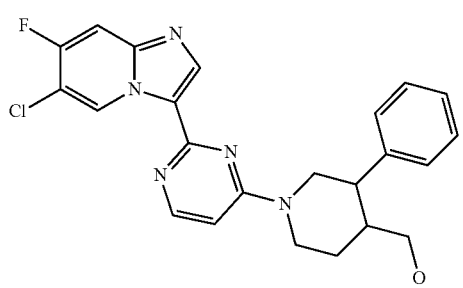
I-84 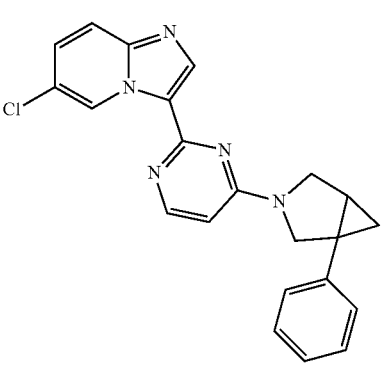
I-85 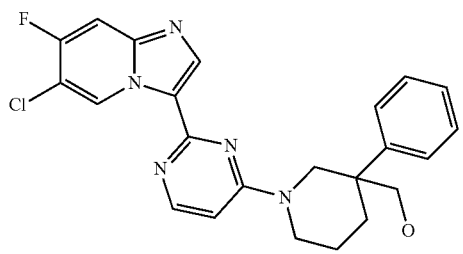

I-86
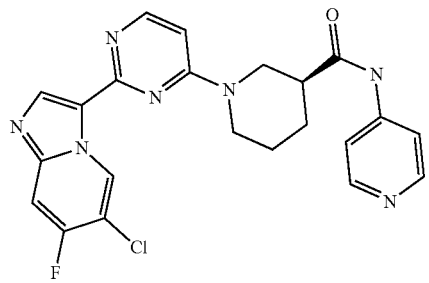
I-91
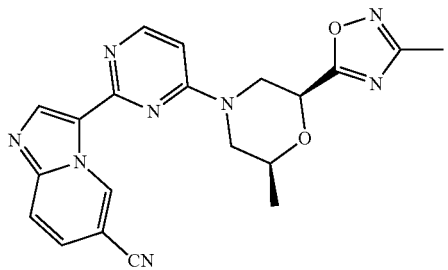
I-87
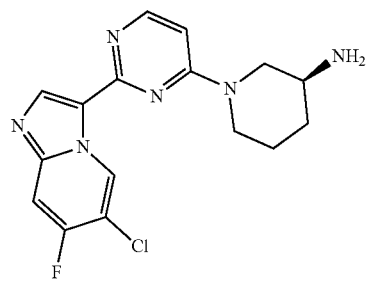
I-92
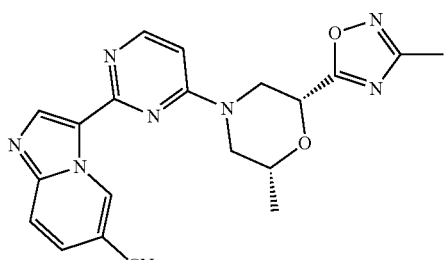
I-88
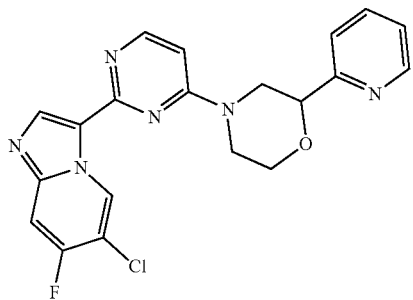
I-93
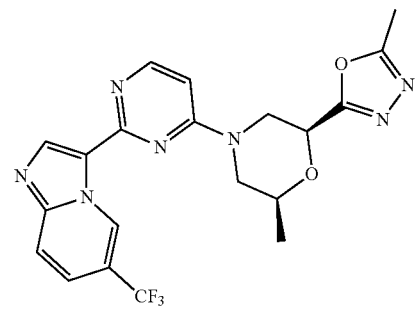
I-89
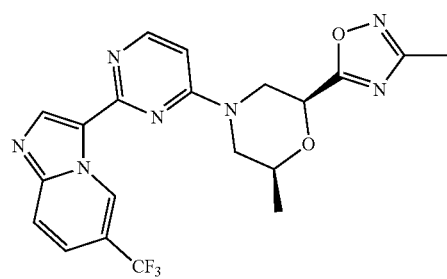
I-94
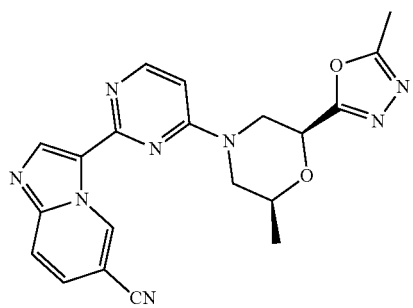
I-90
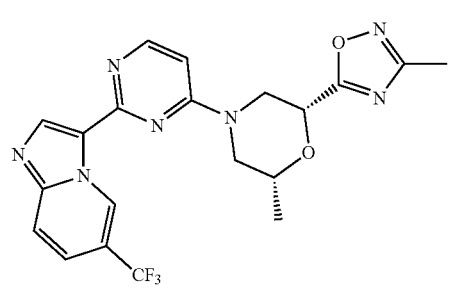
I-95
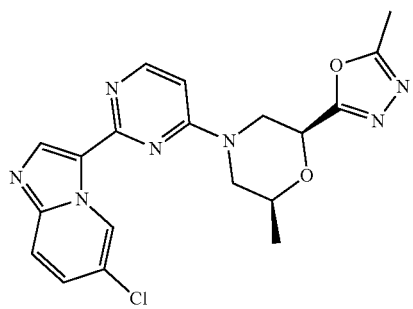

I-96 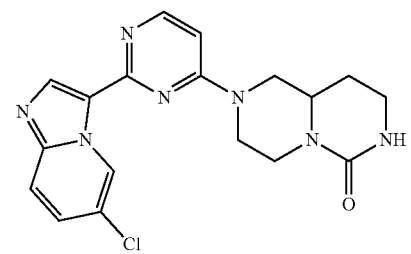
I-97 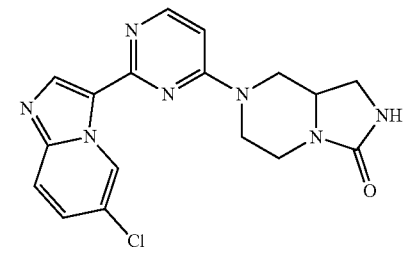
I-98 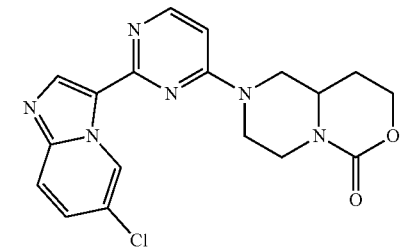
I-99 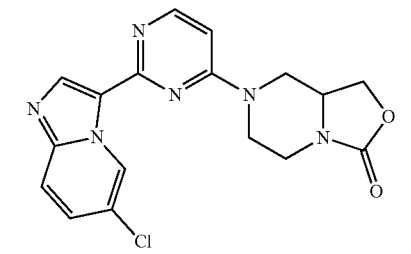
I-100 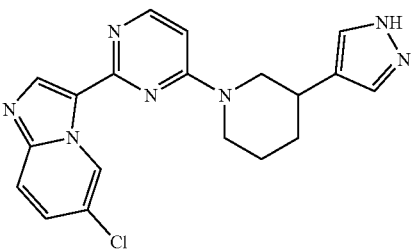
I-101 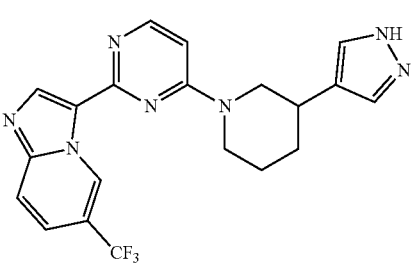
I-102 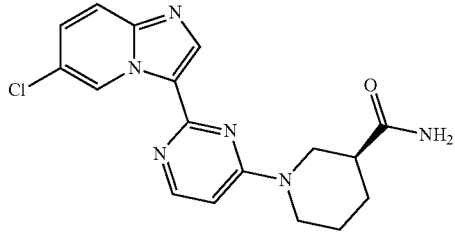
I-103 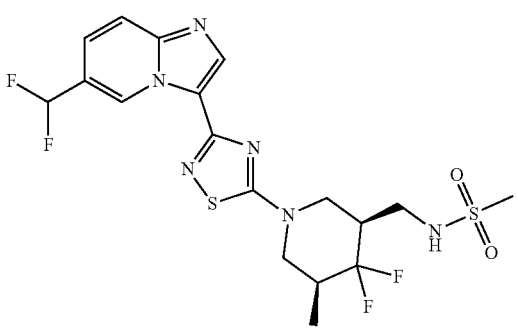
I-104 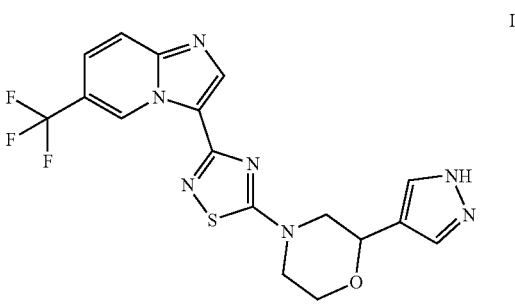
I-105 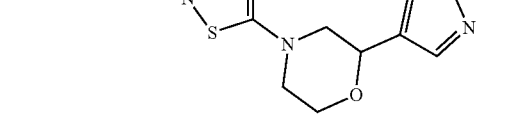
I-106 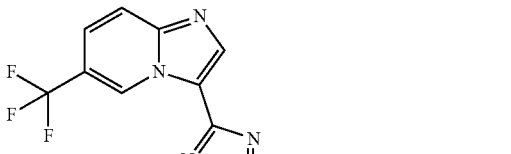

I-107
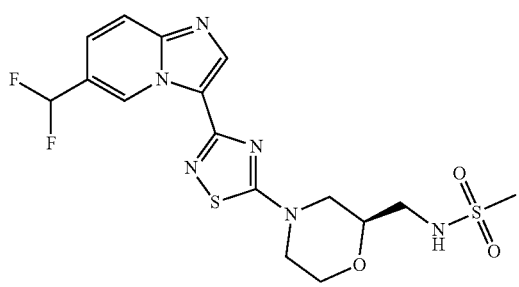
I-108
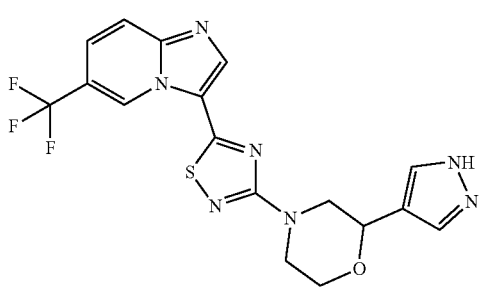
I-109
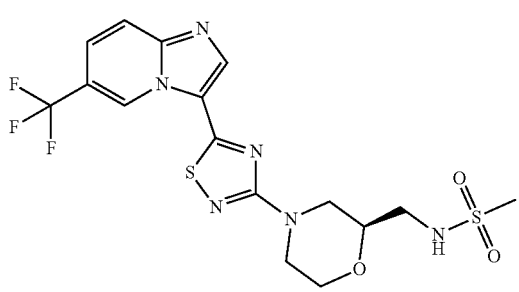
I-110
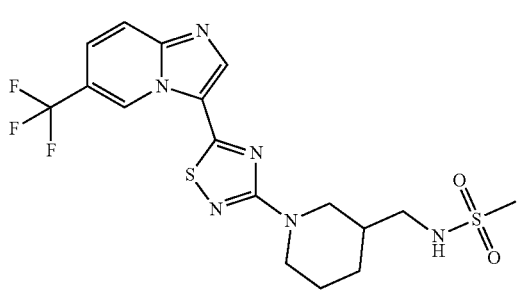
I-111
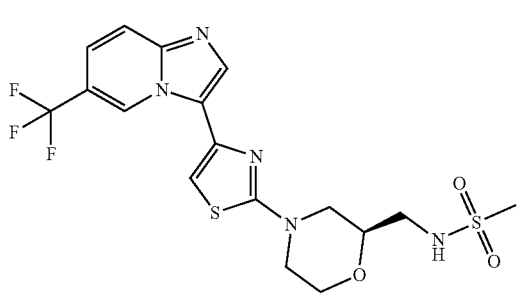
I-112
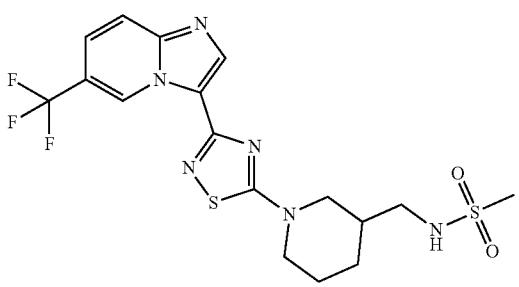
I-113
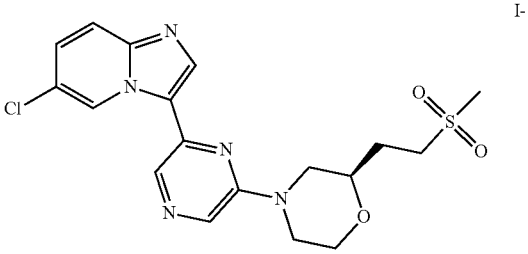
I-114
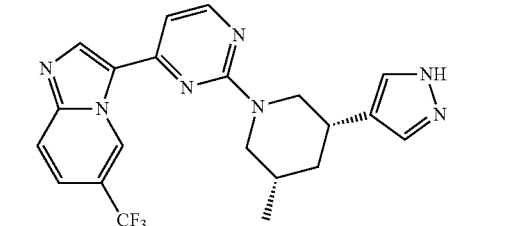
I-115
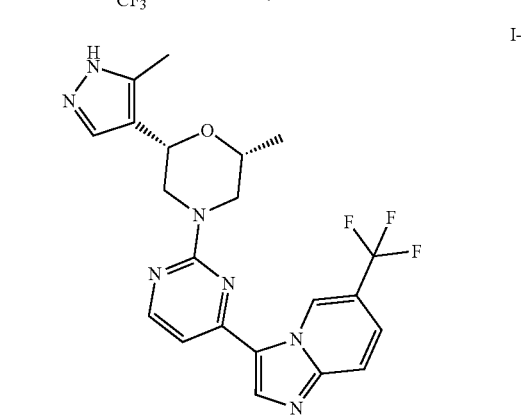
I-116
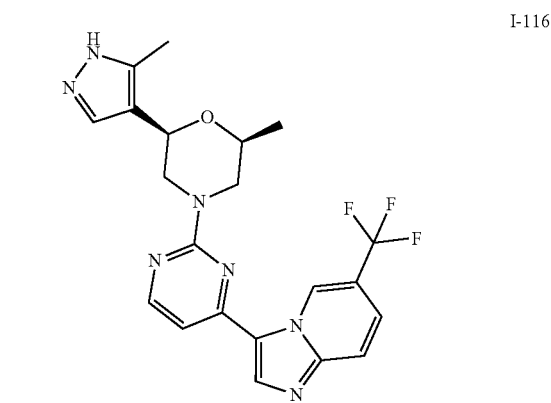

I-117
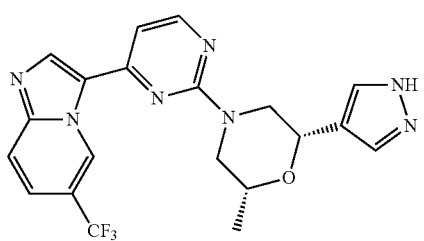
I-119
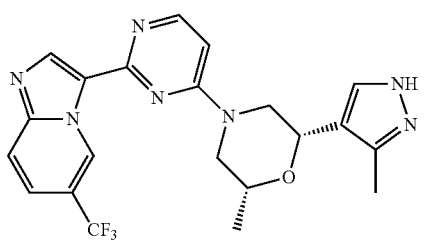
I-120
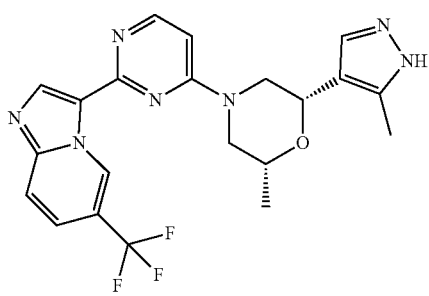
I-122
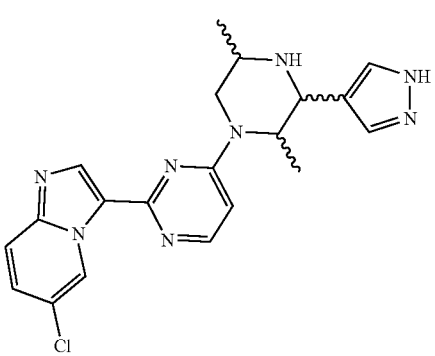
I-123
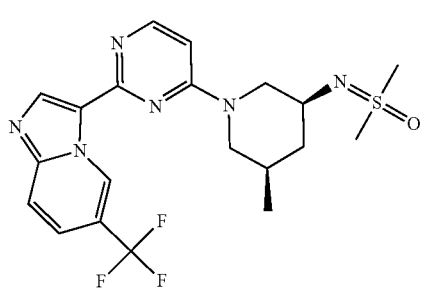
I-124
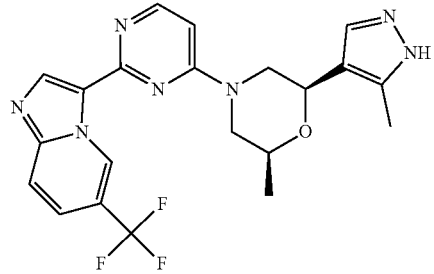
I-125
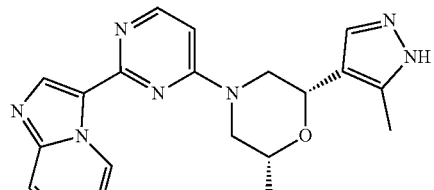
I-126
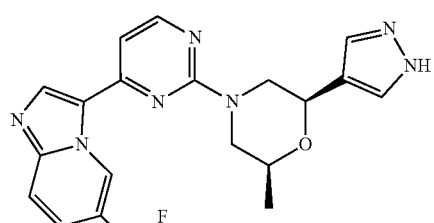
I-127
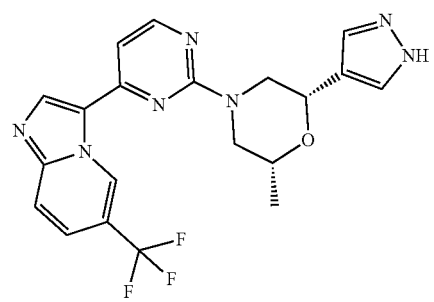
I-128
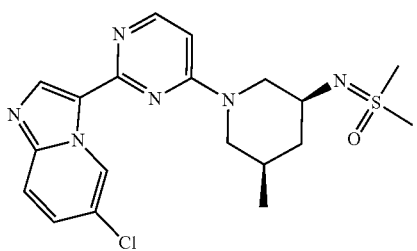

I-129
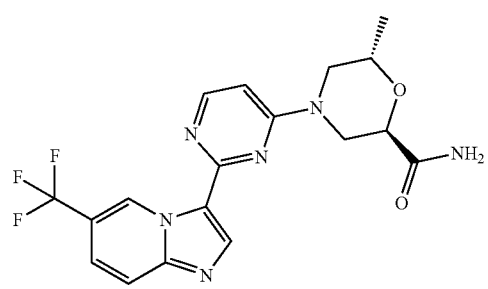
I-130
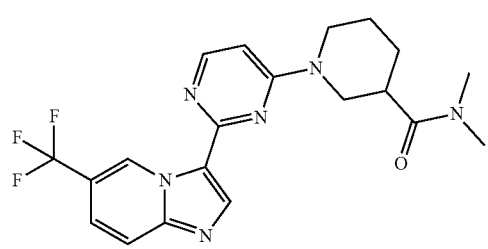
I-131
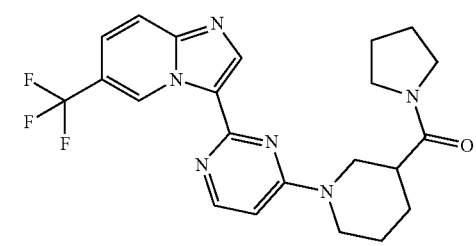
I-132
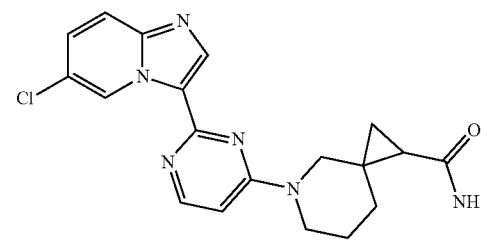
I-133
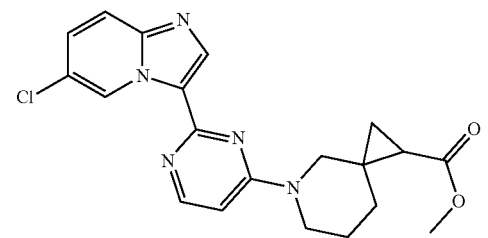
I-134
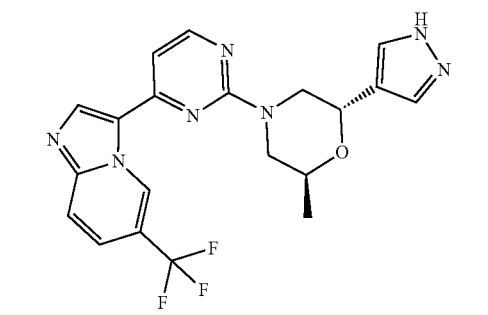
I-135
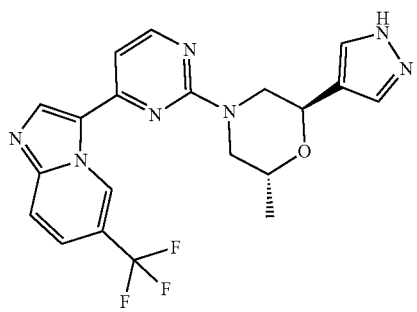
I-136
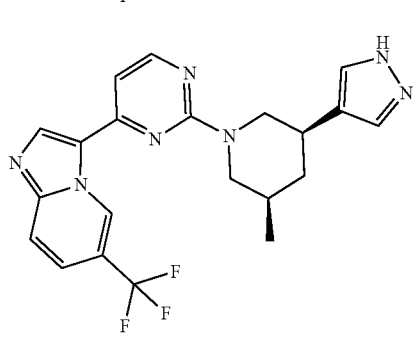
I-137
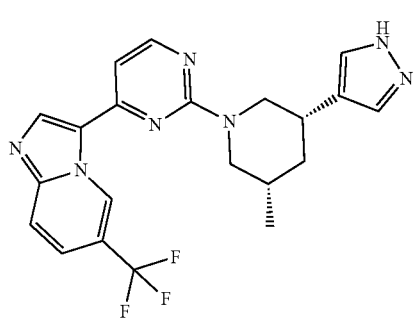
I-138
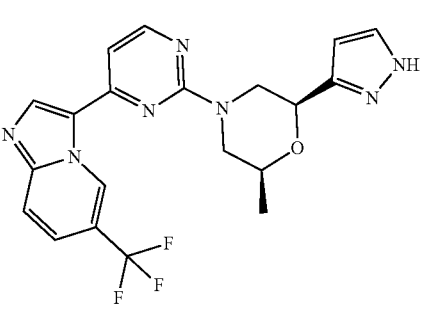
I-139
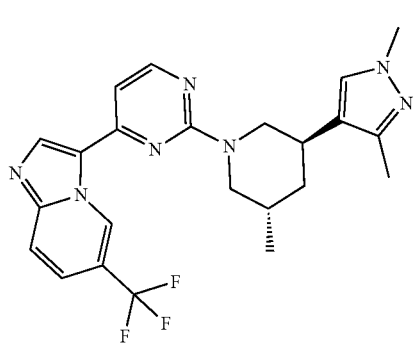

I-140
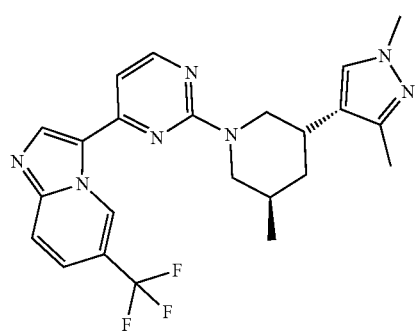
I-141
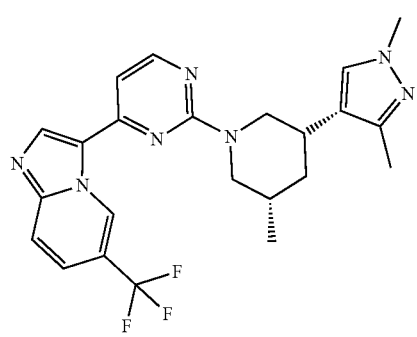
I-142
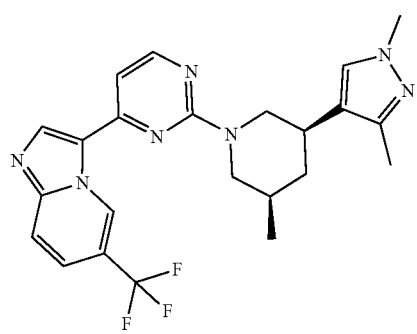
I-143
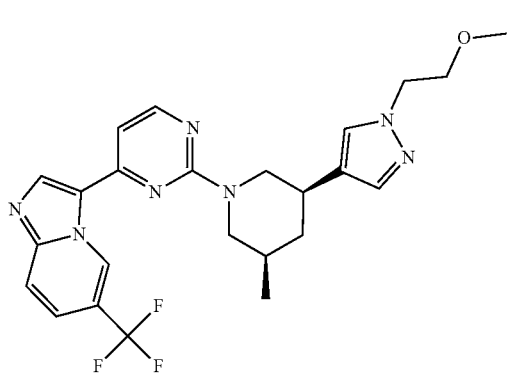
I-144
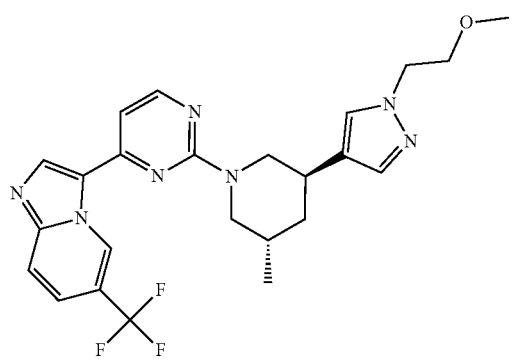
I-145
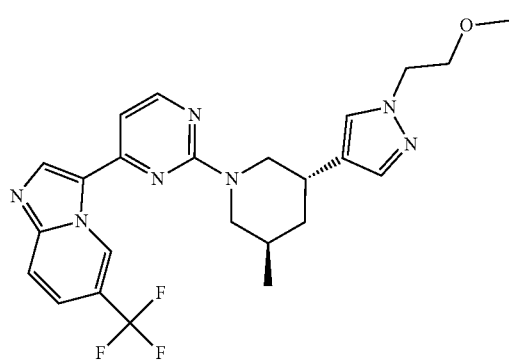
I-146
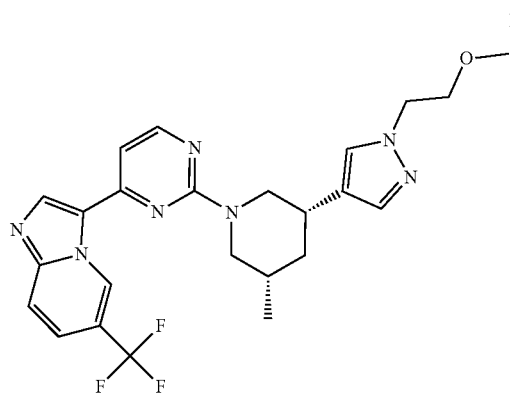
I-147
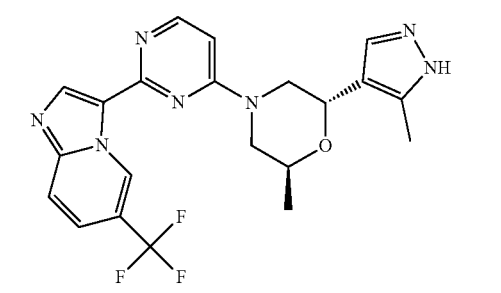

I-148
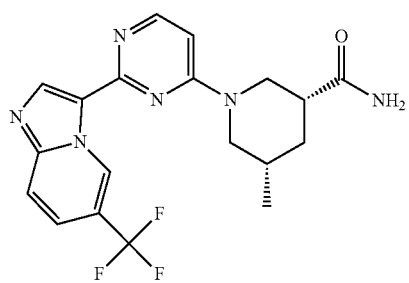
I-149
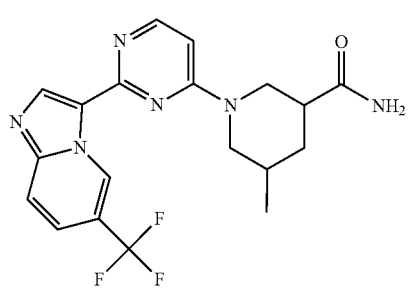
I-150
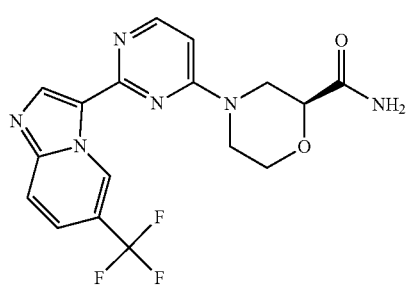
I-151
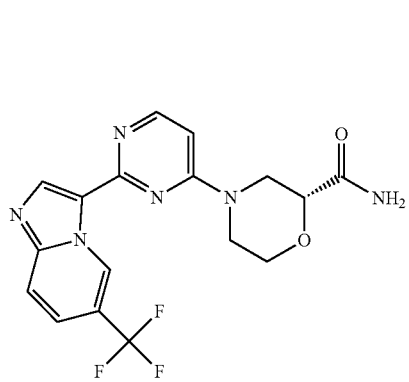
I-152
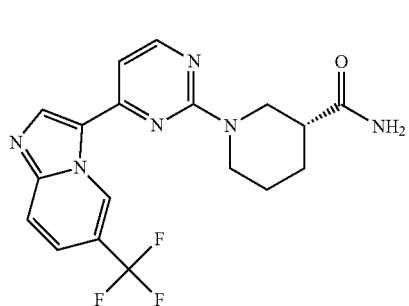
I-153
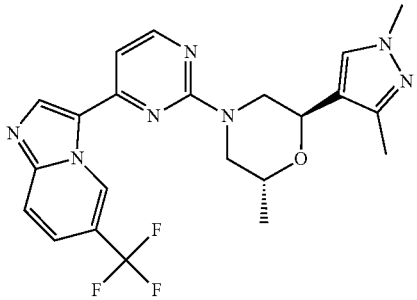
I-154
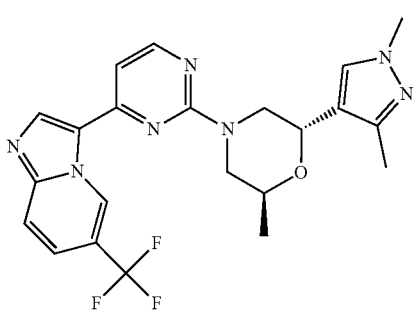
I-155
I-156
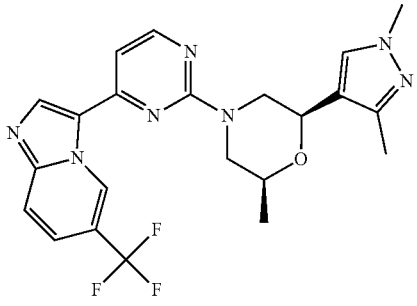
I-157

-continued
I-158
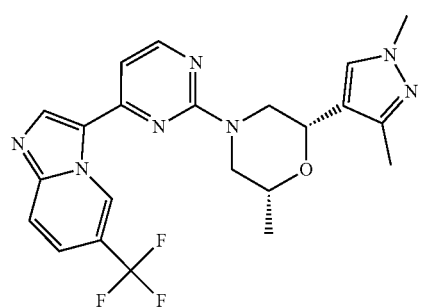
I-159
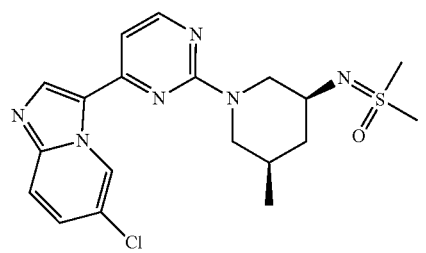
I-160
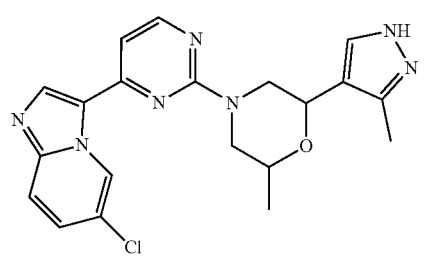
I-161
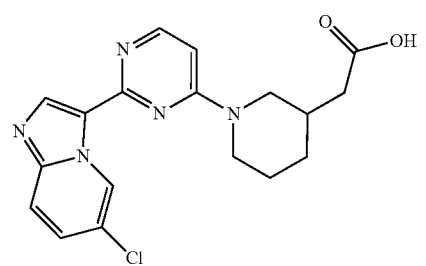
I-162
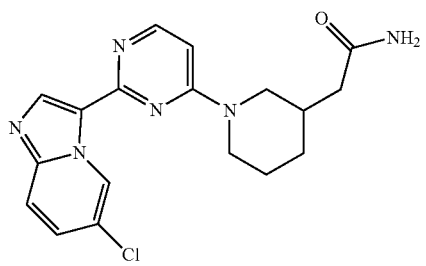
I-163
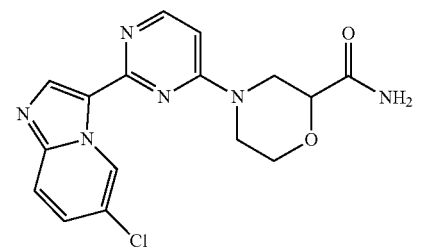
-continued
I-164
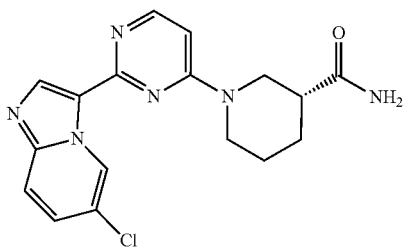
I-165
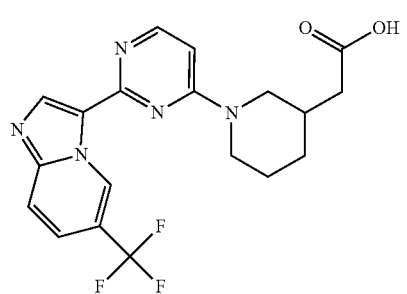
I-166
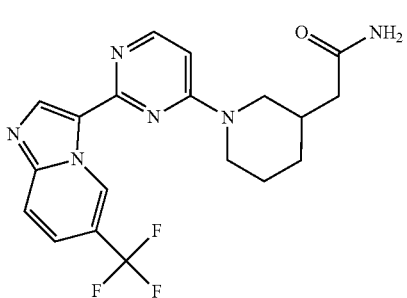
I-167
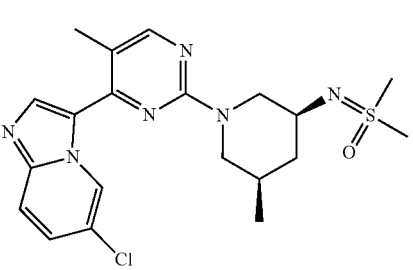
I-168
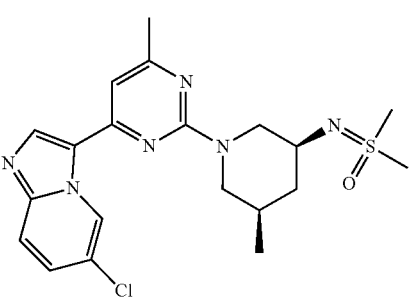

I-169
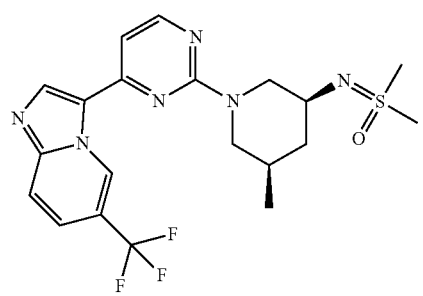
I-170
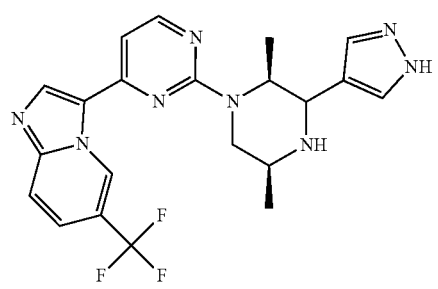
I-171
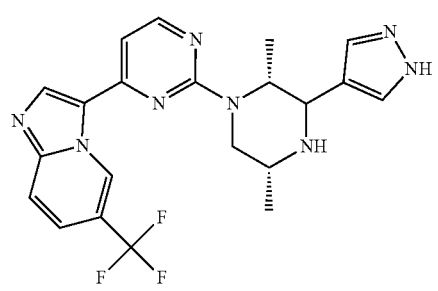
I-172
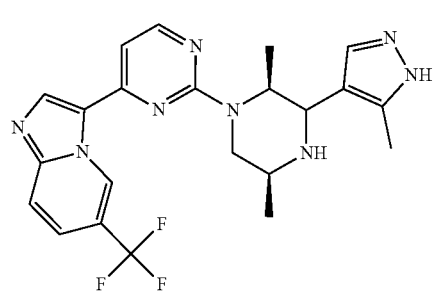
I-173
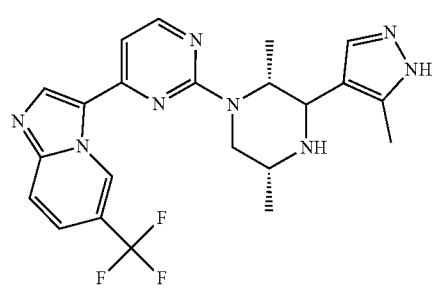
I-174
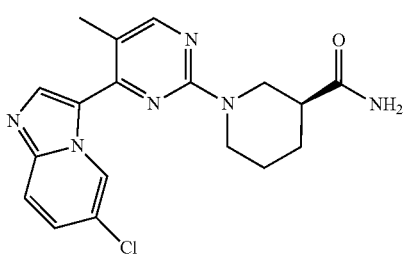
I-175
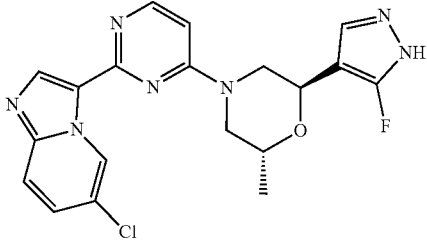
I-176
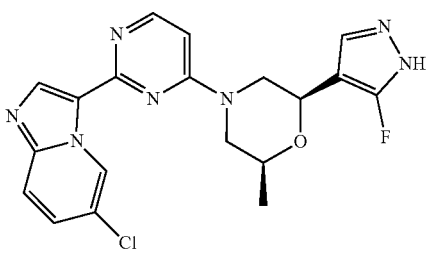
I-177
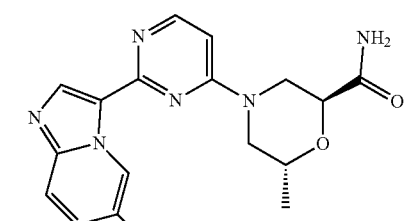
I-178
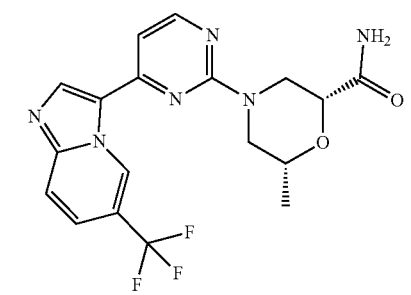
I-179
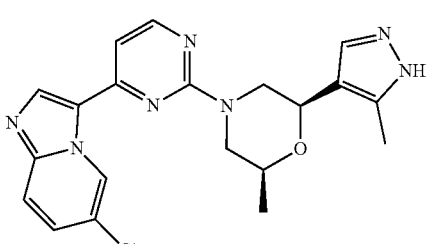

I-180
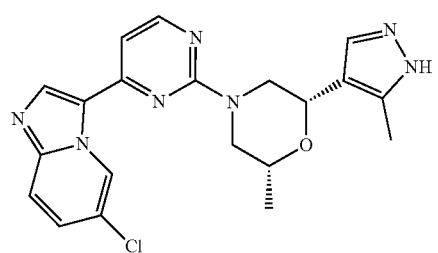
I-181
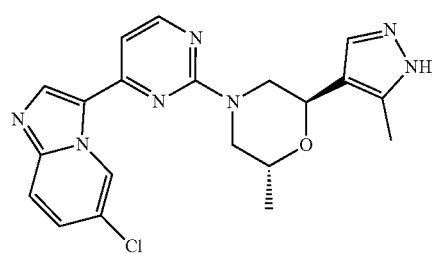
I-182
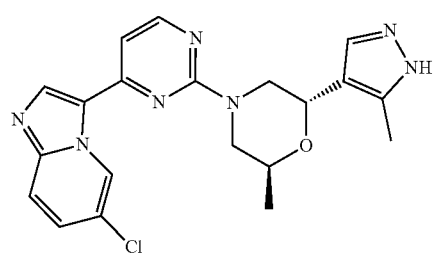
I-183
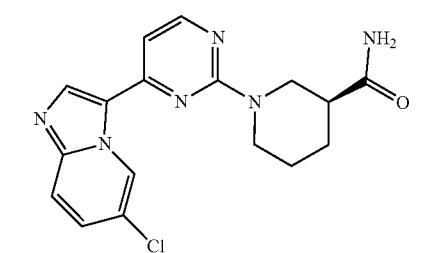
I-184
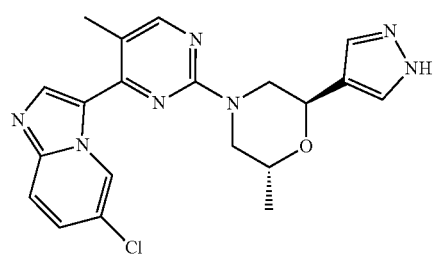
I-185
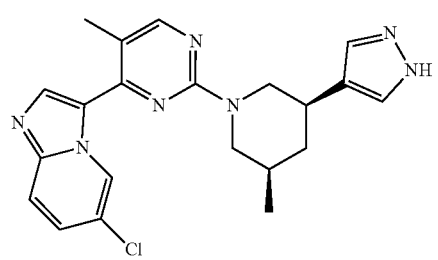
I-186
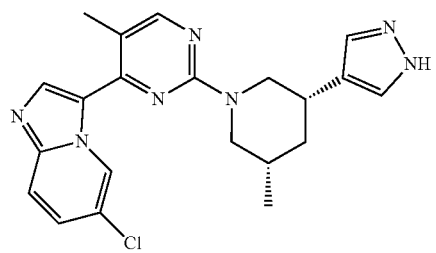
I-187
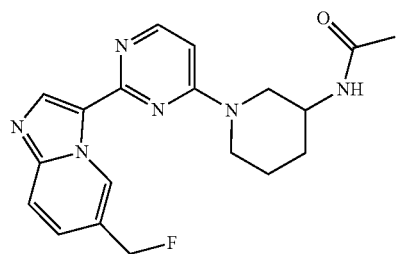
I-188
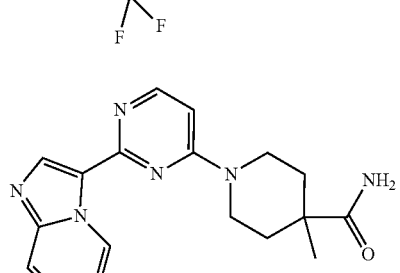
I-189
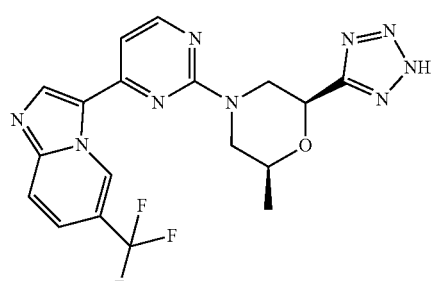
I-190
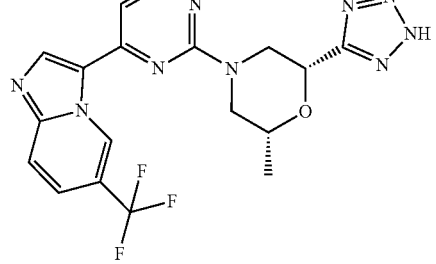

I-191 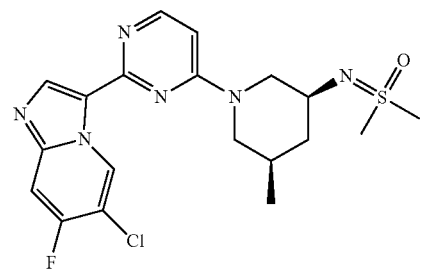
I-192 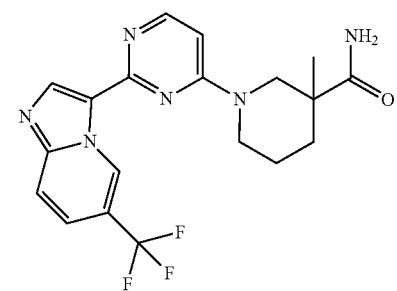
I-193 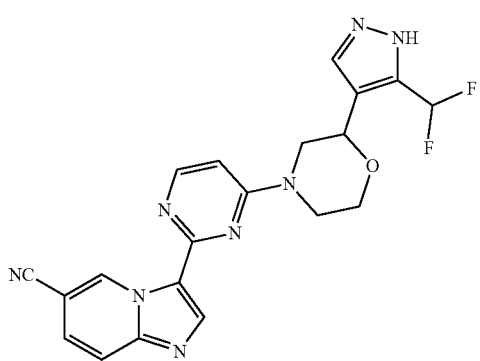
I-195 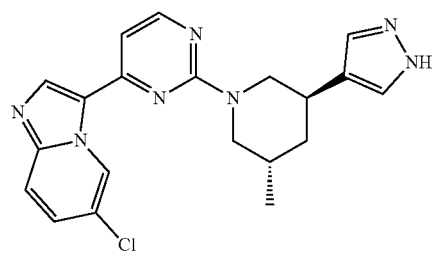
I-196 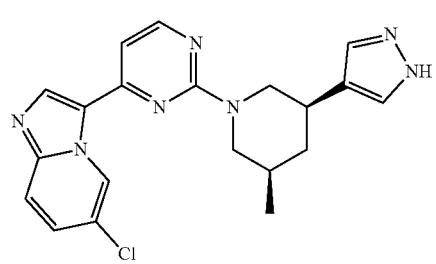
I-197 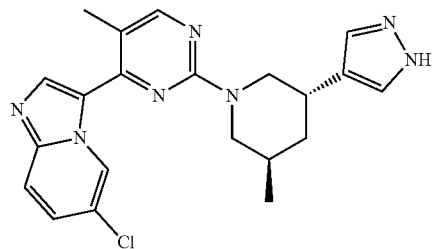
I-198 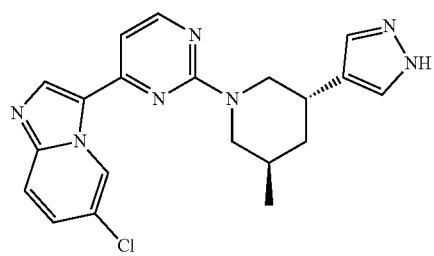
I-199 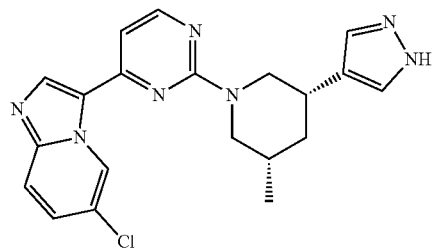
I-200 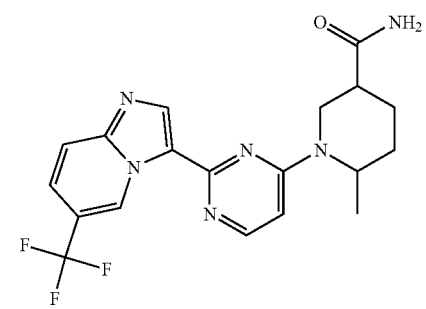
I-201 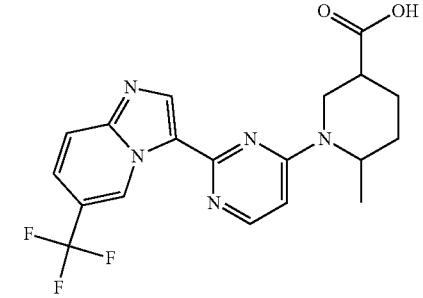

I-202 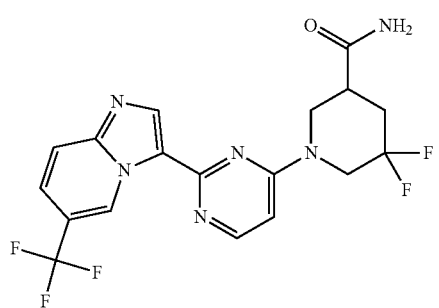
I-203 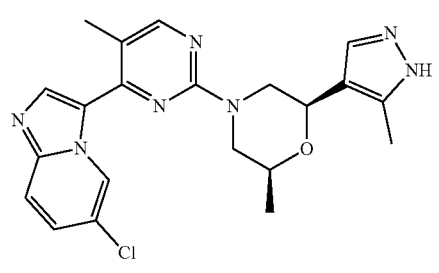
I-204 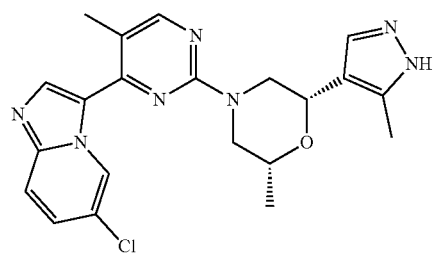
I-205 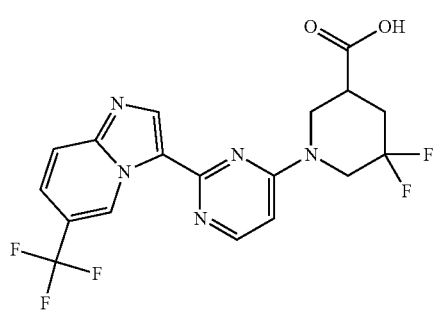
I-206 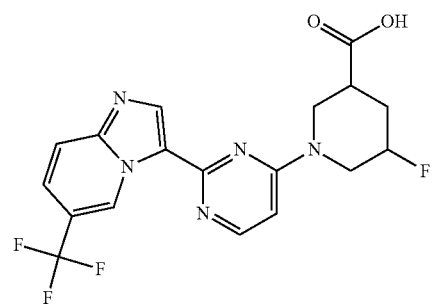
I-207 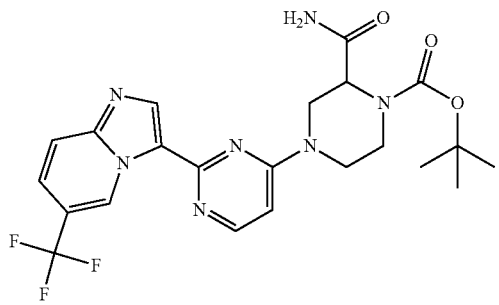
I-208 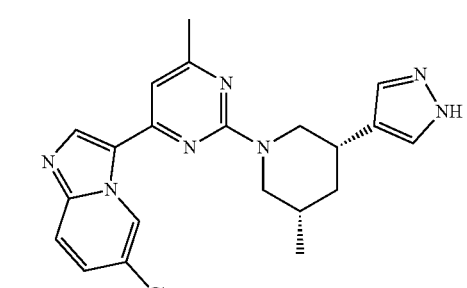
I-209 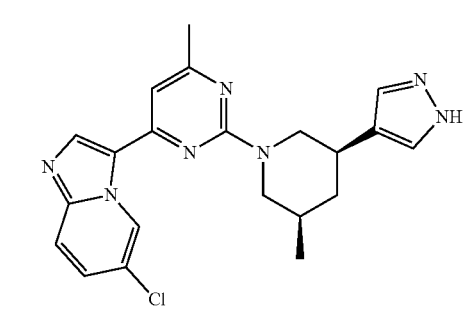
I-210 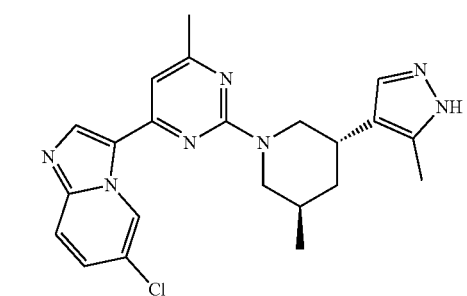
I-211 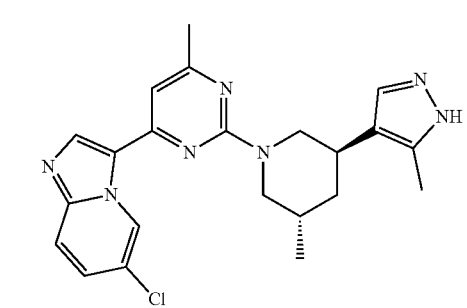

I-212 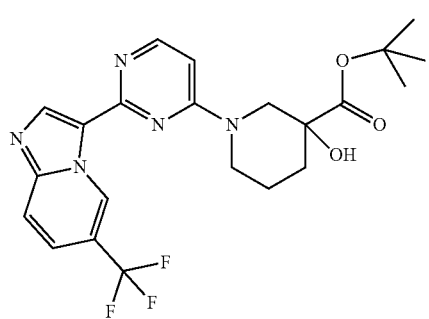
I-213 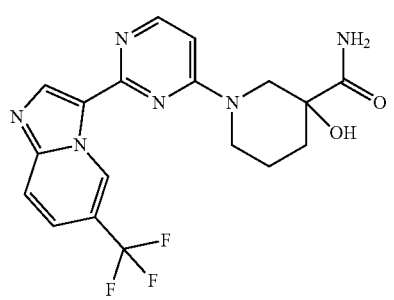
I-214 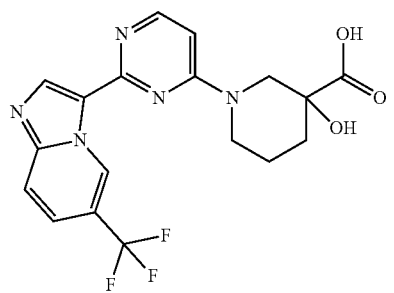
I-217 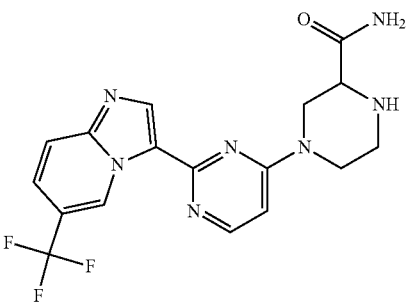
I-218 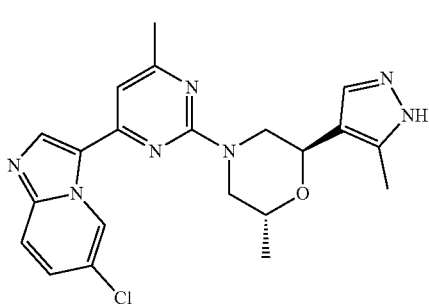
I-219 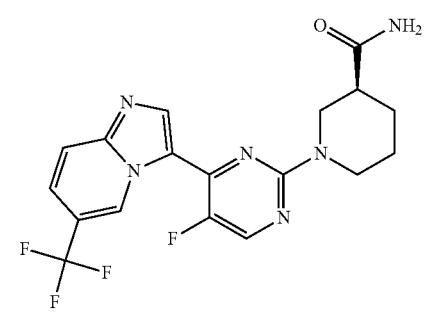
I-220 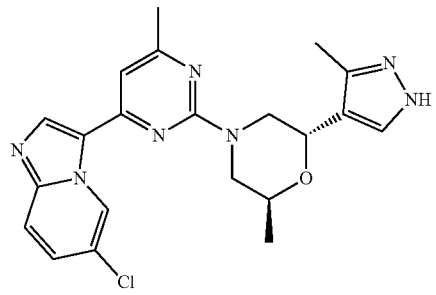
I-221 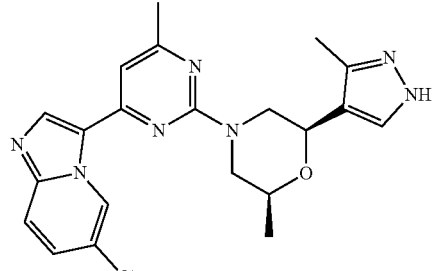
I-222 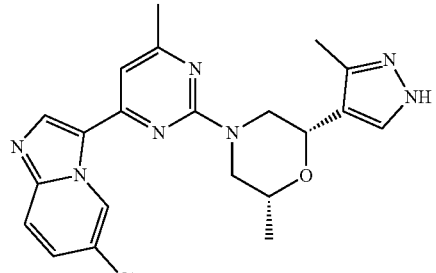
I-223

I-224 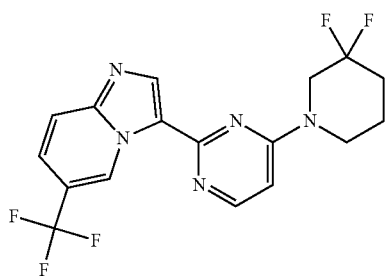
I-225 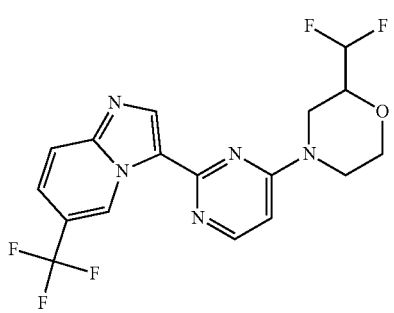
I-226 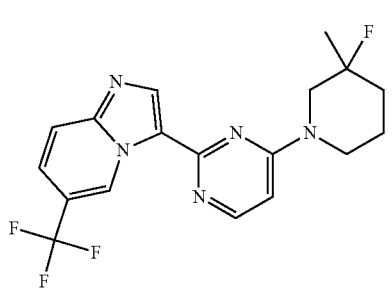
I-227 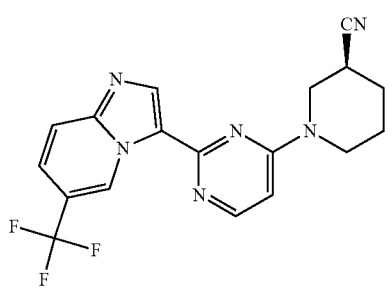
I-228 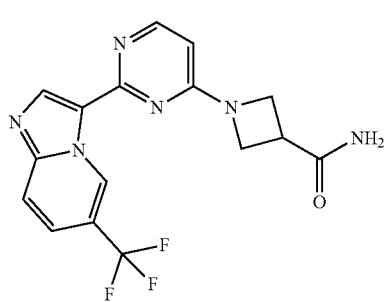
I-229 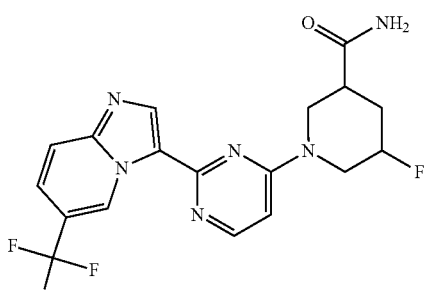
I-230 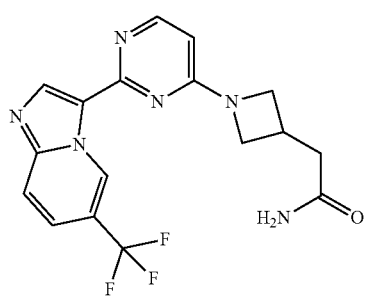
I-231 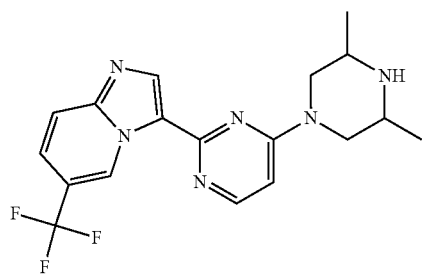
I-232 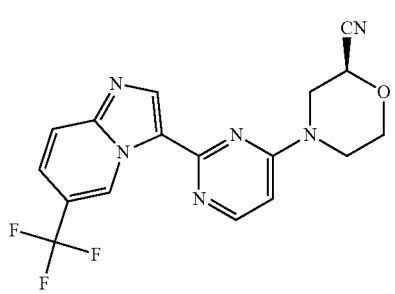
I-233 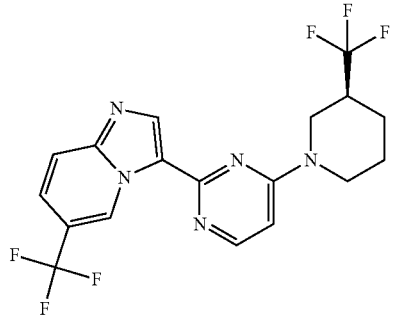

I-234
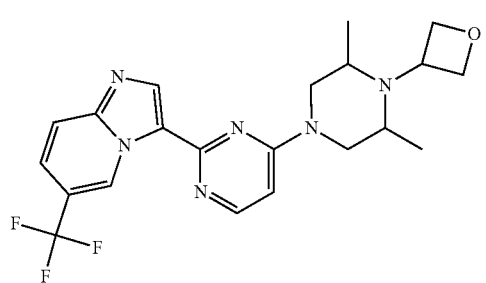
I-235
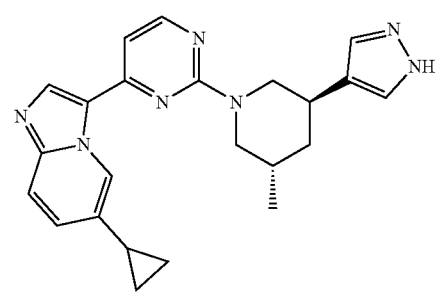
I-236
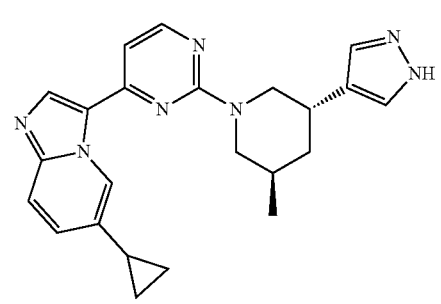
I-237
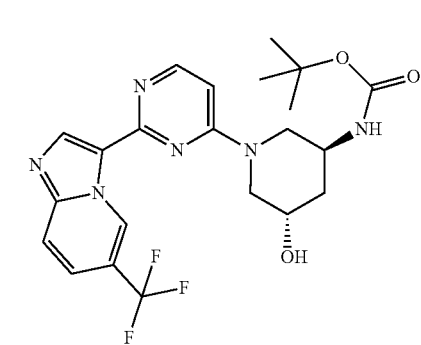
I-238
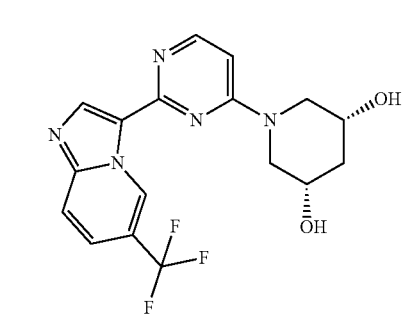
I-239
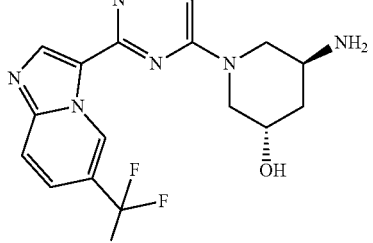
I-240
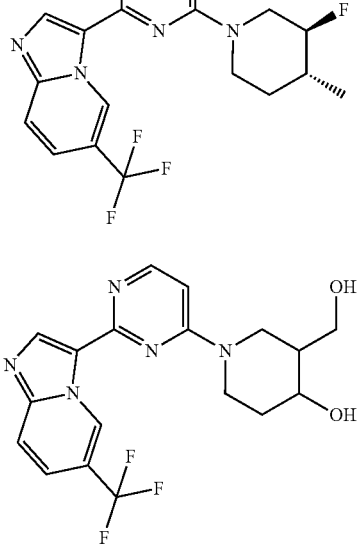
I-241
I-242
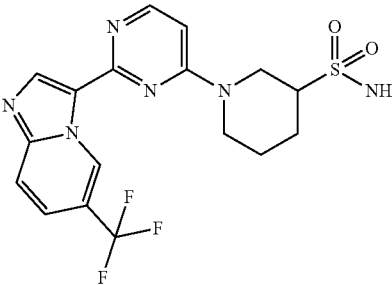
I-243
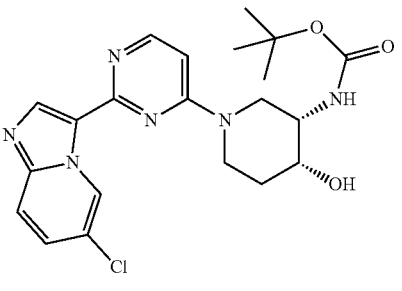

I-244 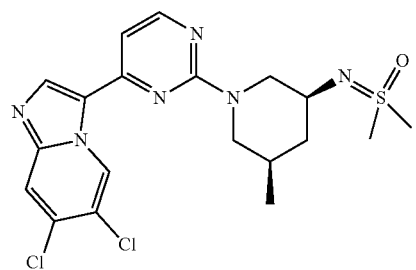
I-245 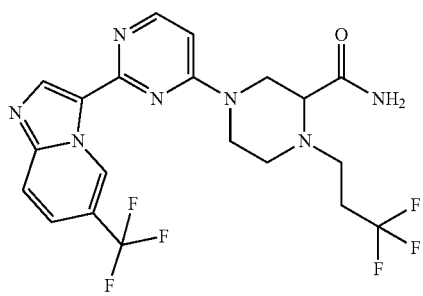
I-246 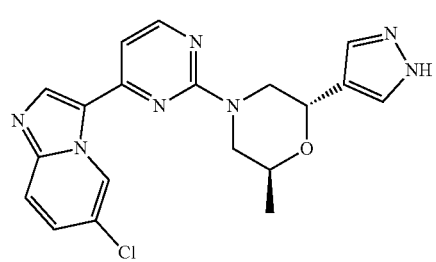
I-247 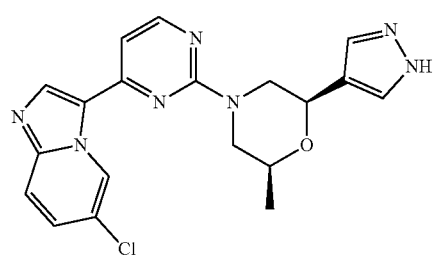
I-248 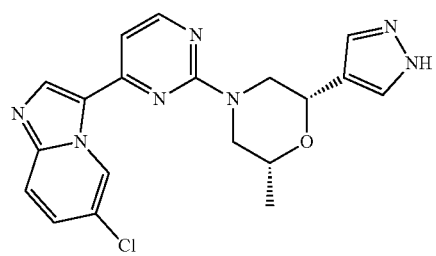
I-249 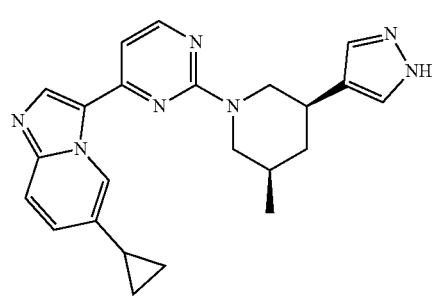
I-250 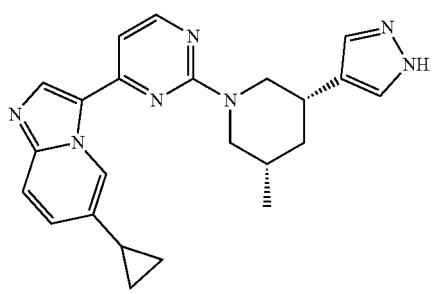
I-251 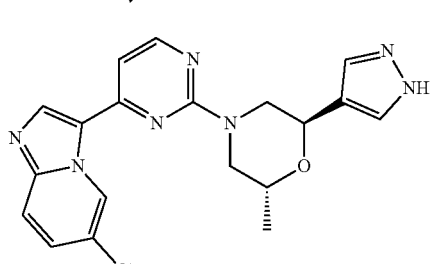
I-252 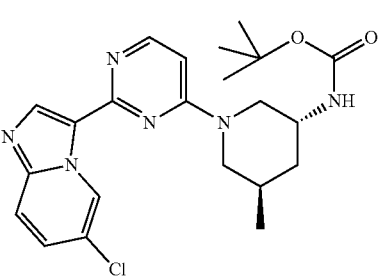
I-253 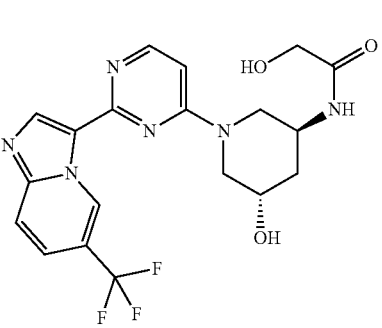
I-254 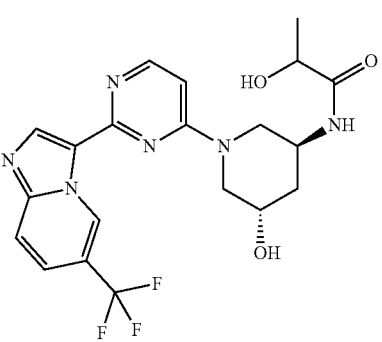

I-255 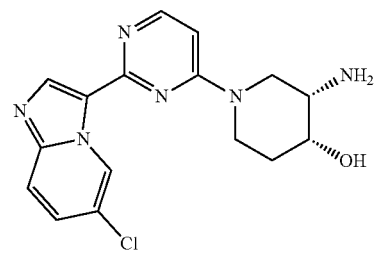
I-256 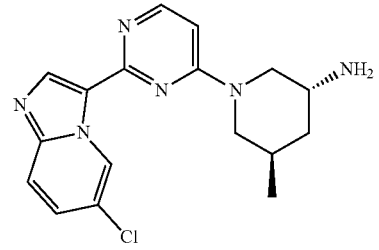
I-257 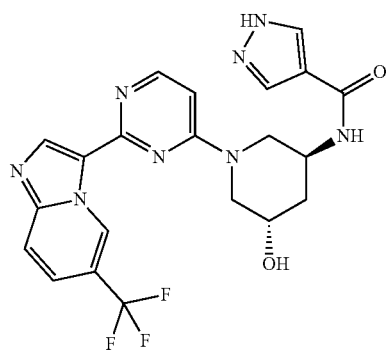
I-258 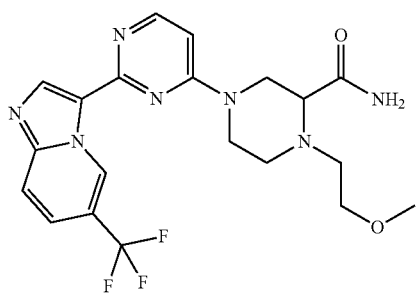
I-259 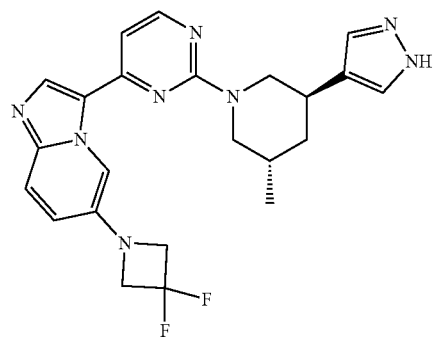
I-260 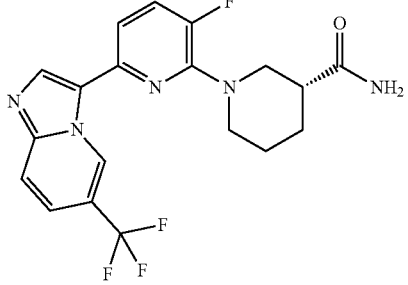
I-261 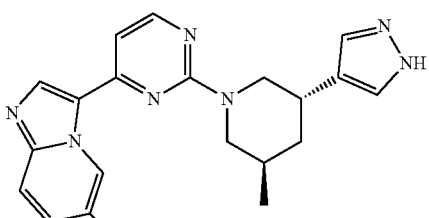
I-262 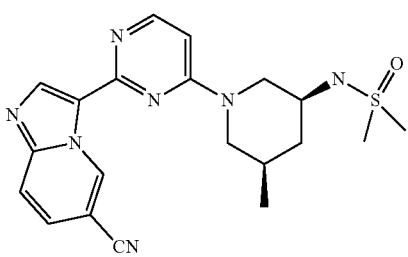
I-263 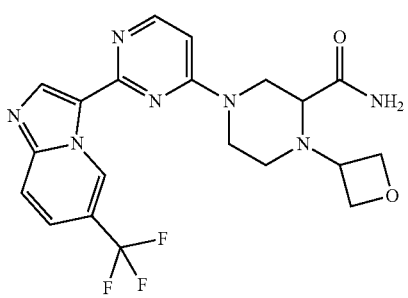
I-264 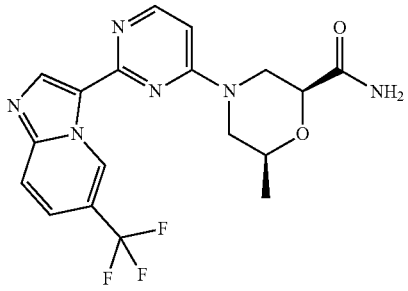

I-265
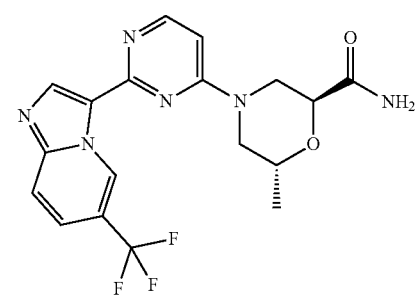
I-266
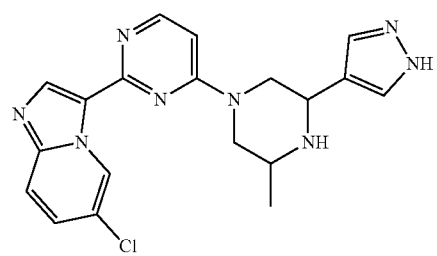
I-267
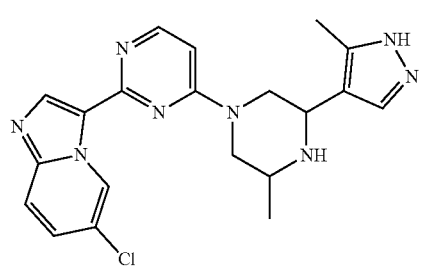
I-268
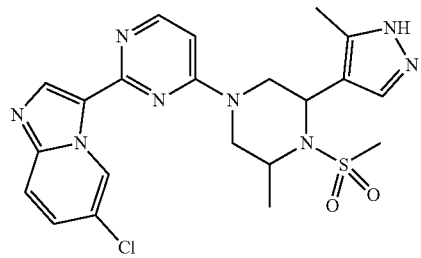
I-269
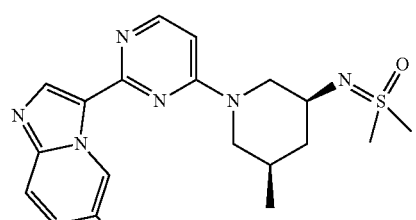
I-270
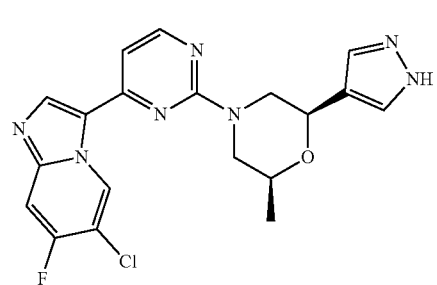
I-271
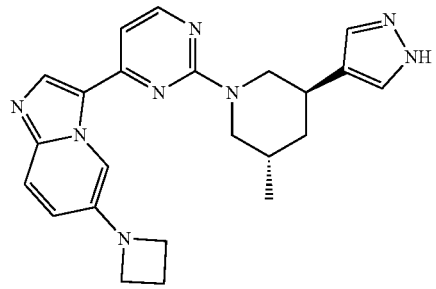
I-272
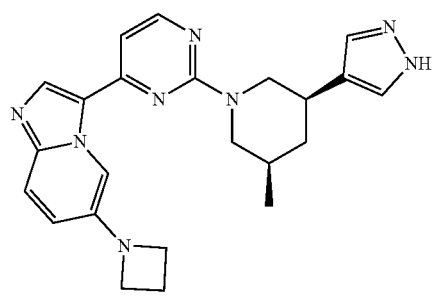
I-273
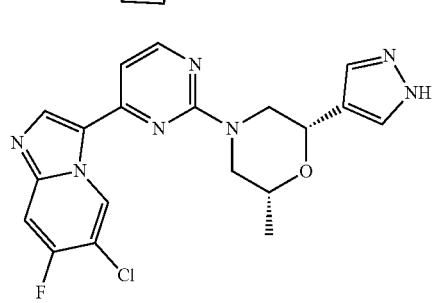
I-274
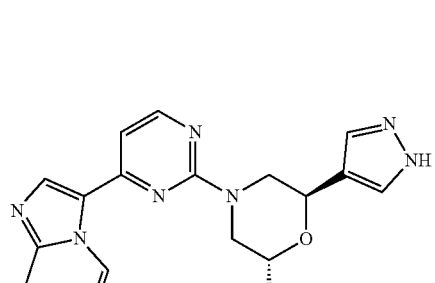
I-275
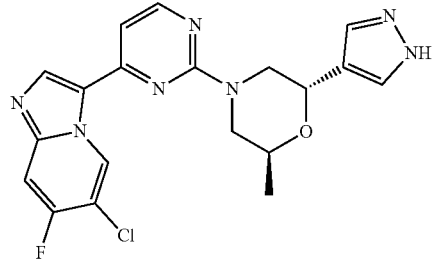

I-276
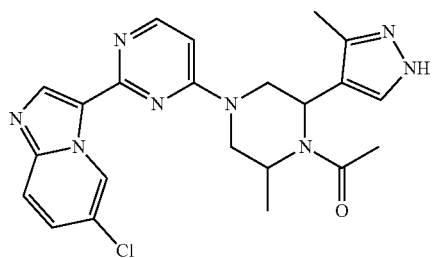
I-277
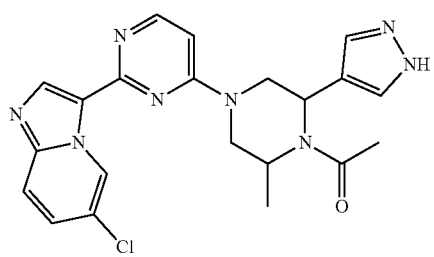
I-278
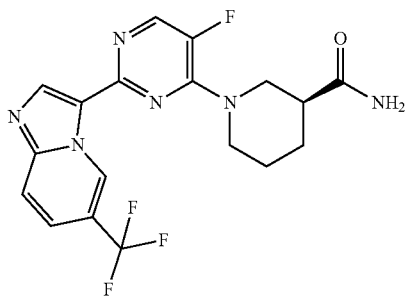
I-279
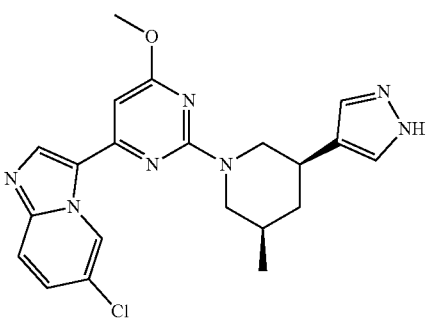
I-280
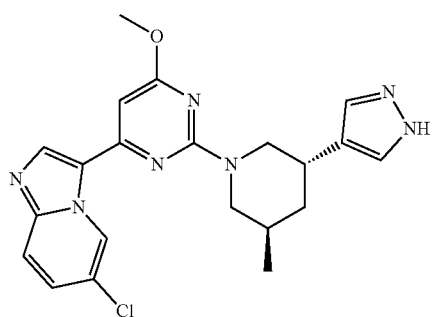
I-281
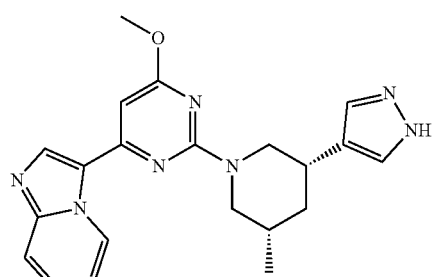
I-282
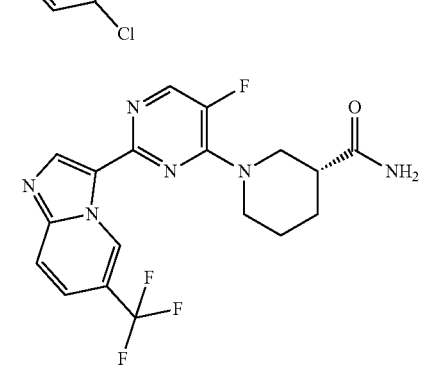
I-283
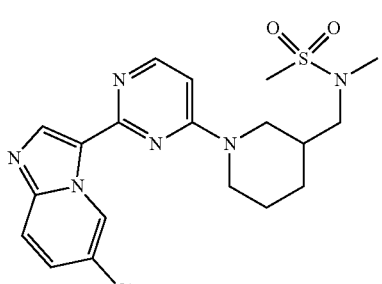
I-284
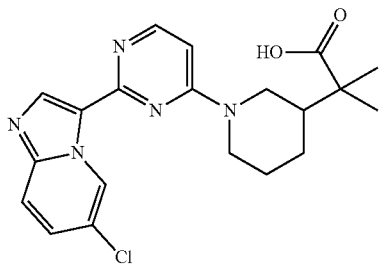
I-285
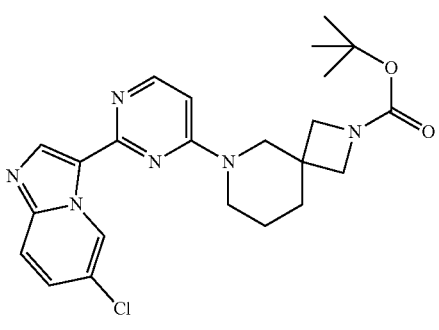

I-286 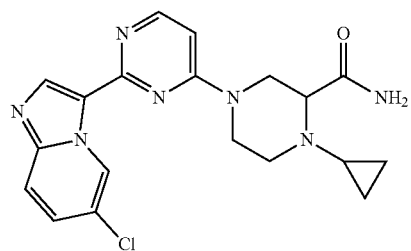
I-291 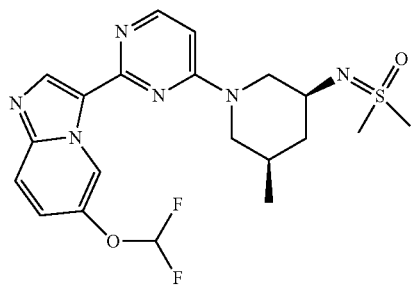
I-287 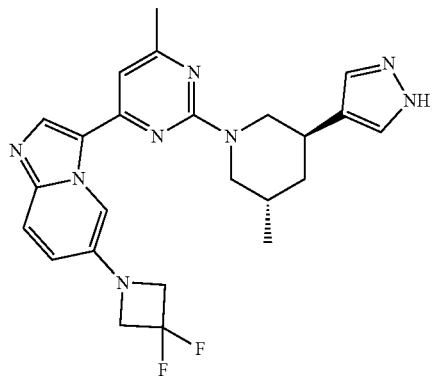
I-292 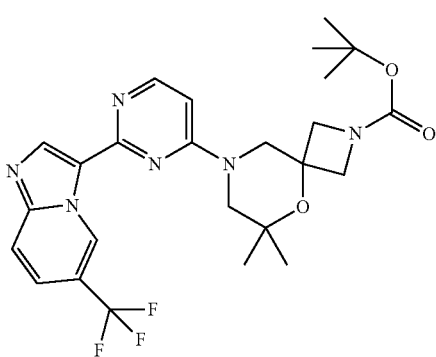
I-288 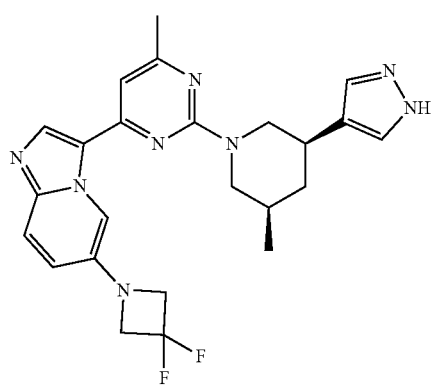
I-293 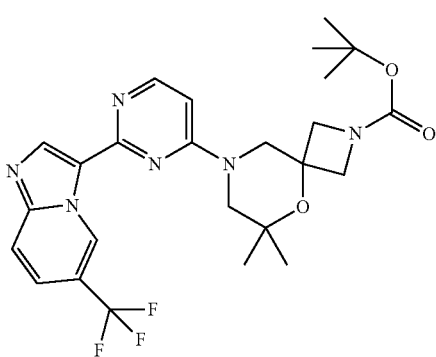
I-289 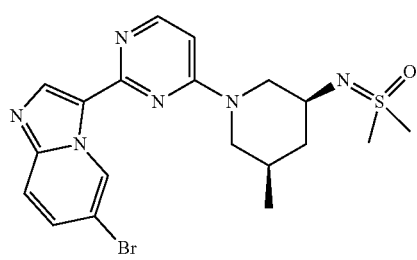
I-294 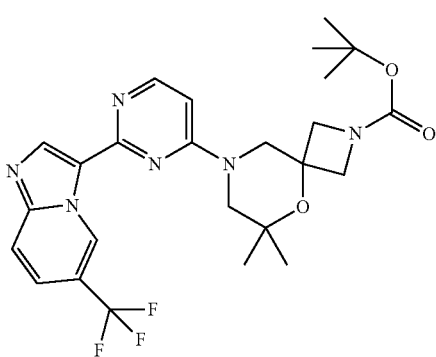
I-290 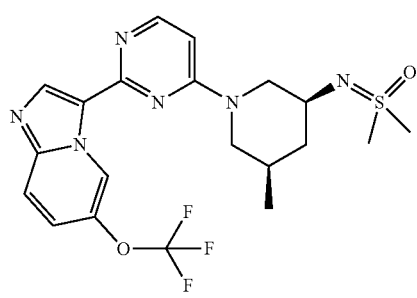
I-295 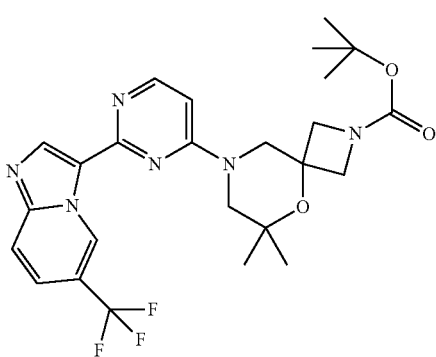

I-296 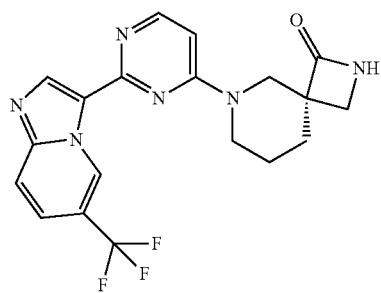
I-297 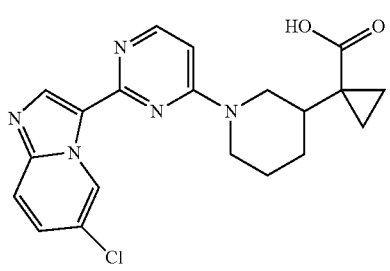
I-298 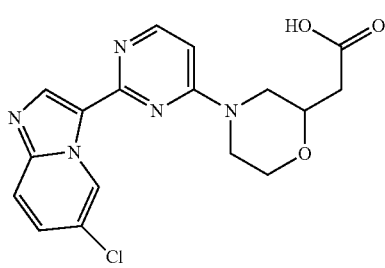
I-299 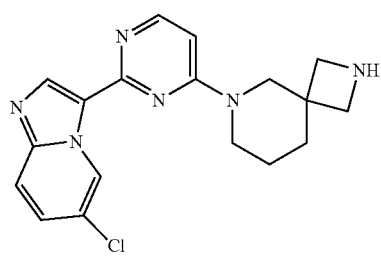
I-300 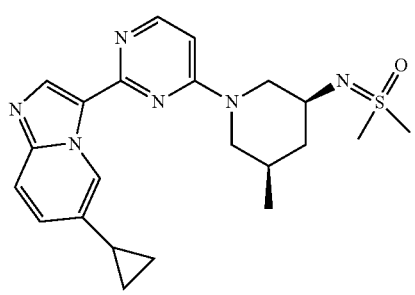
I-301 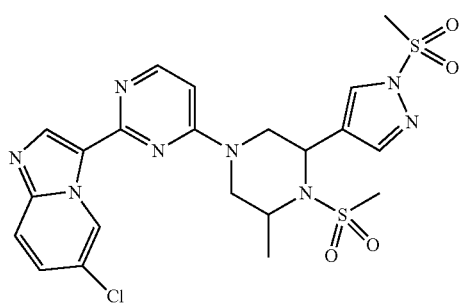
I-302 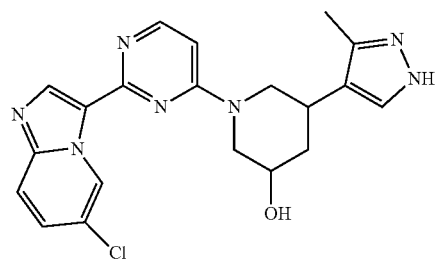
I-303 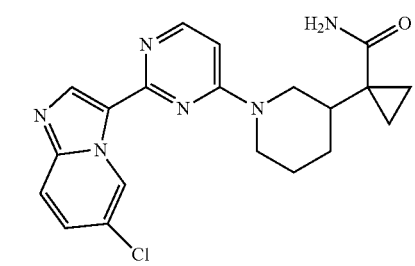
I-304 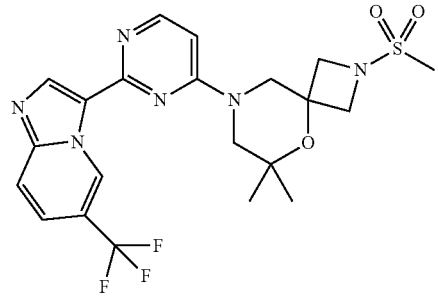
I-305 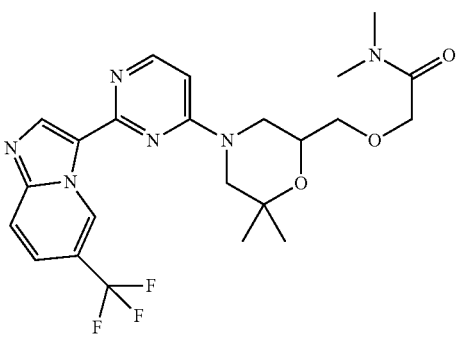

-continued
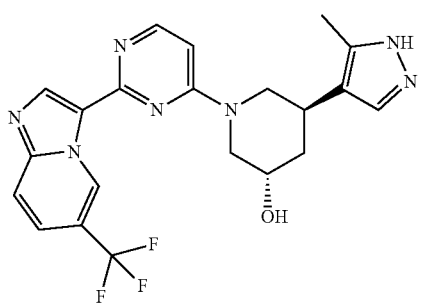
I-307
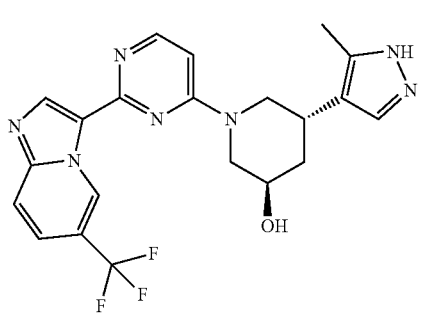
I-308
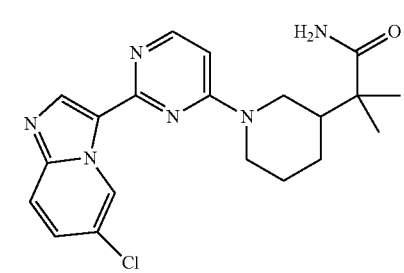
I-309
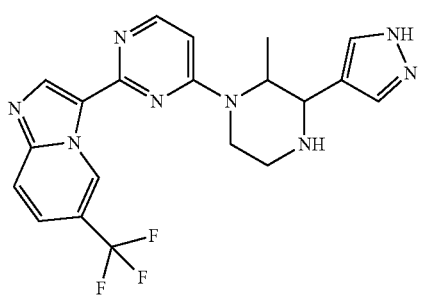
I-310
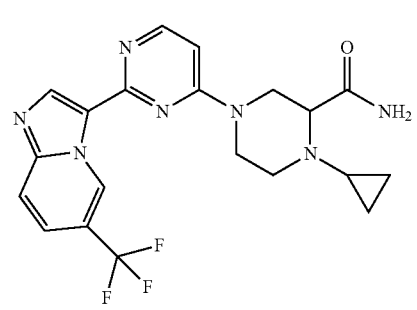
I-311
-continued
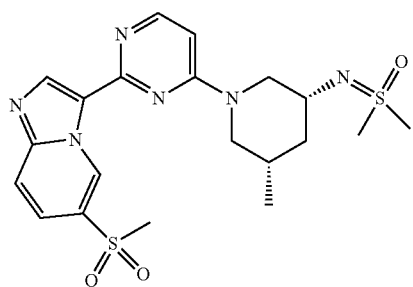
I-312
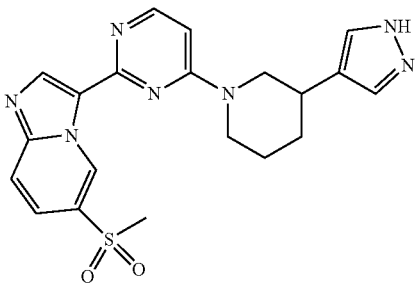
I-313
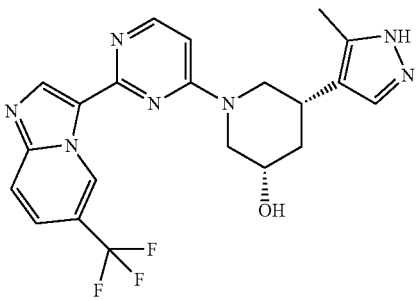
I-314
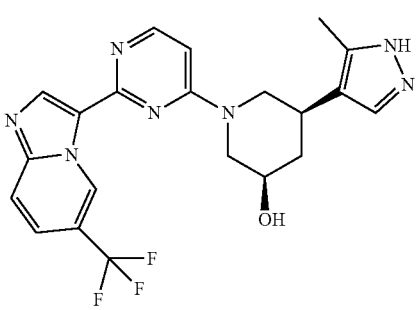
I-315
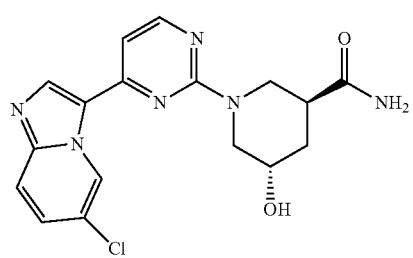
I-316

413
-continued
I-317
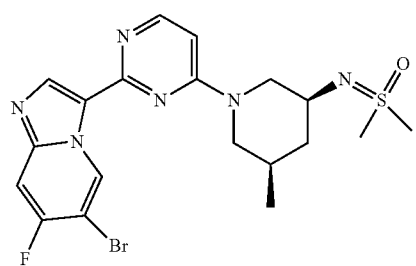
I-318
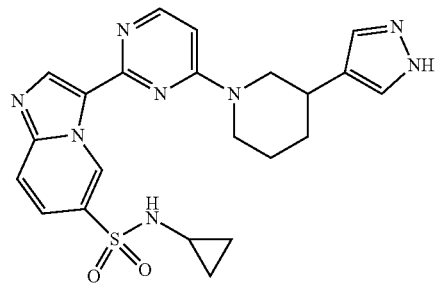
I-319
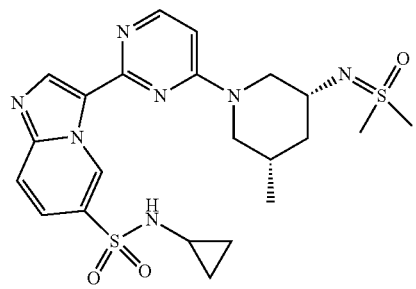
I-320
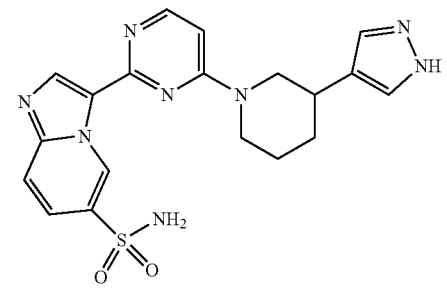
I-321
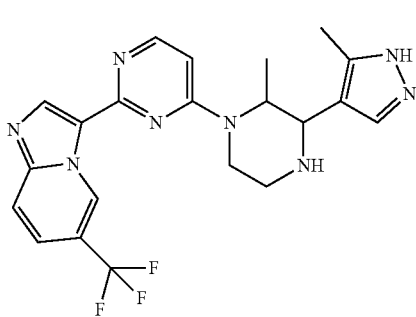
414
-continued
I-322
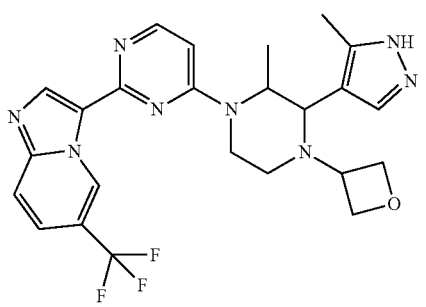
I-323
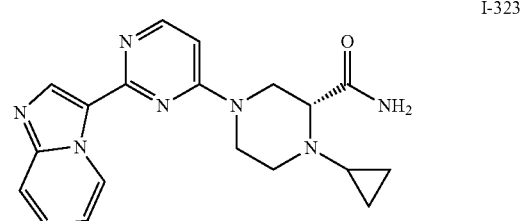
I-324
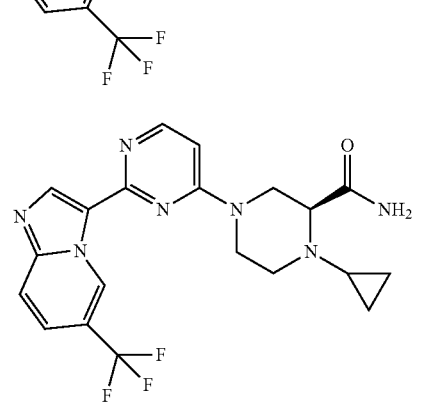
I-325
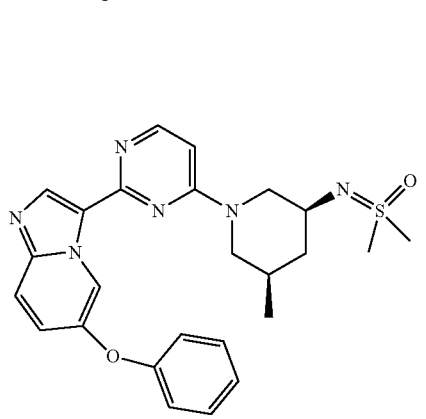
I-326
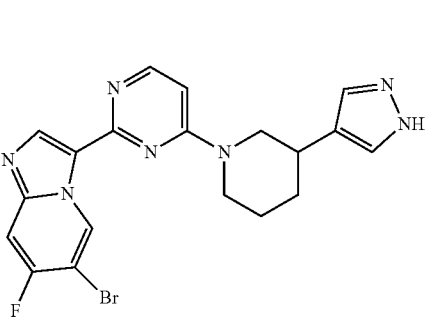

I-327 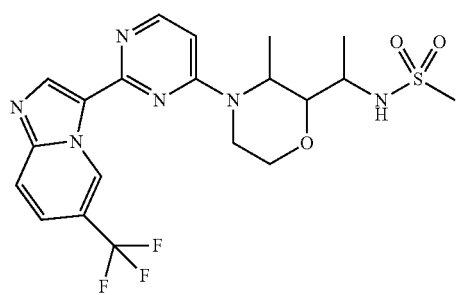
I-328 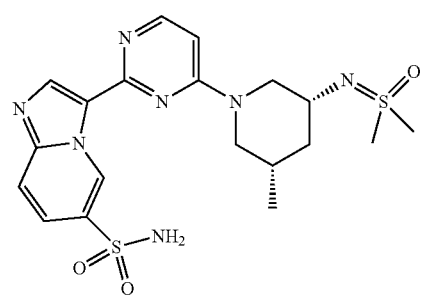
I-329 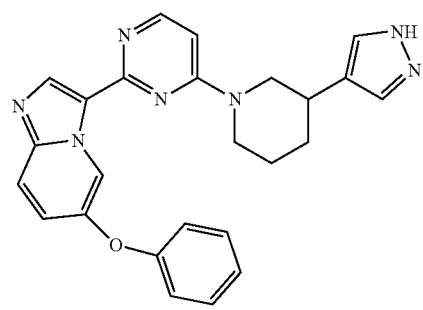
I-330 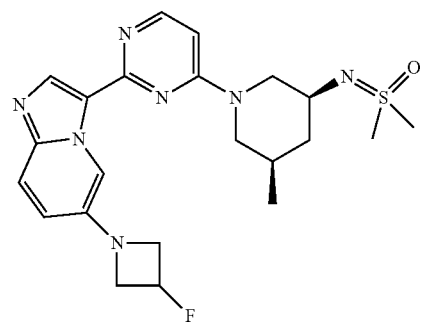
I-331 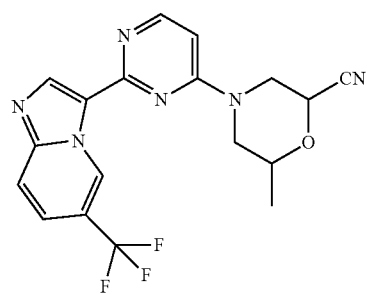
I-332 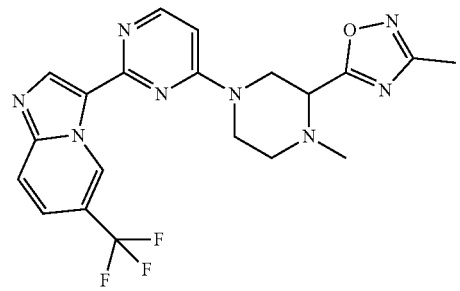
I-333 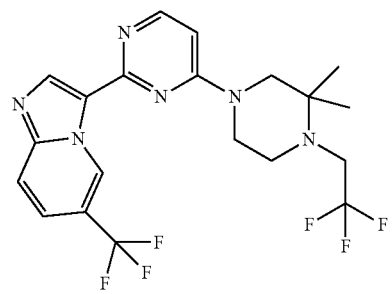
I-334 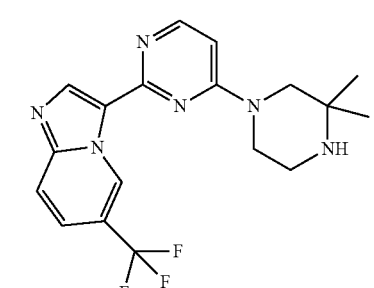
I-335 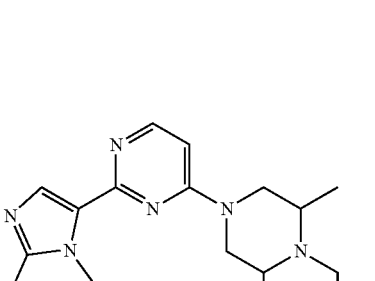
I-336 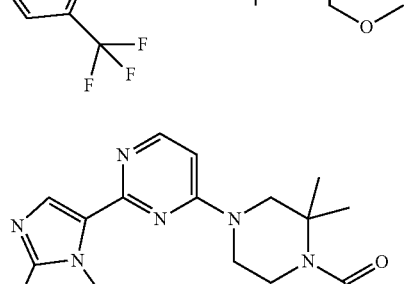

I-337
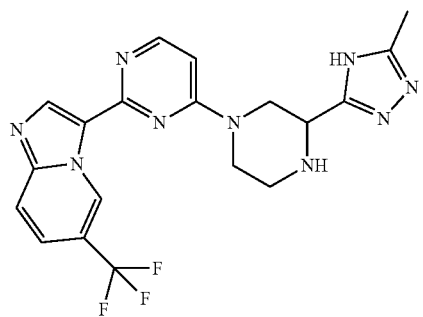
I-338
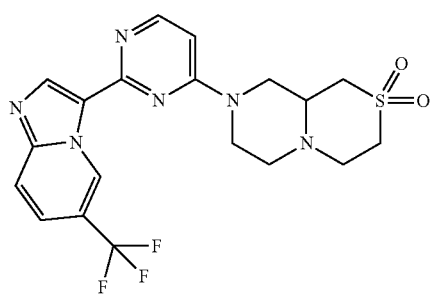
I-339
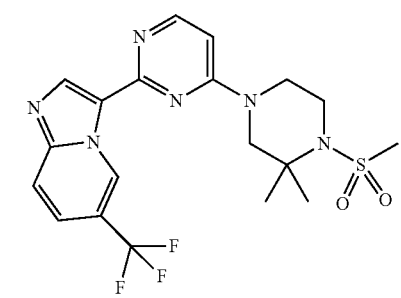
I-340
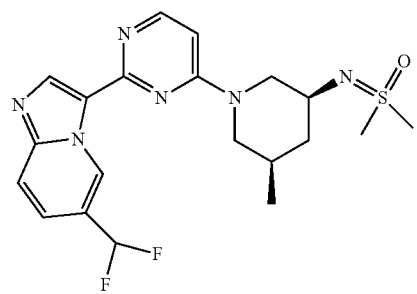
I-341
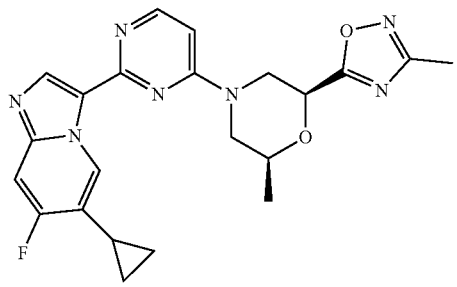
I-342
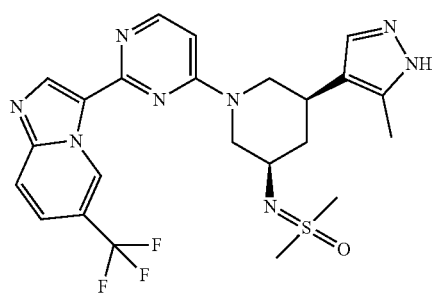
I-343
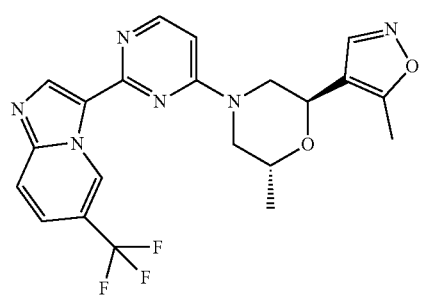
I-344
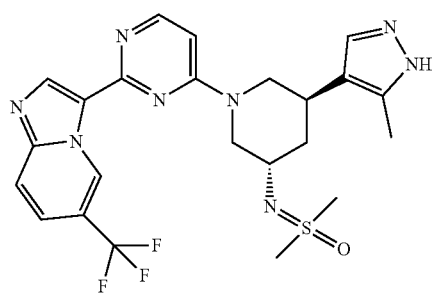
I-345
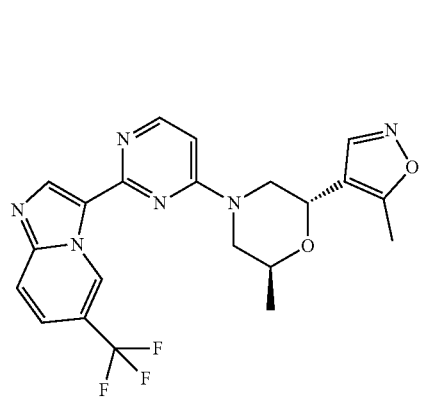
I-346
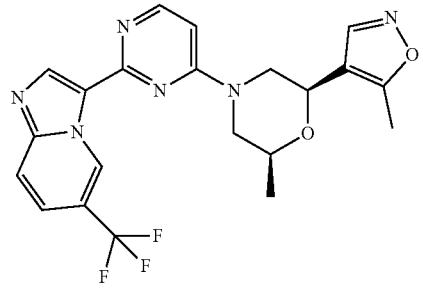

I-347
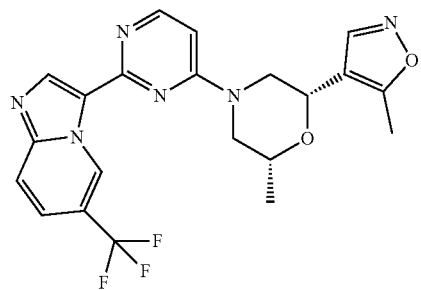
I-348
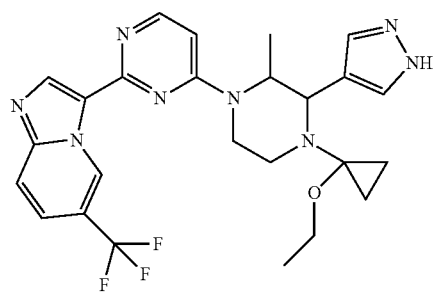
I-349
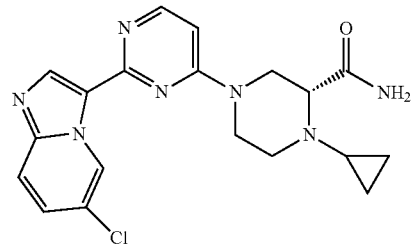
I-350
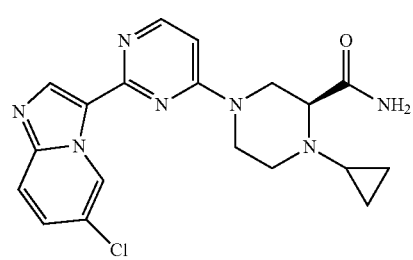
I-351
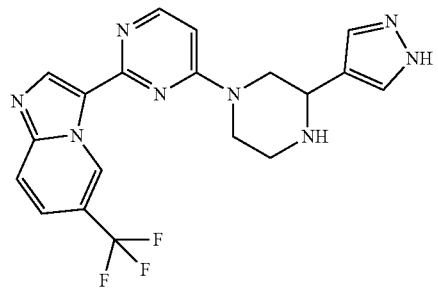
I-352
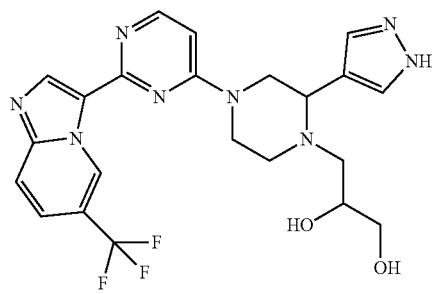
I-353
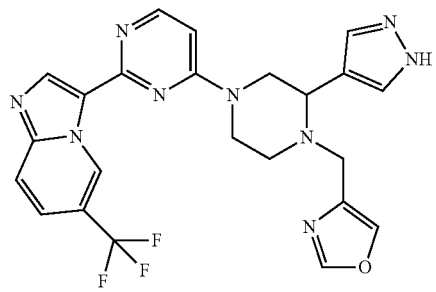
I-354
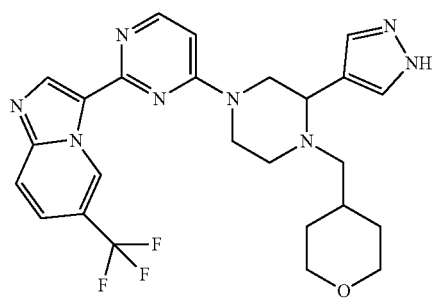
I-355
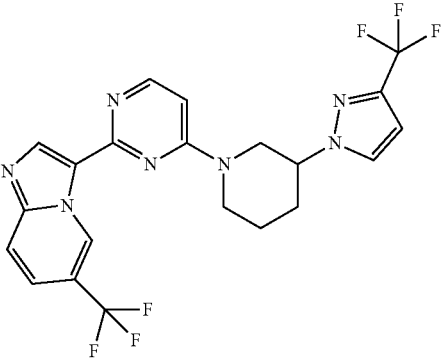
I-356
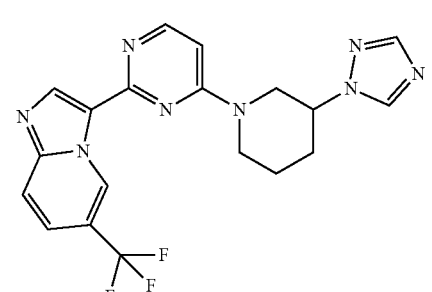

-continued
I-357
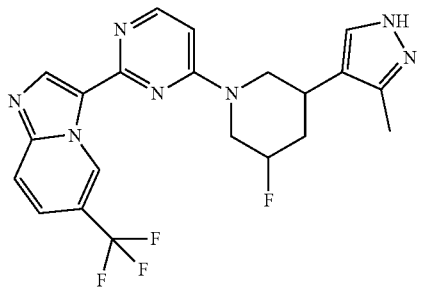
I-358
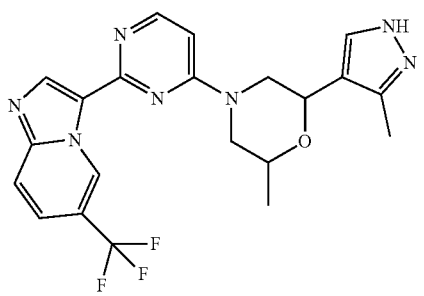
I-359
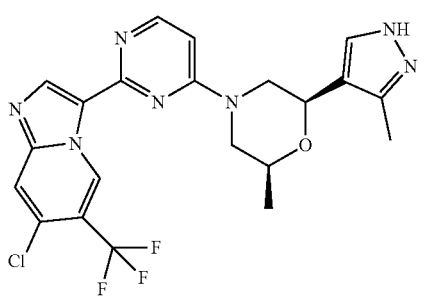
I-360
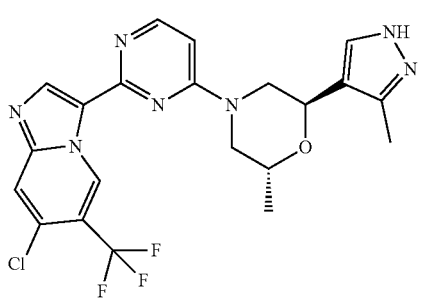
I-361
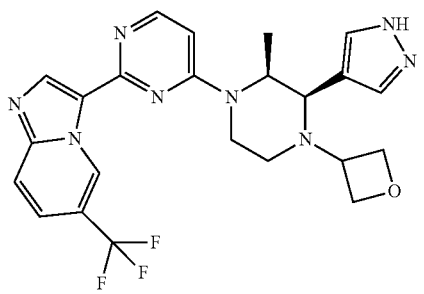
-continued
I-362
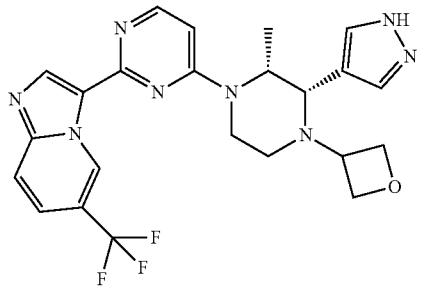
I-363
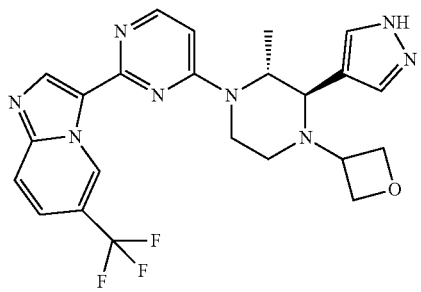
I-364
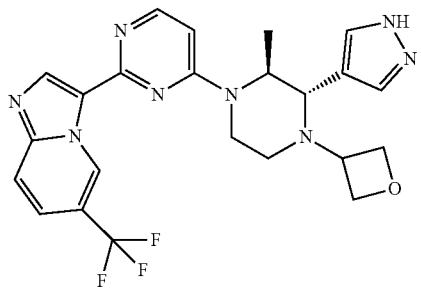
I-365
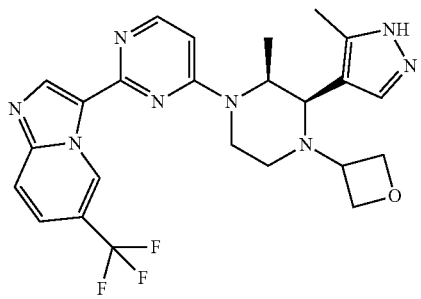
I-366

I-367
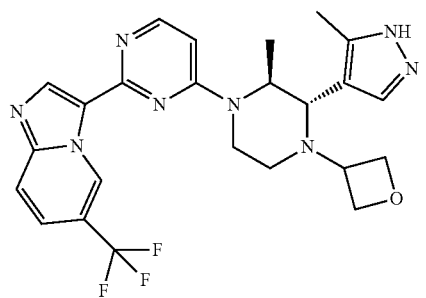
I-368
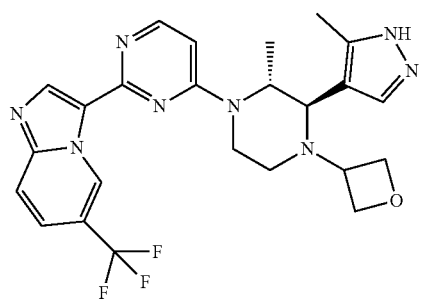
I-369
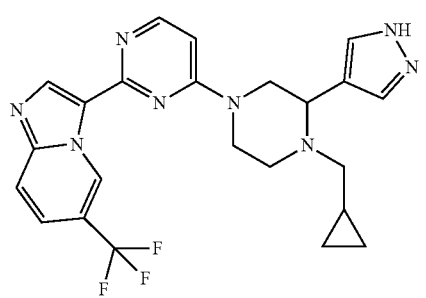
I-370
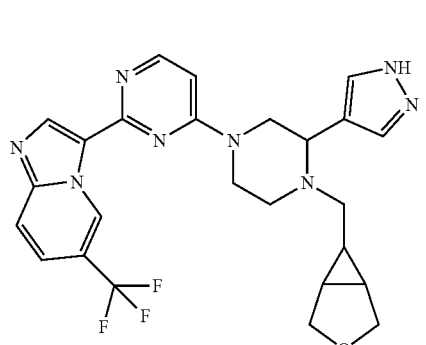
I-371
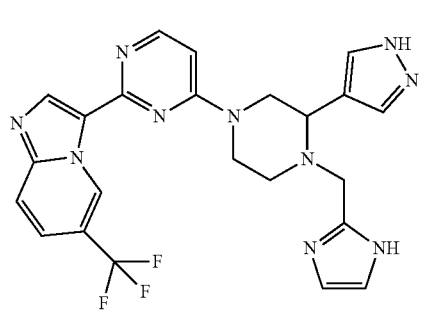
I-372
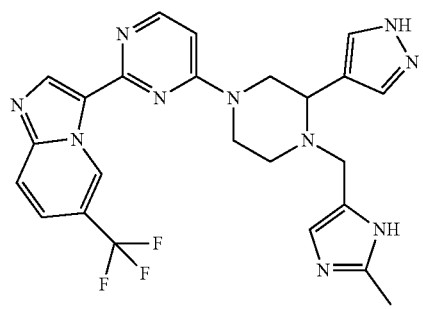
I-373
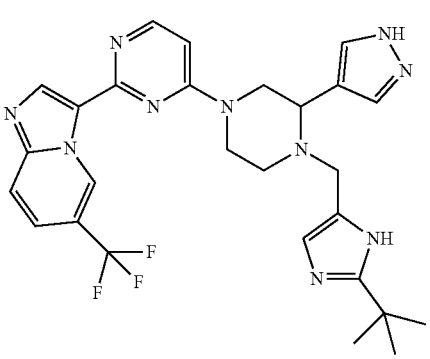
I-374
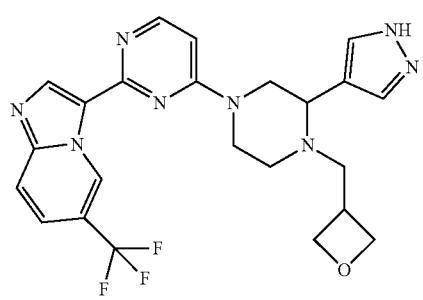
I-375
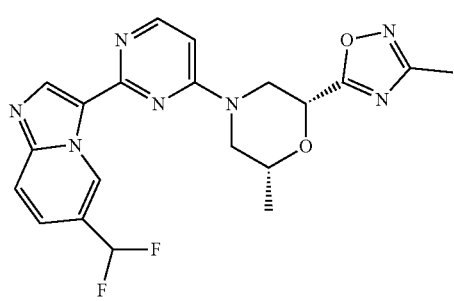
I-376
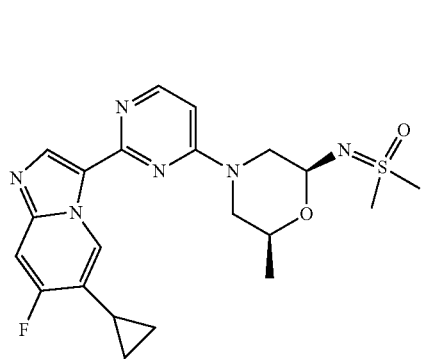

I-377 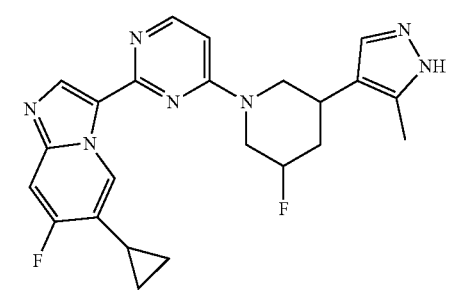
I-378 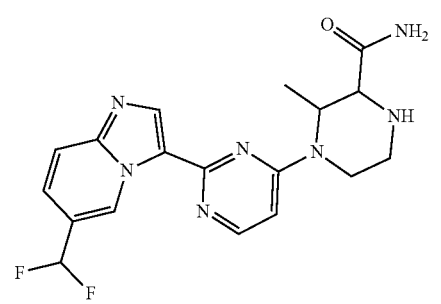
I-379 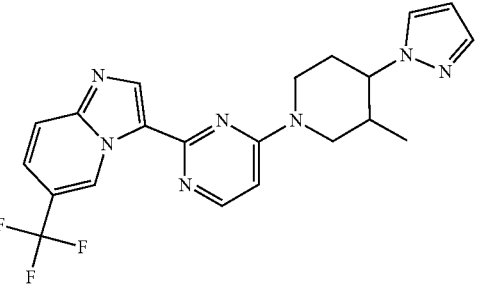
I-380 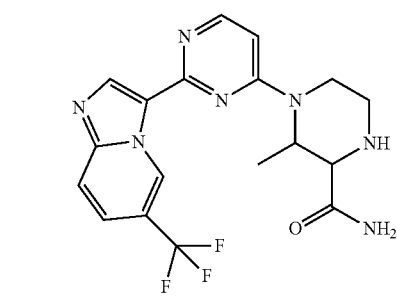
I-382 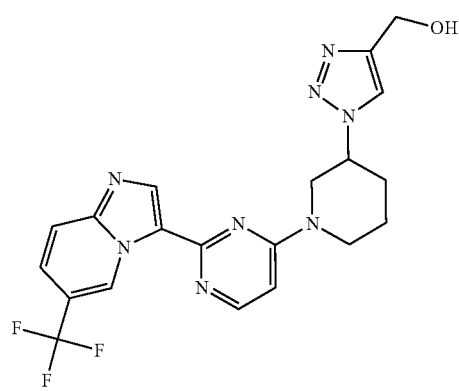
I-383 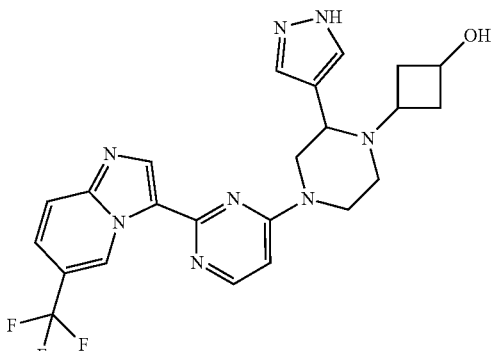
I-384 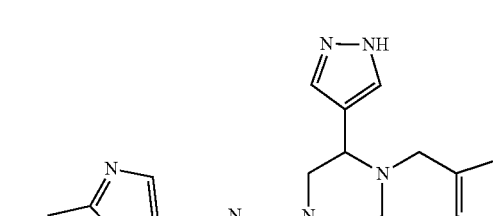
I-385 
I-386 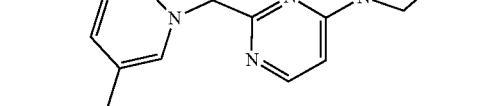

I-387
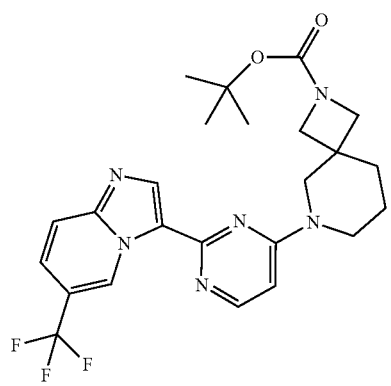
I-388
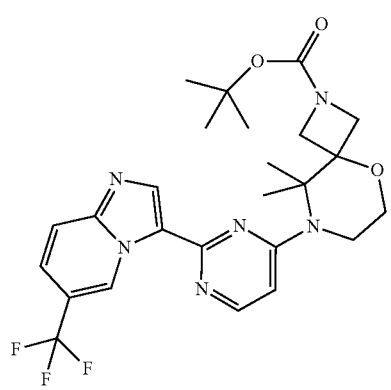
I-389
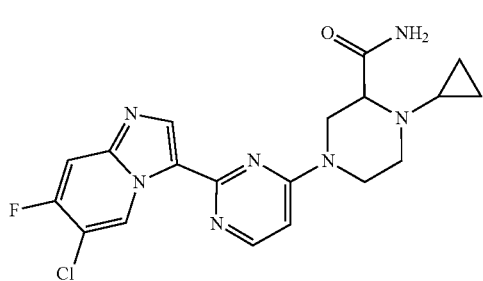
I-390
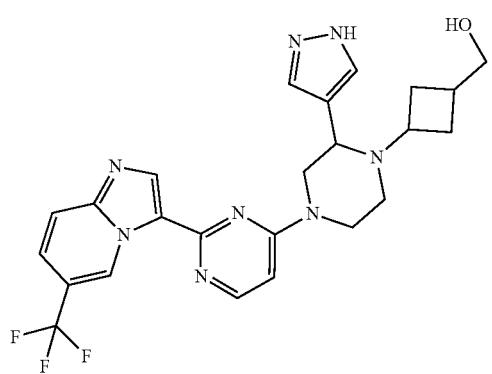
I-391
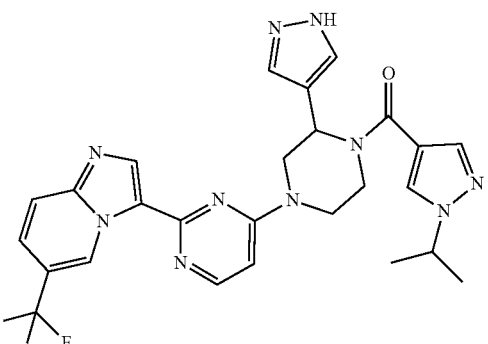
I-392
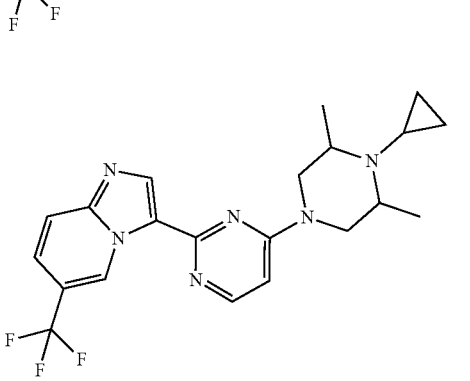
I-393
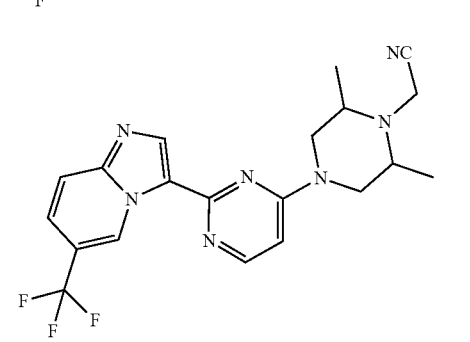
I-394
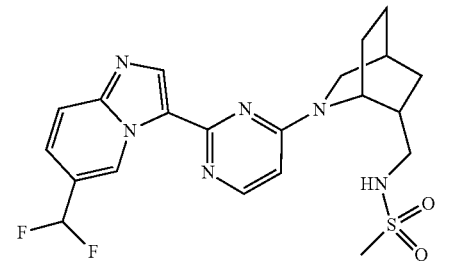
I-395
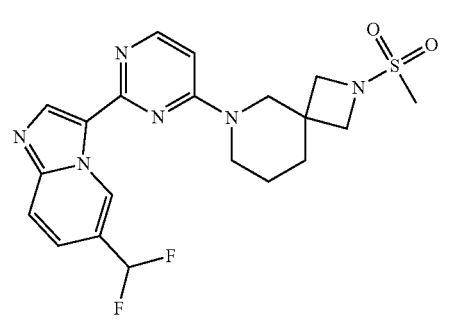

I-396 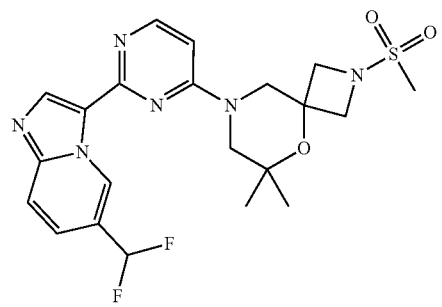
I-397 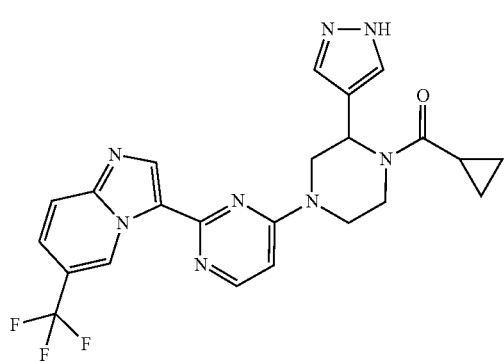
I-398 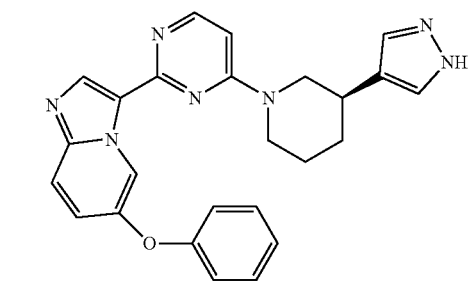
I-399 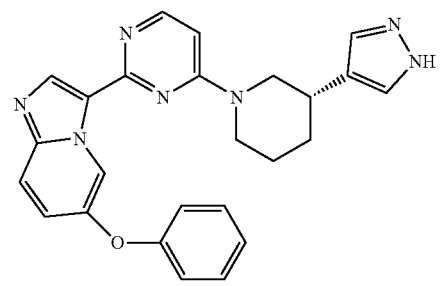
I-400 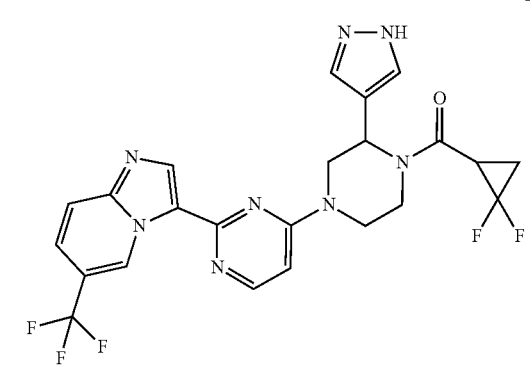
I-401 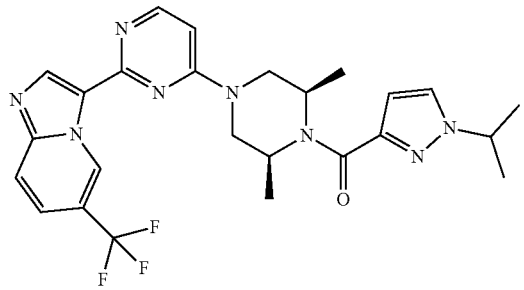
I-402 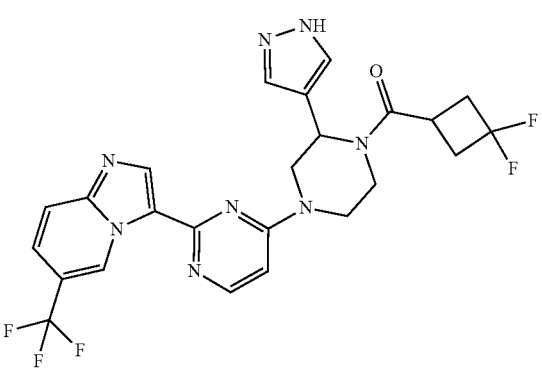
I-403 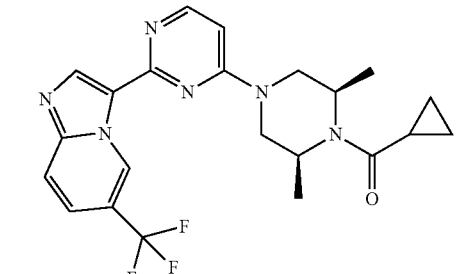
I-404 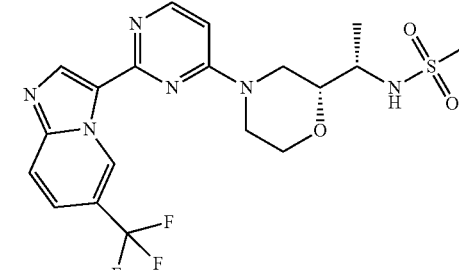
I-405 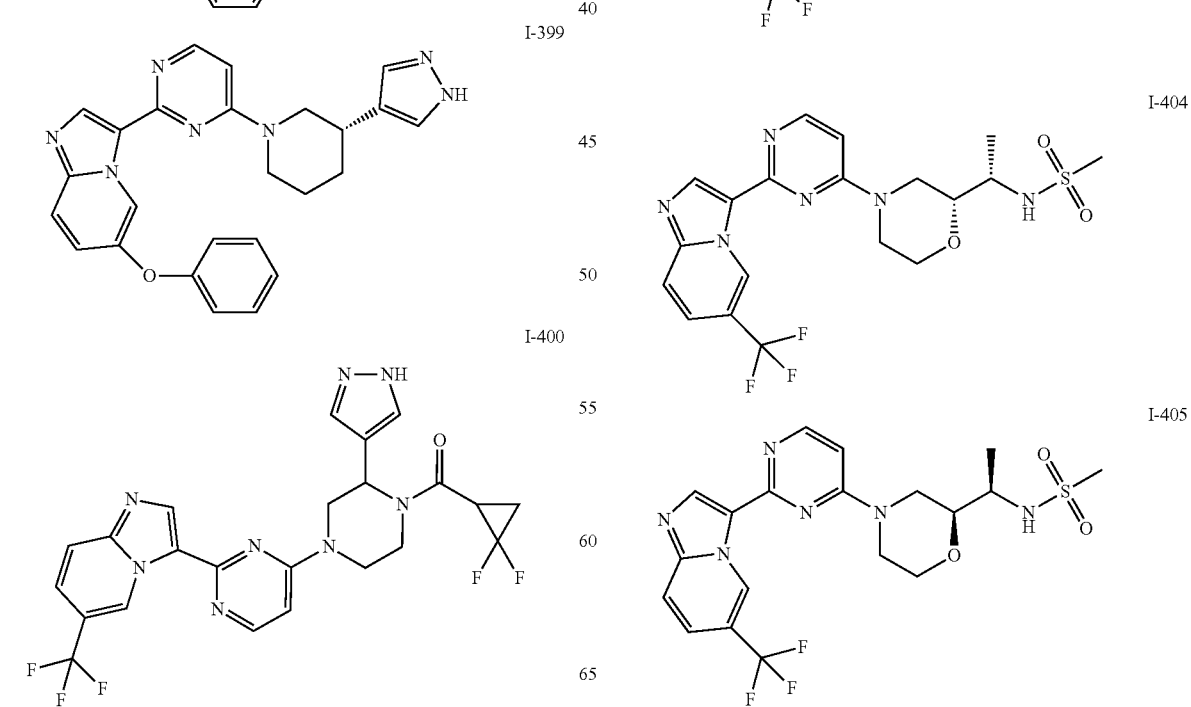

I-406
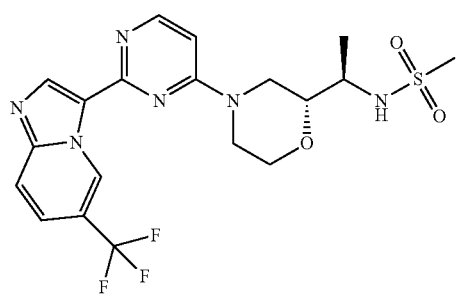
I-407
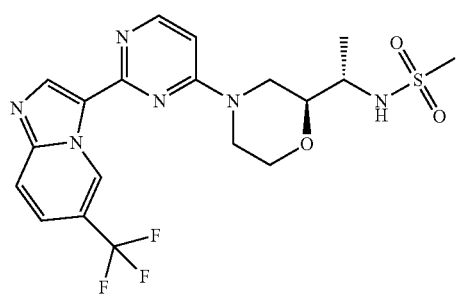
I-408
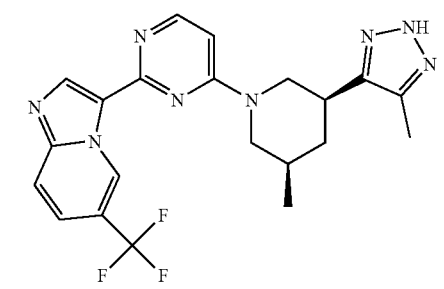
I-409
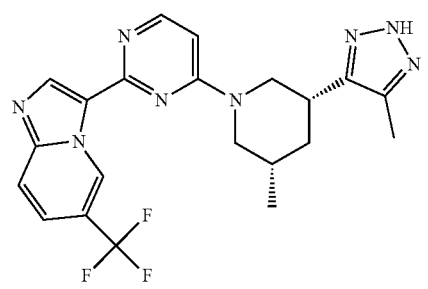
I-410
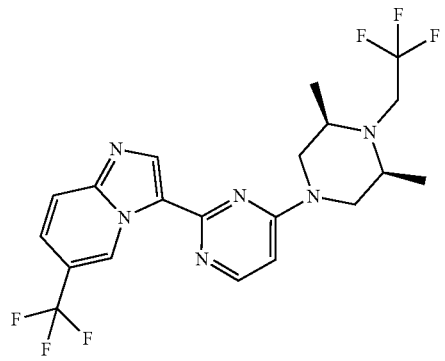
I-411
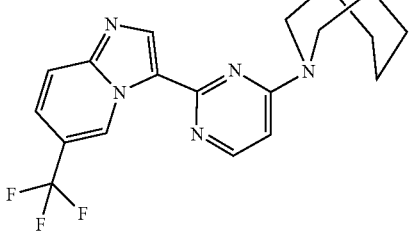
I-412
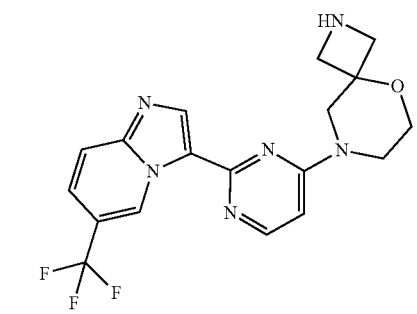
I-413
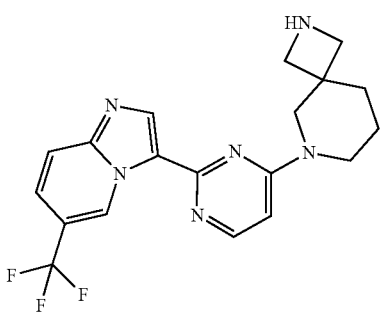
I-414
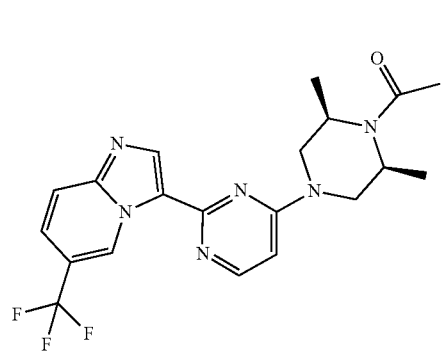

-continued
I-415
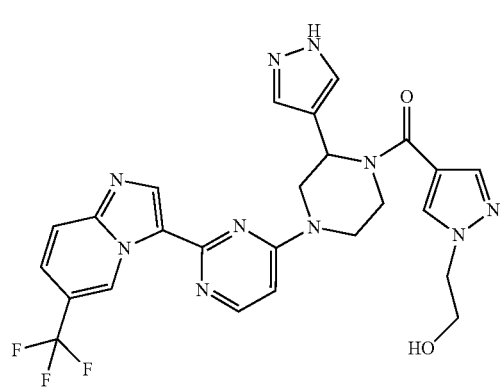
I-416
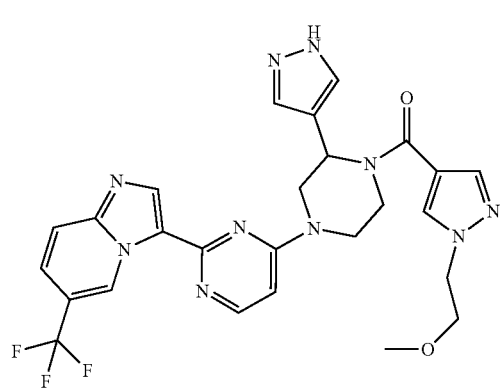
I-417
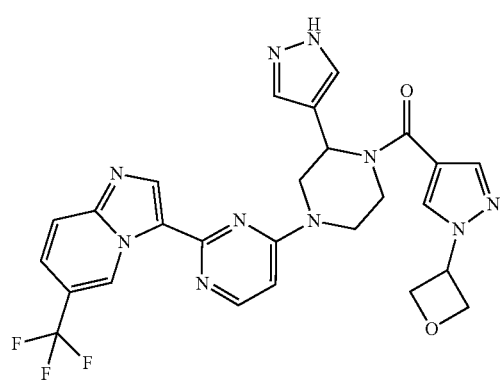
I-418
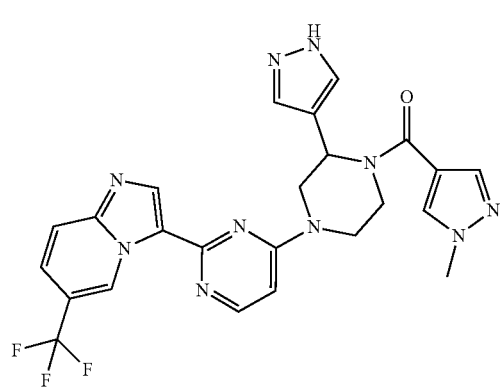
-continued
I-419
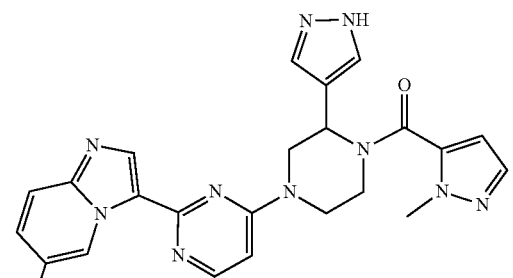
I-420
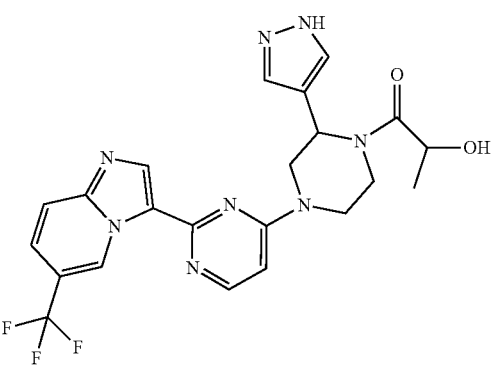
I-421
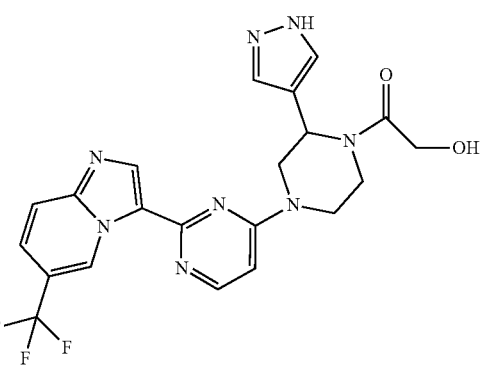
I-422
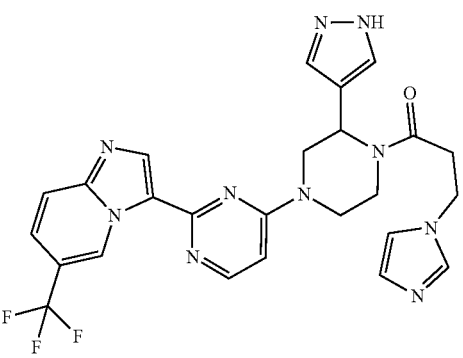

I-423
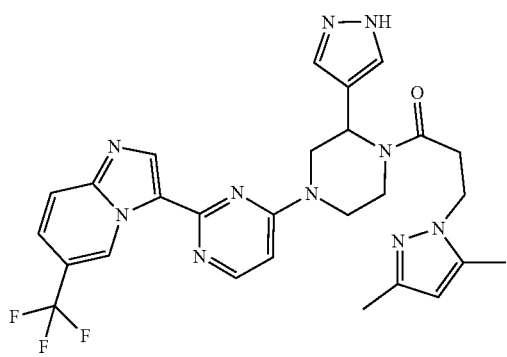
I-424
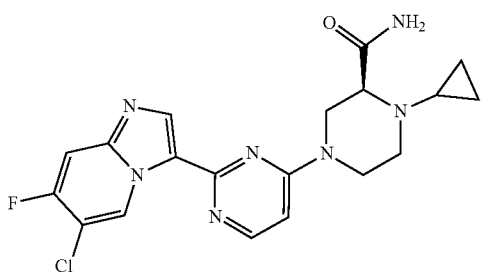
I-425
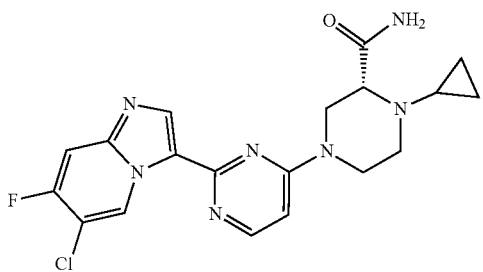
I-428
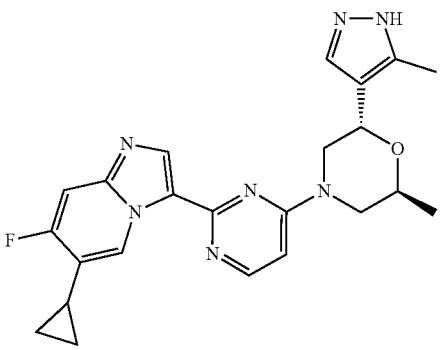
I-429
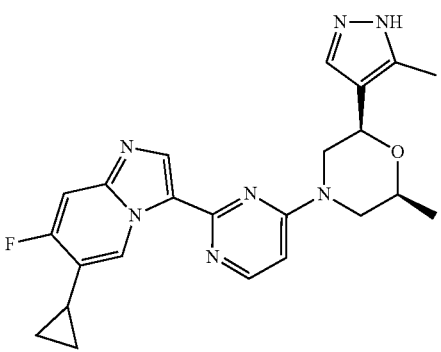
I-426
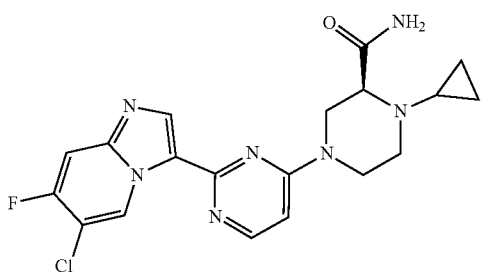
I-427
I-432
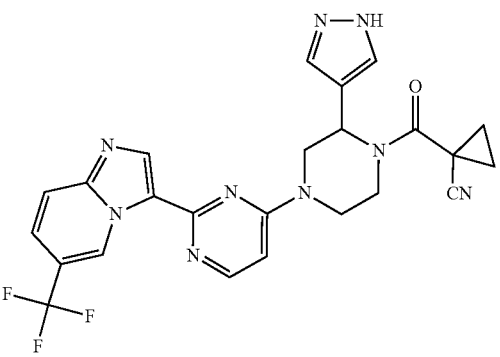
I-433
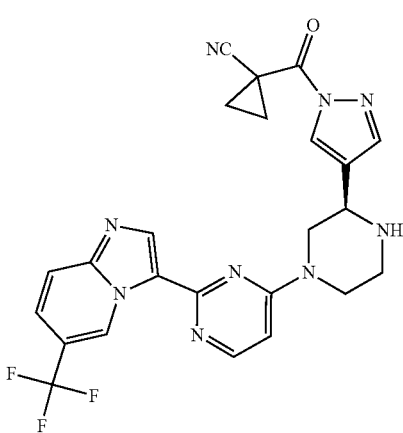

I-434
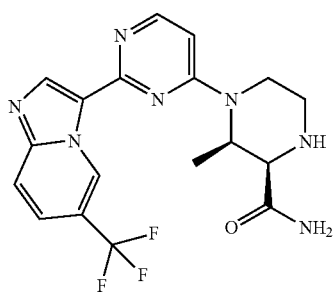
I-435
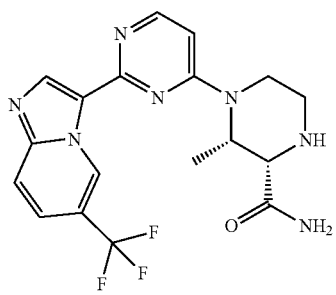
I-436
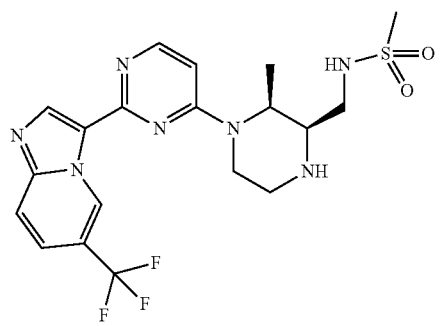
I-437
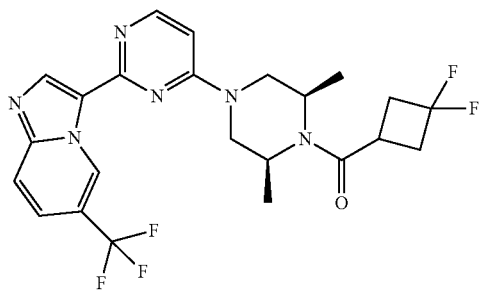
I-438
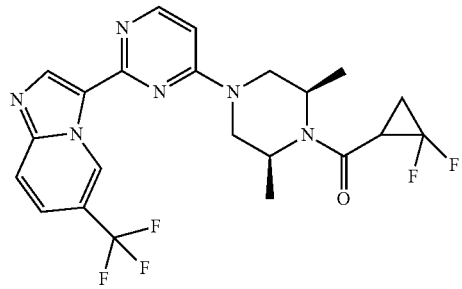
I-439
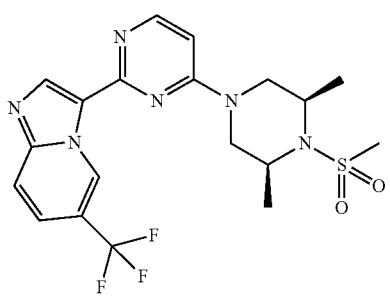
I-440
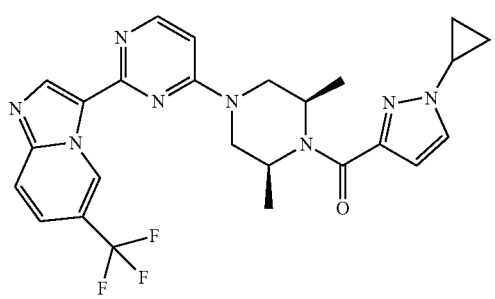
I-441
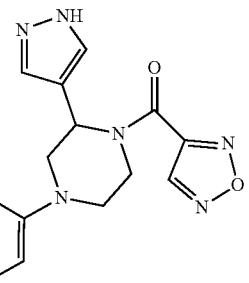
I-442
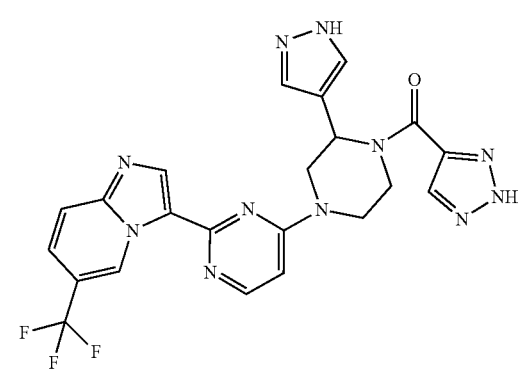

I-443 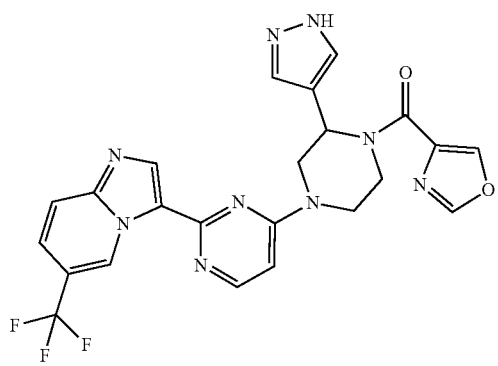
I-444 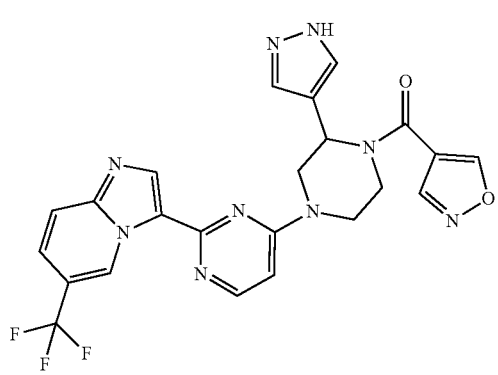
I-445 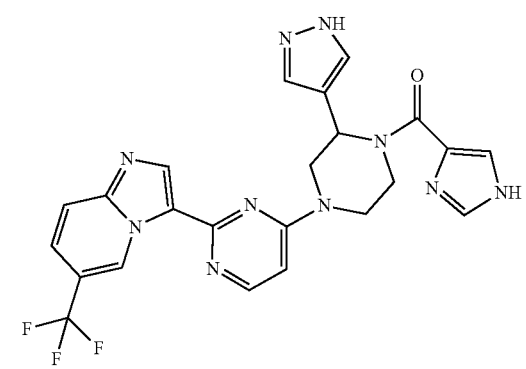
I-446 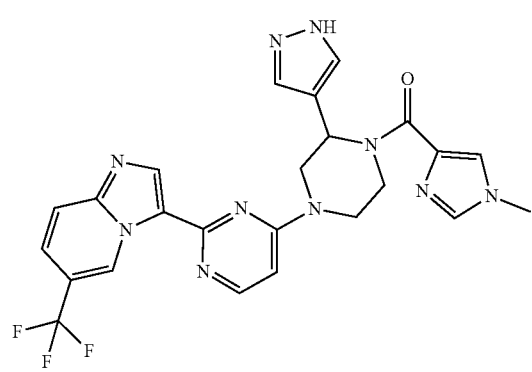
I-447 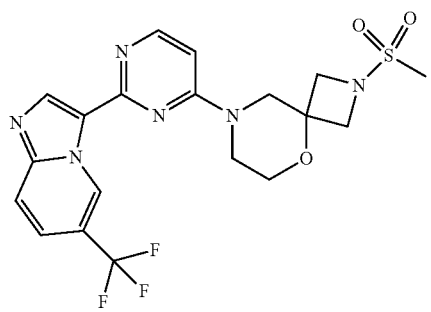
I-448 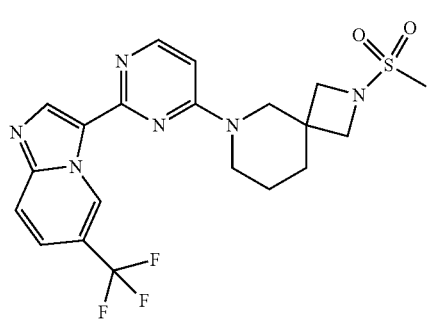
I-449 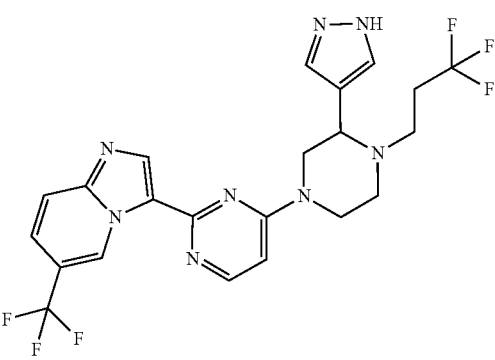
I-450
I-451 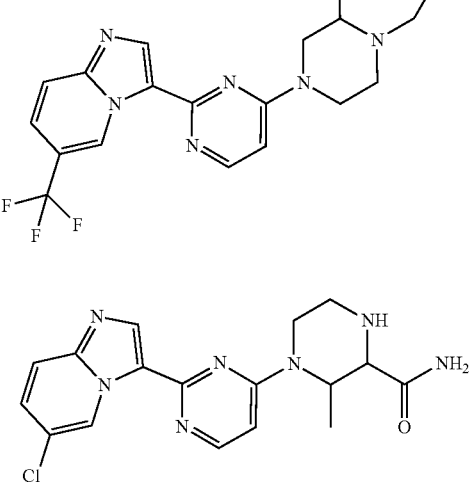

I-452 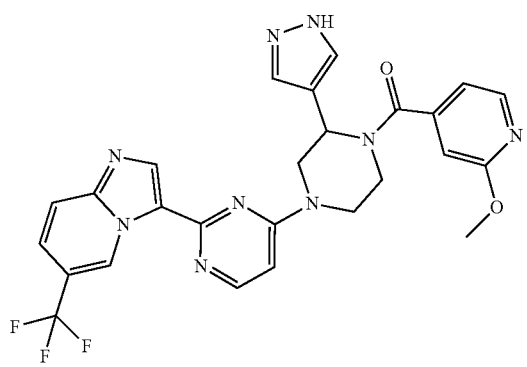
I-454 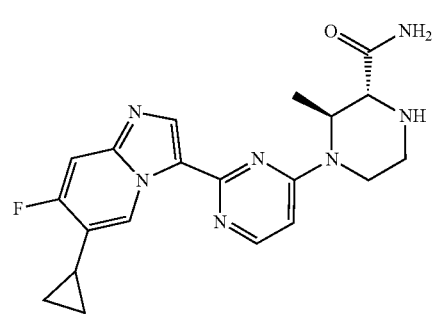
I-455 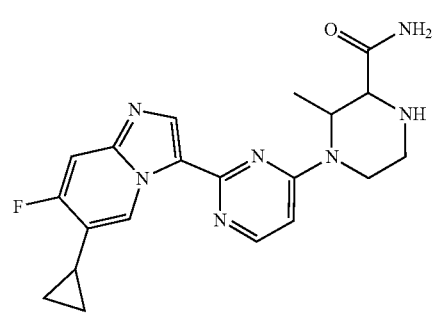
I-456 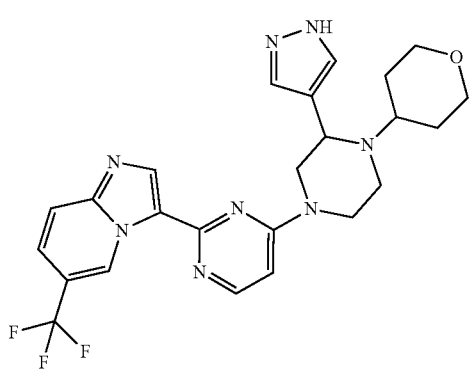
I-457 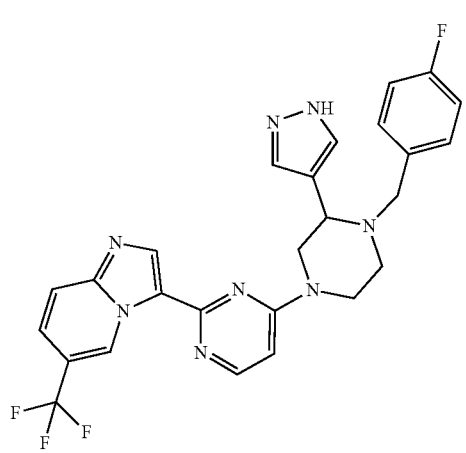
I-458 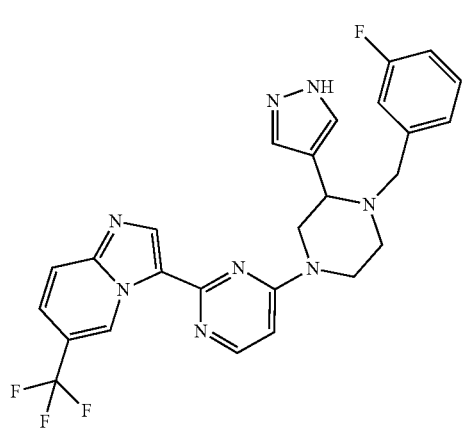
I-459 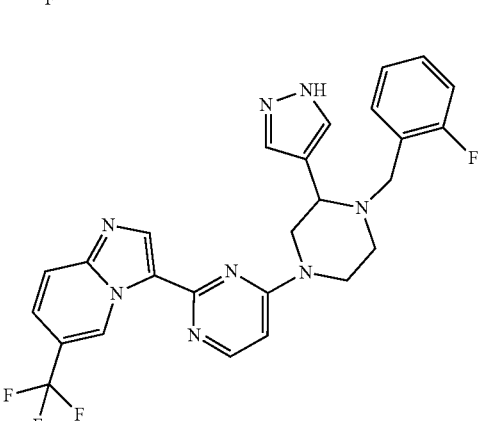
I-460 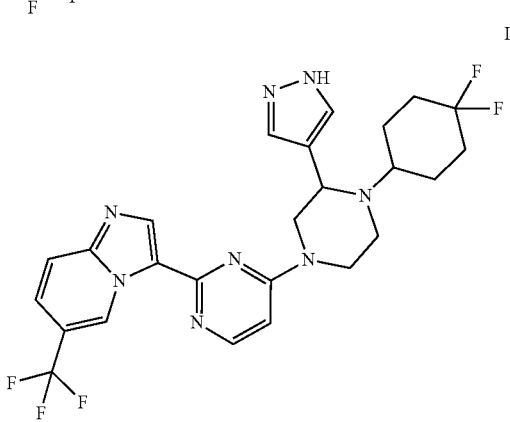

I-461 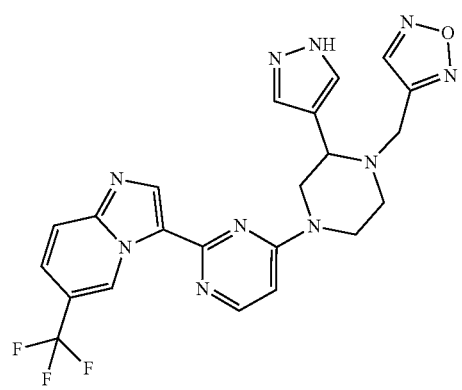
I-462 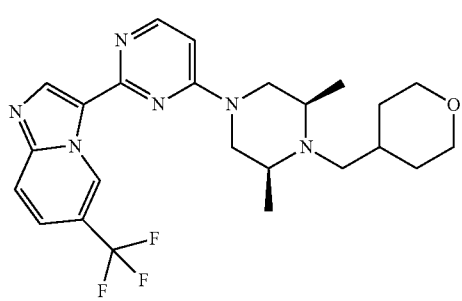
I-463 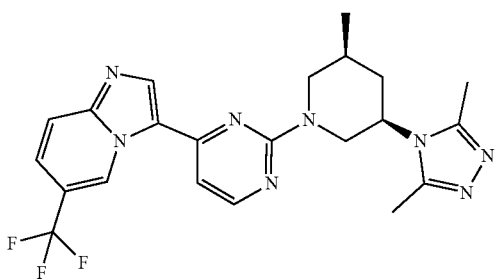
I-464 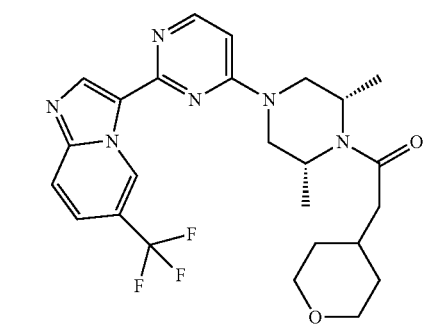
I-465 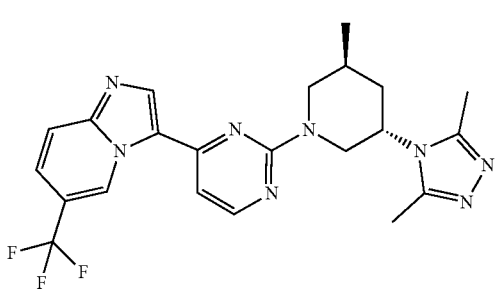
I-466 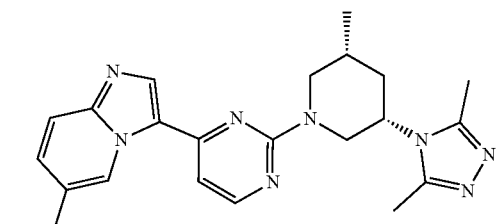
I-467 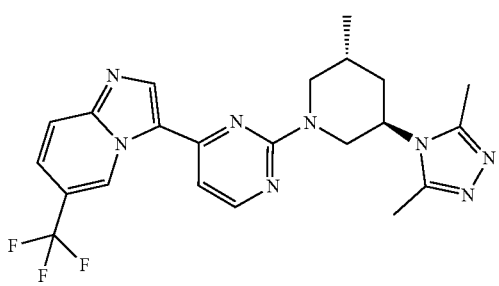
I-468 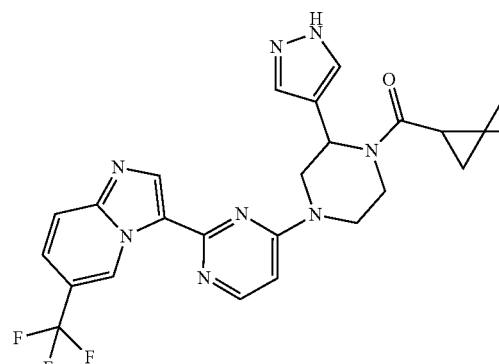
I-469 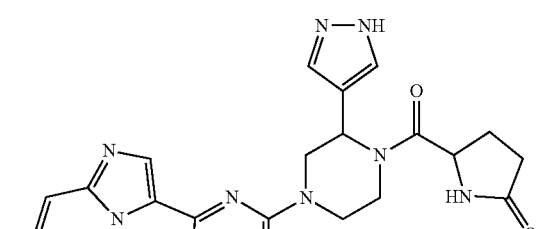
I-470 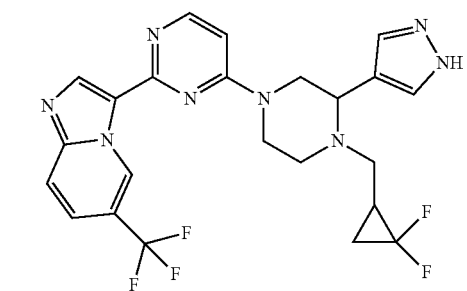

I-471
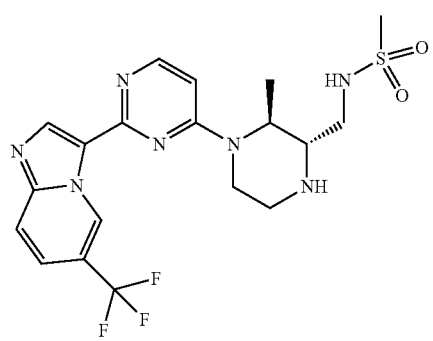
I-472
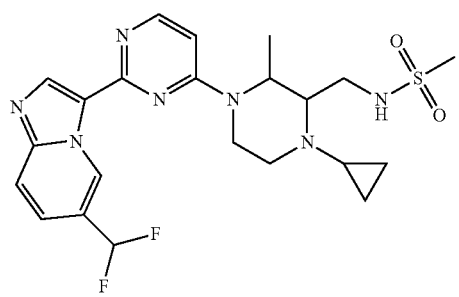
I-473
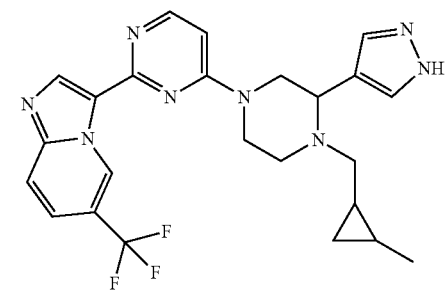
I-474
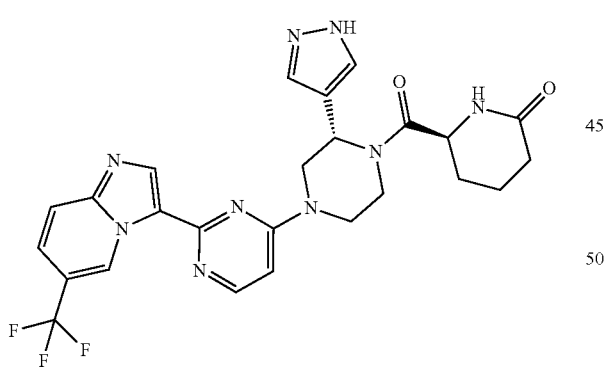
I-475
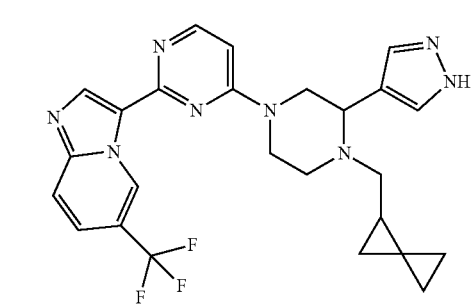
I-476
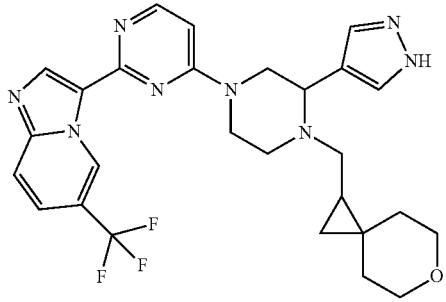
I-477
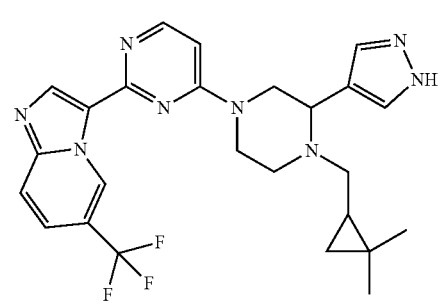
I-478
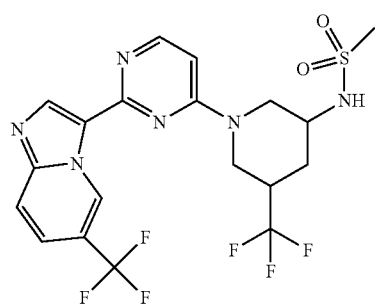
I-479
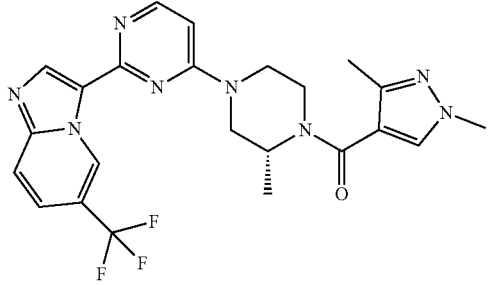
I-480
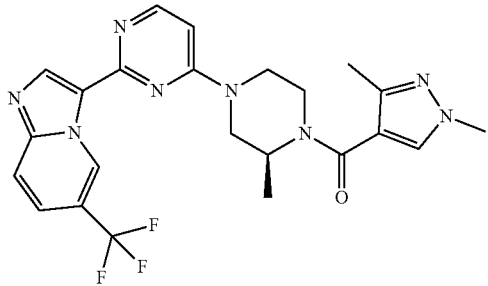

I-481 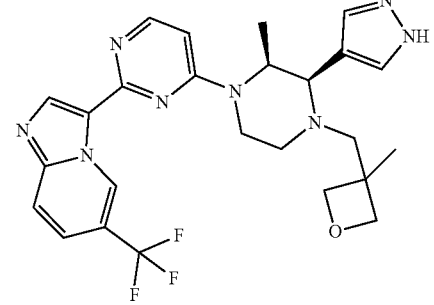
I-482 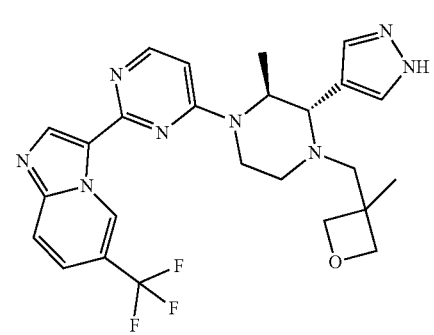
I-483 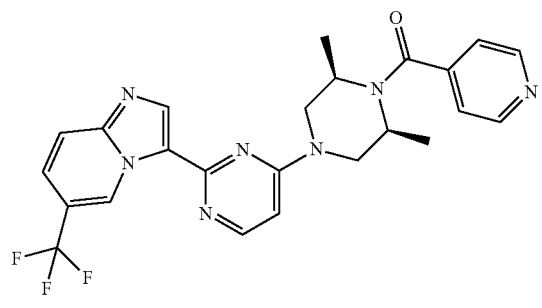
I-484 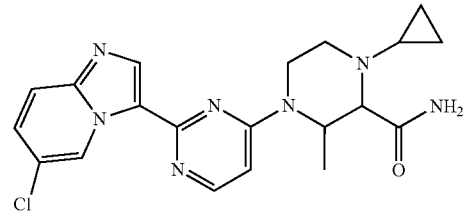
I-485 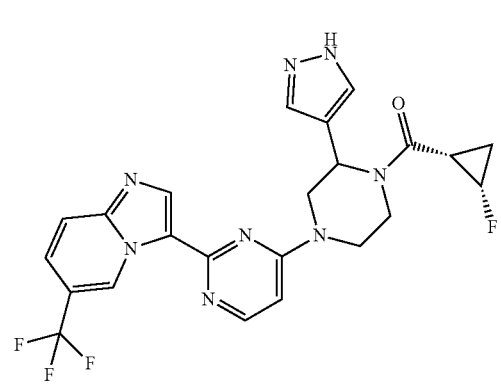
I-486 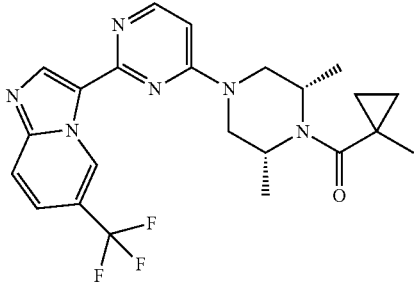
I-487 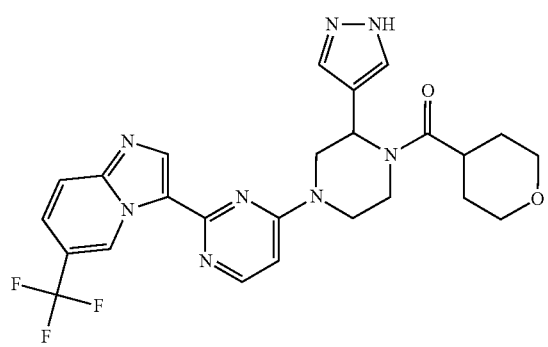
I-488 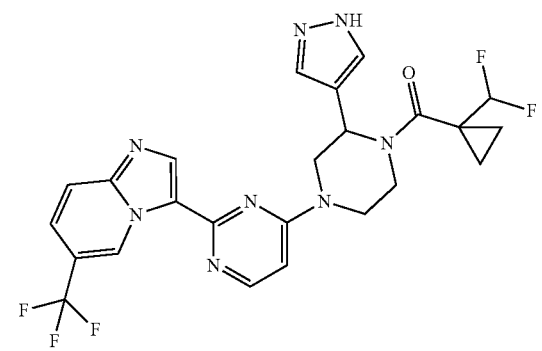
I-489 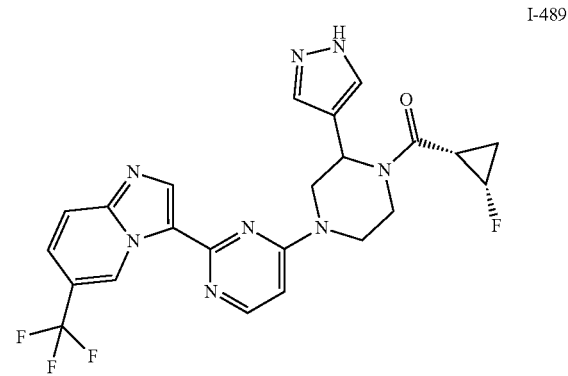

449
-continued
I-490
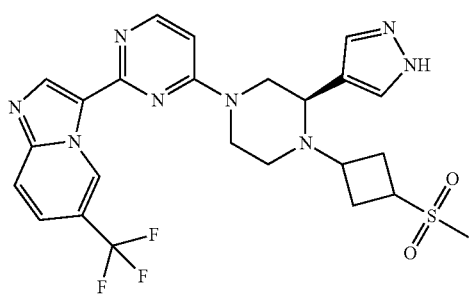
I-491
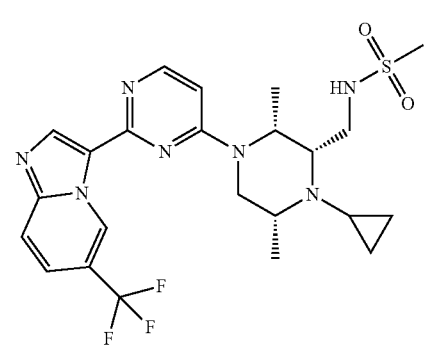
I-492
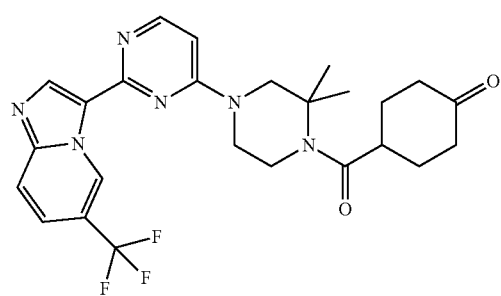
I-493
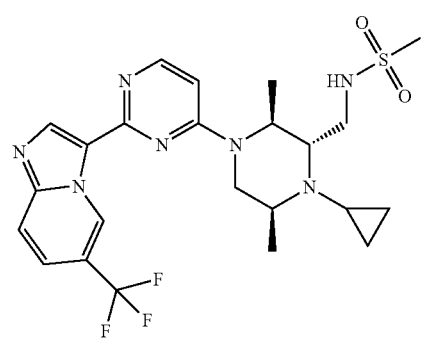
I-494
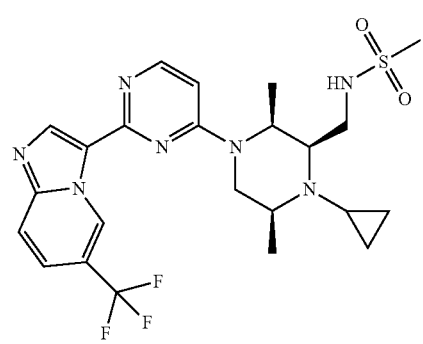
450
-continued
I-495
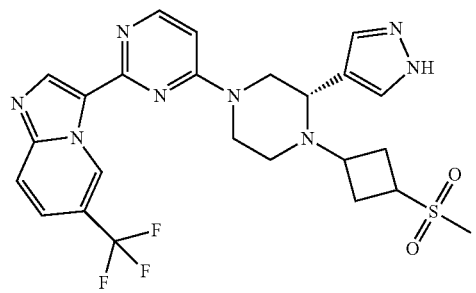
I-496
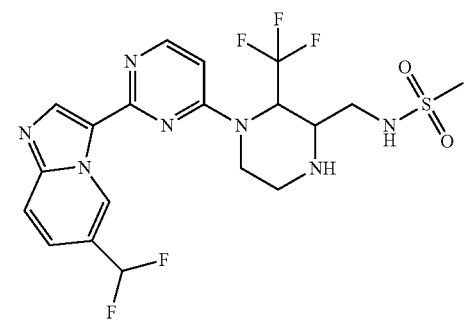
I-497
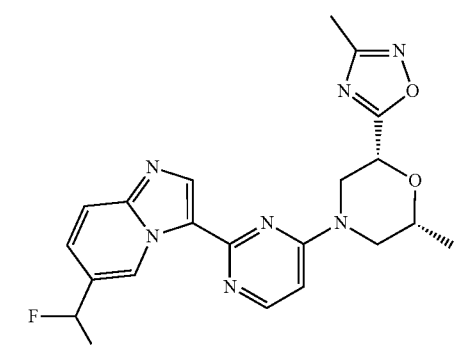
I-498
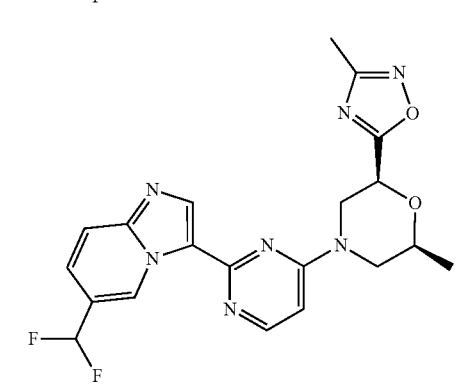
I-499
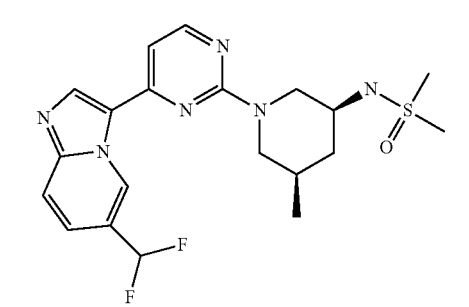

-continued
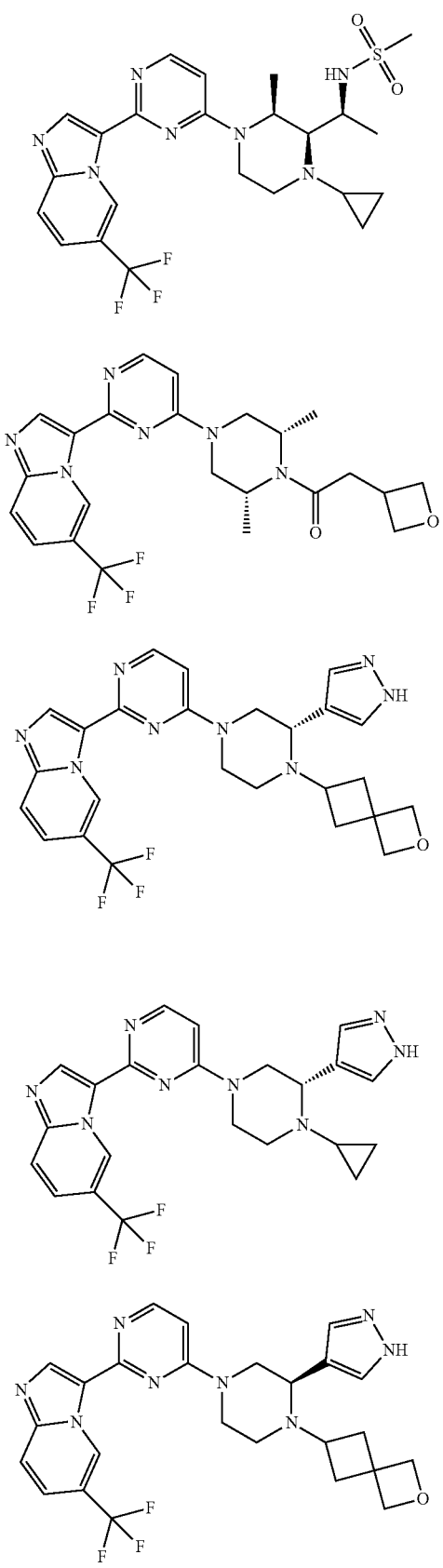
I-500
I-501
I-502
I-503
I-504
-continued
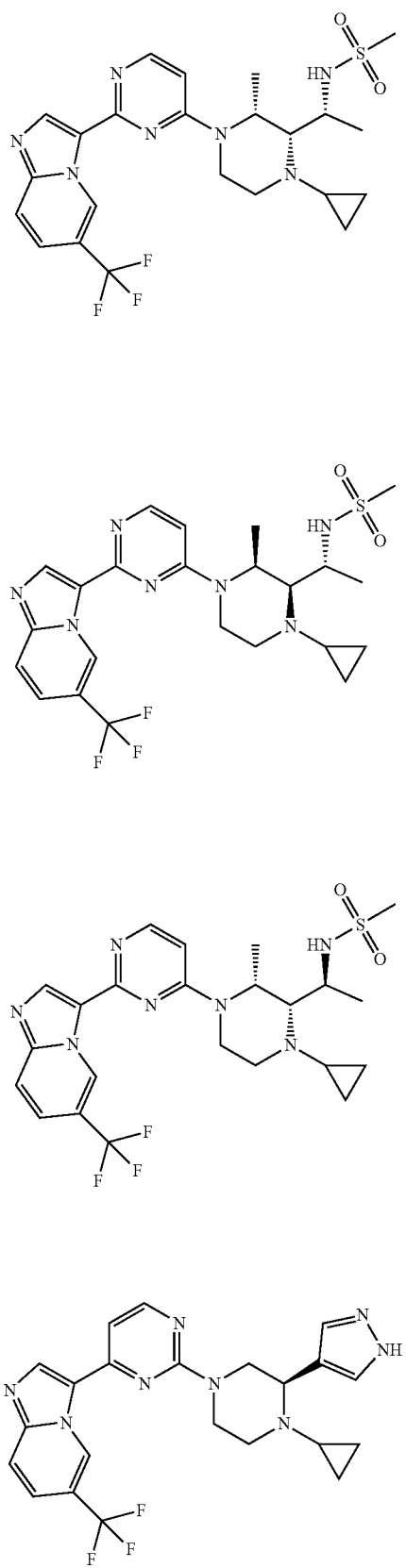
I-505
I-506
I-507
I-508

I-509
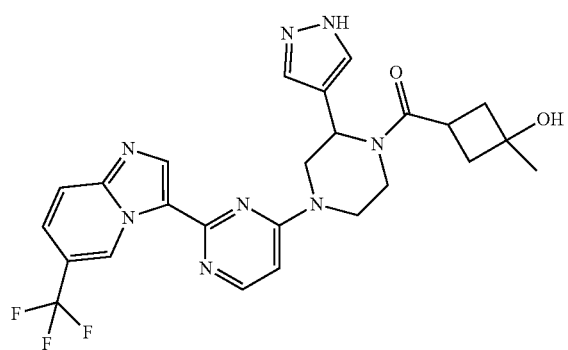
I-510
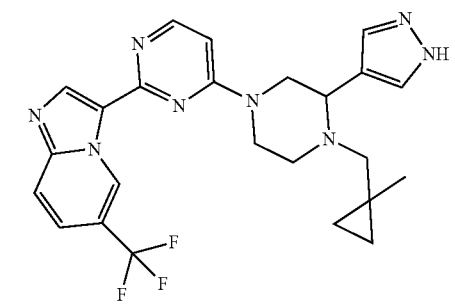
I-511
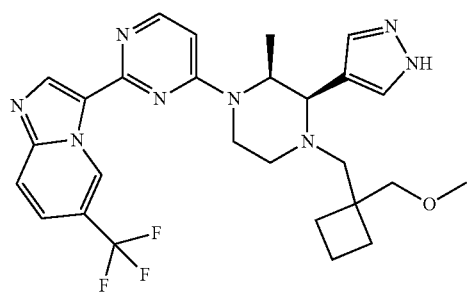
I-512
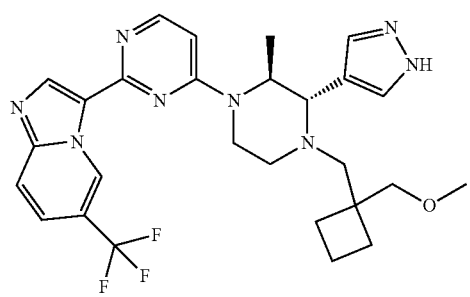
I-513
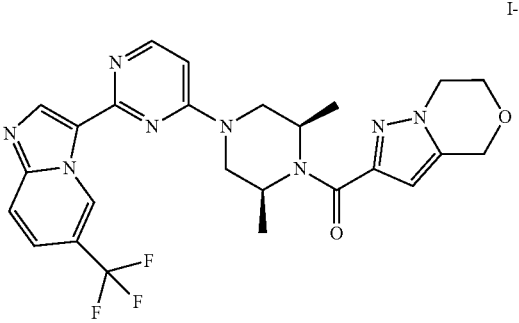
I-514
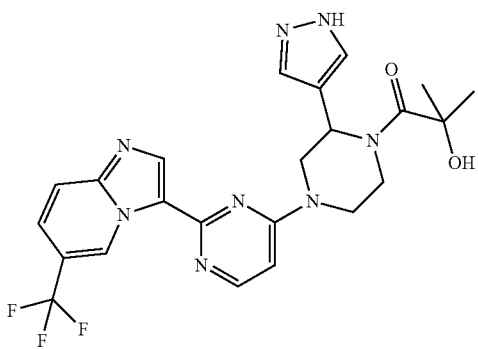
I-515
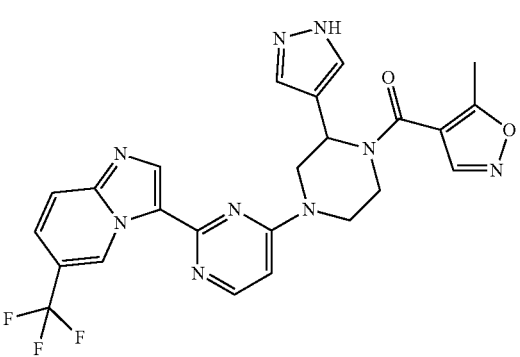
I-516
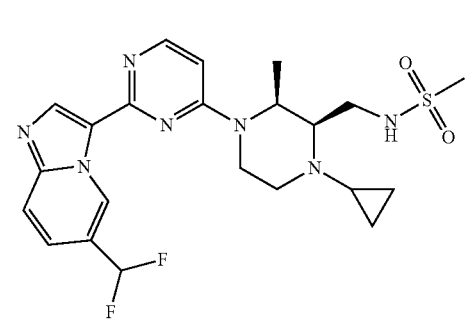
I-517
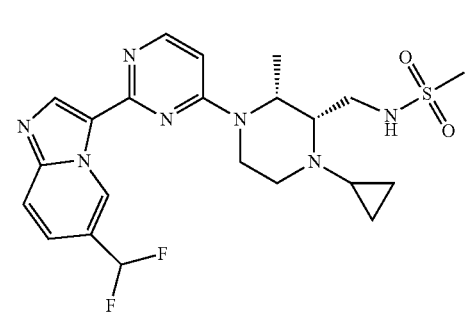

I-518
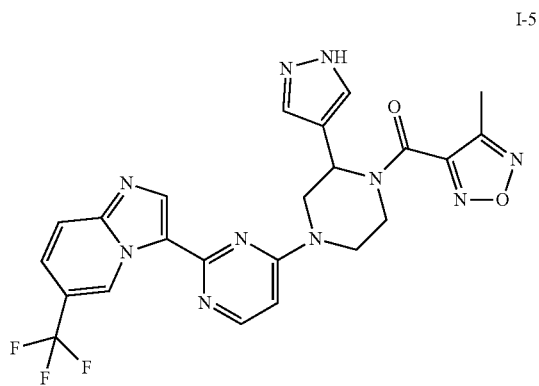
I-519
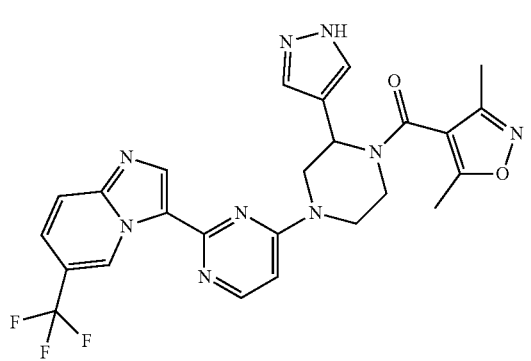
I-520
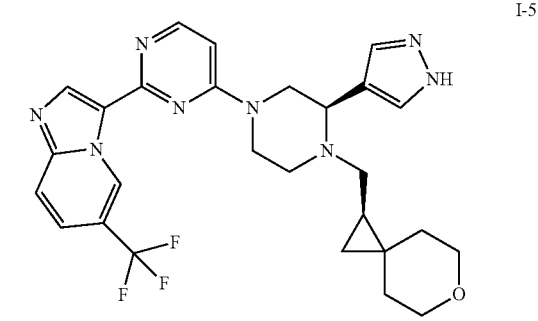
I-521
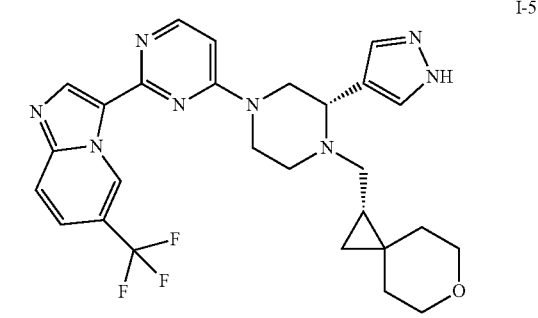
I-522
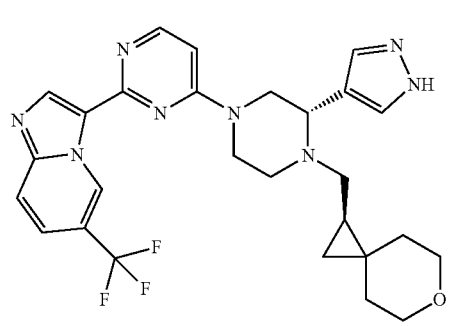
I-523
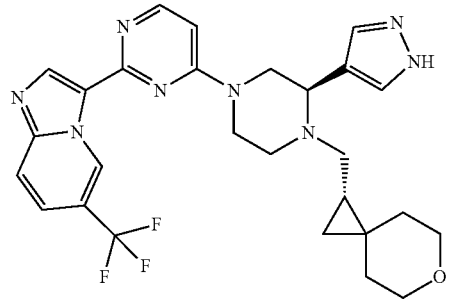
I-524
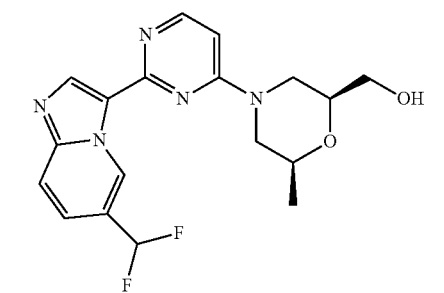
I-525
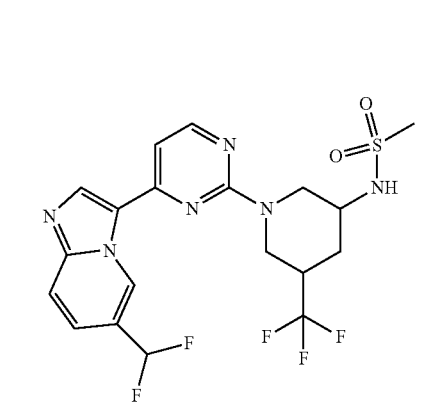
I-526
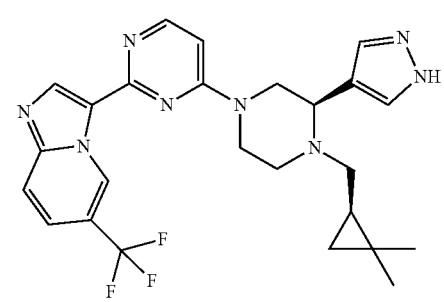

I-527 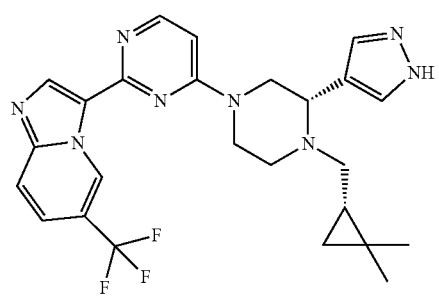
I-528 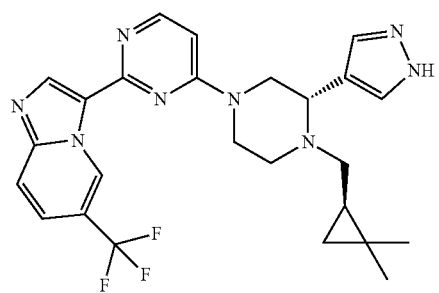
I-529 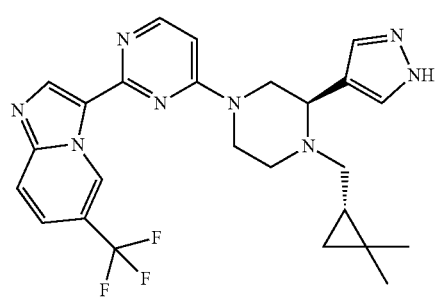
I-530 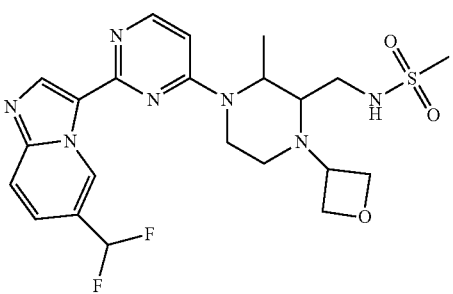
I-531 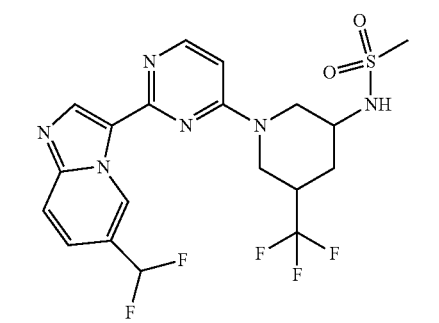
I-532 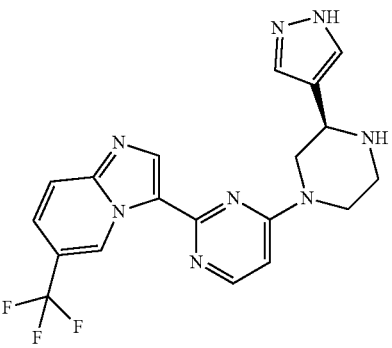
I-533 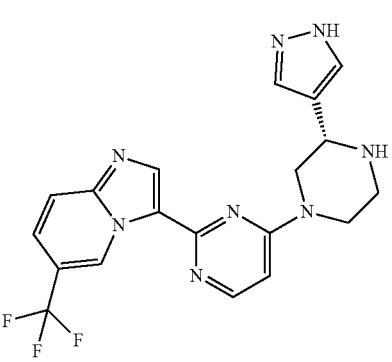
I-534 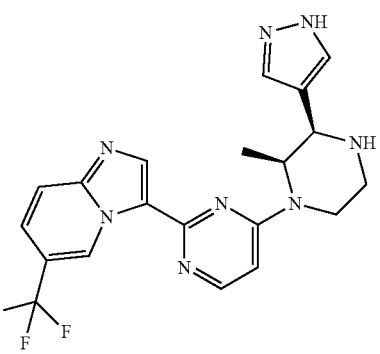
I-535 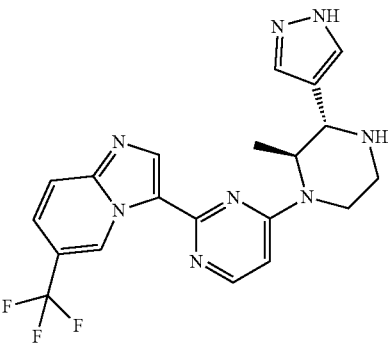

-continued
I-536
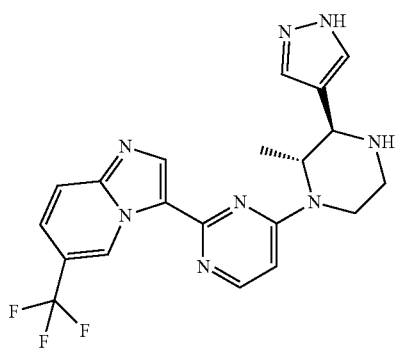
I-537
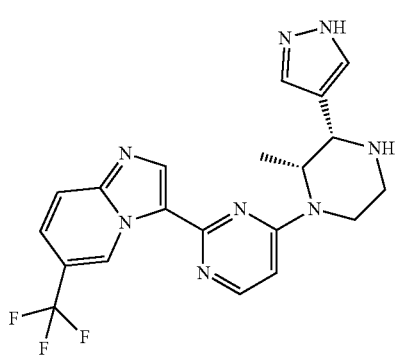
I-538
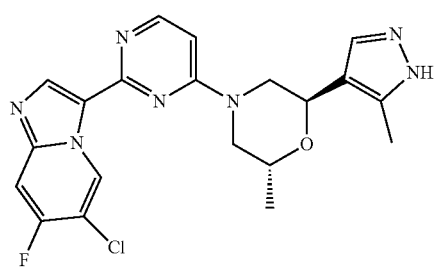
I-539
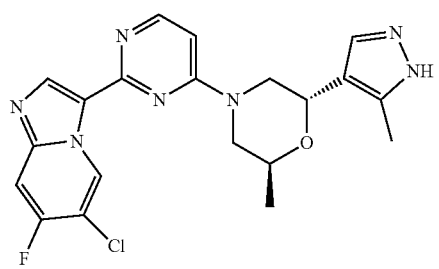
I-540
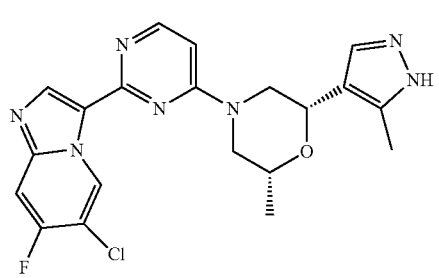
-continued
I-541
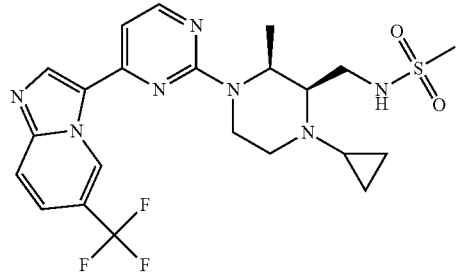
I-542
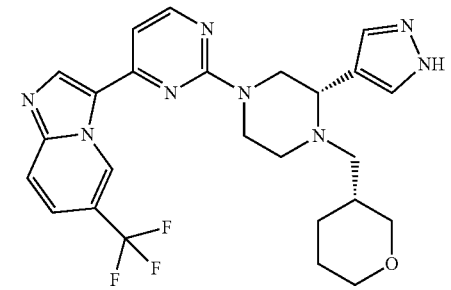
I-543
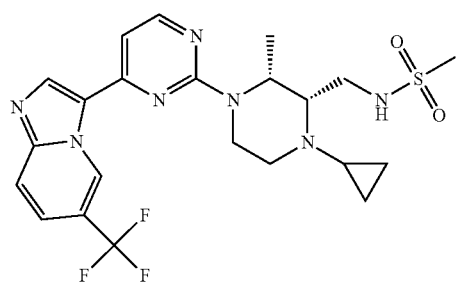
I-544
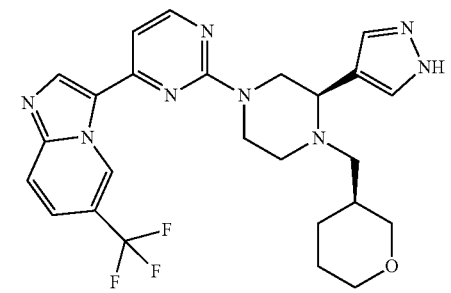
I-545
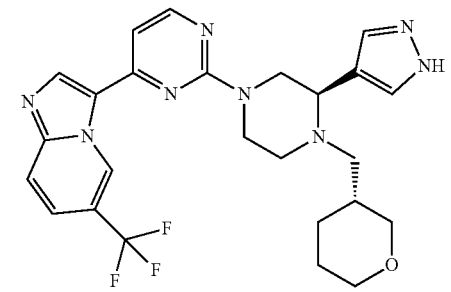

I-546 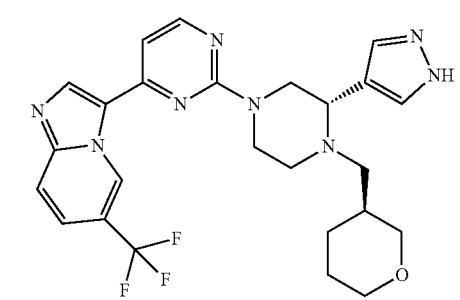
I-547 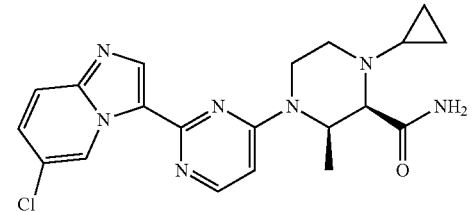
I-548 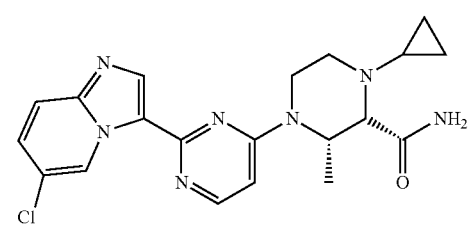
I-549 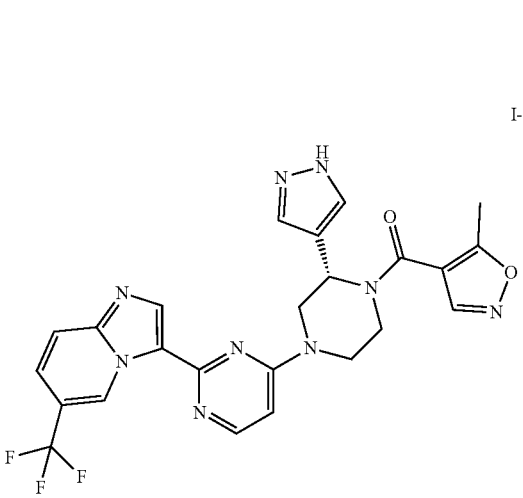
I-550 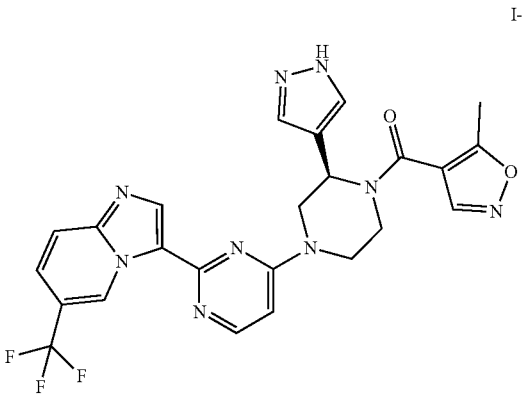
I-551 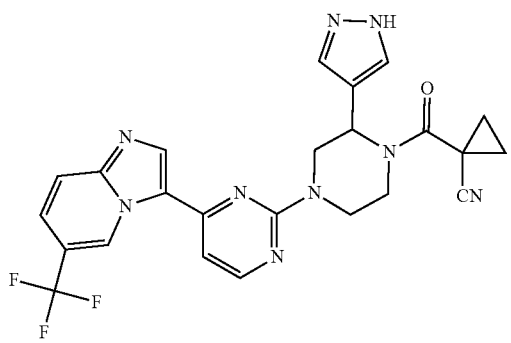
I-552 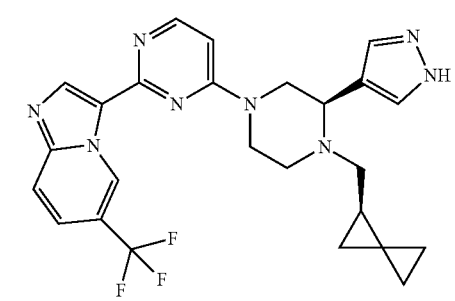
I-553 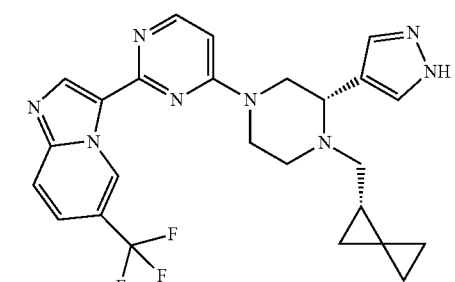
I-554 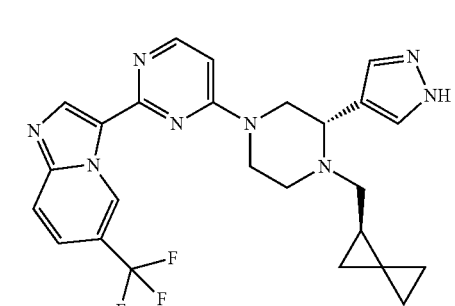
I-555 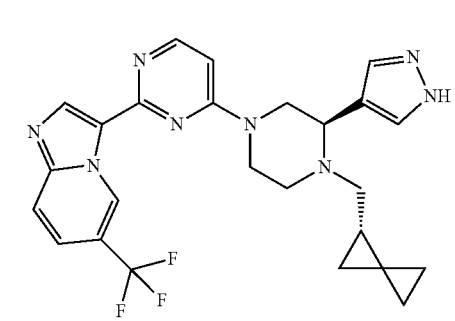

I-556
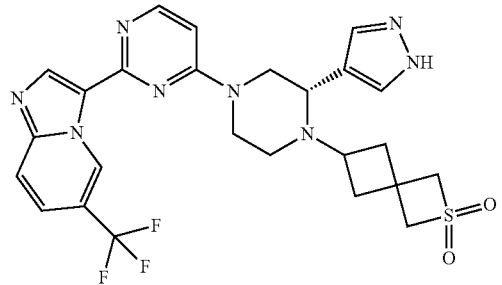
I-557
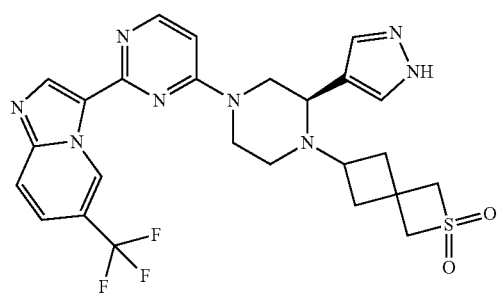
I-558
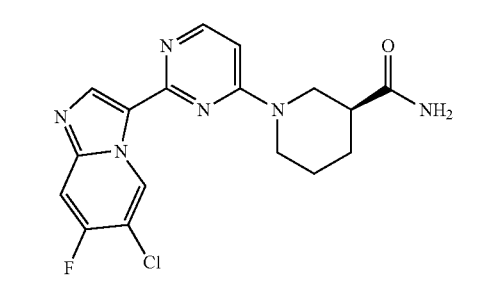
I-559
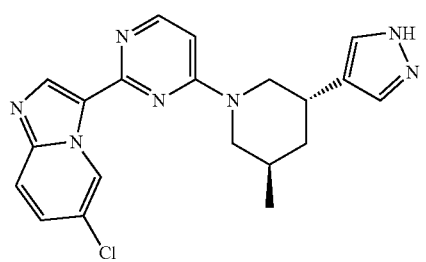
I-560
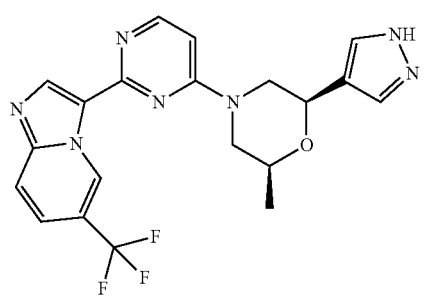
I-561
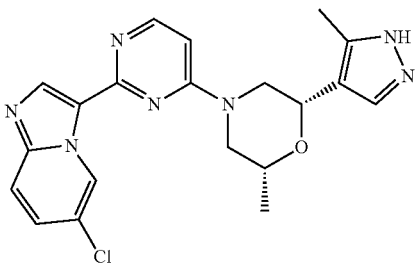
I-562
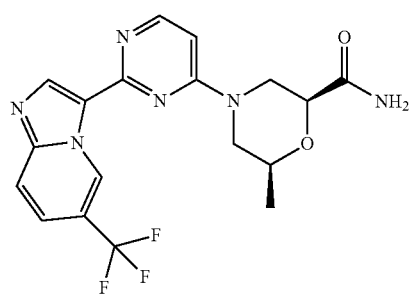
I-563
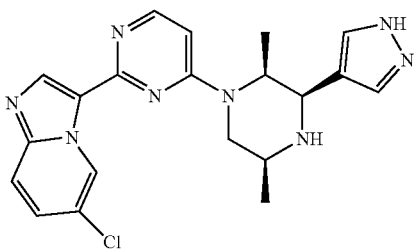
I-564
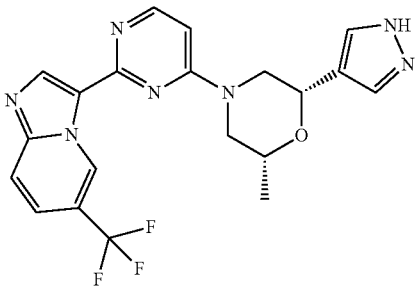
I-565
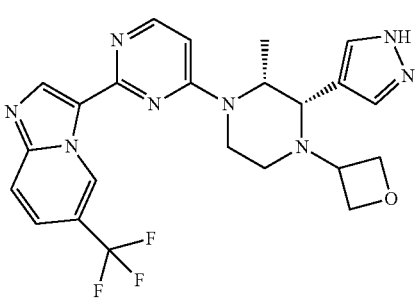

—S(NH$_2$)$_2$(O)OH, —N=S(O)R$_2$, —CH$_3$, —CH$_2$OH, —CH$_2$NHSO$_2$CH$_3$, —CD$_3$, —CD$_2$NRS(O)$_2$R, or R.

6. The compound of claim 1, wherein two R$^1$ groups are taken together to form a bivalent C$_{2-4}$ alkylene chain.

7. The compound of claim 1, wherein two R$^1$ groups are taken together to form =O or =NH.

8. The compound of claim 5, wherein each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

9. The compound of claim 5, wherein R is hydrogen.

10. The compound of claim 5, wherein R is an optionally substituted C$_{1-6}$ aliphatic.

11. The compound of claim 5, wherein R is an optionally substituted 3-8 membered saturated or partially unsaturated monocyclic carbocyclic ring.

12. The compound of claim 5, wherein R is an optionally substituted phenyl.

13. The compound of claim 5, wherein R is an optionally substituted 8-10 membered bicyclic aromatic carbocyclic ring.

14. The compound of claim 5, wherein R is an optionally substituted 4-8 membered saturated or partially unsaturated monocyclic heterocyclic ring having 1-2 heteroatoms independently selected from nitrogen, oxygen, or sulfur.

15. The compound of claim 5, wherein R is an optionally substituted 5-6 membered monocyclic heteroaromatic ring having 1-4 heteroatoms independently selected from nitrogen, oxygen, or sulfur.

16. The compound of claim 5, wherein R is an optionally substituted 8-10 membered bicyclic heteroaromatic ring having 1-5 heteroatoms independently selected from nitrogen, oxygen, or sulfur.

17. The compound of claim 5, wherein two R groups are taken together to form a bivalent C$_{2-4}$ alkylene chain.

18. The compound of claim 5, wherein two R groups are taken together with their intervening atoms to form an optionally substituted 3-7 membered saturated or partially unsaturated monocyclic ring having 0-4 heteroatoms independently selected from nitrogen, oxygen or sulfur.

19. The compound of claim 1, wherein a R$^1$ group is selected from the group consisting of: fluoro, chloro, methyl, ethyl, —OH, —OCH$_3$, —CH$_2$OH, —CH$_2$CN, —CF$_3$, —CH$_2$NH$_2$, —COOH, —NH$_2$, or a pharmaceutically acceptable salt thereof.

4. A pharmaceutical composition comprising a compound according to claim 1, and a pharmaceutically acceptable carrier, adjuvant, or vehicle.

5. The compound of claim 1, wherein R$^1$ is hydrogen, halogen, —CN, —C(O)R, —C(O)OR, —C(O)NR$_2$, —C(O)NRS(O)$_2$R, —C(O)N=S(O)R$_2$, —NR$_2$, —NRC(O)R, —NRC(O)NR$_2$, —NRC(O)OR, —NRS(O)$_2$R, —NRS(O)$_2$NR$_2$, —OR, —ON(R)SO$_2$R, —P(O)R$_2$, —SR, —S(O)R, —S(O)$_2$R, —S(O)(NH)R, —S(O)$_2$N(R)$_2$,

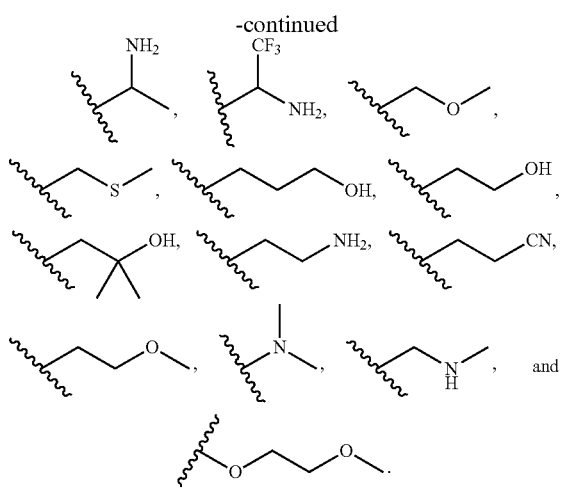
20. The compound of claim 1, wherein a $R^1$ group is selected from the group consisting of:
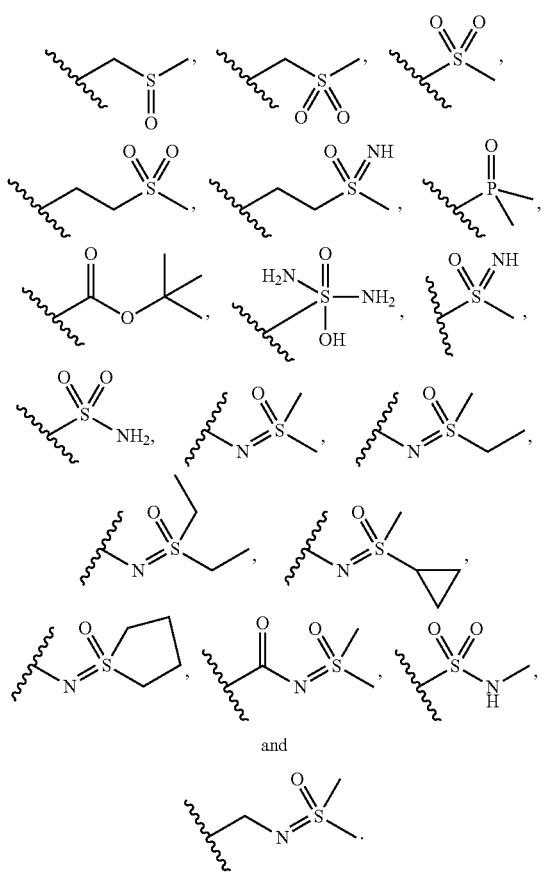
21. The compound of claim 1, wherein a $R^1$ group is selected from the group consisting of:
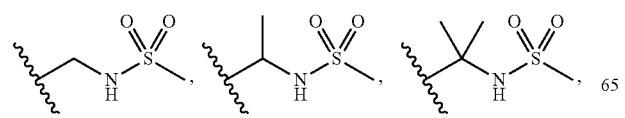
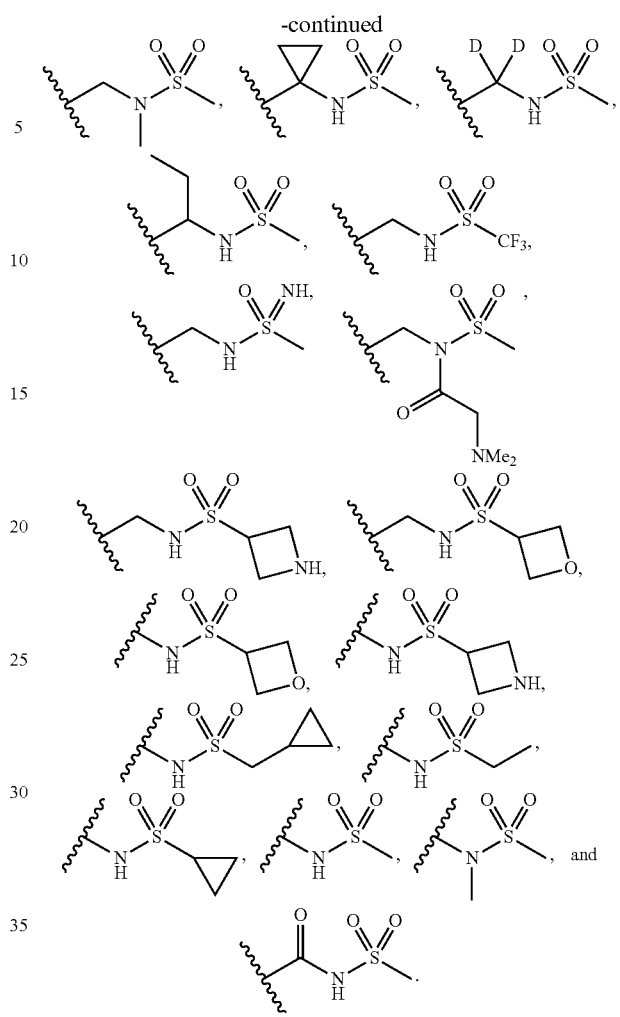
22. The compound of claim 1, wherein a $R^1$ group is selected from the group consisting of:
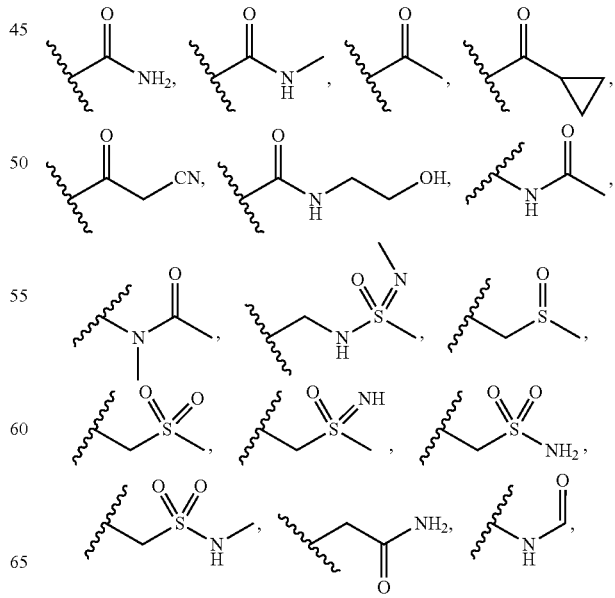

469
-continued
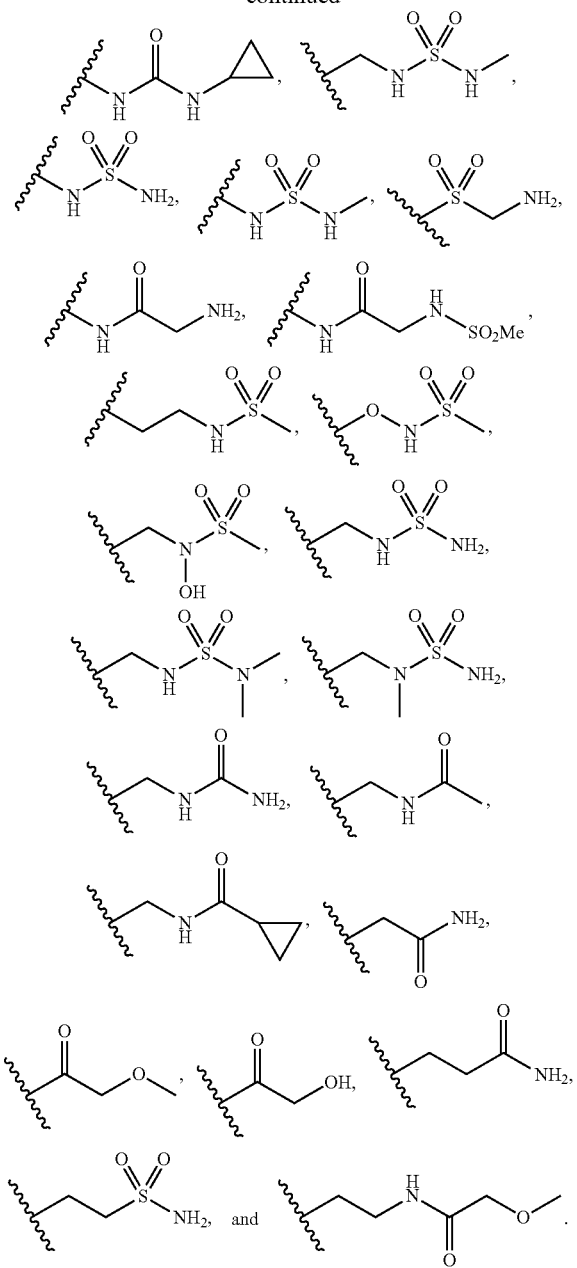
23. The compound of claim 1, wherein a $R^1$ group is selected from the group consisting of:
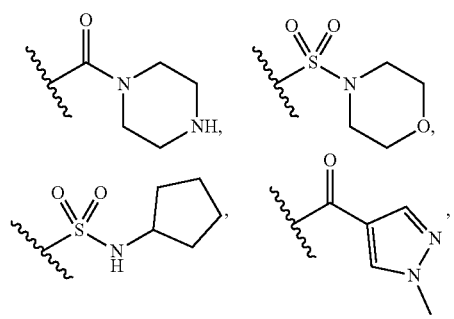
470
-continued
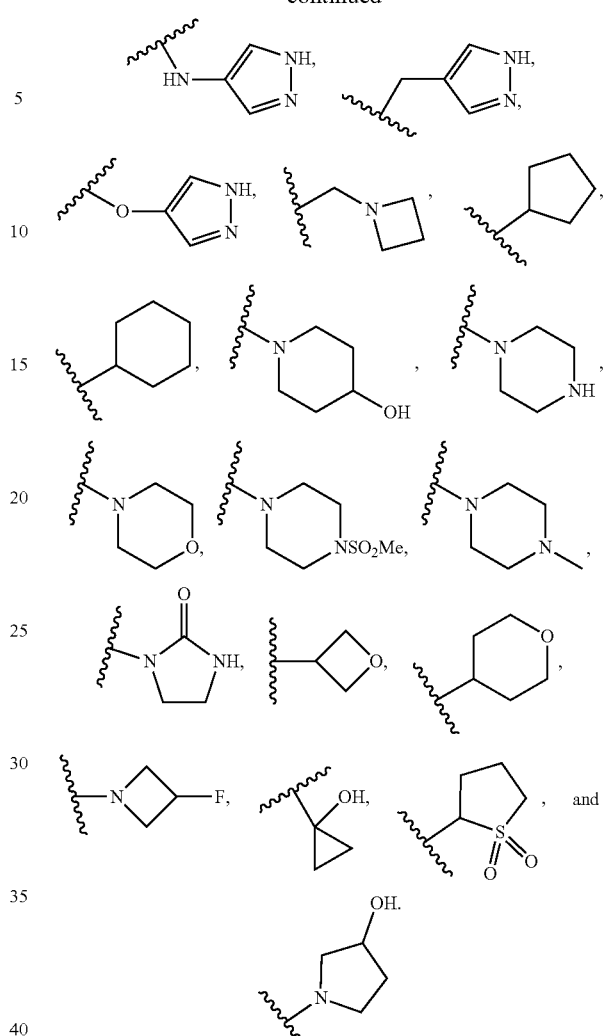
24. The compound of claim 1, wherein a $R^1$ group is selected from the group consisting of:
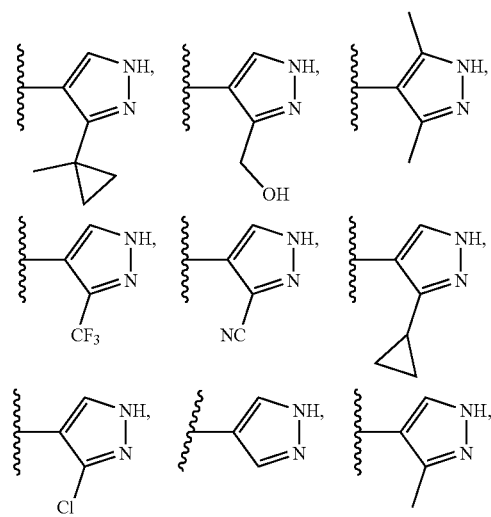

-continued
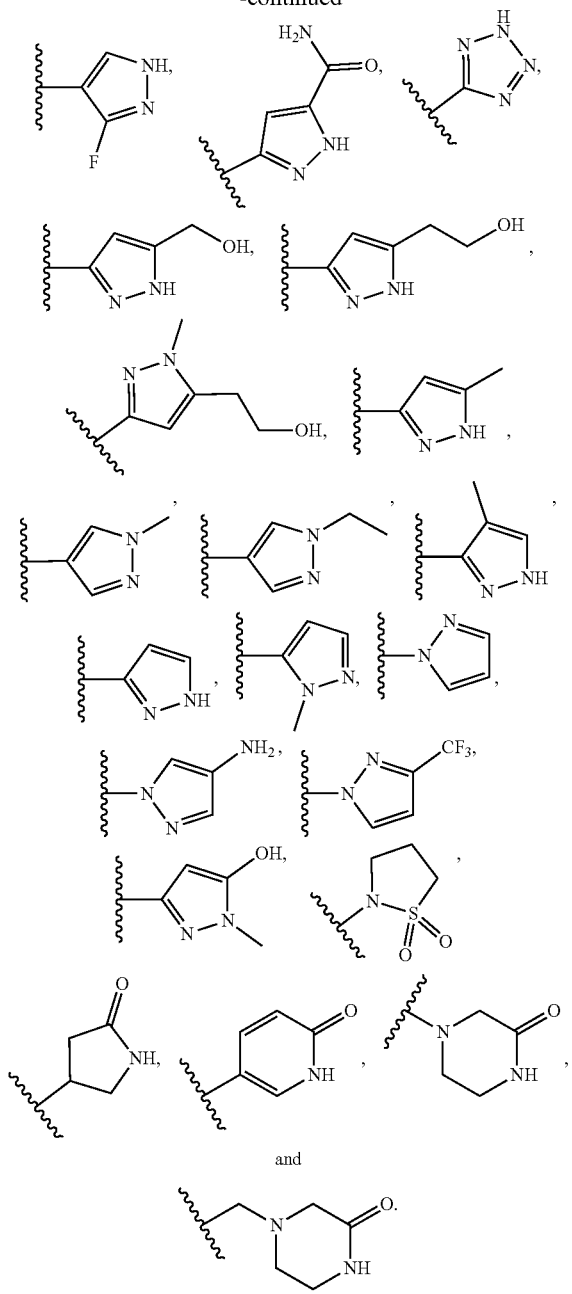
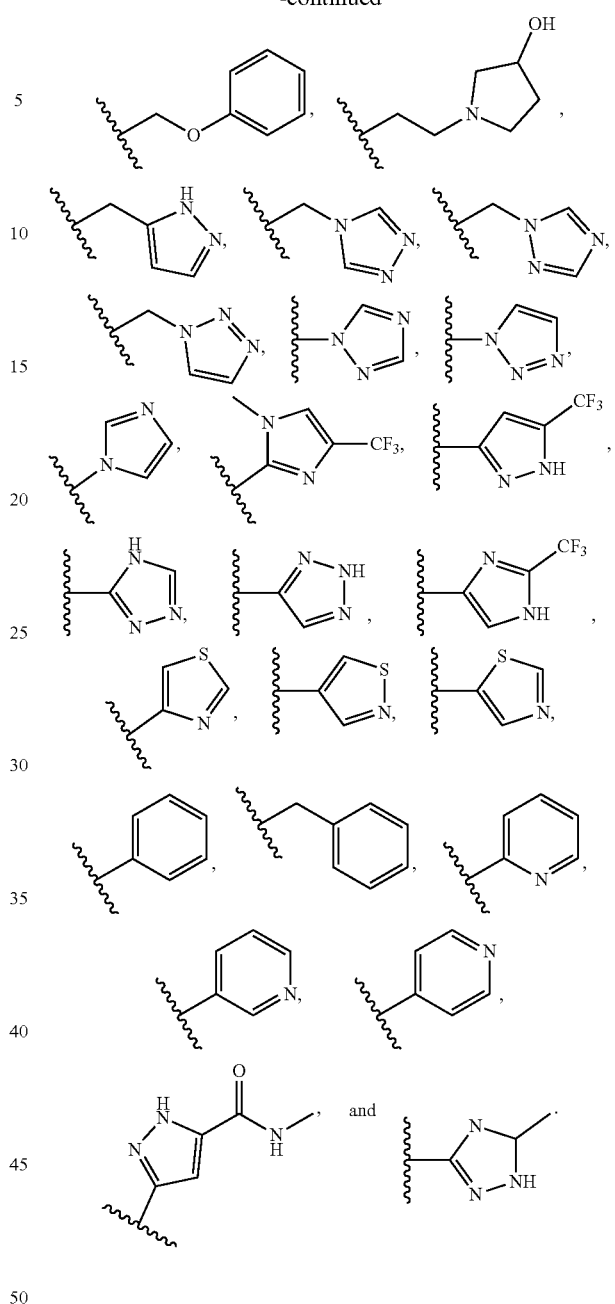
25. The compound of claim 1, wherein a $R^1$ group is selected from the group consisting of:
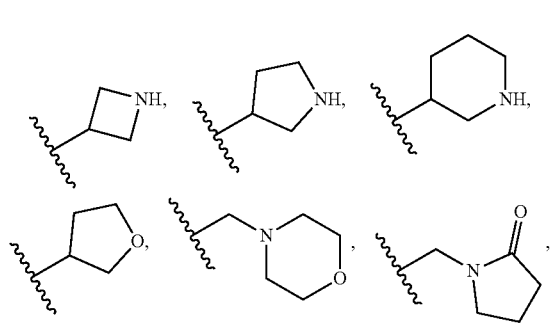
26. The compound of claim 1, wherein a $R^1$ group is selected from the group consisting of:
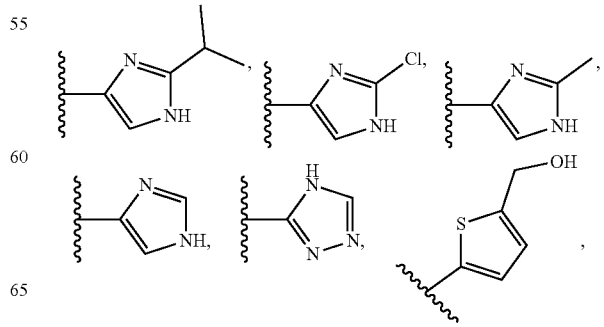

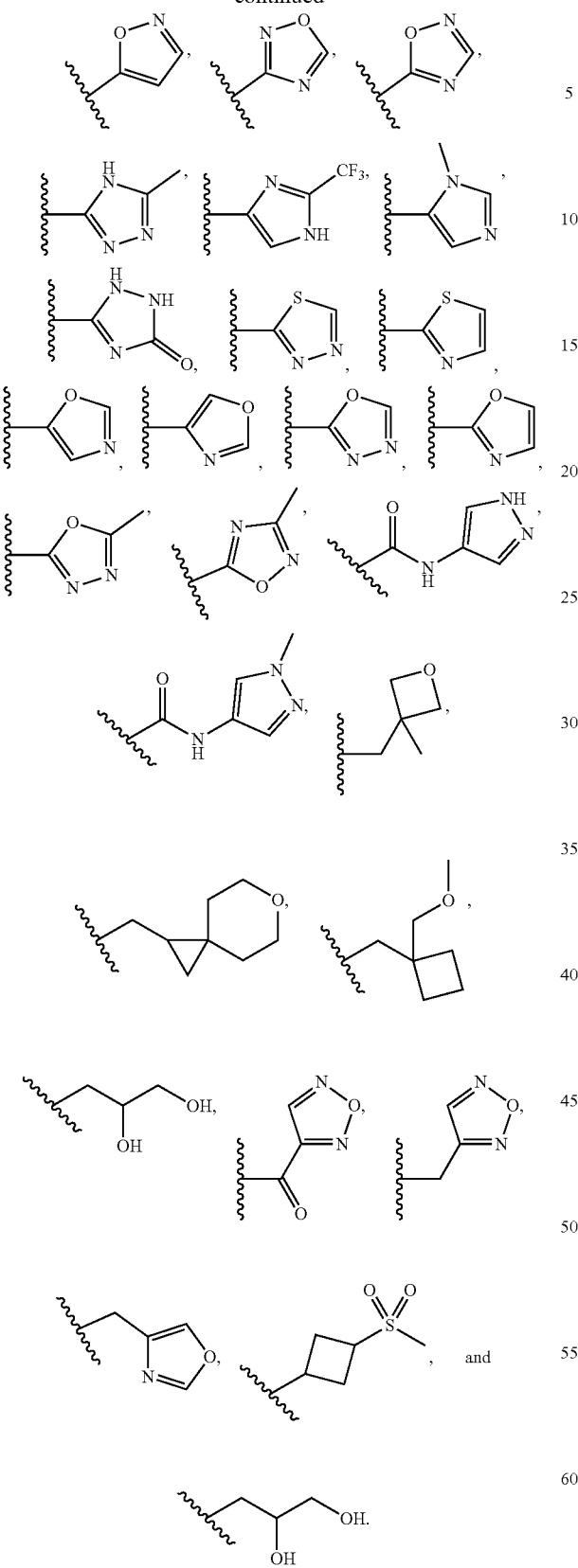
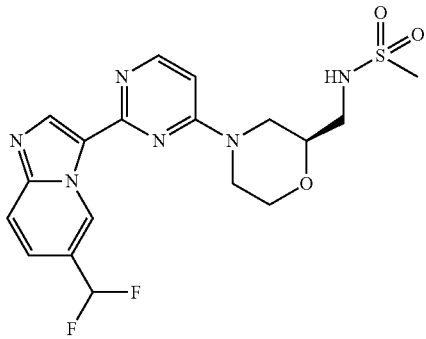
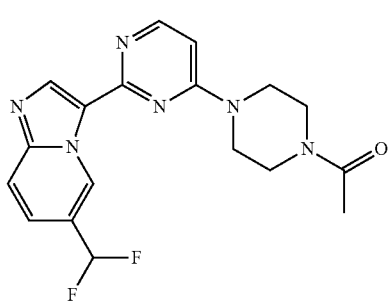
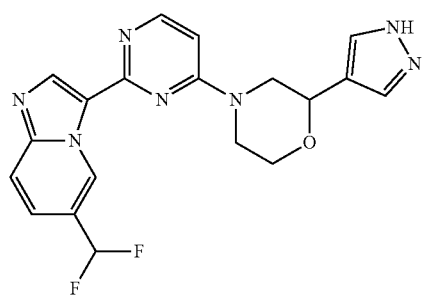
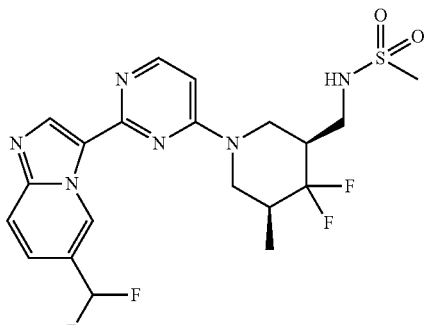
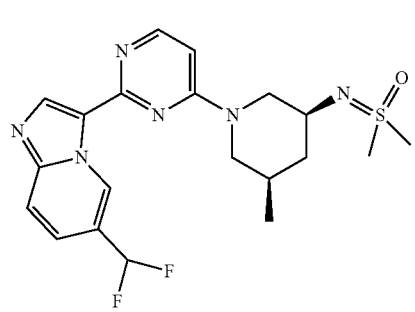
27. The compound of claim 1, wherein the compound is selected from the group consisting of:

I-375
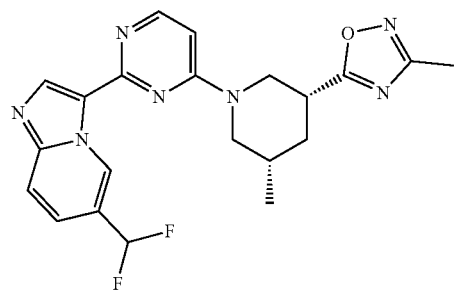
I-378
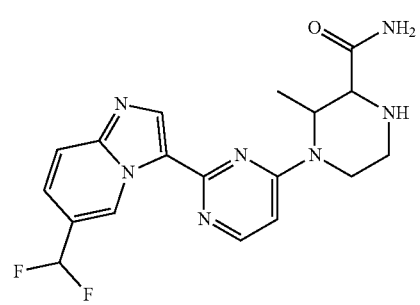
I-394
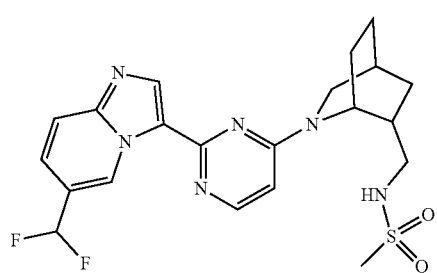
I-472
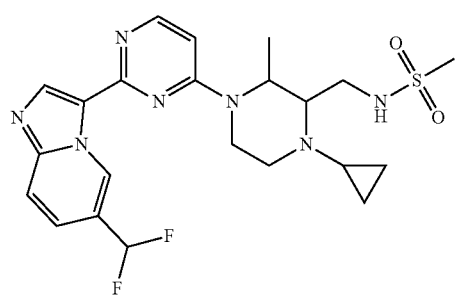
I-496
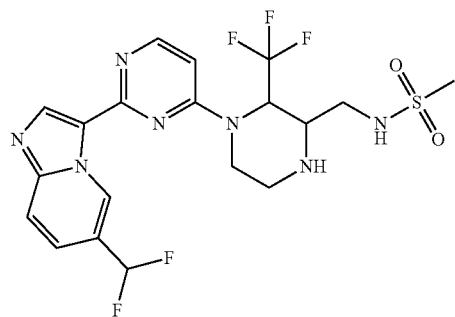
I-497
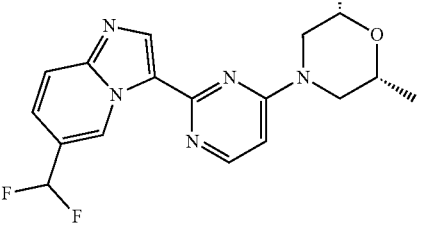
I-498
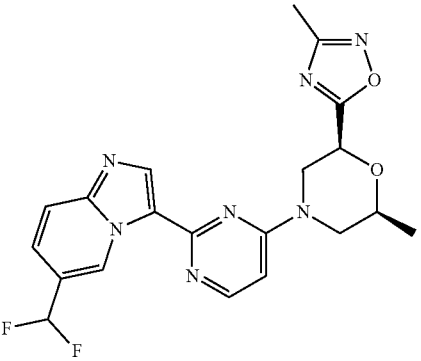
I-516
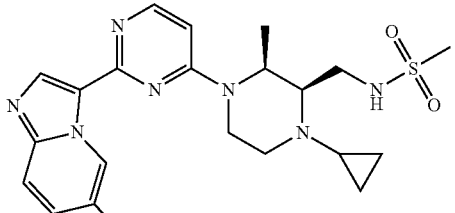
I-517
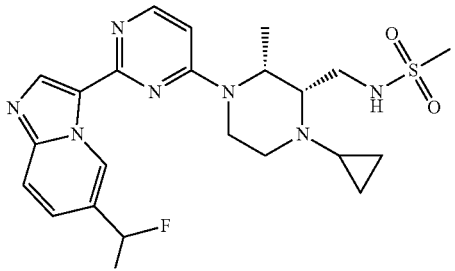
I-524
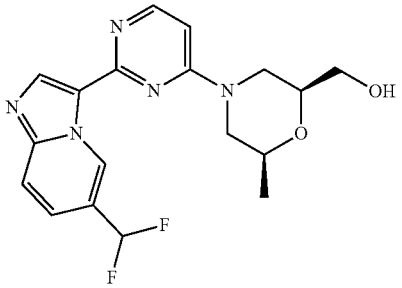

-continued
I-530
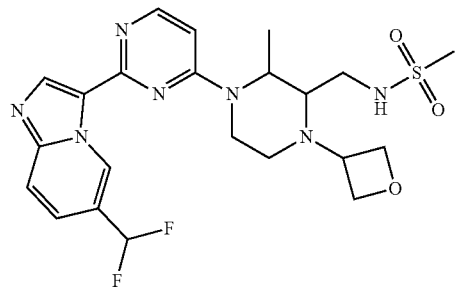
I-531
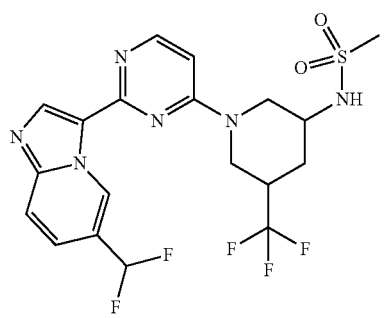
-continued
I-569
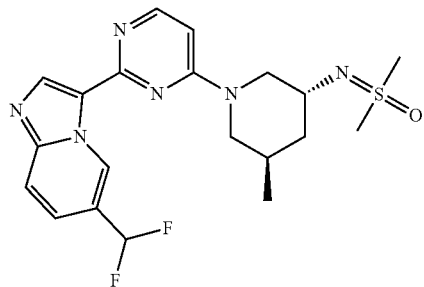
or a pharmaceutically acceptable salt thereof.
28. A pharmaceutical composition comprising a compound according to claim 3, and a pharmaceutically acceptable carrier, adjuvant, or vehicle.
* * * * *